(12) United States Patent
Muto et al.

(10) Patent No.: US 8,507,714 B2
(45) Date of Patent: Aug. 13, 2013

(54) 7-MEMBERED RING COMPOUND AND METHOD OF PRODUCTION AND PHARMACEUTICAL APPLICATION THEREOF

(75) Inventors: Tsuyoshi Muto, Mishima-gun (JP); Taisaku Tanaka, Ibaraki (JP); Hiroshi Maruoka, Mishima-gun (JP); Seiichi Imajo, Ikeda (JP); Yoshiaki Tomimori, Kyoto (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 12/984,195

(22) Filed: Jan. 4, 2011

(65) Prior Publication Data

US 2011/0166342 A1    Jul. 7, 2011

Related U.S. Application Data

(63) Continuation of application No. 11/791,828, filed as application No. PCT/JP2005/022591 on Dec. 1, 2005, now Pat. No. 7,888,348.

(30) Foreign Application Priority Data

Dec. 2, 2004 (JP) .................................. 2004-350153

(51) Int. Cl.
    *C07C 229/38* (2006.01)
(52) U.S. Cl.
    USPC ........................................... 560/37; 562/442
(58) Field of Classification Search
    None
    See application file for complete search history.

(56) References Cited

U.S. PATENT DOCUMENTS

| | | | |
|---|---|---|---|
| 5,663,333 A | 9/1997 | Hodge et al. | |
| 2002/0183249 A1 * | 12/2002 | Taylor et al. | ............... 514/12 |
| 2004/0254167 A1 | 12/2004 | Biftu et al. | |

FOREIGN PATENT DOCUMENTS

| | | |
|---|---|---|
| CN | 1435408 | 8/2003 |
| DE | 2257171 | 11/1972 |
| EP | 1099690 A1 | 5/2001 |
| JP | 36-9868 | 7/1961 |
| JP | 76009750 B * | 3/1976 |
| JP | 2000095770 A | 4/2000 |
| JP | 2003-342265 | 12/2003 |
| JP | 2004-067584 | 3/2004 |
| RU | 2301803 C2 | 6/2007 |
| SU | 403677 A1 | 10/1973 |
| WO | WO-0005204 A1 | 2/2000 |
| WO | 00/51640 | 9/2000 |
| WO | 01/32214 | 5/2001 |
| WO | 01/62292 | 8/2001 |
| WO | 01/62293 | 8/2001 |
| WO | 01/62294 | 8/2001 |
| WO | 02/32881 | 4/2002 |
| WO | 02/083649 | 10/2002 |
| WO | 03/007964 | 1/2003 |
| WO | 03/035654 | 5/2003 |
| WO | 03/078419 | 9/2003 |
| WO | 2004/007464 | 1/2004 |
| WO | WO-2004065382 A1 | 8/2004 |
| WO | 2005/000825 | 1/2005 |
| WO | WO-2005021508 A1 | 3/2005 |
| WO | 2005/051304 A2 | 6/2005 |
| WO | 2005/073214 | 8/2005 |

OTHER PUBLICATIONS

Rouhi, Chemical and Engineering News, The Right Stuff, 2003, 81(8), pp. 32-35.*
Maruoka et al, Bioorganic & Medicinal Chemistry Letters, Development of 6-Benzyl Substituted 4-Aminocarbonyl-1, 4-diazepane-2, 5-diones as Orally Active Human Chymase Inhibitors, 2007, 17, pp. 3435-3439.*
Amendment filed Aug. 11, 2010, in European Patent Office in European Patent Application No. 05814413.0-2117.
Schechter, Norman, "Chymotrypsin-like Proteinases of Human Skin Mast Cells" in Mast Cell Proteases in Immunology and Biology, Editor, George H. Caughey, 1995, pp. 47-69, Marcel Dekker, Inc., New York, Basel, Hong Kong.
Irani, Anne-Marie A., "Tissue and Developmental Variation of Protease Expression in Human Mast Cells", in Mast Cell Proteases in Immunology and Biology ed. George H. Caughey, 1995, pp. 127-143, Marcel Dekker, Inc., New York, Basel, Hong Kong.
Urata et al., "Identification of a Highly Specific Chymase as the Major Angiotensin II-forming Enzyme in the Human Heart", Journal of Biological Chemistry, Dec. 25, 1990, pp. 22348-22357, vol. 265, No. 36, The American Society for Biochemistry and Molecular Biology, Inc., USA.
Vartio et al., "Susceptibility of Soluble and Matrix Fibronectins to Degradation by Tissue Proteinases, Mast Cell Chymase and Cathepsin G", Journal of Biological Chemistry, Jan. 10, 1981, pp. 471-477, vol. 256, No. 1. USA.

(Continued)

Primary Examiner — Paul A Zucker
(74) Attorney, Agent, or Firm — Drinker Biddle & Reath LLP

(57) ABSTRACT

A 7-membered heterocyclic compound having the formula (I), or its salt, or a solvate thereof with a chymase inhibitory action and useful for the prevention or treatment of various diseases, in which chymase is involved:

(I)

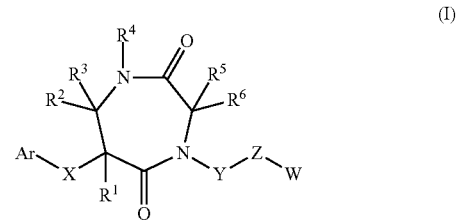

a method for producing the same, and a pharmaceutical composition useful for the prevention or treatment of diseases, in which chymase is involved, including the compound of having the formula (I), or its pharmaceutically acceptable salt, or a solvate thereof are provided.

3 Claims, No Drawings

(56) References Cited

OTHER PUBLICATIONS

Saarinen, Juhani et al., "Activation of Human Intersititial Procollagenase through Direct Cleavage of the Leu$^{83}$—Thr$^{84}$ Bond by Mast Cell Chymase", Journal of Biological Chemistry, Jul. 8, 1994, pp. 18134-18140, vol. 269, No. 27, The American Society for Biochemistry and Molecular Biology, Inc., USA.
Kofford et al., "Cleavage of Type I Procollagen by Human Mast Cell Chymase Initiates Collagen Fibril Formation and Generates a Unique Carboxyl-terminal Propetide", Journal of Biological Chemistry, Mar. 14, 1997, pp. 7127-7131, vol. 272, No. 11; The American Society for Biochemistry and Molecular Biology, Inc., USA.
Taipale et al., "Human Mast Cell Chymase and Leukocyte Elastase Release Latent Transforming Growth Factor β1 from the Extracellular Matrix of Cultured Human Epithelial and Endothelial Cells", Journal of Biological Chemistry, Mar. 3, 1995, pp. 4689-4696, vol. 270, No. 9; The American Society for Biochemistry and Molecular Biology, Inc., USA.
Lindstedt et al., "Activation of Paracrine TGF-β1 Signaling Upon Stimulation and Degranulation of Rat Serosal Mast Cells: A Novel Function for Chymase", The FASEB Journal, Jun. 2001, vol. 15, pp. 1377-1388.
Mizutani et al., "Rapid and Specific Conversion of Precursor Interleukin 1β (IL-1β) to an Active IL-1 Species by Human Mast Cell Chymase", J. Exp. Med, Oct. 1991, pp. 821-825, vol. 174; The Rockefeller University Press.
Longley et al., "Chymase Cleavage of Stem Cell Factor Yields a Bioactive, Soluble Product", Proc. National Academy of Science, USA; Aug. 1997, vol. 94, pp. 9017-9021.
Kokkonen et al., "Low Density Lipoprotein Degradation by Secretory Granules of Rat Mast Cells", Journal of Biological Chemistry; vol. 261, No. 34, Dec. 5, 1986; pp. 16067-16072; The American Society of Biological Chemists, Inc.
Lindstedt et al., "Chymase in Exocytosed Rat Mast Cell Granules Effectively Proteolyzes Apolipoprotein A1-containing Lipoproteins, So Reducing the Cholesterol Efflux-inducing Ability of Serum and Aortic Intimal Fluid", J. Clin. Invest., vol. 97, No. 10, May 1996, pp. 2174-2182; The American Society for Clinical Investigation, Inc.
Nakano et al., "Selective Conversion of Big Endothelins to Tracheal Smooth Muchle-Constricting 31-Amino Acid-Length Endothelins by Chymase from Human Mast Cells"; J. Immunology; vol. 159; 1997; pp. 1987-1992.
Schick et al., "Rat Serosal Mast Cell Degranulation Mediated by Chymase, An Endogenous Secretory Granule Protease: Active Site-Dependent Initiation at 1°C"; The Journal of Immunology; vol. 136, No. 10, May 15, 1986, pp. 3812-3818.
He et al., Human Mast Cell Chymase Induces the Accumulation of Neutrophils, Eosinophils and Other Inflammatory Cells in vivo; British Journal of Pharmacology, (1998) 125, pp. 1491-1500.
He et al., "The Induction of A Prolonged Increase in Microvascular Permeability by Human Mast Cell Chymase"; Elsevier, European Journal of Pharmacology 352 (1998) pp. 91-98.
Powers et al., "Inhibitors of Serine Proteinases" in Proteinase Inhibitors, pp. 55-152; (1986), Editors Barrett and Salvensen.
Fukami et al., "Chymase: Its Pathophysiological Roles and Inhibitors"; Curr. Pharmaceutical Design, vol. 4; Institute for Biomedical Research, Research Center, Suntory Ltd, Japan; 1998; pp. 439-453.
Aoyama, "Non-Peptidic Chymase Inhibitors"; Ashley Publications; 2001; pp. 1423-1429.
Muto et al., "Recent Chymase Inhibitors and Their Effects in in vivo Models"; IDrugs 2002 5(12); pp. 1141-1150.
Matsumoto et al., "Chymase Inhibition Prevents Cardiac Fibrosis and Improves Diastolic Dysfunction in the Progression of Heart Failure"; Circulation, vol. 107; May 27, 2003; pp. 2555-2558.
Jin et al., "Beneficial Effects of Cardiac Chymase Inhibition During the Acute Phase of Myocardial Infarction"; Life Sciences 71 (2002) pp. 437-446.
Takai et al., "A Single Treatment With a Specific Chymase Inhibitor, TY-51184, Prevents Vascular Proliferation in Canine Grafted Veins"; J. Pharmacological Sciences (2004); vol. 94, pp. 443-448.
Lampariello et al., "Solid-Phase Synthesis of Conformationally Constrained Peptidomimetics Based on a 3,6-Disubstituted-1,4-diazepan-2,5-dione Core"; J. Org. Chem. (2003); vol. 68, pp. 7893-7895.
Müller-Hartwieg et al., "Synthesis and Conformational Investigation of Cyclic Dipeptides: 7-Membered Rings Containing α- and β-Amino Acids"; Journal of Peptide Science; (2003) vol. 9, pp. 187-199.
Gates, "New Synthesis of Diazepam"; J. Org. Chem (1980) vol. 45, pp. 1675-1681.
Search Report dated Jan. 24, 2006 for International Application No. PCT/JP2005/022591 filed Dec. 1, 2005 [translated].
Raffaella Lampariello, Lucia et al., "Solid-Phase Synthesis of Conformationally Constrained Peptidomimetics Based on a 3,6-Disubstituted-1,4-diazepan-2,5-dione Core", The Journal of Organic Chemistry, Oct. 3, 2003, pp. 7893-7895, vol. 68, No. 20, American Chemical Society, Columbus, Ohio, USA.
Muller-Hartwieg, J. Constanze D. et al., "Synthesis and Conformational Investigation of Cyclic Dipeptides: 7-Membered Rings Containing α- and β-Amino Acids", Journal of Peptide Science, Mar. 2003, pp. 187-199, vol. 9, No. 3.
Gates, Marshall, "New Synthesis of Diazepam", Journal of Organic Chemistry, Apr. 25, 1980, pp. 1675-1681, vol. 45, No. 9, American Chemical Society, Columbus, Ohio, USA.
Muñoz-Muñiz, Omar et al., "Enantioselective Alkylation and Protonation of Prochiral Enolates in the Asymmetric Synthesis of β-Amino Acids", Tetrahedron, Jun. 2, 2003, pp. 4223-4229, vol. 59, No. 23, Pergamon Press, Oxford, England.
Richter et al., "Polymer Bound 3-Hydroxy-2-methylidenepropionic Acids. A Template for Multiple Core Structure Libraries", Journal of Organic Chemistry, 1999, vol. 64, No. 4, pp. 1362-1365.
Tanaka et al., "Identification of 6-substituted 4-arylsulfonyl-1,4-diazepane-2,5-diones as Novel Scaffold for Human Chymase Inhibitors", Bioorganic & Medicinal Chemistry Letters, vol. 17, 2007, pp. 3431-3434.
Maruoka et al., "Development of 6-benzyl substituted 4-aminocarbonyl-1,4-diazepane-2,5-diones as Orally Active Human Chymase Inhibitors", Bioorganic & Medicinal Chemistry Letters, vol. 17, 2007, pp. 3435-3439.
European Search Report dated Nov. 9, 2009 in European Application No. 05 81 4413.0.
English-language translation of Decision to Grant issued by Russian Patent Office in PCT/JP2005/022591.
Office Action issued Nov. 29, 2011, in Japanese Application No. 2006-546761.
Decision to Grant issued Oct. 12, 2011, in Russian Application No. 2007124585.
Chen et al., "Asymmetric Synthesis of a Novel Phenylogous Amino Acid Mimicking an Extended Dipeptide," Tetrahedron Letters, vol. 36, No. 46, 1995, pp. 8715-8718.
European Search Report mailed May 11, 2012, in European Patent Application No. EP. 12 15 6735.

\* cited by examiner

7-MEMBERED RING COMPOUND AND METHOD OF PRODUCTION AND PHARMACEUTICAL APPLICATION THEREOF

CROSS REFERENCE TO RELATED APPLICATIONS

This application is a continuation of application Ser. No. 11/791,828, filed Apr. 29, 2008, which is a National Stage of International Application No. PCT/JP2005/022591, filed Dec. 1, 2005, which claims the benefit of Japanese Patent Application No. 2004-350153, filed Dec. 2, 2004, and which are incorporated by reference herein in their entirety.

TECHNICAL FIELD

The present invention relates to a 7-membered ring compound having a chymase inhibitory activity and useful as a pharmaceutical for the prevention and/or treatment of diseases, in which chymase is involved, such as bronchial asthma, urticaria, atopic dermatitis, allergic conjunctivitis, rhinitis, rheumatoid arthritis, mastocytosis, scleroderma, heart failure, cardiac hypertrophy, congestive heart failure, hypertension, atherosclerosis, myocardial ischemia, myocardial infarction, restenosis after PTCA, restenosis after bypass graft surgery, ischemic peripheral circulatory disorders, hyperaldosteronism, diabetic retinopathy, diabetic nephropathy, nephritis, glomerulosclerosis, renal insufficiency, psoriasis, solid tumor, postoperative adhesion, glaucoma, and ocular hypertension, and the method of production thereof and starting compounds useful for the same.

BACKGROUND ART

Chymase is stored as an ingredient in granules of mast cells (MC), which are one of the inflammatory cells closely related to inflammation, and is widely present mainly in the tissue such as skin, heart, vascular walls, intestines etc. (see Non-Patent Document 1). Human chymase is known as an enzyme for specifically producing angiotensin II (i.e., Ang II) from angiotensin I (i.e., Ang I) independently from angiotensin converting enzyme. There is a report that, in human cardiac tissue, 80% of the production of angiotensin II is derived from by chymase (see Non-Patent Document 2). Ang II is known to be closely related to regulation of the blood pressure, diuretic regulation, and hypertrophy and remodeling of the cardiovascular system, that is, the migration and proliferation of smooth muscle cells etc. and the growth of the extracellular matrix in the cardiovascular system tissue. From these findings, it is suggested that chymase is closely related to cardiovascular lesions through production of Ang II. In addition to production of Ang II, it is reported that chymase has the following actions based on its protease activity: 1) degradation of the extracellular matrix (see Non-Patent Document 3), activation of collagenase (see Non-Patent Document 4), and production of collagen (see Non-Patent Document 5); 2) processing and activation of inflammatory cytokine, for example, release of latent TGF β1 from extracellular matrix (see Non-Patent Document 6), activation of latent TGFβ1 to active TGFβ1 (see Non-Patent Document 7), and activation of IL-1β (see Non-Patent Document 8); 3) activation of stem cell factor (SCF) which induces differentiation and proliferation of MCs (see Non-Patent Document 9); 4) degradation of apolipoprotein B in LDL (see Non-Patent Document 10) and degradation of apolipoprotein A in HDL (see Non-Patent Document 11); and 5) conversion of big endothelin to a bioactive peptide comprised of 31 amino acid residues (ET(1-31)) (see Non-Patent Document 12). Further, it is reported that chymase stimulates rat peritoneal mast cells to induce degranulation (see Non-Patent Document 13) and that administration of human chymase intraperitoneally to mice or subcutaneously to guinea pigs induces infiltration of eosinophil and other leukocytes (see Non-Patent Document 14), and causes continuous increase of vascular permeability not through the action of histamine (see Non-Patent Document 15). These various reports relating to the action of chymase suggest that chymase plays an important role in the processes of tissue inflammation, repair, and healing, and in allergic conditions. It is believed that in these processes, the excessive reaction of chymase is involved in various diseases.

From the above-mentioned findings, a chymase inhibitor can be expected to be useful as a pharmaceutical for the prevention or treatment of for example, bronchial asthma, urticaria, atopic dermatitis, allergic conjunctivitis, rhinitis, rheumatoid arthritis, mastocytosis, scleroderma, heart failure, cardiac hypertrophy, congestive heart failure, hypertension, atherosclerosis, myocardial ischemia, myocardial infarction, restenosis after PTCA, restenosis after bypass graft surgery, ischemic peripheral circulatory disorders, hyperaldosteronism, diabetic retinopathy, diabetic nephropathy, nephritis, glomerulosclerosis, renal insufficiency, psoriasis, solid tumor, postoperative adhesion, glaucoma, and ocular hypertension, and other diseases.

On the other hand, small molecule chymase inhibitors are already shown in books (see Non-Patent Document 16) or review articles (see Non-Patent Documents 17, 18, and 19). The efficacy of several inhibitors among these in animal disease models has been reported (vascular lipid deposition: see Patent Document 1, heart failure: see Non-Patent Document 20, myocardial infarction: see Patent Document 2, see Non-Patent Document 21, see Non-Patent Document 22, aortic aneurysm: see Patent Document 3, restenosis: see Patent Document 4, atopic dermatitis: see Patent Document 5, pruritus: see Patent Document 6, eosinphilia: see Patent Document 7, fibrosis: see Patent Document 8). Further, recently, in addition to the chymase inhibitors described in the above-mentioned books and review articles, imidazolidinedione derivatives (see Patent Document 9), phosphonic acid derivatives (see Patent Document 10), benzothiophensulfonamide derivatives (see Patent Document 11), imidazole derivatives (see Patent Document 12), triazolidine derivatives (see Patent Document 13), pyridone derivatives (see Patent Document 14), thiazolimine and oxazolimine derivatives (see Patent Document 15), and enamide derivatives (see Patent Document 16) are disclosed as novel chymase inhibitors. However, there are no examples of the above chymase inhibitors being practically used as pharmaceuticals.

Further, 1,4-diazepan-2,5-dione skeleton compounds similar in structure to the present invention are disclosed in documents (see Non-Patent Documents 23 and 24) etc., but none has the electron withdrawing group such as a carbonyl group, sulfonyl group, or other electron withdrawing group at the 4-position nitrogen atom like in the present invention. Further, there is no disclosure at all of chymase inhibitory activity like in the present invention. Further, Patent Document 17 and Non-Patent Document 25 disclose a 1,4-benzodiazepine derivative as a 7-membered lactam derivative having a carbonyl group, sulfonyl group, or other electron withdrawing group at the 4-position nitrogen atom, but these derivatives differ in skeleton from the present invention. Further, there is no disclosure at all of chymase inhibitory activity like in the present invention.

Further, as examples of production of a non-fused 1,4-diazepan-2,5-dione derivative similar to the present invention, a 7-membered ring closure reaction using lactamization etc. are reported in Non-Patent Documents 26 and 27. However, up to now, there has been no report of a production method characterized by introducing an electron withdrawing group at the 4-position nitrogen atom of a 1,4-diazepan-2,5-dione derivative, like in the present invention. Further, there has been no report up to now of a production method of 1,4-diazepan-2,5-dione derivative characterized by an intramolecular alkylation reaction at the portions corresponding to the 4-position nitrogen atom and 3-position carbon atom, like in the present invention.

[Patent Document 1] WO01-32214
[Patent Document 2] WO03-07964
[Patent Document 3] WO03-07964
[Patent Document 4] WO02-32881
[Patent Document 5] WO01-62294
[Patent Document 6] WO00-51640
[Patent Document 7] WO01-62293
[Patent Document 8] WO01-62292
[Patent Document 9] WO02-83649
[Patent Document 10] WO03-35654
[Patent Document 11] WO03-78419
[Patent Document 12] WO04-07464
[Patent Document 13] Japanese Patent Publication (A) No. 2003-342265
[Patent Document 14] Japanese Patent Publication (A) No. 2004-67584
[Patent Document 15] WO05-000825
[Patent Document 16] WO05-073214
[Patent Document 17] DE 2257171
[Non-Patent Document 1] Mast Cell Proteases in Immunology and Biology; Caughey, G. H., Ed; Marcel Dekker, Inc.: New York, 1995
[Non-Patent Document 2] J. Biol. Chem., 1990, 265 (36), 22348
[Non-Patent Document 3] J. Biol. Chem., 1981, 256 (1), 471
[Non-Patent Document 4] J. Biol. Chem., 1994, 269 (27), 18134
[Non-Patent Document 5] J. Biol. Chem., 1997, 272 (11), 7127
[Non-Patent Document 6] J. Biol. Chem., 1995, 270 (9), 4689
[Non-Patent Document 7] FASEB J., 2001, 15 (8), 1377
[Non-Patent Document 8] J. Exp. Med., 1991, 174 (4), 821
[Non-Patent Document 9] Proc. Natl. Acad. Sci. USA., 1997, 94 (17), 9017
[Non-Patent Document 10] J. Biol. Chem., 1986, 261 (34), 16067
[Non-Patent Document 11] J. Clin. Invest., 1996, 97 (10), 2174
[Non-Patent Document 12] J. Immunol., 1997, 159 (4), 1987
[Non-Patent Document 13] J. Immunol., 1986, 136 (10), 3812
[Non-Patent Document 14] Br. J. Pharmacol., 1998, 125 (7), 1491
[Non-Patent Document 15] Eur. J. Pharmacol., 1998, 352 (1), 91
[Non-Patent Document 16] Protease Inhibitors; Barrett et. al., Eds; Elsevier Science B. V.: Amsterdam, 1986
[Non-Patent Document 17] Curr. Pharm. Des., 1998, 4 (6), 439
[Non-Patent Document 18] Exp. Opin. Ther. Patents, 2001, 11, 1423
[Non-Patent Document 19] Idrugs, 2002, 5 (12), 1141
[Non-Patent Document 20] Circulation, 2003, 107 (20), 2555
[Non-Patent Document 21] Life Sci., 2002, 71 (4), 437-46
[Non-Patent Document 22] J. Pharmacol. Sci., 2004, 94 (4), 443
[Non-Patent Document 23] J. Org. Chem., 2003, 68 (20), 7893
[Non-Patent Document 24] J. Pept. Sci. 2003, 9 (3), 187
[Non-Patent Document 25] J. Org. Chem., 1980, 45 (9), 1675
[Non-Patent Document 26] J. Org. Chem., 2003, 68 (20), 7893
[Non-Patent Document 27] J. Pept. Sci. 2003, 9 (3), 187

DISCLOSURE OF THE INVENTION

As explained above, at present, several types of small molecule chymase inhibitors have been disclosed. However, up until now, no clinically applicable chymase inhibitors have been found. Development of a clinically applicable chymase inhibitor leading to the prevention or treatment of bronchial asthma, urticaria, atopic dermatitis, allergic conjunctivitis, rhinitis, rheumatoid arthritis, mastocytosis, scleroderma, heart failure, cardiac hypertrophy, congestive heart failure, hypertension, atherosclerosis, myocardial ischemia, myocardial infarction, restenosis after PTCA, restenosis after bypass graft surgery, ischemic peripheral circulatory disorders, hyperaldosteronism, diabetic retinopathy, diabetic nephropathy, nephritis, glomerulosclerosis, renal insufficiency, psoriasis, solid tumor, postoperative adhesion, glaucoma, and ocular hypertension, and other diseases in which chymase is involved is therefore desired.

To solve this issue, the present invention provides a compound having the following formula (I) characterized in chemical structure with a 7-membered ring skeleton:

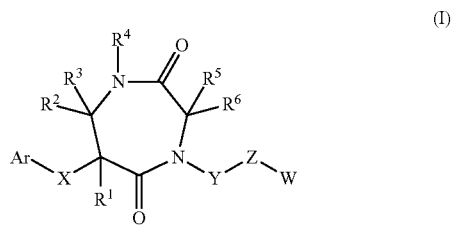

wherein, Ar indicates (1) a $C_6$ to $C_{14}$ aromatic hydrocarbon group, (2) a 5- to 8-membered aromatic heterocyclic group including 1 to 4 hetero atoms selected from a nitrogen atom, sulfur atom, and oxygen atom, other than a carbon atom, or (3) a bicyclic or tricyclic aromatic group formed by condensation of the above aromatic heterocyclic group and a $C_6$ to $C_{14}$ aromatic hydrocarbon ring, wherein, the groups (1) to (3) of the above Ar may optionally be substituted with any 1 to 5 groups selected from the group consisting of (i) a halogen atom, (ii) nitro, (iii) cyano, (iv) $C_1$ to $C_6$ alkyl which may optionally be substituted with 1 to 3 halogen atoms, (v) $C_2$ to $C_6$ alkenyl which may optionally be substituted with 1 to 3 halogen atoms, (vi) $C_2$ to $C_6$ alkynyl which may optionally be substituted with 1 to 3 halogen atoms, (vii) $C_3$ to $C_6$ cycloalkyl, (viii) hydroxyl, (ix) $C_1$ to $C_6$ alkoxy which may optionally be substituted with 1 to 3 groups selected from a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl, (x) $C_1$ to $C_5$ alkylenedioxy, (xi) $C_1$ to $C_6$ alkylthio which may optionally be substituted with 1 to 3 groups selected from a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxy-carbonyl, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xviii) $C_1$ to $C_6$ alkoxycarbonyl, (xix) carbamoyl, (xx) thiocarbamoyl, (xxi) mono-$C_1$ to $C_6$ alkylcarbamoyl, (xxii) di-$C_1$ to $C_6$ alkylcarbamoyl, (xxiii) 5- to 6-membered cyclic aminocarbonyl, (xxiv) sulfo, (xxv) $C_1$ to $C_6$ alkylsulfonyl, (xxvi) $C_1$ to $C_6$ alkoxycarbonylamino, (xxvii) $C_1$ to $C_6$ alkylcarbonylamino, (xxviii) mono- or di-$C_1$ to $C_6$ alkylaminocarbonylamino, (xxix) aminosulfonyl, and (xxx) mono- or di-$C_1$ to $C_6$ alkylaminosulfonyl, W indicates (1) a hydrogen atom, (2) a $C_6$ to $C_{14}$ aromatic hydrocarbon group, (3) a 5- to 8-membered aromatic heterocyclic group including 1 to 4 hetero atoms selected from a nitrogen atom, a sulfur atom, and an oxygen atom, other than a carbon atom, (4) a bicyclic or tricyclic aromatic group formed by condensation of the above aromatic heterocyclic group and a $C_6$ to $C_{14}$ aromatic hydrocarbon ring, (5) $C_1$ to $C_6$ alkyl, or (6) a 5- to 7-membered heterocycloalkyl group which may optionally be substituted with 1 to 3 groups selected from oxo and phenyl, wherein each of the groups (2) to (4) of the above W may optionally be substituted with 1 to 5 groups selected from the group consisting of (i) a halogen atom, (ii) nitro, (iii) cyano, (iv) $C_1$ to $C_6$ alkyl which may optionally be substituted with a halogen atom, amino, $C_1$ to $C_6$ alkoxycarbonyl, $C_1$ to $C_6$ alkoxycarbonylamino, and carboxyl, (v) $C_2$ to $C_6$ alkenyl which may optionally be substituted with 1 to 3 halogen atoms, (vi) $C_2$ to $C_6$ alkynyl which may optionally be substituted with 1 to 3 halogen atoms, (vii) $C_3$ to $C_6$ cycloalkyl, (viii) hydroxyl, (ix) $C_1$ to $C_6$ alkoxy which may optionally be substituted with 1 to 3 groups selected from a halogen atom, hydroxyl, $C_1$ to $C_6$ alkoxy, amino, and mono- or di-$C_1$ to $C_6$ alkylamino, (x) $C_1$ to $C_5$ alkylenedioxy, (xi) $C_1$ to $C_6$ alkylthio which may optionally be substituted with 1 to 3 groups selected from a halogen atom, hydroxyl, $C_1$ to $C_6$ alkoxy, amino, and mono- or di-$C_1$ to $C_6$ alkylamino, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xviii) $C_1$ to $C_6$ alkoxycarbonyl which may be substituted with a halogen atom, (xix) $C_7$ to $C_{16}$ aralkyloxycarbonyl which may optionally be substituted with a halogen atom, (xx) carbamoyl, (xxi) mono-$C_1$ to $C_6$ alkylcarbamoyl which may optionally be substituted with 1 to 3 groups selected from a halogen atom, hydroxyl, carboxyl, $C_1$ to $C_6$ alkoxy, amino, and mono- or di-$C_1$ to $C_6$ alkylamino, (xxii) di-$C_1$ to $C_6$ alkylcarbamoyl which may optionally be substituted with hydroxyl, (xxiii) 5- to 6-membered cyclic aminocarbonyl which may optionally be substituted with $C_1$ to $C_6$ alkoxycarbonyl, (xxiv) $C_6$ to $C_{10}$ arylcarbamoyl, (xxv) $C_1$ to $C_{10}$ heteroarylcarbamoyl, (xxvi) $C_7$ to $C_{16}$ aralkylcarbamoyl, (xxvii) $C_1$ to $C_{10}$ heteroaryl-$C_1$ to $C_6$ alkylcarbamoyl, (xxviii) N—$C_1$ to $C_6$ alkyl-N—$C_6$ to $C_{12}$ arylcarbamoyl, (xxix) $C_3$ to $C_6$ cycloalkylcarbamoyl, (xxx) sulfo, (xxxi) $C_1$ to $C_6$ alkylsulfonyl, (xxxii) $C_1$ to $C_6$ alkylsulfonylamino, (xxxiii) $C_6$ to $C_{12}$ arylsulfonylamino which may optionally be substituted with $C_1$ to $C_6$ alkyl, (xxxiv) $C_1$ to $C_{10}$ heteroarylsulfonylamino, (xxxv) $C_1$ to $C_6$ alkoxycarbonylamino, (xxxvi) $C_1$ to $C_6$ alkylcarbonylamino, (xxxvii) mono- or di-$C_1$ to $C_6$ alkylaminocarbonylamino, (xxxviii) $C_6$ to $C_{12}$ aryl, (xxxix) $C_1$ to $C_{10}$ heteroaryl, (xl) $C_6$ to $C_{10}$ aryloxy, (xli) $C_1$ to $C_{10}$ heteroaryloxy, (xlii) $C_7$ to $C_{16}$ aralkyloxy, (xliii) $C_1$ to $C_{10}$ heteroaryl-$C_1$ to $C_6$ alkyloxy, (xliv) aminosulfonyl, (xlv) mono- or di-$C_1$ to $C_6$ alkylaminosulfonyl, (xlvi) $C_7$ to $C_{16}$ aralkyloxycarbamoyl, and (xlvii) $C_1$ to $C_{10}$ heteroaryl-$C_1$ to $C_6$ alkyloxycarbamoyl, X indicates (1) a bond, (2) linear or branched $C_1$ to $C_6$ alkylene, (3) an oxygen atom, (4) $NR^{13}$, wherein $R^{13}$ indicates a hydrogen atom or a $C_1$ to $C_6$ alkyl group, or (5) —S(O)$_m$—, [where, m indicates an integer of 0 to 2], Y indicates (1) —S(O)$_n$—, wherein n indicates an integer of 1 or 2, (2) —S(O)$_n$NH—, wherein n indicates an integer of 1 or 2], (3) —C(=O)—, (4) —C(=O)NH—, or (5) —C(=O)NR$^{14}$—, wherein R$^{14}$ indicates a $C_1$ to $C_6$ alkyl group, Z indicates (1) a bond or (2) $CR^7R^8$, wherein $R^7$ and $R^8$ are, independently, (A) a hydrogen atom, (B) $C_1$ to $C_6$ alkyl which may be substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, and (vi) a halogen atom, (C) $C_6$ to $C_{12}$ aryl or $C_1$ to $C_{10}$ heteroaryl which may optionally be substituted with 1 to 5 groups selected from the group consisting of (i) a halogen atom and (ii) an alkyl group which may optionally be substituted with 1 to 3 halogen atoms, (D) $C_3$ to $C_6$ cycloalkyl which may optionally be substituted with 1 to 5 groups selected from (i) a halogen atom and (ii) an alkyl group which may optionally be substituted with 1 to 3 halogen atoms, (E) —COOR$^9$ wherein R$^9$ indicates a hydrogen atom or $C_1$ to $C_6$ alkyl, or (F) CONR$^{10}$R$^{11}$ wherein R$^{10}$ and R$^{11}$ are independently, (a) hydrogen atom, (b) $C_1$ to $C_6$ alkyl which may optionally be substituted with 1 to 3 groups selected from the group consisting of (i) a halogen atom, (ii) $C_3$ to $C_6$ cycloalkyl, (iii) carboxyl, (iv) $C_1$ to $C_6$ alkoxycarbonyl, (v) $C_1$ to $C_6$ alkylcarbonyl, (vi) carbamoyl, (vii) mono-$C_1$ to $C_6$ alkylcarbamoyl, (viii) di-$C_1$ to $C_6$ alkylcarbamoyl, (ix) $C_6$ to $C_{12}$ aryl, and (x) $C_1$ to $C_{10}$ heteroaryl, (c) OR$^{12}$ wherein R$^{12}$ indicates a hydrogen atom or $C_1$ to $C_6$ alkyl, or (d) (1) a $C_6$ to $C_{14}$ aromatic hydrocarbon group, (2) a 5- to 8-membered aromatic heterocyclic group including 1 to 4 hetero atoms selected from a nitrogen atom, a sulfur atom, and an oxygen atom, other than a carbon atom, or (3) a bicyclic or tricyclic aromatic group formed by condensation of the above aromatic heterocyclic group and a $C_6$ to $C_{14}$ aromatic hydrocarbon ring, wherein each of the groups (1) to (3) may be optionally substituted with 1 to 5 groups selected from the group consisting of (i) a halogen atom, (ii) nitro, (iii) cyano, (iv) $C_1$ to $C_6$ alkyl which may optionally be substituted with 1 to 3 halogen atoms, (v) $C_2$ to $C_6$ alkenyl which may optionally be substituted with 1 to 3 halogen atoms, (vi) $C_2$ to $C_6$ alkynyl which may optionally be substituted with 1 to 3 halogen atoms, (vii) $C_3$ to $C_6$ cycloalkyl, (viii) hydroxyl, (ix) $C_1$ to $C_6$ alkoxy which may optionally be substituted with 1 to 3 halogen atoms, (x) $C_1$ to $C_5$ alkylenedioxy, (xi) $C_1$ to $C_6$ alkylthio which may optionally be substituted with 1 to 3 halogen atoms, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xviii) $C_1$ to $C_6$ alkoxycarbonyl, (xix) carbamoyl, (xx) thiocarbamoyl, (xxi) mono-$C_1$ to $C_6$ alkylcarbamoyl, (xxii) di-$C_1$ to $C_6$ alkylcarbamoyl, (xxiii) $C_6$ to $C_{10}$ arylcarbamoyl, (xxiv) $C_1$ to $C_{10}$ heteroarylcarbamoyl, (xxv) sulfo, (xxvi) $C_1$ to $C_6$ alkylsulfonyl, (xxvii) aminosulfonyl, and (xxviii) mono- or di-$C_1$ to $C_6$ alkylaminosulfonyl, $R^1$ indicates (1) a hydrogen atom, (2) a halogen atom, or (3) $C_1$ to $C_6$ alkyl, or $R^1$ forms —CH= together with X, $R^2$ and $R^3$ are independently (1) a hydrogen atom, (2) a halogen atom, or (3) $C_1$ to $C_6$ alkyl, $R^5$ and $R^6$ are independently (1) a hydrogen atom or (2) $C_1$ to $C_6$ alkyl which may optionally be substituted with a group selected from the group consisting of i) carboxyl, (ii) $C_1$ to $C_6$ alkoxy, (iii) $C_1$ to $C_6$ alkoxycarbonyl, (iv) $C_6$ to $C_{12}$ aryloxycarbonyl, (v) $C_1$ to $C_{10}$ heteroaryloxycarbonyl, and (vi) amino, $R^2$ and $R^3$ and also $R^5$ and $R^6$ may independently form a 3- to 8-membered ring, and $R^4$ indicates a (1) a hydrogen atom, (2) $C_1$ to $C_6$ alkylcarbamoyl, or (3) $C_1$ to $C_6$ alkyl which may optionally be substituted with 1 to 3 groups selected from the group consisting of (i) carbamoyl, (ii) mono- or di-$C_1$ to $C_6$ alkylcarbamoyl, (iii) mono- or di-$C_6$ to $C_{12}$ arylcarbamoyl, (iv) mono- or di-$C_1$ to $C_{10}$ heteroarylcarbamoyl, (v) N—$C_1$ to $C_6$ alkyl-N—$C_6$ to $C_{12}$ arylcarbamoyl, (vi) N—$C_1$ to $C_6$ alkyl-N—$C_1$ to $C_{10}$ heteroarylcarbamoyl, (vii) mono- or di-$C_7$ to $C_{16}$ aralkylcarbamoyl, (viii) mono- or di-$C_1$ to $C_{10}$ heteroaryl-$C_1$ to $C_6$ alkylcarbamoyl, (ix) carboxyl, and (x) $C_1$ to $C_6$ alkoxycarbonyl, or its salt or solvate thereof.

Further, the present invention provides a pharmaceutical composition comprising the compound having the formula (I), or its pharmaceutically acceptable salt, or solvate thereof as the active ingredient, and a chymase inhibitor comprising the compound having the formula (I).

Further, the present invention provides a method of production of the compound having the formula (I), or its salt, or solvate thereof. Specifically, it provides the following methods:

[Method of Production (A)]

A method for producing the compound having formula (I), or its salt, or solvate thereof, comprising a cyclization reaction of a compound having the formula (II):

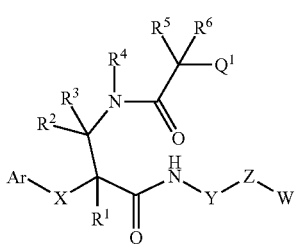

(II)

wherein Ar, W, X, Y, Z, $R^1$, $R^2$, $R^3$, $R^4$, $R^5$, and $R^6$ are the same as defined in the above formula (I), $Q^1$ indicates a halogen atom, a $C_6$ to $C_{10}$ arylsulfonyloxy group which may optionally be substituted with 1 to 3 halogen atoms, or $C_1$ to $C_4$ alkylsulfonyloxy group which may optionally be substituted with 1 to 3 halogen atoms

[Method of Production (B)]

A method for producing a compound, or its salt or a solvate thereof having the formula (I), wherein Y is —S(O)$_n$NH— (wherein n indicates an integer of 1 or 2) or —C(=O)NH—, comprising the coupling reaction of the compound, or a salt thereof, having the formula (III):

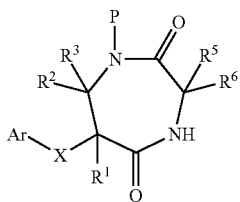

(III)

wherein Ar, X, $R^1$, $R^2$, $R^3$, $R^5$, and $R^6$ are the same as defined in the above formula (I), and P indicates a protective group selected from the group consisting of (1) allyl, (2) allyloxycarbonyl, (3) 9-fluorenylmethylcarbonyl, (4) linear or branched $C_1$ to $C_6$ alkyloxycarbonyl which may optionally be substituted with 1 to 3 halogen atoms, (5) linear or branched $C_1$ to $C_6$ alkylcarbonyl which may optionally be substituted with 1 to 3 halogen atoms, (6) $C_7$ to $C_{16}$ aralkyl which may optionally be substituted with 1 to 3 groups selected from (i) a halogen atom, (ii) $C_1$ to $C_6$ alkyl, (iii) $C_1$ to $C_6$ alkoxy, and (iv) nitro, (7) $C_5$ to $C_{16}$ arylcarbonyl which may optionally be substituted with 1 to 3 groups selected from (i) a halogen atom, (ii) $C_1$ to $C_6$ alkyl, (iii) $C_1$ to $C_6$ alkoxy, and (iv) nitro, (8) $C_7$ to $C_{16}$ aralkyloxycarbonyl which may be substituted with 1 to 3 groups selected from (i) a halogen atom, (ii) $C_1$ to $C_6$ alkyl, (iii) $C_1$ to $C_6$ alkoxy, and (iv) nitro, or (9) $C_5$ to $C_{16}$ arylsulfonyl which may optionally be substituted with 1 to 3 groups selected from (i) a halogen atom, (ii) $C_1$ to $C_6$ alkyl, (iii) $C_1$ to $C_6$ alkoxyl, and (iv) nitro, or $R^4$, wherein $R^4$ is the same as defined in the above formula (I), the compound (IV), or a salt thereof, having the formula (IV):

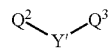

(IV)

wherein $Q^2$ and $Q^3$ indicate, independently, nitro, $C_6$ to $C_{10}$ aryloxy group which may optionally be substituted with 1 to 3 halogen atoms, or a halogen atom, and Y' indicates —S(O)$_n$— (wherein n indicates an integer of 1 or 2) or C(=O), and the compound (V), or a salt thereof, having the formula (V):

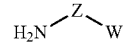

(V)

wherein W and Z are the same as defined as in the above formula (I), and the optional deprotection reaction of the coupling product described above.

Further, as another aspect of the present invention, there is provided the compound, or its salt, or a solvate thereof, having the formula (Va), which is useful as starting materials to produce the compound having the formula (I):

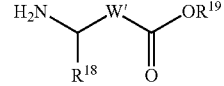

(Va)

wherein W' indicates (1) a 6-membered aromatic hydrocarbon group or (2) a 6-membered aromatic heterocyclic group having 1 to 4 hetero atoms selected from a nitrogen atom, a sulfur atom, and an oxygen atom, other than a carbon atom, wherein the groups (1) and (2) of W' may optionally be substituted with 1 to 4 groups selected from the group consisting of (i) a halogen atom, (ii) nitro, (iii) cyano, (iv) $C_1$ to $C_6$ alkyl which may optionally be substituted with 1 to 3 groups selected from a halogen atom, amino, $C_1$ to $C_6$ alkoxycarbonyl, $C_1$ to $C_6$ alkoxycarbonylamino, and carboxyl, (v) $C_2$ to $C_6$ alkenyl which may optionally be substituted with 1 to 3 halogen atoms, (vi) $C_2$ to $C_6$ alkynyl which may optionally be substituted with 1 to 3 halogen atoms, (vii) $C_3$ to $C_6$ cycloalkyl, (viii) hydroxyl, (ix) $C_1$ to $C_6$ alkoxy which may optionally be substituted with 1 to 3 groups selected from a halogen atom, hydroxyl, $C_1$ to $C_6$ alkoxy, amino, and mono- or di-$C_1$ to $C_6$ alkylamino, (x) $C_1$ to $C_5$ alkylenedioxy, (xi) $C_1$ to $C_6$ alkylthio which may optionally be substituted with 1 to 3 groups selected from a halogen atom, hydroxyl, $C_1$ to $C_6$ alkoxy, amino, and mono- or di-$C_1$ to $C_6$ alkylamino, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xviii) $C_1$ to $C_6$ alkoxycarbonyl, (xix) $C_7$ to $C_{16}$ aralkyloxycarbonyl, (xx) carbamoyl, (xxi) mono-$C_1$ to $C_6$ alkylcarbamoyl which may optionally be substituted with 1 to 3 groups selected from a halogen atom, hydroxyl, carboxyl, $C_1$ to $C_6$ alkoxy, amino, and mono- or di-$C_1$ to $C_6$ alkylamino, (xxii) di-$C_1$ to $C_6$ alkylcarbamoyl which may optionally be substituted with hydroxyl, (xxiii) 5- to 6-membered cyclic aminocarbonyl which may optionally be substituted with $C_1$ to $C_6$ alkoxycarbonyl, (xxiv) $C_6$ to $C_{10}$ arylcarbamoyl, (xxv) $C_1$ to $C_{10}$ heteroarylcarbamoyl, (xxvi) $C_7$ to $C_{16}$ aralkylcarbamoyl, (xxvii) $C_1$ to $C_{10}$ heteroaryl-$C_1$ to $C_6$ alkylcarbamoyl, (xxviii) N—$C_1$ to $C_6$ alkyl-N—$C_6$ to $C_{12}$ arylcarbamoyl, (xxix) $C_3$ to $C_6$ cycloalkylcarbamoyl, (xxx) sulfo, (xxxi) $C_1$ to $C_6$ alkylsulfonyl, (xxxii) $C_1$ to $C_6$ alkylsulfonylamino, (xxxiii) $C_6$ to $C_{12}$ arylsulfonylamino which may be substituted with $C_1$ to $C_6$ alkyl, (xxxiv) $C_1$ to $C_{10}$ heteroarylsulfonylamino, (xxxv) $C_1$ to $C_6$ alkoxycarbonylamino, (xxxvi) $C_1$ to $C_6$ alkylcarbonylamino, (xxxvii) mono- or di-$C_1$ to $C_6$ alkylaminocarbonylamino, (xxxviii) $C_6$ to $C_{12}$ aryl, (xxxix) $C_1$ to $C_{10}$ heteroaryl, (xl) $C_6$ to $C_{10}$ aryloxy, (xli) $C_1$ to $C_{10}$ heteroaryloxy, (xlii) $C_7$ to $C_{16}$ aralkyloxy, (xliii) $C_1$ to $C_{10}$ heteroaryl-$C_1$ to $C_6$ alkyloxy, (xliv) aminosulfonyl, (xlv) mono- or di-$C_1$ to $C_6$ alkylaminosulfonyl, (xlvi) $C_7$ to $C_{16}$ aralkyloxycarbamoyl, and (xlvii) $C_1$ to $C_{10}$ heteroaryl-$C_1$ to $C_6$ alkyloxycarbamoyl, $R^{18}$ indicates a $C_2$ to $C_4$ alkyl group which may optionally be substituted with 1 to 3 halogen atoms, and $R^{19}$ indicates a hydrogen atom, $C_1$ to $C_6$ alkyl group which may optionally be substituted with 1 to 3 halogen atoms, or $C_7$ to $C_{16}$ aralkyl group which may optionally be substituted with 1 to 3 halogen atoms.

Among the compounds having the formula (Va), when W' indicates phenyl and the $NH_2$—$CH(R^{18})$— group and $R^{19}O$—$C(=O)$— group are 1,4 substituted, W' is preferably substituted with 1 to 4 groups selected from the group consisting of (ii) nitro, (iv) $C_1$ to $C_6$ alkyl substituted with 1 to 3 groups selected from amino, $C_1$ to $C_6$ alkoxycarbonyl, $C_1$ to $C_6$ alkoxycarbonylamino, and carboxyl, (v) $C_2$ to $C_6$ alkenyl which may optionally be substituted with 1 to 3 halogen atoms, (vi) $C_2$ to $C_6$ alkynyl which may optionally be substituted with 1 to 3 halogen atoms, (vii) $C_3$ to $C_6$ cycloalkyl, (viii) hydroxyl, (ix) $C_1$ to $C_6$ alkoxy substituted with 1 to 3 groups selected from hydroxyl, $C_1$ to $C_6$ alkoxy, amino, and mono- or di-$C_1$ to $C_6$ alkylamino, (x) $C_1$ to $C_5$ alkylenedioxy, (xi) $C_1$ to $C_6$ alkylthio which may optionally be substituted with 1 to 3 groups selected from a halogen atom, hydroxyl, $C_1$ to $C_6$ alkoxy, amino, and mono- or di-$C_1$ to $C_6$ alkylamino, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xviii) $C_1$ to $C_6$ alkoxycarbonyl, (xix) $C_7$ to $C_{16}$ aralkyloxycarbonyl, (xx) carbamoyl, (xxi) mono-$C_1$ to $C_6$ alkylcarbamoyl which may optionally be substituted with 1 to 3 groups selected from a halogen atom, hydroxyl, carboxyl, $C_1$ to $C_6$ alkoxy, amino, and mono- or di-$C_1$ to $C_6$ alkylamino, (xxii) di-$C_1$ to $C_6$ alkylcarbamoyl which may optionally be substituted with hydroxyl, (xxiii) 5- to 6-membered cyclic aminocarbonyl which may optionally be substituted with $C_1$ to $C_6$ alkoxycarbonyl, (xxiv) $C_6$ to $C_{10}$ arylcarbamoyl, (xxv) $C_1$ to $C_{10}$ heteroarylcarbamoyl, (xxvi) $C_7$ to $C_{16}$ aralkylcarbamoyl, (xxvii) $C_1$ to $C_{10}$ heteroaryl-$C_1$ to $C_6$ alkylcarbamoyl, (xxviii) N—$C_1$ to $C_6$ alkyl-N—$C_6$ to $C_{12}$ arylcarbamoyl, (xxix) $C_3$ to $C_6$ cycloalkylcarbamoyl, (xxx) sulfo, (xxxi) $C_1$ to $C_6$ alkylsulfonyl, (xxxii) $C_1$ to $C_6$ alkylsulfonylamino, (xxxiii) $C_6$ to $C_{12}$ arylsulfonylamino which may optionally be substituted with $C_1$ to $C_6$ alkyl, (xxxiv) $C_1$ to $C_{10}$ heteroarylsulfonylamino, (xxxv) $C_1$ to $C_6$ alkoxycarbonylamino, (xxxvi) $C_1$ to $C_6$ alkylcarbonylamino, (xxxvii) mono- or di-$C_1$ to $C_6$ alkylaminocarbonylamino, (xxxviii) $C_6$ to $C_{12}$ aryl, (xxxix) $C_1$ to $C_{10}$ heteroaryl, (xl) $C_6$ to $C_{10}$ aryloxy, (xli) $C_1$ to $C_{10}$ heteroaryloxy, (xlii) $C_7$ to $C_{16}$ aralkyloxy, (xliii) $C_1$ to $C_{10}$ heteroaryl-$C_1$ to $C_6$ alkyloxy, (xliv) aminosulfonyl, (xlv) mono- or di-$C_1$ to $C_6$ alkylaminosulfonyl, (xlvi) $C_7$ to $C_{16}$ aralkyloxycarbamoyl, and (xlvii) $C_1$ to $C_{10}$ heteroaryl-$C_1$ to $C_6$ alkyloxycarbamoyl. More preferably, W' may be substituted with (ii) nitro, (viii) hydroxyl, and (xii) amino.

Further, as another aspect of the present invention, there is provided a compound, or its salt or a solvate thereof, having of the formula (VIa), which is useful as starting materials to produce the compound having the formula (I):

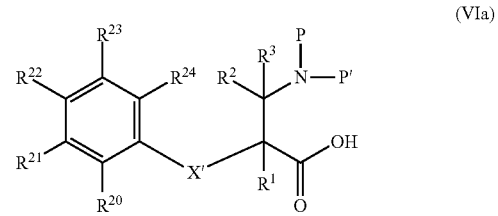

(VIa)

wherein $R^1$, $R^2$, and $R^3$ are the same as defined in the above formula (I), P is the same as defined in the above formula (III), X' indicates methylene, or X' forms —CH= together with $R^1$, P' indicates a protective group selected from the group consisting of (1) allyl, (2) allyloxycarbonyl, (3) 9-fluorenylmethylcarbonyl, (4) linear or branched $C_1$ to $C_6$ alkyloxycarbonyl which may optionally be substituted with 1 to 3 halogen atoms, (5) linear or branched $C_1$ to $C_6$ alkylcarbonyl which may optionally be substituted with 1 to 3 halogen atoms, (6) $C_7$ to $C_{16}$ aralkyl which may optionally be substituted with 1 to 3 of (i) a halogen atom, (ii) $C_1$ to $C_6$ alkyl, (iii) $C_1$ to $C_6$ alkoxy, or (iv) nitro, (7) $C_5$ to $C_{16}$ arylcarbonyl which may optionally be substituted with 1 to 3 of (i) a halogen atom, (ii) $C_1$ to $C_6$ alkyl, (iii) $C_1$ to $C_6$ alkoxy, or (iv) nitro, (8) $C_7$ to $C_{16}$ aralkyloxycarbonyl which may optionally be substituted with 1 to 3 of (i) a halogen atom, (ii) $C_1$ to $C_6$ alkyl, (iii) $C_1$ to $C_6$ alkoxy, or (iv) nitro, and (9) $C_5$ to $C_{16}$ arylsulfonyl which may optionally be substituted with 1 to 3 of (i) a halogen atom, (ii) $C_1$ to $C_6$ alkyl, (iii) $C_1$ to $C_6$ alkoxy, or (iv) nitro, or a hydrogen atom, $R^{20}$ is (1) a halogen atom, (2) nitro, (3) cyano, (4) $C_1$ to $C_6$ alkyl which may optionally be substituted with 1 to 3 halogen atoms, (5) hydroxyl, or (6) $C_1$ to $C_6$ alkoxy which may be substituted with 1 to 3 groups selected from a halogen atom, $C_1$ to $C_6$ alkoxy, carboxyl, and $C_1$ to $C_6$ alkoxycarbonyl, $R^{21}$, $R^{22}$, $R^{23}$, and $R^{24}$ are, independently, (1) a halogen atom, (2) nitro, (3) cyano, (4) $C_1$ to $C_6$ alkyl which may be substituted with 1 to 3 halogen atoms, (5) hydroxyl, or (6) $C_1$ to $C_6$ alkoxy which may optionally be substituted with 1 to 3 groups selected from a halogen atom, $C_1$ to $C_6$ alkoxy, carboxyl, and $C_1$ to $C_6$ alkoxycarbonyl, or a hydrogen atom, provided that the following compounds are excluded:
(1) Compounds where $R^{20}$ and $R^{24}$ are chlorine atoms and $R^{21}$, $R^{22}$, and $R^{23}$ are hydrogen atoms,
(2) Compounds where $R^{20}$, $R^{22}$, and $R^{24}$ are methyl and $R^{21}$ and $R^{23}$ are hydrogen atoms, and
(3) Compounds where $R^{20}$ is a chlorine atom or bromine atom and $R^{21}$, $R^{22}$, $R^{23}$, and $R^{24}$ are hydrogen atoms.

When the compounds, or a salt thereof, having the formulae (I), (II), (III), (V), (Va), and (VIa) have asymmetric carbon atoms in their structures, their optically active compounds and their mixtures are also included in the scope of the present invention. When they have two or more asymmetric carbon atoms, the diastereomer mixtures are also included in the scope of the present invention. Further, when the compounds, or a salt thereof, having the formulae (I), (II), (III), (V), (Va), and (VIa) have double bonds in their structures, all of the cis-forms, trans-forms, and their mixtures are also included in the scope of the present invention.

Further, the compounds having the formula (I) or a salt thereof, may be brought into contact with, or recrystallized from the solvent such as water, methanol, ethanol, 1-propanol, 2-propanol, 1-butanol, 2-butanol, 2-methyl-1-propanol, 1-pentanol, 3-methyl-1-butanol, 2-methoxyethanol, 2-ethoxyethanol, formic acid, ethyl formate, acetic acid, methyl acetate, ethyl acetate, propyl acetate, isobutyl acetate, acetone, methylethylketone, methylisobutylketone (preferably, water, ethanol, 1-propanol, 2-propanol, 1-butanol, acetic acid, ethyl acetate, acetone, etc.), or other solvents, or mixed solvents including the same so as to form their solvates. These solvates are also included in the scope of the present invention.

The compounds having the formula (I), or its salt, or a solvate thereof, of the present invention have a chymase inhibitory activity and are useful as a pharmaceutical for the prevention or treatment of bronchial asthma, urticaria, atopic dermatitis, allergic conjunctivitis, rhinitis, rheumatoid arthritis, mastocytosis, scleroderma, heart failure, cardiac hypertrophy, congestive heart failure, hypertension, atherosclerosis, myocardial ischemia, myocardial infarction, restenosis after PTCA, restenosis after bypass graft surgery, ischemic peripheral circulatory disorders, hyperaldosteronism, diabetic retinopathy, diabetic nephropathy, nephritis, glomerulosclerosis, renal insufficiency, psoriasis, solid tumor, postoperative adhesion, glaucoma, and ocular hypertension, and other diseases.

Further, the production method of the present invention provides a practical production method of 1,4-diazepan-2,5-dione derivative having an electronic withdrawing group at its 4-position nitrogen atom, which are not reported hereinbefore.

BEST MODE FOR CARRYING OUT THE INVENTION

In the description, the terms "alkyl", "alkenyl", "alkynyl", "alkoxy", and "alkylene" include both linear and branched forms.

[1. Explanation of Compounds Having Formula (I)]

In the above-mentioned formula (I), as examples of the "$C_6$ to $C_{14}$ aromatic hydrocarbon group" expressed by Ar, a monocyclic or polycyclic aromatic hydrocarbon group, more specifically, phenyl, biphenyl, naphthyl, indenyl, anthryl, phenanthryl (preferably, phenyl, biphenyl, naphthyl, etc., particularly preferably phenyl etc.), or other 6- to 14-membered monocyclic or polycyclic aromatic hydrocarbon group etc. may be mentioned.

Further, as examples of the "5- to 8-membered aromatic heterocyclic group including 1 to 4 hetero atoms selected from a nitrogen atom, sulfur atom, and oxygen atom, other than a carbon atom" expressed by Ar, for example a monocyclic group including 1 or more (for example, 1 to 4, preferably 1 to 3) hetero atoms which consist of 1 or 2 species of hetero atoms selected from a nitrogen atom, oxygen atom, and sulfur atom, other than a carbon atom, or its condensed aromatic heterocyclic group, more specifically, thienyl, furyl, pyrrolyl, imidazolyl, pyrazolyl, triazolyl, tetrazolyl, thiazolyl, isothiazolyl, oxazolyl, isoxazolyl, pyridyl, pyradinyl, pyrimidinyl, pyridazinyl, naphthylidinyl, purinyl, and other aromatic heterocyclic groups (preferably pyridyl, thienyl, and furyl) etc. may be mentioned.

Further, as examples of the "bicyclic or tricyclic aromatic group formed by condensation of the above aromatic heterocyclic group and a $C_6$ to $C_{14}$ aromatic hydrocarbon ring" expressed by Ar, benzothienyl, benzofuryl, indolyl, isoindolyl, benzimidazolyl, benzopyrazolyl, benzotriazolyl, benzothiazolyl, benzisothiazolyl, benzoxazolyl, benzisoxazolyl, benzodioxolyl, quinolyl, isoquinolyl, quinoxalinyl, phthalazinyl (preferably, benzothienyl, benzofuryl, benzodioxolyl, and quinolyl), etc. may be mentioned.

Among these, as examples of the above-mentioned (1) aromatic hydrocarbon group, (2) aromatic heterocyclic group, or (3) bicyclic or tricyclic aromatic group formed by condensation of the above aromatic heterocyclic group and a $C_6$ to $C_{14}$ aromatic hydrocarbon group, expressed by Ar, phenyl and naphthyl are particularly preferred.

Next, the substituent groups (i) to (xxx) of the groups expressed by Ar in the above-mentioned formula (I) are shown together with specific examples:
(i) a halogen atom (for example, fluorine, chlorine, bromine, and iodine may be mentioned)
(ii) nitro
(iii) cyano
(iv) $C_1$ to $C_6$ alkyl which may optionally be substituted with 1 to 3 halogen atoms (as the halogen atom, fluorine, chlorine, bromine, and iodine may be mentioned, and as the $C_1$ to $C_6$ alkyl, methyl, ethyl, n-propyl, i-propyl, n-butyl, i-butyl, s-butyl, t-butyl, n-pentyl, n-hexyl, etc. may be mentioned. As specific examples, methyl, fluoromethyl, difluoromethyl, trifluoromethyl, chloromethyl, dichloromethyl, trichloromethyl, ethyl, 2,2,2-trifluoroethyl, n-propyl, i-propyl, n-butyl, i-butyl, s-butyl, t-butyl, n-pentyl, n-hexyl, etc. (preferably methyl, ethyl, trifluoromethyl, etc.) may be mentioned),
(v) $C_2$ to $C_6$ alkenyl which may optionally be substituted with 1 to 3 halogen atoms (as the halogen atom, fluorine, chlorine, bromine, and iodine may be mentioned, and as the $C_2$ to $C_6$ alkenyl, for example, vinyl, propenyl, isopropenyl, 2-buten-1-yl, 4-penten-1-yl, 5-hexen-1-yl, etc. may be mentioned)
(vi) $C_2$ to $C_6$ alkynyl which may optionally be substituted with 1 to 3 halogen atoms (as the halogen atom, fluorine, chlorine, bromine, and iodine may be mentioned, and as the $C_2$ to $C_6$ alkynyl, for example, 2-butyn-1-yl, 4-pentyn-1-yl, 5-hexyn-1-yl, etc. may be mentioned),
(vii) $C_3$ to $C_6$ cycloalkyl (for example cyclopropyl, cyclobutyl, cyclopentyl, cyclohexyl, etc. may be mentioned)

(viii) hydroxyl (ix) $C_1$ to $C_6$ alkoxy which may optionally be substituted with 1 to 3 groups selected from a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl (as the $C_1$ to $C_6$ alkoxy, for example, methoxy, ethoxy, n-propoxy, i-propoxy, n-butoxy, i-butoxy, s-butoxy, t-butoxy, n-pentyloxy, n-hexyloxy, etc. may be mentioned. As the substituent of alkoxy group, fluorine, chlorine, bromine, iodine, methylamino, dimethylamino, methoxy, ethoxy, N-methylcarbamoyl, N,N-dimethylcarbamoyl, N-benzylcarbamoyl, N-(2-picolyl)carbamoyl, methoxycarbonyl, t-butoxycarbonyl, carboxyl, etc. may be mentioned. As specific examples, methoxy, ethoxy, n-propoxy, i-propoxy, n-butoxy, i-butoxy, t-butoxy, trifluoromethyloxy, trichloromethyloxy, methoxymethyloxy, ethoxymethyloxy, N-methyl-carbamoylmethyloxy, N,N-dimethylcarbamoylmethyloxy, N-benzylcarbamoylmethyloxy, N-(2-picolyl)-carbamoylmethyloxy, methoxycarbonylmethyloxy, t-butoxycarbonylmethyloxy, carboxylmethyloxy, etc. (preferably methoxy, ethoxy, N-methylcarbamoylmethyloxy, N-benzylcarbamoylmethyloxy, N-(2-picolyl)-carbamoylmethyloxy, methoxycarbonylmethyloxy, t-butoxycarbonylmethyloxy, and carboxylmethyloxy) may be mentioned)

(x) $C_1$ to $C_5$ alkylenedioxy (for example methylenedioxy, ethylenedioxy, etc. may be mentioned), (xi) $C_1$ to $C_6$ alkylthio which may optionally be substituted with 1 to 3 groups selected from a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl (as the $C_1$ to $C_6$ alkylthio, for example methylthio, ethylthio, n-propylthio, i-propylthio, n-butylthio, i-butylthio, s-butylthio, t-butylthio, n-pentylthio, n-hexylthio, etc. may be mentioned, as examples of substituent groups of $C_1$ to $C_6$ alkylthio, fluorine, chlorine, bromine, iodine, methylamino, dimethylamino, methoxy, ethoxy, N-methylcarbamoyl, N,N-dimethylcarbamoyl, N-benzylcarbamoyl, N-(2-picolyl)-carbamoyl, methoxycarbonyl, t-butoxycarbonyl, carboxyl, etc. may be mentioned. As specific examples, methylthio, ethylthio, n-propylthio, i-propylthio, n-butylthio, i-butylthio, t-butylthio, trifluoromethylthio, trichloromethylthio, methoxymethylthio, ethoxymethylthio, N-methylcarbamoylmethylthio, N-benzylcarbamoylmethylthio, N-(2-picolyl)-carbamoylmethylthio, methoxycarbonylmethylthio, t-butoxycarbonylmethylthio, carboxylmethylthio, etc. may be mentioned)

(xii) amino (xiii) mono-$C_1$ to $C_6$ alkylamino (for example, N-methylamino etc. may be mentioned)

(xiv) di-$C_1$ to $C_6$ alkylamino (for example, N,N-dimethylamino etc. may be mentioned)

(xv) 5- to 6-membered cyclic amino (for example, morpholino, piperidino, piperazino, etc. may be mentioned)

(xvi) $C_1$ to $C_6$ alkylcarbonyl (for example, acetyl, propanoyl, butyryl, isobutyryl, pivaroyl, etc. may be mentioned)

(xvii) carboxyl (xviii) $C_1$ to $C_6$ alkoxycarbonyl (for example methoxycarbonyl, ethoxycarbonyl, etc. may be mentioned)

(xix) carbamoyl (xx) thiocarbamoyl (xxi) mono-$C_1$ to $C_6$ alkylcarbamoyl (for example, N-methylcarbamoyl, N-ethylcarbamoyl, etc. may be mentioned)

(xxii) di-$C_1$ to $C_6$ alkylcarbamoyl (for example, N,N-dimethylcarbamoyl, N,N-diethylcarbamoyl, etc. may be mentioned)

(xxiii) 5- to 6-membered cyclic aminocarbonyl (for example, morpholinocarbonyl, piperidinocarbonyl, piperadinocarbonyl, etc. may be mentioned)

(xxiv) sulfo (xxv) $C_1$ to $C_6$ alkylsulfonyl (for example, methanesulfonyl etc. may be mentioned)

(xxvi) $C_1$ to $C_6$ alkoxycarbonylamino (for example, methoxycarbonylamino, ethoxycarbonylamino, etc. may be mentioned)

(xxvii) $C_1$ to $C_6$ alkylcarbonylamino (for example, acetoamide group etc. may be mentioned)

(xxviii) mono- or di-$C_1$ to $C_6$ alkylaminocarbonylamino (for example, N-methylaminocarbonylamino etc. may be mentioned)

(xxix) aminosulfonyl and (xxx) mono- or di-$C_1$ to $C_6$ alkylaminosulfonyl (for example, methylaminosulfonyl etc. may be mentioned).

Among the substituent groups of the groups expressed by above-mentioned Ar, (i) a halogen atom, (iv) $C_1$ to $C_6$ alkyl which may be substituted with 1 to 3 halogen atoms, and (ix) $C_1$ to $C_6$ alkoxy which may optionally be substituted with 1 to 3 groups selected from a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl are particularly preferable.

As examples of the "$C_6$ to $C_{14}$ aromatic hydrocarbon group", "5- to 8-membered aromatic heterocyclic group including 1 to 4 hetero atoms selected from a nitrogen atom, sulfur atom, and oxygen atom other than a carbon atom", and "bicyclic or tricyclic aromatic group formed by condensation of the above aromatic heterocyclic group and a $C_6$ to $C_{14}$ aromatic hydrocarbon group" expressed by W, ones the same as the examples of the "$C_6$ to $C_{14}$ aromatic hydrocarbon group", "5- to 8-membered aromatic heterocyclic group including 1 to 4 hetero atoms selected from a nitrogen atom, sulfur atom, and oxygen atom other than a carbon atom", and "bicyclic or tricyclic aromatic group formed by condensation of the above aromatic heterocyclic group and a $C_6$ to $C_{14}$ aromatic hydrocarbon" expressed by the Ar may be mentioned.

As examples of the "$C_6$ to $C_{14}$ aromatic hydrocarbon group", "5- to 8-membered aromatic heterocyclic group including 1 to 4 hetero atoms selected from a nitrogen atom, sulfur atom, and oxygen atom, other than a carbon atom", and "bicyclic or tricyclic aromatic group formed by the condensation of the above aromatic heterocyclic group and a $C_6$ to $C_{14}$ aromatic hydrocarbon group" expressed by W, phenyl, pyridyl, thienyl, and furyl are particularly preferred.

Next, the substituent groups (i) to (xlvii) of the "$C_6$ to $C_{14}$ aromatic hydrocarbon group", "5- to 8-membered aromatic heterocyclic group including 1 to 4 hetero atoms selected from a nitrogen atom, sulfur atom, and oxygen atom, other than a carbon atom", and "bicyclic or tricyclic aromatic group formed by the condensation of the above aromatic heterocyclic group and a $C_6$ to $C_{14}$ aromatic hydrocarbon group" expressed by W in the above-mentioned formula (I) are shown together with specific examples.

(i) a halogen atom (for example fluorine, chlorine, bromine, iodine may be mentioned)

(ii) nitro (iii) cyano (iv) $C_1$ to $C_6$ alkyl which may optionally be substituted with 1 to 3 groups selected from a halogen atom, amino, $C_1$ to $C_6$ alkoxycarbonyl, $C_1$ to $C_6$ alkoxycarbonylamino, and carboxyl (as $C_1$ to $C_6$ alkyl, methyl, ethyl, n-propyl, i-propyl, n-butyl, i-butyl, s-butyl, t-butyl, n-pentyl, n-hexyl, etc. may be mentioned, and as a substituent group of $C_1$ to $C_6$ alkyl, fluorine, chlorine, bromine, iodine, amino, methoxycarbonyl, ethoxycarbonyl, methoxycarbonylamino, ethoxycarbonylamino, t-butoxycarbonylamino, and carboxyl may be mentioned. As specific examples, methyl, fluoromethyl, difluoromethyl, trifluoromethyl, chloromethyl, dichloromethyl, trichloromethyl, carboxylmethyl, ethyl, 2,2,2-trifluoroethyl, aminoethyl, methoxycarbonylethyl, t-butoxycarbonylaminoethyl, carboxylethyl, n-propyl, i-propyl, n-butyl, i-butyl, s-butyl, t-butyl, n-pentyl, n-hexyl, etc. (preferably, methyl, ethyl, trifluoromethyl, aminoethyl, carboxylmethyl, etc.) may be mentioned)

(v) $C_2$ to $C_6$ alkenyl which may optionally be substituted with 1 to 3 halogen atoms (as a halogen atom, fluorine, chlorine, bromine, and iodine may be mentioned, and as $C_2$ to $C_6$ alkenyl, for example, vinyl, propenyl, isopropenyl, 2-buten-1-yl, 4-pentene-1-yl, 5-hexen-1-yl, etc. may be mentioned)

(vi) $C_2$ to $C_6$ alkynyl which may optionally be substituted with 1 to 3 halogen atoms (as a halogen atom, fluorine, chlorine, bromine, and iodine may be mentioned, as $C_2$ to $C_6$ alkynyl, for example, 2-buten-1-yl, 4-pentyne-1-yl, 5-hexyne-1-yl, etc. may be mentioned)

(vii) $C_3$ to $C_6$ cycloalkyl (for example, cyclopropyl, cyclobutyl, cyclopentyl, cyclohexyl, etc. may be mentioned.)

(viii) hydroxyl (ix) $C_1$ to $C_6$ alkoxy which may optionally be substituted with 1 to 3 groups selected from a halogen atom, hydroxyl, $C_1$ to $C_6$ alkoxy, amino, and mono- or di-$C_1$ to $C_6$ alkylamino (as $C_1$ to $C_6$ alkoxy, for example, methoxy, ethoxy, n-propoxy, i-propoxy, n-butoxy, i-butoxy, s-butoxy, t-butoxy, n-pentyloxy, n-hexyloxy, etc. may be mentioned. As a substituent group of alkoxy, fluorine, chlorine, bromine, iodine, methylamino, dimethylamino, methoxy, ethoxy, N-methylcarbamoyl, N,N-dimethylcarbamoyl, N-benzylcarbamoyl, N-(2-picolyl)-carbamoyl, methoxycarbonyl, t-butoxycarbonyl, carboxyl, etc. may be mentioned. As specific examples, methoxy, ethoxy, n-propoxy, i-propoxy, n-butoxy, i-butoxy, t-butoxy, trifluoromethyloxy, trichloromethyloxy, methoxymethyloxy, ethoxymethyloxy, N-methyl-carbamoylmethyloxy, N-benzylcarbamoylmethyloxy, N-(2-picolyl)-carbamoylmethyloxy, methoxycarbonylmethyloxy, t-butoxycarbonylmethyloxy, carboxylmethyloxy, etc. (preferably, methoxy, ethoxy, N-methyl-carbamoylmethyloxy, N-benzylcarbamoylmethyloxy, N-(2-picolyl)-carbamoylmethyloxy, methoxycarbonylmethyloxy, t-butoxycarbonylmethyloxy, and carboxylmethyloxy) may be mentioned)

(x) $C_1$ to $C_5$ alkylenedioxy (for example methylenedioxy, ethylenedioxy, etc. may be mentioned)

(xi) $C_1$ to $C_6$ alkylthio which may optionally be substituted with 1 to 3 groups selected form a halogen atom, hydroxyl, $C_1$ to $C_6$ alkoxy, amino, and mono- or di-$C_1$ to $C_6$ alkylamino (as $C_1$ to $C_6$ alkylthio, for example, methylthio, ethylthio, n-propylthio, i-propylthio, n-butylthio, i-butylthio, s-butylthio, t-butylthio, n-pentylthio, n-hexylthio, etc. may be mentioned, and as examples of substituent groups of $C_1$ to $C_6$ alkylthio, fluorine, chlorine, bromine, iodine, methylamino, dimethylamino, methoxy, ethoxy, N-methylcarbamoyl, N,N-dimethylcarbamoyl, N-benzylcarbamoyl, N-(2-picolyl)-carbamoyl, methoxycarbonyl, t-butoxycarbonyl, carboxyl, etc. may be mentioned. As specific examples, methylthio, ethylthio, n-propylthio, i-propylthio, n-butylthio, i-butylthio, t-butylthio, trifluoromethylthio, trichloromethylthio, methoxymethylthio, ethoxymethylthio, N-methylcarbamoylmethylthio, N-benzylcarbamoylmethylthio, N-(2-picolyl)-carbamoylmethylthio, methoxycarbonylmethylthio, t-butoxycarbonylmethylthio, carboxylmethylthio, etc. may be mentioned)

(xii) amino (xiii) mono-$C_1$ to $C_6$ alkylamino (for example, N-methylamino etc. may be mentioned)

(xiv) di-$C_1$ to $C_6$ alkylamino (for example, N,N-dimethylamino etc. may be mentioned)

(xv) 5- to 6-membered cyclic amino (for example morpholino, piperidino, piperazino, etc. may be mentioned)

(xvi) $C_1$ to $C_6$ alkylcarbonyl (for example acetyl, propanoyl, butyryl, isobutyryl, pivaloyl, etc. may be mentioned)

(xvii) carboxyl (xviii) $C_1$ to $C_6$ alkoxycarbonyl which may optionally be substituted with a halogen atom (for example, methoxycarbonyl, ethoxycarbonyl, etc. may be mentioned)

(xix) $C_7$ to $C_{16}$ aralkyloxycarbonyl which may optionally be substituted with a halogen atom (for example, benzyloxycarbonyl etc. may be mentioned)

(xx) carbamoyl (xxi) mono-$C_1$ to $C_6$ alkyl-carbamoyl which may optionally be substituted with 1 to 3 groups selected from a halogen atom, hydroxyl, carboxyl, $C_1$ to $C_6$ alkoxy, amino, and mono- or di-$C_1$ to $C_6$ alkylamino (as a mono-$C_1$ to $C_6$ alkylcarbamoyl, for example, N-methylcarbamoyl, N-ethylcarbamoyl, etc. may be mentioned, and as a substituent group of mono-$C_1$ to $C_6$ alkylcarbamoyl, fluorine, chlorine, bromine, iodine, hydroxyl, carboxyl, methoxy, ethoxy, amino, N-methylamino, N,N-dimethylamino, etc. may be mentioned)

(xxii) di-$C_1$ to $C_6$ alkylcarbamoyl which may optionally be substituted with hydroxyl (for example, N,N-dimethylcarbamoyl, N,N-diethylcarbamoyl, N-hydroxyethyl-N-methylcarbamoyl, etc. may be mentioned)

(xxiii) 5- to 6-membered cyclic aminocarbonyl which may optionally be substituted with $C_1$ to $C_6$ alkoxycarbonyl (for example, morpholinocarbonyl, piperidinocarbonyl, piperazinocarbonyl, t-butoxycarbonylpiperazinolcarbonyl, etc. may be mentioned)

(xxiv) $C_6$-$C_{10}$ arylcarbamoyl (for example, phenylcarbamoyl etc. may be mentioned)

(xxv) $C_1$ to $C_{10}$ heteroarylcarbamoyl (for example, pyridylcarbamoyl etc. may be mentioned)

(xxvi) $C_7$ to $C_{16}$ aralkylcarbamoyl (for example, benzylaminocarbonyl etc. may be mentioned)

(xxvii) $C_1$ to $C_{10}$ heteroaryl-$C_1$ to $C_6$ alkylcarbamoyl (for example, pyridylmethylcarbamoyl, pyridylethylcarbamoyl, etc. may be mentioned)

(xxviii) N—$C_1$ to $C_6$ alkyl-N—$C_6$ to $C_{12}$ aryl-carbamoyl (for example, N-methyl-N-phenylcarbamoyl etc. may be mentioned)

(xxix) $C_3$ to $C_6$ cycloalkylcarbamoyl (for example, cyclopropylcarbamoyl, cyclohexylcarbamoyl, etc. may be mentioned)

(xxx) sulfo (xxxi) $C_1$ to $C_6$ alkylsulfonyl (for example, methane sulfonyl etc. may be mentioned)

(xxxii) $C_1$ to $C_6$ alkylsulfonylamino (for example, methane sulfonylamino etc. may be mentioned)

(xxxiii) $C_6$ to $C_{12}$ arylsulfonylamino which may optionally be substituted with $C_1$ to $C_6$ alkyl (for example, benzenesulfonylamino, methylbenzenesulfonylamino, etc. may be mentioned.)

(xxxiv) $C_1$ to $C_{10}$ heteroarylsulfonylamino (for example, pyridylsulfonylamino etc. may be mentioned)

(xxxv) $C_1$ to $C_6$ alkoxycarbonylamino (for example, methoxycarbonylamino, ethoxycarbonylamino, t-butoxycarbonylamino, etc. may be mentioned)

(xxxvi) $C_1$ to $C_6$ alkylcarbonylamino (for example, acetoamide etc. may be mentioned)

(xxxvii) mono- or di-$C_1$ to $C_6$ alkylaminocarbonylamino (for example, N-methylaminocarbonylamino, N-ethylaminocarbonylamino, etc. may be mentioned)

(xxxviii) $C_6$ to $C_{12}$ aryl (for example, phenyl etc. may be mentioned)

(xxxix) $C_1$ to $C_{10}$ heteroaryl ($C_1$ to $C_{10}$ heteroaryl including 1 to 4 hetero atoms selected from a nitrogen atom, sulfur atom, and oxygen atom (for example, pyridyl, pyrazolyl, imidazolyl, etc.) may be mentioned)

(xl) $C_6$ to $C_{10}$ aryloxy (for example, phenoxy etc. may be mentioned)

(xli) $C_1$ to $C_{10}$ heteroaryloxy ($C_1$ to $C_{10}$ heteroaryloxy including 1 to 4 hetero atoms selected from a nitrogen atom, sulfur atom, and oxygen atom (for example, pyridyloxy, pyrazolyloxy, imidazolyloxy, etc.) may be mentioned)

(xlii) $C_7$ to $C_{16}$ aralkyloxy (for example, benzyloxy etc. may be mentioned)

(xliii) $C_1$ to $C_{10}$ heteroaryl-$C_1$ to $C_6$ alkyloxy ($C_1$ to $C_{10}$ heteroaryl-$C_1$ to $C_6$ alkyloxy including 1 to 4 hetero atoms selected from a nitrogen atom, sulfur atom, and oxygen atom (for example, pyridylmethyloxy, pyrazolylmethyloxy, imidazolylmethyloxy, etc.) may be mentioned)

(xliv) aminosulfonyl (xlv) mono- or di-$C_1$ to $C_6$ alkylaminosulfonyl (for example, N-methylaminosulfonyl etc. may be mentioned)

(xlvi) $C_7$ to $C_{16}$ aralkyloxy-carbamoyl (for example, benzyloxycarbamoyl etc. may be mentioned)

(xlvii) $C_1$ to $C_{10}$ heteroaryl-$C_1$ to $C_6$ alkyloxy-carbamoyl ($C_1$ to $C_{10}$ heteroaryl-$C_1$ to $C_6$ alkyloxycarbamoyl including 1 to 4 hetero atoms selected from a nitrogen atom, sulfur atom, and oxygen atom (for example, pyridylmethyloxycarbamoyl, pyrazolylmethyloxycarbamoyl, imidazolylmethyloxycarbamoyl, etc.) may be mentioned)

As examples of the $C_1$ to $C_6$ alkyl expressed by W in the above-mentioned formula (I), methyl, ethyl, n-propyl, i-propyl, n-butyl, i-butyl, s-butyl, t-butyl, n-pentyl, n-hexyl, etc. may be mentioned.

As examples of the heterocycloalkyl group of the 5- to 7-membered heterocycloalkyl group which may optionally be substituted with 1 to 3 groups selected from oxo and phenyl expressed by W in the above-mentioned formula (I), pyrrolidine, imidazolidine, piperidine, piperazine, etc. may be mentioned.

In the above-mentioned formula (I), X indicates (1) a bond, (2) linear or branched $C_1$ to $C_6$ alkylene, (3) oxygen atom, (4) $NR^{13}$, where, $R^{13}$ indicates a hydrogen atom or $C_1$ to $C_6$ alkyl group, or (5) —$S(O)_m$—, where m indicates an integer of 0 to 2.

As specific examples of the "linear or branched $C_1$ to $C_6$ alkylene" expressed by X, methylene, 1,1-ethylene, 1,2-ethylene, 1,1-propylene, etc. may be mentioned. Further, as specific examples of the "$NR^{13}$, where $R^{13}$ indicates a hydrogen atom or $C_1$ to $C_6$ alkyl group" expressed by X, —NH—, —NMe—, —NEt-, —N$^n$Pr—, —N$^i$Pr—, etc. may be mentioned. As X, a methylene group is particularly preferable.

In the above-mentioned formula (I), Y indicates (1) —S(O)$_n$—, where n indicates an integer of 1 or 2, (2) —S(O)$_n$NH—, where n indicates an integer of 1 or 2, (3) —C(=O)—, (4) —C(=O)NH—, or (5) —C(=O)NR$^{14}$—, where R$^{14}$ indicates a $C_1$ to $C_6$ alkyl group. As specific examples of the "—C(=O)NR$^{14}$—, where R$^{14}$ indicates a $C_1$ to $C_6$ alkyl group" expressed by Y, —C(=O)NMe—, —C(=O)NEt-, —C(=O)N$^n$Pr—, —C(=O)N$^i$Pr—, etc. may be mentioned. As Y, —SO$_2$— and —C(=O)NH— are particularly preferable.

Next, in the above-mentioned formula (I), the (A) to (F), which the R$^7$ and R$^8$ of "CR$^7$R$^8$" expressed by Z independently indicate, are shown below along with specific examples:

(A) a hydrogen atom (B) $C_1$ to $C_6$ alkyl which may optionally be substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, and (vi) a halogen atom (as examples of $C_1$ to $C_6$ alkyl, methyl, ethyl, n-propyl, i-propyl, n-butyl, i-butyl, s-butyl, t-butyl, n-pentyl, n-hexyl, etc. may be mentioned. As examples of a substituent group of $C_1$ to $C_6$ alkyl, carboxyl, methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, phenyl, hydroxyl, methoxy, ethoxy, n-propoxy, i-propoxy, n-butoxy, i-butoxy, t-butoxy, fluorine, chlorine, bromine, iodine, etc. may be mentioned)

(C) $C_6$ to $C_{12}$ aryl or $C_1$ to $C_{10}$ heteroaryl which may optionally be substituted with 1 to 5 groups selected from the group consisting of (i) a halogen atom and (ii) an alkyl group which may optionally be substituted with 1 to 3 halogen atoms (as examples of $C_6$ to $C_{12}$ aryl or $C_1$ to $C_{10}$ heteroaryl, phenyl, pyridyl, pyrazolyl, imidazolyl, etc. may be mentioned. As examples of a substituent group, fluorine, chlorine, bromine, iodine, methyl, ethyl, trifluoromethyl, etc. may be mentioned)

(D) $C_3$ to $C_6$ cycloalkyl which may optionally be substituted with 1 to 5 groups selected from the group consisting of (i) a halogen atom and (ii) an alkyl group which may optionally be substituted with 1 to 3 halogen atoms (as examples of $C_3$ to $C_6$ cycloalkyl, cyclopropyl, cyclohexyl, etc. may be mentioned. As examples of the substituent group, fluorine, chlorine, bromine, iodine, methyl, ethyl, trifluoromethyl, etc. may be mentioned)

(E) —COOR$^9$ (R$^9$ indicates a hydrogen atom or $C_1$ to $C_6$ alkyl) (as specific examples, carboxyl, methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, etc. may be mentioned)

(F) CONR$^{10}$R$^{11}$ (where, specific examples of (a) to (d) which R$^{10}$ and R$^{11}$ show independently are as follows)

(a) hydrogen atom (b) $C_1$ to $C_6$ alkyl which may optionally be substituted with 1 to 3 groups selected from the group consisting of (i) a halogen atom, (ii) $C_3$ to $C_6$ cycloalkyl, (iii) carboxyl, (iv) $C_1$ to $C_6$ alkoxycarbonyl, (v) $C_1$ to $C_6$ alkylcarbonyl, (vi) carbamoyl, (vii) mono-$C_1$ to $C_6$ alkylcarbamoyl, (viii) di-$C_1$ to $C_6$ alkylcarbamoyl, (ix) $C_6$ to $C_{12}$ aryl and (x) $C_1$ to $C_{10}$ heteroaryl (as specific examples of a $C_1$ to $C_6$ alkyl group, methyl, ethyl, n-propyl, i-propyl, n-butyl, i-butyl, s-butyl, t-butyl, n-pentyl, n-hexyl, etc. may be mentioned. Here, as examples of the substituent groups (i) to (x) of a $C_1$ to $C_6$ alkyl group, (i) a halogen atom (for example, fluorine, chlorine, bromine, iodine)

(ii) $C_3$ to $C_6$ cycloalkyl (for example, cyclopropyl, cyclobutyl, cyclopentyl, cyclohexyl, etc.)

(iii) carboxyl (iv) $C_1$ to $C_6$ alkoxycarbonyl (for example, methoxycarbonyl, ethoxycarbonyl, etc.)

(v) $C_1$ to $C_6$ alkyl-carbonyl (for example, acetyl, propanoyl, butyryl, isobutyryl, pivaroyl, etc.)

(vi) carbamoyl (vii) mono-$C_1$ to $C_6$ alkylcarbamoyl (for example, N-methylcarbamoyl, N-ethylcarbamoyl, etc.)

(viii) di-$C_1$ to $C_6$ alkylcarbamoyl (for example, N,N-dimethylcarbamoyl, N,N-diethylcarbamoyl, etc.)
(ix) $C_6$ to $C_{12}$ aryl (for example, phenyl, tolyl, xylyl, biphenyl, naphthyl, indenyl, etc.)
(x) $C_1$ to $C_{10}$ heteroaryl (for example thienyl, furyl, pyrrolyl, imidazolyl, pyrazolyl, triazolyl, tetrazolyl, thiazolyl, isothiazolyl, oxazolyl, isoxazolyl, pyridyl, pyrazinyl, pyrimidinyl, pyridazinyl, benzothienyl, benzofuryl, indolyl, isoindolyl, benzimidazolyl, benzopyrazolyl, benzotriazolyl, benzothiazolyl, benzisothiazolyl, benzoxazolyl, benzisoxazolyl, quinolyl, isoquinolyl, quinoxalinyl, phthalazinyl, naphthylidinyl, purinyl, etc.) may be mentioned.)
(c) $OR^{12}$ ($R^{12}$ indicates a hydrogen atom or $C_1$ to $C_6$ alkyl) (as specific examples, hydroxyl, methoxy, ethoxy, n-propoxy, i-propoxy, n-butoxy, i-butoxy, s-butoxy, t-butoxy, n-pentyloxy, n-hexyloxy, etc. may be mentioned)
(d) (1) $C_6$ to $C_{14}$ aromatic hydrocarbon group, (2) a 5- to 8-membered aromatic heterocyclic group including 1 to 4 hetero atoms selected from a nitrogen atom, sulfur atom, and oxygen atom, other than a carbon atom, or (3) a bicyclic or tricyclic aromatic group formed by condensation of the above aromatic heterocyclic group and a $C_6$ to $C_{14}$ aromatic hydrocarbon ring (specific examples of the groups (1) to (3) being the same as the "$C_6$ to $C_{14}$ aromatic hydrocarbon group", "5- to 8-membered aromatic heterocyclic group including 1 to 4 hetero atoms selected from a nitrogen atom, sulfur atom, and oxygen atom other than a carbon atom", and "bicyclic or tricyclic aromatic group formed by condensation of the above aromatic heterocyclic group and a $C_6$ to $C_{14}$ aromatic hydrocarbon ring" in the above Ar. As preferable examples of the groups (1) to (3) in $R^{10}$ and $R^{11}$, phenyl, naphthyl, pyridyl, pyrrolyl, tetrazolyl, pyrrolyl, etc. may be mentioned)

Specific examples of the substituent groups (i) to (xxviii) which the groups (1) to (3) may have 1 to 5 of are shown.

(i) a halogen atom (for example, fluorine, chlorine, bromine, iodine)
(ii) nitro
(iii) cyano
(iv) $C_1$ to $C_6$ alkyl which may optionally be substituted with 1 to 3 halogen atoms (for example, $C_1$ to $C_6$ alkyl (for example, methyl, ethyl, n-propyl, i-propyl, n-butyl, i-butyl, s-butyl, t-butyl, n-pentyl, n-hexyl, etc.) which may optionally be substituted with 1 to 3 halogen atoms selected from fluorine, chlorine, bromine, and iodine, may be mentioned. As specific examples, methyl, fluoromethyl, difluoromethyl, trifluoromethyl, chloromethyl, dichloromethyl, trichloromethyl, ethyl, 2,2,2-trifluoroethyl, n-propyl, i-propyl, n-butyl, i-butyl, s-butyl, t-butyl, n-pentyl, n-hexyl, etc., (preferably, methyl, ethyl, trifluoromethyl, etc.) may be mentioned)
(v) $C_2$ to $C_6$ alkenyl which may optionally be substituted with 1 to 3 halogen atoms (for example, $C_2$ to $C_6$ alkenyl (for example, vinyl, propenyl, isopropenyl, 2-buten-1-yl, 4-penten-1-yl, 5-hexen-1-yl, etc.) which may optionally be substituted with 1 to 3 halogen atoms selected from fluorine, chlorine, bromine, and iodine may be mentioned)
(vi) $C_2$ to $C_6$ alkynyl which may optionally be substituted with 1 to 3 halogen atoms (for example $C_2$ to $C_6$ alkynyl (for example, 2-butyn-1-yl, 4-pentyn-1-yl, 5-hexyn-1-yl, etc.) which may optionally be substituted with 1 to 3 halogen atoms selected from fluorine, chlorine, bromine, and iodine may be mentioned)
(vii) $C_3$ to $C_6$ cycloalkyl (for example cyclopropyl, cyclobutyl, cyclopentyl, cyclohexyl, etc. may be mentioned)
(viii) hydroxyl
(ix) $C_1$ to $C_6$ alkoxy which may optionally be substituted with 1 to 3 halogen atoms (for example, methoxy, ethoxy, n-propoxy, i-propoxy, n-butoxy, i-butoxy, t-butoxy, trifluoromethyloxy, trichloromethyloxy, etc.)
(x) $C_1$ to $C_5$ alkylenedioxy (for example, methylenedioxy, ethylenedioxy, etc. may be mentioned)
(xi) $C_1$ to $C_6$ alkylthio which may optionally be substituted with 1 to 3 halogen atoms (for example, methylthio, ethylthio, n-propylthio, i-propylthio, n-butylthio, i-butylthio, s-butylthio, t-butylthio, n-pentylthio, n-hexylthio, trifluoromethylthio, trichloromethylthio, etc. may be mentioned)
(xii) amino
(xiii) mono-$C_1$ to $C_6$ alkylamino (for example, N-methylamino, etc. may be mentioned)
(xiv) di-$C_1$ to $C_6$ alkylamino (for example, N,N-dimethylamino etc. may be mentioned)
(xv) 5- to 6-membered cyclic amino (for example, morpholino, piperidino, piperazino, etc. may be mentioned)
(xvi) $C_1$ to $C_6$ alkylcarbonyl (for example, acetyl, propanoyl, butyryl, isobutyryl, pivaroyl, etc. may be mentioned)
(xvii) carboxyl
(xviii) $C_1$ to $C_6$ alkoxycarbonyl (for example, methoxycarbonyl, ethoxycarbonyl, etc. may be mentioned)
(xix) carbamoyl
(xx) thiocarbamoyl
(xxi) mono-$C_1$ to $C_6$ alkylcarbamoyl (for example, N-methylcarbamoyl, N-ethylcarbamoyl, etc. may be mentioned)
(xxii) di-$C_1$ to $C_6$ alkylcarbamoyl (for example, N,N-dimethylcarbamoyl, N,N-diethylcarbamoyl, etc. may be mentioned)
(xxiii) $C_6$-$C_{10}$ arylcarbamoyl (for example, phenylcarbamoyl etc. may be mentioned)
(xxiv) $C_1$ to $C_{10}$ heteroarylcarbamoyl (for example, pyridylcarbamoyl etc. may be mentioned)
(xxv) sulfo
(xxvi) $C_1$ to $C_6$ alkylsulfonyl (for example, methanesulfonyl etc. may be mentioned)
(xxvii) aminosulfonyl and
(xxviii) mono- or di-$C_1$ to $C_6$ alkylaminosulfonyl (for example, N-methylaminosulfonyl etc. may be mentioned)

In the above-mentioned formula (I), as specific examples of the halogen atom expressed by $R^1$, $R^2$, and $R^3$, fluorine, chlorine, bromine, and iodine may be mentioned.

In the above-mentioned formula (I), as specific examples of the $C_1$ to $C_6$ alkyl group expressed by $R^1$, $R^2$ and $R^3$, methyl, ethyl, n-propyl, i-propyl, n-butyl, i-butyl, s-butyl, t-butyl, n-pentyl, n-hexyl, etc. may be mentioned.

In the above-mentioned formula (I), as the "$C_1$ to $C_6$ alkyl group" expressed by $R^5$ and $R^6$, methyl, ethyl, n-propyl, i-propyl, n-butyl, i-butyl, s-butyl, t-butyl, n-pentyl, and n-hexyl may be mentioned, and as the substituent group which the "$C_1$ to $C_6$ alkyl group" may have, (i) carboxyl, (ii) $C_1$ to $C_6$ alkoxy (for example, methoxy and ethoxy), (iii) $C_1$ to $C_6$ alkoxycarbonyl (for example, methoxycarbonyl and ethoxycarbonyl), (iv) $C_6$ to $C_{12}$ aryloxycarbonyl (for example, phenoxycarbonyl), (v) $C_1$ to $C_{10}$ heteroaryloxycarbonyl (for example, pyridyloxycarbonyl), and (vi) amino may be mentioned. As specific examples, methyl, ethyl, n-propyl, i-propyl, n-butyl, i-butyl, s-butyl, t-butyl, n-pentyl, n-hexyl, methoxymethyl, ethoxymethyl, carboxymethyl, 2-carboxyethyl, methoxycarbonylmethyl, 2-(methoxycarbonyl)ethyl, aminomethyl, aminoethyl, aminopropyl, etc. may be mentioned.

In the above-mentioned formula (I), as specific examples of the 3- to 8-membered ring formed by $R^2$ and $R^3$ or $R^5$ and $R^6$, cyclopropyl, cyclobutyl, cyclopentyl, cyclohexyl, etc. may be mentioned.

In the above-mentioned formula (I), as specific examples of the $C_1$ to $C_6$ alkylcarbamoyl expressed by $R^4$, N-methylaminocarbonyl, N-ethylaminocarbonyl, etc. may be mentioned.

In the above-mentioned formula (I), as specific examples of "$C_1$ to $C_6$ alkyl group" expressed by $R^4$, methyl, ethyl, n-propyl, i-propyl, n-butyl, i-butyl, s-butyl, t-butyl, n-pentyl, and n-hexyl may be mentioned, and as the 1 to 3 substituent groups which the "$C_1$ to $C_6$ alkyl group" may have, (i) carbamoyl, (ii) mono- or di-$C_1$ to $C_6$ alkylcarbamoyl (for example, N-methylcarbamoyl etc.), (iii) mono- or di-$C_6$ to $C_{12}$ arylcarbamoyl, (for example, N-phenylcarbamoyl etc.), (iv) mono- or di-$C_1$ to $C_{10}$ heteroarylcarbamoyl (for example, N-pyridylcarbamoyl), (v) N—$C_1$ to $C_6$ alkyl-N—$C_6$ to $C_{12}$ arylcarbamoyl (for example, N-methyl-N-phenylcarbamoyl), (vi) N—$C_1$ to $C_6$ alkyl-N—$C_1$ to $C_{10}$ heteroarylcarbamoyl (for example, N-methyl-N-pyridylcarbamoyl), (vii) mono- or di-$C_7$ to $C_{16}$ aralkylcarbamoyl (for example, N-benzylcarbamoyl), (viii) mono- or di-$C_1$ to $C_{10}$ heteroaryl-$C_1$ to $C_6$ alkylcarbamoyl (for example, N-pyridylmethylcarbamoyl etc.), (ix) carboxyl, and (x) $C_1$ to $C_6$ alkoxycarbonyl (for example, methoxycarbonyl, ethoxycarbonyl, etc.) may be mentioned. As specific examples, methyl, ethyl, n-propyl, i-propyl, carbamoylmethyl, N-phenylcarbamoylmethyl, N-pyridylcarbamoylmethyl, N-methyl-N-phenylcarbamoylmethyl, N-benzylcarbamoylmethyl, carbamoylethyl, N-phenylcarbamoylethyl, N-pyridylcarbamoylethyl, N-methyl-N-phenylcarbamoylethyl, N-benzylcarbamoylethyl, carboxylmethyl, carboxylethyl, methoxycarbonylmethyl, methoxycarbonylethyl, ethoxycarbonylmethyl, ethoxycarbonylethyl, etc. may be mentioned.

As preferable examples of the compounds having the above-mentioned formula (I), the following may be mentioned.

1. A compound, or its salt, or a solvate thereof, where, in the formula (I), X is linear or branched $C_1$ to $C_6$ alkylene, $R^1$ indicates (1) a hydrogen atom, (2) halogen atom, or (3) $C_1$ to $C_6$ alkyl or $R^1$ forms —CH= together with X, and Y is —$SO_2$— or —C(=O)NH—.

2. A compound, or its salt, or a solvate thereof, where, in the formula (I), Ar is a $C_6$ to $C_{14}$ aromatic hydrocarbon group.

3. A compound, or its salt, or a solvate thereof, where, in the formula (I), Ar is a phenyl group, the Ar group may optionally be substituted with 1 to 5 groups selected from the group consisting of (i) a halogen atom, (ii) nitro, (iii) cyano, (iv) $C_1$ to $C_6$ alkyl which may optionally be substituted with 1 to 3 halogen atoms, (v) hydroxyl, and (vi) $C_1$ to $C_6$ alkoxy which may optionally be substituted with 1 to 3 halogen atoms, and $R^2$, $R^3$, $R^4$, $R^5$, and $R^6$ are all hydrogen atoms.

4. A compound, or its salt, or a solvate thereof, where, in the formula (I), W is a (1) $C_6$ to $C_{14}$ aromatic hydrocarbon group or (2) 5- to 8-membered aromatic heterocyclic group including 1 to 4 hetero atoms selected from a nitrogen atom, sulfur atom, and oxygen atom, other than a carbon atom.

5. A compound, or its salt, or a solvate thereof, where, in the formula (I), W is a (1) $C_6$ to $C_{14}$ aromatic hydrocarbon group or (2) 5- to 8-membered aromatic heterocyclic group including 1 to 4 hetero atoms selected from a nitrogen atom, sulfur atom, and oxygen atom, other than a carbon atom, and Z is a (1) a bond or (2) $CR^7R^8$, where $R^7$ and $R^8$ independently indicate, (A) a hydrogen atom (B) $C_1$ to $C_6$ alkyl which may optionally be substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, and (vi) a halogen atom.

6. A compound, or its salt, or a solvate thereof, where, in the formula (I), W is a hydrogen atom.

7. A compound, or its salt, or a solvate thereof, where, in the formula (I), W is a hydrogen atom, and Z is $CR^7R^8$, where $R^7$ and $R^8$ independently indicate, (A) a hydrogen atom (B) $C_1$ to $C_6$ alkyl which may optionally be substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, and (vi) halogen atom (E) —$COOR^9$, where $R^9$ indicates a hydrogen atom or $C_1$ to $C_6$ alkyl or (F) $CONR^{10}R^{11}$, where $R^{10}$ and $R^{11}$ independently indicate, (a) a hydrogen atom (b) $C_1$ to $C_6$ alkyl which may optionally be substituted with 1 to 3 groups selected from the group consisting of (i) a halogen atom, (ii) $C_3$ to $C_6$ cycloalkyl, (iii) carboxyl, (iv) $C_1$ to $C_6$ alkoxycarbonyl, (v) $C_1$ to $C_6$ alkyl-carbonyl, (vi) carbamoyl, (vii) mono-$C_1$ to $C_6$ alkylcarbamoyl, (viii) di-$C_1$ to $C_6$ alkylcarbamoyl, (ix) $C_6$ to $C_{12}$ aryl, and (x) $C_1$ to $C_{10}$ heteroaryl (c) $OR^{12}$, where, $R^{12}$ indicates a hydrogen atom or $C_1$ to $C_6$ alkyl or (d) (1) $C_6$ to $C_{14}$ aromatic hydrocarbon group, (2) 5- to 8-membered aromatic heterocyclic group including 1 to 4 hetero atoms selected from a nitrogen atom, sulfur atom, and oxygen atom, other than a carbon atom, or (3) a bicyclic or tricyclic aromatic group formed by condensation of the above aromatic heterocyclic group and a $C_6$ to $C_{14}$ aromatic hydrocarbon ring, where the groups (1) to (3) may optionally be substituted with 1 to 5 groups selected from the group consisting of a (i) halogen atom, (ii) nitro, (iii) cyano, (iv) $C_1$ to $C_6$ alkyl which may optionally be substituted with 1 to 3 halogen atoms, (v) $C_2$ to $C_6$ alkenyl which may optionally be substituted with 1 to 3 halogen atoms, (vi) $C_2$ to $C_6$ alkynyl which may optionally be substituted with 1 to 3 halogen atoms, (vii) $C_3$ to $C_6$ cycloalkyl, (viii) hydroxyl, (ix) $C_1$ to $C_6$ alkoxy which may optionally be substituted with 1 to 3 halogen atoms, (x) $C_1$ to $C_5$ alkylenedioxy, (xi) $C_1$ to $C_6$ alkylthio which may optionally be substituted with 1 to 3 halogen atoms, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xviii) $C_1$ to $C_6$ alkoxycarbonyl, (xix) carbamoyl, (xx) thiocarbamoyl, (xxi) mono-$C_1$ to $C_6$ alkylcarbamoyl, (xxii) di-$C_1$ to $C_6$ alkylcarbamoyl, (xxiii) $C_6$-$C_{10}$ arylcarbamoyl, (xxiv) $C_1$ to $C_{10}$ heteroarylcarbamoyl, (xxv) sulfo, (xxvi) $C_1$ to $C_6$ alkylsulfonyl, (xxvii) aminosulfonyl, and (xxviii) mono- or di-$C_1$ to $C_6$ alkylaminosulfonyl.

As particularly preferable specific examples, the following compounds may be mentioned.

3-[(1R)-1-({[(6R)-6-(5-chloro-2-methoxybenzyl)-3,7-dioxo-1,4-diazepan-1-yl]carbonyl}amino)propyl]benzoic acid, or its salt, or a solvate thereof.

2-amino-4-[(1R)-1-({[(6R)-6-(5-chloro-2-methoxybenzyl)-3,7-dioxo-1,4-diazepan-1-yl]carbonyl}amino)propyl]benzoic acid, or its salt, or a solvate thereof.

2-amino-4-[(1R)-1-({[(6S)-6-(5-chloro-2-methoxybenzyl)-3,7-dioxo-1,4-diazepan-1-yl]carbonyl}amino)propyl]benzoic acid, or its salt, or a solvate thereof.

6-(5-chloro-2-methoxybenzyl)-4-[(4-chlorophenyl)sulfonyl]-1,4-diazepan-2,5-dione, or its salt, or a solvate thereof.

4-[(3-amino-4-chlorophenyl)sulfonyl]-6-(5-chloro-2-methoxybenzyl)-1,4-diazepan-2,5-dione, or its salt, or a solvate thereof.

When the compound having formula (I) has an amine or other basic group as a substituent group, it may also be formed a salt with an inorganic acid (for example, hydrochloric acid, hydrogen bromic acid, sulfuric acid, etc.) or a salt with an organic acid (for example, methanesulfonic acid, benzenesulfonic acid, toluenesulfonic acid, etc.) When the compound having the formula (I) has a carboxylic acid and other acid group as a substituent group, it may also be formed a salt with an inorganic base (for example, sodium, potassium, calcium, magnesium, or other alkali metal or alkali earth metal etc., or ammonia etc.) or a salt with an organic base (for example, triethanolamine, 2-aminoethanol, 2,2'-iminobis(ethanol), etc.).

The compound having the formula (I) or a salt thereof may also be a nonsolvate or a solvate with water, methanol, ethanol, 1-propanol, 2-propanol, 1-butanol, 2-butanol, 2-methyl-1-propanol, 1-pentanol, 3-methyl-1-butanol, 2-methoxyethanol, 2-ethoxyethanol, formic acid, ethyl formate, acetic acid, methyl acetate, ethyl acetate, propyl acetate, isobutyl acetate, acetone, methylethylketone, methylisobutylketone (preferably, water, ethanol, 1-propanol, 2-propanol, 1-butanol, acetic acid, ethyl acetate, acetone, etc.) and other solvents.

[2. Method of Production of Compound Having Formula (I) or Salt or Solvate Thereof]

Below, a production method of a compound having the formula (I) or its salt or solvate thereof will be explained. A compound having the formula (I), or its salt, or a solvate thereof may be produced by a method of one or both of the following explained two methods of production (A) and (B).

[Method of Production (A)]

The compound having the formula (I) or its salt, or solvate thereof may be produced by a cyclization reaction of a compound having the formula (II):

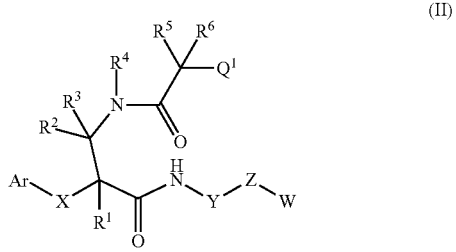

(II)

where Ar, W, X, Y, Z, $R^1$, $R^2$, $R^3$, $R^4$, $R^5$, and $R^6$ are the same as defined above, $Q^1$ indicates a halogen atom, $C_6$ to $C_{10}$ arylsulfonyloxy group which may optionally be substituted with 1 to 3 halogen atoms, or $C_1$ to $C_4$ alkylsulfonyloxy group which may optionally be substituted with 1 to 3 halogen atoms.

As the group expressed by $Q^1$, a halogen atom (for example, chlorine, bromine, iodine, etc.), $C_6$ to $C_{10}$ arylsulfonyloxy group which may optionally be substituted with 1 to 3 halogen atoms (for example, benzenesulfonyloxy, p-toluene sulfonyloxy, etc.), $C_1$ to $C_4$ alkylsulfonyloxy group which may optionally be substituted with 1 to 3 halogen atoms (for example, methane sulfonyloxy etc.), etc. may be used.

Usually, this reaction may be carried out in the presence of a base. As the base, for example, sodium hydride, potassium hydride, and other alkali metal hydrides, sodium carbonate, sodium hydrogencarbonate, potassium carbonate, potassium hydrogencarbonate, and other alkali metal carbonates, trisodium phosphate, disodium hydrogenphosphate, sodium dihydrogenphosphate, tripotassium phosphate, dipotassium hydrogenphosphate, potassium dihydrogenphosphate, and other alkali metal phosphates, n-butyllithium and other organic alkali metals, lithium diisopropylamide and other organometallic amides, potassium t-butoxide, and other alkali metal alkoxides etc. may be used.

Further, usually, this reaction may be carried out in the presence of a solvent. As the solvent, for example, 2-propanol and other alcohols, dioxane, tetrahydrofuran, and other ethers, benzene, toluene, xylene, and other aromatic hydrocarbons, acetonitrile and other nitriles, N,N-dimethylformamide, N,N-dimethylacetoamide, N-methylpyrrolidone, and other amides, dimethylsulfoxide and other sulfoxides, etc. may be used as single solvents or mixed solvents.

The reaction temperature of the present invention method is preferably about −80° C. to about 100° C., while the reaction time is preferably about 30 minutes to about 48 hours. Further, the reaction may be carried out using an additive for promoting the reaction. As such an additive, for example, sodium iodide, potassium iodide, etc. may be used.

[Method of Production (B)]

Among the compounds having the formula (I) or a salt thereof, compounds where Y is —S(O)$_n$NH— (where n indicates an integer of 1 or 2) or —C(═O)NH— may be produced by the coupling reaction of the compound, or a salt thereof, having the formula (III):

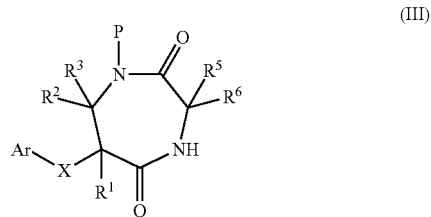

(III)

where Ar, X, $R^1$, $R^2$, $R^3$, $R^5$, and $R^6$ are the same as defined above, and P indicates a protective group such as an allyl, allyloxycarbonyl, 9-fluorenylmethylcarbonyl, linear or branched $C_1$ to $C_6$ alkyloxycarbonyl which may optionally be substituted with 1 to 3 halogen atoms, linear or branched $C_1$ to $C_6$ alkylcarbonyl which may optionally be substituted with 1 to 3 halogen atoms, $C_7$ to $C_{16}$ aralkyl which may optionally be substituted with 1 to 3 groups selected from (i) a halogen atom, (ii) $C_1$ to $C_6$ alkyl, (iii) $C_1$ to $C_6$ alkoxy, and (iv) nitro, $C_5$ to $C_{16}$ arylcarbonyl which may optionally be substituted with 1 to 3 groups selected from (i) a halogen atom, (ii) $C_1$ to $C_6$ alkyl, (iii) $C_1$ to $C_6$ alkoxy, and (iv) nitro, $C_7$ to $C_{16}$ aralkyloxycarbonyl which may optionally be substituted with 1 to 3 groups selected from (i) a halogen atom, (ii) $C_1$ to $C_6$ alkyl, (iii) $C_1$ to $C_6$ alkoxy, and (iv) nitro, or $C_5$ to $C_{16}$ arylsulfonyl which may optionally be substituted with 1 to 3 groups selected from (i) a halogen atom, (ii) $C_1$ to $C_6$ alkyl, (iii) $C_1$ to $C_6$ alkoxyl, and (iv) nitro, or $R^4$, where $R^4$ is as defined above, the compound (IV), or a salt thereof, having formula (IV):

where $Q^2$ and $Q^3$ independently indicate $C_6$ to $C_{10}$ aryloxy group which may optionally be substituted with 1 to 3 halogen atoms or nitro, or a halogen atom, and Y' indicates —S(O)$_n$— (where n indicates an integer of 1 or 2) or C(=O), and the compound (V), or a salt thereof, having the formula (V):

where W and Z are the same as defined as above, and the optional deprotection reaction of the coupling product described above.

In the production method, as the compound (V), it is possible to use a compound, or a salt thereof, having the formula (Va):

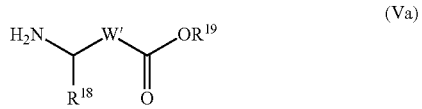

where W' $R^{18}$, and $R^{19}$ are the same as defined above.

The compound (Va) may be acquired or synthesized according to the method for the compound (V) explained later.

As the "protective group" expressed by P, for example, allyl, allyloxycarbonyl, 9-fluorenylmethylcarbonyl, linear or branched $C_1$ to $C_6$ alkyloxycarbonyl which may optionally be substituted with 1 to 3 halogen atoms (for example, t-butyloxycarbonyl etc.), linear or branched $C_1$ to $C_6$ alkylcarbonyl which may optionally be substituted with 1 to 3 halogen atoms (for example, trifluoroacetyl etc.), $C_7$ to $C_{16}$ aralkyl which may optionally be substituted with 1 to 3 of (i) a halogen atom, (ii) $C_1$ to $C_6$ alkyl, (iii) $C_1$ to $C_6$ alkoxy, or (iv) nitro (for example, benzyl, p-methoxybenzyl, 2,4-dimethoxybenzyl, 2,4,6-trimethoxybenzyl, etc.), $C_5$ to $C_{16}$ arylcarbonyl which may optionally be substituted with 1 to 3 of (i) a halogen atom, (ii) $C_1$ to $C_6$ alkyl, (iii) $C_1$ to $C_6$ alkoxy, or (iv) nitro (for example, benzoyl and p-nitrobenzoyl), $C_7$ to $C_{16}$ aralkyloxycarbonyl which may optionally be substituted with 1 to 3 of (i) a halogen atom, (ii) $C_1$ to $C_6$ alkyl, (iii) $C_1$ to $C_6$ alkoxy, or (iv) nitro (for example, benzyloxycarbonyl etc.), $C_5$ to $C_{16}$ arylsulfonyl which may optionally be substituted with 1 to 3 of (i) a halogen atom, (ii) $C_1$ to $C_6$ alkyl, (iii) $C_1$ to $C_6$ alkoxy, or (iv) nitro (for example, p-toluene sulfonyl etc.) etc. may be used. When P is such a "protective group", the protective group may be removed by an ordinary method after the compounds (III), (IV), and (V) are reacted.

As the substituent group expressed by $Q^2$ and $Q^3$, a $C_6$ to $C_{10}$ aryloxy group which may optionally be substituted with 1 to 3 halogen atoms or nitro (for example, phenyloxy, p-nitrophenyloxy, p-chlorophenyloxy, 2-chlorophenyloxy, etc.) or a halogen atom (for example, chlorine, bromine, iodine, etc.) etc. may be used.

The reaction used in the present invention may be a one-pot reaction of the compounds (III), (IV), and (V) (including the compound (Va)) in the same system, may be a stepwise reaction, that is, a reaction of the compound (III) and the compound (IV) followed by a reaction with the compound (V) (including the compound (Va)), or may be a stepwise reaction, that is, a reaction of the compound (IV) and compound (V) followed by a reaction with the compound (III). When the reaction is performed divided into two stages, it is possible to use the reaction intermediate obtained by the first stage reaction for the second stage reaction without purification, or possible to purify the reaction intermediate, then use it for the second stage reaction.

Usually, the reaction is preferably carried out in the presence of a base. When the reaction is performed divided into two stages, the reaction is preferably carried out in the presence of a base at least one of the stages. As the base, for example sodium hydride, potassium hydride, or other hydrated alkali metal, n-butyllithium, or other organic alkali metal, lithium diisopropylamide or other alkali metal amide, potassium t-butoxide or other alkali metal alkoxide, triethylamine or other alkylamine, etc. may be used.

This reaction may be carried out in inert solvent such as dioxane, tetrahydrofuran, diethylether, t-butylmethylether, or another ether, benzene, toluene, xylene, or other aromatic hydrocarbon, hexane, pentane, or other aliphatic hydrocarbon, acetonitrile or other nitrile, N,N-dimethylformamide, N,N-dimethylacetoamide, N-methylpyrrolidone, or other amide, or mixed solvents of the same.

In this reaction, the compound (IV) and compound (V) (including the compound (Va)) preferably used in amounts of about 1 to about 5 moles, preferably about 1 to about 2 moles based upon 1 mole of the compound (III) or its salt. The reaction temperature is preferably about −100° C. to about 100° C. The reaction time is preferably about 30 minutes to 48 hours.

Further, this reaction may be carried out using an additive for promoting the reaction. As the additive, for example; 4-dimethylaminopyridine, 1-hydroxybenzotriazole, etc. may be used.

The compound (I) of the present invention or a salt thereof produced by the method of (A) or (B) and the starting compounds (II), (III), and (V) (including compound (Va)) and synthesis intermediate for production of the compound (I) may be purified by known means, for example, solvent extraction, pH change, solvent exchange, salting out, crystallization, recrystallization, chromatography, etc. When the compound (I) of the present invention, the starting compounds (II), (III), and (V) (including the compound (Va)), and the synthesis intermediate for production of the compound (I) (including the compound (Va)) or a salt thereof are optically active compounds and another optical isomer is included, a general optical resolution method may be used for separation into the enantiomers.

It is possible, optionally, to manipulate the functional group of the compound (I) of the present invention produced by the method of (A) or (B), to obtain a functional group converted compound (I) by 1 to 5 steps of an ordinary reaction such as deprotection reaction when it has a protective group, the hydrogenation reaction when X forms a double bond (—CH=) together with $R^1$, or other portion has a double bond, the reduction reaction when it has a nitro group, the esterification reaction and amidation reaction when it has a carboxylic acid, the hydrolysis reaction when it has an ester group, the (i) alkylation reaction, (ii) acylation reaction, and (iii) sulfonylation reaction when it has an amino group or hydroxyl group, the (i) alkylation reaction, (ii) acylation reaction, and (iii) sulfonylation reaction when it has a primary or secondary amide group, and the oxidation reaction to a sulfonyl group or sulfonic acid when it has an alkylthio group.

When the compound (I) of the present invention produced by the method (A) or (B) has an amine or other basic functional group as a substituent group, it is possible to use an ordinary method to form a salt with an inorganic acid (for example hydrochloric acid, hydrogen bromic acid, sulfuric acid, etc.) or a salt with an organic acid (for example, methanesulfonic acid, benzenesulfonic acid, toluenesulfonic acid, etc.). When the compound (I) has a carboxylic acid or other acid group as a substituent group, it is possible to use an ordinary method to form a salt with an inorganic base (for example, sodium, potassium, calcium, magnesium, or another alkali metal, an alkali earth metal etc., ammonia, etc.) or a salt with an organic base (for example, triethanolamine, 2-aminoethanol, 2,2'-iminobis(ethanol), etc.)

The compound (I) of the present invention or its salt produced by the above method (A) or (B) may be brought into contact with, or recrystallized from the solvent such as water, methanol, ethanol, 1-propanol, 2-propanol, 1-butanol, 2-butanol, 2-methyl-1-propanol, 1-pentanol, 3-methyl-1-butanol, 2-methoxyethanol, 2-ethoxyethanol, formic acid, ethyl formate, acetic acid, methyl acetate, ethyl acetate, propyl acetate, isobutyl acetate, acetone, methylethylketone, methylisobutylketone, or other solvent (preferably, water, ethanol, 1-propanol, 2-propanol, 1-butanol, acetic acid, ethyl acetate, acetone, etc.), or other solvents, or a mixed solvent including the same so as to form its solvates.

[3. Method of Production of Starting Material for Producing the Compound Having Formula (I) or a Salt or Solvate Thereof]

A production method of the starting material compounds (II), (III), and (V) (including the compound (Va)) used for the production of the compound (I), or its salt, or a solvate thereof, and the production method of the starting compound (VI) (including the compound (VIa)) for the production of the compounds (II), (III) will be explained.

The starting compound (II) may, for example, be obtained by the method of the scheme:

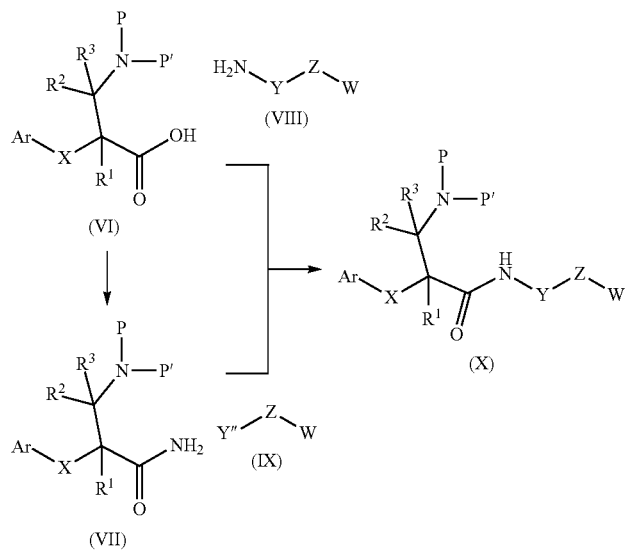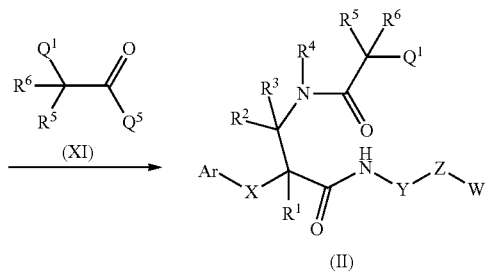

where Ar, W, X, Y, Z, P, $Q^1$, $R^1$, $R^2$, $R^3$, $R^4$, $R^5$, and $R^6$ are the same as defined above, Y" indicates an isocyanate group (—NCO), halocarbonyl group (for example, chlorocarbonyl, bromocarbonyl, etc.), halosulfonyl group (for example, chlorosulfonyl, bromosulfonyl, etc.), or a $C_6$ to $C_{10}$ aryloxycarbonyl group which may optionally be substituted with 1 to 3 halogen atoms or nitro (for example, 4-nitrophenylcarbonyl, 2-chlorophenylcarbonyl, 2,4-dichlorophenylcarbonyl, etc.), P' indicates a protective group such as an allyl, allyloxycarbonyl, 9-fluorenylmethylcarbonyl, a linear or branched $C_1$ to $C_6$ alkyloxycarbonyl which may optionally be substituted with 1 to 3 halogen atoms, linear or branched $C_1$ to $C_6$ alkylcarbonyl which may optionally be substituted with 1 to 3 halogen atoms, $C_7$ to $C_{16}$ aralkyl which may optionally be substituted with 1 to 3 groups selected from (i) a halogen atom, (ii) $C_1$ to $C_6$ alkyl, (iii) $C_1$ to $C_6$ alkoxy, and (iv) nitro, $C_5$ to $C_{16}$ arylcarbonyl which may optionally be substituted with 1 to 3 groups selected from (i) a halogen atom, (ii) $C_1$ to $C_6$ alkyl, (iii) $C_1$ to $C_6$ alkoxy, and (iv) nitro, $C_7$ to $C_{16}$ aralkyloxycarbonyl which may optionally be substituted with 1 to 3 groups selected from (i) a halogen atom, (ii) $C_1$ to $C_6$ alkyl, (iii) $C_1$ to $C_6$ alkoxy, and (iv) nitro, or $C_5$ to $C_{16}$ arylsulfonyl which may optionally be substituted with 1 to 3 groups selected from (i) a halogen atom, (ii) $C_1$ to $C_6$ alkyl, (iii) $C_1$ to $C_6$ alkoxy, and (iv) nitro, or a hydrogen atom, and $Q^5$ indicates a halogen atom or OH.

First, from the compound (VI), for example a condensation reaction using a general condensing agent (for example, DCC, 1,1'-carbonyl diimidazole, etc.), the Yamaguchi method, or other known method may be used for condensation with the compound (VIII) to obtain the compound (X). Alternatively, from the compound (VI), for example, a condensation reaction with ammonia using a general condensing agent (for example, DCC, 1,1'-carbonyl diimidazole, etc.) or other known method to obtain the compound (VII), and subsequent reaction of obtained compound (VII) with the compound (IX) in the presence of sodium hydride, potassium t-butoxide, or other bases may also be used to obtain the compound (X).

Next, from the obtained compound (X), if necessary, the ordinarily-used deprotection reaction for removing the P' group, and then, when $Q^5$ in compound (XI) is a halogen atom, for example a reaction with the compound (XI) in the presence of triethylamine, sodium hydroxide, or other base or, when $Q^5$ in compound (XI) is an OH group, for example, a condensation reaction with the compound (XI) using a general condensing agent (for example DCC etc.) may be used to obtain the compound (II). At this time, when P is not $R^4$ but a protective group, before or after the reaction of the above-mentioned compound (X) and compound (XI), it is possible to remove the P group by an ordinary method for conversion to a compound where $R^4$ is a hydrogen atom.

In the above method of production, as the compound (VI), it is possible to use a compound of the formula (VIa):

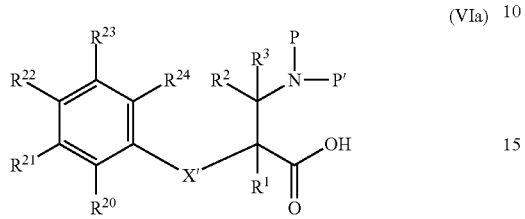

(VIa)

{where $R^1, R^2, R^3, P, P', X', R^{20}, R^{21}, R^{22}, R^{23}$, and $R^{24}$ are the same as defined above.

However, the following compounds are excluded:
(1) Compounds wherein $R^{20}$ and $R^{24}$ are chlorine atoms and $R^{21}, R^{22}$, and $R^{23}$ are hydrogen atoms,
(2) Compounds wherein $R^{20}, R^{22}$, and $R^{24}$ are methyl and $R^{21}$ and $R^{23}$ are hydrogen atoms, and
(3) Compounds wherein $R^{20}$ is a chlorine atom or bromine atom and $R^{21}, R^{22}, R^{23}$, and $R^{24}$ are hydrogen atoms}.

The compound (VIa) may be acquired or synthesized according to the method for the compound (VI) explained later.

The compound (IX) used in above-mentioned reaction may be a commercially available product or known compound. The compound (IX) used in above-mentioned reaction, for example, may be one synthesized by a known chlorosulfonylation reaction etc. described in J. Am. Chem. Soc., 1940, 62, 511 or Chem. Ber., 1957, 90, 841, etc. The compound (IX) may also be one synthesized from a known carboxylic acid compound by, for example, the known acid chloride synthesis method. Further, the compound (IX) may also be synthesized from the compound (V) (including the compound (Va)) by for example the known isocyanate synthesis method using diphosgene, triphosgene, etc.

The compound (VIII) used in above-mentioned reaction may be a commercially available product or known compound. Further, the compound (VIII) may be obtained by the compound (IX) by, for example, a condensation reaction with ammonia or other known method. The compound (VIII) can be obtained by, for example, the known aminosulfonylation reaction described in Bioorg. Med. Chem. Lett., 2003, 13 (5), 837 etc.

The starting compound (III) may, for example, be synthesized by the method of the scheme:

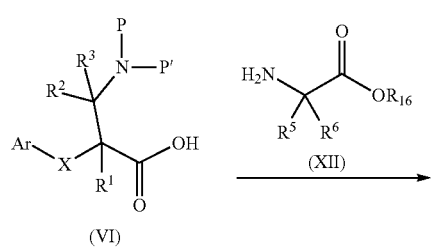

(VI)

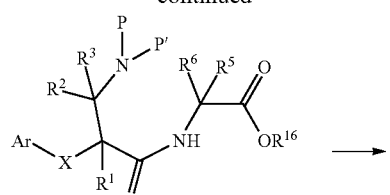

(XIII)

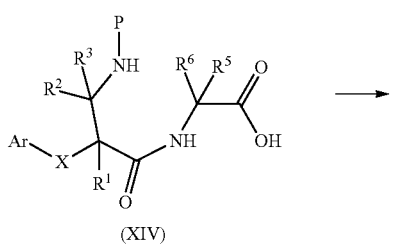

(XIV)

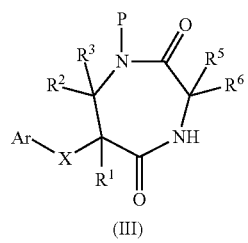

(III)

where Ar, X, P, P', $R^1, R^2, R^3, R^5, R^4$, and $R^6$ are the same as defined above, and $R^{16}$ indicates a $C_1$ to $C_6$ alkyl group or $C_7$ to $C_{16}$ aralkyl group.

First, it is possible to use a condensation reaction, for example, the reaction using a generally used condensing agent (for example, DCC etc.) or other known reaction, for condensation of the compound (VI) and compound (XII) or its salt to obtain the compound (XIII). The compound (XII) used in this reaction may be a commercially available product or known amino acid derivative.

Next, from the obtained compound (XIII), for example, a hydrolysis reaction using sodium hydroxide etc. or other known method may be used for hydrolysis to obtain the compound (XIV). If necessary at this time, before and/or after the hydrolysis reaction, for example, a known method using an acid, base, etc. may be used to remove the P', but this is not absolutely necessary when P' is a hydrogen atom.

Next, from the obtained compound (XIV), for example, a condensing reaction using a general condensing agent (for example, DCC etc.) or other known method may be used for cyclization reaction to obtain the compound (III).

In the above production method, as the compound (VI), the above-mentioned compound (VIa) may also be used.

Among the starting compounds (III), a compound where X is an oxygen atom, $NR^{13}$, or $-S(O)m-$ (where m indicates an integer of 0 to 2) may be synthesized by the method shown in, for example, the scheme:

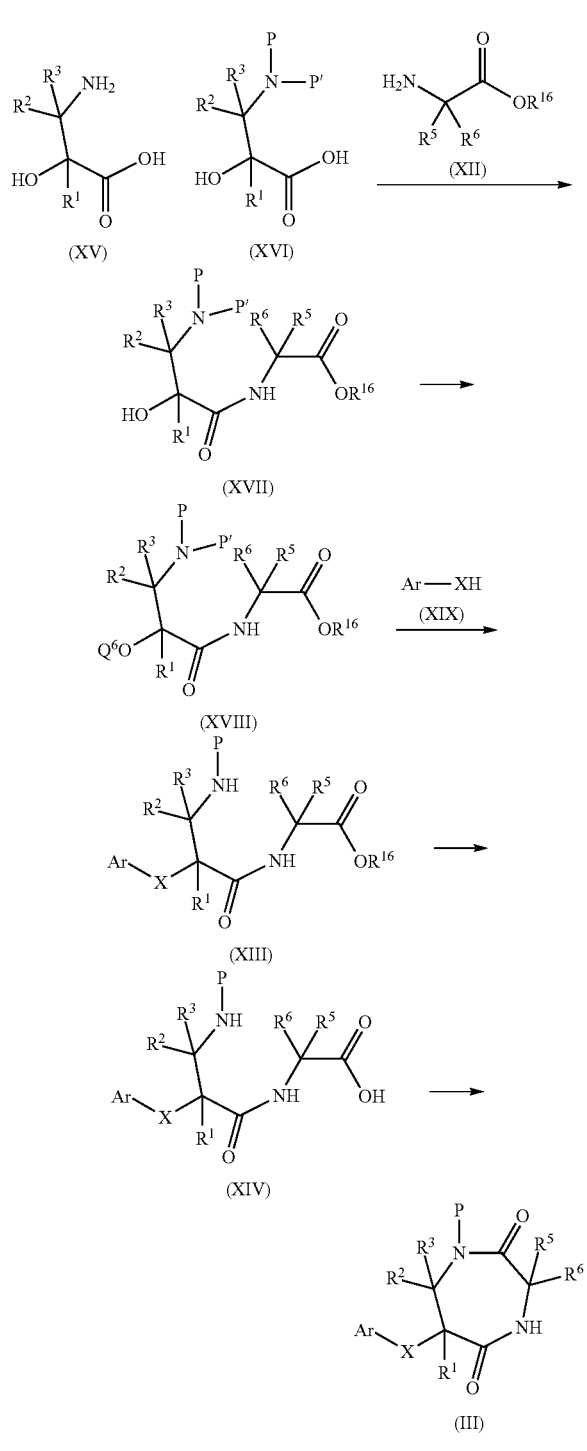

(XV) (XVI) (XVII) (XVIII) (XIII) (XIV) (III)

where Ar, P, P', $R^1$, $R^2$, $R^3$, $R^5$, $R^4$, $R^6$, and $R^{16}$ are the same as defined above, $Q^6$ together with the adjoining oxygen atom indicates $C_6$ to $C_{10}$ arylsulfonyloxy which may optionally be substituted with 1 to 3 halogen atoms or $C_1$ to $C_4$ alkylsulfonyloxy which may optionally be substituted with 1 to 3 halogen atoms. Here, X indicates an oxygen atom, $NR^{13}$, or —S(O)m-, where m indicates an integer of 0 to 2.

That is, from a commercially available or known β-alanine derivative (XV), for example, a reaction for introducing the protective group, reductive alkylation reaction or other known method which is used in general for amino groups may be used to introduce a P group (protective group or $R^4$ group) or optionally a P' group (protective group or hydrogen atom) to obtain the compound (XVI). Next, for example, a condensation reaction using a general condensing agent (for example, DCC etc.) or other known method may be used to condense the compound (XVI) and the compound (XII) or its salt to obtain the compound (XVII), then the hydroxyl group of obtained compound (XVII) converted to a leaving group, that is, a $OQ^6$ group, to obtain the compound (XVIII). Further, it is possible to perform a nuclear substitution reaction using the compound (XIX) on the obtained compound (XVIII) to obtain the compound (XIII). From the obtained compound (XIII), it is possible to use the methods described above to obtain the compound (III).

The starting compound (III) may be synthesized by the method shown in, for example, the scheme:

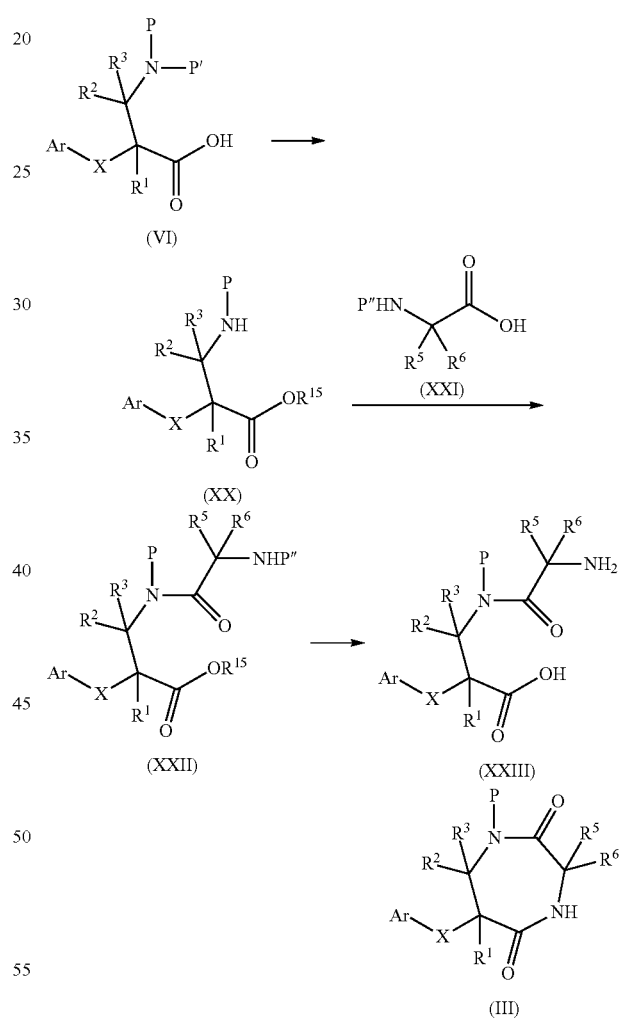

(VI) (XX) (XXI) (XXII) (XXIII) (III)

where Ar, X, $R^1$, $R^2$, $R^3$, $R^4$, $R^5$, $R^6$, P, and P' have the same meaning as above. $R^{15}$ indicates a $C_1$ to $C_6$ alkyl group or $C_7$ to $C_{16}$ aralkyl group, and P" indicates a protective group, the same or different, such as allyl, allyloxycarbonyl, 9-fluorenylmethylcarbonyl, linear or branched $C_1$ to $C_6$ alkyloxycarbonyl which may optionally be substituted with 1 to 3 halogen atoms, linear or branched $C_1$ to $C_6$ alkylcarbonyl which may optionally be substituted with 1 to 3 halogen atoms, $C_7$ to $C_{16}$ aralkyl which may optionally be substituted with 1 to 3 of (i)

a halogen atom, (ii) $C_1$ to $C_6$ alkyl, (iii) $C_1$ to $C_6$ alkoxy, or (iv) nitro, $C_5$ to $C_{16}$ arylcarbonyl which may optionally be substituted with 1 to 3 of (i) a halogen atom, (ii) $C_1$ to $C_6$ alkyl, (iii) $C_1$ to $C_6$ alkoxy, or (iv) nitro, $C_7$ to $C_{16}$ aralkyloxycarbonyl which may optionally be substituted with 1 to 3 of (i) a halogen atom, (ii) $C_1$ to $C_6$ alkyl, (iii) $C_1$ to $C_6$ alkoxy, or (iv) nitro, $C_5$ to $C_{16}$ arylsulfonyl which may optionally be substituted with 1 to 3 of (i) a halogen atom, (ii) $C_1$ to $C_6$ alkyl, (iii) $C_1$ to $C_6$ alkoxy, or (iv) nitro.

First, from the compound (VI), for example, an esterification reaction using a general condensing agent (for example, DCC etc.), and subsequent deprotection of the P' group, or other known method may be used to obtain the compound (XX).

Next, from the compound (XX), for example, a condensation reaction using a general condensing agent (for example, DCC etc.) and other known method may be used to condense the compound (XXI) to obtain the compound (XXII). The starting compound (XXI) used in this reaction may be a commercially available product or known amino acid derivative.

Next, from the compound (XXII), for example a deprotection reaction using an acid, base, etc. or other known method may be used to remove the P'' group and $R^{15}$ group simultaneously or in stages so as to obtain the compound (XXIII).

Next, from the compound (XXIII), for example, condensation reaction using a general condensing agent (for example, DCC etc.) or other known method may be used for cyclization reaction to obtain the compound (III).

In the above production method, as the compound (VI), the above-mentioned compound (VIa) may be used.

The starting compound (V) used in above-mentioned reactions may be a commercially available product or known compound. Further, among the starting compounds (V), a compound where W is not a hydrogen atom and Z is $CR^7R^8$, where $R^8$ is a hydrogen atom, may also be synthesized by the method of the scheme:

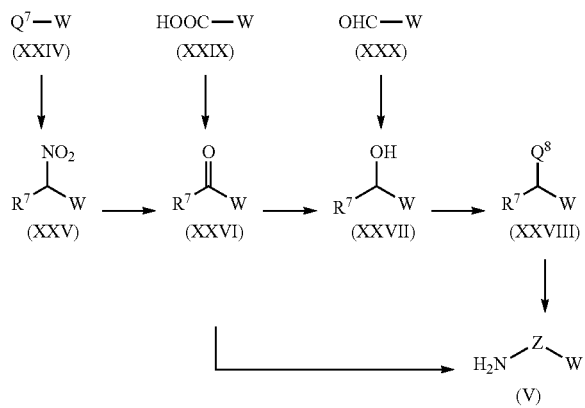

where W has the same definition as the above-mentioned W (but W is not a hydrogen atom), Z is $CR^7R^8$, $R^8$ is a hydrogen atom, $R^7$ is the same as defined above, $Q^7$ indicates a halogen atom, and $Q^8$ indicates a halogen atom, a $C_6$ to $C_{10}$ arylsulfonyloxy group which may optionally be substituted with 1 to 3 halogen atoms, or a $C_1$ to $C_4$ alkylsulfonyloxy group which may be substituted with 1 to 3 halogen atoms.

First, from the starting compound (XXIV), for example, a coupling reaction with nitroalkane using a palladium catalyst (for example, palladium acetate, tris(dibenzylideneacetone) dipalladium) or another transition metal catalyst, or other known method may be used to obtain the compound (XXV).

Next, from the compound (XXV), for example, an Nef reaction or other known method may be used to obtain the compound (XXVI). The compound (XXVI) can be obtained by an alkylation reaction, using organometallic reagent etc., of an acid chloride, Weinreb amide, or other reactive compound, which can be obtained from the compound (XXIX) by using a known method. Above-mentioned starting material compounds (XXIV) and (XXIX) used can be commercially available products or known compounds.

Next, from the compound (XXVI), for example a reduction reaction using sodium boron hydride or other generally used reducing agent may be used to obtain the compound (XXVII). At this time, for example, the asymmetric reduction reaction described in Angew. Chem. Int. Ed., 1998, 37, 1986, J. Org. Chem., 1985, 50, 5446, etc. may be used to obtain an optically active compound (XXVII). The compound (XXVII) can also be obtained from the compound (XXX) by, for example, an alkylation reaction using a Grignard reagent or other organometallic reagent. At this time, for example the asymmetric alkylation reaction described in Chem. Rev., 2001, 101, 757 etc. may be used to obtain the optically active compound (XXVII). Above-mentioned starting material compounds (XXVI) and (XXX) used may be commercially available products or known compounds.

Next, from the compound (XXVII), for example, an alkylsulfonylation reaction, arylsulfonylation reaction, halogenation reaction, or other known method may be used for conversion of hydroxyl group of compound (XXVII) to a generally used leaving group to obtain the compound (XXVIII).

Next, from the compound (XXVIII), for example, a substitution reaction using sodium azide, potassium phthalimide, or other suitable nitrogen nucleophilic agent to obtain an amine precursor, and subsequent reaction for obtained amine precursor such as a reduction, hydrolysis etc. may be used to obtain the compound (V). The above-mentioned amine precursor may be directly obtained by, for example, Mitsunobu reaction or other method from the compound (XXVII). The compound (V) may also be obtained by, for example, hydrogenation etc. of oxime which can be obtained from the compound (XXVI) by a known method. Further, from the compound (XXVI), for example, an asymmetric amination reaction described in Angew. Chem. Int. Ed., 2003, 42 (44), 5472 etc. may be used to obtain an optically active compound (V).

It is possible, optionally, to manipulate the functional group of the compound (V) to obtain a functional group converted compound (V) by 1 to 5 steps of an ordinary reaction such as deprotection reaction when it has a protective group, a hydrogenation reaction when it has an alkenyl group or alkynyl group, a reduction when it has a nitro group, an esterification reaction and amidation reaction when it has a carboxylic acid, a hydrolysis when it has an ester group, (i) alkylation reaction, (ii) acylation reaction, and (iii) sulfonylation reaction when it has an amino group or hydroxyl group, (i) alkylation reaction, (ii) acylation reaction, and (iii) sulfonylation reaction when it has a primary or secondary amide group, and an oxidation reaction to a sulfonyl group or sulfonic acid when it has an alkylthio group, etc.

Among the starting material compounds (V), a compound expressed by the formula (Va):

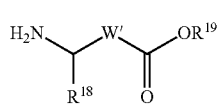

where W', $R^{18}$ and $R^{19}$ are the same as defined above may also be synthesized according to the production method of the compound (V) using the corresponding starting compound.

When the compounds (V) and (Va) obtained by the above methods have asymmetric centers, it is possible to use an ordinary method for optical resolution to obtain an enantiomer of one of the compounds (V) and (Va).

Next, the synthesis method of the compound (VI) as the common starting material for producing the compounds (II) and (III) will be explained.

Among the compounds (VI), a compound where $R^1$ forms —CH= together with X, or a compound where $R^1$ is a hydrogen atom and X is an alkylene may be synthesized by the method of scheme:

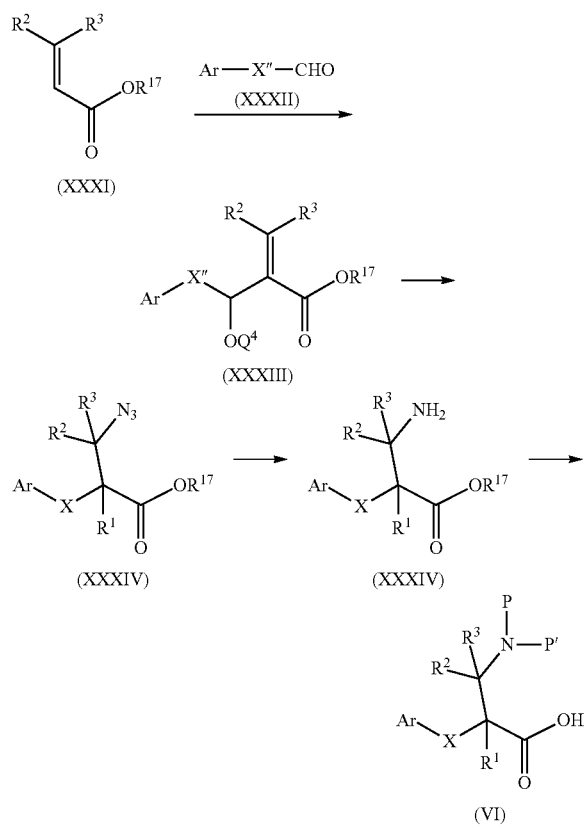

where Ar, P, P', $R^2$, and $R^3$ are the same as defined above, $R^{17}$ indicates $C_1$ to $C_6$ alkyl or $C_7$ to $C_{16}$ aralkyl, X" indicates a bond or $C_1$ to $C_5$ alkylene, $Q^4$ together with the adjoining oxygen atom indicates $C_6$ to $C_{10}$ arylsulfonyloxy which may optionally be substituted with 1 to 3 halogen atoms, $C_1$ to $C_4$ alkylsulfonyloxy which may optionally be substituted with 1 to 3 halogen atoms, $C_1$ to $C_6$ alkylcarbonyloxy, or $C_7$ to $C_{16}$ aralkylcarbonyloxy. Here, $R^1$ forms —CH=, together with X, or $R^1$ is a hydrogen atom and X is alkylene.

That is, a coupling reaction of the compound (XXXI) and compound (XXXII), for example, the Baylis-Hillman reaction and other known method, and if necessary, subsequent conversion of a free hydroxyl group etc. of coupling product to a leaving group, that is, $OQ^4$ group may be used for a reaction to obtain the compound (XXXIII). The starting compound (XXXI) or (XXXII) used in this reaction may be a commercially available product or known compound. Among the compounds (XXXII), a compound where X" is a bond may be obtained by formylation reaction, for example, a Vilsmeier reaction or other known method, of a commercially available or known aromatic compound. Next, from the obtained compound (XXXIII), for example, an azidation reaction using sodium azide etc. or other known method may be used for conversion to the compound (XXXIV), then for example a Staudinger reaction, hydrogenation, or other known method may be used for reduction of an azide group of compound (XXXIV), and optionally a double bond, to obtain the compound (XXXV). Further, from the obtained compound (XXXV), for example, a reaction for introduction of a protective group, reductive alkylation reaction, or other known method used in general for an amino group may be used to introduce a P group (protective group or $R^4$ group), and optionally a P' group (protective group or hydrogen atom), and further, for example, a hydrolysis reaction using sodium hydroxide etc. or another known method may be used for hydrolysis to obtain the compound (VI). Further, from the compound (XXXV), it is also possible to first perform a hydrolysis reaction, then perform a reaction to introduce a P group (optionally, a P' group) so as to obtain the compound (VI).

Among the compounds (VI), a compound where $R^2$ and $R^3$ both indicate hydrogen atoms can also be synthesized by the method of the scheme:

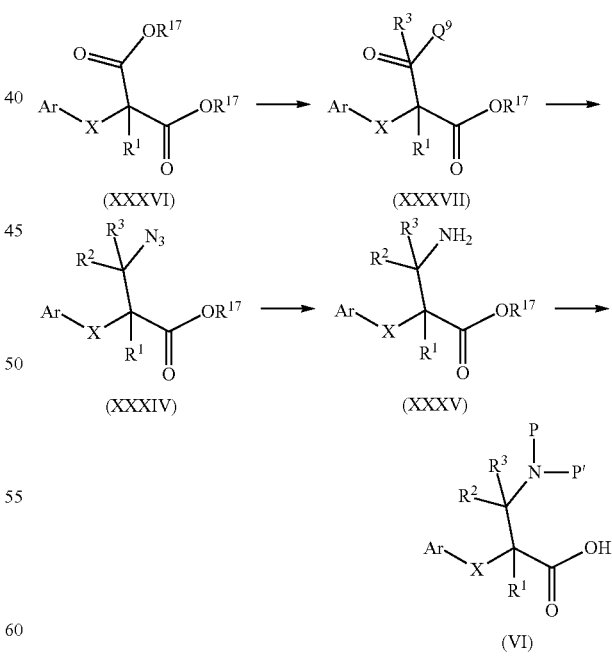

where, Ar, X, P, P', $R^1$, and $R^{17}$ have the same meaning as above. $Q^9$ is $C_6$ to $C_{10}$ arylsulfonyloxy which may optionally be substituted with 1 to 3 halogen atoms, $C_1$ to $C_4$ alkylsulfonyloxy which may optionally be substituted with 1 to 3 halogen atoms, or a halogen atom. $R^2$ and $R^3$ both indicate a hydrogen atom here. For example, it is possible to use the compound (XXXVI) as a starting material to obtain a compound (XXXVII) having the leaving group $Q^9$ by using a series of known method, which is, for example, selective hydrolysis of one ester moiety of compound (XXXVI), conversion of the resulting carboxylic acid to acid chloride, selective reduction of the acid chloride to alcohol, and a sulfonylation reaction or halogenation reaction. Next, from the obtained compound (XXXVII), for example an azidation reaction using sodium azide or other known method may be used to obtain the compound (XXIV). From the obtained compound (XXXIV), the above-mentioned method may be used to obtain the compound (VI). The starting compound (XXXVI) may be easily obtained by a substitution reaction of the ArX group on a commercially available or known halomalonic acid ester, a Knoevenagel reaction from a commercially available or known malonic acid ester, an alkylation reaction of a malonic acid ester, or other generally used known reaction or, if necessary, subsequent hydrogenation reaction for above obtained compound using a transition metal catalyst or other known method.

Among the compounds (VI), a compound where $R^2$ and $R^3$ both indicate hydrogen atoms can also be synthesized by the method of the scheme:

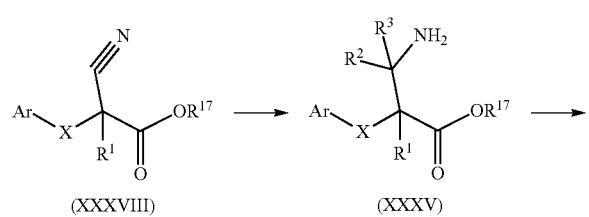

where, Ar, X, P, P', $R^1$, and $R^{17}$ are the same as defined above, and $R^2$ and $R^3$ both indicate a hydrogen atom. That is, for example, by using a compound (XXXVIII) as a starting material, which is easily obtained by a substitution reaction of an ArX group on a commercially available or known halocyanoacetic acid ester, a Knoevenagel reaction of a commercially available or known cyanoacetic acid ester, an alkylation reaction of a cyanoacetic acid ester, or other generally used known reaction or, if necessary, subsequent hydrogenation reaction using a transition metal catalyst or other known method, it is possible to selectively reduce the nitrile groups by, for example, the method described in J. Am. Chem. Soc., 1982, 104, 6801, to obtain the compound (XXXV) or its salt. From the obtained compound (XXXV), the above-mentioned methods may be used to obtain the compound (VI).

Among the compounds (VI), a compound where $R^1$ forms —CH= together with X, or $R^1$ is a hydrogen atom and X indicates alkylene can also be synthesized by the scheme:

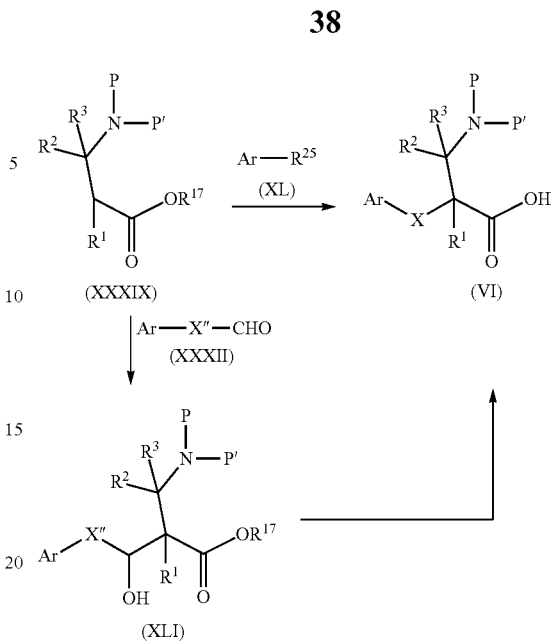

where $R^{25}$ indicates halogenated alkyl, for example, a halogenated methyl group, and Ar, P, P', $R^2$, $R^3$, $R^{17}$, and X" are the same as defined above. Here, $R^1$ forms —CH= together with X, or $R^1$ is hydrogen and X is an alkylene. That is, it is also possible to synthesize the compound (VI) by an alkylation reaction of the compound (XXXIX) using the compound (XL) and the succeeding hydrolysis reaction. Further, an aldol reaction of the compound (XXXIX) and compound (XXXII) may be used for conversion to the compound (XLI), then a dehydration, deoxygenation, or other known reaction, and the following hydrolysis reaction may be used for synthesis of the compound (VI). The starting materials used in this reaction, that is, the compounds (XXXIX), (XL), and (XXXII), can be commercially available products or known compounds. The compound (XXXIX) may be used one synthesized by using a reaction for introduction of a protective group, reductive alkylation reaction, or other known reaction used in general for an amino group, to introduce a P group (protective group or $R^4$ group) and, optionally, a P' group (protective group or hydrogen atom) to a commercially available or known β-amino acid ester.

Among the compounds (XXXII), a compound where X" is a bond may be synthesized by formylation reaction, for example a Vilsmeier reaction or other known method, of a commercially available or known aromatic compound.

Among the compounds (VI), a compound where $R^1$ forms —CH= together with X, or $R^1$ is a hydrogen atom and X is alkylene can also be synthesized by the scheme:

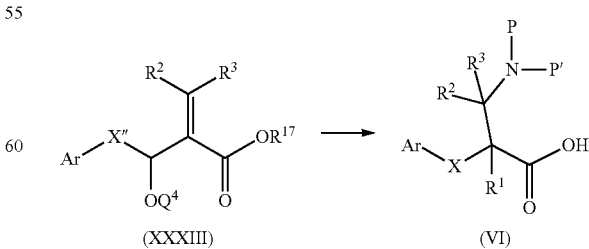

where, Ar, $R^2$, $R^3$, $R^{17}$, P, P', $Q^4$, and X" are the same as defined above. Here, $R^1$ forms —CH= together with X, or $R^1$ is a hydrogen atom and X is alkylene. That is, from the above-mentioned compound (XXXIII), it is possible to synthesize the compound (VI) where $R^1$ forms —CH=, together with X by the reaction with PP'—$NH_2$, and subsequent hydrolysis using sodium hydroxide etc. or other known method. Further, before or after hydrolysis in this reaction, it is possible to perform a hydrogenation reaction using for example a transition metal catalyst, or other known method to synthesize a compound (VI) where $R^1$ is a hydrogen atom and X is an alkylene.

Among the compounds (VI), a compound having the formula (VIa):

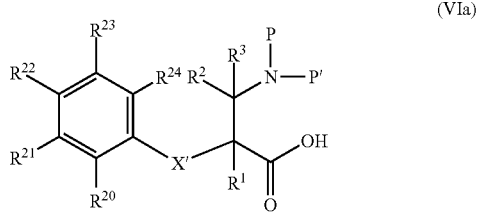

(VIa)

where $R^1$, $R^2$, $R^3$, P, P', X', $R^{20}$, $R^{21}$, $R^{22}$, $R^{23}$, and $R^{24}$ are the same as defined above, and except for the following compounds:
(1) Compounds where $R^{20}$ and $R^{24}$ are chlorine atoms and $R^{21}$, $R^{22}$, and $R^{23}$ are hydrogen atoms,
(2) Compounds where $R^{20}$, $R^{22}$, and $R^{24}$ are methyl and $R^{21}$ and $R^{23}$ are hydrogen atoms, and
(3) Compounds where $R^{20}$ is a chlorine atom or bromine atom and $R^{21}$, $R^{22}$, $R^{23}$, and $R^{24}$ are hydrogen atoms can also be synthesized using the corresponding starting compounds according to the production method of the compound (VI).

Among the compounds (VI), a compound, where X is an oxygen atom, $NR^{13}$, or —S(O)m- can be synthesized by the method described in, for example, J. Org. Chem., 1994, 59, 3123, Tetrahedron, 1987, 43 (17), 3881, Chem. Lett., 1997, 4, 375 or Tetrahedron Lett., 1991, 32 (27), 3151.

It is possible, optionally, to manipulate the functional group of the compound (VI) or compound (VIa) obtained by the above methods to produce a functional group converted compound (VI) or compound (VIa) by 1 to 5 steps of an ordinary reaction such as a deprotection reaction when it has a protective group, a hydrogenation reaction when it has an alkenyl group or alkynyl group, a reduction reaction when it has a nitro group, an esterification reaction and amidation reaction when it has an carboxylic acid, a hydrolysis reaction when it has an ester group, an (i) alkylation reaction, (ii) acylation reaction, and (iii) sulfonylation reaction when it has an amino group or hydroxyl group, an (i) alkylation reaction, (ii) acylation reaction, and (iii) sulfonylation reaction when it has a primary or secondary amide group, and an oxidation reaction to a sulfonyl group, sulfonic acid, etc. when it has an alkylthio group.

When the compounds (VI) and (VIa) obtained by the above-mentioned methods include asymmetric centers, it is also possible use an ordinary method for optical resolution to obtain an enantiomer of one of the compounds (VI) and (VIa).

The compound (I), or its salt or a solvate thereof of the present invention, have superior chymase inhibitory activity and have low toxicity ($LD_{50}$>1 g/kg), so can be safely used for mammals (for example, humans, rat, mice, dogs, cattle, etc.) for the prevention and/or treatment of bronchial asthma, urticaria, atopic dermatitis, allergic conjunctivitis, rhinitis, rheumatoid arthritis, mastocytosis, scleroderma, heart failure, cardiac hypertrophy, congestive heart failure, hypertension, atherosclerosis, myocardial ischemia, myocardial infarction, restenosis after PTCA, restenosis after bypass graft surgery, ischemic peripheral circulatory disorders, hyperaldosteronism, diabetic retinopathy, diabetic nephropathy, nephritis, glomerulosclerosis, renal insufficiency, psoriasis, solid tumor, postoperative adhesion, glaucoma, and ocular hypertension, and other diseases.

The administration route of the pharmaceutical for prevention or treatment of above-mentioned diseases may be oral or parenteral.

The preparation used in the present invention may also contain, as active ingredients, other pharmaceutical ingredients in addition to the compound (I) or its pharmaceutically acceptable salt or solvate thereof.

As such a pharmaceutical active ingredient, for example, steroids (for example, betamethasone etc.), immunosuppressants (for example, tacrolimus, pimecrolimus etc.), antiallergic agent (clemastine fumarate, d-chlorpheniramine maleate, cyproheptadine hydrochloride, promethazine hydrochloride, homochlorcyclizine hydrochloride, mequitazine, diphenhydramine hydrochloride, ebastine, cetirizine hydrochloride, olopatadine hydrochloride, fexofenadine hydrochloride, sodium cromoglicate, emedastine difumarate, suplatast tosilate, epinastine hydrochloride, etc.) etc. may be mentioned. These ingredients are not particularly limited so long as the object of the present invention is achieved, and may be used in approximate ratios. As specific examples of the dosage forms, for example, tablets (including sugar-coated tablets and film-coated tablets), pills, capsules (including microcapsules), granules, fine subtilaes, powders, syrups, emulsions, suspensions, injections, inhalants, ointments, eye drops, etc. may be used. These drug products may be prepared according to ordinary methods (for example, methods described in the Japan Pharmacopeia etc.)

In the preparations of the present invention, the content of the compound according to the present invention differs according to the type of the preparation, but usually is about 0.01 to about 100% by weight, based upon the total weight of the preparation, preferably about 0.1 to about 50% by weight, more preferably about 0.5 to about 20% by weight or so.

Specifically, tablets can be produced by granulating a homogenous mixture of pharmaceutical as it is or with an excipient, binder, disintegrating agent, or other suitable additives by a suitable method, then adding a lubricant agent, and subjecting the mixture to compressive shaping; directly subjecting a homogenous mixture of pharmaceutical as it is or with an excipient, binder, disintegrating agent, or other suitable additives by a suitable method, to compressive shaping; or directly subjecting a homogenous mixture of granules of pharmaceutical as it is prepared in advance or with suitable additives, to compressive shaping. Further, these tablets may, if necessary, be given a coloring agent, flavoring agent, and may be coated with a suitable coating agent.

As the production method of an injections, it is possible to dissolve, suspend, or emulsify a certain amount of the pharmaceutical in injection water, physiological saline, Ringer's solution, etc. in the case of a water-based solvent, or in an ordinary vegetable oil etc. in the case of a non-water-based solvent, to obtain a certain volume, or to take a certain amount of the pharmaceutical and seal it in an injection use container.

As the carriers for oral preparations, for example starch, mannitol, crystalline cellulose, sodium carboxylmethylcellulose, and other substances commonly used in the field of preparations may be used. As the carriers for injections, for example, distilled water, physiological saline, glucose solution, transfusions, etc. may be used. In addition, it is possible to suitably add additives generally used in preparations.

The dosage of these preparations differs according to age, body weight, symptoms, route of administration, number of dosages, etc., but for example for an adult patient, daily dose of these preparation is usually about 0.1 to about 100 mg/kg, preferably about 1 to 50 mg/kg, more preferably about 1 to about 10 mg/kg, based on daily dose of active ingredient (the compound of the present invention), administered orally once or in three portions daily.

EXAMPLES

Reference Examples, Examples, and Test Examples will now be used to explain the present invention in more detail, but the present invention is not limited thereto. The fractions including the desired substances in the Examples and Reference Examples were detected by TLC (thin-layer chromatography). In TLC observation, As a TLC plate, a Merch $60F_{254}$ was used, while as the detection method, a UV detector was used. For the MS, the ESI method (i.e., electron spray ionization method) was used to detect the positive ions.

Reference Example 1

5-chloro-2-anisaldehyde (Compound S1)

To 5-chloro-2-salicylaldehyde (10 g) in an N,N-dimethylformamide (70 ml) solution, methyl iodide (8 ml) and potassium carbonate (9 g) were added and the mixture was stirred at room temperature for 3 hours. Distilled water was added to the reaction solution and the mixture was extracted with diethylether. The organic layer was successively washed with saturated sodium thiosulfate aqueous solution, distilled water, and saturated saline, dried over with anhydrous sodium sulfate, then concentrated. The residue was dried in vacuo to obtain the title compound (9.1 g).

NMR (CDCl$_3$): δ10.4 (1H, s), 7.78 (1H, d, J=2.7 Hz), 7.48 (1H, dd, J=8.9, 2.7 Hz), 6.94 (1H, d, J=8.9 Hz), 3.93 (3H, s)

Reference Example 2

Methyl 2-[(5-chloro-2-methoxyphenyl)(hydroxy)methyl]propenoate (Compound S2)

A reaction mixture of the compound S1 (7 g), methyl acrylate (6 ml), 1,4-diazabicyclo[2.2.2]octane (4.6 g), lanthanum trifluoromethanesulfonate (1.2 g), and diethanol amine (2.7 ml) was stirred at room temperature for 60 hours. Distilled water and saturated potassium hydrogensulfate aqueous solution were added to the reaction solution, and the mixture was extracted with ethyl acetate. The organic layer was successively washed with distilled water and saturated saline, dried over with anhydrous sodium sulfate, then concentrated. The residue was dried in vacuo to obtain the title compound (11.1 g).

NMR (CDCl$_3$): δ7.37 (1H, d, J=2.9 Hz), 7.22 (1H, dd, J=8.7, 2.9 Hz), 6.8 (1H, d, J=8.7 Hz), 6.31 (1H, m), 5.83 (1H, d, J=5.8 Hz), 5.69 (1H, m), 3.81 (3H, s), 3.77 (3H, s)

Reference Example 3

Methyl 2-[(5-chloro-2-methoxyphenyl)(acetoxy)methyl]propenoate (Compound S3)

To the compound S2 (11 g) in methylene chloride (100 ml) solution, pyridine (3.5 ml) and acetylchloride (3.1 ml) were added under ice cooling and the mixture was stirred at that temperature for 1 hour. Distilled water was added to the reaction solution, methylene chloride was distilled off in vacuo, and the remaining aqueous layer was extracted with ethyl acetate. The organic layer was successively washed with saturated potassium hydrogensulfate aqueous solution, distilled water, saturated sodium hydrogencarbonate aqueous solution, and saturated saline, dried over with anhydrous sodium sulfate, then concentrated. The residue was dried in vacuo to obtain the title compound (11.8 g).

Reference Example 4

Methyl (2E)-2-(azide methyl)-3-(5-chloro-2-methoxyphenyl)-2-propenoate (Compound S4)

To the compound S3 (11.8 g) in dimethylsulfoxide (70 ml) solution, sodium azide (3.9 g) was added and the mixture was stirred at room temperature for 30 minutes. Distilled water was added to the reaction solution, and the mixture was extracted with diethylether. The organic layer was successively washed with distilled water and saturated saline, dried over with anhydrous sodium sulfate, and concentrated. The residue was dried in vacuo to obtain the title compound (10.1 g).

Reference Example 5

(2E)-2-(aminoethyl)-3-(5-chloro-2-methoxyphenyl)-2-propenoic Acid (Compound S5)

To the compound S4 (10 g) in tetrahydrofuran (70 ml) solution, triphenylphosphine (9.4 g) and distilled water (1 ml) were added and the mixture was stirred at room temperature for 15 hours. Next, tetrahydrofuran was distilled off in vacuo, methanol (70 ml) and 2N sodium hydroxide aqueous solution (35 ml) were added to the remaining mixture, and the mixture was stirred at room temperature for 2 hours. Next, the methanol was distilled off in vacuo and the remaining aqueous layer was washed with ethyl acetate. Further, the aqueous layer was neutralized by hydrochloric acid, then precipitate was collected by filtration, was washed with diethylether, and was dried in vacuo to obtain the title compound (6.3 g).

Reference Example 6

(2E)-3-(5-chloro-2-methoxyphenyl)-2-{[(trifluoroacetyl)amino]methyl}-2-propenoic Acid (Compound S6)

To the compound S5 (3 g) in tetrahydrofuran (15 ml) suspension, anhydrous trifluoroacetic acid (2.3 ml) was added under ice cooling and the mixture was stirred at room temperature for 2 hours. The reaction solution was concentrated, ethyl acetate was added to the residue, and the obtained solution was successively washed with saturated potassium hydrogensulfate aqueous solution and saturated saline and dried over with anhydrous sodium sulfate and concentrated. The residue was recrystallized from ethyl acetate/hexane to obtain the title compound (3.07 g).

NMR (CDCl$_3$): δ8.01 (1H, s), 7.39 (1H, d, J=2.4 Hz), 7.35 (1H, dd, J=8.8, 2.4 Hz), 7.01 (1H, br), 6.88 (1H, d, J=8.8 Hz), 4.33 (2H, d, J=6 Hz), 3.84 (3H, s)

MS: 360 (M+Na)$^+$

Reference Example 7

(2E)-2-{[(tert-butoxycarbonyl)amino]methyl}-3-phenyl-2-propenoic Acid (Compound S7)

Instead of the starting material in Reference Example 2, that is, the compound S1, benzaldehyde was used for the similar procedure as in Reference Example 2 to Reference Example 4. To the obtained methyl (2E)-2-(azide methyl)-3-phenyl-2-propenoate (1.62 g) in tetrahydrofuran (20 ml) solution, triphenylphosphine (1.96 g) and distilled water (0.2 ml) were added and the mixture was stirred at room temperature for 6 hours. Next, di-tert-butyldicarbonate (1.72 g) was added to the reaction solution, the mixture was stirred at room temperature for 15 minutes, then the reaction solution was concentrated. The residue was purified by silica gel column chromatography (hexane/ethyl acetate=4/1). To 1 g of the obtained methyl (2E)-2-{[(tert-butoxycarbonyl)amino]methyl}-3-phenyl-2-propenoate (1.68 g), ethanol (8 ml) and 2M sodium hydroxide aqueous solution (2 ml) were added and the mixture was stirred at room temperature for 2 hours. The reaction solution was diluted with distilled water, and the ethanol was distilled off in vacuo. The obtained aqueous solution was made acidic by a 10% potassium hydrogensulfate aqueous solution and the mixture was extracted with diethylether. The organic layer was successively washed with distilled water and saturated saline, dried over with anhydrous sodium sulfate, and concentrated to obtain the title compound (818 mg).

NMR (CDCl$_3$): δ7.98-7.73 (1H, br), 7.60-7.30 (5H, br), 6.75 (0.5H, brs), 5.14 (0.5H, brs), 4.25 (2H, d, J=5.9 Hz), 1.60-1.15 (9H, br)

MS: 278 (M+H)$^+$

Reference Example 8

(2E)-3-phenyl-2-{[(trifluoroacetyl)amino]methyl}-2-propenoic Acid (Compound S8)

Instead of the starting material in Reference Example 2, that is, the compound S1, benzaldehyde was used for successively the similar procedures as in Reference Example 2 to Reference Example 6 to obtain the title compound.

NMR (DMSO-d$_6$): δ12.79 (1H, brs), 9.64 (1H, br), 7.81 (1H, s), 7.53-7.35 (5H, m), 4.18 (2H, d, J=4.2 Hz)

Reference Example 9

(2E)-3-(5-chloro-2-nitrophenyl)-2-{[(trifluoroacetyl)amino]methyl}-2-propenoic Acid (Compound S9)

Instead of the starting material in Reference Example 2, that is, the compound S1, 5-chloro-2-nitrobenzaldehyde was used for successively the similar procedures as in Reference Example 2 to Reference Example 6 to obtain the title compound.

NMR (CDCl$_3$): δ8.24 (1H, d, J=8.8 Hz), 8.19 (1H, s), 7.58 (1H, dd, J=8.8, 2.2 Hz), 7.51 (1H, d, J=2.2 Hz), 7.05 (1H, br), 4.16 (2H, d, J=6.3 Hz)

MS: 375 (M+Na)$^+$

Reference Example 10

(2E)-3-(5-fluoro-2-methoxyphenyl)-2-{[(trifluoroacetyl)amino]methyl}-2-propenoic Acid (Compound S10)

Instead of the starting material compound in Reference Example 1, that is, the 5-chloro-2-salicylaldehyde, 5-fluoro-2-hydroxybenzaldehyde was used for successively the similar procedures as in Reference Example 1 to Reference Example 6 to obtain the title compound.

NMR (CDCl$_3$): δ8.05 (1H, s), 7.21 (1H, dd, J=8.6, 3 Hz), 7.14-6.96 (2H, m), 6.88 (1H, dd, J=9.1, 4.3 Hz), 4.35 (2H, d, J=5.9 Hz), 3.84 (3H, s)

MS: 344 (M+Na)$^+$

Reference Example 11

(2E)-3-(2-methoxymethoxy-5-methylphenyl)-2-{[(trifluoroacetyl)amino]methyl}-2-propenoic Acid (Compound S11)

Instead of the starting material in Reference Example 2, that is, the compound S1,2-methoxymethoxy-5-methylbenzaldehyde was used for successively the similar procedures as in Reference Example 2 to Reference Example 6 to obtain the title compound.

NMR (DMSO-d$_6$): δ12.72 (1H, brs), 9.60 (1H, br), 7.87 (1H, s), 7.17 (1H, d, J=8.3 Hz), 7.09 (1H, s), 7.06 (1H, d, J=8.3 Hz), 5.20 (2H, s), 4.12 (2H, d, J=4.4 Hz), 3.36 (3H, s), 2.22 (3H, s)

MS: 370 (M+Na)$^+$

Reference Example 12

(2E)-3-(3-chloro-5-fluoro-2-methoxyphenyl)-2-{[(trifluoroacetyl)amino]methyl}-2-propenoic Acid (Compound S12)

Instead of the starting material compound in Reference Example 1, that is, the 5-chloro-2-salicylaldehyde, 3-chloro-5-fluoro-2-hydroxybenzaldehyde was used for successively the similar procedures as in Reference Example 1 to Reference Example 6 to obtain the title compound.

NMR (CDCl$_3$): δ8.00 (1H, s), 7.22 (1H, dd, J=7.6, 2.7 Hz), 7.15 (1H, dd, J=8.6, 2.7 Hz), 7.10 (1H, br), 4.34 (2H, d, J=6.1 Hz), 3.78 (3H, s)

MS: 378 (M+Na)$^+$

Reference Example 13

(2E)-3-(5-chloro-2-ethoxyphenyl)-2-{[(trifluoroacetyl)amino]methyl}-2-propenoic Acid (Compound S13)

Instead of the starting material in Reference Example 2, that is, the compound S1,5-chloro-2-ethoxybenzaldehyde was used for successively the similar procedures as in Reference Example 2 to Reference Example 6 to obtain the title compound.

NMR (CDCl$_3$): δ8.04 (1H, s), 7.40 (1H, d, J=2.5 Hz), 7.32 (1H, dd, J=8.9, 2.5 Hz), 7.02 (1H, br), 6.86 (1H, d, J=8.9 Hz), 4.36 (2H, d, J=6 Hz), 4.07 (2H, q, J=6.9 Hz), 1.41 (3H, t, J=6.9 Hz)

MS: 374 (M+Na)$^+$

Reference Example 14

(2E)-3-(2-methoxy-5-trifluoromethylphenyl)-2-{[(trifluoroacetyl)amino]methyl}-2-propenoic Acid (Compound S14)

Instead of the starting material compound in Reference Example 2, that is, the compound S2, 2-methoxy-5-trifluoromethylbenzaldehyde was used for successively the similar procedures as in Reference Example 2 to Reference Example 6 to obtain the title compound.

NMR (DMSO-$d_6$): $\delta$12.90 (1H, brs), 9.67 (1H, t, J=4.4 Hz), 7.82 (1H, s), 7.77 (1H, dd, J=8.7, 2.1 Hz), 7.62 (1H, d, J=2.1 Hz), 7.28 (1H, d, J=8.7 Hz), 4.04 (2H, d, J=4.4 Hz), 3.90 (3H, s)

MS: 394 (M+Na)$^+$

Reference Example 15

(2E)-3-(4-chloro-5-fluoro-2-methoxyphenyl)-2-{[(trifluoroacetyl)amino]methyl}-2-propenoic Acid (Compound S15)

To 2-chloro-1-fluoro-4-methoxybenzene (5 g) in methylene chloride (30 ml) solution, titanium tetrachloride (5.8 ml) and α,α-dichloromethylmethylether (2.8 ml) were added under ice cooling, the mixture was stirred at 2° C. for 11.5 hours, then the reaction solution was poured into ice. Next, the methylene chloride layer was separated, washed with saturated saline, dried over with anhydrous sodium sulfate, and concentrated. The obtained residue was recrystallized from ethylether. The thus obtained 4-chloro-5-fluoro-2-methoxybenzaldehyde (3.41 g) was used instead of the starting material in Reference Example 2, that is, the compound S1, for successively the similar procedure as in Reference Example 2 to Reference Example 6 to obtain the title compound.

NMR (CDCl$_3$): $\delta$7.96 (1H, s), 7.37 (1H, d, J=9.0 Hz), 7.06 (1H, br), 6.96 (1H, d, J=5.9 Hz), 4.33 (2H, d, J=6.1 Hz), 3.84 (3H, s)

MS: 378 (M+Na)$^+$

Reference Example 16

(2E)-3-(2,5-dimethoxyphenyl)-2-{[(trifluoroacetyl)amino]methyl}-2-propenoic Acid (Compound S16)

Instead of the starting material compound of Reference Example 1, that is, the 5-chloro-2-salicylaldehyde, 2,5-dihydroxybenzaldehyde was used for successively the similar procedure as in Reference Example 1 to Reference Example 6 to obtain the title compound.

NMR (CDCl$_3$): $\delta$8.11 (1H, s), 7.11 (1H, br), 7.03 (1H, d, J=2.9 Hz), 6.95 (1H, dd, J=9.0, 2.9 Hz), 6.88 (1H, d, J=9.0 Hz), 4.39 (2H, d, J=5.9 Hz), 3.82 (6H, s)

MS: 356 (M+Na)$^+$

Reference Example 17

(2E)-3-benzo[1,3]-dioxol-5-yl-2-{[(trifluoroacetyl)amino]methyl}-2-propenoic Acid (Compound S17)

Instead of the starting material in Reference Example 2, that is, the compound S1, 3,4-methylenedioxybenzaldehyde was used for successively the similar procedure as in Reference Example 2 to Reference Example 6 to obtain the title compound.

NMR (CDCl$_3$): $\delta$7.89 (1H, s), 7.12-7.03 (1H, m), 7.10 (1H, d, J=1.6 Hz), 7.04 (1H, dd, J=8.1, 1.6 Hz), 6.89 (1H, d, J=8.1 Hz), 6.04 (2H, s), 4.49 (2H, d, J=5.9 Hz)

MS: 340 (M+Na)$^+$

Reference Example 18

(2E)-3-(2-fluoro-5-methoxyphenyl)-2-{[(trifluoroacetyl)amino]methyl}-2-propenoic Acid (Compound S18)

Instead of the starting material in Reference Example 2, that is, the compound S1, 2-fluoro-5-methoxybenzaldehyde was used for successively the similar procedure as in Reference Example 2 to Reference Example 6 to obtain the title compound.

NMR (CDCl$_3$): $\delta$8.00 (1H, s), 7.12 (1H, dd, J=5.8, 3.1 Hz), 7.11-7.02 (1H, m), 7.06 (1H, t, J=9.1 Hz), 6.98-6.91 (1H, m), 4.41 (2H, d, J=6 Hz), 3.85 (3H, s)

MS: 344 (M+Na)$^+$

Reference Example 19

(2E)-3-(2-chlorophenyl)-2-{[(trifluoroacetyl)amino]methyl}-2-propenoic Acid (Compound S19)

Instead of the starting material in Reference Example 2, that is, the compound S1, 2-chlorobenzaldehyde was used for successively the similar procedure as in Reference Example 2 to Reference Example 6 to obtain the title compound.

NMR (DMSO-$d_6$): $\delta$12.98 (1H, brs), 9.59 (1H, br), 7.79 (1H, s), 7.59-7.53 (1H, m), 7.52-7.48 (1H, m), 7.47-7.38 (2H, m), 4.08 (2H, d, J=4.7 Hz)

Reference Example 20

(2E)-3-(3,5-dichlorophenyl)-2-{[(trifluoroacetyl)amino]methyl}-2-propenoic Acid (Compound S20)

Instead of the starting material in Reference Example 2, that is, the compound S1, 3,5-dichlorobenzaldehyde was used for successively the similar procedure as in Reference Example 2 to Reference Example 6 to obtain the title compound.

NMR (DMSO-$d_6$): $\delta$12.98 (1H, brs), 9.64 (1H, t, J=4.7 Hz), 7.72 (1H, s), 7.65 (1H, t, J=1.9 Hz), 7.525 (1H, d, J=1.9 Hz), 7.523 (1H, d, J=1.9 Hz), 4.13 (2H, d, J=4.7 Hz)

Reference Example 21

(2E)-3-(5-chloro-2-ethoxymethoxyphenyl)-2-{[(trifluoroacetyl)amino]methyl}-2-propenoic Acid (Compound S21)

To 5-chloro-2-salicylaldehyde (25 g) in methylene chloride (250 ml) solution, ethoxymethylchloride (15 ml) and N,N-diisopropylethylamine (33 ml) were added under ice cooling and the mixture was stirred at room temperature for 4 hours. The reaction solution was concentrated, then the residue was diluted with diethylether and the insoluble compound was filtered out. The filtrate was successively washed with distilled water, 1N sodium hydroxide aqueous solution, and saturated saline, dried over with anhydrous sodium sulfate, then concentrated. The thus obtained 5-chloro-2-ethoxymethoxybenzaldehyde as a crude product (32.4 g) was used for the similar procedure as in Reference Example 2 to Reference Example 6 to obtain the title compound.

NMR (CDCl$_3$): δ8.02 (1H, s), 7.40 (1H, d, J=2.4 Hz), 7.33 (1H, dd, J=8.9, 2.4 Hz), 7.16 (1H, d, J=8.9 Hz), 7.05 (1H, br), 5.23 (2H, s), 4.36 (2H, d, J=6 Hz), 3.71 (2H, q, J=7.0 Hz), 1.22 (3H, t, J=7.0 Hz)
MS: 404 (M+Na)$^+$

Reference Example 22

(2E)-3-(2-methoxy-5-methoxymethoxyphenyl)-2-{[(trifluoroacetyl)amino]methyl}-2-propenoic Acid (Compound S22)

To 2,5-dihydroxybenzaldehyde (15 g) in acetone (105 ml) solution, methoxymethyl chloride (8.25 ml) in ethyl acetate (16.5 ml) solution and potassium carbonate (15 g) were added under ice cooling and the mixture was stirred at room temperature for 17 hours. Saturated ammonium chloride aqueous solution was added to the reaction solution, then the mixture was extracted with ethyl acetate. The organic layer was washed with saturated saline, then was extracted with 1N sodium hydroxide aqueous solution. The aqueous layer was neutralized by 1N hydrochloric acid, then the mixture was extracted with ethyl acetate. The organic layer was dried over with anhydrous sodium sulfate, then concentrated. The residue was purified by silica gel column chromatography (hexane/ethyl acetate=4/1). The thus obtained 2-hydroxy-5-methoxymethoxybenzaldehyde (1.75 g) was used for the similar procedure as in Reference Example 1 to Reference Example 6 to obtain the title compound.
NMR (CDCl$_3$): δ8.09 (1H, s), 7.14-7.00 (3H, m), 6.87 (1H, d, J=8.8 Hz), 5.16 (2H, s), 4.36 (2H, d, J=5.7 Hz), 3.82 (3H, s), 3.48 (3H, s)
MS: 386 (M+Na)$^+$ Reference Example 23

(2E)-2-{[(tert-butoxycarbonyl)amino]methyl}-3-(5-chloro-2-methoxyphenyl)-2-propenoic Acid (Compound S23)

To the compound S5 (15 g) in tetrahydrofuran (300 ml) suspension, 2N sodium hydroxide aqueous solution (70 ml) and di-tert-butyldicarbonate (15 g) were added and the mixture was stirred at room temperature for 1 hour. Next, tetrahydrofuran was distilled off in vacuo, the obtained aqueous mixture was acidified by adding saturated potassium hydrogensulfate aqueous solution, then the mixture was extracted with ethyl acetate. The organic layer was washed with saturated saline and dried over with anhydrous sodium sulfate and concentrated. The residue was recrystallized from ethyl acetate/hexane to obtain the title compound (19.8 g).
NMR (CDCl$_3$): δ7.93 (0.5H, br), 7.78 (0.5H, br), 7.42 (0.5H, br), 7.30 (1H, dd, J=8.8, 2.4 Hz), 7.19 (0.5H, br), 6.84 (1H, d, J=8.8 Hz), 6.76 (0.5H, br), 5.12 (0.5H, br), 4.14 (2H, br), 3.84 (3H, s), 1.55-1.15 (9H, m)
MS: 364 (M+Na)$^+$ Reference Example 24

(2E)-2-{[(tert-butoxycarbonyl)amino]methyl}-3-(4-cyanophenyl)-2-propenoic Acid (Compound S24)

Instead of the starting material in Reference Example 2, that is, the compound S1, 4-cyanobenzaldehyde was used for the similar procedure as in Reference Example 2 to Reference Example 5 and Reference Example 23 to obtain the title compound.
NMR (DMSO-d$_6$): δ12.77 (1H, brs), 7.89 (2H, d, J=8.4 Hz), 7.70-7.62 (3H, m), 6.94 (1H, br), 3.90 (2H, d, J=4.6 Hz), 1.36 (9H, s)
MS: 303 (M+H)$^+$ Reference Example 25

(2E)-2-{[(tert-butoxycarbonyl)amino]methyl}-3-(naphthyl-2-yl)-2-propenoic Acid (Compound S25)

Instead of the starting material in Reference Example 2, that is, the compound S1, 2-naphthylaldehyde was used for the similar procedure as in Reference Example 2 to Reference Example 5 and Reference Example 23 to obtain the title compound.
NMR (CDCl$_3$): δ8.12-7.94 (2H, m), 7.92-7.80 (3H, m), 7.68-7.58 (1H, m), 7.58-7.50 (2H, m), 5.20 (1H, brs), 4.35 (2H, d, J=6 Hz), 1.48 (9H, br)
MS: 350 (M+Na)$^+$ Reference Example 26

(2E)-2-{[(tert-butoxycarbonyl)amino]methyl}-3-(4-fluorophenyl)-2-propenoic Acid (Compound S26)

Instead of the starting material in Reference Example 2, that is, the compound S1, 4-fluorobenzaldehyde was used for the similar procedure as in Reference Example 2 to Reference Example 5 and Reference Example 23 to obtain the title compound.
NMR (CDCl$_3$): δ7.85-7.31 (2H, m), 7.12 (2H, t, J=8.2 Hz), 6.72 (1H, br), 5.16 (1H, br), 4.22 (2H, d, J=6.1 Hz), 1.28 (9H, br)
MS: 318 (M+Na)$^+$ Reference Example 27

(2E)-2-{[(tert-butoxycarbonyl)amino]methyl}-3-(4-chlorophenyl)-2-propenoic Acid (Compound S27)

Instead of the starting material in Reference Example 2, that is, the compound S1, 4-chlorobenzaldehyde was used for the similar procedure as in Reference Example 2 to Reference Example 5 and Reference Example 23 to obtain the title compound.
NMR (CDCl$_3$): δ7.82-7.70 (1H, m), 7.48-7.22 (3H, m), 6.77 (1H, br), 5.14 (1H, br), 4.21 (2H, d, J=6.3 Hz), 1.28 (9H, br)
MS: 334 (M+Na)$^+$ Reference Example 28

(2E)-2-{[(tert-butoxycarbonyl)amino]methyl}-3-(3-chlorophenyl)-2-propenoic Acid (Compound S28)

Instead of the starting material in Reference Example 2, that is, the compound S1, 3-chlorobenzaldehyde was used for the similar procedure as in Reference Example 2 to Reference Example 5 and Reference Example 23 to obtain the title compound.
NMR (CDCl$_3$): δ7.85-7.65 (2H, m), 7.51-7.35 (2H, m), 6.80 (1H, br), 5.10 (1H, br), 4.21 (2H, d, J=3.5 Hz), 1.258 (9H, br)

MS: 334 (M+Na)+

Reference Example 29

(2E)-2-{[(tert-butoxycarbonyl)amino]methyl}-3-(3-methylphenyl)-2-propenoic Acid (Compound S29)

Instead of the starting material in Reference Example 2, that is, the compound S1, 3-methylbenzaldehyde was used for the similar procedure as in Reference Example 2 to Reference Example 5 and Reference Example 23 to obtain the title compound.
NMR (DMSO-$d_6$): δ12.56 (1H, brs), 7.62 (1H, s), 7.35-7.25 (3H, m), 7.20 (1H, d, J=7.1 Hz), 6.87 (1H, br), 3.93 (2H, d, J=4.7 Hz), 2.32 (3H, s), 1.39 (9H, s)
MS: 314 (M+Na)+

Reference Example 30

(2E)-2-{[(tert-butoxycarbonyl)amino]methyl}-3-(3-trifluoromethylphenyl)-2-propenoic Acid (Compound S30)

Instead of the starting material in Reference Example 2, that is, the compound S1, 3-trifluoromethylbenzaldehyde was used for the similar procedure as in Reference Example 2 to Reference Example 5 and Reference Example 23 to obtain the title compound.
NMR (DMSO-$d_6$): δ12.75 (1H, brs), 7.87 (1H, s), 7.81-7.71 (3H, m), 7.66 (1H, t, J=7.7 Hz), 6.98 (1H, br), 3.89 (2H, d, J=4.3 Hz), 1.37 (9H, s)
MS: 368 (M+Na)+

Reference Example 31

(2E)-2-{[(tert-butoxycarbonyl)amino]methyl}-3-(3-cyanophenyl)-2-propenoic Acid (Compound S31)

Instead of the starting material in Reference Example 2, that is, the compound S1, 3-cyanobenzaldehyde was used for the similar procedure as in Reference Example 2 to Reference Example 5 and Reference Example 23 to obtain the title compound.
NMR (DMSO-$d_6$): δ12.78 (1H, brs), 7.94 (1H, s), 7.84 (1H, d, 7.6 Hz), 7.80 (1H, d, 7.8 Hz), 7.66-7.60 (2H, m), 6.97 (1H, br), 3.90 (2H, d, 4.2 Hz), 1.37 (9H, s)
MS: 325 (M+Na)+

Reference Example 32

(2E)-2-{[(allyloxycarbonyl)amino]methyl}-3-(4-methoxymethoxyphenyl)-2-propenoic Acid (Compound S32)

Instead of the starting material in Reference Example 2, that is, the compound S1, 4-methoxymethoxybenzaldehyde was used for the similar procedure as in Reference Example 2 to Reference Example 4. To the obtained compound (6.1 g) in tetrahydrofuran (70 ml) solution, triphenylphosphine (5.8 g) and distilled water (0.6 ml) were added and the mixture was stirred at room temperature for 13 hours. 2N hydrochloric acid (10 ml) was added to the reaction solution, then tetrahydrofuran was distilled off in vacuo. The obtained aqueous solution was washed with ethyl acetate, then a 4N sodium hydroxide aqueous solution (20 ml) was added. Tetrahydrofuran (50 ml) was added to this, allyl chlorocarbonate (2.8 ml) was added under ice cooling, and the mixture was stirred at room temperature for 3 hours. The tetrahydrofuran was distilled off in vacuo, then ethanol (50 ml) and a 4N sodium hydroxide aqueous solution (10 ml) were added to the obtained aqueous mixture and the mixture was stirred at room temperature for 18 hours. The ethanol was distilled off in vacuo, then the obtained aqueous mixture was washed with diethylether-hexane (3:1), was acidified by adding a potassium hydrogensulfate aqueous solution, and was extracted with diethylether. The organic layer was successively washed with water and saturated saline, dried over with anhydrous sodium sulfate, then concentrated. The residue was recrystallized from diethylether/hexane to obtain the title compound (3.8 g).
NMR (CDCl$_3$): δ7.86 (1H, s), 7.56 (2H, d, J=8.1 Hz), 7.09 (2H, d, J=8.1 Hz), 6.00-5.88 (1H, m), 5.39 (1H, br), 5.36-5.15 (4H, m), 4.58 (2H, d, J=5 Hz), 4.32 (2H, d, J=5.9 Hz), 3.48 (3H, s)
MS: 344 (M+Na)+

Reference Example 33

N-(tert-butoxycarbonyl)-2-(3-chlorobenzyl)-β-alanine (Compound S33)

To a suspension of the compound S28 (500 mg) and platinum oxide (50 mg) in methanol (25 ml) was stirred under hydrogen atmosphere at room temperature for 45 minutes. The insoluble compound was filtered out, then the filtrate was concentrated to obtain the title compound as a crude product (440 mg).
NMR (CDCl$_3$): δ7.30-7.00 (4H, m), 4.94 (1H, br), 3.43-3.20 (2H, m), 3.10-2.60 (3H, m), 1.45 (9H, s)
MS: 336 (M+Na)+

Reference Example 34

Methyl 3-(benzoylamino)-2-[(5-chloro-2-methoxyphenyl)(hydroxy)methyl]butanoate (Compound S34)

To methyl 3-(benzoylamino)butanoate (1.65 g) in tetrahydrofuran (30 ml) solution, lithium diisopropylamide (2M heptane/tetrahydrofuran/ethylbenzene solution) (8.2 ml) was added at −78° C. and the mixture was stirred at −45° C. for 30 minutes. The reaction solution was again cooled to −78° C., then the compound of Reference Example 1 (1.5 g) in tetrahydrofuran (3 ml) solution was added and, while gradually raising the temperature to room temperature, the mixture was stirred for 16 hours. Saturated ammonium chloride solution was added to the reaction solution, then tetrahydrofuran was distilled off in vacuo. The remaining solution was extracted with ethyl acetate. The organic layer was washed with saturated saline, dried over with anhydrous sodium sulfate, then concentrated. The residue was purified by silica gel column chromatography (hexane/ethyl acetate=3/1 to 2/1) to obtain the title compound (2.27 g).

Reference Example 35

Methyl 6-(5-chloro-2-methoxyphenyl)-4-methyl-2-phenyl-5,6-dihydro-4H-1,3-oxazine-5-carboxylate (Compound S35)

To the compound S34 (3.07 g) in trifluoroacetic acid (7 ml) solution, concentrated sulfuric acid (0.4 ml) was added and the mixture was stirred at room temperature for 1 hour. 2N sodium hydroxide aqueous solution was added to the reaction solution and the mixture concentrated in vacuo. The residue was diluted with ethyl acetate, then the obtained solution was successively washed with distilled water, saturated sodium hydrogencarbonate aqueous solution, and saturated saline, dried over with anhydrous sodium sulfate, then concentrated. The residue was purified by silica gel column chromatography (hexane/ethyl acetate=2/1) to obtain the title compound (2.17 g) as a mixture of two types of diastereomers (A and B).
(Diastereomer A)
NMR (CDCl$_3$): δ7.95-7.90 (2H, m), 7.47-7.31 (4H, m), 7.28 (1H, dd, J=8.8, 2.6 Hz), 6.84 (1H, d, J=8.8 Hz), 5.64 (1H, d, J=10.5 Hz), 4.02 (1H, dd, J=10.5, 6.7 Hz), 3.79 (3H, s), 3.55 (3H, s), 2.64 (1H, t, J=10.5 Hz), 1.34 (3H, d, J=6.7 Hz)
(Diastereomer B)
NMR (CDCl$_3$): δ7.93 (2H, d, J=7.2 Hz), 7.47-7.31 (3H, m), 7.29-7.24 (1H, m), 7.2 (1H, d, J=2.5 Hz), 6.86 (1H, d, J=8.7 Hz), 5.83 (1H, d, J=6.9 Hz), 3.92 (1H, dd, J=6.7, 5.5 Hz), 3.83 (3H, s), 3.66 (3H, s), 3.24 (1H, dd, J=6.9, 5.5 Hz), 1.32 (3H, d, J=6.7 Hz)

Reference Example 36

Methyl (2E)-2-[1-(benzoylamino)ethyl]-3-(5-chloro-2-methoxyphenyl)-2-propenoate (Compound S36)

To the compound S35 (2.17 g) in tetrahydrofuran (20 ml) solution, potassium tert-butoxide (0.69 g) was added and the mixture was stirred at room temperature for 2 hours. Saturated potassium hydrogensulfate aqueous solution was added to the reaction solution, then the mixture was extracted with ethyl acetate. The organic layer was successively washed with saturated saline, dried over with anhydrous sodium sulfate, then concentrated. The residue was purified by silica gel column chromatography (hexane/ethyl acetate=2/1 to 1/1) to obtain the title compound (0.44 g).
NMR (CDCl$_3$): δ7.80-7.75 (2H, m), 7.71 (1H, s), 7.58-7.38 (5H, m), 7.3 (1H, dd, J=8.8, 1.4 Hz), 6.84 (1H, d, J=8.8 Hz), 5.56-5.45 (1H, m), 3.86 (3H), 3.81 (3H), 1.47 (3H, d, J=7 Hz)

Reference Example 37

Methyl (2E)-2-{1-[benzoyl(tert-butoxycarbonyl)amino]ethyl}-3-(5-chloro-2-methoxyphenyl)-2-propenoate (Compound S37)

To the compound S36 (400 mg) in tetrahydrofuran (3 ml) solution, 4-dimethylaminopyridine (88 mg) and di-tert-butyldicarbonate (1.5 g) were added in three additions during stirring at room temperature over 28 hours, then the reaction solution was diluted with ethyl acetate, was washed with saturated potassium hydrogensulfate aqueous solution, dried over with anhydrous sodium sulfate, then concentrated. The residue was purified by silica gel column chromatography (hexane/ethyl acetate=5/1) to obtain the title compound (413 mg).

Reference Example 38

Methyl (2E)-2-{1-[(tert-butoxycarbonyl)amino]ethyl}-3-(5-chloro-2-methoxyphenyl)-2-propenoate (Compound S38)

To the compound S37 (400 mg) in tetrahydrofuran (2 ml) solution, 2N lithium hydroxide aqueous solution (2 ml) and methanol (4 ml) were added and the mixture was stirred at room temperature for 8 hours. The methanol and tetrahydrofuran were distilled off in vacuo. The reaction solution was diluted with ethyl acetate, then the mixture was washed with saturated potassium hydrogensulfate aqueous solution, dried over with anhydrous sodium sulfate, then concentrated. The residue was recrystallized from hexane/ethyl acetate to obtain the title compound (211 mg).
NMR (CDCl$_3$): δ7.76 (1H, br), 7.29 (1H, dd, J=8.9, 2.4 Hz), 7.29-7.22 (2H, m), 6.84 (1H, d, J=8.9 Hz), 4.92 (1H, br), 3.83 (3H, s), 1.60-1.15 (3H, m)

Reference Example 39

Ethyl (2E)-3-(5-chloro-2-methoxyphenyl)-2-cyano-2-propenoate (Compound S39)

To the compound S1 (500 mg) and methyl cyanoacetate (497 mg) in ethanol (10 ml) solution, sodium ethoxide (300 mg) was added under ice cooling and the mixture was stirred at room temperature for 2 hours. Saturated ammonium chloride aqueous solution was added to the reaction solution, and the mixture was extracted with ethyl acetate. The extract was washed with saturated saline, dried over with anhydrous sodium sulfate, then concentrated. The residue was diluted with hexane/diethylether, then the precipitated solid was collected by filtration to obtain the title compound (730 mg).

Reference Example 40

Ethyl 3-(5-chloro-2-methoxyphenyl)-2-cyanopropanoate (Compound S40)

To the compound S39 (591 mg) in ethanol (18 ml) solution, 5% platinum carbon (sulfided catalyst) (118 mg) was added and the mixture was stirred under hydrogen atmosphere at room temperature for 4 hours. The insoluble compound was filtered out, then the filtrate was concentrated. The residue was purified by silica gel column chromatography (hexane/ethyl acetate=3/1) to obtain the title compound (313 mg).

Reference Example 41

Methyl 3-(5-chloro-2-methoxyphenyl)-2-cyano-2-methylpropanoate (Compound S41)

To the compound S40 (301 mg) in methanol (6 ml) solution, sodium methoxide (0.54 mg) and methyl iodide (0.14 ml) were added and the mixture was stirred at room temperature for 3 hours. The reaction solution was concentrated, then chloroform and saturated ammonium chloride aqueous solution were added to the residue. The organic layer was separated, then washed with saturated saline, dried over with anhydrous sodium sulfate, then concentrated. The residue was purified by silica gel column chromatography (hexane/ethyl acetate=3/1) to obtain the title compound (147 mg).
NMR (CDCl$_3$): δ7.23 (1H, dd, J=8.8, 2.6 Hz), 7.14 (1H, d, J=2.6 Hz), 6.81 (1H, d, J=8.8 Hz), 3.8 (3H, s), 3.79 (3H, s), 3.21 (1H, d, J=13.5 Hz), 3.15 (1H, d, J=13.5 Hz), 1.6 (3H, s)

Reference Example 42

Methyl 3-amino-2-(5-chloro-2-methoxybenzyl)-2-methylpropanoate (Compound S42)

To the compound S41 (147 mg) and cobalt (II) chloride 6 hydrate (261 mg) in methanol (7.4 ml) solution, sodium boron hydride (208 mg) was added in several additions batches and the mixture was stirred at room temperature for 30 minutes. 2N hydrochloric acid was added to the reaction solution, methanol was distilled off in vacuo, and the remaining solution was washed with ethyl acetate. A 1N sodium hydroxide aqueous solution was added to the aqueous layer, and the mixture was extracted with ethyl acetate. The organic layer was successively washed with saturated saline, dried over with anhydrous sodium sulfate, and concentrated to obtain the title compound (71 mg).

NMR (CDCl$_3$): δ7.2 (1H, dd, J=8.8, 2.5 Hz), 7.03 (1H, d, J=2.5 Hz), 6.92 (1H, d, J=8.8 Hz), 3.79 (3H, s), 3.68 (3H, s), 3.34-3.29 (2H, m), 2.91 (2H, br), 1.18 (3H, s)

Reference Example 43

2-(5-chloro-2-methoxybenzyl)-2-methyl-β-alanine (Compound S43)

To the compound S42 (60 mg) in methanol (0.6 ml) solution, 1N sodium hydroxide aqueous solution (0.3 ml) was added and the mixture was stirred at 60° C. for 1.5 hours. The methanol was distilled off in vacuo, 1N hydrochloric acid was added to the remaining solution to acidify (pH was 4), and the mixture was washed with ethyl acetate. The aqueous layer was stirred for a while, and the precipitated solid was collected by filtration to obtain the title compound (32.4 mg).

Reference Example 44

2-(5-chloro-2-methoxybenzyl)-2-methyl-N-(trifluoroacetyl)-β-alanine (Compound S44)

To the compound S43 (32 mg) in tetrahydrofuran (0.32 ml) solution, anhydrous trifluoroacetic acid (26 μl) was added and the mixture was stirred at room temperature for 1 hour. The reaction solution was concentrated, then the residue was diluted with ethyl acetate and washed with saturated saline. The organic layer was concentrated, the residue was diluted with hexane/ethyl acetate, and the precipitated solid was collected by filtration to obtain the title compound (33.8 mg).

NMR (CDCl$_3$): δ7.29 (1H, br), 7.21 (1H, dd, J=8.8, 2.7 Hz), 7.12 (1H, d, J=2.7 Hz), 6.82 (1H, d, J=8.8 Hz), 3.83 (3H, s), 3.44 (1H, dd, J=14.0, 6.9 Hz), 3.38 (1H, dd, J=14.0, 6.2 Hz), 3.03 (1H, d, J=13.9 Hz), 2.92 (1H, d, J=13.9 Hz), 1.29 (3H, s)

Reference Example 45

Diethyl 2-(5-chloro-2-methoxybenzyl)malonate (Compound S45)

To the compound S1 (23 g) in toluene (230 ml) solution, diethyl malonate (20 ml) and piperadine acetate (3.9 g) were added. The mixture was stirred at reflux for 4 hours with Dean-Stark apparatus for removing water. The reaction solution was successively washed with distilled water and saturated saline, dried over with anhydrous sodium sulfate, then concentrated. The residue was dissolved in ethanol (450 ml), platinum oxide (2 g) was added to the solution, then the mixture was stirred at room temperature under hydrogen atmosphere at 5 atm for 14 hours. The insoluble compound was filtered out, then the filtrate was concentrated. The residue was purified by silica gel column chromatography (hexane/ethyl acetate=2/1) to obtain the title compound (39 g).

Reference Example 46

Diethyl 2-(5-chloro-2-methoxybenzyl)-2-fluoromalonate (Compound S46)

To the compound S45 (39 g) in tetrahydrofuran (400 ml) solution, sodium hydride (60% mineral oil dispersion) (5 g) was added under ice cooling and the mixture was stirred at that temperature for 1 hour. Next, N-fluoro-2,4,6-trimethylpiperidium trifurate (36 g) was added to the reaction solution and the mixture was stirred at room temperature for 4 hours. Saturated potassium hydrogensulfate aqueous solution was added to the reaction solution, and the mixture was extracted with ethyl acetate. The organic layer was washed with saturated saline, dried over with anhydrous sodium sulfate, then concentrated. The residue was purified by silica gel column chromatography (hexane/ethyl acetate=3/1 to 2/1) to obtain the title compound (43 g).

NMR (CDCl$_3$): δ7.20-7.14 (2H, m), 6.75 (1H, d, J=7.0 Hz), 4.32-4.19 (4H, m), 3.76 (3H, s), 3.5 (2H, d, J=23.4 Hz), 1.31-1.22 (6H, m)

Reference Example 47

Monoethyl 2-(5-chloro-2-methoxybenzyl)-2-fluoromalonate (Compound S47)

To the compound S46 (41 g) in tetrahydrofuran (200 ml)/ethanol (200 ml) solution, 1N sodium hydroxide aqueous solution (125 ml) was added and the mixture was stirred at room temperature for 24 hours. The reaction solution was concentrated, diethylether was added to the residue, and the mixture was extracted with distilled water. The aqueous layer was neutralized by 1N hydrochloric acid, and the mixture was extracted with diethylether. The organic layer was washed with saturated saline, dried over with anhydrous sodium sulfate, and concentrated to obtain the title compound (27 g).

Reference Example 48

Ethyl 2-(5-chloro-2-methoxybenzyl)-2-fluoro-3-hydroxypropanoate (Compound S48)

To the compound S47 (14 g) in methylene chloride (420 ml) solution, N,N-dimethylformamide (1 drop) and oxalyl chloride (25 ml) were added, the mixture was stirred under heating and reflux for 2 hours, then the reaction solution was concentrated. To the residue in tetrahydrofuran (420 ml) solution, lithium tri-tert-butoxy aluminum hydride (15.5 g) was added at −78° C. and the mixture was stirred at that temperature for 1.5 hours. To the reaction solution, a Rochelle salt aqueous solution was added, then the mixture was stirred for 30 minutes and was extracted with ethyl acetate. The organic layer was washed with saturated saline, dried over with anhydrous sodium sulfate, then concentrated. The residue was purified by silica gel column chromatography (hexane/ethyl acetate=2/1 to 1/1) to obtain the title compound (5 g).

Reference Example 49

Ethyl 3-azide-2-(5-chloro-2-methoxybenzyl)-2-fluoropropanoate (Compound S49)

To the compound S48 (2.43 g) in methylene chloride (48 ml) solution, 2,6-di-tert-butyl-4-methylpyridine (2.57 g) and trifluoromethane sulfonic acid anhydride (2.1 ml) were added under ice cooling and the mixture was stirred at that temperature for 30 minutes. Distilled water was added to the reaction solution and the mixture was extracted with chloroform. The organic layer was washed with saturated saline, dried over with anhydrous sodium sulfate, then concentrated. The residue was diluted with chloroform, the insoluble compound was filtered out, and the filtrate was concentrated. To the residue in N,N-dimethylformamide (48 ml) solution, sodium azide (1.09 g) was added and the mixture was stirred at 60° C. for 1 hour. Distilled water was added to the reaction solution, and the mixture was extracted with ethyl acetate. The organic layer was washed with saturated saline, dried over with anhydrous sodium sulfate, then concentrated. The residue was purified by silica gel column chromatography (hexane/ethyl acetate=3/1) to obtain the title compound (1.64 g).

NMR (CDCl$_3$): δ7.21 (1H, dd, J=8.8, 2.3 Hz), 7.16 (1H, d, J=2.3 Hz), 6.78 (1H, d, J=8.8 Hz), 4.32-4.19 (2H, m), 3.79 (3H, s), 3.67 (1H, dd, J=28.2, 13.4 Hz), 3.5 (1H, dd, J=14.7, 13.4 Hz), 3.29 (1H, dd, J=21.0, 14.3 Hz), 3.12 (1H, dd, J=21.1, 14.3 Hz), 1.27 (3H, t, J=7.2 Hz)

Reference Example 50

3-azide-2-(5-chloro-2-methoxybenzyl)-2-fluoropropanoic Acid (Compound S50)

To the compound S49 (1.64 g) in tetrahydrofuran (16 ml)/methanol (16 ml) solution, 2N sodium hydroxide aqueous solution (8 ml) was added and the mixture was stirred at room temperature for 1 hour. Saturated potassium hydrogensulfate aqueous solution was added the reaction solution, and the mixture was extracted with ethyl acetate. The organic layer was washed with saturated saline, dried over with anhydrous sodium sulfate, then concentrated. The residue was diluted with hexane/ethyl acetate, then the precipitate was collected by filtration to obtain the title compound (1.36 g).

Reference Example 51

N-(tert-butoxycarbonyl)-2-(5-chloro-2-methoxybenzyl)-2-fluoro-β-alanine (Compound S51)

To the compound S50 (1.36 g) in tetrahydrofuran (14 ml) solution, distilled water (0.14 ml) and triphenylphosphine (1.24 g) were added under ice cooling and the mixture was stirred at room temperature for 5 hours. The reaction solution was concentrated, ethyl acetate was added to the residue, and the precipitate was collected by filtration. To the filtrate in tetrahydrofuran (15 ml) solution, 2N sodium hydroxide aqueous solution (6.5 ml) and di-tert-butyl-dicarbonate (1.5 g) were added and the mixture was stirred at room temperature for 4 hours. Saturated potassium hydrogensulfate aqueous solution was added to the reaction solution, and the mixture was extracted with ethyl acetate. The organic layer was washed with saturated saline, dried over with anhydrous sodium sulfate, then concentrated. The residue was purified by silica gel column chromatography (ethyl acetate to chloroform/methanol=3/1) to obtain the title compound (1.43 g).

NMR (CDCl$_3$): δ7.22-7.15 (2H, m), 6.78 (1H, d, J=9.1 Hz), 3.78 (3H, s), 3.57-3.01 (5H, m), 1.42 (9H, s)

Reference Example 52 tert-butyl (6-chloro-2-oxo-2H-chromen-3-yl)methylcarbamate (Compound S52)

To the compound S5 (5.0 g) in acetic acid (90 ml) solution, 30% hydrogen bromide/acetic acid solution (10 ml) was added and the mixture was stirred at 100° C. for 63 hours. The precipitated solid was collected by filtration, 1,4-dioxane (27 ml), a 4M sodium hydroxide aqueous solution (5.4 ml), and di-tert-butyl-dicarbonate (2.2 g) were added, and the mixture was stirred at room temperature for 2 hours. The 1,4-dioxane was distilled off in vacuo, distilled water (30 ml) was added, and 1N hydrochloric acid was added to adjust the pH to 5. The precipitated solid was collected by filtration to obtain the title compound (2.82 g).

NMR (CDCl$_3$): δ7.63 (1H, s), 7.48-7.42 (2H, m), 7.30-7.24 (1H, m), 5.24 (1H, br), 4.19 (2H, d, J=6.5 Hz), 1.44 (9H, s)

Reference Example 53

(2Z)-2-{[(tert-butoxycarbonyl)amino]ethyl}-3-(2-butoxy-5-chlorophenyl)-2-propenoic Acid (Compound S53)

To the compound S52 (2.0 g), methanol (40 ml), tetrahydrofuran (40 ml), and 4M sodium hydroxide (3.9 ml) were added and the mixture was stirred for 2 hours. 4M sodium hydroxide (1 ml) was additionally added and the mixture was stirred for 15 minutes, then the reaction solution was concentrated. To 700 mg of the obtained residue, N,N-dimethylformamide (7 ml) and n-butyl iodide (0.55 ml) were added and the mixture was stirred at room temperature for 16 hours. The reaction solution was concentrated, distilled water was added, and the mixture was extracted with ethyl acetate. The organic layer was successively washed with saturated sodium hydrogencarbonate aqueous solution and saturated saline, dried over with anhydrous sodium sulfate, then concentrated. Methanol (6.5 ml), tetrahydrofuran (6.5 ml), and 1M sodium hydroxide (6.5 ml) were added to the residue, and the mixture was stirred at room temperature for 21 hours. Methanol and tetrahydrofuran were distilled off in vacuo, distilled water was added, then 1N hydrochloric acid was added to the obtained aqueous solution to adjust the pH to 4 and the mixture was extracted with chloroform. The organic layer was washed with saturated saline, dried over with anhydrous sodium sulfate, and concentrated to obtain the title compound (560.9 mg).

Reference Example 54

Methyl 5-(aminosulfonyl)-2-chlorobenzoate (Compound S54)

To methyl 5-amino-2-chlorobenzoate (16.2 g) in concentrated hydrochloric acid (40 ml)/acetic acid (120 ml) suspension, a sodium nitrite (7.6 g) aqueous solution (20 ml) was added under ice cooling and the mixture was stirred at that temperature for 45 minutes. Next, the inside temperature of the reaction vessel was cooled to −5° C., copper (II) chloride 2-hydrate (3.7 g) and a 21% sulfur dioxide in acetic acid solution (60 ml) were added, and the mixture was raised to room temperature and stirred at 12 hours. Under ice cooling, distilled water was added to the reaction solution, the mixture was stirred at that temperature for 30 minutes, and the precipitate was collected by filtration. The filtrate was dissolved in tetrahydrofuran (50 ml), 28% ammonia water (10 ml) was added under ice cooling, and the mixture was stirred at that temperature for 15 minutes. The tetrahydrofuran was distilled off in vacuo, then ethyl acetate/hexane was added. The precipitate was collected by filtration to obtain the title compound (10.9 g).

Reference Example 55

5-(aminosulfonyl)-2-chlorobenzoic Acid (Compound S55)

To the compound S54 (10.9 g) in methanol (120 ml) solution, 2N sodium hydroxide aqueous solution (40 ml) was added and the mixture was stirred at room temperature for 3 hours. The methanol was distilled off in vacuo, then the remaining solution was made acidic by 6M hydrochloric acid and the precipitated solid was collected by filtration to obtain the title compound (10 g).

Reference Example 56

Tert-butyl 5-(aminosulfonyl)-2-chlorobenzoate (Compound S56)

To the compound S55 (10 g) in methylene chloride (80 ml)/tert-butyl alcohol (80 ml) solution, N,N'-diisopropyl-O-tert-butylisourea (40 ml) was added and the mixture was stirred under heating and reflux for 1 hour. The insoluble compound was filtered out, then the filtrate was concentrated. The residue was purified by silica gel column chromatography (chloroform/ethyl acetate=6/1 to 4/1) to obtain the title compound (8.68 g).

NMR (DMSO-$d_6$): δ8.09 (1H, d, J=2.3 Hz), 7.92 (1H, dd, J=8.4, 2.3 Hz), 7.78 (1H, d, J=8.4 Hz), 7.57 (2H, brs), 1.57 (9H, s)

Reference Example 57

N-[5-(aminosulfonyl)-2-chlorophenyl]-2,2,2-trifluoroacetoamide (Compound S57)

A solution of 3-amino-4-chlorobenzenesulfonamide (3.1 g) and trifluoroacetic acid anhydride (2.2 ml) in tetrahydrofuran (30 ml) was stirred at room temperature for 4 hours. The reaction solution was concentrated and the residue was recrystallized from hexane-ethyl acetate to obtain the title compound (3.07 g).

Reference Example 58

3-amino-4-methylbenzenesulfonamide (Compound S58)

A solution of 4-methyl-3-nitrobenzenesulfonamide (2.1 g) and platinum oxide (210 mg) in methanol (50 ml) was stirred under hydrogen atmosphere at room temperature for 6 hours. The insoluble compound was filtered out, then the filtrate was concentrated. The residue was recrystallized from hexane/acetone to obtain the title compound (1.23 g).

Reference Example 59

3-(tert-butoxycarbonyl)amino-4-methylbenzenesulfonamide (Compound S59)

To the compound S58 (1.2 g) in 1,4-dioxane (50 ml) solution, di-tert-butyl-dicarbonate (1.69 g) was added and the mixture was stirred under heating and reflux for 22 hours. The reaction solution was concentrated, distilled water was added, and the mixture was extracted with ethyl acetate. The organic layer was washed with saturated saline, dried over with anhydrous magnesium sulfate, then concentrated. The residue was recrystallized from hexane/ethyl acetate to obtain the title compound (0.84 g).

NMR (DMSO-$d_6$): δ8.74 (1H, s), 7.88 (1H, s), 7.45 (1H, d, J=8 Hz), 7.34 (1H, d, J=8 Hz), 7.27 (2H, s), 2.25 (3H, s), 1.47 (9H, s)

MS: 309 (M+Na)$^+$

Reference Example 60

3-(tert-butoxycarbonyl)amino-4-chlorobenzenesulfonamide (Compound S60)

Instead of the starting material compound of Reference Example 58, that is, the 4-methyl-3-nitrobenzenesulfonamide, 4-chloro-3-nitrobenzenesulfonamide was used for successively the similar procedure as in Reference Example 58 and Reference Example 59 to obtain the title compound.

NMR (CDCl$_3$): δ8.78 (1H, d, J=1.9 Hz), 7.52 (1H, dd, J=8.3, 1.9 Hz), 7.47 (1H, d, J=8.3 Hz), 7.11 (1H, brs), 4.91 (2H, brs), 1.54 (9H, s)

MS: 329 (M+Na)$^+$

Reference Example 61

3-(tert-butoxycarbonyl)amino-4-methoxybenzenesulfonamide (Compound S61)

Instead of the starting material compound of Reference Example 58, that is, the 4-methyl-3-nitrobenzenesulfonamide, 4-methoxy-3-nitrobenzenesulfonamide was used for successively the similar procedure as in Reference Example 58 and Reference Example 59 to obtain the title compound.

NMR (DMSO-$d_6$): δ7.11 (1H, d, J=2.4 Hz), 7.05 (1H, dd, J=8.5, 2.4 Hz), 6.94 (1H, d, J=8.5 Hz), 5.21 (2H, brs), 3.84 (3H, s), 1.30 (9H, s)

MS: 325 (M+Na)$^+$

Reference Example 62

3-(tert-butoxycarbonyl)aminobenzenesulfonamide (Compound S62)

Instead of the starting material compound of Reference Example 58, that is, 4-methyl-3-nitrobenzenesulfonamide, 3-nitrobenzenesulfonamide was used for successively the similar procedure as in Reference Example 58 and Reference Example 59 to obtain the title compound.

NMR (DMSO-$d_6$): δ9.67 (1H, s), 8.12 (1H, s), 7.53-7.39 (3H, m), 7.30 (2H, s), 1.48 (9H, s)

MS: 272 (M+H)$^+$

Reference Example 63

4-(tert-butoxycarbonyl)aminobenzenesulfonamide (Compound S63)

Instead of the starting material compound of Reference Example 58, that is, 4-methyl-3-nitrobenzenesulfonamide, 4-nitrobenzenesulfonamide was used for successively the similar procedure as in Reference Example 58 and Reference Example 59 to obtain the title compound.

NMR (DMSO-d$_6$): δ9.70 (1H, brs), 7.69 (2H, d, J=8.4 Hz), 7.58 (2H, d, J=8.4 Hz), 7.16 (2H, s), 1.48 (9H, s)

Reference Example 64

4-(tert-butoxycarbonyl)amino-5-chloro-2-thiophen-sulfonamide (Compound S64)

Instead of the starting material compound of Reference Example 58, that is, 4-methyl-3-nitrobenzenesulfonamide, 5-chloro-4-nitrothiophen-2-sulfonamide was used for successively the similar procedure as in Reference Example 58 and Reference Example 59 to obtain the title compound.

NMR (DMSO-d$_6$): δ9.30 (1H, brs), 7.80 (2H, brs), 7.68 (1H, brs), 1.46 (9H, s)

Reference Example 65

4-(tert-butoxycarbonyl)aminoethylbenzenesulfonamide (Compound S65)

Instead of the starting material compound in Reference Example 59, that is, the 4-methyl-3-nitrobenzenesulfonamide, 4-aminoethylbenzenesulfonamide was used for the similar procedure as in Reference Example 59 to obtain the title compound.

NMR (DMSO-d$_6$): δ7.73 (2H, d, J=8.2 Hz), 7.37 (2H, d, J=8.2 Hz), 7.26 (2H, brs), 6.90 (1H, br), 3.20-3.10 (2H, m), 2.76 (2H, t, J=7.2 Hz), 1.36 (9H, s)

MS: 323 (M+Na)$^+$

Reference Example 66

4-chloro-3-{[(ethylamino)carbonyl]amino}benzenesulfonamide (Compound S66)

To 3-amino-4-chlorobenzenesulfonamide (420 mg) in tetrahydrofuran (2 ml) solution, ethylisocyanate (180 μl) was added and the mixture was stirred under heating and reflux for 15 hours. The reaction solution was concentrated, then the residue was recrystallized from chloroform/methanol to obtain the title compound as a crude product (550 mg).

NMR (DMSO-d$_6$): δ8.73 (1H, d, J=2.2 Hz), 8.19 (1H, brs), 7.59 (1H, d, J=8.4 Hz), 7.42-7.35 (3H, m), 7.10 (1H, t, J=5.3 Hz), 3.19-3.09 (2H, m), 1.06 (3H, t, J=7.3 Hz)

Reference Example 67

Tert-butyl 2-amino-4-aminosulfonylbenzoate (Compound S67)

To tert-butyl 4-aminosulfonyl-2-(benzyloxycarbonyl)aminobenzoate (5.0 g) in tetrahydrofuran solution (50 ml), 5% palladium carbon (500 mg) was added and the mixture was stirred under hydrogen atmosphere at room temperature for 1 hour. The insoluble compound was filtered out, and the filtrate was concentrated. The residue was diluted with ethyl acetate, then the insoluble compound was again filtered out. The filtrate was concentrated, and the residue was recrystallized from ethyl acetate/hexane to obtain the title compound (2.9 g).

NMR (DMSO-d$_6$): δ7.77 (1H, d, J=8.3 Hz), 7.35 (2H, s), 7.23 (1H, s), 6.93 (2H, s), 6.89 (1H, d, J=8.3 Hz), 1.54 (9H, s)

Reference Example 68

N-(dimethylamino)methylidene-4-{3-(dimethylamino)-2-propenoyl}benzenesulfonamide (Compound S68)

To 4-aminosulfonylacetophenone (2.5 g) in 1,4-dioxane (30 ml) solution, N,N-dimethylformamide dimethylacetal (30 ml) was added and the mixture was stirred at 90° C. for 24 hours. The precipitate was collected by filtration and washed with ethyl acetate to obtain the title compound (3 g).

Reference Example 69

4-(1H-pyrazol-3-yl)benzenesulfonamide (Compound S69)

To the compound S68 (3 g) in methanol (50 ml) solution, hydrazine-hydrate (1.6 ml) was added and the mixture was stirred under heating and reflux for 3 hours. The reaction solution was concentrated, then the residue was recrystallized from methanol/diethylether to obtain the title compound (1.3 g).

NMR (DMSO-d$_6$): δ13.1 (1H, br), 7.98 (2H, d, J=8 Hz), 7.84 (2H, d, J=8 Hz), 7.32 (2H, brs), 6.82 (1H, s)

Reference Example 70

N-tert-butoxycarbonyl-N'-(4-chlorophenyl)-N'-methylsulfonylurea (Compound S70)

To chlorosulfonylisocyanate (1.1 g) in methylene chloride (10 ml) solution, 2-methyl-2-propanol (0.75 ml) was added under ice cooling and the mixture was stirred at that temperature for 10 hours. Triethylamine (2.2 ml) and 4-chloro-N-methylaniline (0.96 ml) were added to the reaction solution under ice cooling and the mixture was stirred at room temperature for 5 days. Distilled water was added to the reaction solution, then this was extracted with chloroform. The organic layer was washed with 1N hydrochloric acid and saturated saline, dried over with anhydrous magnesium sulfate, then concentrated. The residue was purified by silica gel column chromatography (hexane/ethyl acetate=6/1 to 1/1) to obtain the title compound (2.2 g).

Reference Example 71

N-(4-chlorophenyl)-N-methylsulfamide (Compound S71)

To the compound S70 (2.2 g), a 4M hydrochloric acid/1,4-dioxane solution (20 ml) was added and the mixture was stirred at room temperature for 1.5 hours. The reaction mixture was concentrated to obtain the title compound (1.5 g).

Reference Example 72

N-[(1R)-1-phenylethyl]urea (Compound S72)

To (1R)-1-phenylethylamine (1 g) and triethylamine (1.15 ml) in tetrahydrofuran (25 ml) solution, 4-nitrophenylchlorocarbonate (1.66 g) was added at −20° C. and the mixture was stirred at room temperature for 30 minutes. Further, 28% ammonia water (4 ml) was added to the reaction solution and the mixture was stirred at room temperature for 30 minutes. The tetrahydrofuran was distilled off in vacuo, and the mixture was extracted with ethyl acetate. The organic layer was successively washed with 2N sodium hydroxide aqueous solution, distilled water, saturated potassium hydrogensulfate aqueous solution, and saturated saline and dried over with anhydrous sodium sulfate, then concentrated. The residue was recrystallized from ethyl acetate/hexane to obtain the title compound (860 mg).

Reference Example 73

N-benzyloxycarbonyl-(1R)-1-(1H-tetrazol-5-yl)propylamine (Compound S73)

To N-benzyloxycarbonyl-(1R)-1-cyanopropylamine (85.6 mg) in suspension (3 ml), sodium azide (28 mg) and zinc bromide (88.3 mg) were added and the mixture was stirred under heating and reflux for 24 hours. 3N hydrochloric acid and ethyl acetate were added to the reaction solution and the mixture was stirred until there were no longer any insolubles. The obtained solution was extracted with ethyl acetate, then the organic layer was concentrated. 0.25N sodium hydroxide aqueous solution was added to the residue, the mixture was stirred for 30 minutes, and the insoluble compound was filtered. 6N hydrochloric acid was added to the filtrate to adjust to pH 1, then this was concentrated. The residue was diluted with 1N hydrochloric acid, then the solids were collected by filtration to obtain the title compound (60.4 mg).

Reference Example 74

(1R)-1-(1H-tetrazol-5-yl)propylamine Hydrochloride (Compound S74)

To the compound S73 (31.6 mg) in ethanol (2 ml) solution, 10% palladium carbon (4.7 mg) was added and the mixture was stirred under hydrogen atmosphere at room temperature for 4 days. The insoluble compound was filtered out, then the filtrate was concentrated. The residue was diluted with 4N hydrogen chloride/ethyl acetate solution, then concentrated. Distilled water was added to the residue, then the obtained aqueous solution was washed with ethyl acetate, then concentrated to obtain the title compound (20.8 mg).

NMR (DMSO-$d_6$): δ8.30 (3H, brs), 4.65 (1H, t, 7.2 Hz), 2.06-1.90 (2H, m), 0.81 (3H, t, 7.5 Hz)

MS: 128 (M+H)$^+$

Reference Example 75

Tert-butyl 2-fluoro-5-(1-nitropropyl)benzoate (Compound S75)

To tert-butyl 5-bromo-2-fluorobenzoate (1.26 g) in dimethoxyethane (22.9 ml) solution, tris(dibenzylideneacetone)dipalladium (0.10 g), 2-(di-tert-butylphosphino)-2'-methylbiphenyl (0.14 g), tripotassium phosphate (1.07 g), and 1-nitropropane (0.82 ml) were added, the mixture was stirred at room temperature for 1 minute, then the mixture was stirred under heating and reflux for 15 hours. The insoluble compound was filtered out, then the filtrate was concentrated. The residue was purified by silica gel column chromatography (hexane/ethyl acetate, ethyl acetate: 0 to 10%) to obtain the title compound (392 mg).

Reference Example 76 tert-butyl 2-fluoro-5-(N-hydroxypropanimidoyl)benzoate (Compound S76)

To the compound S75 (392 mg) in 1,4-dioxane (15 ml)/distilled water (1 ml) solution, potassium tert-butoxide (202 mg) was added and the mixture was stirred at room temperature for 45 hours. 1N hydrochloric acid was added to the reaction solution under ice cooling, and the mixture was extracted with ethyl acetate. The organic layer was washed with saturated saline, dried over with anhydrous sodium sulfate, then concentrated. Sodium acetate (255 mg) and hydroxylamine hydrochloride (159 mg) were added to the residue in ethanol (10 ml) solution, then the mixture was stirred under heating and reflux for 55 hours. The reaction solution was concentrated, then the residue was diluted with ethyl acetate. The obtained solution was successively washed with distilled water and saturated saline, dried over with anhydrous sodium sulfate, then concentrated. The residue was purified by silica gel column chromatography (hexane/ethyl acetate, ethyl acetate: 10 to 30%) to obtain the title compound (413 mg).

Reference Example 77 tert-butyl 5-(1-aminopropyl)-2-fluorobenzoate Hydrochloride (Compound S77)

A suspension of the compound S76 (413 mg) and 10% palladium carbon (124 mg) in ethanol (20 ml) was stirred at a 4 atm hydrogen atmosphere and the mixture was stirred at room temperature for 7 hours. The insoluble compound was filtered out, then the filtrate was concentrated. The residue was diluted with ethyl acetate, 4N hydrogen chloride/ethyl acetate solution (0.39 ml) was added, and the precipitate was collected by filtration to obtain the title compound (244 mg).

NMR (DMSO-$d_6$): δ8.41 (3H, br), 7.91 (1H, dd, 6.8, 2.2 Hz), 7.74-7.69 (1H, m), 7.35 (1H, dd, 10.5, 8.6 Hz), 4.20 (1H, dd, 9.0, 5.6 Hz), 1.99-1.85 (1H, m), 1.82-1.70 (1H, m), 1.51 (9H, s), 0.72 (3H, t, 7.4 Hz)

MS: 237 (M–$NH_2$)$^+$

Reference Example 78

Tert-butyl 4-(1-aminopropyl)-2-hydroxybenzoate (Compound S78)

Instead of the starting material compound of Reference Example 75, that is tert-butyl 5-bromo-2-fluorobenzoate, tert-butyl 4-bromo-2-hydroxybenzoate was used for successively the similar procedure as in Reference Example 75 to Reference Example 77 to obtain the title compound.

NMR (DMSO-$d_6$): δ7.69 (1H, d, J=8.2 Hz), 6.97 (1H, d, J=1.4 Hz), 6.92 (1H, dd, J=8.2, 1.4 Hz), 3.82 (1H, t, J=6.8 Hz), 3.31 (2H, br), 1.71-1.54 (2H, m), 1.57 (9H, s), 0.76 (3H, t, J=7.4 Hz)

MS: 235 (M–$NH_2$)$^+$

Reference Example 79

Tert-butyl 5-(1-aminopropyl)-2-aminobenzoate Dihydrochloride (Compound S79)

Instead of the starting material compound of Reference Example 75, that is, tert-butyl 5-bromo-2-fluorobenzoate, tert-butyl 5-chloro-2-nitrobenzoate was used for successively the similar procedure as in Reference Example 75 to Reference Example 77 to obtain the title compound.

NMR (DMSO-d$_6$): δ8.22 (3H, brs), 7.67 (1H, d, 1.2 Hz), 7.30 (1H, dd, 8.6, 1.2 Hz), 6.76 (1H, d, 8.6 Hz), 5.50-4.40 (3H, br), 3.95-3.86 (1H, m), 1.94-1.83 (1H, m), 1.79-1.65 (1H, m), 1.51 (9H, s), 0.72 (3H, t, 7.4 Hz)

MS: 234 (M−NH$_2$)$^+$

Reference Example 80 tert-butyl 4-(1-aminopropyl)-2-aminobenzoate (Compound S80)

Instead of the starting material compound of Reference Example 75, that is, tert-butyl 5-bromo-2-fluorobenzoate, tert-butyl 2-amino-4-chlorobenzoate was used for successively the similar procedure as in Reference Example 75 to Reference Example 77 to obtain the title compound.

NMR (CDCl$_3$): δ7.44 (1H, d, 8.3 Hz), 6.58 (1H, d, 1.6 Hz), 6.54 (1H, dd, 8.3, 1.6 Hz), 5.66 (2H, brs), 3.68 (1H, t, 6.7 Hz), 1.68-1.59 (2H, m), 1.56 (9H, s), 0.85 (3H, t, 7.3 Hz)

MS: 234 (M−NH$_2$)$^+$

Reference Example 81 tert-butyl 4-(1-aminopropyl)-2-fluorobenzoate Hydrochloride (Compound S81)

Instead of the starting material compound of Reference Example 75, that is, tert-butyl 5-bromo-2-fluorobenzoate, tert-butyl 4-bromo-2-fluorobenzoate was used for successively the similar procedure as in Reference Example 75 to Reference Example 77 to obtain the title compound.

NMR (DMSO-d$_6$): δ8.50 (3H, br), 7.83 (1H, t, 7.9 Hz), 7.48-7.44 (1H, m), 7.37 (1H, dd, 7.9, 1.4 Hz), 4.21 (1H, dd, 8.8, 5.7 Hz), 1.99-1.85 (1H, m), 1.83-1.71 (1H, m), 1.51 (9H, s), 0.73 (3H, t, 7.4 Hz)

MS: 237 (M−NH$_2$)$^+$

Reference Example 82 tert-butyl 3-[(1S)-1-hydroxypropyl]benzoate (Compound S82)

To the (1S,2R)-2-di-n-butylamino-1-phenyl-1-propanol (200 mg) in toluene (7 ml) solution, tert-butyl 3-formylbenzoate (3 g) in hexane (7 ml) solution was added and the mixture was stirred at room temperature for 20 minutes. Next, diethylzinc in 1N hexane solution (33 ml) was added to the reaction solution under ice cooling and the mixture was stirred at that temperature for 18 hours. Saturated ammonium chloride aqueous solution was added to the reaction solution, the mixture was stirred at 20 minutes, and 1N hydrochloric acid was added. The obtained mixed solution was extracted with ethyl acetate. The organic layer was dried over with anhydrous sodium sulfate, then concentrated to obtain the title compound (3.5 g).

Reference Example 83 tert-butyl 3-[(1R)-1-aminopropyl]benzoate L-tartrate (Compound S83)

To the compound S82 (4.5 g) in tetrahydrofuran (100 ml) solution, phthalimide (3.4 g), triphenylphosphine (6 g), and diethylazodicarboxylate (0.40% toluene solution) (10 g) were added and the mixture was stirred at room temperature for 4 hours. The reaction solution was concentrated, and the residue was purified by silica gel column chromatography (hexane/ethyl acetate=5/1). To the obtained compound (3.5 g) in methanol (25 ml) solution, hydrazine hydrate (1.6 ml) was added and the mixture was stirred under heating and reflux for 2 hours. The precipitate of the reaction solution was filtered out, and the filtrate was concentrated. The residue was diluted with ethyl acetate and was successively washed with distilled water and saturated saline. The organic layer was dried over with anhydrous sodium sulfate, then concentrated. The residue was diluted with methanol, L-tartaric acid (1.34 g) was added, then the mixture was concentrated. The obtained residue was recrystallized from ethyl acetate/ethanol to obtain the title compound (2.01 g).

NMR (DMSO-d$_6$): δ8.05 (1H, s), 8.01 (1H, d, J=7.7 Hz), 7.65 (1H, d, J=7.7 Hz), 7.57 (1H, t, J=7.7 Hz), 4.84 (3H, br), 4.26 (1H, dd, J=9.1, 6.0 Hz), 2.12-1.92 (2H, m), 1.61 (9H, s), 0.90 (3H, t, J=7.3 Hz)

MS: 219 (M−NH$_2$)$^+$

Reference Example 84 tert-butyl 3-[(1S)-1-aminopropyl]benzoate D-tartrate (Compound S84)

To tert-butyl 3-formylbenzoate (2.9 g) and R-(+)-phenyl lactic acid (1 g) in methylene chloride (30 ml) solution, titanium tetraisopropoxide (5.8 ml) and diethylzinc in 1M hexane solution (42 ml) were added under ice cooling and the mixture was stirred at room temperature for 16 hours. 1N hydrochloric acid was added to the reaction solution under ice cooling and the precipitated compound was filtered out. The filtrate was extracted with ethyl acetate. The organic layer was successively washed with saturated sodium hydrogencarbonate aqueous solution, distilled water, saturated potassium hydrogensulfate aqueous solution, and saturated saline, dried over with anhydrous sodium sulfate, then concentrated. The obtained compound (3.07 g) was used instead of the starting material of Reference Example 83, that is, the compound S82, while D-tartaric acid was used instead of L-tartaric acid for the similar procedure as in Reference Example 83 to obtain the title compound.

Reference Example 85 tert-butyl 5-[(1R)-1-aminopropyl]-2-furancarboxylate D-tartrate (Compound S85)

Instead of the starting material compound of Reference Example 82, that is, the tert-butyl 3-formylbenzoate, tert-butyl 5-formyl-2-furancarboxylate was used for the similar procedure as in Reference Example 82, while D-tartaric acid was used instead of L-tartaric acid for the similar procedure as in Reference Example 83 to obtain the title compound.

NMR (DMSO-d$_6$): δ8.25-7.30 (3H, br), 7.16 (1H, d, J=3.5 Hz), 6.59 (1H, d, J=3.5 Hz), 4.15 (1H, t, J=6.8 Hz), 3.95 (2H, s), 1.89-1.70 (2H, m), 1.51 (9H, s), 0.85 (3H, dt, J=7.3, 2.3 Hz)

MS: 226 (M+H)$^+$

Reference Example 86 tert-butyl 4-(1-aminopropyl)benzoate Hydrochloride (Compound S86)

To copper (I) iodide (3.1 g) in diethylether (70 ml) suspension, ethylmagnesium bromide (0.89M tetrahydrofuran solution) (35 ml) was added at −23° C. and the mixture was stirred at that temperature for 20 minutes. Next, tert-butyl 4-formylbenzoate (3 g) in diethylether (10 ml) solution was added to the reaction solution and the mixture was stirred at −23° C. for 30 minutes. Saturated ammonium chloride aqueous solution and 28% ammonia water were added to the reaction solution, the mixture was stirred at room temperature for 40 minutes, and the mixture was extracted with ethyl acetate. The organic layer was successively washed with distilled water and saturated saline, dried over with anhydrous sodium sulfate, then concentrated. The obtained compound (3.7 g) was used as an starting material instead of the starting material of Reference Example 83, that is, the compound S82, while 4N hydrochloric acid/ethyl acetate was used instead of L-tartaric acid for the similar procedure as in Reference Example 83 to obtain the title compound.

NMR (DMSO-$d_6$): δ8.04 (2H, d, J=8.4 Hz), 7.51 (2H, d, J=8.4 Hz), 4.84 (3H, br), 4.25 (1H, dd, J=9, 6 Hz), 2.10-1.90 (2H, m), 1.60 (9H, s), 0.90 (3H, t, J=7.4 Hz)
MS: 219 (M−$NH_2$)$^+$

Reference Example 87 tert-butyl 3-(1-aminopropyl)benzoate Hydrochloride (Compound S87)

Instead of the starting material compound of Reference Example 86, that is, tert-butyl 4-formylbenzoate, tert-butyl 3-formylbenzoate was used for the similar procedure as in Reference Example 86 to obtain the title compound.

NMR (DMSO-$d_6$): δ8.05 (1H, s), 8.01 (1H, d, J=7.7 Hz), 7.65 (1H, d, J=7.7 Hz), 7.57 (1H, t, J=7.7 Hz), 4.84 (3H, br), 4.26 (1H, dd, J=9.1, 6.0 Hz), 2.12-1.92 (2H, m), 1.61 (9H, s), 0.90 (3H, t, J=7.3 Hz)
MS: 219 (M−$NH_2$)$^+$

Reference Example 88 tert-butyl 3-(1-aminopropyl)-2-benzyloxybenzoate Hydrochloride (Compound S88)

Instead of the starting material compound of Reference Example 86, that is, tert-butyl 4-formylbenzoate, tert-butyl 2-benzyloxy-3-formylbenzoate was used for the similar procedure as in Reference Example 86 to obtain the title compound.
MS: 364 (M+Na)$^+$

Reference Example 89 tert-butyl 5-(1-aminopropyl)-2-benzyloxybenzoate Hydrochloride (Compound S89)

Instead of the starting material compound of Reference Example 86, that is tert-butyl 4-formylbenzoate, tert-butyl 2-benzyloxy-5-formylbenzoate was used for the similar procedure as in Reference Example 86 to obtain the title compound.

NMR (DMSO-$d_6$): δ7.66 (1H, d, J=2.5 Hz), 7.51-7.47 (3H, m), 7.39-7.30 (3H, m), 7.22 (1H, d, J=8.7 Hz), 5.19 (2H, s), 4.82 (3H, s), 4.14 (1H, dd, J=9.3, 5.9 Hz), 2.09-1.88 (2H, m), 1.50 (9H, s), 0.89 (3H, t, J=7.3 Hz)
MS: 364 (M+Na)$^+$

Reference Example 90 tert-butyl 5-(1-aminopropyl)-2-thiophencarboxylate Hydrochloride (Compound S90)

Instead of the starting material compound of Reference Example 86, that is, tert-butyl 4-formylbenzoate, tert-butyl 5-formylthiophencarboxylate was used for the similar procedure as in Reference Example 86 to obtain the title compound.

NMR (DMSO-$d_6$): δ8.67-8.43 (2H, br), 7.64 (1H, d, J=3.7 Hz), 7.28 (1H, d, J=3.7 Hz), 4.55-4.45 (1H, br), 2.04-1.77 (2H, m), 1.49 (9H, s), 0.80 (3H, t, J=7.4 Hz)
MS: 242 (M+H)$^+$

Reference Example 91 tert-butyl 5-(1-aminopropyl)-2-furancarboxylate Hydrochloride (Compound S91)

Instead of the starting material compound of Reference Example 86, that is, tert-butyl 4-formylbenzoate, tert-butyl 5-formylfurancarboxylate was used for the similar procedure as in Reference Example 86 to obtain the title compound.

NMR (DMSO-$d_6$): δ8.67-8.43 (2H, br), 7.17 (1H, d, J=3.5 Hz), 6.71 (1H, d, J=3.5 Hz), 4.41-4.31 (1H, br), 1.95-1.83 (2H, m), 1.49 (9H, s), 0.82 (3H, t, J=7.4 Hz)
MS: 226 (M+H)$^+$

Reference Example 92 tert-butyl 6-(1-aminopropyl)-2-pyridinecarboxylate Dihydrochloride (Compound S92)

Instead of the starting material compound of Reference Example 86, that is, tert-butyl 4-formylbenzoate, tert-butyl 6-formylpicolinate was used for the similar procedure as in Reference Example 86 to obtain the title compound.

NMR (CDCl$_3$): δ9.12-8.90 (3H, br), 7.96 (1H, d, J=7.7 Hz), 7.84 (1H, t, J=7.7 Hz), 7.57 (1H, d, J=7.7 Hz), 4.67-4.59 (1H, br), 2.40-2.25 (1H, m), 2.15-2.02 (1H, m), 1.59 (9H, s), 0.92 (3H, t, J=7.4 Hz)
MS: 237 (M+H)$^+$

Reference Example 93 tert-butyl 5-(1-aminopropyl)-nicotinate Dihydrochloride (Compound S93)

Instead of the starting material compound of Reference Example 86, that is, tert-butyl 4-formylbenzoate, tert-butyl 5-formyl nicotinate was used for the similar procedure as in Reference Example 86 to obtain the title compound.

NMR (DMSO-$d_6$): δ9.01 (1H, d, J=2.0 Hz), 8.87 (1H, d, J=2.2 Hz), 8.85-8.65 (3H, br), 8.42 (1H, brs), 4.41-4.32 (1H, br), 2.10-1.96 (1H, m), 1.92-1.79 (1H, m), 1.55 (9H, s), 0.75 (3H, t, J=7.4 Hz)
MS: 237 (M+H)$^+$

Reference Example 94

1-(3-tert-butoxyisoxazol-5-yl)propylamine (Compound S94)

Instead of the starting material compound of Reference Example 86, that is, tert-butyl 4-formylbenzoate, 3-tert-butoxy-5-isoxazole carboaldehyde was used for the similar procedure as in Reference Example 86 to obtain the title compound.

NMR (CDCl$_3$): δ5.65 (1H, s), 3.84 (1H, t, 6.6 Hz), 1.86-1.66 (2H, m), 1.52 (9H, s), 0.96 (3H, t, 7.5 Hz)

MS: 199 (M+H)$^+$

Reference Example 95

1-(4-bromo-3-nitrophenyl)-1-propanone (Compound S95)

To fuming nitric acid (200 ml), 1-(4-bromophenyl)-1-propanone (40 g) was added while keeping the inside temperature of the mixture at 5 to 10° C. The reaction solution was stirred at that temperature for 30 minutes and then poured into ice. The precipitate was collected by filtration, washed with distilled water, and recrystallized from methanol to obtain the title compound (18 g).

NMR (CDCl$_3$): δ8.38 (1H, d, J=2.0 Hz), 7.99 (1H, dd, J=8.2, 2.0 Hz), 7.86 (1H, d, J=8.2 Hz), 3.01 (2H, q, J=7.1 Hz), 1.25 (3H, t, J=7.1 Hz)

Reference Example 96

2-nitro-4-propionylbenzonitrile (Compound S96)

To the compound S95 (100 g) in N,N-dimethylformamide (200 ml) solution, copper cyanide (34.7 g) was added and stirred at 100° C. for 1 hour. Iron (III) chloride (180 g) in concentrated hydrochloric acid (45 ml)/distilled water (270 ml) solution was added to the reaction solution, the mixture was stirred at 70° C. for 30 minutes, then this was extracted with a hexane/ethyl acetate=1/2 mixed solvent. The organic layer was successively washed with 1N hydrochloric acid, 1N sodium hydroxide aqueous solution, and saturated saline, was filtered by a column packed with anhydrous sodium sulfate and silica gel, and the filtrate was concentrated. Methonal was added to the residue, then the mixture was ice-cooled. The precipitated solid was collected by filtration to obtain the title compound (33 g).

NMR (CDCl$_3$): δ8.84 (1H, d, J=1.6 Hz), 8.35 (1H, dd, J=7.9, 1.6 Hz), 8.04 (1H, d, J=7.9 Hz), 3.09 (2H, q, J=7.1 Hz), 1.29 (3H, t, J=7.1 Hz)

Reference Example 97

2-nitro-4-propionylbenzoic Acid (Compound S97)

A reaction mixture of the compound S96 (168 g), concentrated sulfuric acid (462 ml), and distilled water (378 ml) was stirred at 110° C. for 12 hours. The reaction solution was poured into ice water, then the mixture was extracted with ethyl acetate. The organic layer was extracted with 2N sodium hydroxide aqueous solution. The aqueous layer was neutralized by hydrochloric acid and the mixture was extracted with ethyl acetate. The organic layer was successively washed with saturated saline, dried over with anhydrous sodium sulfate, then concentrated. The residue was dried in vacuo to obtain the title compound (159 g).

NMR (CDCl$_3$): δ8.43 (1H, s), 8.3 (1H, d, J=7.9 Hz), 7.98 (1H, d, J=7.9 Hz), 3.14 (2H, q, J=7.0 Hz), 1.09 (3H, t, J=7.0 Hz)

Reference Example 98 tert-butyl 2-nitro-4-propionylbenzoate (Compound S98)

To magnesium sulfate (227 g) in methylene chloride (840 ml) suspension, concentrated sulfuric acid (20 ml) was added and the mixture was stirred at room temperature for 15 minutes. Next, the compound S97 (84 g) and tert-butyl alcohol (219 ml) were successively added to the mixture and the mixture was stirred at room temperature for 4 days. Silica gel was added to the reaction solution which was then filtered. The filtrate was concentrated, hexane was added to the residue, and the precipitated solid was collected by filtration to obtain the title compound (92 g).

NMR (CDCl$_3$): δ8.41 (1H, d, J=1.5 Hz), 8.2 (1H, dd, J=7.9, 1.5 Hz), 7.8 (1H, d, J=7.9 Hz), 3.04 (2H, q, J=7.2 Hz), 1.58 (9H, s), 1.26 (3H, t, J=7.2 Hz)

Reference Example 99 tert-butyl 4-[(1S)-1-hydroxypropyl]-2-nitrobenzoate (Compound S99)

To the compound S98 (139 g) in tetrahydrofuran (695 ml) solution, (−)-B-chlorodiisopinocampheylborane was added dropwise under ice cooling, then the mixture was stirred at that temperature for 2 hours. The reaction solution was concentrated, and the residue was diluted with diethylether (21). Diethanol amine (145 ml) was added to the obtained solution under ice cooling and the mixture was stirred at room temperature for 2 hours. The precipitate was filtered out, and the filtrate was concentrated. The residue was purified by silica gel column chromatography (hexane/ethyl acetate=10/1 to 4/1) to obtain the title compound (109 g).

NMR (CDCl$_3$): δ7.81 (1H, s), 7.71 (1H, d, J=7.9 Hz), 7.6 (1H, d, J=7.9 Hz), 4.79-4.70 (1H, m), 1.85-1.75 (2H, m), 1.56 (9H, s), 1.00-0.90 (3H, m)

Reference Example 100 tert-butyl 4-[(1R)-1-azide propyl]-2-nitrobenzoate (Compound S100)

To the compound S99 (109 g) in tetrahydrofuran (436 ml) solution, triethylamine (108 ml) and methanesulfonyl chloride (36 ml) were added under ice cooling and the mixture was stirred for 15 minutes. Distilled water was added to the reaction solution, and the mixture was extracted with ethyl acetate. The organic layer was washed with saturated saline, dried over with anhydrous sodium sulfate, then concentrated. To the thus obtained tert-butyl 4-[(1S)-1-[(methylsulfonyl)oxy]propyl-2-nitrobenzoate (137 g) in N,N-dimethylformamide (685 ml) solution, sodium azide (16.3 g) was added under ice cooling and the mixture was stirred at room temperature for 1 hour. Distilled water was added to the reaction solution, and the mixture was extracted with ethyl acetate. The organic layer was washed with saturated saline, dried over with anhydrous sodium sulfate, then concentrated. The residue was dried in vacuo to obtain the title compound (139 g).

NMR (CDCl$_3$): δ8.01 (1H, s), 7.74 (1H, d, J=8.1 Hz), 7.56 (1H, d, J=8.1 Hz), 4.5 (1H, t, J=7 Hz), 1.93-1.78 (2H, m), 1.56 (9H, s), 0.96 (3H, t, J=7.3 Hz)

Reference Example 101 tert-butyl 4-[(1R)-1-aminopropyl]-2-nitrobenzoate Hydrochloride (Compound S101)

To the compound S100 (139 g) in tetrahydrofuran (1.4l) solution, distilled water (70 ml) and triphenylphosphine (119 g) were added under ice cooling and the mixture was stirred at 50° C. for 20 hours. The reaction solution was concentrated, toluene and 0.5N hydrochloric acid were added, and the aqueous layer and the organic layer were separated. Hexane was added to the organic layer, and the mixture was extracted with 0.5N hydrochloric acid. A sodium hydroxide aqueous solution was added to the combined aqueous layer, then the obtained alkali aqueous solution was extracted with ethyl acetate. The organic layer was washed with saturated saline, dried over with anhydrous sodium sulfate, and concentrated to obtain tert-butyl 4-[(1R)-1-aminopropyl]-2-nitrobenzoate. The obtained tert-butyl 4-[(1R)-1-aminopropyl]-2-nitrobenzoate was diluted with ethyl acetate, 4N hydrogen chloride/ethyl acetate (110 ml) was added, and the precipitate was collected by filtration. The filtrate was recrystallized from N,N-dimethylformamide/ethyl acetate to obtain the title compound (45.8 g).

NMR (DMSO-$d_6$): δ8.66 (3H, br), 8.22 (1H, s), 7.96-7.89 (2H, m), 4.38 (1H, dd, 8.9, 5.8 Hz), 2.04-1.93 (1H, m), 1.92-1.80 (1H, m), 1.50 (9H, s), 0.77 (3H, t, 7.4 Hz)

MS: 281 (M+H)$^+$

Reference Example 102 tert-butyl 2-amino-4-[(1R)-1-aminopropyl]benzoate D-tartrate (Compound S102)

The tert-butyl 4-[(1R)-1-aminopropyl]-2-nitrobenzoate (4.66 g) obtained at the step of Reference Example 101 was dissolved in ethanol (150 ml), 10% palladium carbon (1 g) was added, and the mixture was stirred under hydrogen atmosphere at room temperature for 8 hours. The insoluble compound was filtered out, and the filtrate was concentrated. Ethanol was added to the residue and the mixture was stirred under heating and reflux until dissolving. Next, ethyl acetate was added, the mixture was cooled to room temperature, and the precipitated crystal was collected by filtration to obtain the title compound (5.42 g).

NMR (CDCl$_3$): δ7.67 (1H, d, J=8.2 Hz), 6.73 (1H, d, J=1.4 Hz), 6.67 (2H, s), 6.58 (1H, dd, J=8.2, 1.4 Hz), 3.96-3.89 (1H, m), 3.85 (2H, s), 1.92-1.64 (2H, m), 1.52 (9H, s), 0.76 (3H, t, J=7.4 Hz)

MS: 234 (M−NH$_2$)$^+$

Reference Example 103 tert-butyl 5-[(1R)-1-aminopropyl]-nicotinate D-tartrate (Compound S103)

Instead of the starting material of Reference Example 56, that is, the compound S55, the 5-bromonicotinic acid was used for the similar procedure as in Reference Example 56. To the obtained tert-butyl 5-bromonicotinate (22.4 g), dimethylacetoamide (112 ml), tris(dibenzylideneacetone)dipalladium (1.59 g), zinc cyanide (6.1 g), diphenylphosphinoferrocene (1.92 g), and zinc powder (0.68 g) were added and the mixture was stirred under argon atmosphere at 120° C. for 1.5 hours. The reaction solution was filtered by sellite, which was then washed with ethyl acetate, and the filtrate was washed with saturated saline. The organic layer was dried over with anhydrous sodium sulfate, then concentrated. The obtained residue was purified by silica gel column chromatography (hexane/ethyl acetate=3/1) to obtain tert-butyl 5-cyanonicotinate (13.1 g).

To copper (I) iodide (1.0 g) in tetrahydrofuran (18 ml) suspension, ethylmagnesium bromide (0.86M tetrahydrofuran solution (12.3 ml) was added under cooling at −20° C., the mixture was stirred at 0° C. for 30 minutes, then the tert-butyl 5-cyanonicotinate (0.9 g) obtained above in tetrahydrofuran (9 ml) solution was added at the similar temperature. After stirring for 1 hour, saturated ammonium chloride aqueous solution and ethyl acetate were added to the mixture and the solution separated. The aqueous layer was extracted with ethyl acetate, while the combined organic layer was washed with saturated saline, then was dried over with anhydrous sodium sulfate and concentrated. The obtained residue was purified by silica gel column chromatography (hexane/ethyl acetate=3/1). The obtained tert-butyl 5-propionylnicotinate was used successively instead of the starting material compound of Reference Example 99, that is, the compound S98, for the similar procedure as in Reference Example 99 and Reference Example 100, then D-tartaric acid was used instead of the 4N hydrogen chloride/ethyl acetate used as the reagent in Reference Example 101 for the similar procedure as in Reference Example 101 to obtain the title compound.

NMR (DMSO-$d_6$): δ8.99 (1H, d, J=2.0 Hz), 8.81 (1H, d, J=2.1 Hz), 8.33 (1H, t, J=2.0 Hz), 7.75-6.95 (3H, br), 4.31 (0.5H, d, J=2.6 Hz), 4.18 (1H, t, J=6.4 Hz), 4.04-3.99 (0.5H, br), 3.86 (1H, s), 1.95-1.71 (2H, m), 1.57 (9H, s), 0.78 (3H, t, J=7.4 Hz)

MS: 237 (M+H)$^+$

Reference Example 104 tert-butyl 5-[(1R)-1-aminopropyl]-3-furancarboxylate D-tartrate (Compound S104)

To 3-furancarboxylic acid (1.12 g), nitromethane (10 ml), indium (III) trifluoromethane sulfonate (56 mg), lithium perchlorate (1.06 g), and propionic anhydride (1.28 ml) were added and the mixture was stirred at 50° C. for 3 hours. Water was added to the reaction solution and the solution separated. The aqueous layer was extracted with ethyl acetate. The combined organic layer was washed with saturated saline, dried over with anhydrous sodium sulfate, and concentrated. The obtained 5-propionyl-3-furancarboxylic acid was used instead of the starting material of Reference Example 56, that is, the compound S55, for the similar procedure as in Reference Example 56 to obtain tert-butyl 5-propionyl-3-furancarboxylate. This was used instead of the starting material compound of Reference Example 99, that is, the compound S98, for the similar procedure as in Reference Example 99 and Reference Example 100, then D-tartaric acid was used successively instead of the 4N hydrogen chloride/ethyl acetate used as the reagent in Reference Example 101 for the similar procedure as in Reference Example 101 to obtain the title compound.

NMR (DMSO-$d_6$): δ8.28 (1H, s), 6.65 (1H, s), 4.12 (1H, t, J=6.3 Hz), 3.91 (2H, s), 1.89-1.72 (2H, m), 1.50 (9H, s), 0.82 (3H, t, J=7.4 Hz)

MS: 209 (M−NH$_2$)$^+$

Reference Example 105 tert-butyl 2-[(1R)-1-aminopropyl]-isonicotinate D-tartrate (Compound S105)

Instead of the starting material compound of Reference Example 103, that is, 5-bromonicotinic acid, 2-chloroisonicotinic acid was used for the similar procedure as in Reference Example 103 to obtain the title compound.

NMR (DMSO-d$_6$): δ8.81 (1H, d, J=4.9 Hz), 7.90 (1H, d. J=1.5 Hz), 7.77 (1H, dd, J=4.9, 1.5 Hz), 4.39 (1H, t, J=6.8 Hz), 3.83 (2H, s), 1.90-1.76 (2H, m), 1.57 (9H, s), 0.80 (3H, t, J=7.5 Hz)

MS: 237 (M+H)$^+$

Reference Example 106 tert-butyl 6-[(1R)-1-aminopropyl]-nicotinate D-tartrate (Compound S106)

Instead of the starting material compound of Reference Example 103, that is, 5-bromonicotinic acid, 6-chloronicotinic acid was used for the similar procedure as in Reference Example 103 to obtain the title compound.

NMR (DMSO-d$_6$): δ9.04 (1H, d, J=2.1 Hz), 8.29 (1H, dd. J=8.1, 2.1 Hz), 7.62 (1H, d, J=8.1 Hz), 4.34 (1H, t, J=6.8 Hz), 3.84 (2H, s), 1.90-1.74 (2H, m), 1.57 (9H, s), 0.79 (3H, t, J=7.5 Hz)

MS: 237 (M+H)$^+$

Reference Example 107 tert-butyl 5-[(1S)-1-hydroxypropyl]-thiophen-3-carboxylate (Compound S107)

Instead of the starting material compound of Reference Example 104, that is, 3-furan carboxylic acid, 3-thiophencarboxylic acid was used for the similar procedure as in Reference Example 104 to obtain tert-butyl 5-propionyl-3-thiophencarboxylate.

To (R)-tetrahydro-1-methyl-3,3-diphenyl-1H,3H-pyrrolo[1,2-c][1,3,2]oxaborole (1M toluene solution) (21 μl) in toluene (0.21 ml) solution, a boranedimethylaniline complex (74 μl) was added under ice cooling, then the tert-butyl 5-propionyl-thiophen-2-carboxylate (100 mg) obtained by the above procedure in tetrahydrofuran (0.5 ml) solution was added dropwise and the mixture was stirred at that temperature for 1 hour. Methanol was added to the reaction solution, the mixture was stirred for 10 minutes, then 1N hydrochloric acid was added and the mixture was extracted with ethyl acetate. The organic layer was washed with saturated saline, dried over with anhydrous sodium sulfate, then concentrated. The residue was purified by silica gel column chromatography (hexane/ethyl acetate=3/1) to obtain the title compound (97.8 mg).

Reference Example 108 tert-butyl 5-[(1R)-1-aminopropyl]-thiophen-3-carboxylate D-tartrate (Compound S108)

Instead of the starting material of Reference Example 100, that is, the compound S99, the compound S107 was used for the similar procedure as with Reference Example 100, then further, instead of the 4N hydrogen chloride/ethyl acetate used as the reagent in Reference Example 101, D-tartaric acid was used for the similar procedure as in Reference Example 101 to obtain the title compound.

NMR (DMSO-d$_6$): δ8.17 (1H, s), 7.41 (1H, s), 4.35 (1H, t, J=7.8 Hz), 3.93 (2H, s), 1.92-1.70 (2H, m), 1.51 (9H, s), 0.84 (3H, t, J=7.3 Hz)

MS: 225 (M+H)$^+$

Reference Example 109

4-(1-aminopropyl)aniline hydrochloride (Compound S109)

To 1-(4-aminophenyl)propan-1-on oxime (2.75 g) in ethanol (60 ml) solution, 10% palladium carbon (280 mg) was added, then the mixture was stirred under 4 to 5 atm hydrogen atmosphere at room temperature for 16 hours. The insoluble compound was filtered out, then a 4N hydrogen chloride/1,4-dioxane solution (6 ml) was added to the filtrate. The ethanol was distilled off in vacuo, then the precipitate was collected by filtration to obtain the title compound (1.2 g).

NMR (DMSO-d$_6$): δ8.55 (3H, brs), 7.51 (2H, d, J=8.3 Hz), 7.27 (2H, d, J=8.3 Hz), 4.12-4.01 (1H, m), 2.00-1.89 (1H, m), 1.84-1.70 (1H, m), 0.71 (3H, t, J=7.4 Hz)

MS: 134 (M–NH$_2$)$^+$

Reference Example 110

1-(3-aminosulfonylphenyl)propylamine Hydrochloride (Compound S110)

To 3-aminosulfonylbenzoic acid (4.0 g), N,N-dimethylformamide (53 ml), 1-(3-dimethylaminopropyl)-3-ethylcarbodiimide hydrochloride (3.8 g), 1-hydroxybenzotriazole (2.7 g), N,O-dimethylhydroxylamine hydrochloride (1.9 g), and triethylamine (2.8 ml) were added under ice cooling and the mixture was stirred at room temperature for 12 hours. A potassium hydrogensulfate aqueous solution and ethyl acetate were added to the reaction solution and the mixture was separated. The aqueous layer was extracted with ethyl acetate. The combined organic layer was successively washed with distilled water, saturated sodium hydrogencarbonate aqueous solution, and saturated saline, dried over with anhydrous sodium sulfate, then concentrated. The obtained residue was purified by silica gel column chromatography (hexane/ethyl acetate=1/2). To the obtained N-methoxy-N-methyl-3-aminosulfonylbenzamide (1.8 g), tetrahydrofuran (36 ml) and ethyl magnesium bromide (0.89M tetrahydrofuran solution, 41 ml) were added under ice cooling, the mixture was stirred at room temperature for 3 hours, then saturated ammonium chloride aqueous solution and ethyl acetate were added to reaction solution, the mixture was separated, then organic layer was successively washed with saturated saline, dried over with anhydrous sodium sulfate, then concentrated. The obtained residue was purified by silica gel column chromatography (hexane/ethyl acetate=1/1). To the obtained 3-propionylbenzenesulfonamide (0.97 g), ethanol (2.5 ml), sodium acetate (0.56 g), and hydroxylamine hydrochloride (0.35 g) were added and the mixture was stirred at 90° C. for 3 hours. Ethyl acetate and water were added to the reaction solution, the mixture was separated, then the organic layer was successively washed with saturated saline, dried over with anhydrous sodium sulfate, then concentrated. The obtained 3-(N-hydroxypropanimidoyl)benzenesulfonamide was used instead of the starting material compound of Reference Example 109, that is, 1-(4-aminophenyl)propan-1-on oxime, for the similar procedure as with Reference Example 109 to obtain the title compound.

NMR (DMSO-d$_6$): δ8.50-8.36 (3H, br), 7.92 (1H, s), 7.83 (1H, d, J=7.5 Hz), 7.71-7.60 (2H, m), 7.42 (2H, s), 4.33-4.21 (1H, br), 2.00-1.70 (2H, m), 0.75 (3H, t, J=7.4 Hz)

MS: 215 (M+H)$^+$

Reference Example 111

1-(4-aminosulfonylphenyl)propylamine Hydrochloride (Compound S111)

Instead of the starting material compound of Reference Example 110, that is, 3-aminosulfonylbenzoic acid, 4-aminosulfonylbenzoic acid was used for the similar procedure as with Reference Example 110 to obtain the title compound.

NMR (DMSO-$d_6$): δ8.60-8.45 (3H, br), 7.85 (2H, d, J=8.2 Hz), 7.63 (2H, d, J=8.2 Hz), 7.39 (2H, s), 4.29-4.20 (1H, br), 2.03-1.74 (2H, m), 0.74 (3H, t, J=7.4 Hz)

MS: 215 (M+H)$^+$

Reference Example 112

1-(3-methane sulfonylphenyl)propylamine Hydrochloride (Compound S112)

To 1-(3-methane sulfonylphenyl)propan-1-one (188 g), ethanol (4.7 ml), sodium acetate (1.09 g), and hydroxylamine hydrochloride (0.68 g) were added and the mixture was stirred at 90° C. for 3 hours. Ethyl acetate and water were added to the reaction solution, the mixture was separated, then the organic layer was successively washed with saturated saline, dried over with anhydrous sodium sulfate, then concentrated. The obtained 1-(3-methane sulfonylphenyl)propan-1-one oxime was used instead of the starting material compound 1-(4-aminophenyl)propan-1-on oxime of Reference Example 109 for the similar procedure as with Reference Example 109 to obtain the title compound.

NMR (DMSO-$d_6$): δ8.55-8.35 (2H, br), 8.06 (1H, s), 7.94 (1H, d, J=7.6 Hz), 7.80 (1H, brd, J=8.3 Hz), 7.71 (1H, t, J=7.6 Hz), 4.38-4.29 (1H, br), 3.22 (3H, s), 2.03-1.78 (2H, m), 0.76 (3H, t, J=7.3 Hz)

MS: 214 (M+H)$^+$

Reference Example 113

1-(4-methane sulfonylphenyl)propylamine Hydrochloride (Compound S113)

Instead of the starting material compound of Reference Example 112, that is, 1-(3-methane sulfonylphenyl)propan-1-on, 1-(4-methane sulfonylphenyl)propan-1-on was used for the similar procedure as in Reference Example 112 to obtain the title compound.

NMR (DMSO-$d_6$): δ8.60-8.40 (2H, br), 7.99 (2H, d, J=8.3 Hz), 7.72 (2H, d, J=8.3 Hz), 4.33-4.23 (1H, br), 3.22 (3H, s), 2.02-1.72 (2H, m), 0.75 (3H, t, J=7.4 Hz)

MS: 214 (M+H)$^+$

Reference Example 114 tert-butyl 3-(1-aminopropyl)-4-methoxybenzoate (Compound S114)

Instead of the starting material of Reference Example 56, that is, the compound S55, 3-bromo-4-methoxybenzoic acid was used for the similar procedure as in Reference Example 56, Reference Example 75, Reference Example 76, and Reference Example 164 to obtain the title compound.

NMR (CDCl$_3$): δ7.88 (1H, d, 1.7 Hz), 7.85 (1H, dd, 8.5, 1.7 Hz), 6.84 (1H, d, 8.5 Hz), 4.05 (1H, t, 6.9 Hz), 3.86 (3H, s), 1.82-1.60 (2H, m), 1.56 (9H, S), 0.88 (3H, s, 7.4 Hz)

MS: 249 (M–NH$_2$)$^+$

Reference Example 115 tert-butyl 4-[(1R)-1-aminopropyl]-2-nitrobenzoate Hydrochloride (Compound S101)

A mixed solution of the compound S97 (703 mg), (R)-2,2'-bis(di-4-methylphenylphosphino)-1,1'-binaphthyl ruthenium (II) chloride complex (51 mg), ammonium formate (3.15 g), and 2M ammonia/methanol solution (20 ml) was stirred under a nitrogen atmosphere at 85° C. for 18 hours. Next, ethyl formate (4 ml) was added to the reaction solution and the mixture was stirred at 85° C. for 18 hours. The reaction solution was concentrated, saturated potassium hydrogensulfate aqueous solution and saturated saline were added, and the mixture was extracted with ethyl acetate. The organic layer was dried over with anhydrous sodium sulfate, then concentrated. Ethanol (10 ml), distilled water (2.5 ml), and concentrated hydrochloric acid (2.5 ml) were added to the residue, the mixture was stirred at 85° C. for 40 minutes, then the reaction solution was concentrated to obtain 4-[(1R)-1-aminopropyl]-2-nitrobenzoic acid hydrochloride (745 mg). To 500 mg of the obtained 4-[(1R)-1-aminopropyl]-2-nitrobenzoic acid hydrochloride, methylene chloride (20 ml) and anhydrous magnesium sulfate (3.5 g) were added and the mixture was stirred at room temperature for 15 minutes. Next, concentrated sulfuric acid (186 μl) was added to the reaction solution, the mixture was stirred at room temperature for 5 minutes, then isobutene (3.5 ml) was added and the mixture was stirred at room temperature for 24 hours. Saturated sodium hydrogencarbonate aqueous solution was added to the reaction solution and the mixture was extracted with ethyl acetate. The organic layer was washed with saturated saline, dried over with anhydrous sodium sulfate, then concentrated. The residue was diluted with ethyl acetate, then 4N hydrogen chloride/ethyl acetate solution (0.5 ml) was added dropwise in the obtained solution. The precipitate was collected by filtration to obtain the title compound (358 mg).

NMR (DMSO-$d_6$): δ8.66 (3H, br), 8.22 (1H, s), 7.96-7.89 (2H, m), 4.38 (1H, dd, 8.9, 5.8 Hz), 2.04-1.93 (1H, m), 1.92-1.80 (1H, m), 1.50 (9H, s), 0.77 (3H, t, 7.4 Hz)

MS: 281 (M+H)$^+$

Reference Example 116 tert-butyl 4-[(1R)-1-isocyanatepropyl]-2-nitrobenzoate (Compound S116)

Saturated sodium hydrogencarbonate aqueous solution (15 ml) was added to the compound S101 (1 g) in methylene chloride (15 ml) solution under ice cooling and the mixture was stirred at that temperature for 10 minutes. Next, under ice cooling, trichloromethyl chloroformate (0.38 ml) was added to the reaction solution and the mixture was stirred at that temperature for 20 minutes. The reaction solution was extracted with methylene chloride. The extract was washed with saturated saline, dried over with anhydrous sodium sulfate, and concentrated to obtain the title compound as a crude product (1.02 g).

NMR (CDCl$_3$): δ7.76 (1H, d, J=1.7 Hz), 7.73 (1H, d, J=7.9 Hz), 7.57 (1H, dd, J=7.9, 1.7 Hz), 4.73 (1H, dd, J=7.5, 5.4 Hz), 1.95-1.80 (2H, m), 1.56 (9H, s), 1.01 (3H, t, J=7.3 Hz)

Reference Example 117

N-[(2E)-3-(5-chloro-2-methoxyphenyl)-2-({[(4-chlorophenyl)sulfonyl]amino}carbonyl)-2-propenyl]-2,2,2-trifluoroacetoamide (Compound S117)

To the compound S6 (620 mg) and 4-chlorobenzenesulfonamide (350 mg) in methylene chloride (10 ml) solution, 4-dimethylaminopyridine (225 mg) and 1-(3-dimethylaminopropyl)-3-ethylcarbodiimide hydrochloride (460 mg) were added and the mixture was stirred at room temperature for 2 hours. The methylene chloride was distilled off in vacuo, then ethyl acetate was added. The ethyl acetate solution was successively washed with distilled water, saturated potassium hydrogensulfate aqueous solution, distilled water, and saturated saline, dried over with anhydrous sodium sulfate, then concentrated. The residue was dried in vacuo to obtain the title compound (1.04 g).

Reference Example 118

N-(2-chloro-5-{[((2E)-3-(5-chloro-2-methoxyphenyl)-2-{[(trifluoroacetyl)amino]methyl}-2-propenoyl)amino]sulfonyl}phenyl)-2,2,2-trifluoroacetoamide (Compound S118)

Instead of the starting material compound of Reference Example 117, that is, 4-chlorobenzenesulfonamide, the compound S57 was used for the similar procedure as in Reference Example 117 to obtain the title compound.

Reference Example 119 tert-butyl (2E)-2-({[(4-chlorophenyl)sulfonyl]amino}carbonyl)-3-(4-fluorophenyl)-2-propenylcarbamate (Compound S119)

Instead of the compound S6 of Reference Example 117, the compound S26 was used for the similar procedure as in Reference Example 117 to obtain the title compound.
NMR (CDCl$_3$): δ8.07 (2H, d, J=8.6 Hz), 7.8 (1H, s), 7.5 (2H, d, J=8.6 Hz), 7.21 (2H, dd, J=8.7, 5.4 Hz), 7.1 (2H, t, J=8.7 Hz), 4.91 (1H, br), 4.11 (2H, d, J=6.9 Hz), 1.5 (9H, s)

Reference Example 120

N-[(2E)-2-(aminomethyl)-3-(4-fluorophenyl)-2-propenoyl]-4-chlorobenzenesulfonamide Hydrochloride (Compound S120)

A 1M hydrogen chloride/acetic acid solution (10 ml) was added to the compound S119 (828 mg) and the mixture was stirred at room temperature for 1.5 hours. The reaction solution was diluted with diethylether and the mixture was stirred under ice cooling for 30 minutes. The precipitated solid was collected by filtration to obtain the title compound (614 mg).
NMR (CD3OD): δ8.08 (2H, d, J=8.7 Hz), 7.86 (1H, s), 7.63 (2H, d, J=8.7 Hz), 7.47 (2H, dd, J=8.7, 5.3 Hz), 7.24 (2H, t, J=8.7 Hz), 3.87 (2H, s)

Reference Example 121

Allyl(2E)-2-({[(4-chlorophenyl)sulfonyl]amino}carbonyl)-3-(4-methoxymethoxyphenyl)-2-propenylcarbamate (Compound S121)

To the compound S32 (1.2 g) and 4-chlorobenzenesulfonamide (710 mg) in methylene chloride (25 ml) solution, 4-dimethylaminopyridine (460 mg) and 1-(3-dimethylaminopropyl)-3-ethylcarbodiimide hydrochloride (930 mg) were added and the mixture was stirred at room temperature for 1.5 hours. The methylene chloride was distilled off in vacuo, then ethyl acetate was added. The ethyl acetate solution was successively washed with distilled water, saturated potassium hydrogensulfate aqueous solution, distilled water, and saturated saline, dried over with anhydrous sodium sulfate, then concentrated. The residue was dried in vacuo to obtain the title compound (1.88 g).
NMR (CDCl$_3$): δ8.07 (2H, d, J=8.6 Hz), 7.7 (1H, s), 7.5 (2H, d, J=8.6 Hz), 7.30-7.21 (2H, m), 7.06 (2H, d, J=8.7 Hz), 5.92 (1H, ddd, J=16.0, 10.0, 5.7 Hz), 5.33 (1H, d, J=16.0 Hz), 5.26 (1H, d, J=10.0 Hz), 5.25-5.15 (3H, m), 4.65 (2H, d, J=5.7 Hz), 4.2 (2H, d, J=6.7 Hz), 3.47 (3H, s)

Reference Example 122

2-bromo-N-[(2E)-3-(5-chloro-2-methoxyphenyl)-2-({[(4-chlorophenyl)sulfonyl]amino}carbonyl)-2-propenyl]acetoamide (Compound S122)

To the compound S117 (1.01 g) in methanol (9 ml) solution, 2N sodium hydroxide aqueous solution (2.2 ml) was added and the mixture was stirred at room temperature for 2 hours. The methanol was distilled off in vacuo, the mixture was diluted with methylene chloride (15 ml), then bromoacetyl chloride (0.18 ml) was added under ice cooling and the mixture was stirred at that temperature for 20 minutes. Next, methylene chloride was distilled off in vacuo and the remaining aqueous mixture was extracted with ethyl acetate. The organic layer was successively washed with saturated sodium hydrogencarbonate aqueous solution, saturated saline, saturated potassium hydrogensulfate aqueous solution, saturated saline, dried over with anhydrous sodium sulfate, and concentrated to obtain the title compound (930 mg).

Reference Example 123

N-[(2E)-2-(aminomethyl)-3-(4-methoxymethoxyphenyl)-2-propenoyl]-4-chlorobenzenesulfonamide Hydrochloride (Compound S123)

To the compound S121 (500 mg) in tetrahydrofuran (15 ml) suspension, formic acid (0.12 ml), triphenylphosphine (52 mg), and tris(dibenzylideneacetone)dipalladium (46 mg) were added and the mixture was stirred at room temperature for 2 hours. A 4M hydrogen chloride/dioxane solution was added to the reaction solution, then tetrahydrofuran was distilled off in vacuo. The residue was diluted with methanol, then the insoluble compound was filtered out and the filtrate was concentrated. The residue was recrystallized from methanol/diethylether to obtain the title compound (216 mg).

Reference Example 124

2-bromo-N-[(2E)-2-({[(4-chlorophenyl)sulfonyl]amino}carbonyl)-3-(4-fluorophenyl)-2-propenyl]acetoamide (Compound S124)

To the compound S120 (599 mg) in methylene chloride (10 ml)/distilled water (3 ml) solution, triethylamine (0.6 ml) and bromoacetyl bromide (0.19 ml) were added under ice cooling and the mixture was stirred at room temperature for 20 minutes. The reaction solution was diluted with ethyl acetate, was successively dried by saturated sodium hydrogencarbonate aqueous solution, distilled water, saturated potassium hydrogensulfate aqueous solution, distilled water, and saturated saline, dried over with anhydrous sodium sulfate, then concentrated. The residue was washed with hexane/ethyl acetate to obtain the title compound as a crude product (522 mg).

NMR (DMSO-d6): δ8.46 (1H, br), 7.97 (2H, d, J=8.6 Hz), 7.71 (2H, d, J=8.6 Hz), 7.60-7.50 (3H, m), 7.27 (2H, t, J=8.8 Hz), 3.99 (2H, d, J=5.0 Hz), 3.77 (2H, s)

Example 1

(6E)-6-(5-chloro-2-methoxybenzylidene)-4-[(4-chlorophenyl)sulfonyl]-1,4-diazepan-2,5-dione (Compound 1)

To the compound S122 (915 mg) in N,N-dimethylformamide (50 ml) solution, sodium hydride (60% mineral oil dispersion) (80 mg) was added and the mixture was stirred at 60 to 80° C. for 19 hours. Acetic acid (1 ml) was added to the reaction solution and the mixture concentrated. Ethyl acetate was added to the residue, then the obtained solution was successively washed with saturated sodium hydrogencarbonate aqueous solution, distilled water, saturated potassium hydrogensulfate aqueous solution, and saturated saline, dried over with anhydrous sodium sulfate, then concentrated. The residue was recrystallized from ethyl acetate to obtain the title compound (373 mg).

NMR (DMSO-d$_6$): δ8.07-8.02 (1H, br), 7.95 (2H, d, J=8.6 Hz), 7.75 (2H, d, J=8.6 Hz), 7.54 (1H, s), 7.47 (1H, dd, J=8.8, 2.5 Hz), 7.27 (1H, d, J=2.5 Hz), 7.11 (1H, d, J=8.8 Hz), 4.72 (2H, s), 4.18 (2H, d, J=4.2 Hz), 3.80 (3H, s), 3.31 (2H, s)

MS: 455 (M+H)$^+$

The β-amino acid derivative and sulfonamide derivative shown in Table I as starting material compounds were used for the synthesis methods shown in Table I to obtain the title compounds of Examples 2 to 21. Note that the β-amino acid derivative and sulfonamide derivative shown in Table I are compounds shown in the reference examples, commercially available compounds, or compounds obtained by derivation from the commercially available compounds by known methods.

The Synthesis Method A of Table I is a method successively performing operations similar to Reference Example 117, Reference Example 122, and Example 1, while the Synthesis Method B is a method successively performing operations similar to Reference Example 119, Reference Example 120, Reference Example 124, and Example 1.

TABLE I

| Ex. No. | β-amino acid derivative used as starting material | Sulfonamide derivative used as starting material | Synthesis method |
|---|---|---|---|
| Ex. 2 | Compound S26 | 4-Cl-C$_6$H$_4$-SO$_2$NH$_2$ | B |
| Ex. 3 | Compound S25 | 4-Cl-C$_6$H$_4$-SO$_2$NH$_2$ | B |
| Ex. 4 | Compound S8 | 4-CN-C$_6$H$_4$-SO$_2$NH$_2$ | A |
| Ex. 5 | Compound S9 | 4-Cl-C$_6$H$_4$-SO$_2$NH$_2$ | A |
| Ex. 6 | Compound S10 | 4-Cl-3-NO$_2$-C$_6$H$_3$-SO$_2$NH$_2$ | A |
| Ex. 7 | Compound S31 | 4-Cl-C$_6$H$_4$-SO$_2$NH$_2$ | B |
| Ex. 8 | Compound S6 | 4-Cl-2-OMe-C$_6$H$_3$-SO$_2$NH$_2$ | A |
| Ex. 9 | Compound S6 | 4-Cl-2-F-C$_6$H$_3$-SO$_2$NH$_2$ | A |
| Ex. 10 | Compound S6 | Compound S66 | A |
| Ex. 11 | Compound S6 | 4-Cl-C$_6$H$_4$-CH$_2$-SO$_2$NH$_2$ | A |
| Ex. 12 | Compound S6 | Compound S69 | A |
| Ex. 13 | Compound S10 | 6-Cl-pyridin-3-yl-SO$_2$NH$_2$ | A |

TABLE I-continued

| Ex. No. | β-amino acid derivative used as starting material | Sulfonamide derivative used as starting material | Synthesis method |
|---|---|---|---|
| Ex. 14 | Compound S10 | 5-chloro-2-thiophenesulfonamide (H₂N-SO₂-thiophene-Cl) | A |
| Ex. 15 | Compound S6 | 5-chloro-4-fluoro-2-methoxybenzenesulfonamide | A |
| Ex. 16 | Compound S6 | 2,5-dimethoxybenzenesulfonamide | A |
| Ex. 17 | Compound S6 | 2-methoxy-5-methylbenzenesulfonamide | A |
| Ex. 18 | Compound S6 | 2-methoxy-5-(trifluoromethyl)benzenesulfonamide | A |
| Ex. 19 | Compound S6 | 2-methoxy-5-nitrobenzenesulfonamide | A |
| Ex. 20 | Compound S12 | 4-chlorobenzenesulfonamide | A |
| Ex. 21 | Compound S10 | methyl 3-(aminosulfonyl)propanoate (H₂N-SO₂-CH₂CH₂-C(O)-O-CH(CH₃)... methyl ester) | A |

Example 2

(6E)-6-(4-fluorobenzylidene)-4-[(4-chlorophenyl)sulfonyl]-1,4-diazepan-2,5-dione (Compound 2)

NMR (CDCl$_3$): δ8.03 (2H, d, J=8.6 Hz), 7.62 (1H, s), 7.52 (2H, d, J=8.6 Hz), 7.27-7.21 (2H, m), 7.12 (2H, t, J=8.6 Hz), 5.91-5.84 (1H, br), 4.7 (2H, s), 4.32 (2H, d, J=4.4 Hz)
MS: 409 (M+H)$^+$

Example 3

(6E)-4-[(4-chlorophenyl)sulfonyl]-6-(2-naphthylmethylene)-1,4-diazepan-2,5-dione (Compound 3)

NMR (CDCl$_3$): δ8.05 (2H, d, J=8.7 Hz), 7.90-7.81 (4H, m), 7.74 (1H, s), 7.58-7.50 (4H, m), 7.35 (1H, dd, J=8.5, 1.4 Hz), 5.92-5.87 (1H, br), 4.74 (2H, s), 4.44 (2H, d, J=3.8 Hz)
MS: 441 (M+H)$^+$

Example 4

4-{[(6E)-6-benzylidene-3,7-dioxo-1,4-diazepan-1-yl]sulfonyl}benzonitrile (Compound 4)

NMR (DMSO-d$_6$): δ8.17 (2H, d, J=8.4 Hz), 8.15-8.05 (1H, br), 8.11 (2H, d, J=8.4 Hz), 7.56 (1H, s), 7.51-7.38 (5H, m), 4.75 (2H, s), 4.3 (2H, d, J=4.3 Hz)
MS: 382 (M+H)$^+$
Melting point: 239° C. (decomposition)

Example 5

(6E)-6-(5-chloro-2-nitrobenzylidene)-4-[(4-chlorophenyl)sulfonyl]-1,4-diazepan-2,5-dione (Compound 5)

NMR (CDCl$_3$): δ8.18 (1H, d, J=8.8 Hz), 8.02 (2H, d, J=8.7 Hz), 7.72 (1H, s), 7.58-7.52 (3H, m), 7.23 (1H, d, J=2 Hz), 5.82 (1H, br), 4.69 (2H, s), 4.05 (1H, d, J=4.4 Hz), 4.04 (1H, d, J=4.3 Hz)
MS: 470 (M+H)$^+$

Example 6

(6E)-4-[(4-dimethylamino-3-nitrophenyl)sulfonyl]-6-(5-fluoro-2-methoxybenzylidene)-1,4-diazepan-2,5-dione (Compound 6)

NMR (DMSO-d$_6$): δ8.28 (1H, d, J=2.4 Hz), 8.04 (1H, br), 7.86 (1H, dd, J=9.3, 2.4 Hz), 7.56 (1H, s), 7.31 (1H, d, J=9.3 Hz), 7.26 (1H, dt, J=8.8, 3 Hz), 7.13-7.07 (2H, m), 4.68 (2H, s), 4.17 (2H, d, J=4.5 Hz), 3.79 (3H, s), 2.96 (6H, s)
MS: 493 (M+H)$^+$

Example 7

(6E)-4-[(4-chlorophenyl)sulfonyl]-6-(3-cyanobenzylidene)-1,4-diazepan-2,5-dione (Compound 7)

NMR (DMSO-$d_6$): δ8.09 (1H, br), 7.96 (2H, d, J=8.7 Hz), 7.90-7.84 (2H, m), 7.77-7.63 (4H, m), 7.50 (1H, s), 4.70 (2H, s), 4.28-4.24 (2H, m)
MS: 416 (M+H)$^+$

Example 8

(6E)-6-(5-chloro-2-methoxybenzylidene)-4-[(4-chloro-2-methoxyphenyl)sulfonyl]-1,4-diazepan-2,5-dione (Compound 8)

NMR (CDCl$_3$): δ8.06 (1H, d, J=8.6 Hz), 7.69 (1H, s), 7.32 (1H, dd, J=8.9, 2.5 Hz), 7.12 (1H, dd, J=8.6, 1.8 Hz), 7.04 (1H, d, J=2.5 Hz), 6.99 (1H, d, J=1.8 Hz), 6.85 (1H, d, J=8.9 Hz), 5.88 (1H, br), 4.77 (2H, s), 4.18 (2H, d, J=4.5 Hz), 3.94 (3H, s), 3.80 (3H, s)
MS: 485 (M+H)$^+$

Example 9

(6E)-4-[(4-chloro-2-fluorophenyl)sulfonyl]-6-(5-chloro-2-methoxybenzylidene)-1,4-diazepan-2,5-dione (Compound 9)

NMR (DMSO-$d_6$): δ8.08 (1H, t, J=4.3 Hz), 8.00 (1H, t, J=8.3 Hz), 7.83 (1H, dd, J=10.3, 1.8 Hz), 7.62-7.58 (2H, m), 7.47 (1H, dd, J=9.0, 2.5 Hz), 7.27 (1H, d, J=2.5 Hz), 7.12 (1H, d, J=9.0 Hz), 4.70 (2H, s), 4.18 (2H, d, J=4.3 Hz), 3.8 (3H, s)
MS: 473 (M+H)$^+$

Example 10

N-(2-chloro-5-{[(6E)-6-(5-chloro-2-methoxybenzylidene)-3,7-dioxo-1,4-diazepan-1-yl]sulfonyl}phenyl)-N'-ethylurea (Compound 10)

NMR (DMSO-$d_6$): δ8.90 (1H, d, J=2.2 Hz), 8.31 (1H, s), 8.05 (1H, br), 7.68 (1H, d, J=8.4 Hz), 7.53 (1H, s), 7.46 (1H, dd, J=9.0, 2.5 Hz), 7.41 (1H, dd, J=8.4, 2.2 Hz), 7.27 (1H, d, J=2.5 Hz), 7.15 (1H, t, J=5.2 Hz), 7.11 (1H, d, J=9.0 Hz), 4.68 (2H, s), 4.17 (2H, br), 3.80 (3H, s), 3.20-3.11 (2H, m), 1.09 (3H, t, J=7.2 Hz)
MS: 541 (M+H)$^+$

Example 11

(6E)-4-[(4-chlorobenzyl)sulfonyl]-6-(5-chloro-2-methoxybenzylidene)-1,4-diazepan-2,5-dione (Compound 11)

NMR (CDCl$_3$): δ7.76 (1H, s), 7.39-7.32 (5H, m), 7.10 (1H, d, J=2.5 Hz), 6.89 (1H, d, J=8.9 Hz), 5.96 (1H, br), 4.83 (2H, s), 4.11 (2H, d, J=4.2 Hz), 4.02 (2H, s), 3.86 (3H, s)
MS: 469 (M+H)$^+$

Example 12

(6E)-6-(5-chloro-2-methoxybenzylidene)-4-{[4-(1H-pyrazol-3-yl)phenyl]sulfonyl}-1,4-diazepan-2,5-dione (Compound 12)

NMR (DMSO-$d_6$): δ13.15 (1H, br), 8.10-8.00 (3H, m), 7.95 (2H, d, J=8.4 Hz), 7.85 (1H, br), 7.52 (1H, d, J=2.1 Hz), 7.45 (1H, dd, J=8.9, 2.5 Hz), 7.27 (1H, d, J=2.5 Hz), 7.10 (1H, d, J=8.9 Hz), 6.89 (1H, d, J=2.1 Hz), 4.73 (2H, s), 4.18 (2H, d, J=3.7 Hz), 3.78 (3H, s)
MS: 487 (M+H)$^+$

Example 13

(6E)-4-[(6-chloro-3-pyridyl)sulfonyl]-6-(5-fluoro-2-methoxybenzylidene)-1,4-diazepan-2,5-dione (Compound 13)

NMR (DMSO-$d_6$): δ8.93 (1H, d, J=2.5 Hz), 8.36 (1H, dd, J=8.5, 2.5 Hz), 8.12 (1H, br), 7.86 (1H, d, J=8.5 Hz), 7.59 (1H, s), 7.27 (1H, dt, J=8.7, 3.1 Hz), 7.12-7.07 (2H, m), 4.72 (2H, s), 4.18 (2H, d, J=4.1 Hz), 3.79 (3H, s)
MS: 440 (M+H)$^+$

Example 14

(6E)-4-[(5-chloro-2-thienyl)sulfonyl]-6-(5-fluoro-2-methoxybenzylidene)-1,4-diazepan-2,5-dione (Compound 14)

NMR (CDCl$_3$): δ7.77 (1H, s), 7.72 (1H, d, J=4.1 Hz), 7.12-7.06 (1H, m), 6.96 (1H, d, J=4.1 Hz), 6.90-6.82 (2H, m), 5.97 (1H, br), 4.61 (2H, s), 4.209 (1H, d, J=4.5 Hz), 4.208 (1H, d, J=3.7 Hz), 3.82 (3H, s)
MS: 445 (M+H)$^+$
Melting point: 150-153° C.

Example 15

(6E)-4-[(5-chloro-4-fluoro-2-methoxyphenyl)sulfonyl]-6-(5-chloro-2-methoxybenzylidene)-1,4-diazepan-2,5-dione (Compound 15)

NMR (CDCl$_3$): δ8.21 (1H, d, J=8.1 Hz), 7.72 (1H, s), 7.33 (1H, dd, J=8.8, 2.5 Hz), 7.05 (1H, d, J=2.5 Hz), 6.86 (1H, d, J=8.8 Hz), 6.80 (1H, d, J=10.3 Hz), 5.90 (1H, br), 4.76 (2H, s), 4.19 (2H, d, J=4.4 Hz), 3.93 (3H, s), 3.81 (3H, s)
MS: 503 (M+H)$^+$

Example 16

(6E)-6-(5-chloro-2-methoxybenzylidene)-4-[(2,5-dimethoxyphenyl)sulfonyl]-1,4-diazepan-2,5-dione (Compound 16)

NMR (CDCl$_3$): δ7.65 (1H, s), 7.64 (1H, d, J=3.0 Hz), 7.32 (1H, dd, J=8.8, 2.6 Hz), 7.13 (1H, dd, J=9.0, 3.0 Hz), 7.06 (1H, d, J=2.6 Hz), 6.94 (1H, d, J=9.0 Hz), 6.85 (1H, d, J=8.8 Hz), 5.88 (1H, br), 4.77 (2H, s), 4.177 (1H, d, J=3.8 Hz), 4.176 (1H, d, J=4.5 Hz), 3.90 (3H, s), 3.85 (3H, s), 3.80 (3H, s)
MS: 481 (M+H)$^+$

Example 17

(6E)-6-(5-chloro-2-methoxybenzylidene)-4-[(2-methoxy-5-methylphenyl)sulfonyl]-1,4-diazepan-2,5-dione (Compound 17)

NMR (CDCl$_3$): δ7.94 (1H, d, J=2.0 Hz), 7.66 (1H, s), 7.37 (1H, dd, J=8.5, 2.0 Hz), 7.31 (1H, dd, J=8.9, 2.5 Hz), 7.05 (1H, d, J=2.5 Hz), 6.90 (1H, d, J=8.5 Hz), 6.85 (1H, d, J=8.9 Hz), 5.91 (1H, br), 4.78 (2H, s), 4.17 (2H, d, J=4.0 Hz), 3.91 (3H, s), 3.79 (3H, s), 2.38 (3H, s)
MS: 465 (M+H)$^+$

Example 18

(6E)-6-(5-chloro-2-methoxybenzylidene)-4-{[2-methoxy-5-(trifluoromethyl)phenyl]sulfonyl}-1,4-diazepan-2,5-dione (Compound 18)

NMR (CDCl$_3$): δ8.42 (1H, d, J=2.0 Hz), 7.83 (1H, dd, J=8.8, 2.0 Hz), 7.71 (1H, s), 7.32 (1H, dd, J=8.8, 2.5 Hz), 7.1 (1H, d, J=8.8 Hz), 7.05 (1H, d, J=2.5 Hz), 6.86 (1H, d, J=8.8 Hz), 5.97 (1H, br), 4.79 (2H, s), 4.20 (2H, d, J=4.4 Hz), 4.01 (3H, s), 3.81 (3H, s)
MS: 519 (M+H)$^+$

Example 19

(6E)-6-(5-chloro-2-methoxybenzylidene)-4-[(2-methoxy-5-nitrophenyl)sulfonyl]-1,4-diazepan-2,5-dione (Compound 19)

NMR (CDCl$_3$): δ9.04 (1H, d, J=2.8 Hz), 8.47 (1H, dd, J=9.1, 2.8 Hz), 7.75 (1H, s), 7.33 (1H, dd, J=8.8, 2.5 Hz), 7.12 (1H, d, J=9.1 Hz), 7.04 (1H, d, J=2.5 Hz), 6.86 (1H, d, J=8.8 Hz), 5.80 (1H, br), 4.80 (2H, s), 4.22 (2H, d, J=4.4 Hz), 4.08 (3H, s), 3.81 (3H, s)
MS: 496 (M+H)$^+$

Example 20

(6E)-6-(3-chloro-5-fluoro-2-methoxybenzylidene)-4-[(4-chlorophenyl)sulfonyl]-1,4-diazepan-2,5-dione (Compound 20)

NMR (CDCl$_3$): δ8.03 (2H, d, J=8.8 Hz), 7.60 (1H, s), 7.53 (2H, d, J=8.8 Hz), 7.19 (1H, dd, J=7.7, 3.0 Hz), 7.78 (1H, dd, J=8.3, 3.0 Hz), 5.8 (1H, br), 4.72 (2H, s), 4.153 (1H, d, J=3.6 Hz), 1.151 (1H, d, J=4.7 Hz), 3.72 (3H, s)
MS: 473 (M+H)$^+$

Example 21

Methyl 3-{[(6E)-6-(5-fluoro-2-methoxybenzylidene)-3,7-dioxo-1,4-diazepan-1-yl]sulfonyl}propanoatetartrate (Compound 21)

NMR (CDCl$_3$): δ7.83 (1H, s), 7.10 (1H, dt, J=8.9, 3.0 Hz), 6.92-6.86 (2H, m), 5.92 (1H, br), 4.56 (2H, s), 4.252 (1H, d, J=3.7 Hz), 4.251 (1H, d, J=4.6 Hz), 3.98 (2H, t, J=7.4 Hz), 3.85 (3H, s), 3.73 (3H, s), 2.88 (2H, t, J=7.4 Hz)
MS: 415 (M+H)$^+$

Example 22

(6E)-4-[(3-amino-4-chlorophenyl)sulfonyl]-6-(5-chloro-2-methoxybenzylidene)-1,4-diazepan-2,5-dione (Compound 22)

To the compound S118 (2.25 g), methanol (20 ml) and a 2M sodium hydroxide aqueous solution (5.8 ml) were added, the mixture was stirred at room temperature for 23 hours, then the mixture was further stirred at 60° C. for 7 hours. The methanol was distilled off in vacuo, methylene chloride (20 ml) was added to the remaining aqueous solution, bromoacetyl bromide (0.35 ml) was further added under ice cooling, then the mixture was stirred at that temperature for 20 minutes. The methylene chloride was distilled off in vacuo, ethyl acetate and saturated sodium hydrogencarbonate aqueous solution were added to the remaining solution, and the aqueous layer and the organic layer were separated. The organic layer was washed with saturated saline, dried over with anhydrous sodium sulfate, and diluted with N,N-dimethylformamide (100 ml). The ethyl acetate was distilled off in vacuo. The remaining N,N-dimethylformamide solution was stirred at 60° C. for 14 hours. The reaction solution was concentrated, then the residue was diluted with ethyl acetate. The obtained solution was successively washed with distilled water and saturated saline, dried over with anhydrous sodium sulfate, then concentrated. The residue was purified by silica gel column chromatography (chloroform/acetone=4/1) to obtain the title compound (520 mg).

NMR (DMSO-d$_6$): δ8.04 (1H, t, J=4.4 Hz), 7.54 (1H, s), 7.46 (1H, dd, J=9.0, 2.5 Hz), 7.47-7.41 (2H, m), 7.27 (1H, d, J=2.5 Hz), 7.11 (1H, d, J=9.0 Hz), 6.98 (1H, dd, J=8.3, 2.2 Hz), 5.96 (2H, s), 4.66 (2H, s), 4.16 (2H, d, J=4.4 Hz), 3.8 (3H, s)
MS: 470 (M+H)$^+$

Reference Example 125 tert-butyl (2E)-2-({[(4-chloroanilino)carbonyl]amino}carbonyl)-3-(5-chloro-2-methoxyphenyl)-2-propenylcarbamate (Compound S125)

To N-(4-chlorophenyl)urea (1.9 g) in N,N-dimethylformamide (35 ml) solution, sodium hydride (60% mineral oil dispersion) (460 mg) was added and the mixture was stirred at room temperature for 1 hour. Next, to the reaction mixture, a mixed solution obtained by adding 1,1'-carbonyldiimidazole (1.9 g) to the compound S23 (4 g) in tetrahydrofuran (35 ml) solution under ice cooling and stirring the mixture at room temperature for 45 minutes was added and the reaction mixture was stirred at room temperature for 16 hours. The reaction mixture was diluted with ethyl acetate and saturated potassium hydrogensulfate aqueous solution, and the obtained solution was separated. The organic layer was washed with saturated saline, dried over with anhydrous sodium sulfate, then concentrated. The residue was purified by silica gel column chromatography (hexane/ethyl acetate=1/1) to obtain the title compound (2.6 g).

NMR (CDCl$_3$): δ10.79 (1H, br), 9.46 (1H, br), 7.7 (1H, s), 7.5 (2H, d, J=8.8 Hz), 7.33 (1H, dd, J=8.8, 2.5 Hz), 7.30-7.20 (3H, m), 6.87 (1H, d, J=8.8 Hz), 4.92 (1H, br), 4.15 (2H, d, J=6.4 Hz), 3.84 (3H, s), 1.46 (9H, s)

Reference Example 126

2-bromo-N-[(2E)-2-({[(4-chloroanilino)carbonyl]amino}carbonyl)-3-(5-chloro-2-methoxyphenyl)-2-propenyl]acetoamide (Compound S126)

A mixed solution of the compound S125 (2.6 g) and a 1M hydrochloric acid/acetic acid solution (15 ml) was stirred at room temperature for 1 hour. The reaction solvent was distilled off in vacuo. The residue was diluted with methylene chloride (50 ml) and distilled water (10 ml), bromoacetyl chloride (0.5 ml) and triethylamine (1.7 ml) were added to the obtained solution under ice cooling, and the mixture was stirred at that temperature for 20 minutes. The reaction solution was diluted with N,N-dimethylformamide and ethyl acetate, was successively washed with distilled water, saturated sodium hydrogencarbonate aqueous solution, distilled water, saturated potassium hydrogensulfate aqueous solution, and saturated saline, dried over with anhydrous sodium sulfate, then concentrated. The residue was washed with ethyl acetate to obtain the title compound (2.5 g).

NMR (DMSO-$d_6$): δ10.8 (1H, s), 10.69 (1H, s), 8.55 (1H, br), 7.65-7.55 (3H, m), 7.51 (1H, s), 7.45 (1H, dd, J=9.0, 2.2 Hz), 7.4 (2H, d, J=8.8 Hz), 7.12 (1H, d, J=9.0 Hz), 4.09 (2H, d, J=5.0 Hz), 3.86 (2H, s), 3.82 (3H, s)

Example 23

(6E)-6-(5-chloro-2-methoxybenzylidene)-N-(4-chlorophenyl)-3,7-dioxo-1,4-diazepan-1-carboxamide (Compound 23)

To the compound S126 (2.08 g) in N,N-dimethylformamide (150 ml) solution, sodium hydride (60% mineral oil dispersion) (150 mg) was added. The mixture was stirred at room temperature for 30 minutes, then warmed to 60° C. and stirred for 1 hour. Next, acetic acid (0.5 ml) was added to the reaction solution and the mixture concentrated. The residue was diluted with ethyl acetate. The obtained solution was successively washed with saturated sodium hydrogencarbonate aqueous solution, distilled water, saturated potassium hydrogensulfate aqueous solution, and saturated saline, dried over with anhydrous sodium sulfate, then concentrated. The residue was recrystallized from hexane/ethyl acetate to obtain the title compound (1.26 g).

NMR (CDCl$_3$): δ11.23 (1H, s), 7.52 (2H, d, J=8.8 Hz), 7.48 (1H, s), 7.35 (1H, dd, J=8.8, 2.5 Hz), 7.29 (2H, d, J=8.8 Hz), 7.14 (1H, d, J=2.5 Hz), 6.89 (1H, d, J=8.8 Hz), 5.90-5.84 (1H, br), 4.74 (2H, s), 4.30 (2H, dd, J=3.3, 1.9 Hz), 3.87 (3H, s)

MS: 434 (M+H)$^+$

Example 24

(6E)-6-(5-chloro-2-methoxybenzylidene)-3,7-dioxo-N-[(1R)-1-phenylethyl]-1,4-diazepan-1-carboxamide (Compound 24) (Enantiomer of Compound 25)

Instead of the starting material compound of Reference Example 125, that is, N-(4-chlorophenyl)urea, the compound S72 was used to successively perform the similar procedures as with Reference Example 125, Reference Example 126, and Example 23 to obtain the title compound.

NMR (CDCl$_3$): δ9.41 (1H, d, J=7.4 Hz), 7.40 (1H, s), 7.37-7.21 (6H, m), 7.11 (1H, d, J=2.4 Hz), 6.87 (1H, d, J=8.8 Hz), 6.53-6.47 (1H, br), 5.12-5.03 (1H, m), 4.71 (1H, d, J=16.5 Hz), 4.57 (1H, d, J=16.5 Hz), 4.23 (2H, t, J=1.4 Hz), 3.84 (3H, s), 1.58 (3H, d, J=6.9 Hz)

MS: 428 (M+H)$^+$

Example 25

(6E)-6-(5-chloro-2-methoxybenzylidene)-3,7-dioxo-N-[(1S)-1-phenylethyl]-1,4-diazepan-1-carboxamide (Compound 25) (Enantiomer of Compound 24)

Instead of the starting material compound of Reference Example 125, that is, N-(4-chlorophenyl)urea, N-[(1S)-1-phenylethyl]urea was used to successively perform the similar procedures as with Reference Example 125, Reference Example 126, and Example 23 to obtain the title compound.

MS: 428 (M+H)$^+$

Example 26

(6E)-6-(5-chloro-2-methoxybenzylidene)-N-(5-chloro-2-pyridyl)-3,7-dioxo-1,4-diazepan-1-carboxamide (Compound 26)

Instead of the starting material compound of Reference Example 125, that is, N-(4-chlorophenyl)urea, N-(2-pyridyl)urea was used to successively perform the similar procedures as with Reference Example 125, Reference Example 126, and Example 23 to obtain the title compound.

NMR (DMSO-$d_6$): δ11.68 (1H, s), 8.40 (1H, d, J=2.5 Hz), 8.03 (1H, d, J=9.0 Hz), 7.98 (1H, dd, J=9.0, 2.5 Hz), 7.93-7.89 (1H, br), 7.51 (1H, s), 7.47 (1H, dd, J=8.8, 2.6 Hz), 7.39 (1H, d, J=2.6 Hz), 7.14 (1H, d, J=8.8 Hz), 4.59 (2H, s), 4.21 (2H, s), 3.84 (3H, s)

MS: 435 (M+H)$^+$

Reference Example 127 tert-butyl (2E)-3-(5-chloro-2-methoxyphenyl)-2-{[(trifluoroacetyl)amino]methyl}-2-propenoate (Compound S127)

To the compound S6 (2.81 g) in methylene chloride (15 ml)/tert-butyl alcohol (15 ml) solution, N,N'-diisopropyl-O-tert-butylisourea (7 ml) was added and the mixture was stirred at room temperature for 17 hours. The reaction solution was concentrated, the precipitate was removed by filtration, then the filtrate was concentrated. The residue was purified by silica gel column chromatography (hexane/ethyl acetate, ethyl acetate: 10 to 20%) to obtain the title compound (1.79 g).

Reference Example 128 tert-butyl (2E)-3-(5-chloro-2-methoxyphenyl)-2-{[methyl(trifluoroacetyl)amino]methyl}-2-propenoate (Compound S128)

To the compound S127 (1.79 g) in tetrahydrofuran (50 ml) solution, sodium hydride (60% mineral oil dispersion) (0.2 g) was added under ice cooling and the mixture was stirred at that temperature for 10 minutes. Next, methyl iodide (0.42 ml) was added to the reaction solution under ice cooling, and the mixture was stirred at room temperature for 14 hours. Distilled water was added to the reaction solution and the mixture was extracted with ethyl acetate. The organic layer was washed with saturated saline, dried over with anhydrous magnesium sulfate, then concentrated. The residue was purified by silica gel column chromatography (hexane/ethyl acetate, ethyl acetate: 10 to 50%) to obtain the title compound (1.62 g).

Reference Example 129 tert-butyl (2E)-3-(5-chloro-2-methoxyphenyl)-2-[(methylamino)methyl]-2-propenoate (Compound S129)

To the compound S128 (1.62 g) in ethanol (50 ml) solution, 1N sodium hydroxide aqueous solution was added and the mixture was stirred at room temperature for 3 hours. The reaction solution was concentrated, distilled water was added to the residue, and the mixture was extracted with ethyl acetate. The organic layer was washed with saturated saline, dried over with anhydrous magnesium sulfate, then concentrated to obtain the title compound (1.21 g).

Reference Example 130 tert-butyl (2E)-2-{[{[(tert-butoxycarbonyl)amino]acetyl}(methyl)amino]methyl}-3-(5-chloro-2-methoxyphenyl)-2-propenoate (Compound S130)

To the compound S129 (1.21 g) in methylene chloride (50 ml) solution, N-tert-butoxycarbonyl glycine (0.68 g) and 1-(3-dimethylaminopropyl)-3-ethylcarbodiimide hydrochloride (0.89 g) were added and the mixture was stirred at room temperature for 15 hours. The reaction solution was concentrated, distilled water was added to the residue, and the mixture was extracted with ethyl acetate. The organic layer was washed with saturated saline, dried over with anhydrous magnesium sulfate, then concentrated. The residue was purified by silica gel column chromatography (hexane/ethyl acetate, ethyl acetate: 20 to 50%) to obtain the title compound (1.58 g).

Reference Example 131

(2E)-2-{[(aminoacetyl)(methyl)amino]methyl}-3-(5-chloro-2-methoxyphenyl)-2-propenoic Acid (Compound S131)

A mixed solution of the compound S130 (1.58 g) and a 4N hydrogen chloride/1,4-dioxane solution (50 ml) was stirred at room temperature for 22 hours. The reaction solution was concentrated, diethylether was added to the precipitated solid, and the insoluble compound was collected by filtration to obtain the title compound (1.09 g).

Reference Example 132

(6E)-6-(5-chloro-2-methoxybenzylidene)-1-methyl-1,4-diazepan-2,5-dione (Compound S132)

To the compound S131 (1.09 g) in methylene chloride (312 ml) solution, 1-(3-dimethylaminopropyl)-3-ethylcarbodiimide hydrochloride (1.2 g) and 1-hydroxybenzotriazole (0.84 g) were added and the mixture was stirred at room temperature for 19 hours. The reaction solution was concentrated, distilled water was added to the residue, and the mixture was extracted with ethyl acetate. The organic layer was successively washed with saturated potassium hydrogensulfate aqueous solution, saturated saline, saturated sodium hydrogencarbonate aqueous solution, and saturated saline, dried over with anhydrous magnesium sulfate, then concentrated. Diethylether was added to the precipitated solid, and the insoluble compound was collected by filtration to obtain the title compound (0.61 g).
NMR (DMSO-$d_6$): δ8.19 (1H, br), 7.62 (1H, s), 7.42 (1H, dd, J=8.9, 2.5 Hz), 7.22 (1H, d, J=2.5 Hz), 7.11 (1H, d, J=8.9 Hz), 4.32 (2H, s), 3.88 (2H, d, J=5.5 Hz), 3.81 (3H, s), 2.69 (3H, s)

Reference Example 133

4-nitrophenyl(6E)-6-(5-chloro-2-methoxybenzylidene)-4-methyl-3,7-dioxo-1,4-diazepan-1-carboxylate (Compound S133)

To the compound S132 (503 mg) in tetrahydrofuran (40 ml) solution, p-nitrophenyl chlorocarbonate (2.58 g) and triethylamine (1.78 ml) were added in stages until the compound of Reference Example 132 disappeared. The mixture was stirred at room temperature for a total of 23 hours. The reaction solution was concentrated, distilled water was added to the residue, and the mixture was extracted with ethyl acetate. The organic layer was washed with saturated saline, dried over with anhydrous magnesium sulfate, then concentrated. The residue was purified by silica gel column chromatography (hexane/ethyl acetate, ethyl acetate: 50 to 100%) to obtain the title compound (225 mg).

Example 27

(6E)-6-(5-chloro-2-methoxybenzylidene)-4-methyl-3,7-dioxo-N-[(1R)-1-phenylethyl]-1,4-diazepan-1-carboxamide (Compound 27)

To the compound S133 (103 mg) in 1,4-dioxane (5 ml) suspension, (R)-(+)-1-phenylethylamine (29 µl) was added and the mixture was stirred at room temperature for 2.5 hours. The reaction solution was concentrated, then the residue was purified by silica gel column chromatography (hexane/ethyl acetate, ethyl acetate: 50% to 100%) to obtain the title compound (101 mg).
NMR (DMSO-$d_6$): δ9.37 (1H, d, J=7.3 Hz), 7.45 (1H, dd, J=8.9, 2.6 Hz), 7.39-7.31 (6H, m), 7.29-7.22 (1H, m), 7.12 (1H, d, J=8.9 Hz), 4.95-4.86 (1H, m), 4.58 (1H, d, J=15.4 Hz), 4.53 (1H, d, J=15.4 Hz), 4.38 (1H, d, J=16.8 Hz), 4.33 (1H, d, J=16.8 Hz), 3.81 (3H, s), 2.78 (3H, s), 1.44 (3H, d, J=6.9 Hz)
MS: 442 (M+H)$^+$

Example 28

(6E)-N-benzyl-6-(5-chloro-2-methoxybenzylidene)-N,4-dimethyl-3,7-dioxo-1,4-diazepan-1-carboxamide (Compound 28)

Instead of the starting material compound of Example 27, that is, (R)-(+)-1-phenylethylamine, N-methylbenzylamine was used for the similar procedure as with Example 27 to obtain the title compound.
NMR (DMSO-$d_6$): δ7.65 (1H, br), 7.45 (1H, dd, J=8.8, 2.5 Hz), 7.40-7.31 (4H, m), 7.30-7.25 (2H, m), 7.13 (1H, d, J=8.8 Hz), 4.58 (2H, br), 4.38 (2H, br), 4.30 (2H, br), 3.82 (3H, s), 2.78 (6H, s)
MS: 422 (M+H)$^+$

Example 29

6-(5-chloro-2-methoxybenzyl)-4-[(4-chlorophenyl)sulfonyl]-1,4-diazepan-2,5-dione (Compound 29)

To the compound 1 (1.26 g) in tetrahydrofuran (400 ml) solution, 5% platinum carbon (sulfided catalyst) (400 mg) was added and the mixture was stirred under hydrogen atmosphere at room temperature for 15 hours. Next, the catalyst was filtered out and the filtrate was concentrated. The residue was purified by silica gel column chromatography (hexane/ethyl acetate=3/2 to 2/1), then the obtained purified product was recrystallized from hexane/ethyl acetate to obtain the title compound (915 mg).
NMR (CDCl$_3$): δ7.96 (2H, d, J=8.7 Hz), 7.52 (2H, d, J=8.7 Hz), 7.19 (1H, dd, J=8.8, 2.6 Hz), 7.01 (1H, d, J=2.6 Hz), 6.77 (1H, d, J=8.8 Hz), 5.71 (1H, br), 5.00 (1H, d, J=17.7 Hz), 4.39 (1H, d, J=17.7 Hz), 3.79 (3H, s), 3.50-3.40 (1H, m), 3.26-3.09 (3H, m), 2.52 (1H, dd, J=14.1, 9.1 Hz)
MS: 457 (M+H)$^+$
Melting point: 110-112° C.

As the starting material compounds, the benzylidene derivatives or β-amino acid derivatives and sulfonamide derivatives shown in Table II to Table VI were used by the synthesis methods shown in Table II to Table VI to obtain the compounds of Example 30 to Example 89. Note that the β-amino acid derivatives, sulfonamide derivatives, and benzylidene derivatives shown in Table II to Table VI are compounds shown in the reference examples or examples and commercially available compounds or compounds obtained by derivation from commercially available compounds by known methods.

The Synthesis Method C shown in Table II to Table VI is a method the similar as that of Example 29, the Synthesis Method D is a method successively performing the similar procedures as Reference Example 119, Reference Example 120, Reference Example 124, Example 1, and Example 29, and the Synthesis Method E is a method successively performing the similar procedures as in Reference Example 117, Reference Example 122, Example 1, and Example 29.

TABLE II

| Ex. no. | Benzylidene derivative used as material | β-amino acid derivative used as material | Sulfonamide derivative used as material | Synthesis method |
|---|---|---|---|---|
| Ex. 30 | — | Compound S7 | 4-Cl, 4-H$_2$NO$_2$S-C$_6$H$_3$ | D |
| Ex. 31 | — | Compound S28 | 4-Cl, 4-H$_2$NO$_2$S-C$_6$H$_3$ | D |
| Ex. 32 | — | Compound S27 | 4-Cl, 4-H$_2$NO$_2$S-C$_6$H$_3$ | D |
| Ex. 33 | Compound 2 | — | — | C |
| Ex. 34 | — | Compound S24 | 4-Cl, 4-H$_2$NO$_2$S-C$_6$H$_3$ | D |
| Ex. 35 | Compound 3 | — | — | C |
| Ex. 36 | Compound 4 | — | — | C |
| Ex. 37 | — | Compound S29 | 4-Cl, 4-H$_2$NO$_2$S-C$_6$H$_3$ | D |
| Ex. 38 | — | Compound S30 | 4-Cl, 4-H$_2$NO$_2$S-C$_6$H$_3$ | D |

TABLE II-continued

| Ex. no. | Benzylidene derivative used as material | β-amino acid derivative used as material | Sulfonamide derivative used as material | Synthesis method |
|---|---|---|---|---|
| Ex. 39 | — | Compound S13 | 4-Cl, 4-H$_2$NO$_2$S-C$_6$H$_3$ | E |
| Ex. 40 | — | Compound S53 | 4-Cl, 4-H$_2$NO$_2$S-C$_6$H$_3$ | D |
| Ex. 41 | — | Compound S10 | 4-Cl, 4-H$_2$NO$_2$S-C$_6$H$_3$ | E |

TABLE III

| Ex. no. | Benzylidene derivative used as material | β-amino acid derivative used as material | Sulfonamide derivative used as material | Synthesis method |
|---|---|---|---|---|
| Ex. 42 | — | Compound S6 | 4-Cl, 2-CH$_3$, H$_2$NO$_2$S-C$_6$H$_2$ | E |
| Ex. 43 | — | Compound S23 | 2,5-diCl, H$_2$NO$_2$S, COOCH$_3$-C$_6$H | D |
| Ex. 44 | — | Compound S38 | 4-Cl, 4-H$_2$NO$_2$S-C$_6$H$_3$ | D |
| Ex. 45 | — | Compound S38 | 4-Cl, 4-H$_2$NO$_2$S-C$_6$H$_3$ | D |
| Ex. 46 | — | Compound S10 | Compound S60 | E |
| Ex. 47 | — | Compound S21 | 4-Cl, 4-H$_2$NO$_2$S-C$_6$H$_3$ | E |
| Ex. 48 | Compound 8 | — | — | C |
| Ex. 49 | Compound 9 | — | — | C |
| Ex. 50 | — | Compound S6 | Compound S67 | E |
| Ex. 51 | — | Compound S6 | Compound S61 | E |

TABLE III-continued

| Ex. no. | Benzylidene derivative used as material | β-amino acid derivative used as material | Sulfonamide derivative used as material | Synthesis method |
|---|---|---|---|---|
| Ex. 52 | — | Compound S6 | Compound S59 | E |
| Ex. 53 | Compound 7 | — | — | C |

TABLE IV

| Ex. no. | Benzylidene derivative used as material | β-amino acid derivative used as material | Sulfonamide derivative used as material | Synthesis method |
|---|---|---|---|---|
| Ex. 54 | — | Compound S14 | 4-Cl-C6H4-SO2NH2 | E |
| Ex. 55 | Compound 10 | — | — | C |
| Ex. 56 | Compound 11 | — | — | C |
| Ex. 57 | Compound 195 | — | — | C |
| Ex. 58 | Compound 12 | — | — | C |
| Ex. 59 | — | Compound S11 | 4-Cl-C6H4-SO2NH2 | E |
| Ex. 60 | Compound 183 | — | — | C |
| Ex. 61 | Compound 182 | — | — | C |
| Ex. 62 | — | Compound S6 | Compound S65 | E |
| Ex. 63 | Compound 182 | — | — | C |
| Ex. 64 | Compound 184 | — | — | C |
| Ex. 65 | Compound 13 | — | — | C |

TABLE V

| Ex. no. | Benzylidene derivative used as material | β-amino acid derivative used as material | Sulfonamide derivative used as material | Synthesis method |
|---|---|---|---|---|
| Ex. 66 | Compound 14 | — | — | C |
| Ex. 67 | — | Compound S15 | 4-Cl-C6H4-SO2NH2 | E |
| Ex. 68 | Compound 15 | — | — | C |
| Ex. 69 | Compound 16 | — | — | C |
| Ex. 70 | Compound 17 | — | — | C |
| Ex. 71 | Compound 18 | — | — | C |
| Ex. 72 | — | Compound S10 | 4-CF3-C6H4-SO2NH2 | E |
| Ex. 73 | — | Compound S10 | 4-CH3-C6H4-SO2NH2 | E |
| Ex. 74 | — | Compound S10 | 4-NO2-C6H4-SO2NH2 | E |
| Ex. 75 | — | Compound S10 | 4-Br-C6H4-SO2NH2 | E |

TABLE V-continued

| Ex. no. | Benzylidene derivative used as material | β-amino acid derivative used as material | Sulfonamide derivative used as material | Synthesis method |
|---|---|---|---|---|
| Ex. 76 | — | Compound S10 | 4-F-C6H4-SO2NH2 | E |
| Ex. 77 | — | Compound S10 | 4-MeO-C6H4-SO2NH2 | E |

TABLE VI

| Ex. no. | Benzylidene derivative used as material | β-amino acid derivative used as material | Sulfonamide derivative used as material | Synthesis method |
|---|---|---|---|---|
| Ex. 78 | Compound 21 | — | — | C |
| Ex. 79 | — | Compound S19 | 4-Cl-C6H4-SO2NH2 | E |
| Ex. 80 | — | Compound S20 | 4-Cl-C6H4-SO2NH2 | E |
| Ex. 81 | — | Compound S16 | 4-Cl-C6H4-SO2NH2 | E |
| Ex. 82 | — | Compound S17 | 4-Cl-C6H4-SO2NH2 | E |
| Ex. 83 | — | Compound S18 | 4-Cl-C6H4-SO2NH2 | E |
| Ex. 84 | Compound 23 | — | — | C |
| Ex. 85 | Compound 24 | — | — | C |
| Ex. 86 | Compound 25 | — | — | C |
| Ex. 87 | Compound 26 | — | — | C |
| Ex. 88 | Compound 27 | — | — | C |
| Ex. 89 | Compound 28 | — | — | C |

Example 30

6-benzyl-4-(phenylsulfonyl)-1,4-diazepan-2,5-dione (Compound 30)

NMR (CDCl$_3$): δ8.03 (2H, d, J=7.6 Hz), 7.66 (1H, t, J=7.6 Hz), 7.55 (2H, t, J=7.6 Hz), 7.32-7.20 (3H, m), 7.11 (2H, d, J=6.9 Hz), 5.73 (1H, br), 5.02 (1H, d, J=17.7 Hz), 4.42 (1H, d, J=17.7 Hz), 3.38-3.12 (4H, m), 2.53 (1H, dd, J=14.3, 9.0 Hz)

MS: 359 (M+H)$^+$

Example 31

6-(3-chlorobenzyl)-4-[(4-chlorophenyl)sulfonyl]-1,4-diazepan-2,5-dione (Compound 31)

NMR (CDCl$_3$): δ7.96 (2H, d, J=8.5 Hz), 7.52 (2H, d, J=8.5 Hz), 7.24-7.22 (2H, m), 7.11 (1H, s), 7.05-6.98 (1H, m), 5.67 (1H, br), 5.00 (1H, d, J=17.7 Hz), 4.42 (1H, d, J=17.7 Hz), 3.39-3.25 (2H, m), 3.23-3.14 (2H, m), 2.53 (1H, dd, J=14.4, 8.4 Hz)

MS: 427 (M+H)$^+$

Example 32

6-(4-chlorobenzyl)-4-[(4-chlorophenyl)sulfonyl]-1,4-diazepan-2,5-dione (Compound 32)

NMR (CDCl$_3$): δ7.95 (2H, d, J=8.7 Hz), 7.51 (2H, d, J=8.7 Hz), 7.30-7.24 (2H, m), 7.06 (2H, d, J=8.3 Hz), 5.68 (1H, br), 4.98 (1H, d, J=17.7 Hz), 4.41 (1H, d, J=17.7 Hz), 3.36-3.24 (2H, m), 3.22-3.13 (2H, m), 2.54 (1H, dd, J=14.3, 8.0 Hz)

MS: 427 (M+H)$^+$

Example 33

6-(4-fluorobenzyl)-4-[(4-chlorophenyl)sulfonyl]-1,4-diazepan-2,5-dione (Compound 33)

NMR (CDCl$_3$): δ7.96 (2H, d, J=8.7 Hz), 7.52 (2H, d, J=8.7 Hz), 7.09 (2H, dd, J=8.5, 5.4 Hz), 6.98 (2H, t, J=8.5 Hz), 5.69 (1H, br), 4.98 (1H, d, J=17.7 Hz), 4.42 (1H, d, J=17.7 Hz), 3.35-3.25 (2H, m), 3.21-3.12 (2H, m), 2.54 (1H, dd, J=14.3, 8.0 Hz)

MS: 411 (M+H)$^+$

Example 34

6-(4-cyanobenzyl)-4-[(4-chlorophenyl)sulfonyl]-1,4-diazepan-2,5-dione (Compound 34)

NMR (DMSO-d$_6$): δ7.92 (2H, d, J=8.8 Hz), 7.86 (1H, br), 7.74 (2H, d, J=8.1 Hz), 7.72 (2H, d, J=8.8 Hz), 7.43 (2H, d, J=8.1 Hz), 4.90 (1H, d, J=17.6 Hz), 4.54 (1H, d, J=17.6 Hz), 3.89-3.79 (1H, m), 3.07-2.94 (3H, m), 2.61 (1H, dd, J=14.5, 8.3 Hz)
MS: 418 (M+H)$^+$

Example 35

4-[(4-chlorophenyl)sulfonyl]-6-(2-naphthylmethyl)-1,4-diazepan-2,5-dione (Compound 35)

NMR (CDCl$_3$): δ7.97 (2H, d, J=8.6 Hz), 7.82-7.73 (3H, m), 7.56 (1H, s), 7.54-7.42 (4H, m), 7.23 (1H, dd, J=8.4, 1.5 Hz), 5.76 (1H, br), 4.97 (1H, d, J=17.6 Hz), 4.43 (1H, d, J=17.6 Hz), 3.49-3.18 (4H, m), 2.72 (1H, dd, J=14.0, 8.6 Hz)
MS: 443 (M+H)$^+$

Example 36

4-[(6-benzyl-3,7-dioxo-1,4-diazepan-1-yl)sulfonyl]benzonitrile (Compound 36)

NMR (CDCl$_3$): δ8.14 (2H, d, J=8.5 Hz), 7.84 (2H, d, J=8.5 Hz), 7.34-7.22 (3H, m), 7.11 (2H, d, J=6.9 Hz), 5.67 (1H, br), 4.96 (1H, d, J=17.6 Hz), 4.46 (1H, d, J=17.6 Hz), 3.39-3.28 (2H, m), 3.25-3.15 (2H, m), 2.57 (1H, dd, J=14.3, 8.7 Hz)
MS: 384 (M+H)$^+$

Example 37

4-[(4-chlorophenyl)sulfonyl]-6-(3-methylbenzyl)-1,4-diazepan-2,5-dione (Compound 37)

NMR (CDCl$_3$): δ7.96 (2H, d, J=8.7 Hz), 7.51 (2H, d, J=8.7 Hz), 7.25 (1H, s), 7.18 (1H, t, J=7.5 Hz), 7.05 (1H, d, J=7.5 Hz), 6.95-6.86 (2H, m), 6.03-5.98 (1H, br), 4.95 (1H, d, J=17.6 Hz), 4.42 (1H, d, J=17.6 Hz), 3.34-3.23 (2H, m), 3.20-3.10 (2H, m), 2.50 (1H, dd, J=14.5, 9.1 Hz), 2.31 (3H, s)
MS: 407 (M+H)$^+$
Melting point: 64-66° C.

Example 38

4-[(4-chlorophenyl)sulfonyl]-6-[3-(trifluoromethyl)benzyl]-1,4-diazepan-2,5-dione (Compound 38)

NMR (CDCl$_3$): δ7.96 (2H, d, J=8.7 Hz), 7.52 (3H, d, J=8.7 Hz), 7.42 (1H, t, J=7.8 Hz), 7.39 (1H, s), 7.33 (1H, d, J=7.8 Hz), 5.68-5.62 (1H, br), 5.02 (1H, d, J=17.6 Hz), 4.42 (1H, d, J=17.6 Hz), 3.40-3.16 (4H, m), 2.63 (1H, dd, J=14.3, 7.8 Hz)
MS: 461 (M+H)$^+$

Example 39

6-(5-chloro-2-ethoxybenzyl)-4-[(4-chlorophenyl)sulfonyl]-1,4-diazepan-2,5-dione (Compound 39)

NMR (CDCl$_3$): δ7.96 (2H, d, J=8.5 Hz), 7.52 (2H, d, J=8.5 Hz), 7.16 (1H, dd, J=8.8, 2.4 Hz), 7.02 (1H, d, J=2.4 Hz), 6.75 (1H, d, J=8.8 Hz), 5.68 (1H, br), 5.01 (1H, d, J=17.8 Hz), 4.36 (1H, d, J=17.8 Hz), 4.01 (2H, q, J=7.0 Hz), 3.52-3.42 (1H, m), 3.28-3.06 (3H, m), 2.56 (1H, dd, J=14.1, 9.0 Hz), 1.37 (3H, t, J=7.0 Hz)
MS: 471 (M+H)$^+$

Example 40

6-(5-chloro-2-butoxybenzyl)-4-[(4-chlorophenyl)sulfonyl]-1,4-diazepan-2,5-dione (Compound 40)

NMR (CDCl$_3$): δ7.96 (2H, d, J=8.6 Hz), 7.52 (2H, d, J=8.6 Hz), 7.17 (1H, dd, J=8.7, 2.5 Hz), 7.02 (1H, d, J=2.5 Hz), 6.76 (1H, d, J=8.7 Hz), 5.66-5.61 (1H, br), 5.02 (1H, d, J=17.6 Hz), 4.36 (1H, d, J=17.6 Hz), 3.94 (2H, t, J=6.5 Hz), 3.51-3.43 (1H, m), 3.29-3.07 (3H, m), 2.53 (1H, dd, J=14.0, 9.0 Hz), 1.77-1.68 (2H, m), 1.47-1.38 (2H, m), 0.95 (3H, t, J=7.4 Hz)
MS: 499 (M+H)$^+$

Example 41

4-[(4-chlorophenyl)sulfonyl]-6-(5-fluoro-2-methoxybenzyl)-1,4-diazepan-2,5-dione (Compound 41)

NMR (CDCl$_3$): δ7.96 (2H, d, J=7.0 Hz), 7.52 (2H, d, J=7.0 Hz), 6.97-6.90 (1H, m), 6.82-6.76 (2H, m), 5.70-5.65 (1H, br), 5.00 (1H, d, J=17.6 Hz), 4.40 (1H, d, J=17.6 Hz), 3.79 (3H, s), 3.52-3.40 (1H, m), 3.29-3.21 (1H, m), 3.19-3.09 (2H, m), 2.55 (1H, dd, J=14.0, 8.8 Hz)
MS: 439 (M+H)$^+$

Example 42

6-(5-chloro-2-methoxybenzyl)-4-[(4-chloro-2-methylphenyl)sulfonyl]-1,4-diazepan-2,5-dione (Compound 42)

NMR (CDCl$_3$): δ8.10 (1H, d, J=8.6 Hz), 7.37 (1H, dd, J=8.6, 2 Hz), 7.29 (1H, d, J=2.0 Hz), 7.19 (1H, dd, J=8.8, 2.6 Hz), 6.97 (1H, d, J=2.6 Hz), 6.78 (1H, d, J=8.8 Hz), 5.82 (1H, br), 5.11 (1H, d, J=17.9 Hz), 4.42 (1H, d, J=17.9 Hz), 3.80 (3H, s), 3.49-3.40 (1H, m), 3.29-3.14 (2H, m), 3.09 (1H, dd, J=14.2, 4.6 Hz), 2.52 (3H, s), 2.49 (1H, dd, J=14.2, 9.3 Hz)
MS: 471 (M+H)$^+$

Example 43

Methyl 2,4-dichloro-5-{[6-(5-chloro-2-methoxybenzyl)-3,7-dioxo-1,4-diazepan-1-yl]sulfonyl}benzoate (Compound 43)

NMR (CDCl$_3$): δ8.79 (1H, s), 7.60 (1H, s), 7.18 (1H, dd, J=8.9, 2.6 Hz), 6.97 (1H, d, J=2.6 Hz), 6.78 (1H, d, J=8.9 Hz), 5.99 (1H, br), 5.12 (1H, d, J=18.0 Hz), 4.46 (1H, d, J=18.0 Hz), 3.98 (3H, s), 3.81 (3H, s), 3.52-3.42 (1H, m), 3.30-3.26 (2H, m), 3.06 (1H, dd, J=14.2, 4.9 Hz), 2.51 (1H, dd, J=14.2, 9.0 Hz)
MS: 548 (M+H)$^+$

Example 44 rel-(6R,7R)-6-(5-chloro-2-methoxybenzyl)-4-[(4-chlorophenyl)sulfonyl]-7-methyl-1,4-diazepan-2,5-dione (Compound 44)

NMR (CDCl$_3$): δ7.93 (2H, d, J=8.6 Hz), 7.46 (2H, d, J=8.6 Hz), 7.17 (1H, dd, J=8.7, 2.5 Hz), 7.11 (1H, d, J=2.5 Hz), 6.75

(1H, d, J=8.7 Hz), 5.40 (1H, br), 4.74 (1H, d, J=16.9 Hz), 4.47 (1H, d, J=19.6 Hz), 3.80 (3H, s), 3.39-3.29 (1H, m), 3.14-3.01 (2H, m), 2.79 (1H, d, J=10.1 Hz), 1.33 (3H, d, J=6.3 Hz)
MS: 471 (M+H)$^+$

Example 45 rel-(6R,7S)-6-(5-chloro-2-methoxybenzyl)-4-[(4-chlorophenyl)sulfonyl]-7-methyl-1,4-diazepan-2,5-dione (Compound 45)

NMR (CDCl$_3$): δ7.97 (2H, d, J=8.7 Hz), 7.52 (2H, d, J=8.7 Hz), 7.18 (1H, dd, J=8.7, 2.6 Hz), 7.00 (1H, d, J=2.6 Hz), 6.67 (1H, d, J=8.7 Hz), 5.97 (1H, brd, J=4.0 Hz), 5.07 (1H, d, J=18.0 Hz), 4.31 (1H, d, J=18.0 Hz), 3.78 (3H, s), 3.60-3.56 (1H, m), 3.42-3.33 (1H, m), 3.03 (1H, dd, J=14.2, 5.4 Hz), 2.57 (1H, dd, J=14.2, 8.8 Hz), 0.97 (3H, d, J=6.6 Hz)
MS: 471 (M+H)$^+$

Example 46

4-[(3-amino-4-chlorophenyl)sulfonyl]-6-(5-fluoro-2-methoxybenzyl)-1,4-diazepan-2,5-dione Hydrochloride (Compound 46)

NMR (DMSO-d$_6$): δ7.83 (1H, br), 7.43 (1H, d, J=8.3 Hz), 7.39 (1H, d, J=2.2 Hz), 7.12-6.91 (4H, m), 4.85 (1H, d, J=17.5 Hz), 4.47 (1H, d, J=17.5 Hz), 3.88-3.42 (1H, m), 3.74 (3H, s), 3.02-2.97 (2H, m), 2.85 (1H, dd, J=14.3, 4.7 Hz), 2.58-2.48 (1H, m)
MS: 456 (M+H)$^+$

Example 47

6-(5-chloro-2-ethoxymethoxybenzyl)-4-[(4-chlorophenyl)sulfonyl]-1,4-diazepan-2,5-dione (Compound 47)

NMR (CDCl$_3$): δ7.97 (2H, d, J=8.7 Hz), 7.53 (2H, d, J=8.7 Hz), 7.17 (1H, dd, J=8.4, 2.6 Hz), 7.04 (1H, d, J=8.4 Hz), 7.03 (1H, d, J=2.6 Hz), 5.81-5.73 (1H, br), 5.21 (2H, dd, J=11.3, 6.9 Hz), 5.01 (1H, d, J=17.6 Hz), 4.38 (1H, d, J=17.6 Hz), 3.66 (2H, dd, J=14.1, 6.9 Hz), 3.51-3.42 (1H, m), 3.32-3.12 (3H, m), 2.55 (1H, dd, J=14.2, 9.2 Hz), 1.21 (3H, t, J=7.0 Hz)
MS: 523 (M+Na)$^+$

Example 48

6-(5-chloro-2-methoxybenzyl)-4-[(4-chloro-2-methoxyphenyl)sulfonyl]-1,4-diazepan-2,5-dione (Compound 48)

NMR (CDCl$_3$): δ8.04 (1H, d, J=8.5 Hz), 7.19 (1H, dd, J=8.8, 2.6 Hz), 7.13 (1H, dd, J=8.5, 2.6 Hz), 7.00-6.97 (2H, m), 6.78 (1H, d, J=8.8 Hz), 5.79 (1H, br), 5.14 (1H, d, J=18.1 Hz), 4.40 (1H, d, J=18.1 Hz), 3.87 (3H, s), 3.81 (3H, s), 3.50-3.40 (1H, m), 3.25-3.14 (2H, m), 3.10 (1H, dd, J=14.2, 4.4 Hz), 2.49 (1H, dd, J=14.2, 9.3 Hz)
MS: 487 (M+H)$^+$

Example 49

4-[(4-chloro-2-fluorophenyl)sulfonyl]-6-(5-chloro-2-methoxybenzyl)-1,4-diazepan-2,5-dione (Compound 49)

NMR (CDCl$_3$): δ8.05 (1H, t, J=8.2 Hz), 7.35 (1H, d, J=8.2 Hz), 7.24-7.17 (2H, m), 6.99 (1H, d, J=2.5 Hz), 6.78 (1H, d, J=8.5 Hz), 5.91 (1H, br), 5.09 (1H, d, J=18.0 Hz), 4.41 (1H, d, J=18.0 Hz), 3.81 (3H, s), 3.51-3.42 (1H, m), 3.34-3.21 (2H, m), 3.08 (1H, dd, J=14.2, 4.8 Hz), 2.51 (1H, dd, J=14.2, 9.1 Hz)
MS: 475 (M+H)$^+$

Example 50 tert-butyl 2-amino-4-{[6-(5-chloro-2-methoxybenzyl)-3,7-dioxo-1,4-diazepan-1-yl]sulfonyl}benzoate (Compound 50)

NMR (DMSO-d$_6$): δ7.84 (1H, br), 7.81 (1H, d, 8.5 Hz), 7.41 (1H, d, 1.4 Hz), 7.26-7.23 (2H, m), 7.03 (2H, s), 6.97 (1H, d, 8.4 Hz), 6.86 (1H, dd, 8.5, 1.4 Hz), 4.88 (1H, d, 17.5 Hz), 4.48 (1H, d, 17.5 Hz), 3.75 (3H, s), 3.73-3.62 (1H, m), 3.02-2.98 (2H, m), 2.84 (1H, dd, 14.3, 4.9 Hz), 2.56-2.48 (1H, m), 1.54 (9H, s)
MS: 482 (M-tBu)$^+$

Example 51 tert-butyl 5-{[6-(5-chloro-2-methoxybenzyl)-3,7-dioxo-1,4-diazepan-1-yl]sulfonyl}-2-methoxyphenylcarbamate (Compound 51)

NMR (DMSO-d$_6$): δ8.32-8.30 (2H, m), 7.81 (1H, br), 7.59 (1H, dd, 8.7, 2.3 Hz), 7.26-7.21 (3H, m), 6.97 (1H, d, 8.9 Hz), 4.85 (1H, d, 17.4 Hz), 4.50 (1H, d, 17.4 Hz), 3.91 (3H, s), 3.75 (3H, s), 3.69-3.60 (1H, m), 3.01-2.96 (2H, m), 2.83 (1H, dd, 14.2, 4.6 Hz), 2.55-2.49 (1H, m), 1.48 (9H, s)
MS: 512 (M-tBu)$^+$

Example 52 tert-butyl 5-{[6-(5-chloro-2-methoxybenzyl)-3,7-dioxo-1,4-diazepan-1-yl]sulfonyl}-2-methylphenylcarbamate (Compound 52)

NMR (DMSO-d$_6$): δ8.83 (1H, s), 8.01 (1H, m), 7.82 (1H, br), 7.51 (1H, dd, 8.0, 1.8 Hz), 7.42 (1H, d, 8.0 Hz), 7.27-7.23 (2H, m), 6.97 (1H, d, 9.5 Hz), 4.86 (1H, d, 17.5 Hz), 4.50 (1H, d, 17.5 Hz), 3.74 (3H, s), 3.69-3.60 (1H, m), 3.03-2.93 (2H, m), 2.83 (1H, dd, 14.3, 4.6 Hz), 2.55-2.48 (1H, m), 2.29 (3H, s), 1.49 (9H, s)
MS: 496 (M-tBu)$^+$

Example 53

3-({1-[(4-chlorophenyl)sulfonyl]-3,7-dioxo-1,4-diazepan-6-yl}methyl)benzonitrile (Compound 53)

NMR (CDCl$_3$): δ7.95 (2H, d, 8.7 Hz), 7.58-7.51 (3H, m), 7.47-7.38 (3H, m), 5.79 (1H, br), 5.01 (1H, d, 17.7 Hz), 4.41 (1H, d, 17.7 Hz), 3.42-3.18 (4H, m), 2.60 (1H, dd, 14.5, 7.5 Hz)
MS: 418 (M+H)$^+$

Example 54

4-[(4-chlorophenyl)sulfonyl]-6-[2-methoxy-5-(trifluoromethyl)benzyl]-1,4-diazepan-2,5-dione (Compound 54)

NMR (CDCl$_3$): δ7.97 (2H, d, J=8.7 Hz), 7.52 (3H, d, J=8.7 Hz), 7.31 (1H, s), 6.92 (1H, d, J=8.6 Hz), 5.70-5.64 (1H, br), 5.02 (1H, d, J=17.7 Hz), 4.39 (1H, d, J=17.7 Hz), 3.88 (3H, s), 3.48-3.40 (1H, m), 3.26-3.15 (3H, m), 2.61 (1H, dd, J=14.2, 8.9 Hz)
MS: 491 (M+H)$^+$

Example 55

N-(2-chloro-5-{[6-(5-chloro-2-methoxybenzyl)-3,7-dioxo-1,4-diazepan-1-yl]sulfonyl}phenyl)-N'-ethylurea (Compound 55)

NMR (CDCl$_3$): δ8.59 (1H, d, J=2.1 Hz), 7.66 (1H, dd, J=8.5, 2.1 Hz), 7.49 (1H, d, J=8.5 Hz), 7.17 (1H, dd, J=8.8, 2.5 Hz), 7.00 (1H, d, J=2.5 Hz), 6.85 (1H, s), 6.76 (1H, d, J=8.8 Hz), 5.99 (1H, br), 5.06-4.99 (2H, m), 4.44 (1H, d, J=17.9 Hz), 3.80 (3H, s), 3.54-3.45 (1H, m), 3.38-3.18 (4H, m), 3.10 (1H, dd, J=14.1, 4.7 Hz), 2.47 (1H, dd, J=14.1, 9.0 Hz), 1.21 (3H, t, J=7.2 Hz)
MS: 543 (M+H)$^+$

Example 56

4-[(4-chlorobenzyl)sulfonyl]-6-(5-chloro-2-methoxybenzyl)-1,4-diazepan-2,5-dione (Compound 56)

NMR (CDCl$_3$): δ7.28-7.13 (6H, m), 6.83 (1H, d, J=8.7 Hz), 5.82-5.76 (1H, br), 4.80 (1H, d, J=14.0 Hz), 4.70 (1H, d, J=14.0 Hz), 4.38 (1H, d, J=18.0 Hz), 3.84 (3H, s), 3.69 (1H, d, J=18.0 Hz), 3.40-3.29 (3H, m), 3.26-3.16 (1H, m), 2.62 (1H, dd, J=13.9, 7.6 Hz)
MS: 471 (M+H)$^+$

Example 57

4-[(4-chlorophenyl)sulfonyl]-6-(5-hydroxy-2-methoxybenzyl)-1,4-diazepan-2,5-dione (Compound 57)

NMR (CDCl$_3$): δ7.97 (2H, d, J=8.6 Hz), 7.52 (2H, d, J=8.6 Hz), 6.73 (1H, d, J=8.7 Hz), 6.69 (1H, dd, J=8.7, 2.8 Hz), 6.58 (1H, d, J=2.8 Hz), 5.63-5.58 (1H, br), 4.97 (1H, d, J=17.7 Hz), 4.59 (1H, s), 4.41 (1H, d, J=17.7 Hz), 3.76 (3H, s), 3.49-3.40 (1H, m), 3.28-3.20 (1H, m), 3.17-3.06 (2H, m), 2.53 (1H, dd, J=14.0, 8.9 Hz)
MS: 439 (M+H)$^+$

Example 58

6-(5-chloro-2-methoxybenzyl)-4-{[4-(1H-pyrazol-3-yl)phenyl]sulfonyl}-1,4-diazepan-2,5-dione Hydrochloride (Compound 58)

NMR (DMSO-d$_6$): δ8.06 (2H, d, J=8.5 Hz), 7.93 (2H, d, J=8.5 Hz), 7.85-7.81 (2H, m, J=2.1 Hz), 7.27-7.21 (2H, m), 6.96 (1H, d, J=9.5 Hz), 6.89 (1H, d, J=2.3 Hz), 4.90 (1H, d, J=17.5 Hz), 4.57 (1H, d, J=17.5 Hz), 3.74 (3H, s), 3.72-3.64 (1H, m), 3.62-3.58 (1H, m), 3.04-2.94 (2H, m), 2.83 (1H, dd, J=14.3, 4.8 Hz)
MS: 489 (M+H)$^+$

Example 59

4-[(4-chlorophenyl)sulfonyl]-6-[2-(methoxymethoxy)-5-methylbenzyl]-1,4-diazepan-2,5-dione (Compound 59)

NMR (CDCl$_3$): δ7.97 (2H, d, J=8.8 Hz), 7.52 (2H, d, J=8.8 Hz), 7.01 (1H, dd, J=8.3, 1.8 Hz), 6.95 (1H, d, J=8.3 Hz), 6.85 (1H, d, J=1.8 Hz), 5.80-5.74 (1H, br), 5.16 (1H, d, J=6.6 Hz), 5.14 (1H, d, J=6.6 Hz), 4.99 (1H, d, J=17.6 Hz), 4.40 (1H, d, J=17.6 Hz), 3.55-3.40 (1H, m), 3.43 (3H, s), 3.30-3.21 (1H, m), 3.19-3.10 (2H, m), 2.57 (1H, dd, J=14.1, 9.5 Hz), 2.24 (3H, s)
MS: 489 (M+Na)$^+$

Example 60

(3S,6R)-6-(5-chloro-2-methoxybenzyl)-4-[(4-chlorophenyl)sulfonyl]-3-methyl-1,4-diazepan-2,5-dione (Compound 60)

NMR (CDCl$_3$): δ8.02 (2H, d, J=8.7 Hz), 7.52 (2H, d, J=8.7 Hz), 7.20 (1H, dd, J=8.8, 2.6 Hz), 7.08 (1H, d, J=2.6 Hz), 6.79 (1H, d, J=8.8 Hz), 5.95-5.87 (1H, br), 5.12 (1H, q, J=7.4 Hz), 3.81 (3H, s), 3.36-3.21 (4H, m), 2.80 (1H, dd, J=13.2, 8.7 Hz), 1.59 (3H, d, J=7.3 Hz)
MS: 471 (M+H)$^+$

Example 61

(3R,6S)-6-(5-chloro-2-methoxybenzyl)-4-[(4-chlorophenyl)sulfonyl]-3-methyl-1,4-diazepan-2,5-dione (Compound 61)

NMR (CDCl$_3$): δ8.02 (2H, d, J=8.7 Hz), 7.52 (2H, d, J=8.7 Hz), 7.20 (1H, dd, J=8.7, 2.4 Hz), 7.08 (1H, d, J=2.4 Hz), 6.79 (1H, d, J=8.7 Hz), 5.91 (1H, br), 5.12 (1H, q, J=7.4 Hz), 3.81 (3H, s), 3.35-3.20 (4H, m), 2.80 (1H, dd, J=13.1, 8.6 Hz), 1.59 (3H, d, J=7.4 Hz)
MS: 471 (M+H)$^+$
Melting point: 78-80° C.

Example 62 tert-butyl 2-(4-{[6-(5-chloro-2-methoxybenzyl)-3,7-dioxo-1,4-diazepan-1-yl]sulfonyl}phenyl)ethylcarbamate (Compound 62)

NMR (DMSO-d$_6$): δ7.85-7.82 (3H, m), 7.45 (2H, d, 8.2 Hz), 7.26-7.23 (2H, m), 6.97 (1H, d, 8.3 Hz), 6.94-6.92 (1H, m), 4.86 (1H, d, 17.5 Hz), 4.53 (1H, d, 17.5 Hz), 3.74 (3H, s), 3.70-3.60 (1H, m), 3.22-3.16 (2H, m), 2.99-2.95 (2H, m), 2.85-2.78 (3H, m), 2.54-2.47 (1H, m), 1.35 (9H, s)
MS: 466 (M-Boc)$^+$

Example 63

(3R,6R)-6-(5-chloro-2-methoxybenzyl)-4-[(4-chlorophenyl)sulfonyl]-3-methyl-1,4-diazepan-2,5-dione (Compound 63)

NMR (CDCl$_3$): δ7.99 (2H, d, J=8.6 Hz), 7.53 (2H, d, J=8.6 Hz), 7.20 (1H, dd, J=8.8, 2.6 Hz), 6.99 (1H, d, J=2.6 Hz), 6.78 (1H, d, J=8.8 Hz), 5.90 (1H, d, J=6.3 Hz), 5.49 (1H, q, J=7.4 Hz), 3.78 (3H, s), 3.40-3.33 (1H, m), 3.29 (1H, d, J=11.7 Hz), 3.22 (1H, dd, J=14.2, 3.7 Hz), 3.06 (1H, dd, J=11.7, 6.9 Hz), 2.38 (1H, dd, J=14.2, 9.4 Hz), 1.65 (3H, d, J=7.4 Hz)
MS: 471 (M+H)$^+$

Example 64

6-(5-chloro-2-methoxybenzyl)-4-[(4-chlorophenyl)sulfonyl]-4,8-diazaspiro[2.6]nonan-5,9-dione (Compound 64)

NMR (CDCl$_3$): δ8.02 (2H, d, J=8.7 Hz), 7.52 (2H, d, J=8.7 Hz), 7.20 (1H, dd, J=8.8, 2.5 Hz), 7.04 (1H, d, J=2.5 Hz), 6.78

(1H, d, J=8.8 Hz), 5.64 (1H, br), 4.09-4.00 (1H, m), 3.80 (3H, s), 3.25-3.20 (2H, m), 3.15 (1H, dd, J=14.2, 4.7 Hz), 2.43-2.32 (2H, m), 1.66-1.55 (1H, m), 1.42-1.35 (1H, m), 1.15-1.09 (1H, m)

MS: 483 (M+H)⁺

Example 65

4-[(6-chloro-3-pyridyl)sulfonyl]-6-(5-fluoro-2-methoxybenzyl)-1,4-diazepan-2,5-dione (Compound 65)

NMR (CDCl₃): δ8.94 (1H, d, J=2.4 Hz), 8.29 (1H, dd, J=8.7, 2.4 Hz), 7.51 (1H, d, J=8.7 Hz), 6.92 (1H, dt, J=8.9, 3.1 Hz), 6.81-6.75 (2H, m), 5.83 (1H, br), 4.97 (1H, d, J=17.6 Hz), 4.42 (1H, d, J=17.6 Hz), 3.79 (3H, s), 3.55-3.45 (1H, m), 3.27 (1H, dt, J=13.3, 4.3 Hz), 3.19 (1H, dd, J=13.3, 1.5 Hz), 3.10 (1H, dd, J=14.0, 5.1 Hz), 2.57 (1H, dd, J=14.0, 8.7 Hz)

MS: 442 (M+H)⁺

Example 66

4-[(5-chloro-2-thienyl)sulfonyl]-6-(5-fluoro-2-methoxybenzyl)-1,4-diazepan-2,5-dione (Compound 66)

NMR (CDCl₃): δ7.69 (1H, d, J=4.1 Hz), 6.98-6.87 (2H, m), 6.86-6.72 (2H, m), 5.80-5.73 (1H, br), 4.91 (1H, d, J=17.7 Hz), 4.37 (1H, d, J=17.7 Hz), 3.80 (3H, s), 3.51-3.40 (1H, m), 3.28-3.19 (2H, m), 3.19 (1H, dd, J=14.0, 5.0 Hz), 2.63 (1H, dd, J=14.1, 8.8 Hz)

MS: 447 (M+H)⁺

Example 67

6-(4-chloro-5-fluoro-2-methoxybenzyl)-4-[(4-chlorophenyl)sulfonyl]-1,4-diazepan-2,5-dione (Compound 67)

NMR (CDCl₃): δ7.96 (2H, d, J=8.7 Hz), 7.53 (2H, d, J=8.7 Hz), 6.89 (1H, d, J=9.0 Hz), 6.50 (1H, d, J=6.1 Hz), 5.71-5.64 (1H, br), 5.01 (1H, d, J=17.7 Hz), 4.39 (1H, d, J=17.7 Hz), 3.80 (3H, s), 3.48-3.38 (1H, m), 3.27-3.03 (3H, m), 2.57 (1H, dd, J=14.1, 8.8 Hz)

MS: 475 (M+H)⁺

Melting point: 80-90° C.

Example 68

4-[(5-chloro-4-fluoro-2-methoxyphenyl)sulfonyl]-6-(5-chloro-2-methoxybenzyl)-1,4-diazepan-2,5-dione (Compound 68)

NMR (CDCl₃): δ8.20 (1H, d, J=8.0 Hz), 7.21 (1H, dd, J=8.7, 2.6 Hz), 7.02 (1H, d, J=2.6 Hz), 6.80 (1H, d, J=10.1 Hz), 6.80 (1H, d, J=8.8 Hz), 5.76-5.70 (1H, br), 5.12 (1H, d, J=17.9 Hz), 4.42 (1H, d, J=17.9 Hz), 3.87 (3H, s), 3.83 (3H, s), 3.50-3.40 (1H, m), 3.28-3.09 (3H, m), 2.52 (1H, dd, J=14.2, 9.3 Hz)

MS: 505 (M+H)⁺

Example 69

6-(5-chloro-2-methoxybenzyl)-4-[(2,5-dimethoxyphenyl)sulfonyl]-1,4-diazepan-2,5-dione (Compound 69)

NMR (CDCl₃): δ7.62 (1H, d, J=3.1 Hz), 7.19 (1H, dd, J=8.8, 2.7 Hz), 7.14 (1H, dd, J=9.1, 3.1 Hz), 6.99 (1H, d, J=2.7 Hz), 6.93 (1H, d, J=9.1 Hz), 6.79 (1H, d, J=8.8 Hz), 5.72-5.68 (1H, br), 5.18 (1H, d, J=18.1 Hz), 4.42 (1H, d, J=18.1 Hz), 3.86 (3H, s), 3.83 (3H, s), 3.82 (3H, s), 3.51-3.40 (1H, m), 3.22-3.17 (2H, m), 3.12 (1H, dd, J=14.2, 4.4 Hz), 2.50 (1H, dd, J=14.2, 9.5 Hz)

MS: 483 (M+H)⁺

Example 70

6-(5-chloro-2-methoxybenzyl)-4-[(2-methoxy-5-methylphenyl)sulfonyl]-1,4-diazepan-2,5-dione (Compound 70)

NMR (CDCl₃): δ7.93 (1H, d, J=2.0 Hz), 3.39 (1H, dd, J=8.5, 2.0 Hz), 7.19 (1H, dd, J=8.7, 2.6 Hz), 6.98 (1H, d, J=2.6 Hz), 6.89 (1H, d, J=8.5 Hz), 6.79 (1H, d, J=8.7 Hz), 5.78-5.71 (1H, br), 5.19 (1H, d, J=18.1 Hz), 4.41 (1H, d, J=18.1 Hz), 3.84 (3H, s), 3.82 (3H, s), 3.52-3.39 (1H, m), 3.20-3.07 (3H, m), 2.49 (1H, dd, J=14.2, 9.4 Hz), 2.38 (3H, s)

MS: 467 (M+H)⁺

Example 71

6-(5-chloro-2-methoxybenzyl)-4-{[2-methoxy-5-(trifluoromethyl)phenyl]sulfonyl}-1,4-diazepan-2,5-dione (Compound 71)

NMR (CDCl₃): δ8.41 (1H, d, J=2.0 Hz), 7.86 (1H, dd, J=8.7, 2.0 Hz), 7.20 (1H, dd, J=8.8, 2.7 Hz), 7.10 (1H, d, J=8.8 Hz), 6.99 (1H, d, J=2.7 Hz), 6.79 (1H, d, J=8.7 Hz), 5.78-5.71 (1H, br), 5.16 (1H, d, J=18.0 Hz), 4.44 (1H, d, J=18.0 Hz), 3.95 (3H, s), 3.83 (3H, s), 3.50-3.40 (1H, m), 3.28-3.08 (3H, m), 2.52 (1H, dd, J=14.2, 9.4 Hz)

MS: 521 (M+H)⁺

Example 72

6-(5-fluoro-2-methoxybenzyl)-4-{[4-(trifluoromethyl)phenyl]sulfonyl}-1,4-diazepan-2,5-dione (Compound 72)

NMR (CDCl₃): δ8.16 (2H, d, J=8.3 Hz), 7.82 (2H, d, J=8.3 Hz), 6.92 (1H, dt, J=8.8, 3.1 Hz), 6.80-6.75 (2H, m), 5.66 (1H, br), 5.02 (1H, d, J=17.6 Hz), 4.43 (1H, d, J=17.6 Hz), 3.79 (3H, s), 3.53-3.45 (1H, m), 3.26 (1H, dt, J=13.3, 4.3 Hz), 3.18 (1H, dd, J=13.3, 1.6 Hz), 3.11 (1H, dd, J=14.0, 4.9 Hz), 2.57 (1H, dd, J=14.0, 8.7 Hz)

MS: 475 (M+H)⁺

Example 73

6-(5-fluoro-2-methoxybenzyl)-4-[(4-methylphenyl)sulfonyl]-1,4-diazepan-2,5-dione (Compound 73)

NMR (CDCl₃): δ7.91 (2H, d, J=8.3 Hz), 7.34 (2H, d, J=8.3 Hz), 6.96-6.88 (1H, m), 6.79-6.74 (2H, m), 5.71-5.65 (1H, br), 5.04 (1H, d, J=17.6 Hz), 4.39 (1H, d, J=17.6 Hz), 3.79 (3H, s), 3.52-3.44 (1H, m), 3.28-3.10 (3H, m), 2.53 (1H, dd, J=14.0, 9.0 Hz), 2.45 (3H, s)

MS: 421 (M+H)⁺

Example 74

4-[(4-aminophenyl)sulfonyl]-6-(5-fluoro-2-methoxybenzyl)-1,4-diazepan-2,5-dione (Compound 74)

NMR (CDCl₃): δ7.80 (2H, d, J=8.7 Hz), 6.96-6.87 (1H, m), 6.83-6.72 (2H, m), 6.68 (2H, d, J=8.7 Hz), 5.73-5.69 (1H, br), 5.02 (1H, d, J=17.7 Hz), 4.37 (1H, d, J=17.7 Hz), 4.26 (2H, s), 3.79 (3H, s), 3.50-3.37 (1H, m), 3.20-3.07 (3H, m), 2.54 (1H, dd, J=14.1, 9.1 Hz)

MS: 422 (M+H)$^+$

Example 75

4-[(4-bromophenyl)sulfonyl]-6-(5-fluoro-2-methoxybenzyl)-1,4-diazepan-2,5-dione (Compound 75)

NMR (CDCl$_3$): δ7.89 (2H, d, J=8.6 Hz), 7.69 (2H, d, J=8.6 Hz), 6.98-6.88 (1H, m), 6.82-6.76 (2H, m), 5.81-5.76 (1H, br), 5.00 (1H, d, J=17.8 Hz), 4.41 (1H, d, J=17.8 Hz), 3.79 (3H, s), 3.54-3.39 (1H, m), 3.30-3.05 (3H, m), 2.55 (1H, dd, J=14.1, 8.9 Hz)

MS: 485 (M+H)$^+$

Example 76

6-(5-fluoro-2-methoxybenzyl)-4-[(4-fluorophenyl)sulfonyl]-1,4-diazepan-2,5-dione (Compound 76)

NMR (CDCl$_3$): δ8.06 (2H, dd, J=8.8, 4.9 Hz), 7.22 (2H, t, J=8.8 Hz), 6.97-6.89 (1H, m), 6.80-6.73 (2H, m), 5.78-5.72 (1H, br), 5.01 (1H, d, J=17.8 Hz), 4.41 (1H, d, J=17.8 Hz), 3.80 (3H, s), 3.53-3.43 (1H, m), 3.29-3.23 (1H, m), 3.20-3.10 (2H, m), 2.56 (1H, dd, J=14.0, 8.8 Hz)

MS: 425 (M+H)$^+$

Example 77

6-(5-fluoro-2-methoxybenzyl)-4-[(4-methoxyphenyl)sulfonyl]-1,4-diazepan-2,5-dione (Compound 77)

NMR (CDCl$_3$): δ7.97 (2H, d, J=9.0 Hz), 7.00 (2H, d, J=9.0 Hz), 6.94-6.86 (1H, m), 6.80-6.72 (2H, m), 5.75-5.70 (1H, br), 5.03 (1H, d, J=17.8 Hz), 4.39 (1H, d, J=17.8 Hz), 3.89 (3H, s), 3.79 (3H, s), 3.52-3.40 (1H, m), 3.26-3.17 (1H, m), 3.17-3.08 (2H, m), 2.54 (1H, dd, J=14.1, 8.9 Hz)

MS: 437 (M+H)$^+$

Example 78

Methyl 3-{[6-(5-fluoro-2-methoxybenzyl)-3,7-dioxo-1,4-diazepan-1-yl]sulfonyl}propanoate (Compound 78)

NMR (CDCl$_3$): δ6.99-6.87 (2H, m), 6.84-6.79 (1H, m), 5.80-5.74 (1H, br), 4.78 (1H, d, J=17.7 Hz), 4.31 (1H, d, J=17.7 Hz), 3.91 (2H, t, J=7.3 Hz), 3.84 (3H, s), 3.73 (3H, s), 3.59-3.48 (1H, m), 3.42-3.19 (3H, m), 3.84 (2H, dt, J=7.3, 1.8 Hz), 2.67 (1H, dd, J=14.1, 8.7 Hz)

MS: 417 (M+H)$^+$

Example 79

6-(2-chlorobenzyl)-4-[(4-chlorophenyl)sulfonyl]-1,4-diazepan-2,5-dione (Compound 79)

NMR (CDCl$_3$): δ7.96 (2H, d, J=8.7 Hz), 7.52 (2H, d, J=8.7 Hz), 7.36 (1H, dd, J=5.8, 2.4 Hz), 7.25-7.16 (3H, m), 5.97 (1H, br), 4.99 (1H, d, J=17.7 Hz), 4.41 (1H, d, J=17.7 Hz), 3.57-3.48 (1H, m), 3.34-3.18 (3H, m), 2.72 (1H, dd, J=14.2, 8.2 Hz)

MS: 427 (M+H)$^+$

Example 80

4-[(4-chlorophenyl)sulfonyl]-6-(3,5-dichlorobenzyl)-1,4-diazepan-2,5-dione (Compound 80)

NMR (CDCl$_3$): δ7.95 (2H, d, J=8.7 Hz), 7.52 (2H, d, J=8.7 Hz), 7.25 (1H, d, J=1.7 Hz), 7.02 (2H, d, J=1.7 Hz), 5.81 (1H, br), 5.02 (1H, d, J=17.8 Hz), 4.42 (1H, d, J=17.8 Hz), 3.38-3.13 (4H, m), 2.5 (1H, dd, J=14.4, 7.8 Hz)

MS: 461 (M+H)$^+$

Example 81

4-[(4-chlorophenyl)sulfonyl]-6-(2,5-dimethoxybenzyl)-1,4-diazepan-2,5-dione (Compound 81)

NMR (CDCl$_3$): δ7.97 (2H, d, J=8.7 Hz), 7.52 (2H, d, J=8.7 Hz), 6.78-6.71 (2H, m), 6.62 (1H, d, J=2.7 Hz), 5.61-5.57 (1H, br), 4.99 (1H, d, J=17.6 Hz), 4.41 (1H, d, J=17.6 Hz), 3.76 (3H, s), 3.74 (3H, s), 3.50-3.40 (1H, m), 3.28-3.19 (1H, m), 3.16-3.07 (2H, m), 2.55 (1H, dd, J=14.1, 9.3 Hz)

MS: 453 (M+H)$^+$

Example 82

6-(1,3-benzodioxol-5-ylmethyl)-4-[(4-chlorophenyl)sulfonyl]-1,4-diazepan-2,5-dione (Compound 82)

NMR (CDCl$_3$): δ7.97 (2H, d, J=8.7 Hz), 7.52 (2H, d, J=8.7 Hz), 6.73 (1H, d, J=7.8 Hz), 6.60 (1H, d, J=1.4 Hz), 6.56 (1H, dd, J=7.8, 1.4 Hz), 5.95 (2H, s), 5.70-5.63 (1H, br), 4.99 (1H, d, J=17.5 Hz), 4.43 (1H, d, J=17.5 Hz), 3.33-3.19 (2H, m), 3.18-3.08 (2H, m), 2.48 (1H, dd, J=14.4, 8.5 Hz)

MS: 437 (M+H)$^+$

Example 83

4-[(4-chlorophenyl)sulfonyl]-6-(2-fluoro-5-methoxybenzyl)-1,4-diazepan-2,5-dione (Compound 83)

NMR (CDCl$_3$): δ7.97 (2H, d, J=8.7 Hz), 7.52 (2H, d, J=8.7 Hz), 6.95 (1H, t, J=9.2 Hz), 6.78-6.70 (1H, m), 6.68-6.61 (1H, m), 5.81-5.76 (1H, br), 4.99 (1H, d, J=17.6 Hz), 4.42 (1H, d, J=17.6 Hz), 3.76 (3H, s), 3.50-3.33 (1H, m), 3.32-3.11 (3H, m), 2.63 (1H, dd, J=14.4, 8.9 Hz)

MS: 441 (M+H)$^+$

Example 84

6-(5-chloro-2-methoxybenzyl)-N-(4-chlorophenyl)-3,7-dioxo-1,4-diazepan-1-carboxamide (Compound 84)

NMR (DMSO-d$_6$): δ11.08 (1H, s), 7.75 (1H, d, J=3.5 Hz), 7.57 (2H, d, J=8.8 Hz), 7.39 (2H, d, J=8.8 Hz), 7.36 (1H, d, J=2.5 Hz), 7.27 (1H, dd, J=8.8, 2.5 Hz), 7.01 (1H, d, J=8.8 Hz), 4.78 (1H, d, J=17.3 Hz), 4.63 (1H, d, J=17.3 Hz), 4.00-3.90 (1H, m), 3.80 (3H, s), 3.23 (1H, t, J=12.9 Hz), 3.08-2.99 (2H, m), 2.67 (1H, dd, J=14.4, 9.0 Hz)

MS: 436 (M+H)$^+$

Example 85

6-(5-chloro-2-methoxybenzyl)-3,7-dioxo-N-[(1R)-1-phenylethyl]-1,4-diazepan-1-carboxamide (Compound 85)

NMR (CDCl$_3$): δ9.43 (1H, brd, J=7.0 Hz), 7.39-7.30 (4H, m), 7.29-7.25 (1H, m), 7.24-7.20 (1H, m), 7.12 (1H, d, J=2.3

Hz), 6.81 (0.5H, d, J=8.8 Hz), 6.80 (0.5H, d, J=8.8 Hz), 5.77 (0.5H, br), 5.73 (0.5H, br), 5.41 (0.5H, d, J=17.4 Hz), 5.38 (0.5H, d, J=17.4 Hz), 5.10-4.99 (1H, m), 4.12 (0.5H, d, J=17.4 Hz), 4.08 (0.5H, d, J=17.4 Hz), 3.83 (1.5H, s), 3.82 (1.5H, s), 3.73-3.62 (1H, m), 3.35-3.28 (2H, m), 3.08 (1H, dd, J=14.0, 5.1 Hz), 2.64-2.56 (1H, m), 1.55 (1.5H, d, J=7.0 Hz), 1.54 (1.5H, d, J=7.0 Hz)
MS: 430 (M+H)$^+$

Example 86

6-(5-chloro-2-methoxybenzyl)-3,7-dioxo-N-[(1S)-1-phenylethyl]-1,4-diazepan-1-carboxamide (Compound 86)

NMR (CDCl$_3$): δ9.44 (1H, brd, J=6.7 Hz), 7.37-7.17 (6H, m), 7.12 (1H, d, J=2.3 Hz), 6.81 (1H, dd, J=8.7, 2.3 Hz), 5.80 (1H, brd, J=15.3 Hz), 5.42 (0.5H, d, J=17.4 Hz), 5.39 (0.5H, d, J=17.4 Hz), 5.10-4.98 (1H, m), 4.13 (0.5H, d, J=17.4 Hz), 4.08 (0.5H, d, J=17.4 Hz), 3.84 (1.5H, s), 3.83 (1.5H, s), 3.72-3.62 (1H, m), 3.33-3.25 (2H, m), 3.19 (1H, dd, J=14.0, 5.2 Hz), 2.63-2.53 (1H, m), 1.60-1.48 (3H, m)
MS: 430 (M+H)$^+$ Example 87

6-(5-chloro-2-methoxybenzyl)-N-(5-chloro-2-pyridyl)-3,7-dioxo-1,4-diazepan-1-carboxamide (Compound 87)

NMR (DMSO-d$_6$): δ11.64 (1H, s), 8.37 (1H, d, J=2.3 Hz), 8.01 (1H, d, J=8.9 Hz), 7.95 (1H, dd, J=8.9, 2.3 Hz), 7.75 (1H, d, J=3.4 Hz), 7.35 (1H, d, J=2.6 Hz), 7.26 (1H, dd, J=8.8, 2.6 Hz), 7.00 (1H, d, J=8.8 Hz), 4.81 (1H, d, J=17.3 Hz), 4.63 (1H, d, J=17.3 Hz), 4.02-3.91 (1H, m), 3.79 (3H, s), 3.24 (1H, t, J=12.5 Hz), 3.07-2.94 (2H, m), 2.66 (1H, dd, J=14.0, 8.6 Hz)
MS: 437 (M+H)$^+$

Example 88

6-(5-chloro-2-methoxybenzyl)-4-methyl-3,7-dioxo-N-[(1R)-1-phenylethyl]-1,4-diazepan-1-carboxamide (Compound 88)

NMR (DMSO-d$_6$): δ9.39 (0.5H, d, 6.8 Hz), 9.37 (0.5H, d, 6.4 Hz), 7.35-7.29 (5H, m), 7.28-7.24 (2H, m), 7.00-6.97 (1H, m), 4.91-4.84 (2H, m), 4.58 (0.5H, d, 17.1 Hz), 4.55 (0.5H, d, 17.1 Hz), 4.02-3.98 (1H, m), 3.78 (3H, s), 3.17-3.09 (1H, m), 2.98 (1H, dd, 15.0, 5.1 Hz), 2.72 (1.5H, s), 2.68 (1.5H, s), 2.67-2.58 (2H, m), 1.42 (3H, d, 7.0 Hz)
MS: 444 (M+H)$^+$

Example 89

N-benzyl-6-(5-chloro-2-methoxybenzyl)-N,4-dimethyl-3,7-dioxo-1,4-diazepan-1-carboxamide (Compound 89)

NMR (DMSO-d$_6$): δ7.40-7.20 (7H, m), 6.98 (1H, d, 8.9 Hz), 4.81-4.12 (3H, m), 4.01-3.85 (1H, m), 3.84-3.65 (1H, m), 3.78 (3H, s), 3.45-3.10 (4H, m), 3.05-2.88 (1H, m), 2.84-2.55 (5H, m)$^+$
MS: 444 (M+H)$^+$

Reference Example 134

4-[(3-amino-4-chlorophenyl)sulfonyl]-6-(5-chloro-2-methoxybenzyl)-1,4-diazepan-2,5-dione (Compound S134)

To the compound 22 (753 mg) in tetrahydrofuran (25 ml) solution, 5% platinum carbon (sulfur poisoned catalyst) (150 mg) was added and the mixture was stirred under hydrogen atmosphere at room temperature for 15 hours. Next, the catalyst was filtered out and the filtrate was concentrated. The residue was purified by silica gel column chromatography (hexane/ethyl acetate=2/3 to 1/2) to obtain the title compound (559 mg).

Example 90

4-[(3-amino-4-chlorophenyl)sulfonyl]-6-(5-chloro-2-methoxybenzyl)-1,4-diazepan-2,5-dione Hydrochloride (Compound 90)

To the compound S134 (438 mg) in chloroform (5 ml) solution, a 4M hydrogen chloride/1,4-dioxane solution (0.96 ml) was added at room temperature, and the precipitated solid was collected by filtration to obtain the title compound (259 mg).
NMR (DMSO-d$_6$): δ7.85-7.80 (1H, br), 7.44 (1H, d, J=8.3 Hz), 7.40 (1H, d, J=2.3 Hz), 7.28-7.23 (2H, m), 7.00-6.94 (2H, m), 4.86 (1H, d, J=17.5 Hz), 4.47 (1H, d, J=17.5 Hz), 3.76 (3H, s), 3.72-3.65 (1H, m), 3.02-2.98 (2H, br), 2.85 (1H, dd, J=14.2, 4.2 Hz), 2.55-2.45 (1H, m)
MS: 472 (M+H)$^+$
Melting point: 120-122° C.

Reference Example 135

{[(2E)-2-{[(tert-butoxycarbonyl)amino]methyl}-3-(5-chloro-2-methoxyphenyl)-2-propenyl]amino}ethyl Acetate (Compound S135)

To the compound S23 (123 g) in methylene chloride (400 ml) solution, glycine methyl ester hydrochloride (51 g), 1-hydroxybenzotriazole (49 g), triethylamine (53 ml), and 1-(3-dimethylaminopropyl)-3-ethylcarbodiimide hydrochloride (76 g) were added under ice cooling and the mixture was stirred at room temperature for 2 hours. The reaction solution was diluted with distilled water, then the precipitate was filtered out and the filtrate was extracted with ethyl acetate. The organic layer was successively washed with saturated potassium hydrogensulfate aqueous solution, distilled water, saturated sodium hydrogencarbonate aqueous solution, and saturated saline, dried over with anhydrous sodium sulfate, then concentrated. The residue was recrystallized from hexane/ethyl acetate to obtain the title compound (131.5 g).

Reference Example 136

{[(2E)-2-(aminomethyl)-3-(5-chloro-2-methoxyphenyl)-2-propenyl]amino}ethyl acetate Hydrochloride (Compound S136)

A mixed solution of the compound S135 (131.5 g) and a 4M hydrogen chloride/ethyl acetate solution (350 ml) was stirred at room temperature for 20 minutes. The reaction solution was diluted with diethylether, then the precipitate was collected by filtration to obtain the title compound (109.3 g).

Reference Example 137

[((2E)-3-(5-chloro-2-methoxyphenyl)-2-{[(2,4,6-trimethoxybenzyl)amino]methyl}-2-propenyl)amino]ethyl Acetate Hydrochloride (Compound S137)

To the compound S136 (55.8 g) in tetrahydrofuran (800 ml) solution, 2,4,6-trimethoxybenzaldehyde (30.5 g) was added and the mixture was stirred at room temperature for 20 minutes. Next, sodium triacetoxy borohydride (50 g) was added to the reaction solution and the mixture was stirred at room temperature for 1 hour. Distilled water was added to the reaction solution, then tetrahydrofuran was distilled off in vacuo. The remaining aqueous layer was basified by a sodium hydroxide aqueous solution, then the mixture was extracted with ethyl acetate. The organic layer was washed with saturated saline, dried over with anhydrous sodium sulfate, and partially distilled off in vacuo. A 4M hydrogen chloride/ethyl acetate solution was added to the remaining solution and the mixture was stirred under ice cooling for 30 minutes. The precipitate was collected by filtration to obtain the title compound (75.7 g).

NMR (DMSO-$d_6$): δ9.12 (1H, br), 8.58 (1H, br), 7.59 (1H, s), 7.48 (1H, d, J=8.9 Hz), 7.32 (1H, s), 7.13 (1H, d, J=8.9 Hz), 6.23 (2H, s), 4.13 (2H, q, J=7.1 Hz), 3.96 (2H, d, J=5.7 Hz), 3.84-3.70 (16H, m), 1.21 (3H, t, J=7.1 Hz)

Reference Example 138

[((2E)-3-(5-chloro-2-methoxyphenyl)-2-{[(2,4,6-trimethoxybenzyl)amino]methyl}-2-propenyl)amino]acetic Acid Hydrochloride (Compound S138)

To the compound S137 (148.5 g) in methanol (300 ml) solution, 2N sodium hydroxide aqueous solution (300 ml) was added and the mixture was stirred at room temperature for 2 hours. The reaction solution was neutralized by 6M hydrochloric acid (100 ml), then the methanol was distilled off in vacuo. Crystal nuclei were added to the remaining solution and the mixture was stirred under ice cooling for 30 minutes. The precipitate was collected by filtration to obtain the title compound as a crude product (143.1 g).

Reference Example 139

(6E)-6-(5-chloro-2-methoxybenzylidene)-1-(2,4,6-trimethoxybenzyl)-1,4-diazepan-2,5-dione (Compound S139)

A solution of the compound S138 (53 g) and 1-hydroxybenzotriazole (14 g) in N,N-dimethylformamide (1000 ml) was added dropwise to a solution of 1-(3-dimethylaminopropyl)-3-ethylcarbodiimide hydrochloride (24 g) and triethylamine (17 ml) in N,N-dimethylformamide (500 ml) over 2 hours. After dropping, the insoluble compound was filtered out, then the filtrate was concentrated. Ethyl acetate and 1N hydrochloric acid were added to the residue and the mixture was stirred for 30 minutes. The insoluble compound was collected by filtration and washed with distilled water and ethyl acetate. Ethyl acetate and 1N sodium hydroxide aqueous solution were added to the obtained solid and stirred for 30 minutes. The insoluble compound was collected by filtration and washed with distilled water and ethyl acetate. A mixed solvent of tetrahydrofuran/methanol=1/1 was added to the obtained solid and the mixture was stirred under heating and reflux for 30 minutes. The solution was allowed to cool to room temperature, then the mixed solution was filtered by sellite and the filtrate was concentrated. The residue was recrystallized from ethyl acetate to obtain the title compound (22.1 g).

NMR (CDCl$_3$): δ7.6 (1H, s), 7.29-7.19 (1H, m), 6.76-6.69 (2H, m), 6.05 (1H, br), 5.75 (2H, s), 4.52 (2H, s), 4.23 (2H, s), 4.05 (2H, d, J=6.1 Hz), 3.80-3.74 (6H, m), 3.52 (6H, s)

Reference Example 140

6-(5-chloro-2-methoxybenzyl)-1-(2,4,6-trimethoxybenzyl)-1,4-diazepan-2,5-dione (Compound S140A), (6S)-6-(5-chloro-2-methoxybenzyl)-1-(2,4,6-trimethoxybenzyl)-1,4-diazepan-2,5-dione (Compound S140B), and (6R)-6-(5-chloro-2-methoxybenzyl)-1-(2,4,6-trimethoxybenzyl)-1,4-diazepan-2,5-dione (Compound S140C)

To the compound S139 (16.3 g) in tetrahydrofuran (600 ml) solution, 2% platinum carbon (sulfur poisoned catalyst) (7.3 g) was added and the mixture was stirred under hydrogen atmosphere at room temperature for 60 hours. Next, the catalyst was filtered out and the filtrate was concentrated. The residue was purified by silica gel column chromatography (chloroform/ethyl acetate/methanol=7/1/0.5) to obtain the title compound (compound S140A) (13.1 g).

The compound S140A was separated using CHIRALCEL OD-H (Daicel Chemical Industries) (movement phase: acetonitrile/trifluoroacetic acid=100/0.1) to obtain the compound S140B and the compound S140C.

(Compound S140A)
NMR (CDCl$_3$): δ7.14 (1H, dd, J=8.7, 2.5 Hz), 6.88 (1H, d, J=2.5 Hz), 6.69 (1H, d, J=8.7 Hz), 5.98 (2H, s), 5.94 (1H, br), 4.8 (1H, d, J=13.7 Hz), 4.30-4.20 (2H, m), 3.83 (3H, s), 3.78-3.69 (4H, m), 3.63 (6H, s), 3.38 (1H, dd, J=15.4, 12.2 Hz), 3.11 (1H, dd, J=13.0, 3.2 Hz), 2.94 (1H, dd, J=15.4, 4.9 Hz), 2.5 (1H, dd, J=13.0, 10.7 Hz)

(Compound S140B)
NMR (CDCl$_3$): δ7.14 (1H, dd, J=8.7, 2.5 Hz), 6.88 (1H, d, J=2.5 Hz), 6.69 (1H, d, J=8.7 Hz), 5.98 (2H, s), 5.94 (1H, br), 4.8 (1H, d, J=13.7 Hz), 4.30-4.20 (2H, m), 3.83 (3H, s), 3.78-3.69 (4H, m), 3.63 (6H, s), 3.38 (1H, dd, J=15.4, 12.2 Hz), 3.11 (1H, dd, J=13.0, 3.2 Hz), 2.94 (1H, dd, J=15.4, 4.9 Hz), 2.5 (1H, dd, J=13.0, 10.7 Hz)

(Compound S140C)
NMR (CDCl$_3$): δ7.14 (1H, dd, J=8.7, 2.5 Hz), 6.88 (1H, d, J=2.5 Hz), 6.69 (1H, d, J=8.7 Hz), 5.98 (2H, s), 5.94 (1H, br), 4.8 (1H, d, J=13.7 Hz), 4.30-4.20 (2H, m), 3.83 (3H, s), 3.78-3.69 (4H, m), 3.63 (6H, s), 3.38 (1H, dd, J=15.4, 12.2 Hz), 3.11 (1H, dd, J=13.0, 3.2 Hz), 2.94 (1H, dd, J=15.4, 4.9 Hz), 2.5 (1H, dd, J=13.0, 10.7 Hz)

Reference Example 141A 2-chlorophenyl 6-(5-chloro-2-methoxybenzyl)-3,7-dioxo-4-(2,4,6-trimethoxybenzyl)-1,4-diazepan-1-carboxylate (Compound S141A)

To the compound S140A (4.07 g) in tetrahydrofuran (200 ml) solution, a 1.59M hexane solution of n-butyllithium (6 ml) was added at −78° C. and the mixture was stirred at that temperature for 20 minutes. Next, 2-chlorophenyl chlorocarbonate (1.4 ml) was added to the reaction solution at −78° C.

and the mixture was stirred at that temperature for 20 minutes. The reaction solution was diluted with saturated potassium hydrogensulfate aqueous solution and distilled water, and the mixture was extracted with ethyl acetate. The organic layer was successively washed with saturated saline and distilled water, dried over with anhydrous sodium sulfate, then concentrated. The residue was purified by silica gel column chromatography (hexane/ethyl acetate/methanol=1/2/0 to 3/3/1) to obtain the title compound (4.21 g).

NMR (CDCl$_3$): δ7.44-7.40 (1H, m), 7.33-7.12 (4H, m), 6.93 (1H, d, J=2.6 Hz), 6.73 (1H, d, J=8.8 Hz), 6.05 (2H, s), 5.06 (1H, d, J=17.6 Hz), 4.83 (1H, d, J=13.7 Hz), 4.44 (1H, d, J=17.6 Hz), 4.34 (1H, d, J=13.7 Hz), 3.83 (3H, s), 3.77 (3H, s), 3.7 (6H, s), 3.57-3.45 (1H, m), 3.29-3.14 (2H, m), 3.07 (1H, dd, J=14.1, 3.8 Hz), 2.38 (1H, dd, J=14.1, 9.8 Hz)

Reference Example 141B (6S)-2-chlorophenyl 6-(5-chloro-2-methoxybenzyl)-3,7-dioxo-4-(2,4,6-trimethoxybenzyl)-1,4-diazepan-1-carboxylate (Compound S141B)

Instead of the starting material compound of Reference Example 141A, that is, the compound S140A, the compound S140B was used for the similar procedure as in Reference Example 141A to obtain the title compound.

NMR (CDCl$_3$): δ7.44-7.40 (1H, m), 7.33-7.12 (4H, m), 6.93 (1H, d, J=2.6 Hz), 6.73 (1H, d, J=8.8 Hz), 6.05 (2H, s), 5.06 (1H, d, J=17.6 Hz), 4.83 (1H, d, J=13.7 Hz), 4.44 (1H, d, J=17.6 Hz), 4.34 (1H, d, J=13.7 Hz), 3.83 (3H, s), 3.77 (3H, s), 3.7 (6H, s), 3.57-3.45 (1H, m), 3.29-3.14 (2H, m), 3.07 (1H, dd, J=14.1, 3.8 Hz), 2.38 (1H, dd, J=14.1, 9.8 Hz)

Reference Example 141C (6R)-2-chlorophenyl 6-(5-chloro-2-methoxybenzyl)-3,7-dioxo-4-(2,4,6-trimethoxybenzyl)-1,4-diazepan-1-carboxylate (Compound S141C)

Instead of the starting material compound of Reference Example 141A, that is, the compound S140A, the compound S140C was used for the similar procedure as in Reference Example 141A to obtain the title compound.

NMR (CDCl$_3$): δ7.44-7.40 (1H, m), 7.33-7.12 (4H, m), 6.93 (1H, d, J=2.6 Hz), 6.73 (1H, d, J=8.8 Hz), 6.05 (2H, s), 5.06 (1H, d, J=17.6 Hz), 4.83 (1H, d, J=13.7 Hz), 4.44 (1H, d, J=17.6 Hz), 4.34 (1H, d, J=13.7 Hz), 3.83 (3H, s), 3.77 (3H, s), 3.7 (6H, s), 3.57-3.45 (1H, m), 3.29-3.14 (2H, m), 3.07 (1H, dd, J=14.1, 3.8 Hz), 2.38 (1H, dd, J=14.1, 9.8 Hz)

Reference Example 142A tert-butyl 3-[(1R)-1-({[(6R)-6-(5-chloro-2-methoxybenzyl)-3,7-dioxo-4-(2,4,6-trimethoxybenzyl)-1,4-diazepan-1-yl]carbonyl}amino)propyl]benzoate (Compound S142A) and tert-butyl 3-[(1R)-1-({[(6S)-6-(5-chloro-2-methoxybenzyl)-3,7-dioxo-4-(2,4,6-trimethoxybenzyl)-1,4-diazepan-1-yl]carbonyl}amino)propyl]benzoate (Compound S142B)

To the compound S141A (3 g) in N,N-dimethylformamide (6 ml) solution, 4-dimethylaminopyridine was added under ice cooling and the mixture was stirred at that temperature for 30 minutes. Next, the compound S83 (2 g) and triethylamine (1.6 ml) were added to the reaction solution and the mixture was stirred under ice cooling for 14 hours. The reaction solution was diluted with ethyl acetate, then was successively washed with distilled water, saturated potassium hydrogensulfate aqueous solution, and saturated saline, dried over with anhydrous sodium sulfate, then concentrated. The residue was purified by silica gel column chromatography (hexane/ethyl acetate=2/3 to 1/2) to obtain the title compound (compound S142A) (1.21 g) and the title compound (compound S142B) (1.34 g).

(Compound S142A)

NMR (CDCl$_3$): δ9.49 (1H, d, J=7.3 Hz), 7.89 (1H, s), 7.85 (1H, d, J=7.6 Hz), 7.43 (1H, d, J=7.6 Hz), 7.35 (1H, t, J=7.6 Hz), 7.16 (1H, dd, J=8.8, 2.6 Hz), 6.89 (1H, d, J=2.6 Hz), 6.73 (1H, d, J=8.8 Hz), 6.06 (2H, s), 5.28 (1H, d, J=17.4 Hz), 4.82 (1H, q, J=7.3 Hz), 4.76 (1H, d, J=13.8 Hz), 4.31 (1H, d, J=13.8 Hz), 4.19 (1H, d, J=17.4 Hz), 3.82 (3H, s), 3.76 (3H, s), 3.69 (6H, s), 3.57-3.43 (1H, m), 3.1 (1H, dd, J=14.0, 4.4 Hz), 3.05-2.96 (2H, m), 2.37 (1H, dd, J=14.0, 9.6 Hz), 1.90-1.78 (2H, m), 1.57 (9H, s), 0.89 (3H, t, J=7.3 Hz)

(Compound S142B)

NMR (CDCl$_3$): δ9.48 (1H, d, J=7.5 Hz), 7.92-7.88 (2H, m), 7.43 (1H, d, J=7.7 Hz), 7.36 (1H, t, J=7.7 Hz), 7.18 (1H, dd, J=8.7, 2.6 Hz), 6.92 (1H, d, J=2.6 Hz), 6.75 (1H, d, J=8.7 Hz), 5.99 (2H, s), 5.29 (1H, d, J=17.4 Hz), 4.85 (1H, q, J=7.5 Hz), 4.76 (1H, d, J=13.8 Hz), 4.257 (1H, d, J=13.8 Hz), 4.252 (1H, d, J=17.4 Hz), 3.81 (3H, s), 3.77 (3H, s), 3.60-3.48 (1H, m), 3.54 (6H, s), 3.1 (1H, dd, J=13.8, 4.8 Hz), 3.00-2.94 (2H, m), 2.4 (1H, dd, J=13.8, 9.2 Hz), 1.94-1.76 (2H, m), 1.6 (9H, s), 0.9 (3H, t, J=7.5 Hz)

Reference Example 142B tert-butyl 3-[(1R)-1-({[(6R)-6-(5-chloro-2-methoxybenzyl)-3,7-dioxo-4-(2,4,6-trimethoxybenzyl)-1,4-diazepan-1-yl]carbonyl}amino)propyl]benzoate (compound S142A)

To the compound S142B (400 mg) in N,N-dimethylformamide (3 ml) solution, 1,8-diazabicyclo[5.4.0]undeca-7-ene was added and the mixture was stirred at room temperature for 24 hours. The reaction solution was diluted with ethyl acetate, then was successively washed saturated potassium hydrogensulfate aqueous solution, distilled water, and saturated saline, dried over with anhydrous sodium sulfate, then concentrated. The residue was purified by silica gel column chromatography (hexane/ethyl acetate=1/1 to 2/3) to obtain the title compound (163 mg) and, as a recovered starting material, the compound S142B (200 mg).

NMR (CDCl$_3$): δ9.49 (1H, d, J=7.3 Hz), 7.89 (1H, s), 7.85 (1H, d, J=7.6 Hz), 7.43 (1H, d, J=7.6 Hz), 7.35 (1H, t, J=7.6 Hz), 7.16 (1H, dd, J=8.8, 2.6 Hz), 6.89 (1H, d, J=2.6 Hz), 6.73 (1H, d, J=8.8 Hz), 6.06 (2H, s), 5.28 (1H, d, J=17.4 Hz), 4.82 (1H, q, J=7.3 Hz), 4.76 (1H, d, J=13.8 Hz), 4.31 (1H, d, J=13.8 Hz), 4.19 (1H, d, J=17.4 Hz), 3.82 (3H, s), 3.76 (3H, s), 3.69 (6H, s), 3.57-3.43 (1H, m), 3.1 (1H, dd, J=14.0, 4.4 Hz), 3.05-2.96 (2H, m), 2.37 (1H, dd, J=14.0, 9.6 Hz), 1.90-1.78 (2H, m), 1.57 (9H, s), 0.89 (3H, t, J=7.3 Hz)

Example 91

3-[(1R)-1-({[(6R)-6-(5-chloro-2-methoxybenzyl)-3,7-dioxo-1,4-diazepan-1-yl]carbonyl}amino)propyl]benzoic Acid (Compound 91)

To the compound S142A (1.92 g), 1M hydrogen chloride/acetic acid solution (15 ml) was added and the mixture was stirred at room temperature for 18 hours. The reaction solution was concentrated, then the residue was successively purified by silica gel column chromatography (chloroform/ethyl acetate/methanol/acetic acid=8/8/1/0.08), silica gel column chromatography (hexane/ethyl acetate/methanol/acetic acid=5/5/1/0.1), and florisil column chromatography (ethyl acetate/isopropanol, isopropanol: 0 to 20%). Hexane was added to the obtained purified product in ethyl acetate solution, then the precipitated solid was collected by filtration to obtain the title compound (0.5 g).

NMR (DMSO-$d_6$): δ13.01 (1H, br), 9.48 (1H, d, J=7.3 Hz), 7.86 (1H, s), 7.82 (1H, d, J=7.7 Hz), 7.67 (1H, d, J=3.5 Hz), 7.55 (1H, d, J=7.7 Hz), 7.46 (1H, t, J=7.7 Hz), 7.33 (1H, d, J=2.6 Hz), 7.27 (1H, dd, J=8.8, 2.6 Hz), 7.00 (1H, d, J=8.8 Hz), 4.79-4.69 (2H, m), 4.49 (1H, d, J=17.2 Hz), 3.91-3.81 (1H, m), 3.79 (3H, s), 3.16 (1H, t, J=12.6 Hz), 3.05-2.96 (2H, m), 2.67 (1H, dd, J=14.3, 9.3 Hz), 1.89-1.74 (2H, m), 0.84 (3H, t, J=7.3 Hz)

MS: 488 (M+H)$^+$

Instead of the starting material compound of Reference Example 142A, that is, the compound S83, the amine derivatives of Table VII to Table IX were used for the similar procedure as with Reference Example 142A and Example 91 to obtain the title compounds of Examples 92 to 149. Note that the amine derivatives shown in Table VII to Table IX are compounds shown in the reference examples and also commercially available compounds or compounds obtained by derivation from commercially available compounds by known methods.

TABLE VII

| Ex. no. | Amine derivative used as material |
|---|---|
| Ex. 92 | |
| Ex. 93 | |
| Ex. 94 | |
| Ex. 95 | |
| Ex. 96 | |
| Ex. 97 | |
| Ex. 98 | |
| Ex. 99 | |
| Ex. 100 | |
| Ex. 101 | |
| Ex. 102 | |
| Ex. 103 | |
| Ex. 104 | |
| Ex. 105 | |

TABLE VII-continued

| Ex. no. | Amine derivative used as material |
|---|---|
| Ex. 106 | 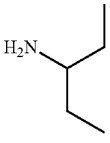 |
| Ex. 107 | 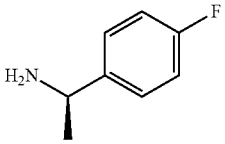 |
| Ex. 108 | 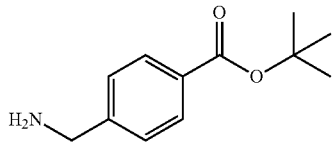 |
| Ex. 109 | 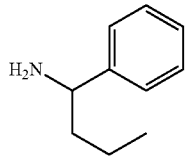 |
| Ex. 110 | 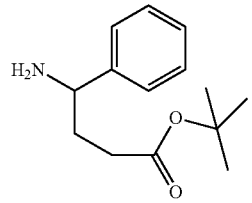 [SMILES: CC(C)(C)OC(=O)CCC(N)c1ccccc1] |
| Ex. 111 | 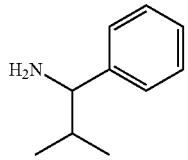 |

TABLE VIII

| Ex. no. | Amine derivative used as material |
|---|---|
| Ex. 112 | 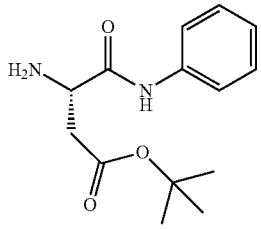 [SMILES: CC(C)(C)OC(=O)C[C@H](N)C(=O)Nc1ccccc1] |
| Ex. 113 | Compound S86 |
| Ex. 114 | Compound S86 |
| Ex. 115 | 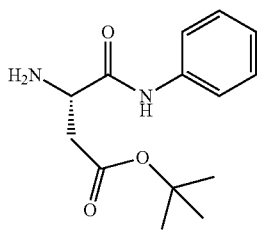 [SMILES: CC(C)(C)OC(=O)C[C@H](N)C(=O)Nc1ccccc1] |

TABLE VIII-continued

| Ex. no. | Amine derivative used as material |
|---|---|
| Ex. 116 | 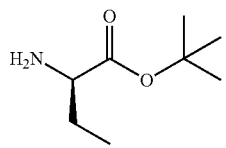 |
| Ex. 117 | 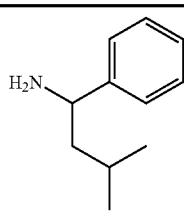 |
| Ex. 118 | Compound S87 |
| Ex. 119 | 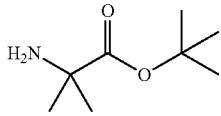 |
| Ex. 120 | Compound S74 |
| Ex. 121 | Compound S87 |
| Ex. 122 | Compound S109 |
| Ex. 123 | Compound S109 |
| Ex. 124 | Compound S84 |
| Ex. 125 | Compound S83 |
| Ex. 126 | Compound S84 |
| Ex. 127 | Compound S112 |
| Ex. 128 | Compound S113 |
| Ex. 129 | Compound S113 |
| Ex. 130 | Compound S78 |
| Ex. 131 | Compound S90 |

TABLE IX

| Ex. no. | Amine derivative used as material |
|---|---|
| Ex. 132 | Compound S90 |
| Ex. 133 | Compound S91 |
| Ex. 134 | Compound S91 |
| Ex. 135 | Compound S110 |
| Ex. 136 | Compound S111 |
| Ex. 137 | Compound S92 |
| Ex. 138 | Compound S93 |
| Ex. 139 | Compound S79 |
| Ex. 140 | Compound S77 |
| Ex. 141 | Compound S77 |
| Ex. 142 | Compound S114 |
| Ex. 143 | Compound S114 |
| Ex. 144 | Compound S80 |
| Ex. 145 | Compound S80 |
| Ex. 146 | Compound S81 |
| Ex. 147 | Compound S81 |
| Ex. 148 | Compound S85 |
| Ex. 149 | Compound S78 |

Example 92

(2S)-2-({[6-(5-chloro-2-methoxybenzyl)-3,7-dioxo-1,4-diazepan-1-yl]carbonyl}amino)-3-phenylpropanoic Acid (Compound 92)

NMR (DMSO-$d_6$): δ13.04 (1H, br), 9.31 (0.5H, d, 7.7 Hz), 9.27 (0.5H, d, 6.8 Hz), 7.67 (1H, br), 7.34-7.20 (5H, m), 7.19-7.10 (2H, m), 6.99 (1H, d, 8.8 Hz), 4.76 (0.5H, d, 17.3 Hz), 4.75 (0.5H, d, 17.4 Hz), 4.59-4.49 (2H, m), 3.90-3.81 (1H, m), 3.77 (3H, s), 3.19-2.99 (4H, m), 2.98-2.85 (1H, m), 2.68-2.55 (1H, m)
MS: 474 (M+H)$^+$

Example 93

(2S)-({[6-(5-chloro-2-methoxybenzyl)-3,7-dioxo-1,4-diazepan-1-yl]carbonyl}amino)(phenyl)acetic Acid (Compound 93)

NMR (DMSO-$d_6$): δ13.25 (1H, br), 9.96 (0.5H, d, 6.3 Hz), 9.88 (0.5H, d, 6.3 Hz), 7.69 (0.5H, br), 7.65 (0.5H, br), 7.45-7.30 (6H, m), 7.26 (1H, d, 8.8 Hz), 6.99 (1H, d, 8.8 Hz), 5.29 (1H, d, 6.3 Hz), 4.77 (0.5H, d, 17.2 Hz), 4.74 (0.5H, d, 17.2 Hz), 4.54 (0.5H, d, 17.2 Hz), 4.50 (0.5H, d, 17.2 Hz), 3.95-3.85 (1H, m), 3.78 (3H, s), 3.19-2.90 (3H, m), 2.69-2.59 (1H, m)
MS: 460 (M+H)$^+$

Example 94

N-{[6-(5-chloro-2-methoxybenzyl)-3,7-dioxo-1,4-diazepan-1-yl]carbonyl}-3-phenyl-β-alanine (Compound 94)

NMR (DMSO-$d_6$): δ12.54-12.00 (1H, br), 9.71 (0.5H, d, 8.1 Hz), 9.66 (0.5H, d, 8.1 Hz), 7.69-7.60 (1H, m), 7.40-7.18 (7H, m), 6.99 (1H, d, 8.7 Hz), 5.22-5.13 (1H, m), 4.77 (0.5H, d, 17.1 Hz), 4.75 (0.5H, d, 17.1 Hz), 4.52 (0.5H, d, 17.1 Hz), 4.48 (0.5H, d, 17.1 Hz), 3.93-3.82 (1H, m), 3.78 (3H, s), 3.15-3.07 (1H, m), 3.05-2.92 (2H, m), 2.91-2.75 (2H, m), 2.69-2.58 (1H, m)
MS: 474 (M+H)$^+$

Example 95

N-benzhydryl-6-(5-chloro-2-methoxybenzyl)-3,7-dioxo-1,4-diazepan-1-carboxamide (Compound 95)

NMR (CDCl$_3$): δ9.93 (1H, d, 7.9 Hz), 7.40-7.15 (10H, m), 7.22 (1H, dd, 8.8, 2.5 Hz), 7.12 (1H, d, 2.5 Hz), 6.81 (1H, d, 8.8 Hz), 6.20 (1H, d, 7.9 Hz), 5.70 (1H, br), 5.42 (1H, d, 17.6 Hz), 4.13 (1H, d, 17.6 Hz), 3.83 (3H, s), 3.78-3.64 (1H, m), 3.38-3.25 (2H, m), 3.19 (1H, dd, 13.9, 5.1 Hz), 2.60 (1H, dd, 13.9, 8.5 Hz)
MS: 492 (M+H)$^+$

Example 96

6-(5-chloro-2-methoxybenzyl)-3,7-dioxo-N-(1-phenylpropyl)-1,4-diazepan-1-carboxamide (Compound 96)

NMR (CDCl$_3$): δ9.49 (1H, brd, 7.7 Hz), 7.39-7.21 (6H, m), 7.13 (1H, d, 2.5 Hz), 6.81 (0.5H, d, 8.7 Hz), 6.80 (0.5H, d, 8.8 Hz), 5.64 (0.5H, br), 5.60 (0.5H, br), 5.40 (0.5H, d, 17.6 Hz), 5.38 (0.5H, d, 17.6 Hz), 4.85-4.76 (1H, m), 4.12 (0.5H, d, 17.6 Hz), 4.07 (0.5H, d, 17.6 Hz), 3.84 (1.5H, s), 3.82 (1.5H, s), 3.72-3.62 (1H, m), 3.35-3.27 (2H, m), 3.19 (1H, dd, 13.9, 5.2 Hz), 2.65-2.59 (1H, m), 1.95-1.79 (2H, m), 0.95-0.86 (3H, m)
MS: 444 (M+H)$^+$

Example 97

6-(5-chloro-2-methoxybenzyl)-N-[1-(1-naphthyl)ethyl]-3,7-dioxo-1,4-diazepan-1-carboxamide (Compound 97)

NMR (CDCl$_3$): δ9.54 (0.5H, d, 6.9 Hz), 9.52 (0.5H, d, 6.3 Hz), 8.14 (1H, d, 8.4 Hz), 7.87 (1H, d, 8.0 Hz), 7.79 (1H, t, 7.8 Hz), 7.59-7.45 (4H, m), 7.25-7.19 (1H, m), 7.10 (1H, s), 6.81 (0.5H, d, 8.8 Hz), 6.79 (0.5H, d, 8.8 Hz), 5.95-5.84 (1H, m), 5.68 (0.5H, br), 5.62 (0.5H, br), 5.46 (0.5H, d, 17.7 Hz), 5.42 (0.5H, d, 17.7 Hz), 4.15 (0.5H, d, 17.7 Hz), 4.10 (0.5H, d, 17.7 Hz), 3.83 (1.5H, s), 3.81 (1.5H, s), 3.73-3.65 (1H, m), 3.35-3.30 (1H, m), 3.29-3.24 (1H, m), 3.16 (1H, dd, 13.9, 5.0 Hz), 2.62-2.55 (1H, m), 1.70 (3H, d, 6.8 Hz)
MS: 480 (M+H)$^+$

Example 98

6-(5-chloro-2-methoxybenzyl)-N-(1,2-diphenylethyl)-3,7-dioxo-1,4-diazepan-1-carboxamide (Compound 98)

NMR (CDCl$_3$): δ9.63-9.56 (1H, m), 7.35-7.12 (11H, m), 7.09-7.07 (1H, m), 6.81 (0.5H, d, 8.7 Hz), 6.80 (0.5H, d, 8.7 Hz), 5.70-5.65 (1H, m), 5.33 (0.5H, d, 17.6 Hz), 5.32 (0.5H, d, 17.6 Hz), 5.19-5.11 (1H, m), 4.05 (0.5H, d, 17.6 Hz), 4.04 (0.5H, d, 17.6 Hz), 3.83 (1.5H, s), 3.82 (1.5H, s), 3.70-3.60 (1H, m), 3.33-3.25 (2H, m), 3.22-3.05 (3H, m), 2.65-2.55 (1H, m)
MS: 506 (M+H)$^+$

Example 99

6-(5-chloro-2-methoxybenzyl)-N-(2-methoxyphenyl)-3,7-dioxo-1,4-diazepan-1-carboxamide (Compound 99)

NMR (DMSO-$d_6$): δ11.55 (1H, s), 8.12 (1H, d, J=7.7 Hz), 7.71 (1H, d, J=3.5 Hz), 7.36 (1H, d, J=2.6 Hz), 7.27 (1H, dd, J=8.8, 2.6 Hz), 7.08-7.04 (2H, m), 7.01 (1H, d, J=8.8 Hz), 6.98-6.92 (1H, m), 4.90 (1H, d, J=17.3 Hz), 4.60 (1H, d, J=17.3 Hz), 4.00-3.91 (1H, m), 3.87 (3H, s), 3.80 (3H, s), 3.19 (1H, t, J=12.8 Hz), 3.07-2.99 (2H, m), 2.69 (1H, dd, J=14.3, 9.1 Hz)
MS: 432 (M+H)$^+$

Example 100

(2R)-2-({[6-(5-chloro-2-methoxybenzyl)-3,7-dioxo-1,4-diazepan-1-yl]carbonyl}amino)propanoic Acid (Compound 100)

NMR (CDCl$_3$): δ9.45-9.40 (1H, m), 7.23-7.19 (1H, m), 7.15 (0.5H, d, 2.3 Hz), 7.12 (0.5H, d, 2.4 Hz), 6.99 (0.5H, br), 6.81 (0.5H, d, 8.8 Hz), 6.80 (0.5H, d, 8.8 Hz), 6.57 (0.5H, br), 5.32 (0.5H, d, 17.3 Hz), 5.29 (0.5H, d, 17.3 Hz), 4.55-4.45 (1H, m), 4.17 (0.5H, d, 17.3 Hz), 4.15 (0.5H, d, 17.3 Hz), 3.84 (3H, s), 3.75-3.65 (1H, m), 3.40-3.30 (2H, m), 3.25-3.15 (1H, m), 2.68-2.57 (1H, m), 1.52 (1.5H, d, 7.2 Hz), 1.49 (1.5H, d, 7.3 Hz)
MS: 398 (M+H)$^+$

Example 101

6-(5-chloro-2-methoxybenzyl)-N-[(1S)-2-hydroxy-1-phenylethyl]-3,7-dioxo-1,4-diazepan-1-carboxamide (Compound 101)

NMR (CDCl$_3$): δ9.75 (0.5H, d, 7.5 Hz), 9.73 (0.5H, d, 7.5 Hz), 7.42-7.30 (5H, m), 7.22 (1H, dd, 8.7, 2.5 Hz), 7.15 (1H, d, 2.5 Hz), 6.82 (0.5H, d, 8.7 Hz), 6.81 (0.5H, d, 8.7 Hz), 5.73 (0.5H, br), 5.69 (0.5H, br), 5.38 (1H, d, 17.7 Hz), 5.29-5.21 (1H, m), 4.43-4.28 (2H, m), 4.14 (0.5H, d, 17.7 Hz), 4.10 (0.5H, d, 17.7 Hz), 3.84 (1.5H, s), 3.83 (1.5H, s), 3.74-3.67 (1H, m), 3.39-3.30 (2H, m), 3.20 (1H, dd, 13.9, 5.1 Hz), 2.69-2.60 (1H, m)

MS: 446 (M+H)$^+$

Example 102

N-benzyl-6-(5-chloro-2-methoxybenzyl)-N-methyl-3,7-dioxo-1,4-diazepan-1-carboxamide (Compound 102)

NMR (CDCl$_3$): δ7.42-7.25 (5H, m), 7.20 (1H, dd, 8.7, 2.5 Hz), 7.13 (1H, m), 6.80 (1H, d, 8.7 Hz), 5.85-5.75 (1H, m), 4.80-4.19 (4H, m), 3.84 (3H, s), 3.49-3.38 (1H, m), 3.37-3.20 (2H, m), 3.05-2.79 (4H, m), 2.70-2.55 (1H, m)

MS: 430 (M+H)$^+$

Example 103

N-benzyl-6-(5-chloro-2-methoxybenzyl)-3,7-dioxo-1,4-diazepan-1-carboxamide (Compound 103)

NMR (CDCl$_3$): δ9.37 (1H, br), 7.39-7.29 (5H, m), 7.21 (1H, dd, 8.7, 2.6 Hz), 7.11 (1H, d, 2.6 Hz), 6.80 (1H, d, 8.7 Hz), 5.76 (1H, br), 5.45 (1H, d, 17.5 Hz), 4.51 (2H, d, 5.5 Hz), 4.14 (1H, d, 17.5 Hz), 3.83 (3H, s), 3.75-3.68 (1H, m), 3.36-3.31 (2H, m), 3.16 (1H, dd, 13.9, 5.4 Hz), 2.58 (1H, dd, 13.9, 8.2 Hz)

MS: 416 (M+H)$^+$

Example 104

6-(5-chloro-2-methoxybenzyl)-3,7-dioxo-N-(2-phenylethyl)-1,4-diazepan-1-carboxamide (Compound 104)

NMR (CDCl$_3$): δ9.06 (1H, br), 7.36-7.21 (6H, m), 7.13 (1H, d, 2.6 Hz), 6.80 (1H, d, 8.7 Hz), 5.72 (1H, br), 5.41 (1H, d, 17.4 Hz), 4.10 (1H, d, 17.4 Hz), 3.83 (3H, s), 3.75-3.65 (1H, m), 3.64-3.52 (2H, m), 3.38-3.27 (2H, m), 3.14 (1H, dd, 13.9, 5.7 Hz), 2.88 (2H, t, 7.3 Hz), 2.59 (1H, d, 13.9, 7.9 Hz)

MS: 430 (M+H)$^+$

Example 105

6-(5-chloro-2-methoxybenzyl)-N-[(1R)-1-cyclohexylethyl]-3,7-dioxo-1,4-diazepan-1-carboxamide (Compound 105)

NMR (CDCl$_3$): δ8.98 (1H, d, 8.2 Hz), 7.21 (1H, dd, 8.8, 2.6 Hz), 7.13 (0.5H, d, 2.6 Hz), 7.12 (0.5H, d, 2.6 Hz), 6.81 (1H, d, 8.8 Hz), 5.74 (1H, br), 5.43 (1H, d, 17.6 Hz), 5.11 (1H, d, 17.6 Hz), 3.84 (1.5H, s), 3.83 (1.5H, s), 3.82-3.75 (1H, m), 3.72-3.64 (1H, m), 3.35-3.30 (2H, m), 3.22-3.17 (1H, m), 2.60 (1H, dd, 14.0, 8.5 Hz), 1.81-1.65 (5H, m), 1.48-0.85 (6H, m), 1.15 (1.5H, d, 5.7 Hz), 1.13 (1.5H, d, 5.6 Hz)

MS: 436 (M+H)$^+$

Example 106

6-(5-chloro-2-methoxybenzyl)-N-(1-ethylpropyl)-3,7-dioxo-1,4-diazepan-1-carboxamide (Compound 106)

NMR (CDCl$_3$): δ8.86 (1H, d, 8.1 Hz), 7.21 (1H, dd, 8.8, 2.5 Hz), 7.12 (1H, d, 2.5 Hz), 6.81 (1H, d, 8.8 Hz), 5.81 (1H, brs), 5.42 (1H, d, 17.5 Hz), 4.12 (1H, d, 17.5 Hz), 3.84 (3H, s), 3.78-3.65 (2H, m), 3.34-3.30 (2H, m), 3.18 (1H, dd, 14.0, 5.2 Hz), 2.61 (1H, dd, 14.0, 8.5 Hz), 1.65-1.43 (4H, m), 0.96-0.89 (6H, m)

MS: 396 (M+H)$^+$

Example 107

6-(5-chloro-2-methoxybenzyl)-N-[(1R)-1-(4-fluorophenyl)ethyl]-3,7-dioxo-1,4-diazepan-1-carboxamide (Compound 107)

NMR (CDCl$_3$): δ9.42-9.38 (1H, m), 7.35-7.28 (2H, m), 7.22 (1H, dd, 8.7, 2.2 Hz), 7.12 (0.5H, d, 2.2 Hz), 7.11 (0.5H, d, 2.2 Hz), 7.07-7.00 (2H, m), 6.81 (0.5H, d, 8.7 Hz), 6.80 (0.5H, d, 8.7 Hz), 5.80-5.73 (1H, m), 5.39 (0.5H, d, 17.6 Hz), 5.37 (0.5H, d, 17.6 Hz), 5.05-4.99 (1H, m), 4.12 (0.5H, d, 17.6 Hz), 4.08 (0.5H, d, 17.6 Hz), 3.83 (1.5H, s), 3.82 (1.5H, s), 3.72-3.65 (1H, m), 3.35-3.29 (2H, m), 3.17 (1H, dd, 14.0, 5.2 Hz), 2.65-2.58 (1H, m), 1.529 (1.5H, d, 7.0 Hz), 1.524 (1.5H, d, 6.9 Hz)

MS: 448 (M+H)$^+$

Example 108

4-[({[6-(5-chloro-2-methoxybenzyl)-3,7-dioxo-1,4-diazepan-1-yl]carbonyl}amino)methyl]benzoic Acid (Compound 108)

NMR (DMSO-d$_6$): δ13.15-12.53 (1H, br), 9.41 (1H, t, 5.9 Hz), 7.89 (2H, d, 8.2 Hz), 7.68 (1H, d, 3.7 Hz), 7.38 (2H, d, 8.2 Hz), 7.32 (1H, d, 2.7 Hz), 7.25 (1H, dd, 8.8, 2.7 Hz), 6.99 (1H, d, 8.8 Hz), 4.78 (1H, d, 17.2 Hz), 4.53 (1H, d, 17.2 Hz), 4.46 (1H, d, 5.9 Hz), 4.45 (1H, d, 5.9 Hz), 3.91-3.82 (1H, m), 3.78 (3H, s), 3.14 (1H, t, 12.6 Hz), 3.08-2.95 (2H, m), 2.62 (1H, dd, 14.3, 8.6 Hz)

MS: 460 (M+H)$^+$

Example 109

6-(5-chloro-2-methoxybenzyl)-3,7-dioxo-N-(1-phenylbutyl)-1,4-diazepan-1-carboxamide (Compound 109)

NMR (CDCl$_3$): δ9.48 (1H, brd, 7.5 Hz), 7.39-7.20 (6H, m), 7.13 (1H, d, 2.6 Hz), 6.81 (0.5H, d, 8.8 Hz), 6.80 (0.5H, d, 8.8 Hz), 5.76 (0.5H, br), 5.71 (0.5H, br), 5.39 (0.5H, d, 17.5 Hz), 5.37 (0.5H, d, 17.5 Hz), 4.93-4.84 (1H, m), 4.11 (0.5H, d, 17.5 Hz), 4.06 (0.5H, d, 17.5 Hz), 3.84 (1.5H, s), 3.82 (1.5H, s), 3.72-3.62 (1H, m), 3.38-3.28 (2H, m), 3.19 (1H, dd, 14.0, 5.2 Hz), 2.66-2.59 (1H, m), 1.91-1.71 (2H, m), 1.45-1.23 (2H, m), 0.98-0.87 (3H, m)

MS: 458 (M+H)$^+$

Example 110

4-({[6-(5-chloro-2-methoxybenzyl)-3,7-dioxo-1,4-diazepan-1-yl]carbonyl}amino)-4-phenylbutanoic Acid (Compound 110)

NMR (DMSO-d$_6$): δ12.29-12.00 (1H, br), 9.39 (0.5H, d, 7.7 Hz), 9.38 (0.5H, d, 6.4 Hz), 7.70-7.61 (1H, m), 7.50-7.20 (7H, m), 6.99 (1H, d, 8.9 Hz), 4.85-4.77 (1H, m), 4.72 (1H, d, 17.2 Hz), 4.51 (0.5H, d, 17.2 Hz), 4.47 (0.5H, d, 17.2 Hz), 3.90-3.80 (1H, m), 3.78 (1.5H, s), 3.77 (1.5H, s), 3.22-3.08 (1H, m), 3.04-2.92 (2H, m), 2.70-2.60 (1H, m), 2.25-1.90 (4H, m)
MS: 488 (M+H)$^+$

Example 111

6-(5-chloro-2-methoxybenzyl)-N-(2-methyl-1-phenylpropyl)-3,7-dioxo-1,4-diazepan-1-carboxamide (Compound 111)

NMR (CDCl$_3$): δ9.64 (1H, d, 8.1 Hz), 7.38-7.21 (6H, m), 7.15 (1H, s), 6.81 (0.5H, d, 8.7 Hz), 6.80 (0.5H, d, 8.8 Hz), 5.71 (0.5H, br), 5.65 (0.5H, br), 5.40 (0.5H, d, 17.6 Hz), 5.37 (0.5H, d, 17.6 Hz), 4.75-4.65 (1H, m), 4.12 (0.5H, d, 17.6 Hz), 4.06 (0.5H, d, 17.6 Hz), 3.84 (1.5H, s), 3.83 (1.5H, s), 3.72-3.64 (1H, m), 3.38-3.29 (2H, m), 3.26-3.20 (1H, m), 2.63 (1H, dd, 13.9, 8.4 Hz), 2.12-2.02 (1H, m), 0.90-0.87 (6H, m)
MS: 458 (M+H)$^+$

Example 112

6-(5-chloro-2-methoxybenzyl)-N-(3-methyl-1-phenylbutyl)-3,7-dioxo-1,4-diazepan-1-carboxamide (Compound 112)

NMR (CDCl$_3$): δ9.45-9.42 (1H, m), 7.39-7.20 (6H, m), 7.13 (1H, d, 2.5 Hz), 6.81 (0.5H, d, 8.7 Hz), 6.80 (0.5H, d, 8.7 Hz), 5.74 (0.5H, br), 5.69 (0.5H, br), 5.38 (0.5H, d, 17.5 Hz), 5.36 (0.5H, d, 17.5 Hz), 5.00-4.89 (1H, m), 4.11 (0.5H, d, 17.5 Hz), 4.05 (0.5H, d, 17.5 Hz), 3.84 (1.5H, s), 3.82 (1.5H, s), 3.72-3.62 (1H, m), 3.38-3.27 (2H, m), 3.18 (1H, dd, 14.0, 5.1 Hz), 2.60 (1H, dd, 14.0, 8.5 Hz), 1.82-1.73 (1H, m), 1.69-1.49 (2H, m), 0.99-0.85 (6H, m)
MS: 472 (M+H)$^+$

Example 113 rel-(1R,6R)-4-[1-({[6-(5-chloro-2-methoxybenzyl)-3,7-dioxo-1,4-diazepan-1-yl]carbonyl}amino)propyl]benzoic Acid (Compound 113)

NMR (DMSO-d$_6$): δ12.73 (1H, br), 9.48 (1H, d, J=7.5 Hz), 7.89 (2H, d, J=8.2 Hz), 7.67 (1H, d, J=3.2 Hz), 7.41 (2H, d, J=8.2 Hz), 7.32 (1H, d, J=2.6 Hz), 7.26 (1H, dd, J=8.9, 2.6 Hz), 7.00 (1H, d, J=8.9 Hz), 4.79-4.70 (2H, m), 4.48 (1H, d, J=17.1 Hz), 3.91-3.81 (1H, m), 3.78 (3H, s), 3.15 (1H, t, J=12.7 Hz), 3.05-2.93 (2H, m), 2.66 (1H, dd, J=14.3, 9.1 Hz), 1.85-1.73 (2H, m), 0.83 (3H, t, J=7.2 Hz)
MS: 488 (M+H)$^+$

Example 114 rel-(1R,6S)-4-[1-({[6-(5-chloro-2-methoxybenzyl)-3,7-dioxo-1,4-diazepan-1-yl]carbonyl}amino)propyl]benzoic Acid (Compound 114)

NMR (DMSO-d$_6$): δ12.71 (1H, br), 9.43 (1H, d, J=7.5 Hz), 7.88 (2H, d, J=8.2 Hz), 7.63 (1H, d, J=3.6 Hz), 7.4 (2H, d, J=8.2 Hz), 7.31 (1H, d, J=2.6 Hz), 7.24 (1H, dd, J=8.9, 2.6 Hz), 6.98 (1H, d, J=8.9 Hz), 4.79-4.69 (2H, m), 4.50 (1H, d, J=17.1 Hz), 3.90-3.80 (1H, m), 3.76 (3H, s), 3.11 (1H, t, J=13.0 Hz), 3.00-2.91 (2H, m), 2.63 (1H, dd, J=14.4, 9.0 Hz), 1.84-1.69 (2H, m), 0.81 (3H, t, J=7.3 Hz)
MS: 488 (M+H)$^+$

Example 115

N-{[6-(5-chloro-2-methoxybenzyl)-3,7-dioxo-1,4-diazepan-1-yl]carbonyl}-2-methylalanine (Compound 115)

NMR (CDCl$_3$): δ9.43 (1H, s), 7.19 (1H, dd, 8.7, 2.5 Hz), 7.11 (1H, d, 2.5 Hz), 6.79 (1H, d, 8.7 Hz), 6.65 (1H, s), 5.26 (1H, d, 17.7 Hz), 4.13 (1H, d, 17.7 Hz), 3.82 (3H, s), 3.75-3.65 (1H, m), 3.36-3.29 (2H, m), 3.17 (1H, dd, 13.9, 5.0 Hz), 2.56 (1H, dd, 13.9, 8.4 Hz), 1.56 (6H, s)
MS: 412 (M+H)$^+$

Example 116

(3S)-4-anilino-3-({[6-(5-chloro-2-methoxybenzyl)-3,7-dioxo-1,4-diazepan-1-yl]carbonyl}amino)-4-oxobutanoic Acid (Compound 116)

NMR (DMSO-d$_6$): δ12.28-12.20 (1H, m), 10.10 (1H, s), 9.62-9.50 (1H, m), 8.20-8.15 (1H, m), 7.53 (2H, d, 8.2 Hz), 7.32-6.89 (6H, m), 4.85-4.69 (1H, m), 4.59-4.45 (1H, m), 4.40-4.35 (1H, m), 3.93-3.89 (1H, m), 3.77 (3H, s), 3.40-2.60 (6H, m)
MS: 517 (M+H)$^+$

Example 117

6-(5-chloro-2-methoxybenzyl)-N-[(3S)-2,5-dioxo-1-phenylpyrrolidinyl]-3,7-dioxo-1,4-diazepan-1-carboxamide (Compound 117)

NMR (DMSO-d$_6$): δ9.55-9.51 (1H, m), 7.70 (1H, br), 7.50-7.44 (2H, m), 7.41-7.35 (1H, m), 7.327 (0.5H, s), 7.321 (0.5H, s), 7.25-7.19 (3H, m), 6.97 (1H, d, 8.8 Hz), 4.98-4.85 (1H, m), 4.77 (0.5H, d, 17.1 Hz), 4.75 (0.5H, d, 17.1 Hz), 4.54 (1H, d, 17.1 Hz), 3.96-3.85 (1H, m), 3.77 (3H, s), 3.20-3.00 (3H, m), 2.96 (1H, dd, 14.4, 5.6 Hz), 2.78-2.70 (1H, m), 2.59 (1H, dd, 14.4, 6.0 Hz)
MS: 499 (M+H)$^+$

Example 118 rel-(1R,6R)-3-[1-({[6-(5-fluoro-2-methoxybenzyl)-3,7-dioxo-1,4-diazepan-1-yl]carbonyl}amino)propyl]benzoic Acid (Compound 118)

NMR (DMSO-d$_6$): δ12.84 (1H, br), 9.45 (1H, d, J=7.3 Hz), 7.83 (1H, s), 7.79 (1H, d, J=7.6 Hz), 7.65 (1H, d, J=3.6 Hz), 7.53 (1H, d, J=7.6 Hz), 7.43 (1H, t, J=7.6 Hz), 7.12 (1H, dd, J=9.4, 3.0 Hz), 7.04-6.92 (2H, m), 4.75-4.65 (2H, m), 4.46 (1H, d, J=17.1 Hz), 3.90-3.79 (1H, m), 3.74 (3H, s), 3.10 (1H, t, J=12.5 Hz), 3.03-2.91 (2H, m), 2.65 (1H, dd, J=14.5, 9.1 Hz), 1.85-1.70 (2H, m), 0.81 (3H, t, J=7.3 Hz)
MS: 472 (M+H)$^+$

Example 119

(2R)-2-({[6-(5-chloro-2-methoxybenzyl)-3,7-dioxo-1,4-diazepan-1-yl]carbonyl}amino)butanoic Acid (Compound 119)

NMR (CDCl$_3$): δ9.45 (0.5H, d, 6.7 Hz), 9.44 (0.5H, d, 6.5 Hz), 7.24-7.20 (1H, m), 7.19-7.10 (0.5H, m), 7.15 (0.5H, d, 2.4 Hz), 7.11 (0.5H, d, 2.5 Hz), 6.95 (0.5H, br), 6.817 (0.5H, d, 8.8 Hz), 6.813 (0.5H, d, 8.7 Hz), 5.38-5.29 (1H, m), 4.48-4.41 (1H, m), 4.23-4.15 (1H, m), 3.84 (3H, s), 3.78-3.65 (1H, m), 3.40-3.33 (2H, m), 3.27-3.15 (1H, m), 2.69-2.58 (1H, m), 2.05-1.80 (2H, m), 1.09-1.00 (3H, m)

MS: 411 (M+H)$^+$

Example 120

6-(5-chloro-2-methoxybenzyl)-3,7-dioxo-N-[(1R)-1-(1H-tetrazol-5-yl)propyl]-1,4-diazepan-1-carboxamide (Compound 120)

NMR (DMSO-d$_6$): δ9.54 (1H, d, 7.4 Hz), 7.66 (1H, br), 7.31 (0.5H, s), 7.30 (0.5H, s), 7.24 (0.5H, d, 8.9 Hz), 7.23 (0.5H, d, 8.9 Hz), 6.98 (1H, d, 8.9 Hz), 5.09-5.00 (1H, m), 4.78 (0.5H, d, 17.5 Hz), 4.74 (0.5H, d, 17.5 Hz), 4.51 (1H, d, 17.5 Hz), 3.90-3.80 (1H, m), 3.76 (3H, s), 3.17-3.05 (1H, m), 3.04-2.90 (2H, m), 2.70-2.55 (1H, m), 1.95-1.71 (2H, m), 0.87-0.69 (3H, m)

MS: 436 (M+H)$^+$

Example 121 rel-(1R,6S)-3-[1-({[6-(5-fluoro-2-methoxybenzyl)-3,7-dioxo-1,4-diazepan-1-yl]carbonyl}amino)propyl]benzoic Acid (Compound 121)

NMR (DMSO-d$_6$): δ9.42 (1H, d, J=7.5 Hz), 7.81 (1H, s), 7.78 (1H, d, J=7.5 Hz), 7.61 (1H, d, J=3.3 Hz), 7.44 (1H, d, J=7.5 Hz), 7.38 (1H, t, J=7.5 Hz), 7.12 (1H, dd, J=9.4, 3.1 Hz), 7.05-6.92 (2H, m), 4.77-4.68 (2H, m), 4.50 (1H, d, J=17 Hz), 3.91-3.80 (1H, m), 3.75 (3H, s), 3.10 (1H, t, J=12.9 Hz), 3.03-2.92 (2H, m), 2.63 (1H, dd, J=14.5, 9.0 Hz), 1.84-1.69 (2H, m), 0.79 (3H, t, J=7.2 Hz)

MS: 472 (M+H)$^+$

Example 122

N-[1-(4-aminophenyl)propyl]-6-(5-chloro-2-methoxybenzyl)-3,7-dioxo-1,4-diazepan-1-carboxamide hydrochloride (Compound 122) (Diastereomer of Compound 123)

NMR (DMSO-d$_6$): δ9.40 (1H, d, J=7.5 Hz), 7.65 (1H, brd, J=3.6 Hz), 7.35 (2H, d, J=8.1 Hz), 7.33 (1H, d, J=2.6 Hz), 7.27 (1H, dd, J=8.7, 2.6 Hz), 7.19 (2H, d, J=8.1 Hz), 7.01 (1H, d, J=8.7 Hz), 4.75 (1H, d, J=17.2 Hz), 4.68 (1H, dd, J=14.4, 7.3 Hz), 4.53 (1H, d, J=17.2 Hz), 3.93-3.83 (1H, m), 3.79 (3H, s), 3.17-2.95 (3H, m), 2.70-2.61 (1H, m), 1.88-1.70 (2H, m), 0.83 (3H, t, J=7.3 Hz)

MS: 459 (M+H)$^+$

Example 123

N-[1-(4-aminophenyl)propyl]-6-(5-chloro-2-methoxybenzyl)-3,7-dioxo-1,4-diazepan-1-carboxamide hydrochloride (Compound 123) (Diastereomer of Compound 122)

NMR (DMSO-d$_6$): δ9.39 (1H, d, J=7.5 Hz), 7.66 (1H, brd, J=3.6 Hz), 7.34-7.28 (3H, m), 7.24 (1H, dd, J=8.8, 2.6 Hz), 7.14 (2H, d, J=8.0 Hz), 6.98 (1H, d, J=8.8 Hz), 4.70 (1H, d, J=17.2 Hz), 4.64 (1H, dd, J=14.4, 7.2 Hz), 4.46 (1H, d, J=17.2 Hz), 3.89-3.79 (1H, m), 3.76 (3H, s), 3.18-2.91 (3H, m), 2.69-2.60 (1H, m), 1.83-1.69 (2H, m), 0.80 (3H, t, J=7.3 Hz)

MS: 459 (M+H)$^+$

Example 124

3-[(1S)-1-({[(6S)-6-(5-chloro-2-methoxybenzyl)-3,7-dioxo-1,4-diazepan-1-yl]carbonyl}amino)propyl]benzoic Acid (Compound 124)

NMR (DMSO-d$_6$): δ13.01 (1H, br), 9.48 (1H, d, J=7.3 Hz), 7.86 (1H, s), 7.82 (1H, d, J=7.7 Hz), 7.67 (1H, d, J=3.5 Hz), 7.55 (1H, d, J=7.7 Hz), 7.46 (1H, t, J=7.7 Hz), 7.33 (1H, d, J=2.6 Hz), 7.27 (1H, dd, J=8.8, 2.6 Hz), 7.00 (1H, d, J=8.8 Hz), 4.79-4.69 (2H, m), 4.49 (1H, d, J=17.2 Hz), 3.91-3.81 (1H, m), 3.79 (3H, s), 3.16 (1H, t, J=12.6 Hz), 3.05-2.96 (2H, m), 2.67 (1H, dd, J=14.3, 9.3 Hz), 1.89-1.74 (2H, m), 0.84 (3H, t, J=7.3 Hz)

MS: 488 (M+H)$^+$

Example 125

3-[(1R)-1-({[(6S)-6-(5-chloro-2-methoxybenzyl)-3,7-dioxo-1,4-diazepan-1-yl]carbonyl}amino)propyl]benzoic Acid (Compound 125)

NMR (DMSO-d$_6$): δ12.92 (1H, br), 9.45 (1H, d, J=7.4 Hz), 7.86 (1H, s), 7.83 (1H, d, J=7.6 Hz), 7.64 (1H, d, J=3.2 Hz), 7.56 (1H, d, J=7.6 Hz), 7.47 (1H, t, J=7.6 Hz), 7.33 (1H, d, J=2.4 Hz), 7.27 (1H, dd, J=8.9, 2.4 Hz), 7.01 (1H, d, J=8.9 Hz), 4.80-4.72 (2H, m), 4.52 (1H, d, J=17.2 Hz), 3.92-3.82 (1H, m), 3.79 (3H, s), 3.12 (1H, t, J=12.7 Hz), 3.03-2.94 (2H, m), 2.65 (1H, dd, J=14.2, 9.0 Hz), 1.87-1.71 (2H, m), 0.84 (3H, t, J=7.2 Hz)

MS: 488 (M+H)$^+$

Example 126

3-[(1S)-1-({[(6R)-6-(5-chloro-2-methoxybenzyl)-3,7-dioxo-1,4-diazepan-1-yl]carbonyl}amino)propyl]benzoic Acid (Compound 126)

NMR (DMSO-d$_6$): δ12.92 (1H, br), 9.45 (1H, d, J=7.4 Hz), 7.86 (1H, s), 7.83 (1H, d, J=7.6 Hz), 7.64 (1H, d, J=3.2 Hz), 7.56 (1H, d, J=7.6 Hz), 7.47 (1H, t, J=7.6 Hz), 7.33 (1H, d, J=2.4 Hz), 7.27 (1H, dd, J=8.9, 2.4 Hz), 7.01 (1H, d, J=8.9 Hz), 4.80-4.72 (2H, m), 4.52 (1H, d, J=17.2 Hz), 3.92-3.82 (1H, m), 3.79 (3H, s), 3.12 (1H, t, J=12.7 Hz), 3.03-2.94 (2H, m), 2.65 (1H, dd, J=14.2, 9.0 Hz), 1.87-1.71 (2H, m), 0.84 (3H, t, J=7.2 Hz)

MS: 488 (M+H)$^+$

Example 127

6-(5-chloro-2-methoxybenzyl)-N-{1-[3-(methylsulfonyl)phenyl]propyl}-3,7-dioxo-1,4-diazepan-1-carboxamide (Compound 127)

NMR (CDCl$_3$): δ9.56 (1H, brd, J=4.8 Hz), 7.88-7.79 (2H, m), 7.60-7.47 (2H, m), 7.22 (1H, dd, J=8.7, 2.5 Hz), 7.15 (0.5H, d, J=2.5 Hz), 7.14 (0.5H, d, J=2.5 Hz), 6.83 (0.5H, d, J=8.7 Hz), 6.82 (0.5H, d, J=8.7 Hz), 5.70-5.60 (1H, br), 5.35 (0.5H, d, J=17.0 Hz), 5.30 (0.5H, d, J=17.0 Hz), 4.86 (1H, dd, J=14.3, 7.3 Hz), 4.13 (0.5H, d, J=17.0 Hz), 4.11 (0.5H, d, J=17.0 Hz), 3.85 (1.5H, s), 3.84 (1.5H, s), 3.77-3.66 (1H, m), 3.38-3.31 (2H, m), 3.25-3.18 (1H, m), 3.07 (1.5H, s), 3.06 (1.5H, s), 2.70-2.60 (1H, m), 1.94-1.82 (2H, m), 1.00-0.90 (3H, m)
MS: 522 (M+H)$^+$

Example 128

6-(5-chloro-2-methoxybenzyl)-N-{1-[4-(methylsulfonyl)phenyl]propyl}-3,7-dioxo-1,4-diazepan-1-carboxamide (Compound 128) (Diastereomer of Compound 129)

NMR (CDCl$_3$): δ9.57 (1H, d, J=7.1 Hz), 7.91 (2H, d, J=8.2 Hz), 7.48 (2H, d, J=8.2 Hz), 7.23 (1H, dd, J=8.7, 2.7 Hz), 7.15 (1H, d, J=2.7 Hz), 6.82 (1H, d, J=8.7 Hz), 5.75-5.70 (1H, br), 5.32 (1H, d, J=17.3 Hz), 4.85 (1H, dd, J=14.2, 7.1 Hz), 4.09 (1H, d, J=17.3 Hz), 3.83 (3H, s), 3.76-3.67 (1H, m), 3.38-3.30 (2H, m), 3.20 (1H, dd, J=14.0, 5.5 Hz), 3.04 (3H, s), 2.65 (1H, dd, J=14.0, 8.0 Hz), 1.92-1.79 (2H, m), 0.96 (3H, t, J=7.3 Hz)
MS: 522 (M+H)$^+$

Example 129

6-(5-chloro-2-methoxybenzyl)-N-{1-[4-(methylsulfonyl)phenyl]propyl}-3,7-dioxo-1,4-diazepan-1-carboxamide (Compound 129) (Diastereomer of Compound 128)

NMR (CDCl$_3$): δ9.57 (1H, d, J=7.0 Hz), 7.92 (2H, d, J=8.3 Hz), 7.49 (2H, d, J=8.3 Hz), 7.23 (1H, dd, J=8.7, 2.6 Hz), 7.15 (1H, d, J=2.6 Hz), 6.82 (1H, d, J=8.7 Hz), 5.62-5.57 (1H, br), 5.34 (1H, d, J=17.7 Hz), 4.85 (1H, dd, J=14.2, 7.3 Hz), 4.14 (1H, d, J=17.7 Hz), 3.85 (3H, s), 3.76-3.64 (1H, m), 3.35-3.28 (2H, m), 3.20 (1H, dd, J=14.0, 5.5 Hz), 3.06 (3H, s), 2.64 (1H, dd, J=14.0, 8.4 Hz), 1.91-1.78 (2H, m), 0.95 (3H, t, J=7.4 Hz)
MS: 522 (M+H)$^+$

Example 130

4-[1-({[6-(5-chloro-2-methoxybenzyl)-3,7-dioxo-1,4-diazepan-1-yl]carbonyl}amino)propyl]-2-hydroxybenzoic Acid (Compound 130) (Diastereomer of Compound 149)

NMR (DMSO-d$_6$): δ9.44 (1H, d, J=7.4 Hz), 7.74 (1H, d, J=8.6 Hz), 7.67 (1H, d, J=3.4 Hz), 7.34 (1H, d, J=2.6 Hz), 7.27 (1H, dd, J=8.9, 2.6 Hz), 7.01 (1H, d, J=8.9 Hz), 6.87-6.84 (2H, m), 4.73 (1H, d, J=17.2 Hz), 4.68 (1H, q, J=7.4 Hz), 4.50 (1H, d, J=17.2 Hz), 3.92-3.81 (1H, m), 3.79 (3H, s), 3.16 (1H, t, J=12.5 Hz), 3.06-2.94 (2H, m), 2.67 (1H, dd, J=14.3, 9.3 Hz), 1.82-1.72 (2H, m), 0.84 (3H, t, J=7.1 Hz)
MS: 504 (M+H)$^+$

Example 131 rel-(1R,6R)-5-[1-({[6-(5-chloro-2-methoxybenzyl)-3,7-dioxo-1,4-diazepan-1-yl]carbonyl}amino)propyl]-2-thiophen Carboxylic Acid (Compound 131)

NMR (DMSO-d$_6$): δ9.37 (1H, d, J=8.0 Hz), 7.68-7.63 (1H, br), 7.32 (1H, d, J=2.7 Hz), 7.25 (1H, dd, J=8.8, 2.7 Hz), 7.03-6.94 (1H, br), 6.99 (1H, d, J=8.8 Hz), 6.80-6.73 (1H, br), 4.88 (1H, dd, J=14.3, 7.1 Hz), 4.79 (1H, d, J=17.4 Hz), 4.51 (1H, d, J=17.4 Hz), 3.90-3.79 (1H, m), 3.77 (3H, s) 3.18-3.12 (1H, m), 3.03-2.90 (2H, m), 2.67-2.60 (1H, m), 1.86-1.75 (2H, m), 0.86 (3H, t, J=7.3 Hz)
MS: 494 (M+H)$^+$

Example 132 rel-(1R,6S)-5-[1-({[6-(5-chloro-2-methoxybenzyl)-3,7-dioxo-1,4-diazepan-1-yl]carbonyl}amino)propyl]-2-thiophen Carboxylic Acid (Compound 132)

NMR (DMSO-d$_6$): δ9.36 (1H, d, J=8.0 Hz), 7.66-7.62 (1H, br), 7.31 (1H, d, J=2.7 Hz), 7.25 (1H, dd, J=8.7, 2.7 Hz), 7.03-6.93 (1H, br), 6.99 (1H, d, J=8.7 Hz), 6.78-6.72 (1H, br), 4.88 (1H, dd, J=14.3, 7.1 Hz), 4.78 (1H, d, J=17.7 Hz), 4.51 (1H, d, J=17.7 Hz), 3.90-3.79 (1H, m), 3.78 (3H, s) 3.18-3.07 (1H, m), 3.01-2.90 (2H, m), 2.63-2.55 (1H, m), 1.86-1.75 (2H, m), 0.85 (3H, t, J=7.3 Hz)
MS: 494 (M+H)$^+$

Example 133 rel-(1R,6R)-5-[1-({[6-(5-chloro-2-methoxybenzyl)-3,7-dioxo-1,4-diazepan-1-yl]carbonyl}amino)propyl]-2-furan Carboxylic Acid (Compound 133)

NMR (DMSO-d$_6$): δ13.05-12.95 (1H, br), 9.36 (1H, d, J=7.9 Hz), 7.70-7.63 (1H, br), 7.31 (1H, d, J=2.7 Hz), 7.25 (1H, dd, J=8.7, 2.7 Hz), 7.11-7.02 (1H, br), 6.99 (1H, d, J=8.7 Hz), 6.48-6.42 (1H, br), 4.86 (1H, dd, J=14.7, 7.3 Hz), 4.76 (1H, d, J=17.4 Hz), 4.51 (1H, d, J=17.4 Hz), 3.90-3.79 (1H, m), 3.78 (3H, s) 3.18-3.07 (1H, m), 3.04-2.90 (2H, m), 2.63-2.55 (1H, m), 1.90-1.78 (2H, m), 0.85 (3H, t, J=7.3 Hz)
MS: 478 (M+H)$^+$

Example 134 rel-(1R,6S)-5-[1-({[6-(5-chloro-2-methoxybenzyl)-3,7-dioxo-1,4-diazepan-1-yl]carbonyl}amino)propyl]-2-furan Carboxylic Acid (Compound 134)

NMR (DMSO-d$_6$): δ9.35 (1H, d, J=8.2 Hz), 7.66 (1H, brd, J=3.6 Hz), 7.31 (1H, d, J=2.6 Hz), 7.26 (1H, dd, J=8.7, 2.6 Hz), 6.99 (1H, d, J=8.7 Hz), 6.98-6.87 (1H, br), 6.43-6.36 (1H, br), 4.84 (1H, dd, J=14.8, 7.3 Hz), 4.78 (1H, d, J=17.3 Hz), 4.53 (1H, d, J=17.3 Hz), 3.90-3.79 (1H, m), 3.78 (3H, s) 3.15 (1H, t, J=12.9 Hz), 3.01-2.90 (2H, m), 2.64-2.57 (1H, m), 1.88-1.72 (2H, m), 0.84 (3H, t, J=7.3 Hz)
MS: 478 (M+H)$^+$

Example 135

N-{1-[3-(aminosulfonyl)phenyl]propyl}-6-(5-chloro-2-methoxybenzyl)-3,7-dioxo-1,4-diazepan-1-carboxamide (Compound 135)

NMR (DMSO-d$_6$): δ9.47 (0.5H, d, J=7.4 Hz), 9.45 (0.5H, d, J=7.5 Hz), 7.75 (1H, s), 7.73-7.60 (2H, m), 7.56-7.50 (2H, m), 7.35-7.30 (3H, m), 7.26 (1H, dd, J=8.7, 2.7 Hz), 7.00 (1H, d, J=8.7 Hz), 4.79-4.68 (2H, m), 4.52 (0.5H, d, J=17.0 Hz), 4.49 (0.5H, d, J=17.0 Hz), 3.92-3.80 (1H, m), 3.779 (1.5H, s), 3.783 (1.5H, s), 3.20-2.92 (3H, m), 2.70-2.60 (1H, m), 1.94-1.72 (2H, m), 0.85 (3H, t, J=7.1 Hz)
MS: 523 (M+H)$^+$

Example 136

N-{1-[4-(aminosulfonyl)phenyl]propyl}-6-(5-chloro-2-methoxybenzyl)-3,7-dioxo-1,4-diazepan-1-carboxamide (Compound 136)

NMR (DMSO-d$_6$): δ9.46 (0.5H, d, J=7.3 Hz), 9.43 (0.5H, d, J=7.4 Hz), 7.78 (1H, d, J=8.3 Hz), 7.77 (1H, d, J=8.3 Hz), 7.65 (1H, brd, J=8.6 Hz), 7.49 (1H, d, J=8.3 Hz), 7.48 (1H, d, J=8.3 Hz), 7.33 (1H, d, J=2.7 Hz), 7.30-7.22 (3H, m), 7.00 (1H, d, J=8.7 Hz), 4.77-4.69 (2H, m), 4.52 (0.5H, d, J=16.3 Hz), 4.48 (0.5H, d, J=16.4 Hz), 3.93-3.80 (1H, m), 3.78 (3H, s), 3.20-2.92 (3H, m), 2.70-2.60 (1H, m), 1.88-1.70 (2H, m), 0.84 (3H, t, J=7.3 Hz)
MS: 523 (M+H)$^+$

Example 137

6-[1-({[6-(5-chloro-2-methoxybenzyl)-3,7-dioxo-1,4-diazepan-1-yl]carbonyl}amino)propyl]-2-pyridine carboxylic Acid (Compound 137)

NMR (DMSO-d$_6$): δ9.53-9.45 (1H, br), 8.05-7.60 (3H, br), 7.40-7.20 (1H, br), 7.32 (1H, d, J=2.5 Hz), 7.26 (1H, dd, J=8.7, 2.5 Hz), 7.00 (1H, d, J=8.7 Hz), 4.93-4.70 (2H, m), 4.52 (0.5H, d, J=13.0 Hz), 4.48 (0.5H, d, J=17.3 Hz), 3.90-3.80 (1H, m), 3.78 (3H, s), 3.22-2.93 (3H, m), 2.72-2.60 (1H, m), 1.95-1.70 (2H, m), 0.90-0.75 (3H, br)
MS: 489 (M+H)$^+$

Example 138

5-[1-({[6-(5-chloro-2-methoxybenzyl)-3,7-dioxo-1,4-diazepan-1-yl]carbonyl}amino)propyl]nicotinic Acid (Compound 138)

NMR (DMSO-d$_6$): δ9.48 (0.5H, d, J=7.2 Hz), 9.44 (0.5H, d, J=7.3 Hz), 8.91 (1H, brs), 8.50 (1H, brs), 8.08 (1H, brs), 7.69-7.60 (1H, br), 7.32 (1H, d, J=2.3 Hz), 7.25 (1H, dd, J=8.7, 2.3 Hz), 6.99 (1H, d, J=8.7 Hz), 4.79-4.64 (2H, m), 4.52 (0.5H, d, J=18.2 Hz), 4.47 (0.5H, d, J=17.4 Hz), 3.90-3.78 (1H, m), 3.77 (1.5H, s), 3.78 (1.5H, s), 3.20-3.08 (1H, m), 3.02-2.92 (2H, m), 2.70-2.60 (1H, m), 1.92-1.72 (2H, m), 0.84 (3H, t, J=7.3 Hz)
MS: 489 (M+H)$^+$

Example 139

2-amino-5-[1-({[6-(5-chloro-2-methoxybenzyl)-3,7-dioxo-1,4-diazepan-1-yl]carbonyl}amino)propyl]benzoic Acid (Compound 139)

NMR (DMSO-d$_6$): δ9.30 (0.5H, d, 7.6 Hz), 9.27 (0.5H, d, 7.7 Hz), 9.10-7.90 (2H, br), 7.64 (0.5H, d, 3.5 Hz), 7.62 (0.5H, d, 3.8 Hz), 7.56 (0.5H, s), 7.56 (0.5H, s), 7.29 (0.5H, s), 7.29 (0.5H, s), 7.26-7.22 (1H, m), 7.17-7.14 (1H, m), 6.97 (0.5H, d, 8.8 Hz), 6.97 (0.5H, d, 8.9 Hz), 6.69 (0.5H, d, 8.5 Hz), 6.68 (0.5H, d, 8.5 Hz), 4.74 (0.5H, d, 17.2 Hz), 4.72 (0.5H, d, 17.1 Hz), 4.51-4.42 (2H, m), 3.86-3.78 (1H, m), 3.75 (1.5H, s), 3.75 (1.5H, s), 3.10 (0.5H, dd, 17.7, 13.0 Hz), 3.07 (0.5H, dd, 17.7, 12.4 Hz), 2.99-2.86 (2H, m), 2.65-2.56 (1H, m), 1.80-1.62 (2H, m), 0.79-0.74 (3H, m)
MS: 503 (M+H)$^+$

Example 140 rel-(1R,6R)-5-[1-({[6-(5-chloro-2-methoxybenzyl)-3,7-dioxo-1,4-diazepan-1-yl]carbonyl}amino)propyl]-2-fluorobenzoic Acid (Compound 140)

NMR (DMSO-d$_6$): δ13.34-13.01 (1H, br), 9.40 (1H, d, 7.2 Hz), 7.74 (1H, dd, 7.0, 2.3 Hz), 7.65 (1H, d, 3.7 Hz), 7.57-7.53 (1H, m), 7.30 (1H, d, 2.7 Hz), 7.27-7.21 (2H, m), 6.97 (1H, d, 8.8 Hz), 4.71-4.65 (2H, m), 4.45 (1H, d, 17.0 Hz), 3.86-3.81 (1H, m), 3.75 (3H, s), 3.13 (1H, t, 12.9 Hz), 2.99-2.92 (2H, m), 2.66-2.60 (1H, m), 1.88-1.69 (2H, m), 0.80 (3H, t, 7.2 Hz)
MS: 506 (M+H)$^+$

Example 141 rel-(1R,6S)-5-[1-({[6-(5-chloro-2-methoxybenzyl)-3,7-dioxo-1,4-diazepan-1-yl]carbonyl}amino)propyl]-2-fluorobenzoic Acid (Compound 141)

NMR (DMSO-d$_6$): δ13.40-13.10 (1H, br), 9.37 (1H, d, 7.3 Hz), 7.74 (1H, dd, 6.9, 2.1 Hz), 7.63 (1H, d, 3.6 Hz), 7.56-7.53 (1H, m), 7.30 (1H, d, 2.6 Hz), 7.28-7.22 (2H, m), 6.97 (1H, d, 8.8 Hz), 4.75-4.65 (2H, m), 4.49 (1H, d, 17.1 Hz), 3.87-3.81 (1H, m), 3.76 (3H, s), 3.09 (1H, t, 13.0 Hz), 2.98-2.92 (2H, m), 2.66-2.60 (1H, m), 1.88-1.68 (2H, m), 0.80 (3H, t, 7.2 Hz)
MS: 506 (M+H)$^+$

Example 142

3-[1-({[6-(5-chloro-2-methoxybenzyl)-3,7-dioxo-1,4-diazepan-1-yl]carbonyl}amino)propyl]-4-methoxybenzoic Acid (Compound 142) (Diastereomer of Compound 143)

NMR (DMSO-d$_6$): δ12.90-12.30 (1H, br), 9.68 (1H, d, 8.4 Hz), 7.82 (1H, dd, 8.5, 2.0 Hz), 7.71 (1H, d, 2.0 Hz), 7.66 (1H, d, 3.5 Hz), 7.31 (1H, d, 2.6 Hz), 7.23 (1H, dd, 8.7, 2.6 Hz), 7.05 (1H, d, 8.5 Hz), 6.96 (1H, d, 8.7 Hz), 4.95-4.89 (1H, m), 4.73 (1H, d, 17.2 Hz), 4.43 (1H, d, 17.2 Hz), 3.90-3.80 (1H, m), 3.85 (3H, s), 3.75 (3H, s), 3.13 (1H, t, 12.8 Hz), 3.02-2.92 (2H, m), 2.68-2.61 (1H, m), 1.78-1.65 (2H, m), 0.78 (3H, t, 7.3 Hz)
MS: 518 (M+H)$^+$

Example 143

3-[1-({[6-(5-chloro-2-methoxybenzyl)-3,7-dioxo-1,4-diazepan-1-yl]carbonyl}amino)propyl]-4-methoxybenzoic Acid (Compound 143) (Diastereomer of Compound 142)

NMR (DMSO-d$_6$): δ12.80-12.45 (1H, br), 9.64 (1H, d, 8.5 Hz), 7.83 (1H, dd, 8.6, 2.0 Hz), 7.71 (1H, d, 2.0 Hz), 7.62 (1H, d, 3.4 Hz), 7.31 (1H, d, 2.6 Hz), 7.24 (1H, dd, 8.7, 2.6 Hz), 7.08 (1H, d, 8.6 Hz), 6.97 (1H, d, 8.7 Hz), 4.97-4.90 (1H, m), 4.74 (1H, d, 17.1 Hz), 4.49 (1H, d, 17.1 Hz), 3.92-3.80 (1H, m), 3.87 (3H, s), 3.76 (3H, s), 3.03 (1H, t, 12.4 Hz), 2.98-2.93 (2H, m), 2.66-2.59 (1H, m), 1.76-1.68 (2H, m), 0.77 (3H, t, 7.3 Hz)
MS: 518 (M+H)$^+$

Example 144 rel-(1R,6R)-2-amino-4-[1-({[6-(5-chloro-2-methoxybenzyl)-3,7-dioxo-1,4-diazepan-1-yl]carbonyl}amino)propyl]benzoic Acid (Compound 144)

NMR (DMSO-d$_6$): δ9.39 (1H, d, 7.6 Hz), 7.65 (1H, d, 3.7 Hz), 7.61 (1H, d, 8.3 Hz), 7.30 (1H, d, 2.6 Hz), 7.24 (1H, dd, 8.7, 2.6 Hz), 6.97 (1H, d, 8.7 Hz), 6.60 (1H, s), 6.40 (1H, d, 8.3 Hz), 5.72 (2H, s), 4.73 (1H, d, 17.1 Hz), 4.54-4.45 (2H, m), 3.87-3.80 (1H, m), 3.76 (3H, s), 3.12 (1H, t, 12.6 Hz), 3.00-2.91 (2H, m), 2.67-2.60 (1H, m), 1.77-1.49 (2H, m), 0.80 (3H, t, 7.2 Hz)

MS: 503 (M+H)$^+$

Example 145 rel-(1R,6S)-2-amino-4-[1-({[6-(5-chloro-2-methoxybenzyl)-3,7-dioxo-1,4-diazepan-1-yl]carbonyl}amino)propyl]benzoic Acid (Compound 145)

NMR (DMSO-d$_6$): δ9.37 (1H, d, 7.7 Hz), 7.63 (1H, brs), 7.62 (1H, d, 7.6 Hz), 7.30 (1H, d, 2.6 Hz), 7.24 (1H, dd, 8.7, 2.6 Hz), 6.98 (1H, d, 8.7 Hz), 6.57 (1H, s), 6.39 (1H, d, 7.6 Hz), 5.72 (2H, s), 4.76 (1H, d, 17.0 Hz), 4.55-4.46 (2H, m), 3.90-3.81 (1H, m), 3.76 (3H, s), 3.10 (1H, t, 12.7 Hz), 3.00-2.91 (2H, m), 2.65-2.55 (1H, m), 1.74-1.65 (2H, m), 0.79 (3H, t, 7.2 Hz)

MS: 503 (M+H)$^+$

Example 146 rel-(1R,6R)-4-[1-({[6-(5-chloro-2-methoxybenzyl)-3,7-dioxo-1,4-diazepan-1-yl]carbonyl}amino)propyl]-2-fluorobenzoic Acid (Compound 146)

NMR (DMSO-d$_6$): δ13.38-12.86 (1H, br), 9.40 (1H, d, 7.4 Hz), 7.73 (1H, t, 7.8 Hz), 7.65 (1H, d, 3.4 Hz), 7.31 (1H, d, 2.6 Hz), 7.24 (1H, dd, 8.7, 2.6 Hz), 7.20-7.11 (2H, m), 6.98 (1H, d, 8.7 Hz), 4.73-4.66 (2H, m), 4.47 (1H, d, 17.2 Hz), 4.01-3.80 (1H, m), 3.76 (3H, s), 3.13 (1H, t, 12.8 Hz), 3.05-2.90 (2H, m), 2.64 (1H, dd, 11.3, 9.4 Hz), 1.81-1.72 (2H, m), 0.82 (3H, t, 7.2 Hz)

MS: 506 (M+H)$^+$

Example 147 rel-(1R,6S)-4-[1-({[6-(5-chloro-2-methoxybenzyl)-3,7-dioxo-1,4-diazepan-1-yl]carbonyl}amino)propyl]-2-fluorobenzoic Acid (Compound 147)

NMR (DMSO-d$_6$): δ13.40-12.80 (1H, br), 9.37 (1H, d, 7.5 Hz), 7.79-7.70 (1H, br), 7.64 (1H, d, 3.8 Hz), 7.31 (1H, d, 2.6 Hz), 7.27-7.15 (3H, m), 6.98 (1H, d, 8.8 Hz), 4.75-4.67 (2H, m), 4.50 (1H, d, 17.1), 4.00-3.80 (1H, m), 3.76 (3H, s), 3.13 (1H, t, 12.7 Hz), 3.00-2.92 (2H, m), 2.67-2.57 (1H, m), 1.82-1.67 (2H, m), 0.81 (3H, t, 7.2 Hz)

MS: 506 (M+H)$^+$

Example 148

5-[(1R)-1-({[(6R)-6-(5-chloro-2-methoxybenzyl)-3,7-dioxo-1,4-diazepan-1-yl]carbonyl}amino)propyl]-2-furan Carboxylic Acid (Compound 148)

NMR (DMSO-d$_6$): δ9.35 (1H, d, J=7.9 Hz), 7.69-7.60 (1H, br), 7.30 (1H, s), 7.24 (1H, d, J=8.7 Hz), 7.11 (1H, d, J=3.4 Hz), 6.97 (1H, d, J=8.7 Hz), 6.46 (1H, d, J=3.4 Hz), 4.85 (1H, dd, J=14.4, 7.1 Hz), 4.74 (1H, d, J=17.3 Hz), 4.50 (1H, d, J=17.3 Hz), 3.89-3.78 (1H, m), 3.76 (3H, s), 3.17-2.88 (3H, m), 2.65-2.57 (1H, m), 1.89-1.77 (2H, m), 0.84 (3H, t, J=7.3 Hz)

MS: 478 (M+H)$^+$

Example 149

4-[1-({[6-(5-chloro-2-methoxybenzyl)-3,7-dioxo-1,4-diazepan-1-yl]carbonyl}amino)propyl]-2-hydroxybenzoic Acid (Compound 149) (Diastereomer of Compound 130)

NMR (DMSO-d$_6$): δ9.41 (1H, d, J=7.5 Hz), 7.75 (1H, d, J=8.5 Hz), 7.66 (1H, d, J=3.8 Hz), 7.34 (1H, d, J=2.6 Hz), 7.27 (1H, dd, J=8.7, 2.6 Hz), 7.01 (1H, d, J=8.5 Hz), 6.90-6.85 (2H, m), 4.74 (1H, d, J=17.1 Hz), 4.72-4.66 (1H, m), 4.53 (1H, d, J=17.1 Hz), 3.93-3.84 (1H, m), 3.79 (3H, s), 3.14 (1H, t, J=13.1 Hz), 3.05-2.95 (2H, m), 2.66 (1H, dd, J=14.2, 9.2 Hz), 1.83-1.72 (2H, m), 0.84 (3H, t, J=7.3 Hz)

MS: 504 (M+H)$^+$

Example 150

2-amino-4-[(1R)-1-({[(6S)-6-(5-chloro-2-methoxybenzyl)-3,7-dioxo-1,4-diazepan-1-yl]carbonyl}amino)propyl]benzoic Acid (Compound 150)

(Step 1) To the compound S141B (1.5 g) in N,N-dimethylformamide (15 ml) solution, 4-dimethylaminopyridine (0.3 g), the compound S102 (0.97 g), and triethylamine (0.68 ml) were added under ice cooling and the mixture was stirred under ice cooling for 16 hours. Saturated ammonium chloride aqueous solution was added to the reaction solution and the mixture was extracted with ethyl acetate. The organic layer was washed with saturated saline, dried over with anhydrous sodium sulfate, then concentrated. The residue was purified by silica gel column chromatography (hexane/ethyl acetate-1/3) to obtain tert-butyl 2-amino-4-[(1R)-1-({[(6S)-6-(5-chloro-2-methoxybenzyl)-3,7-dioxo-4-(2,4,6-trimethoxybenzyl)-1,4-diazepan-1-yl]carbonyl}amino)propyl]benzoate (1.47 g).

NMR (CDCl$_3$): δ9.42 (1H, d, J=7.9 Hz), 7.77 (1H, d, J=8.7 Hz), 7.18 (1H, dd, J=8.7, 2.6 Hz), 6.93 (1H, d, J=2.6 Hz), 6.75 (1H, d, J=8.8 Hz), 6.55-6.50 (2H, m), 6.01 (2H, s), 5.7 (2H, br), 5.31 (1H, d, J=17.5 Hz), 4.82 (1H, d, J=13.8 Hz), 4.7 (1H, q, J=7.9 Hz), 4.29-4.20 (2H, m), 3.81 (3H, s), 3.77 (3H, s), 3.61-3.50 (7H, m), 3.1 (1H, dd, J=13.7, 4.7 Hz), 3.01-2.95 (2H, m), 2.4 (1H, dd, J=13.7, 9.2 Hz), 1.88-1.71 (2H, m), 1.58 (9H, s), 0.88 (3H, t, J=7.4 Hz)

(Step 2) To tert-butyl 2-amino-4-[(1R)-1-({[(6S)-6-(5-chloro-2-methoxybenzyl)-3,7-dioxo-4-(2,4,6-trimethoxybenzyl)-1,4-diazepan-1-yl]carbonyl}amino)propyl]benzoate (1.47 g), 1M hydrogen chloride/acetic acid solution (15 ml) was added and the mixture was stirred at room temperature for 20 hours. The reaction solution was concentrated, then the residue was purified by silica gel column chromatography (chloroform/ethyl acetate/methanol/acetic acid=8/8/1/0.1) to obtain the title compound (0.28 g).

NMR (DMSO-d$_6$): δ9.41 (1H, d, 7.7 Hz), 7.67 (1H, br), 7.66 (1H, d, 8.2 Hz), 7.33 (1H, d, 2.7 Hz), 7.27 (1H, dd, 8.8, 2.7 Hz), 7.01 (1H, d, 8.8 Hz), 6.64 (1H, d, 1.5 Hz), 6.45 (1H, dd, 8.2, 1.5 Hz), 4.79 (1H, d, 17.2 Hz), 4.59-4.49 (1H, m), 4.53 (1H, d, 17.2 Hz), 3.92-3.84 (1H, m), 3.79 (3H, s), 3.14

(1H, t, 12.8 Hz), 3.00 (1H, dd, 17.0, 12.8 Hz), 2.98 (1H, dd, 14.4, 4.6 Hz), 2.65 (1H, dd, 14.4, 9.2 Hz), 1.79-1.67 (2H, m), 0.83 (3H, t, 7.2 Hz)

MS: 503 (M+H)$^+$

Example 151

5-[(1R)-1-({[(6R)-6-(5-chloro-2-methoxybenzyl)-3,7-dioxo-1,4-diazepan-1-yl]carbonyl}amino)propyl] nicotinic Acid (Compound 151)

The compound S141C was used instead of the starting material compound of Reference Example 142A, that is, the compound S141A, and the compound S103 was used instead of the starting material compound of Reference Example 142A, that is, the compound S83, for the similar procedure as in Reference Example 142A and Example 91 to obtain the title compound.

NMR (DMSO-d$_6$): δ9.48 (1H, d, J=7.1 Hz), 8.93 (1H, d, J=1.8 Hz), 8.71 (1H, brs), 8.17 (1H, s), 7.67 (1H, brd, J=3.8 Hz), 7.34 (1H, d, J=2.7 Hz), 7.27 (1H, dd, J=8.7, 2.7 Hz), 7.01 (1H, d, J=8.7 Hz), 4.79 (1H, dd, J=14.2, 7.0 Hz), 4.69 (1H, d, J=17.1 Hz), 4.49 (1H, d, J=17.1 Hz), 3.92-3.80 (1H, m), 3.79 (3H, s), 3.17 (1H, t, J=12.9 Hz), 3.07-2.97 (2H, m), 2.78-2.65 (1H, m), 1.95-1.78 (2H, m), 0.87 (3H, t, J=7.3 Hz)

MS: 489 (M+H)$^+$

Melting point: 138-140° C.

Example 152

(6R)—N-[1-(3-hydroxy-5-isoxazole)propyl]-6-(5-chloro-2-methoxybenzyl)-3,7-dioxo-1,4-diazepan-1-carboxamide (Compound 152) (Diastereomer of Compound 153)

Instead of the starting material compound of Example 151, that is, the compound S103, the compound S94 was used for the similar procedure as in Example 151 to obtain the title compound.

NMR (DMSO-d$_6$): δ11.45-11.05 (1H, br), 9.37 (1H, d, 7.9 Hz), 7.69 (1H, brd, 3.9 Hz), 7.33 (1H, d, 2.7 Hz), 7.27 (1H, dd, 8.8, 2.7 Hz), 7.00 (1H, d, 8.8 Hz), 5.90 (1H, s), 4.83 (1H, dd, 14.4, 7.9 Hz), 4.75 (1H, d, 17.2), 4.53 (1H, d, 17.2 Hz), 3.92-3.82 (1H, m), 3.79 (3H, s), 3.15 (1H, t, 13.2 Hz), 3.04-2.94 (2H, m), 2.68-2.61 (1H, m), 1.91-1.77 (2H, m), 0.87 (3H, t, 7.3 Hz)

MS: 451 (M+H)$^+$

Example 153

(6S)—N-[1-(3-hydroxy-5-isoxazole)propyl]-6-(5-chloro-2-methoxybenzyl)-3,7-dioxo-1,4-diazepan-1-carboxamide (Compound 153) (Diastereomer of Compound 152)

Instead of the starting material compound of Example 151, that is, the compound S103, the compound S94 was used for the similar procedure as in Example 151 to obtain the title compound.

NMR (DMSO-d$_6$): δ11.50-11.05 (1H, br), 9.37 (1H, d, 8.0 Hz), 7.69 (1H, brd, 3.7 Hz), 7.33 (1H, d, 2.7 Hz), 7.27 (1H, dd, 8.8, 2.7 Hz), 7.01 (1H, d, 8.8 Hz), 5.93 (1H, s), 4.84 (1H, dd, 14.3, 8.0 Hz), 4.76 (1H, d, 17.1 Hz), 4.55 (1H, d, 17.1 Hz), 3.91-3.84 (1H, m), 3.79 (3H, s), 3.16 (1H, t, 13.0 Hz), 3.03-2.94 (2H, m), 2.65 (1H, dd, 14.3, 9.0 Hz), 1.89-1.76 (2H, m), 0.87 (3H, t, 7.3 Hz)

MS: 451 (M+H)$^+$

Example 154

5-[(1R)-1-({[(6R)-6-(5-chloro-2-methoxybenzyl)-3,7-dioxo-1,4-diazepan-1-yl]carbonyl}amino)propyl]-3-furan Carboxylic Acid (Compound 154)

Instead of starting material compound of Example 151, that is, the compound S103, the compound S104 was used for the similar procedure as in Example 151 to obtain the title compound.

NMR (DMSO-d$_6$): δ12.71-12.59 (1H, br), 9.36 (1H, d, J=8.1 Hz), 8.20 (1H, brs), 7.69 (1H, brd, J=3.9 Hz), 7.33 (1H, d, J=2.6 Hz), 7.27 (1H, dd, J=8.8, 2.6 Hz), 7.01 (1H, d, J=8.8 Hz), 6.54 (1H, s), 4.85 (1H, dd, J=14.7, 7.1 Hz), 4.78 (1H, d, J=17.1 Hz), 4.52 (1H, d, J=17.1 Hz), 3.91-3.81 (1H, m), 3.79 (3H, s) 3.15 (1H, t, J=12.5 Hz), 3.07-2.92 (2H, m), 2.68-2.57 (1H, m), 1.89-1.75 (2H, m), 0.86 (3H, t, J=7.3 Hz)

MS: 478 (M+H)$^+$

Example 155

5-[(1R)-1-({[(6R)-6-(5-chloro-2-methoxybenzyl)-3,7-dioxo-1,4-diazepan-1-yl]carbonyl}amino)propyl]-3-thiophencarboxylic Acid (Compound 155)

Instead of the starting material compound of Example 151, that is, the compound S103, the compound S108 was used for the similar procedure as in Example 151 to obtain the title compound.

NMR (DMSO-d$_6$): δ12.80-12.65 (1H, br), 9.42 (1H, d, J=7.8 Hz), 8.09 (1H, brs), 7.69 (1H, brd, J=3.5 Hz), 7.33 (1H, d, J=2.6 Hz), 7.30-7.24 (2H, m), 7.01 (1H, d, J=8.8 Hz), 4.97 (1H, dd, J=14.3, 7.1 Hz), 4.77 (1H, d, J=17.1 Hz), 4.53 (1H, d, J=17.1 Hz), 3.93-3.84 (1H, m), 3.79 (3H, s) 3.15 (1H, t, J=12.5 Hz), 3.07-2.94 (2H, m), 2.68-2.58 (1H, m), 1.94-1.85 (2H, m), 0.89 (3H, t, J=7.3 Hz)

MS: 494 (M+H)$^+$

Example 156

2-[(1R)-1-({[(6R)-6-(5-chloro-2-methoxybenzyl)-3,7-dioxo-1,4-diazepan-1-yl]carbonyl}amino)propyl] isonicotinic Acid (Compound 156)

Instead of the starting material compound of Example 151, that is, the compound S103, the compound S105 was used for the similar procedure as in Example 151 to obtain the title compound.

NMR (DMSO-d$_6$): δ9.75 (1H, d, J=7.6 Hz), 8.75 (1H, d, J=4.9 Hz), 7.81 (1H, brs), 7.75-7.68 (2H, m), 7.34 (1H, d, J=2.7 Hz), 7.27 (1H, dd, J=8.8, 2.7 Hz), 7.01 (1H, d, J=8.8 Hz), 4.96 (1H, dd, J=14.1, 7.0 Hz), 4.77 (1H, d, J=17.2 Hz), 4.50 (1H, d, J=17.2 Hz), 3.94-3.80 (1H, m), 3.79 (3H, s), 3.17 (1H, t, J=13.0 Hz), 3.07-2.97 (2H, m), 2.72-2.64 (1H, m), 1.92-1.80 (2H, m), 0.80 (3H, t, J=7.4 Hz)

MS: 489 (M+H)$^+$

Example 157

6-[(1R)-1-({[(6R)-6-(5-chloro-2-methoxybenzyl)-3,7-dioxo-1,4-diazepan-1-yl]carbonyl}amino)propyl] nicotinic Acid (Compound 157)

Instead of the starting material compound of Example 151, that is, the compound S103, the compound S106 was used for the similar procedure as in Example 151 to obtain the title compound.

NMR (DMSO-d$_6$): δ9.75 (1H, d, J=7.5 Hz), 9.04 (1H, d, J=2.1 Hz), 8.25 (1H, dd, J=8.1, 2.1 Hz), 7.70 (1H, brd, J=3.9 Hz), 7.53 (1H, d, J=8.1 Hz), 7.34 (1H, d, J=2.7 Hz), 7.27 (1H, dd, J=8.7, 2.7 Hz), 7.01 (1H, d, J=8.7 Hz), 4.94 (1H, dd, J=14.1, 7.0 Hz), 4.77 (1H, d, J=17.3 Hz), 4.51 (1H, d, J=17.3 Hz), 3.94-3.82 (1H, m), 3.80 (3H, s), 3.17 (1H, t, J=12.5 Hz), 3.08-2.98 (2H, m), 2.72-2.64 (1H, m), 1.92-1.80 (2H, m), 0.80 (3H, t, J=7.4 Hz)

MS: 489 (M+H)$^+$

Reference Example 143

4-nitrophenyl 6-(5-chloro-2-methoxybenzyl)-3,7-dioxo-4-(2,4,6-trimethoxybenzyl)-1,4-diazepan-1-carboxylate (Compound S143)

To the compound S140A (2.69 g) in tetrahydrofuran (160 ml) solution, a 1.59M hexane solution of n-butyllithium (3.7 ml) was added at of −78° C. and the mixture was stirred at that temperature for 20 minutes. Next, p-nitrophenyl chlorocarbonate (1.3 g) in tetrahydrofuran (10 ml) solution was added to the reaction solution at −78° C. and the mixture was stirred at that temperature for 1 hour. Saturated potassium hydrogensulfate aqueous solution was added to the reaction solution, tetrahydrofuran was distilled off in vacuo, and the remaining aqueous solution was extracted with ethyl acetate. The organic layer was washed with saturated saline, dried over with anhydrous sodium sulfate, and concentrated to obtain the title compound as a crude product (4.05 g).

Reference Example 144 tert-butyl rel-(1R,6R)-5-[1-({[4-(2,4,6-trimethoxy-benzyl)-6-(5-chloro-2-methoxybenzyl)-3,7-dioxo-1,4-diazepan-1-yl]carbonyl}amino)propyl]-2-benzyloxybenzoate (Compound S144)

Instead of the starting material of Reference Example 142A, that is, the compound S141A, the compound S143 was used, while instead of the compound S83, the compound S89 was used for the similar procedure as in Reference Example 142A to obtain the title compound.

NMR (CDCl$_3$): δ9.4 (1H, d, J=7.7 Hz), 7.6 (1H, d, J=2.4 Hz), 7.48-7.44 (2H, m), 7.40-7.35 (2H, m), 7.34-7.28 (2H, m), 7.17 (1H, dd, J=8.8, 2.6 Hz), 6.95-6.88 (2H, m), 6.74 (1H, d, J=8.8 Hz), 6.07 (2H, s), 5.3 (1H, d, J=17.4 Hz), 5.11 (2H, s), 4.82-4.70 (2H, m), 4.32 (1H, d, J=13.7 Hz), 4.19 (1H, d, J=13.7 Hz), 3.83 (3H, s), 3.76 (3H, s), 3.69 (6H, s), 3.58-3.45 (1H, m), 3.1 (1H, dd, J=14.0, 4.3 Hz), 3.05-2.99 (2H, m), 2.37 (1H, dd, J=13.8, 9.5 Hz), 1.90-1.75 (2H, m), 1.51 (9H, s), 0.89 (3H, t, J=7.3 Hz)

Reference Example 145 tert-butyl rel-(1R,6R)-5-[1-({[4-(2,4,6-trimethoxy-benzyl)-6-(5-chloro-2-methoxybenzyl)-3,7-dioxo-1,4-diazepan-1-yl]carbonyl}amino)propyl]-2-hydroxybenzoate (Compound S145)

To the compound S144 (315 mg) in tetrahydrofuran (4 ml) solution, platinum oxide (40 mg) was added and the mixture was stirred under hydrogen atmosphere at room temperature for 18 hours. The insoluble compound was filtered out, then the filtrate was concentrated. The residue was purified by silica gel column chromatography (diethylether/ethyl acetate=10/1) to obtain the title compound (186 mg).

NMR (CDCl$_3$): δ10.97 (1H, s), 9.41 (1H, d, J=7.7 Hz), 7.67 (1H, d, J=2.2 Hz), 7.34 (1H, dd, J=8.6, 2.2 Hz), 7.17 (1H, dd, J=8.7, 2.5 Hz), 6.95-6.89 (2H, m), 6.74 (1H, d, J=8.7 Hz), 6.07 (2H, s), 5.32 (1H, d, J=17.4 Hz), 4.80-4.70 (2H, m), 4.33 (1H, d, J=13.7 Hz), 4.19 (1H, d, J=13.7 Hz), 3.83 (3H, s), 3.76 (3H, s), 3.7 (6H, s), 3.60-3.46 (1H, m), 3.1 (1H, dd, J=13.9, 4.5 Hz), 3.05-2.97 (2H, m), 2.38 (1H, dd, J=13.8, 9.5 Hz), 1.89-1.70 (2H, m), 1.61 (9H, s), 0.89 (3H, t, J=7.2 Hz)

Reference Example 146 tert-butyl rel-(1R,6R)-5-[1-({[4-(2,4,6-trimethoxy-benzyl)-6-(5-chloro-2-methoxybenzyl)-3,7-dioxo-1,4-diazepan-1-yl]carbonyl}amino)propyl]-2-methoxybenzoate (Compound S146)

To the compound S145 (315 mg) in N,N-dimethylformamide (2 ml) solution, methyl iodide (0.06 ml) and potassium carbonate (18 mg) were added and the mixture was stirred at room temperature for 3 hours. The reaction solution was diluted with ethyl acetate, successively washed with saturated sodium thiosulfate aqueous solution, saturated potassium hydrogensulfate aqueous solution, and saturated saline, dried over with anhydrous sodium sulfate, then concentrated. The residue was purified by silica gel column chromatography (hexane/ethyl acetate=2/3) to obtain the title compound (85 mg).

NMR (CDCl$_3$): δ9.41 (1H, d, J=7.6 Hz), 7.62 (1H, d, J=2.4 Hz), 7.35 (1H, dd, J=8.6, 2.4 Hz), 7.17 (1H, dd, J=8.7, 2.5 Hz), 6.93-6.88 (2H, m), 6.74 (1H, d, J=8.7 Hz), 6.07 (2H, s), 5.01 (1H, d, J=17.4 Hz), 4.82-4.72 (2H, m), 4.31 (1H, d, J=13.7 Hz), 4.19 (1H, d, J=13.7 Hz), 3.86 (3H, s), 3.83 (3H, s), 3.76 (3H, s), 3.7 (6H, s), 3.58-3.46 (1H, m), 3.1 (1H, dd, J=14.0, 4.4 Hz), 3.05-2.98 (2H, m), 2.37 (1H, dd, J=13.9, 9.3 Hz), 1.91-1.74 (2H, m), 1.58 (9H, s), 0.89 (3H, t, J=7.3 Hz)

Example 158 rel-(1R,6R)-5-[1-({[6-(5-chloro-2-methoxybenzyl)-3,7-dioxo-1,4-diazepan-1-yl]carbonyl}amino)propyl]-2-hydroxybenzoic Acid (Compound 158)

Instead of the starting material of Example 91, that is, the compound S142A, the compound S145 was used for the similar procedure as in Example 91 to obtain the title compound.

NMR (DMSO-d$_6$): δ9.37 (1H, d, J=7.3 Hz), 7.65 (1H, d, J=3.6 Hz), 7.62 (1H, d, J=2.3 Hz), 7.32 (1H, d, J=2.6 Hz), 7.26 (1H, dd, J=8.8, 2.6 Hz), 7.23-7.18 (1H, m), 6.99 (1H, d, J=8.8 Hz), 6.70 (1H, d, J=8.4 Hz), 4.76 (1H, d, J=17.2 Hz), 4.57 (1H, q, J=7.3 Hz), 4.47 (1H, d, J=17.2 Hz), 3.89-3.78 (1H, m), 3.78 (3H, s), 3.14 (1H, t, J=12.6 Hz), 3.04-2.93 (2H, m), 2.68-2.61 (1H, m), 1.84-1.66 (2H, m), 0.80 (3H, t, J=7.2 Hz)

MS: 504 (M+H)$^+$

Example 159 rel-(1R,6R)-5-[1-({[6-(5-chloro-2-methoxybenzyl)-3,7-dioxo-1,4-diazepan-1-yl]carbonyl}amino)propyl]-2-methoxybenzoic Acid (Compound 159)

Instead of the starting material of Example 91, that is, the compound S142A, the compound S146 was used for the similar procedure as in Example 91 to obtain the title compound.

NMR (DMSO-d$_6$): δ12.60 (1H, brs), 9.39 (1H, d, J=7.4 Hz), 7.66 (1H, d, J=3.6 Hz), 7.54 (1H, d, J=2.2 Hz), 7.43 (1H, dd, J=8.6, 2.2 Hz), 7.32 (1H, d, J=2.6 Hz), 7.26 (1H, dd, J=8.8, 2.6 Hz), 7.08 (1H, d, J=8.6 Hz), 7.00 (1H, d, J=8.8 Hz), 4.73 (1H, d, J=17.0 Hz), 4.64 (1H, q, J=7.4 Hz), 4.48 (1H, d, J=17.0 Hz), 3.90-3.75 (1H, m), 3.80 (3H, s), 3.78 (3H, s), 3.15 (1H, t, J=12.8 Hz), 3.03-2.92 (2H, m), 2.65 (1H, dd, J=14.3, 9.4 Hz), 1.86-1.68 (2H, m), 0.82 (3H, t, J=7.3 Hz)
MS: 518 (M+H)$^+$ Example 160 rel-(1R,6R)-3-[1-({[6-(5-chloro-2-methoxybenzyl)-3,7-dioxo-1,4-diazepan-1-yl]carbonyl}amino)propyl]-2-hydroxybenzoic Acid (Compound 160)

Instead of the starting material of Reference Example 144, that is, the compound S89, the compound S88 was used for the similar procedure as in Reference Example 144, Reference Example 145, and Example 158 to obtain the title compound.
NMR (DMSO-d$_6$): δ9.76 (1H, d, J=8.6 Hz), 7.64 (1H, d, J=3.5 Hz), 7.58 (1H, d, J=7.5 Hz), 7.32 (1H, d, J=2.6 Hz), 7.26 (1H, dd, J=8.7, 2.6 Hz), 7.01-6.98 (2H, m), 6.51 (1H, t, J=7.5 Hz), 4.86-4.78 (2H, m), 4.44 (1H, d, J=17.2 Hz), 3.88-3.78 (1H, m), 3.78 (3H, s), 3.14 (1H, t, J=12.6 Hz), 3.03-2.92 (2H, m), 2.69-2.61 (1H, m), 1.90-1.70 (2H, m), 0.77 (3H, t, J=7.3 Hz)

Example 161 rel-(1R,6R)-3-[1-({[6-(5-chloro-2-methoxybenzyl)-3,7-dioxo-1,4-diazepan-1-yl]carbonyl}amino)propyl]-2-methoxybenzoic Acid (Compound 161)

Instead of the starting material of Reference Example 144, that is, the compound S89, the compound S88 was used for the similar procedure as in Reference Example 144, Reference Example 145, Reference Example 146, and Example 159 to obtain the title compound.
NMR (DMSO-d$_6$): δ9.53 (1H, d, J=8.4 Hz), 7.68 (1H, d, J=3.5 Hz), 7.32 (1H, d, J=2.6 Hz), 7.25 (1H, dd, J=8.7, 2.6 Hz), 7.13 (1H, d, J=7.4 Hz), 6.99 (1H, d, J=8.8 Hz), 6.96 (1H, d, J=7.4 Hz), 6.84 (1H, t, J=7.4 Hz), 4.95-4.88 (1H, m), 4.78 (1H, d, J=17.2 Hz), 4.47 (1H, d, J=17.2 Hz), 3.91-3.78 (1H, m), 3.81 (3H, s), 3.78 (3H, s), 3.15 (1H, t, J=12.4 Hz), 3.08-2.94 (2H, m), 2.69-2.63 (1H, m), 1.79-1.63 (2H, m), 0.81 (3H, t, J=7.4 Hz)
MS: 518 (M+H)$^+$ Example 162 rel-(1R,6R)-4-[1-({[6-(5-chloro-2-methoxybenzyl)-3,7-dioxo-1,4-diazepan-1-yl]carbonyl}amino)propyl]-2-methoxybenzoic Acid (Compound 162)

Instead of the starting material of Reference Example 144, that is, the compound S89, the compound S78 was used for the similar procedure as in Reference Example 144, Reference Example 146, and Example 159 to obtain the title compound.
NMR (DMSO-d$_6$): δ12.47 (1H, brs), 9.42 (1H, d, J=7.5 Hz), 7.68 (1H, d, J=3.7 Hz), 7.59 (1H, d, J=8.1 Hz), 7.33 (1H, d, J=2.6 Hz), 7.27 (1H, dd, J=8.8, 2.6 Hz), 7.07 (1H, s), 7.00 (1H, d, J=8.8 Hz), 6.90 (1H, d, J=8.1 Hz), 4.75-4.70 (2H, m), 4.50 (1H, d, J=17.1 Hz), 3.92-3.83 (1H, m), 3.80 (3H, s), 3.79 (3H, s), 3.17 (1H, t, J=12.9 Hz), 3.08-2.95 (2H, m), 2.66 (1H, dd, J=14.5, 9.1 Hz), 1.85-1.74 (2H, m), 0.86 (3H, t, J=7.2 Hz)
MS: 518 (M+H)$^+$ Example 163 rel-(1R,6S)-4-[1-({[6-(5-chloro-2-methoxybenzyl)-3,7-dioxo-1,4-diazepan-1-yl]carbonyl}amino)propyl]-2-methoxybenzoic Acid (Compound 163)

Instead of the starting material of Reference Example 144, that is, the compound S89, the compound S78 was used for the similar procedure as in Reference Example 144, Reference Example 146, and Example 159 to obtain the title compound.
NMR (DMSO-d$_6$): δ12.48 (1H, br), 9.40 (1H, d, J=7.5 Hz), 7.66 (1H, d, J=3.7 Hz), 7.61 (1H, d, J=7.9 Hz), 7.34 (1H, d, J=1.9 Hz), 7.27 (1H, dd, J=8.7, 1.9 Hz), 7.06 (1H, s), 7.01 (1H, d, J=8.7 Hz), 6.92 (1H, d, J=7.9 Hz), 4.77-4.72 (2H, m), 4.53 (1H, d, J=17.0 Hz), 3.93-3.84 (1H, m), 3.81 (3H, s), 3.79 (3H, s), 3.13 (1H, t, J=12.7 Hz), 3.05-2.96 (2H, m), 2.65 (1H, dd, J=14.3, 9.0 Hz), 1.84-1.75 (2H, m), 0.86 (3H, t, J=7.1 Hz)
MS: 518 (M+H)$^+$ Reference Example 147

6-(5-chloro-2-methoxybenzyl)-N-(3-chlorophenyl)-3,7-dioxo-4-(2,4,6-trimethoxybenzyl)-1,4-diazepan-1-carboxamide (Compound S147)

To the compound S140A (150 mg) in tetrahydrofuran (8 ml) solution, a 1.59M hexane solution of n-butyllithium (0.2 ml) was added at −78° C. and the mixture was stirred at that temperature for 20 minutes. Next, a solution of bis(trichloromethyl)carbonate in tetrahydrofuran 1M solution (0.34 ml) was added to the reaction solution at −78° C. and the mixture was stirred at that temperature for 45 minutes. After this, 3-chloroaniline (0.2 ml) was added to the reaction solution at −78° C. and the mixture was stirred and warmed to 0° C. over 3 hours. Saturated potassium hydrogensulfate aqueous solution was added to the reaction solution, and the mixture was extracted with ethyl acetate. The organic layer was successively washed with saturated saline and distilled water, dried over with anhydrous sodium sulfate, then concentrated. The residue was purified by silica gel column chromatography (hexane/ethyl acetate=2/3 to 1/2) to obtain the title compound (56.8 mg).
NMR (CDCl$_3$): δ11.29 (1H, s), 7.65 (1H, s), 7.38 (1H, d, J=8.0 Hz), 7.30-7.22 (1H, m), 7.2 (1H, dd, J=8.8, 2.6 Hz), 7.08 (1H, d, J=8.0 Hz), 6.96 (1H, d, J=2.6 Hz), 6.77 (1H, d, J=8.8 Hz), 6.07 (2H, s), 5.37 (1H, d, J=17.3 Hz), 4.84 (1H, d, J=13.8 Hz), 4.33 (1H, d, J=17.3 Hz), 4.32 (1H, d, J=13.8 Hz), 3.82 (3H, s), 3.79 (3H, s), 3.7 (6H, s), 3.69-3.59 (1H, m), 3.19-3.00 (3H, m), 2.44 (1H, dd, J=13.9, 8.8 Hz)

Example 164

6-(5-chloro-2-methoxybenzyl)-N-(3-chlorophenyl)-3,7-dioxo-1,4-diazepan-1-carboxamide (Compound 164)

To the compound S147 (50 mg), 1M hydrogen chloride/acetic acid solution (1 ml) was added and the mixture was stirred at room temperature for 24 hours. The reaction solution was concentrated, then the residue was purified by florisil column chromatography (ethyl acetate) and the elute was concentrated. The residue was recrystallized from hexane/ethyl acetate to obtain the title compound (18.2 mg).

NMR (CDCl$_3$): δ11.28 (1H, s), 7.66 (1H, t, J=2.0 Hz), 7.38 (1H, ddd, J=8.1, 2.0, 0.9 Hz), 7.25 (1H, t, J=8.1 Hz), 7.23 (1H, dd, J=8.8, 2.6 Hz), 7.16 (1H, d, J=2.6 Hz), 7.10 (1H, ddd, J=8.1, 2.0, 0.9 Hz), 6.82 (1H, d, J=8.8 Hz), 5.93 (1H, br), 5.44 (1H, d, J=17.4 Hz), 4.1 (1H, d, J=17.4 Hz), 3.85 (3H, s), 3.84-3.75 (1H, m), 3.41-3.35 (2H, m), 3.22 (1H, dd, J=13.9, 5.6 Hz), 2.65 (1H, dd, J=13.9, 8.0 Hz)

MS: 436 (M+H)$^+$

Instead of the starting material compound of Reference Example 147, that is, 3-chloroaniline, the aniline derivatives shown in Table X were used for the similar procedure as in Reference Example 147 and Example 164 to obtain the compounds of Example 165 to Example 172. Note that the aniline derivatives shown in Table X are commercially available compounds or compounds obtained by derivation from commercially available compounds by known methods.

TABLE X

| Ex. no. | Aniline derivative used as material |
|---|---|
| Ex. 165 | H$_2$N–C$_6$H$_4$–CF$_3$ |
| Ex. 166 | H$_2$N–C$_6$H$_4$–OMe |
| Ex. 167 | H$_2$N–(5-pyridyl)–2-Cl |
| Ex. 168 | H$_2$N–C$_6$H$_4$–C(O)O-tBu (para) |
| Ex. 169 | H$_2$N–C$_6$H$_4$–C(O)O-tBu (meta) |
| Ex. 170 | H$_2$N–C$_6$H$_4$–C(O)O-tBu (ortho) |
| Ex. 171 | H$_2$N–C$_6$H$_4$–NH–C(O)O-tBu (meta) |

TABLE X-continued

| Ex. no. | Aniline derivative used as material |
|---|---|
| Ex. 172 | H$_2$N–C$_6$H$_4$–NH–C(O)O-tBu (para) |

Example 165

6-(5-chloro-2-methoxybenzyl)-3,7-dioxo-N-[4-(trifluoromethyl)phenyl]-1,4-diazepan-1-carboxamide (Compound 165)

NMR (CDCl$_3$): δ11.45 (1H, s), 7.67 (2H, d, J=8.7 Hz), 7.59 (2H, d, J=8.7 Hz), 7.24 (1H, dd, J=8.7, 2.6 Hz), 7.17 (1H, d, J=2.6 Hz), 6.83 (1H, d, J=8.7 Hz), 5.86 (1H, br), 5.46 (1H, d, J=17.4 Hz), 4.22 (1H, d, J=17.4 Hz), 3.89-3.77 (1H, m), 3.86 (3H, s), 3.41-3.38 (2H, m), 3.23 (1H, dd, J=13.9, 5.5 Hz), 2.66 (1H, dd, J=13.9, 7.9 Hz)

MS: 470 (M+H)$^+$

Example 166

6-(5-chloro-2-methoxybenzyl)-N-(4-methoxyphenyl)-3,7-dioxo-1,4-diazepan-1-carboxamide (Compound 166)

NMR (CDCl$_3$): δ11.04 (1H, s), 7.43 (2H, d, J=8.9 Hz), 7.23 (1H, dd, J=8.8, 2.6 Hz), 7.16 (1H, d, J=2.6 Hz), 6.87 (2H, d, J=8.9 Hz), 6.82 (1H, d, J=8.8 Hz), 5.81 (1H, br), 5.48 (1H, d, J=17.5 Hz), 4.19 (1H, d, J=17.5 Hz), 3.85 (3H, s), 3.84-3.72 (1H, m), 3.8 (3H, s), 3.40-3.36 (2H, m), 3.22 (1H, dd, J=14.0, 5.5 Hz), 2.65 (1H, dd, J=14.0, 8.1 Hz)

MS: 432 (M+H)$^+$

Example 167

6-(5-chloro-2-methoxybenzyl)-N-(6-chloro-3-pyridyl)-3,7-dioxo-1,4-diazepan-1-carboxamide (Compound 167)

NMR (DMSO-d$_6$): δ11.11 (1H, s), 8.57 (1H, d, J=2.7 Hz), 8.07 (1H, dd, J=8.7, 2.7 Hz), 7.75 (1H, d, J=3.5 Hz), 7.49 (1H, d, J=8.7 Hz), 7.36 (1H, d, J=2.5 Hz), 7.27 (1H, dd, J=8.7, 2.5 Hz), 7.01 (1H, d, J=8.7 Hz), 4.77 (1H, d, J=17.3 Hz), 4.65 (1H, d, J=17.3 Hz), 4.02-3.92 (1H, m), 3.79 (3H, s), 3.22 (1H, t, J=12.6 Hz), 3.06-2.99 (2H, m), 2.67 (1H, dd, J=14.4, 9 Hz)

MS: 437 (M+H)$^+$

Example 168

4-({[6-(5-chloro-2-methoxybenzyl)-3,7-dioxo-1,4-diazepan-1-yl]carbonyl}amino)benzoic Acid (Compound 168)

NMR (DMSO-d$_6$): δ12.68 (1H, br), 11.25 (1H, s), 7.91 (2H, d, J=8.6 Hz), 7.75 (1H, d, J=3.9 Hz), 7.65 (2H, d, J=8.6 Hz), 7.36 (1H, d, J=2.6 Hz), 7.27 (1H, dd, J=8.8, 2.6 Hz), 7.01 (1H, d, J=8.8 Hz), 4.77 (1H, d, J=17.3 Hz), 4.64 (1H, d, J=17.3 Hz), 4.00-3.90 (1H, m), 3.79 (3H, s), 3.24 (1H, t, J=12.6 Hz), 3.07-2.98 (2H, m), 2.67 (1H, dd, J=14.4, 9.0 Hz)

MS: 446 (M+H)$^+$

Example 169

3-({[6-(5-chloro-2-methoxybenzyl)-3,7-dioxo-1,4-diazepan-1-yl]carbonyl}amino)benzoic Acid (Compound 169)

NMR (DMSO-d$_6$): δ11.09 (1H, s), 8.07 (1H, s), 7.74 (1H, d, J=3.7 Hz), 7.68-7.62 (2H, m), 7.40-7.35 (2H, m), 7.27 (1H, dd, J=8.8, 2.7 Hz), 7.01 (1H, d, J=8.8 Hz), 4.78 (1H, d, J=17.4 Hz), 4.62 (1H, d, J=17.4 Hz), 3.99-3.88 (1H, m), 3.79 (3H, s), 3.24 (1H, t, J=12.5 Hz), 3.06-2.97 (2H, m), 2.67 (1H, dd, J=14.3, 9.0 Hz)

MS: 446 (M+H)$^+$

Example 170

2-({[6-(5-chloro-2-methoxybenzyl)-3,7-dioxo-1,4-diazepan-1-yl]carbonyl}amino)benzoic Acid (Compound 170)

NMR (DMSO-d$_6$): δ8.20 (1H, d, J=8.2 Hz), 7.94 (1H, d, J=7.8 Hz), 7.71 (1H, d, J=4.1 Hz), 7.40-7.32 (2H, m), 7.26 (1H, dd, J=8.7, 2.6 Hz), 7.06-6.98 (2H, m), 4.64 (1H, d, J=17.1 Hz), 4.58 (1H, d, J=17.1 Hz), 3.87-3.79 (1H, m), 3.80 (3H, s), 3.15 (1H, t, J=12.9 Hz), 3.05-2.95 (2H, m), 2.63 (1H, dd, J=14.3, 9.5 Hz)

MS: 446 (M+H)$^+$

Example 171

N-(3-aminophenyl)-6-(5-chloro-2-methoxybenzyl)-3,7-dioxo-1,4-diazepan-1-carboxamide (Compound 171)

NMR (DMSO-d$_6$): δ10.91 (1H, s), 7.72 (1H, d, J=3.6 Hz), 7.34 (1H, d, J=2.6 Hz), 7.26 (1H, dd, J=8.8, 2.6 Hz), 7.00 (1H, d, J=8.8 Hz), 6.94 (1H, t, J=8.0 Hz), 6.79 (1H, s), 6.59 (1H, d, J=8 Hz), 6.30 (1H, d, J=8 Hz), 5.13 (2H, brs), 4.80 (1H, d, J=17.2 Hz), 4.58 (1H, d, J=17.2 Hz), 3.98-3.87 (1H, m), 3.79 (3H, s), 3.21 (1H, t, J=12.9 Hz), 3.06-2.94 (2H, m), 2.66 (1H, dd, J=14.3, 8.9 Hz)

MS: 417 (M+H)$^+$

Example 172

N-(4-aminophenyl)-6-(5-chloro-2-methoxybenzyl)-3,7-dioxo-1,4-diazepan-1-carboxamide (Compound 172)

NMR (DMSO-d$_6$): δ10.7 (1H, s), 7.71 (1H, d, J=3.6 Hz), 7.34 (1H, d, J=2.6 Hz), 7.26 (1H, dd, J=8.8, 2.6 Hz), 7.12 (2H, d, J=8.7 Hz), 7.00 (1H, d, J=8.8 Hz), 6.51 (2H, d, J=8.7 Hz), 4.96 (2H, brs), 4.80 (1H, d, J=17.2 Hz), 4.57 (1H, d, J=17.2 Hz), 3.97-3.86 (1H, m), 3.79 (3H, s), 3.19 (1H, t, J=12.9 Hz), 3.06-2.93 (2H, m), 2.65 (1H, dd, J=14.3, 8.9 Hz)

MS: 417 (M+H)$^+$

Reference Example 148 tert-butyl 2-(3-chlorobenzyl)-3-{[(4-nitrophenyl)sulfonyl]amino}-3-oxopropylcarbamate (Compound S148)

To the compound S33 (530 mg) in N,N-dimethylformamide (10 ml) solution, 4-nitrobenzenesulfonamide (512 mg), 4-dimethylaminopyridine (310 mg), and 1-(3-dimethylaminopropyl)-3-ethylcarbodiimide hydrochloride (486 mg) were added and the mixture was stirred at room temperature for 17 hours. The reaction solution was concentrated, then the residue was diluted with chloroform and saturated sodium hydrogencarbonate aqueous solution. The organic layer was separated, successively washed with saturated ammonium chloride aqueous solution and saturated saline, dried over with anhydrous sodium sulfate, then concentrated. The residue was dried in vacuo to obtain the title compound (1.19 g).

Reference Example 149

N-[3-amino-2-(3-chlorobenzyl)propanoyl]-4-nitrobenzenesulfonamide Hydrochloride (Compound S149)

A mixture of the compound S148 (1.19 g) and 1N hydrogen chloride/acetic acid solution (12 ml) were stirred at room temperature for 2 hours. The reaction solution was concentrated, chloroform and 1N sodium hydroxide aqueous solution were added, the pH of the aqueous layer was made 5, and the organic layer was separated. The precipitate of the organic layer was collected by filtration to obtain the title compound (444 mg).

Reference Example 150

2-bromo-N-(2-(3-chlorobenzyl)-3-{[(4-nitrophenyl)sulfonyl]amino}-3-oxopropyl)acetoamide (Compound S150)

To the compound S149 (428 mg) in chloroform (8.6 ml) solution, 2N sodium hydroxide aqueous solution (2.0 ml) and bromoacetyl chloride (0.12 ml) were added and the mixture was stirred at room temperature for 2 hours. Distilled water was added to the reaction solution, then the mixture was extracted with ethyl acetate. The organic layer was washed with saturated saline, dried over with anhydrous sodium sulfate, and concentrated to obtain the title compound (299 mg).

NMR (DMSO-d$_6$): δ8.40-8.25 (3H, m), 8.01 (2H, d, J=8.7 Hz), 7.22-6.89 (4H, m), 3.77 (2H, s), 3.19-3.07 (2H, m), 2.99-2.85 (1H, m), 2.72-2.60 (2H, m)

Example 173

6-(5-chlorobenzyl)-4-[(4-nitrophenyl)sulfonyl]-1,4-diazepan-2,5-dione (Compound 173)

To the compound S150 (295 mg) in N,N-dimethylformamide (29 ml) solution, sodium hydride (60% mineral oil dispersion) (23 mg) was added and the mixture was stirred at 60° C. for 17 hours. The reaction solution was concentrated, ethyl acetate and saturated ammonium chloride aqueous solution were added, and the organic layer was separated. The organic layer was washed with saturated saline, dried over with anhydrous sodium sulfate, then concentrated. The residue was purified by silica gel column chromatography (chloroform/ethyl acetate=1/2) to obtain the title compound (41.6 mg).

NMR (DMSO-d$_6$): δ8.44 (2H, d, J=8.9 Hz), 8.20 (2H, d, J=8.9 Hz), 7.91-7.87 (1H, br), 7.31-7.18 (3H, m), 7.18 (1H, d, J=7.3 Hz), 4.95 (1H, d, J=17.5 Hz), 4.57 (1H, d, J=17.5 Hz), 3.88-3.71 (1H, m), 3.09-3.01 (2H, m), 2.94 (1H, dd, J=14.5, 5.4 Hz), 2.55-2.40 (1H, m)

MS: 438 (M+H)$^+$

Example 174

6-(5-chloro-2-methoxybenzyl)-4-[(4-chlorophenyl)sulfonyl]-6-methyl-1,4-diazepan-2,5-dione (Compound 176)

Instead of the starting material of Reference Example 117, that is, the compound S6, the compound S44 was used for the similar procedure as with Reference Example 117 and Reference Example 122 and Example 1 to obtain the title compound.

NMR (CDCl$_3$): δ7.97 (2H, d, J=8.7 Hz), 7.51 (2H, d, J=8.7 Hz), 7.20 (1H, dd, J=8.7, 2.5 Hz), 6.98 (1H, d, J=2.5 Hz), 6.80 (1H, d, J=8.7 Hz), 6.05-5.99 (1H, br), 4.68 (1H, d, J=15.3 Hz), 4.47 (1H, d, J=15.3 Hz), 3.78 (3H, s), 3.23 (1H, d, J=6.3 Hz), 3.21 (1H, d, J=6.3 Hz), 3.11 (1H, d, J=13.8 Hz), 2.79 (1H, d, J=13.8 Hz), 1.2 (3H, s)

MS: 471 (M+H)$^+$

Example 175

6-(5-chloro-2-methoxybenzyl)-6-fluoro-3,7-dioxo-N-[(1R)-1-phenylpropyl]-1,4-diazepan-1-carboxamide (Compound 175)

To the compound S51 (157 mg) in tetrahydrofuran (1.6 ml) solution, N,N-diisopropylethylamine (83 µl) and 2,4,6-trichlorobenzoylchloride (68 µl) were added and the mixture was stirred at room temperature for 1.5 hours, then 4-dimethylaminopyridine (176 mg) and N-[(1R)-1-phenylpropyl]urea (77 mg) were added and the mixture was stirred at room temperature for 3 hours. Distilled water was added to the reaction solution, and the mixture was extracted with ethyl acetate. The organic layer was successively washed with saturated potassium hydrogensulfate aqueous solution, distilled water, saturated sodium hydrogencarbonate aqueous solution, and saturated saline, dried over with anhydrous sodium sulfate, then concentrated. The residue was purified by silica gel column chromatography (hexane/ethyl acetate=5/1). The thus obtained tert-butyl 2-(5-chloro-2-methoxybenzyl)-2-fluoro-3-oxo-3-[({[(1R)-1-phenylpropyl]amino}carbonyl)amino]propyl carbamate (74 mg) was used instead of the starting material compound of Reference Example 149, that is, the compound S148, for the similar procedure as with Reference Example 149, Reference Example 150, and Example 173 to obtain the title compound.

NMR (CDCl$_3$): δ9.47-9.39 (1H, br), 7.38-7.18 (7H, m), 6.85 (0.5H, d, J=8.7 Hz), 6.77 (0.5H, d, J=8.6 Hz), 5.79-5.71 (1H, br), 4.94 (0.5H, d, J=15.7 Hz), 4.84-4.76 (1.5H, m), 4.51 (0.5H, dd, J=15.8, 3.0 Hz), 4.35 (0.5H, dd, J=15.8, 2.5 Hz), 3.85 (1.5H, s), 3.81-3.64 (1H, m), 3.69 (1.5H, s), 3.55-3.17 (3H, m), 1.98-1.78 (2H, m), 0.96-0.87 (3H, m)

MS: 462 (M+H)$^+$

Example 176

3-[1-({[6-(5-chloro-2-methoxybenzyl)-6-fluoro-3,7-dioxo-1,4-diazepan-1-yl]carbonyl}amino)propyl]benzoic Acid (Compound 176)

(Step 1) To the compound S51 (157 mg) in tetrahydrofuran (1.6 ml) solution, N,N-diisopropylethylamine (83 µl) and 2,4,6-trichlorobenzoylchloride (68 µl) were added and the mixture was stirred at room temperature for 1.5 hours, then concentrated. To the residue, toluene (1.5 ml), 4-dimethylaminopyridine (176 mg), and tert-butyl 3-{1-[(aminocarbonyl)amino]propyl}benzoate (121 mg) obtained by using the compound S87 instead of the starting material compound of Reference Example 72, that is, (1R)-1-phenylethylamine, for the similar procedure as in Reference Example 72 were added and the mixture was stirred at room temperature for 3 hours. Distilled water was added to the reaction solution, then the mixture was extracted with ethyl acetate. The organic layer was successively washed with saturated potassium hydrogensulfate aqueous solution, distilled water, saturated sodium hydrogencarbonate aqueous solution, and saturated saline, dried over with anhydrous sodium sulfate, then concentrated. The residue was purified by silica gel column chromatography (hexane/ethyl acetate=3/1) to obtain tert-butyl 3-[6-(5-chloro-2-methoxybenzyl)-1-ethyl-6-fluoro-11,11-dimethyl-3,5,9-trioxo-10-oxa-2,4,8-triazadodec-1-yl]benzoate (146 mg).

(Step 2) To the obtained tert-butyl 3-[6-(5-chloro-2-methoxybenzyl)-1-ethyl-6-fluoro-11,11-dimethyl-3,5,9-trioxo-10-oxa-2,4,8-triazadodec-1-yl]benzoic acid (108 mg), a 1M hydrochloric acid/acetic acid solution (1 ml) was added and the mixture was stirred at room temperature for 3 hours. Diethyl ether was added to the reaction solution, and the precipitated solid was collected by filtration. To the solid collected by filtration, tetrahydrofuran (1.6 ml), 1N sodium hydroxide aqueous solution (0.43 ml), and di-tert-butyl dicarbonate (47 mg) were added and the mixture was stirred at room temperature for 3 hours. Saturated potassium hydrogensulfate aqueous solution was added to the reaction solution, and the mixture was extracted with ethyl acetate. The organic layer was washed with saturated saline, dried over with anhydrous sodium sulfate, then concentrated. Ethyl acetate/tetrahydrofuran/hexane was added to the residue and the precipitated solid was collected by filtration. To the obtained solid in DMF (1.3 ml) solution, 4-dimethylaminopyridine (20 mg), 1-(3-dimethylaminopropyl)-3-ethylcarbodiimide hydrochloride (32 mg), and benzyl alcohol (12 µl) were added and the mixture was stirred at room temperature for 5 hours. Saturated potassium hydrogensulfate aqueous solution was added to the reaction solution, and the mixture was extracted with ethyl acetate. The organic layer was successively washed with distilled water, saturated sodium hydrogencarbonate aqueous solution, and saturated saline, dried over with anhydrous sodium sulfate, then concentrated. The residue was purified by silica gel column chromatography (hexane/ethyl acetate=4/1) to obtain benzyl 3-[6-(5-chloro-2-methoxybenzyl)-1-ethyl-6-fluoro-11,11-dimethyl-3,5,9-trioxo-10-oxa-2,4,8-triazadodec-1-yl]benzoate (51 mg).

(Step 3) The obtained benzyl 3-[6-(5-chloro-2-methoxybenzyl)-1-ethyl-6-fluoro-11,11-dimethyl-3,5,9-trioxo-10-oxa-2,4,8-triazadodec-1-yl]benzoate was used instead of the starting material compound of Reference Example 149, that is, the compound S148, for the similar procedure as in Reference Example 149, Reference Example 150, and Example 173 to obtain benzyl 3-[1-({[6-(5-chloro-2-methoxybenzyl)-6-fluoro-3,7-dioxo-1,4-diazepan-1-yl]carbonyl}amino)propyl]benzoate.

(Step 4) To the obtained benzyl 3-[1-({[6-(5-chloro-2-methoxybenzyl)-6-fluoro-3,7-dioxo-1,4-diazepan-1-yl]carbonyl}amino)propyl]benzoate (20 mg) in tetrahydrofuran (1 ml) solution, platinum oxide (6 mg) was added and the mixture was stirred under hydrogen atmosphere at room temperature for 1.5 hours. Next, the catalyst was filtered out. and the filtrate was concentrated. The residue was purified by silica gel column chromatography (chloroform/ethyl acetate/methanol/acetic acid=8/8/1/0.1) to obtain the title compound (9.3 mg).

NMR (DMSO-$d_6$): δ13.00-12.89 (1H, br), 9.26 (1H, d, J=7.2 Hz), 8.13-8.07 (1H, br), 7.90-7.79 (2H, m), 7.60-7.42 (2H, m), 7.36-7.17 (2H, m), 7.02 (0.5H, d, J=8.8 Hz), 6.87 (0.5H, d, J=8.8 Hz), 4.80-4.68 (1H, br), 4.56 (0.5H, d, J=15.7 Hz), 4.41 (0.5H, d, J=15.7 Hz), 4.18 (1H, d, J=15.7 Hz), 4.02-3.80 (1H, m), 3.74 (1.5H, s), 3.50 (1.5H, s), 3.40-2.82 (3H, m), 1.90-1.71 (2H, m), 0.89-0.75 (3H, m)

MS: 506 (M+H)$^+$

Example 177

6-benzyl-4-(4-chlorobenzenesulfonyl)-1,4-diazepan-2,5-dione (Compound 177)

N-(tert-butoxycarbonyl)-2-benzyl-β-alanine synthesized by using benzaldehyde as the starting material for the similar procedure as in Reference Examples 2 to 5, Reference Example 23, and Reference Example 33 was used instead of the starting material of Reference Example 148, that is, the compound S33, and 4-chlorobenzenesulfonamide was used instead of 4-nitrobenzenesulfonamide for the similar procedure as in Reference Example 148 to Reference Example 150 and Example 173 to obtain the title compound.

NMR (CDCl$_3$): δ7.96 (2H, d, J=8.6 Hz), 7.51 (2H, d, J=8.6 Hz), 7.32-7.21 (3H, m), 7.11 (2H, d, J=6.8 Hz), 5.87 (1H, br), 4.97 (1H, d, J=17.6 Hz), 4.42 (1H, d, J=17.6 Hz), 3.39-3.12 (4H, m), 2.55 (1H, dd, J=14.4, 8.9 Hz)

MS: 393 (M+H)$^+$

Reference Example 151 tert-butyl(2R)-3-amino-2-(5-chloro-2-methoxybenzyl)-3-oxopropylcarbamate (Compound S151)

(Step 1) To the methyl(2R)-3-amino-2-(5-chloro-2-methoxybenzyl)propanoate tosylate (97.9 g), synthesized from the compound S1 as an starting material in accordance with Japanese Patent Publication (A) No. 2004-300036, in tetrahydrofuran (180 ml)/2M sodium hydroxide (125 ml) solution, di-tert-butyl dicarbonate (55 g) was added under ice cooling and the mixture was stirred at room temperature for 1 hour. Ethyl acetate was added to the reaction solution, and the aqueous layer and the organic layer were separated. The organic layer was washed with saturated saline, dried over with anhydrous sodium sulfate, and concentrated to obtain methyl(2R)-3-[(tert-butoxycarbonyl)amino]-2-(5-chloro-2-methoxybenzyl) propanoate as a crude product (99.8 g).

(Step 2) To the crude product (99.8 g) of step 1 in methanol (180 ml) solution, an 85% potassium hydroxide (30 g) aqueous solution (90 ml) was added under ice cooling and the mixture was stirred at room temperature for 1.5 hours. 2N hydrochloric acid (260 ml) was added to the reaction solution, and the mixture was extracted with ethyl acetate. The organic layer was washed with saturated saline, dried over with anhydrous sodium sulfate, then concentrated. The residue was recrystallized from toluene/hexane to obtain (2R)-3-[(tert-butoxycarbonyl)amino]-2-(5-chloro-2-methoxybenzyl)propanoic acid (73.8 g).

(Step 3) To (2R)-3-[(tert-butoxycarbonyl)amino]-2-(5-chloro-2-methoxybenzyl)propanoic acid (15 g) in tetrahydrofuran (75 ml) solution, 1,1'-carbonyldiimidazole (7.8 g) was added under ice cooling and the mixture was stirred at room temperature for 1 hour. The reaction solution was cooled to 0° C., 28% ammonia water (15 ml) was added, and the mixture was stirred at room temperature for 30 minutes. To the reaction solution, distilled water, ethyl acetate, and tetrahydrofuran were added, the aqueous layer and the organic layer were separated, and the aqueous layer was extracted with ethyl acetate. The combined organic layer was successively washed with saturated potassium hydrogensulfate aqueous solution and saturated saline, dried over with anhydrous sodium sulfate, and concentrated until a small amount of ethyl acetate remained. Hexane was added to the concentrated solution, and the precipitated solid was collected by filtration to obtain the title compound (13.5 g).

NMR (DMSO-$d_6$): δ7.25-7.18 (2H, m), 7.13 (1H, d, J=2.7 Hz), 6.94 (1H, d, J=8.8 Hz), 6.81 (1H, brs), 6.71 (1H, br), 3.76 (3H, s), 3.14-3.02 (1H, m), 2.97-2.85 (1H, m), 2.73-2.52 (3H, m), 1.37 (9H, s)

Reference Example 152 tert-butyl(2S)-3-amino-2-(5-chloro-2-methoxybenzyl)-3-oxopropylcarbamate (Compound S152)

(Step 1) To the methyl (2S)-3-amino-2-(5-chloro-2-methoxybenzyl)propanoate tosylate (97.9 g), synthesized from the compound S1 as an starting material in accordance with Japanese Patent Publication (A) No. 2004-300036, in tetrahydrofuran (100 ml)/1M sodium hydroxide (100 ml) solution, di-tert-butyl dicarbonate (24 g) was added under ice cooling and the mixture was stirred at room temperature for 1 hour. Ethyl acetate was added to the reaction solution, and the aqueous layer and the organic layer were separated. The organic layer was washed with saturated saline, dried over with anhydrous sodium sulfate, and concentrated to obtain methyl(2R)-3-[(tert-butoxycarbonyl)amino]-2-(5-chloro-2-methoxybenzyl)propanoate as a crude product (42.9 g).

(Step 2) To the crude product (42.9 g) of step 1 in methanol (100 ml) solution, a 85% potassium hydroxide (13.3 g) aqueous solution (40 ml) was added under ice cooling and the mixture was stirred at room temperature for 1.5 hours. 2N hydrochloric acid (110 ml) was added to the reaction solution, and the mixture was extracted with ethyl acetate. The organic layer was washed with saturated saline, dried over with anhydrous sodium sulfate, then concentrated. The residue was recrystallized from toluene/hexane to obtain (2R)-3-[(tert-butoxycarbonyl)amino]-2-(5-chloro-2-methoxybenzyl)propanoic acid (30.9 g).

(Step 3) To (2S)-3-[(tert-butoxycarbonyl)amino]-2-(5-chloro-2-methoxybenzyl)propanoic acid (30 g) in tetrahydrofuran (150 ml) solution, 1,1'-carbonyldiimidazole (15.6 g) was added under ice cooling and the mixture was stirred at room temperature for 1 hour. The reaction solution was cooled to 0° C., 28% ammonia water (30 ml) was added, and the mixture was stirred at room temperature for 30 minutes. Distilled water and ethyl acetate were added to the reaction solution, the aqueous layer and the organic layer were separated, and the aqueous layer was extracted with ethyl acetate. The combined organic layer was successively washed with saturated potassium hydrogensulfate aqueous solution and saturated saline, dried over with anhydrous sodium sulfate, then concentrated. Hexane and ethyl acetate were added to the precipitated solid and the mixture was stirred in the suspended state at room temperature. The precipitated solid was collected by filtration to obtain the title compound (29.2 g).

NMR (DMSO-$d_6$): δ7.25-7.18 (2H, m), 7.13 (1H, d, J=2.7 Hz), 6.94 (1H, d, J=8.8 Hz), 6.81 (1H, brs), 6.71 (1H, br), 3.76 (3H, s), 3.14-3.02 (1H, m), 2.97-2.85 (1H, m), 2.73-2.52 (3H, m), 1.37 (9H, s)

Reference Example 153 tert-butyl 4-[(1R,6R)-6-(5-chloro-2-methoxybenzyl)-1-ethyl-11,11-dimethyl-3,5,9-trioxo-10-oxa-2,4,8-triazadodec-1-yl]-2-nitrobenzoate (Compound S153)

To the compound S151 (0.88 g) in N,N-dimethylformamide (30 ml) solution, sodium hydride (60% mineral oil dispersion) (102 mg) was added under ice cooling and the mixture was stirred at room temperature for 15 minutes. Next, the compound S1.16 (0.94 g) in tetrahydrofuran (10 ml) solution was added to the reaction solution under ice cooling and the mixture was stirred at that temperature for 1 hour. Saturated potassium hydrogensulfate aqueous solution was added under ice cooling to the reaction solution, and the mixture was extracted with ethyl acetate. The organic layer was washed with saturated saline, dried over with anhydrous sodium sulfate, then concentrated. The residue was purified by silica gel column chromatography (hexane/ethyl acetate, ethyl acetate: 20 to 50%) to obtain the title compound (0.72 g).

NMR (CDCl$_3$): δ8.75 (1H, d, J=7.1 Hz), 8.02 (1H, s), 7.73-7.69 (2H, m), 7.52 (1H, dd, J=7.9, 1.6 Hz), 7.17 (1H, dd, J=8.8, 2.5 Hz), 7.1 (1H, d, J=2.5 Hz), 6.77 (1H, d, J=8.8 Hz), 5.00-4.89 (1H, m), 4.81 (1H, q, J=7.1 Hz), 3.81 (3H, s), 3.40-3.30 (2H, m), 2.91-2.69 (3H, m), 1.90-1.82 (2H, m), 1.57 (9H, s), 1.43 (9H, s), 0.96 (3H, t, J=7.3 Hz)

Reference Example 154 tert-butyl 4-[(1R,6S)-6-(5-chloro-2-methoxybenzyl)-1-ethyl-11,11-dimethyl-3,5,9-trioxo-10-oxa-2,4,8-triazadodec-1-yl]-2-nitrobenzoate (Compound S154)

To the compound S152 (1.08 g) in N,N-dimethylformamide (7 ml) solution, potassium tert-butoxide (350 mg) was added under ice cooling and the mixture was stirred at that temperature for 10 minutes. Next, the compound S116 (1.04 g) in tetrahydrofuran (2.5 ml) solution was added to the reaction solution under ice cooling and the mixture was stirred at that temperature for 30 minutes. Saturated potassium hydrogensulfate aqueous solution and distilled water were added under ice cooling to the reaction solution and the mixture was extracted with a mixed solvent of hexane/ethyl acetate=1/1. The organic layer was successively washed with distilled water and saturated saline, dried over with anhydrous sodium sulfate, then concentrated. The residue was purified by silica gel column chromatography (hexane/ethyl acetate, 3/2 to 1/1) to obtain the title compound (1.56 g).

NMR (CDCl$_3$): δ8.78 (1H, d, J=7.1 Hz), 8.31 (1H, s), 7.73 (1H, d, J=1.5 Hz), 7.67 (1H, d, J=7.9 Hz), 7.56 (1H, dd, J=7.9, 1.5 Hz), 7.18 (1H, dd, J=8.8, 2.5 Hz), 7.11 (1H, d, J=2.5 Hz), 6.78 (1H, d, J=8.8 Hz), 4.9 (1H, br), 4.82 (1H, q, J=7.1 Hz), 3.84 (3H, s), 3.38-3.27 (2H, m), 3.90-2.69 (3H, m), 1.91-1.80 (2H, m), 1.54 (9H, s), 1.38 (9H, s), 0.96 (3H, t, J=7.3 Hz)

Reference Example 155 tert-butyl 3-[(1R)-1-isocyanatepropyl]benzoate (Compound S155)

To the compound S83 (1 g) in methylene chloride (15 ml)/2M sodium hydroxide aqueous solution (15 ml) solution, trichloromethyl chloroformate (0.31 ml) was added under ice cooling and the mixture was stirred at that temperature for 20 minutes. The reaction solution was extracted with methylene chloride. The extract was washed with saturated saline, dried over with anhydrous sodium sulfate, and concentrated to obtain the title compound as a crude product (653 mg).

NMR (CDCl$_3$): δ7.94-7.88 (2H, m), 7.49-7.44 (1H, m), 7.41 (1H, t, J=7.7 Hz), 4.6 (1H, t, J=6.6 Hz), 1.93-1.84 (2H, m), 1.61 (9H, s), 0.99 (3H, t, J=7.3 Hz)

Reference Example 156 tert-butyl 3-[(1R,6R)-6-(5-chloro-2-methoxybenzyl)-1-ethyl-11,11-dimethyl-3,5,9-trioxo-10-oxa-2,4,8-triazadodec-1-yl]benzoate (Compound S156)

To the compound S151 (775 mg) in N,N-dimethylformamide (4 ml) solution, potassium tert-butoxide (254 mg) was added under ice cooling and the mixture was stirred at that temperature for 15 minutes. Next, the compound S155 (653 mg) in tetrahydrofuran (1 ml) solution was added to the reaction solution under ice cooling and the mixture was stirred at that temperature for 30 minutes. Under ice cooling, saturated potassium hydrogensulfate aqueous solution was added to the reaction solution, and the mixture was extracted with ethyl acetate. The organic layer was successively washed with distilled water and saturated saline, dried over with anhydrous sodium sulfate, and concentrated to obtain the title compound as a crude product (1.45 g).

NMR (CDCl$_3$): δ8.7 (1H, d, J=7.9 Hz), 7.99 (1H, s), 7.9 (1H, s), 7.87 (1H, dd, J=7.3, 1.4 Hz), 7.45-7.36 (2H, m), 7.15 (1H, dd, J=8.7, 2.4 Hz), 7.09 (1H, d, J=2.4 Hz), 6.74 (1H, d, J=8.7 Hz), 4.96 (1H, br), 4.82 (1H, q, J=7.3 Hz), 3.76 (3H, s), 3.39-3.26 (2H, m), 2.93-2.82 (1H, m), 2.80-2.64 (2H, m), 1.94-1.80 (2H, m), 1.59 (9H, s), 1.43 (9H, s), 0.92 (3H, t, J=7.5 Hz)

Reference Example 157 tert-butyl 4-{(1R)-1-[({[(2R)-3-amino-2-(5-chloro-2-methoxybenzyl)propanoyl]amino}carbonyl)amino]propyl}-2-nitrobenzoate Hydrochloride (Compound S157)

A mixed solution of the compound S153 (58.7 mg) and 1N hydrogen chloride/ethyl acetate solution (0.45 ml) was stirred at room temperature for 5 hours. Further, 1N hydrogen chloride/ethyl acetate solution (0.45 ml) was added to the reaction solution and the mixture was stirred at room temperature for 3 hours. Next, the reaction solution was concentrated, and the residue was washed with ethyl acetate, tetrahydrofuran, and hexane to obtain the title compound (42 mg).

Reference Example 158 tert-butyl 4-{(1R)-1-[({[(2R)-3-[(bromoacetyl)amino]-2-(5-chloro-2-methoxybenzyl)propanoyl]amino}carbonyl)amino]propyl}-2-nitrobenzoate (Compound S158)

To the compound S157 (0.37 g) in methylene chloride (10 ml)/1N sodium hydroxide aqueous solution (3 ml) solution, bromoacetyl chloride (126 μM) was added under ice cooling and the mixture was stirred at that temperature for 4.5 hours. Distilled water was added to the reaction solution, and the mixture was extracted with ethyl acetate. The organic layer was successively washed with 1N hydrochloric acid and saturated saline, dried over with anhydrous sodium sulfate, and concentrated to obtain the title compound (403 mg).

NMR (CDCl$_3$): δ9.1 (1H, s), 8.81 (1H, d, J=7.2 Hz), 7.71-7.65 (2H, m), 7.51 (1H, dd, J=8.0, 1.6 Hz), 7.17 (1H, dd,

J=8.8, 2.6 Hz), 7.09 (1H, d, J=2.6 Hz), 6.94 (1H, br), 6.76 (1H, d, J=8.8 Hz), 4.83 (1H, q, J=7.2 Hz), 3.85 (2H, s), 3.76 (3H, s), 3.47 (2H, t, J=6.0 Hz), 2.95-2.84 (2H, m), 2.83-2.75 (1H, m), 1.94-1.80 (2H, m), 1.54 (9H, s), 0.96 (3H, t, J=7.3 Hz)

Reference Example 159 tert-butyl 4-{(1R)-1-[({[(2S)-3-[(bromoacetyl)amino]-2-(5-chloro-2-methoxybenzyl)propanoyl]amino}carbonyl)amino]propyl}-2-nitrobenzoate (Compound S159)

To the compound S154 (1.9 g) in ethyl acetate (11 ml) solution, a 4N hydrogen chloride/ethyl acetate solution (3.7 ml) was added under ice cooling and the mixture was stirred at room temperature for 6 hours. Next, 4M sodium hydroxide aqueous solution (7.4 ml) and bromoacetyl chloride (0.25 ml) were added to the reaction solution under ice cooling and the mixture was stirred at that temperature for 30 minutes. The reaction solution was separated into an aqueous layer and organic layer, and the aqueous layer was extracted with ethyl acetate. The combined organic layer was successively washed with 1N hydrochloric acid and saturated saline, dried over with anhydrous sodium sulfate, then concentrated. The residue was purified by silica gel column chromatography (hexane/ethyl acetate, 1/1 to 1/2) to obtain the title compound (1.04 g).
NMR (CDCl$_3$): δ8.78 (1H, d, J=7.0 Hz), 7.72 (1H, d, J=1.5 Hz), 7.66 (1H, d, J=7.8 Hz), 7.54 (1H, dd, J=7.8, 1.5 Hz), 7.2 (1H, dd, J=8.8, 2.6 Hz), 7.14 (1H, d, J=2.6 Hz), 6.87 (1H, t, J=5.8 Hz), 6.8 (1H, d, J=8.8 Hz), 4.82 (1H, q, J=7.0 Hz), 3.85 (3H, s), 3.8 (2H, s), 3.44 (2H, t, J=5.8 Hz), 2.92-2.77 (3H, m), 1.91-1.81 (2H, m), 1.54 (9H, s), 0.97 (3H, t, J=7.4 Hz)

Reference Example 160 tert-butyl 3-{(1R)-1-[({[(2R)-3-[(bromoacetyl)amino]-2-(5-chloro-2-methoxybenzyl)propanoyl]amino}carbonyl)amino]propyl}benzoate (Compound S160)

To the compound S156 (1.45 g) in ethyl acetate (9 ml) solution, 4N hydrogen chloride/ethyl acetate solution (3 ml) was added under ice cooling and the mixture was stirred at room temperature for 6 hours. Next, a 4M sodium hydroxide aqueous solution (5 ml) was added to the reaction solution under ice cooling, the aqueous layer and the organic layer were separated, and the aqueous layer was extracted with ethyl acetate. To the combined organic layer, saturated sodium hydrogencarbonate aqueous solution (3 ml) was added, then, under ice cooling, bromoacetyl chloride (0.19 ml) was added and the mixture was stirred at that temperature for 20 minutes. The reaction solution was separated into an aqueous layer and organic layer, then the organic layer was successively washed with saturated sodium hydrogencarbonate aqueous solution, distilled water, and saturated saline, dried over with anhydrous sodium sulfate, then concentrated. The residue was purified by silica gel column chromatography (hexane/ethyl acetate, 1/2 to 1/3) to obtain the title compound (960 mg).
NMR (CDCl$_3$): δ8.68 (1H, d, J=7.7 Hz), 8.37 (1H, s), 7.93-7.90 (1H, m), 7.87 (1H, dt, J=7.7, 1.5 Hz), 7.43 (1H, dt, J=7.7, 1.5 Hz), 7.38 (1H, t, J=7.7 Hz), 7.17 (1H, dd, J=8.7, 2.6 Hz), 7.1 (1H, d, J=2.6 Hz), 6.96 (1H, br), 6.75 (1H, d, J=8.7 Hz), 4.83 (1H, q, J=7.7 Hz), 3.85 (2H, s), 3.76 (3H, s), 3.54-3.48 (2H, m), 2.91 (1H, dd, J=13.4, 5.8 Hz), 2.85-2.77 (1H, m), 2.71 (1H, dd, J=13.4, 6.9 Hz), 1.92-1.83 (2H, m), 1.59 (9H, s), 0.93 (3H, t, J=7.3 Hz)

Reference Example 161 tert-butyl 4-[(1R)-1-({[(6R)-6-(5-chloro-2-methoxybenzyl)-3,7-dioxo-1,4-diazepan-1-yl]carbonyl}amino)propyl]-2-nitrobenzoate (Compound S161)

To the compound S158 (200 mg) in N,N-dimethylformamide (10 ml) solution, tripotassium phosphate (63 mg) was added under ice cooling and the mixture was stirred at 50° C. for 8 hours. Saturated potassium hydrogensulfate aqueous solution was added to the reaction solution and the mixture was extracted with a hexane/ethyl acetate=1/1 mixed solvent. The organic layer was washed with saturated saline, dried over with anhydrous sodium sulfate, then concentrated. The residue was purified by silica gel column chromatography (hexane/ethyl acetate=1/1 to 1/2) to obtain the title compound (91.8 mg).
NMR (CDCl$_3$): δ9.57 (1H, d, J=6.8 Hz), 7.72 (1H, d, J=1.5 Hz), 7.69 (1H, d, J=7.9 Hz), 7.55 (1H, dd, J=7.9, 1.5 Hz), 7.22 (1H, dd, J=8.8, 2.6 Hz), 7.13 (1H, d, J=2.6 Hz), 6.81 (1H, d, J=8.8 Hz), 5.9 (1H, br), 5.27 (1H, d, J=17.3 Hz), 4.82 (1H, q, J=6.8 Hz), 4.11 (1H, d, J=17.3 Hz), 3.83 (3H, s), 3.79-3.67 (1H, m), 3.39-3.30 (2H, m), 3.2 (1H, dd, J=13.9, 5.1 Hz), 2.62 (1H, dd, J=13.9, 8.4 Hz), 1.95-1.80 (2H, m), 1.55 (9H, s), 0.97 (3H, t, J=7.3 Hz)

Reference Example 162 tert-butyl 4-[(1R)-1-({[(6S)-6-(5-chloro-2-methoxybenzyl)-3,7-dioxo-1,4-diazepan-1-yl]carbonyl}amino)propyl]-2-nitrobenzoate (Compound S162)

To the compound S159 (10.4 g) in N,N-dimethylformamide (500 ml) solution, tripotassium phosphate (3.3 g) was added under ice cooling and the mixture was stirred at 60° C. for 5 hours. Saturated potassium hydrogensulfate aqueous solution and distilled water were added to the reaction solution, and the mixture was extracted with ethyl acetate. The organic layer was washed with saturated saline, dried over with anhydrous sodium sulfate, then concentrated. The residue was purified by silica gel column chromatography (hexane/ethyl acetate=1/2 to only ethyl acetate) to obtain the title compound (5.32 g).
NMR (CDCl$_3$): δ9.56 (1H, d, J=7.0 Hz), 7.73 (1H, d, J=1.5 Hz), 7.69 (1H, d, J=7.8 Hz), 7.56 (1H, dd, J=7.8, 1.5 Hz), 7.22 (1H, dd, J=8.8, 2.6 Hz), 7.14 (1H, d, J=2.6 Hz), 6.81 (1H, d, J=8.8 Hz), 5.88 (1H, br), 5.3 (1H, d, J=17.4 Hz), 4.84 (1H, q, J=7.0 Hz), 4.19-4.09 (1H, m), 3.84 (3H, s), 3.74-3.65 (1H, m), 3.38-3.30 (2H, m), 3.19 (1H, dd, J=14.0, 5.4 Hz), 2.63 (1H, dd, J=14.0, 8.2 Hz), 1.94-1.80 (2H, m), 1.55 (9H, s), 0.95 (3H, t, J=7.3 Hz)

Reference Example 163 tert-butyl 3-[(1R)-1-({[(6R)-6-(5-chloro-2-methoxybenzyl)-3,7-dioxo-1,4-diazepan-1-yl]carbonyl}amino)propyl]benzoate (Compound S163)

To the compound S160 (955 mg) in N-methyl-2-pyrrolidone (30 ml) solution, tripotassium phosphate (325 mg) was added under ice cooling and the mixture was stirred at 60° C. for 5 hours. Saturated potassium hydrogensulfate aqueous solution and distilled water were added to the reaction solution and the mixture was extracted with a hexane/ethyl acetate=1/1 mixed solvent. The organic layer was washed with saturated saline, dried over with anhydrous sodium sulfate, then concentrated. The residue was purified by silica gel column chromatography (hexane/ethyl acetate=1/2 to 1/3) to obtain the title compound (410 mg).

NMR (CDCl$_3$): δ9.53 (1H, d, J=7.4 Hz), 7.91 (1H, t, J=1.6 Hz), 7.87 (1H, dt, J=7.6, 1.6 Hz), 7.45 (1H, dt, J=7.6, 1.6 Hz), 7.37 (1H, t, J=7.6 Hz), 7.21 (1H, dd, J=8.8, 2.7 Hz), 7.11 (1H, d, J=2.7 Hz), 6.8 (1H, d, J=8.8 Hz), 5.83 (1H, br), 5.33 (1H, d, J=17.5 Hz), 4.81 (1H, q, J=7.4 Hz), 4.07 (1H, d, J=17.5 Hz), 3.82 (3H, s), 3.74-3.64 (1H, m), 3.37-3.29 (2H, m), 3.2 (1H, dd, J=14.0, 4.9 Hz), 2.6 (1H, dd, J=14.0, 8.7 Hz), 1.95-1.80 (2H, m), 1.59 (9H, s), 0.93 (3H, t, J=7.4 Hz)

Reference Example 164 tert-butyl 2-amino-4-[(1R)-1-({[(6R)-6-(5-chloro-2-methoxybenzyl)-3,7-dioxo-1,4-diazepan-1-yl]carbonyl}amino)propyl]benzoate (Compound S164)

To the compound S161 (22.1 mg) in acetic acid (1 ml) solution, zinc powder was added and the mixture was stirred at 50° C. for 3 hours. The insoluble compound was filtered out, and the filtrate was concentrated. Ethyl acetate was added to the residue, then the insoluble compound was filtered out. The filtrate was concentrated to obtain the title compound (19.7 mg).

NMR (CDCl$_3$): δ9.46 (1H, d, J=7.5 Hz), 7.77 (1H, d, J=8.3 Hz), 7.21 (1H, dd, J=8.3, 2.6 Hz), 7.13 (1H, d, J=2.6 Hz), 6.8 (1H, d, J=8.8 Hz), 6.74 (1H, br), 6.58-6.52 (2H, m), 5.36 (1H, d, J=17.4 Hz), 4.66 (1H, q, J=7.5 Hz), 4.08 (1H, d, J=17.4 Hz), 3.83 (3H, s), 3.74-3.63 (1H, m), 3.38-3.31 (2H, m), 3.17 (1H, dd, J=13.9, 5.3 Hz), 2.6 (1H, dd, J=13.9, 8.4 Hz), 1.90-1.74 (2H, m), 1.56 (9H, s), 0.91 (3H, t, J=7.4 Hz)

Reference Example 165 tert-butyl 2-amino-4-[(1R)-1-({[(6S)-6-(5-chloro-2-methoxybenzyl)-3,7-dioxo-1,4-diazepan-1-yl]carbonyl}amino)propyl]benzoate (Compound S165)

To the compound S162 (4.5 g) in acetic acid (225 ml) solution, zinc powder (22.5 g) was added and the mixture was stirred at 50° C. for 3 hours. The insoluble compound was filtered out, ethyl acetate and distilled water were added to the filtrate, and the organic layer and the aqueous layer were separated. The organic layer was washed with saturated saline, dried over with anhydrous sodium sulfate, and concentrated to obtain the title compound (4.4 g).

NMR (CDCl$_3$): δ9.43 (1H, d, J=7.8 Hz), 7.79 (1H, d, J=8.6 Hz), 7.21 (1H, dd, J=8.6, 2.6 Hz), 7.12 (1H, d, J=2.6 Hz), 6.8 (1H, d, J=8.8 Hz), 6.59-6.53 (2H, m), 5.88 (1H, br), 5.72 (2H, br), 5.37 (1H, d, J=17.5 Hz), 4.69 (1H, q, J=7.8 Hz), 4.18-4.08 (1H, m), 3.83 (3H, s), 3.74-3.62 (1H, m), 3.32-3.25 (2H, m), 3.18 (1H, dd, J=14.0, 5.3 Hz), 2.59 (1H, dd, J=14.0, 8.4 Hz), 1.90-1.74 (2H, m), 1.56 (9H, s), 0.89 (3H, t, J=7.5 Hz)

Example 178A 2-amino-4-[(1R)-1-({[(6R)-6-(5-chloro-2-methoxy-benzyl)-3,7-dioxo-1,4-diazepan-1-yl]carbonyl}amino)propyl]benzoic Acid (Compound 178A)

A mixed solution of the compound S164 (1.38 g) and 1N hydrochloric acid/acetic acid solution (27 ml) was stirred at room temperature for 2.5 hours. The reaction solution was concentrated, saturated ammonium chloride was added, and the mixture was extracted with ethyl acetate. The organic layer was washed with saturated saline, dried over with anhydrous sodium sulfate, then concentrated. The residue was diluted with ethyl acetate, then the precipitated crystal was collected by filtration to obtain the title compound (787 mg).

NMR (DMSO-d$_6$): δ9.42 (1H, d, J=7.5 Hz), 7.69 (1H, brd, J=3.9 Hz), 7.64 (1H, d, J=8.2 Hz), 7.33 (1H, d, J=2.7 Hz), 7.27 (1H, dd, J=8.2, 2.7 Hz), 7.01 (1H, d, J=8.9 Hz), 6.64 (1H, d, J=1.4 Hz), 6.44 (1H, dd, J=8.9, 1.4 Hz), 4.76 (1H, d, J=17.4 Hz), 4.59-4.48 (2H, m), 3.93-3.82 (1H, m), 3.79 (3H, s), 3.15 (1H, t, J=13.0 Hz), 3.04-2.94 (2H, m), 2.70-2.64 (1H, m), 1.80-1.67 (2H, m), 0.83 (3H, t, J=7.3 Hz)

MS: 503 (M+H)$^+$

Melting point: 137-139° C.

Example 178B 2-amino-4-[(1R)-1-({[(6R)-6-(5-chloro-2-methoxy-benzyl)-3,7-dioxo-1,4-diazepan-1-yl]carbonyl}amino)propyl]benzoic Acid 2-propanol Solvate (Compound 178B)

The compound 178A (500 mg) was heated and completely dissolved in 2-propanol-water (95:5) (2.5 ml), then the solution was allowed to cool to room temperature for recrystallization to obtain the title compound (370 mg).

NMR (DMSO-d$_6$): δ9.43 (1H, d, J=7.6 Hz), 7.7 (1H, d, J=3.6 Hz), 7.64 (1H, d, J=8.3 Hz), 7.34 (1H, d, J=2.7 Hz), 7.27 (1H, dd, J=8.3, 2.7 Hz), 7.01 (1H, d, J=8.9 Hz), 6.64 (1H, d, J=1.3 Hz), 6.43 (1H, dd, J=8.9, 1.3 Hz), 4.76 (1H, d, J=17.1 Hz), 4.59-4.48 (2H, m), 4.35 (1H, br), 3.93-3.82 (1H, m), 3.81-3.71 (1H, m), 3.79 (3H, s), 3.16 (1H, t, J=13.0 Hz), 3.07-2.95 (2H, m), 2.66 (1H, dd, J=14.3, 9.4 Hz), 1.83-1.65 (2H, m), 1.03 (6H, d, J=6.1 Hz), 0.83 (3H, t, J=7.2 Hz)

MS: 503 (M+H)$^+$

Melting point: 142-145° C.

Example 179A 2-amino-4-[(1R)-1-({[(6S)-6-(5-chloro-2-methoxy-benzyl)-3,7-dioxo-1,4-diazepan-1-yl]carbonyl}amino)propyl]benzoic Acid Hydrochloride (Compound 179A)

A mixed solution of the compound S165 (4.36 g) and an 1N hydrochloric acid/acetic acid solution (87 ml) was stirred at room temperature for 2 hours. Ethyl acetate was added to the reaction solution, and the precipitated crystal was collected by filtration to obtain the title compound (3.25 g).

NMR (DMSO-d$_6$): δ9.41 (1H, d, 7.7 Hz), 7.67 (1H, br), 7.66 (1H, d, 8.3 Hz), 7.33 (1H, d, 2.7 Hz), 7.27 (1H, dd, 8.8, 2.7 Hz), 7.01 (1H, d, 8.8 Hz), 6.65 (1H, s), 6.47 (1H, d, 8.3 Hz), 4.78 (1H, d, 17.3), 4.60-4.49 (2H, m), 3.93-3.84 (1H, m), 3.79 (3H, s), 3.13 (1H, t, 12.6 Hz), 3.05-2.93 (2H, m), 2.70-2.62 (1H, m), 1.79-1.67 (2H, m), 0.83 (3H, t, 7.3 Hz)

MS: 503 (M+H)$^+$

Example 179B 2-amino-4-[(1R)-1-({[(6S)-6-(5-chloro-2-methoxy-benzyl)-3,7-dioxo-1,4-diazepan-1-yl]carbonyl}amino)propyl]benzoic Acid (Compound 150)

To the compound 179A (750 mg), 2-propanol (7.5 ml) was added to obtain a suspension. This was stirred at 60° C. for 1 hour. The mixture was cooled to room temperature, the ice-cooled for 30 minutes. The precipitated solid was collected by filtration to obtain the title compound (674 mg).

NMR (DMSO-d$_6$): δ9.41 (1H, d, 7.7 Hz), 7.67 (1H, br), 7.66 (1H, d, 8.2 Hz), 7.33 (1H, d, 2.7 Hz), 7.27 (1H, dd, 8.8, 2.7 Hz), 7.01 (1H, d, 8.8 Hz), 6.64 (1H, d, 1.5 Hz), 6.45 (1H, dd, 8.2, 1.5 Hz), 4.79 (1H, d, 17.2 Hz), 4.59-4.49 (1H, m), 4.53 (1H, d, 17.2 Hz), 3.92-3.84 (1H, m), 3.79 (3H, s), 3.14 (1H, t, 12.8 Hz), 3.00 (1H, dd, 17.0, 12.8 Hz), 2.98 (1H, dd, 14.4, 4.6 Hz), 2.65 (1H, dd, 14.4, 9.2 Hz), 1.79-1.67 (2H, m), 0.83 (3H, t, 7.2 Hz)

MS: 503 (M+H)$^+$

Melting point: 139-140° C.

Example 179C 2-amino-4-[(1R)-1-({[(6S)-6-(5-chloro-2-methoxybenzyl)-3,7-dioxo-1,4-diazepan-1-yl]carbonyl}amino)propyl]benzoic Acid Monoacetic Acid Solvate (Compound 179B)

The compound 150 (121 mg) was dissolved in acetone (1.2 ml) and concentrated. The obtained amorphous was dissolved in acetic acid (2.4 ml). This solution was stirred under ice cooling for 3 hours, then the appeared precipitated crystal was collected by filtration to obtain the title compound (98 mg).

NMR (DMSO-d$_6$): δ9.41 (1H, d, J=7.7 Hz), 7.70-7.64 (2H, m), 7.33 (1H, d, J=2.7 Hz), 7.27 (1H, dd, J=8.8, 2.7 Hz), 7.01 (1H, d, J=8.7 Hz), 6.63 (1H, s), 6.44 (1H, d, J=8.7 Hz), 4.78 (1H, d, J=17.4 Hz), 4.61-4.51 (2H, m), 3.94-3.82 (1H, m), 3.79 (3H, s), 3.13 (1H, t, J=12.3 Hz), 3.05-2.95 (2H, m), 2.71-2.65 (1H, m), 1.9 (3H, s), 1.79-1.65 (2H, m), 0.83 (3H, t, J=7.2 Hz)

MS: 503 (M+H)$^+$

Melting point: 147-149° C.

Example 180A

3-[(1R)-1-({[(6R)-6-(5-chloro-2-methoxybenzyl)-3,7-dioxo-1,4-diazepan-1-yl]carbonyl}amino)propyl]benzoic Acid (Compound 91)

A mixed solution of the compound S163 (3.1 g) and 1N hydrochloric acid/acetic acid solution (20 ml) was stirred at room temperature for 2 hours. The reaction solution was concentrated, hexane/ethyl acetate/toluene was added to the residue, the mixture was stirred at room temperature, and the precipitated solid was collected by filtration to obtain the title compound (3.02 g).

NMR (DMSO-d$_6$): δ13.01 (1H, br), 9.48 (1H, d, J=7.3 Hz), 7.86 (1H, s), 7.82 (1H, d, J=7.7 Hz), 7.67 (1H, d, J=3.5 Hz), 7.55 (1H, d, J=7.7 Hz), 7.46 (1H, t, J=7.7 Hz), 7.33 (1H, d, J=2.6 Hz), 7.27 (1H, dd, J=8.8, 2.6 Hz), 7.00 (1H, d, J=8.8 Hz), 4.79-4.69 (2H, m), 4.49 (1H, d, J=17.2 Hz), 3.91-3.81 (1H, m), 3.79 (3H, s), 3.16 (1H, t, J=12.6 Hz), 3.05-2.96 (2H, m), 2.67 (1H, dd, J=14.3, 9.3 Hz), 1.89-1.74 (2H, m), 0.84 (3H, t, J=7.3 Hz)

MS: 488 (M+H)$^+$

Melting point: 121-123° C.

Example 180B

Sodium 3-[(1R)-1-({[(6R)-6-(5-chloro-2-methoxybenzyl)-3,7-dioxo-1,4-diazepan-1-yl]carbonyl}amino)propyl]benzoate (Compound 180)

To sodium 2-ethylhexanoate (340 mg) in acetone (10 ml) solution, the compound 91 (1 g) in acetone (15 ml) solution was added dropwise. The precipitated solid was collected by filtration and washed with ethyl acetate to obtain the title compound (437 mg).

NMR (DMSO-d$_6$): δ9.49 (1H, d, J=7.6 Hz), 7.76 (1H, s), 7.75-7.66 (2H, m), 7.33 (1H, d, J=2.7 Hz), 7.26 (1H, dd, J=8.7, 2.7 Hz), 7.25-7.15 (2H, m), 7 (1H, d, J=8.7 Hz), 4.77 (1H, d, J=17.2 Hz), 4.67 (1H, q, J=7.6 Hz), 4.48 (1H, d, J=17.2 Hz), 3.92-3.82 (1H, m), 3.78 (3H, s), 3.16 (1H, t, J=12.9 Hz), 3.05-2.94 (2H, m), 2.67 (1H, dd, J=14.3, 9.5 Hz), 1.88-1.70 (2H, m), 0.82 (3H, t, J=7.3 Hz)

MS: 488 (M+H)$^+$

Melting point: 161-163° C.

Reference Example 166 tert-butyl (2R)-2-{[(4-chlorophenyl)sulfonyl]amino}propanoate (Compound S166)

To D-alanine tert-butyl ester hydrochloride (1 g) in methylene chloride (35 ml) solution, triethylamine (1.7 ml) and 4-chlorobenzenesulfonyl chloride (1.1 g) were added under ice cooling and the mixture was stirred at room temperature for 2 hours. The methylene chloride was distilled off in vacuo, then the residue was diluted with ethyl acetate. The obtained solution was successively washed with distilled water, saturated potassium hydrogensulfate aqueous solution, and saturated saline, dried over with anhydrous sodium sulfate, then concentrated. The residue was recrystallized from ethyl acetate/hexane to obtain the title compound (1.47 g).

NMR (CDCl$_3$): δ7.78 (2H, d, J=8.6 Hz), 7.46 (2H, d, J=8.6 Hz), 5.25 (1H, brd, J=8.5 Hz), 3.90-3.81 (1H, m), 1.36 (3H, d, J=7.2 Hz), 1.30 (9H, s)

Instead of the starting material compound of Reference Example 166, that is, D-alanine tert-butyl ester hydrochloride, the amino acid derivatives shown in Table XI were used for the similar procedure as in Reference Example 166 to obtain the compounds of Reference Examples 167 to 171. Note that the amino acid derivatives shown in Table XI are commercially available compounds or compounds obtained by derivation from commercially available compounds by known methods.

TABLE XI

| Ref. Ex. no. | Amino acid derivative used as material |
|---|---|
| Ref. Ex. 167 | (structure) |
| Ref. Ex. 168 | (structure) |
| Ref. Ex. 169 | (structure) |

TABLE XI-continued

| Ref. Ex. no. | Amino acid derivative used as material |
|---|---|
| Ref. Ex. 170 | H₂N–CH(CH₂–COOBn)–C(=O)–O–C(CH₃)₃ |
| Ref. Ex. 171 | H₂N–CH(CH₂–O–CH₃)–C(=O)–O–C(CH₃)₃ |

Reference Example 167 tert-butyl (2S)-2-{[(4-chlorophenyl)sulfonyl]amino}propanoate (Compound S167)

NMR (CDCl$_3$): δ7.78 (2H, d, J=8.6 Hz), 7.46 (2H, d, J=8.6 Hz), 5.25 (1H, brd, J=8.5 Hz), 3.90-3.81 (1H, m), 1.36 (3H, d, J=7.2 Hz), 1.30 (9H, s)

Reference Example 168

5-benzyl 1-tert-butyl (2R)-2-{[(4-chlorophenyl)sulfonyl]amino}pentanedioate (Compound S168)

NMR (CDCl$_3$): δ7.75 (2H, d, J=8.7 Hz), 7.44 (2H, d, J=8.7 Hz), 7.43-7.31 (5H, m), 5.22 (1H, brd, J=9.2 Hz), 5.13 (2H, s), 3.88-3.80 (1H, m), 2.60-2.47 (2H, m), 2.19-2.09 (1H, m), 1.90-1.79 (1H, m), 1.56 (9H, s)

Reference Example 169 tert-butyl 1-{[(4-chlorophenyl)sulfonyl]amino}cyclopropanecarboxylate (Compound S169)

NMR (CDCl$_3$): δ7.82 (2H, d, J=8.6 Hz), 7.46 (2H, d, J=8.6 Hz), 5.52 (1H, s), 1.50-1.47 (2H, m), 1.37-1.32 (2H, m), 1.21 (9H, s)

Reference Example 170

4-benzyl 1-tert-butyl (2R)-2-{[(4-chlorophenyl)sulfonyl]amino}succinate (Compound S170)

Reference Example 171 tert-butyl 2-{[(4-chlorophenyl)sulfonyl]amino}3-methoxypropanoate (Compound S171)

Reference Example 172 tert-butyl (2R)-2-{[(4-chloro-2-nitrophenyl)sulfonyl]amino}butanoate (Compound S172)

Instead of the starting material compound of Reference Example 166, that is, L-alanine tert-butyl ester hydrochloride, D-2-amino-n-butyric acid tert-butyl ester hydrochloride was used, further, instead of 4-chlorobenzenesulfonyl chloride, 4-chloro-2-nitrobenzenesulfonyl chloride was used for the similar procedure as with Reference Example 167 to obtain the title compound.

NMR (CDCl$_3$): δ8.32 (1H, d, J=2.1 Hz), 7.97 (1H, dd, J=8.4, 2.1 Hz), 7.70 (1H, d, J=8.4 Hz), 5.28 (1H, brd, J=9.2 Hz), 3.85-3.78 (1H, m), 1.89-1.78 (1H, m), 1.75-1.65 (1H, m), 1.30 (9H, s), 0.95 (3H, t, J=7.5 Hz)

Example 181

Benzyl 3-{(2R,6E)-6-(5-chloro-2-methoxybenzylidene)-1-[(4-chlorophenyl)sulfonyl]-3,7-dioxo-1,4-diazepan-2-yl}propanoate (Compound 181)

To the compound S23 (760 mg) in tetrahydrofuran (8 ml) solution, triethylamine (0.31 ml) and 2,4,6-trichlorobenzoyl chloride (0.35 ml) were added and the mixture was stirred at room temperature for 30 minutes. The reaction solution was concentrated, then benzene (8 ml) was added to the residue. To the obtained solution, 4-dimethylaminopyridine (275 mg) and the compound S168 (800 mg) were added and the mixture was stirred under heating and reflux for 1 hour. The reaction solution was diluted with ethyl acetate and successively washed with saturated potassium hydrogensulfate aqueous solution and saturated saline. The organic layer was dried over with anhydrous sodium sulfate and concentrated. The residue was purified by silica gel column chromatography (hexane/chloroform/ethyl acetate=8/8/1 to 7/7/1). To the purified product, a 1M hydrogen chloride/acetic acid solution (5 ml) was added, the mixture was stirred at room temperature for 14 hours, then the reaction solution was concentrated. 1-(3-dimethylaminopropyl)-3-ethylcarbodiimide hydrochloride (180 mg) was added to the residue in methylene chloride (14 ml) solution, and the mixture was stirred at room temperature for 1 minute. Next, triethylamine (0.1 ml) was added to the reaction solution and the mixture was stirred at room temperature for 1 hour. The reaction solution was diluted with ethyl acetate, then was successively washed with distilled water, saturated potassium hydrogensulfate aqueous solution, and saturated saline. The organic layer was dried over with anhydrous sodium sulfate and concentrated. The residue was purified by silica gel column chromatography (hexane/ethyl acetate=1/1) to obtain the title compound (117 mg).

NMR (CDCl$_3$): δ8.10 (2H, d, J=8.6 Hz), 7.67 (1H, s), 7.51 (2H, d, J=8.6 Hz), 7.40-7.26 (6H, m), 7.16 (1H, d, J=2.4 Hz), 6.86 (1H, d, J=8.9 Hz), 6.10-6.03 (1H, br), 5.16-5.08 (1H, m), 5.10 (2H, s), 4.17-4.03 (2H, m), 3.80 (3H, s), 2.49-2.33 (2H, m), 2.30-2.20 (1H, m), 2.03-1.91 (1H, m)

MS: (M+H)$^+$

Example 182

(3R,6E)-6-(5-chloro-2-methoxybenzylidene)-4-[(4-chlorophenyl)sulfonyl]-3-methyl-1,4-diazepan-2,5-dione (Compound 182)

Instead of the starting material of Example 181, that is, the compound S168, the compound S166 was used for the similar procedure as in Example 181 to obtain the title compound.

NMR (CDCl$_3$): δ8.10 (2H, d, J=8.7 Hz), 7.74 (1H, s), 7.55 (2H, d, J=8.7 Hz), 7.34 (1H, dd, J=8.8, 2.5 Hz), 7.15 (1H, d, J=2.5 Hz), 6.86 (1H, d, J=8.8 Hz), 6.26 (1H, brd, J=6.4 Hz), 5.12 (1H, q, J=7.6 Hz), 4.22 (1H, d, J=14.3 Hz), 4.02 (1H, dd, J=14.3, 6.4 Hz), 3.82 (3H, s), 1.36 (3H, d, J=7.6 Hz)

MS: 469 (M+H)$^+$

Example 183

(3S,6E)-6-(5-chloro-2-methoxybenzylidene)-4-[(4-chlorophenyl)sulfonyl]-3-methyl-1,4-diazepan-2,5-dione (Compound 183)

Instead of the starting material of Example 181, that is, the compound S168, the compound S167 was used for the similar procedure as in Example 181 to obtain the title compound.
NMR (CDCl$_3$): δ8.12 (2H, d, J=8.8 Hz), 7.75 (1H, s), 7.57 (2H, d, J=8.8 Hz), 7.36 (1H, dd, J=8.8, 2.6 Hz), 7.16 (1H, d, J=2.6 Hz), 6.87 (1H, d, J=8.8 Hz), 6.24 (1H, brd, J=6.5 Hz), 5.13 (1H, q, J=7.6 Hz), 4.24 (1H, d, J=14.1 Hz), 4.03 (1H, dd, J=14.1, 6.5 Hz), 3.83 (3H, s), 1.38 (3H, d, J=7.6 Hz)
MS: 469 (M+H)$^+$

Example 184

(6E)-6-(5-chloro-2-methoxybenzylidene)-4-[(4-chlorophenyl)sulfonyl]-4,8-diaspiro[2.6]nonane-5,9-dione (Compound 184)

Instead of the starting material of Example 181, that is, the compound S168, the compound S169 was used for the similar procedure as in Example 181 to obtain the title compound.
NMR (CDCl$_3$): δ8.08 (2H, d, J=8.7 Hz), 7.533 (2H, d, J=8.7 Hz), 7.532 (1H, s), 7.33 (1H, dd, J=8.9, 2.5 Hz), 7.15 (1H, d, J=2.5 Hz), 6.86 (1H, d, J=8.9 Hz), 5.87 (1H, br), 4.20 (2H, d, J=3.1 Hz), 3.83 (3H, s), 2.05-1.35 (2H, m), 1.30-1.08 (2H, m)
MS: 481 (M+H)$^+$

Example 185

Benzyl [(2R,6E)-1-[(4-chlorophenyl)sulfonyl]-6-(5-fluoro-2-methoxybenzylidene)-3,7-dioxo-1,4-diazepan-2-yl]acetate (Compound 185)

The compound S177 was used instead of the starting material of Example 181, that is, the compound S23, and the compound S170 was used instead of the compound S168 for the similar procedure as in Example 181 to obtain the title compound.
NMR (CDCl$_3$): δ8.09 (2H, d, J=8.7 Hz), 7.67 (1H, s), 7.45 (2H, d, J=8.7 Hz), 7.40-7.32 (3H, m), 7.32-7.23 (2H, m), 7.12-7.04 (1H, m), 6.91-6.82 (2H, m), 6.22-6.17 (1H, br), 5.56 (1H, t, J=7.0 Hz), 5.01 (1H, d, J=14.2 Hz), 4.93 (1H, d, J=14.2 Hz), 4.21 (1H, d, J=14.5 Hz), 4.04 (1H, dd, J=13.6, 6.0 Hz), 3.79 (3H, s), 2.97 (1H, dd, J=15.8, 7.2 Hz), 2.68 (1H, dd, J=15.8, 7.0 Hz)
MS: (M+H)$^+$

Example 186

(3R,6E)-4-[(4-chloro-3-nitrophenyl)sulfonyl]-3-ethyl-6-(5-fluoro-2-methoxybenzylidene)-1,4-diazepan-2,5-dione (Compound 186)

Instead of the starting material of Example 185, that is, the compound S170, the compound S172 was used for the similar procedure as in Example 185 to obtain the title compound.
NMR (CDCl$_3$): δ8.65 (1H, d, J=2.1 Hz), 8.27 (1H, dd, J=8.5, 2.1 Hz), 7.77 (1H, d, J=8.5 Hz), 7.76 (1H, s), 7.15-7.09 (1H, m), 6.97-7.85 (2H, m), 6.58-6.50 (1H, br), 4.87 (1H, dd, J=9.9, 6.4 Hz), 4.21-4.07 (2H, m), 3.80 (3H, s), 2.13-2.00 (1H, m), 1.87-1.71 (1H, m), 0.89 (3H, t, J=6.6 Hz)
MS: (M+H)$^+$

Example 187

(6E)-6-(5-fluoro-2-methoxybenzylidene)-4-[(4-chlorophenyl)sulfonyl]-3-(methoxymethyl)-1,4-diazepan-2,5-dione (Compound 187)

Instead of the starting material of Example 181, that is, the compound S168, the compound S171 was used for the similar procedure as in Example 181 to obtain the title compound.
NMR (CDCl$_3$): δ8.13 (2H, d, J=8.7 Hz), 7.73 (1H, s), 7.54 (2H, d, J=8.7 Hz), 7.35 (1H, dd, J=8.8, 2.6 Hz), 7.14 (1H, d, J=2.6 Hz), 6.87 (1H, d, J=8.8 Hz), 6.43-6.36 (1H, br), 5.26-5.20 (1H, m), 4.27 (1H, dd, J=14.2, 1.2 Hz), 4.00 (1H, dd, J=14.2, 7.0 Hz), 3.83 (3H, s), 3.79 (1H, dd, J=10.1, 6.3 Hz), 3.39 (1H, dd, J=10.1, 3.8 Hz), 3.00 (3H, s)
MS: 499 (M+H)$^+$

Example 188

3-{(2R,6S)-6-(5-chloro-2-methoxybenzyl)-1-[(4-chlorophenyl)sulfonyl]-3,7-dioxo-1,4-diazepan-2-yl}propanoic Acid (Compound 188)

To a solution of the compound 181 (105 mg) in tetrahydrofuran (3 ml), 10% platinum carbon (sulfur poisoned catalyst) (100 mg) was added and the mixture was stirred under hydrogen atmosphere at room temperature for 18 hours. Next, the catalyst was filtered out, and the filtrate was concentrated. The residue was diluted with chloroform/hexane and the precipitate was collected by filtration to obtain the title compound (43 mg).
NMR (CDCl$_3$): δ7.95 (2H, d, J=8.6 Hz), 7.90 (1H, br), 7.50 (2H, d, J=8.6 Hz), 7.19 (1H, dd, J=8.8, 2.5 Hz), 7.08 (1H, d, J=2.5 Hz), 6.78 (1H, d, J=8.8 Hz), 5.03 (1H, dd, J=11.2, 6.2 Hz), 3.77 (3H, s), 3.67-3.57 (1H, m), 3.25-3.12 (2H, m), 2.98-2.88 (2H, m), 2.59-2.50 (2H, m), 2.30-2.12 (1H, m), 2.10-2.00 (1H, m)
MS: 529 (M+H)$^+$

Example 189

(2R,6S)-1-[(4-chlorophenyl)sulfonyl]-6-(5-fluoro-2-methoxybenzyl)-3,7-dioxo-1,4-diazepan-2-yl]acetic Acid (Compound 189)

Instead of the starting material of Example 188, that is, the compound 181, the compound 185 was used for the similar procedure as in Example 188 to obtain the title compound.
NMR (DMSO-d$_6$): δ12.36 (1H, br), 7.97 (2H, d, J=8.7 Hz), 7.82 (1H, br), 7.73 (2H, d, J=8.7 Hz), 7.25-6.95 (3H, m), 5.33-5.30 (1H, m), 3.87-3.75 (1H, m), 3.76 (3H, s), 3.22 (1H, dd, J=17.1, 8.0 Hz), 3.12-3.07 (2H, m), 2.98 (1H, dd, J=14.2, 4.6 Hz), 2.73 (1H, dd, J=17.1, 5.3 Hz), 2.60-2.50 (1H, m)
MS: 499 (M+H)$^+$

Example 190

(3R,6S)-4-[(3-amino-4-chlorophenyl)sulfonyl]-3-ethyl-6-(5-fluoro-2-methoxybenzyl)-1,4-diazepan-2,5-dione (Compound 190)

Instead of the starting material of Example 188, that is, the compound 181, the compound 186 was used for the similar procedure as in Example 188 to obtain the title compound.

NMR (CDCl$_3$): δ7.42 (1H, d, J=2.1 Hz), 7.37 (1H, d, J=8.4 Hz), 7.28 (1H, dd, J=8.4, 2.1 Hz), 6.95-6.90 (1H, m), 6.84 (1H, dd, J=8.7, 3.1 Hz), 6.79 (1H, dd, J=9.0, 4.4 Hz), 5.92 (1H, br), 4.98 (1H, t, J=7.6 Hz), 4.35 (2H, br), 3.80 (3H, s), 3.48 (1H, ddd, J=15.7, 10.9, 4.8 Hz), 3.25 (1H, dd, J=13.5, 4.7 Hz), 3.22-3.14 (1H, m), 3.12-3.02 (1H, m), 2.88 (1H, dd, J=13.5, 8.6 Hz), 2.01-1.90 (2H, m), 1.01 (3H, t, J=7.4 Hz)

MS: 484 (M+H)$^+$

Example 191 rel-(3R,6S)-6-(5-chloro-2-methoxybenzyl)-4-[(4-chlorophenyl)sulfonyl]-3-(methoxymethyl)-1,4-diazepan-2,5-dione (Compound 191)

Instead of the starting material of Example 188, that is, the compound 181, the compound 187 was used for the similar procedure as in Example 188 to obtain the title compound.

NMR (CDCl$_3$): δ8.08 (2H, d, J=8.7 Hz), 7.54 (2H, d, J=8.7 Hz), 7.19 (1H, dd, J=8.8, 2.6 Hz), 7.09 (1H, d, J=2.6 Hz), 6.79 (1H, d, J=8.8 Hz), 6.03 (1H, br), 5.12 (1H, t, J=3.7 Hz), 4.02 (1H, dd, J=9.7, 3.7 Hz), 3.83 (3H, s), 3.80-3.75 (1H, m), 3.72-3.68 (1H, m), 3.38-3.28 (1H, m), 3.22-3.17 (1H, m), 3.10 (3H, s), 3.02-2.92 (2H, m)

MS: 501 (M+H)$^+$

Example 192

4-[(4-chlorophenyl)sulfonyl]-6-(2-methoxybenzyl)-1,4-diazepan-2,5-dione (Compound 192)

To the compound 29 (40 mg) in acetic acid (2 ml) solution, 5% palladium carbon (60 mg) was added and the mixture was stirred under hydrogen atmosphere at room temperature for 22 hours. Next, the catalyst was filtered out, and the filtrate was concentrated. The residue was purified by preparative thin layer chromatography (diethylether) to obtain the title compound (9.1 mg).

NMR (CDCl$_3$): δ7.97 (2H, d, J=8.8 Hz), 7.51 (2H, d, J=8.8 Hz), 7.22 (1H, d, J=7.7 Hz), 7.03 (1H, d, J=7.2 Hz), 6.90-6.84 (2H, m), 5.67 (1H, br), 4.98 (1H, d, J=17.6 Hz), 4.40 (1H, d, J=17.6 Hz), 3.81 (3H, s), 3.54-3.42 (1H, m), 3.25-3.08 (3H, m), 2.56 (1H, dd, J=14.0, 9.1 Hz)

MS: 423 (M+H)$^+$

Example 193

(6E)-6-(2-hydroxy-5-methylbenzylidene)-4-[(4-chlorophenyl)sulfonyl]-1,4-diazepan-2,5-dione (Compound 193)

To (6E)-6-[2-(methoxymethoxy)-5-methylbenzylidene]-4-[(4-chlorophenyl)sulfonyl]-1,4-diazepan-2,5-dione (95 mg), synthesized by using, instead of the starting material of Reference Example 117, that is, the compound S6, the compound S11 for the similar procedure as in Reference Example 117, Reference Example 122, and Example 1, in methylene chloride (0.48 ml) solution, trifluoroacetic acid (0.48 ml) was added and the mixture was stirred at room temperature for 45 minutes. Next, the reaction solution was concentrated, and the residue was recrystallized from hexane/ethyl acetate to obtain the title compound (87 mg).

NMR (CDCl$_3$): δ8.01 (2H, d, J=8.7 Hz), 7.71 (1H, s), 7.5 (2H, d, J=8.7 Hz), 7.06 (1H, d, J=8.2 Hz), 6.86 (1H, s), 6.75 (1H, d, J=8.2 Hz), 6.01 (1H, br), 4.72 (2H, s), 4.21 (2H, d, J=4.7 Hz), 2.26 (3H, s)

MS: 421 (M+H)$^+$

Example 194

4-[(4-chlorophenyl)sulfonyl]-6-(4-hydroxybenzyl)-1,4-diazepan-2,5-dione (Compound 194)

4-[(4-chlorophenyl)sulfonyl]-6-[4-(methoxymethoxy)benzyl]-1,4-diazepan-2,5-dione, synthesized by using, instead of the starting material of Reference Example 124, that is, the compound S120, the compound S121 for the similar procedure as in Reference Example 124, Example 1, and Example 29, was used instead of the starting material compound of Example 193 that is, (6E)-6-[2-(methoxymethoxy)-5-methylbenzylidene]-4-[(4-chlorophenyl)sulfonyl]-1,4-diazepan-2,5-dione, for the similar procedure as in Example 193 to obtain the title compound.

NMR (DMSO-d$_6$): δ9.21 (1H, s), 7.93 (2H, d, J=8.6 Hz), 7.85 (1H, br), 7.73 (2H, d, J=8.6 Hz), 6.98 (2H, d, J=8.2 Hz), 6.64 (2H, d, J=8.2 Hz), 4.87 (1H, d, J=17.5 Hz), 4.52 (1H, d, J=17.5 Hz), 3.65-3.56 (1H, m), 3.07-2.98 (2H, m), 2.84 (1H, dd, J=14.2, 4.5 Hz), 2.37-2.27 (1H, m)

MS: 409 (M+H)$^+$

Example 195

(6E)-4-[(4-chlorophenyl)sulfonyl]-6-(5-hydroxy-2-methoxybenzylidene)-1,4-diazepan-2,5-dione (Compound 195)

(6E)-6-[2-methoxy-5-(methoxymethoxy)benzylidene]-4-[(4-chlorophenyl)sulfonyl]-1,4-diazepan-2,5-dione, synthesized by using, instead of the starting material of Reference Example 117, that is, the compound S6, the compound S22 for the similar procedure as in Reference Example 117, Reference Example 122, and Example 1, was used instead of the starting material compound of Example 193, that is, (6E)-6-[2-(methoxymethoxy)-5-methylbenzylidene]-4-[(4-chlorophenyl)sulfonyl]-1,4-diazepan-2,5-dione, for the similar procedure as in Example 193 to obtain the title compound.

NMR (CDCl$_3$): δ8.04 (2H, d, J=8.6 Hz), 7.79 (1H, s), 7.52 (2H, d, J=8.6 Hz), 7.08 (1H, br), 6.89 (1H, dd, J=8.9, 2.9 Hz), 6.80 (1H, d, J=8.9 Hz), 6.73 (1H, d, J=2.9 Hz), 4.61 (2H, s), 4.23 (2H, d, J=4.3 Hz), 3.76 (3H, s)

MS: 437 (M+H)$^+$

Example 196

([2-chloro-5-{[(6E)-6-(5-chloro-2-methoxybenzylidene)-3,7-dioxo-1,4-diazepan-1-yl]sulfonyl}benzoic Acid (Compound 196)

Instead of the starting material compound of Reference Example 117, that is, 4-chlorobenzenesulfonamide, the compound S56 was used for the similar procedure as in Reference Example 117, Reference Example 122, Example 1, and Example 251 to obtain the title compound.

NMR (DMSO-d$_6$): δ14.00 (1H, s), 8.28 (1H, d, J=4.3 Hz), 8.06 (1H, t, J=4.9 Hz), 8.03 (1H, dd, J=8.5, 2.4 Hz), 7.85 (1H, d, J=8.5 Hz), 7.54 (1H, s), 7.45 (1H, dd, J=8.9, 2.5 Hz), 7.26 (1H, d, J=2.5 Hz), 7.10 (1H, d, J=8.9 Hz), 4.71 (2H, s), 4.16 (2H, d, J=4.3 Hz), 3.79 (3H, s)

MS: 499 (M+H)$^+$

Example 197

2-chloro-5-{[6-(5-chloro-2-methoxybenzyl)-3,7-dioxo-1,4-diazepan-1-yl]sulfonyl}benzoic Acid (Compound 197)

Instead of the starting material compound of Reference Example 117, that is 4-chlorobenzenesulfonamide, the compound S56 was used for the similar procedure as in Reference Example 117, Reference Example 122, Example 1, Example 29, and Example 251 to obtain the title compound.

NMR (DMSO-$d_6$): δ13.99 (1H, brs), 8.28 (1H, d, J=2.3 Hz), 8.04 (1H, dd, J=8.5, 2.3 Hz), 7.88-7.83 (1H, m), 7.85 (1H, d, J=8.5 Hz), 7.28-7.21 (2H, m), 6.97 (1H, d, J=8.5 Hz), 4.88 (1H, d, J=17.5 Hz), 4.53 (1H, d, J=17.5 Hz), 3.75 (3H, s), 3.72-3.61 (1H, m), 3.03-2.99 (2H, m), 2.84 (1H, dd, J=14.3, 4.8 Hz), 2.57-2.50 (1H, m)

MS: 501 (M+H)$^+$

Reference Example 173

2-benzyl-3-[(benzyloxycarbonyl)amino]propanoic Acid (Compound S173)

To methyl (2E)-2-(azide methyl)-3-phenyl-2-propanoate (10 g), obtained by using, instead of the starting material compound of Reference Example 2, that is, the compound S1, benzaldehyde for the similar procedure as with Reference Example 2 to Reference Example 4, ethanol (200 ml), acetic acid (2.6 ml), and 10% palladium carbon (0.48 g) were added and the mixture was stirred under hydrogen atmosphere at room temperature for 3 hours. The reaction solution was filtered, then the concentrated filtrate was diluted with 2N hydrochloric acid and washed with ethyl acetate. The aqueous phase was basified by a 4N sodium hydroxide aqueous solution, then tetrahydrofuran (50 ml) and benzyl chloroformate (1.2 ml) were added at 0° C. and the mixture was stirred at 0° C. for 2 hours. The organic solvent in the reaction solution was distilled off, then the obtained aqueous mixture was extracted with ethyl acetate. The extract was successively washed with water and saturated saline, was dried over with sodium sulfate, then was concentrated. The obtained residue was purified by silica gel column chromatography (hexane-ethyl acetate=7:1) to obtain methyl 2-benzyl-3-[(benzyloxycarbonyl)amino]propanoate (7.9 g, including benzyl alcohol). Ethanol (60 ml) and 2N sodium hydroxide aqueous solution (15 ml) were added to this, then the mixture was stirred at room temperature for 2 hours. The organic solvent in the reaction solution was distilled off, water (20 ml) was added, the mixture was washed with ethyl acetate, then the obtained aqueous phase was acidified by a 10% potassium hydrogensulfate aqueous solution and extracted with diethylether. The extract was successively washed with water and saturated saline, dried over with anhydrous sodium sulfate, and concentrated to obtain the title compound.

Example 198

3-[(6-benzyl-3,7-dioxo-1,4-diazepan-1-yl)sulfonyl]benzoic Acid (Compound 198)

Instead of the starting material compound of Reference Example 117, that is, the compound S6, the compound S173 was used, and instead of 4-chlorobenzenesulfonamide, 3-(tert-butoxycarbonyl)benzenesulfonamide was used, for the similar procedure as with Reference Example 117 to obtain tert-butyl 3-{[(2-benzyl-3-benzyloxycarbonylamino)propanoyl]aminosulfonyl}benzoate (1.95 g). To this, ethanol (20 ml) and 20% palladium hydroxide on carbon (0.22 g) were added and the mixture was stirred under hydrogen atmosphere at room temperature for 17 hours. The reaction solution was filtered, and the filtrate was concentrated to obtain tert butyl 4-{[(3-amino-2-benzylpropanoyl)amino]sulfonyl}benzoate. This was used instead of the starting material of Reference Example 124, that is, the compound S120, for the similar procedure as with Reference Example 124, Example 1, and Example 251 to obtain the title compound.

NMR (DMSO-$d_6$): δ13.72-13.42 (1H, br), 8.42 (1H, s), 8.27 (1H, d, J=7.8 Hz), 8.15 (1H, d, J=7.8 Hz), 7.86 (1H, br), 7.79 (1H, t, J=7.8 Hz), 7.29-7.12 (5H, m), 4.92 (1H, d, J=17.4 Hz), 4.55 (1H, d, J=17.4 Hz), 3.79-3.69 (1H, m), 3.08-2.91 (3H, m), 2.50-2.41 (1H, m)

MS: 403 (M+H)$^+$

Example 199

2-amino-4-{[6-(5-chloro-2-methoxybenzyl)-3,7-dioxo-1,4-diazepan-1-yl]sulfonyl}benzoic Acid (Compound 199)

Instead of the starting material of Example 178, that is, the compound S164, the compound 50 was used for the similar procedure as in Example 178 to obtain the title compound.

NMR (DMSO-$d_6$): δ7.88-7.85 (1H, m), 7.86 (1H, d, 8.4 Hz), 7.41 (1H, d, 1.9 Hz), 7.29-7.24 (2H, m), 6.98 (1H, d, 9.6 Hz), 6.88 (1H, dd, 8.4, 1.9 Hz), 4.88 (1H, d, 17.5 Hz), 4.48 (1H, d, 17.5 Hz), 3.75 (3H, s), 3.72-3.64 (1H, m), 3.04-2.99 (2H, m), 2.85 (1H, dd, 14.5, 4.9 Hz), 2.56-2.50 (1H, m)

MS: 482 (M+H)$^+$

Example 200

4-[(3-amino-4-methylphenyl)sulfonyl]-6-(5-chloro-2-methoxybenzyl)-1,4-diazepan-2,5-dione Hydrochloride (Compound 200)

Instead of the starting material of Example 178, that is, the compound S164, the compound 52 was used for the similar procedure as in Example 178 to obtain the title compound.

NMR (DMSO-$d_6$): δ7.81 (1H, br), 7.29 (1H, s), 7.26-7.23 (2H, m), 7.19 (1H, d, 8.0 Hz), 7.03 (1H, d, 8.0 Hz), 6.97 (1H, d, 9.5 Hz), 4.83 (1H, d, 17.4 Hz), 4.48 (1H, d, 17.4 Hz), 3.75 (3H, s), 3.69-3.60 (1H, m), 3.00-2.96 (2H, m), 2.83 (1H, dd, 14.3, 4.6 Hz), 2.56-2.49 (1H, m), 2.15 (3H, s)

MS: 452 (M+H)$^+$

Example 201

4-{[6-(5-chloro-2-methoxybenzyl)-3,7-dioxo-1,4-diazepan-1-yl]sulfonyl}-2-hydroxybenzoic Acid (Compound 201)

Instead of the starting material compound of Reference Example 117, that is, 4-chlorobenzenesulfonamide, tert-butyl 4-aminosulfonyl-2-hydroxybenzoate was used for the similar procedure as in Reference Example 117, Reference Example 122, Example 1, Example 29, and Example 178 to obtain the title compound.

NMR (DMSO-$d_6$): δ7.96 (1H, d, 8.2 Hz), 7.87 (1H, br), 7.41-7.37 (2H, m), 7.28-7.21 (2H, m), 6.97 (1H, d, 8.5 Hz), 4.91 (1H, d, 17.5 Hz), 4.52 (1H, d, 17.5 Hz), 3.75 (3H, s), 3.72-3.63 (1H, m), 3.04-2.99 (2H, m), 2.84 (1H, dd, 14.3, 4.9 Hz), 2.56-2.48 (1H, m), 2.30 (3H, s), 2.11 (9H, s)

MS: 483 (M+H)$^+$

Example 202

4-[(4-amino-5-chloro-2-thienyl)sulfonyl]-6-(5-chloro-2-methoxybenzyl)-1,4-diazepan-2,5-dione (Compound 202)

Instead of the starting material compound of Reference Example 117, that is, 4-chlorobenzenesulfonamide, the compound S64 was used for the similar procedure as in Reference Example 117, Reference Example 122, Example 1, Example 29, and Example 178 to obtain the title compound.

NMR (CDCl$_3$): δ7.37 (1H, s), 7.20 (1H, dd, J=8.8, 2.6 Hz), 7.07 (1H, d, J=2.6 Hz), 6.79 (1H, d, J=8.8 Hz), 5.74 (1H, br), 4.89 (1H, d, J=17.8 Hz), 4.34 (1H, d, J=17.8 Hz), 3.82 (2H, s), 3.81 (3H, s), 3.51-3.41 (1H, m), 3.33-3.24 (2H, m), 3.19 (1H, dd, J=14.1, 4.7 Hz), 2.59 (1H, dd, J=14.1, 9.1 Hz)

MS: 478 (M+H)$^+$

Example 203

4-{[4-(2-aminoethyl)phenyl]sulfonyl}-6-(5-chloro-2-methoxybenzyl)-1,4-diazepan-2,5-dione Hydrochloride (Compound 203)

Instead of the starting material of Example 178, that is, the compound S164, the compound 62 was used for the similar procedure as in Example 178 to obtain the title compound.

NMR (DMSO-d$_6$): δ7.95 (3H, br), 7.88 (2H, d, 8.3 Hz), 7.84 (1H, br), 7.54 (2H, d, 8.3 Hz), 7.27-7.22 (2H, m), 6.97 (1H, d, 8.6 Hz), 4.87 (1H, d, 17.5 Hz), 4.55 (1H, d, 17.5 Hz), 3.74 (3H, s), 3.72-3.64 (1H, m), 3.13-3.06 (2H, m), 3.01-2.96 (4H, m), 2.82 (1H, d, 14.3, 4.8 Hz), 2.57-2.49 (1H, m)

MS: 466 (M+H)$^+$

Example 204

(6E)-6-(2-amino-5-chlorobenzylidene)-4-[(4-chlorophenyl)sulfonyl]-1,4-diazepan-2,5-dione (Compound 204)

To the compound 5 (77 mg) in 1,4-dioxane (1.5 ml) solution, acetic acid (0.77 ml) and iron reduced (46 mg) were added at room temperature and the mixture was stirred at 100° C. for 3 hours. Ethyl acetate and distilled water were added to the reaction solution and the mixture separated. The organic layer was dried by anhydrous sodium sulfate, then concentrated. The residue was purified by silica gel column chromatography (hexane/ethyl acetate=1/1), then the obtained purified product was recrystallized from hexane/ethyl acetate to obtain the title compound (41 mg).

NMR (CDCl$_3$): δ8.02 (2H, d, J=8.7 Hz), 7.59 (1H, s), 7.52 (2H, d, J=8.7 Hz), 7.13 (1H, dd, J=8.7, 2.2 Hz), 6.90 (1H, d, J=2.2 Hz), 6.65 (1H, d, J=8.7 Hz), 5.89 (1H, br), 4.74 (2H, s), 4.24 (2H, d, J=5.0 Hz), 3.77 (2H, brs)

MS: 440 (M+H)$^+$

Example 205

4-[(4-aminophenyl)sulfonyl]-6-(3-chlorobenzyl)-1,4-diazepan-2,5-dione (Compound 205)

To the compound 173 (14 mg) in methanol (1.4 ml) solution, platinum oxide (4.2 mg) was added and the mixture was stirred under hydrogen atmosphere at room temperature for 1 hour. The insoluble compound was filtered out, then the filtrate was concentrated. Hexane/ethyl acetate was added to the residue, then the precipitate was collected by filtration to obtain the title compound (9.4 mg).

NMR (DMSO-d$_6$): δ7.76 (1H, br), 7.51 (2H, d, J=8.7 Hz), 7.35 (1H, s), 7.31-7.17 (3H, m), 6.59 (2H, d, J=8.7 Hz), 6.25 (2H, brs), 4.82 (1H, d, J=17.5 Hz), 4.49 (1H, d, J=17.5 Hz), 3.79-3.69 (1H, m), 3.01-2.83 (3H, m), 2.57-2.42 (1H, m)

MS: 408 (M+H)$^+$

Example 206 tert-butyl [4-chloro-2-((E)-{1-[(4-chlorophenyl)sulfonyl]-3,7-dioxo-1,4-diazepan-6-ylidene}methyl)phenoxy]acetate (Compound 206)

To (6E)-6-(5-chloro-2-hydroxybenzylidene)-4-[(4-chlorophenyl)sulfonyl]-1,4-diazepan-2,5-dione (364 mg), synthesized from the compound S21 and 4-chlorobenzenesulfonamide by the similar procedure as with Reference Example 117, Reference Example 122, Example 1, and Example 193, in N,N-dimethylformamide (7.3 ml) solution, sodium hydrogencarbonate (89 mg), sodium iodide (12 mg), and tert-butyl bromoacetate (0.19 ml) were added and the mixture was stirred at room temperature for 17 hours. The reaction solution was diluted with ethyl acetate, then the obtained solution was successively washed with saturated ammonium chloride aqueous solution and saturated saline, dried over with anhydrous sodium sulfate, then concentrated. The residue was purified by silica gel column chromatography (hexane/ethyl acetate=1/1), then the obtained purified product was recrystallized from hexane/ethyl acetate to obtain the title compound (247 mg).

NMR (CDCl$_3$): δ8.03 (2H, d, J=8.7 Hz), 7.60 (1H, s), 7.51 (2H, d, J=8.7 Hz), 7.29-7.26 (1H, m), 7.09 (1H, d, J=2.4 Hz), 6.70 (1H, d, J=8.9 Hz), 6.18-6.12 (1H, br), 4.76 (2H, s), 4.50 (2H, s), 4.18 (2H, dd, J=4.8, 0.9 Hz), 1.59 (5H, s), 1.48 (4H, s)

MS: 499 (M-tBu)$^+$

Example 207 tert-butyl {6-benzyl-4-[(4-chlorophenyl)sulfonyl]-2,5-dioxo-1,4-diazepan-1-yl}acetate (Compound 207)

To the compound 177 (50 mg) in N,N-dimethylformamide (0.5 ml) solution, tert-butyl bromoacetate (0.04 ml) and sodium hydride (60% mineral oil dispersion) (12 mg) were added under ice cooling and the mixture was stirred at room temperature for 1 hour. Saturated ammonium chloride aqueous solution and distilled water were added to the reaction solution, then the mixture was extracted with ethyl acetate. The organic layer was successively washed with saturated saline, dried over with anhydrous sodium sulfate, then concentrated. The residue was purified by silica gel column chromatography (hexane/ethyl acetate=2/1), then the purified product was recrystallized from hexane/ethyl acetate to obtain the title compound (10 mg).

NMR (CDCl$_3$): δ7.97 (2H, d, J=8.6 Hz), 7.50 (2H, d, J=8.6 Hz), 7.33-7.20 (3H, m), 7.13 (2H, d, J=7.1 Hz), 4.99 (1H, d, J=17.6 Hz), 4.55 (1H, d, J=17.6 Hz), 3.86 (1H, d, J=17.1 Hz), 3.80 (1H, d, J=17.1 Hz), 3.53-3.43 (1H, m), 3.31 (1H, t, J=11.9 Hz), 3.27-3.16 (2H, m), 2.58 (1H, dd, J=14.4, 8.3 Hz), 1.39 (9H, s)

MS: 529 (M+Na)$^+$

Example 208

Methyl 2-chloro-5-{[(6E)-6-(5-chloro-2-methoxy-benzylidene)-3,7-dioxo-1,4-diazepan-1-yl]sulfonyl}benzoate (Compound 208)

To the compound 196 (40.6 mg) in ethyl acetate/methanol=3/1 (3 ml) solution, trimethylsilyldiazomethane (10% hexane solution) (0.5 ml) was added and the mixture was stirred at room temperature for 10 minutes. The reaction solution was concentrated, then residue was recrystallized from methylene chloride/hexane to obtain the title compound (15.4 mg).

NMR (CDCl$_3$): δ8.53 (1H, d, J=2.4 Hz), 8.10 (1H, dd, J=8.6, 2.4 Hz), 7.68 (1H, s), 7.63 (1H, d, J=8.6 Hz), 7.32 (1H, dd, J=8.9, 2.4 Hz), 7.05 (1H, d, J=2.4 Hz), 6.85 (1H, d, J=8.9 Hz), 5.97 (1H, br), 4.70 (2H, s), 4.215 (1H, d, J=4.6 Hz), 4.212 (1H, d, J=4.5 Hz), 3.97 (3H, s), 3.81 (3H, s)

MS: 513 (M+H)$^+$

Example 209

Methyl rel-(1R,6S)-3-[1-({[6-(5-chloro-2-methoxy-benzyl)-3,7-dioxo-1,4-diazepan-1-yl]carbonyl}amino)propyl]benzoate (Compound 209)

Instead of the starting material of Reference Example 142A, that is, the compound S83, the compound S87 was used for the similar procedure as with Reference Example 142A, Example 91, and Example 208 to obtain the title compound.

NMR (CDCl$_3$): δ9.49 (1H, d, J=7.5 Hz), 7.96 (1H, s), 7.92 (1H, d, J=7.7 Hz), 7.49 (1H, d, J=7.7 Hz), 7.40 (1H, t, J=7.7 Hz), 7.20 (1H, dd, J=8.7, 2.5 Hz), 7.11 (1H, d, J=2.5 Hz), 6.79 (1H, d, J=8.7 Hz), 5.75 (1H, br), 5.35 (1H, d, J=17.6 Hz), 4.82 (1H, q, J=7.5 Hz), 4.10 (1H, d, J=17.6 Hz), 3.91 (3H, s), 3.82 (3H, s), 3.72-3.61 (1H, m), 3.31-3.27 (2H, m), 3.18 (1H, dd, J=13.9, 5.1 Hz), 2.60 (1H, dd, J=13.9, 8.3 Hz), 1.94-1.79 (2H, m), 0.90 (3H, t, J=7.3 Hz)

MS: 502 (M+H)$^+$

Example 210

Methyl 3-[(6-benzyl-3,7-dioxo-1,4-diazepan-1-yl)sulfonyl]benzoate (Compound 210)

Instead of the starting material of Example 208, that is, the compound 196, the compound 198 was used for the similar procedure as in Example 208 to obtain the title compound.

NMR (DMSO-d$_6$): δ8.43 (1H, s), 8.29 (1H, d, J=8 Hz), 8.18 (1H, d, J=8.0 Hz), 7.85 (1H, br), 7.82 (1H, t, J=8.0 Hz), 7.30-7.14 (5H, m), 4.92 (1H, d, J=17.5 Hz), 4.56 (1H, d, J=17.5 Hz), 3.92 (3H, s), 3.78-3.67 (1H, m), 3.08-2.91 (3H, m), 2.44 (1H, dd, J=14.2, 9.0 Hz)

MS: 417 (M+H)$^+$

Example 211

Methyl 4-[(6-benzyl-3,7-dioxo-1,4-diazepan-1-yl)sulfonyl]benzoate (Compound 211)

4-[(6-benzyl-3,7-dioxo-1,4-diazepan-1-yl)sulfonyl]benzoic acid, synthesized by using 4-(tert-butoxycarbonyl)benzenesulfonamide instead of the starting material compound of Example 198, that is, 3-(tert-butoxycarbonyl)benzenesulfonamide for the similar procedure as in Example 198, was used instead of the starting material of Example 208, that is, the compound 196, for the similar procedure as with Example 208 to obtain the title compound.

NMR (DMSO-d$_6$): δ8.17 (2H, d, J=8.3 Hz), 8.06 (2H, d, J=8.3 Hz), 7.86 (1H, br), 7.29-7.17 (5H, m), 4.93 (1H, d, J=17.5 Hz), 4.55 (1H, d, J=17.5 Hz), 3.91 (3H, s), 3.79-3.68 (1H, m), 3.08-2.90 (3H, m), 2.5.4-2.39 (1H, m)

MS: 417 (M+H)$^+$

Example 212

Methyl 2-amino-4-{[6-(5-chloro-2-methoxybenzyl)-3,7-dioxo-1,4-diazepan-1-yl]sulfonyl}benzoate (Compound 212)

Instead of the starting material of Example 208, that is, the compound 196, the compound 199 was used for the similar procedure as in Example 208 to obtain the title compound.

NMR (DMSO-d$_6$): δ7.87 (1H, d, 8.6 Hz), 7.85 (1H, m), 7.45 (1H, d, 1.4 Hz), 7.26-7.23 (2H, m), 7.08 (2H, s), 6.97 (1H, d, 9.3 Hz), 6.86 (1H, dd, 8.6, 1.4 Hz), 4.88 (1H, d, 17.5 Hz), 4.48 (1H, d, 17.5 Hz), 3.83 (3H, s), 3.75 (3H, s), 3.72-3.63 (1H, m), 3.01-2.98 (2H, m), 2.84 (1H, dd, 14.3, 4.7 Hz), 2.55-2.49 (1H, m)

MS: 496 (M+H)$^+$

Example 213

Methyl 4-{[6-(5-chloro-2-methoxybenzyl)-3,7-dioxo-1,4-diazepan-1-yl]sulfonyl}-2-hydroxybenzoate (Compound 213)

Instead of the starting material of Example 208, that is, the compound 196, the compound 201 was used for the similar procedure as in Example 208 to obtain the title compound.

NMR (DMSO-d$_6$): δ10.88 (1H, brs), 7.90 (1H, d, 8.4 Hz), 7.86 (1H, br), 7.49 (1H, d, 1.7 Hz), 7.39 (1H, dd, 8.4, 1.7 Hz), 7.27-7.23 (2H, m), 6.97 (1H, d, 8.4 Hz), 4.90 (1H, d, 17.5 Hz), 4.51 (1H, d, 17.5 Hz), 3.88 (3H, s), 3.75 (3H, s), 3.74-3.64 (1H, m), 3.03-2.99 (2H, m), 2.84 (1H, dd, 14.2, 4.8 Hz), 2.57-2.49 (1H, m)

MS: 497 (M+H)$^+$

Example 214

Methyl [(2R,6S)-1-[(4-chlorophenyl)sulfonyl]-6-(5-fluoro-2-methoxybenzyl)-3,7-dioxo-1,4-diazepan-2-yl]acetate (Compound 214)

Instead of the starting material of Example 208, that is, the compound 196, the compound 189 was used for the similar procedure as in Example 208 to obtain the title compound.

NMR (CDCl$_3$): δ8.04 (2H, d, J=8.7 Hz), 7.52 (2H, d, J=8.7 Hz), 6.93 (1H, dt, J=8.7, 3.0 Hz), 6.87 (1H, dd, J=8.7, 3.0 Hz), 6.80 (1H, dd, J=8.7, 4 Hz), 5.79 (1H, br), 5.20 (1H, dd, J=7.9, 4.9 Hz), 3.81 (3H, s), 3.75-3.65 (1H, m), 3.60 (3H, s), 3.47-3.21 (4H, m), 2.87 (1H, dd, J=17.2, 4.9 Hz), 2.66 (1H, dd, J=14.0, 9.2 Hz)

MS: 513 (M+H)$^+$

Melting point: 73-76° C.

Example 215

Methyl 3-{(2R,6S)-6-(5-chloro-2-methoxybenzyl)-1-[(4-chlorophenyl)sulfonyl]-3,7-dioxo-1,4-diazepan-2-yl}propanoate (Compound 215)

Instead of the starting material of Example 208, that is, the compound 196, the compound 188 was used for the similar procedure as in Example 208 to obtain the title compound.
NMR (CDCl$_3$): δ7.99 (2H, d, J=8.6 Hz), 7.51 (2H, d, J=8.6 Hz), 7.19 (1H, dd, J=8.7, 2.4 Hz), 7.08 (1H, d, J=2.4 Hz), 6.79 (1H, d, J=8.7 Hz), 5.97 (1H, br), 5.14 (1H, t, J=7.8 Hz), 3.81 (3H, s), 3.69 (3H, s), 3.48 (1H, ddd, J=15.4, 11.3, 4.4 Hz), 3.32-3.19 (2H, m), 3.11 (1H, dt, J=15.4, 5.4 Hz), 2.82 (1H, dd, J=13.5, 8.6 Hz), 2.59-2.42 (2H, m), 2.39-2.28 (1H, m), 2.24-2.15 (1H, m)
MS: 543 (M+H)$^+$

Example 216

Methyl 4-({[6-(5-chloro-2-methoxybenzyl)-3,7-dioxo-1,4-diazepan-1-yl]carbonyl}amino)benzoate (Compound 216)

Instead of the starting material of Example 208, that is, the compound 196, the compound 168 was used for the similar procedure as in Example 208 to obtain the title compound.
NMR (CDCl$_3$): δ11.46 (1H, s), 8.02 (2H, d, J=8.7 Hz), 7.62 (2H, d, J=8.7 Hz), 7.23 (1H, dd, J=8.7, 2.5 Hz), 7.17 (1H, d, J=2.5 Hz), 6.83 (1H, d, J=8.7 Hz), 5.76 (1H, br), 5.46 (1H, d, J=17.5 Hz), 4.22 (1H, d, J=17.5 Hz), 3.91 (3H, s), 3.85 (3H, s), 3.84-3.76 (1H, m), 3.42-3.37 (2H, m), 3.23 (1H, dd, J=13.9, 5.4 Hz), 2.66 (1H, dd, J=13.9, 7.9 Hz)
MS: 460 (M+H)$^+$

Example 217

Methyl 3-({[6-(5-chloro-2-methoxybenzyl)-3,7-dioxo-1,4-diazepan-1-yl]carbonyl}amino)benzoate (Compound 217)

Instead of the starting material of Example 208, that is, the compound 196, the compound 169 was used for the similar procedure as in Example 208 to obtain the title compound.
NMR (CDCl$_3$): δ11.34 (1H, s), 8.12 (1H, s), 7.84 (1H, d, J=8.0 Hz), 7.80 (1H, d, J=8.0 Hz), 7.41 (1H, t, J=8.0 Hz), 7.23 (1H, dd, J=8.7, 2.6 Hz), 7.17 (1H, d, J=2.6 Hz), 6.82 (1H, d, J=8.7 Hz), 5.91 (1H, br), 5.46 (1H, d, J=17.5 Hz), 4.22 (1H, d, J=17.5 Hz), 3.92 (3H, s), 3.85 (3H, s), 3.84-3.36 (1H, m), 3.42-3.36 (2H, m), 3.23 (1H, dd, J=14.0, 5.5 Hz), 2.66 (1H, dd, J=14.0, 8.0 Hz)
MS: 460 (M+H)$^+$

Example 218

Methyl rel-(1R,6R)-3-[1-({[6-(5-chloro-2-methoxybenzyl)-3,7-dioxo-1,4-diazepan-1-yl]carbonyl}amino)propyl]benzoate (Compound 218)

Instead of the starting material of Reference Example 142A, that is, the compound S83, the compound S87 was used for the similar procedure as in Reference Example 142A, Example 91, and Example 208 to obtain the title compound.
NMR (CDCl$_3$): δ9.50 (1H, d, J=7.4 Hz), 7.95 (1H, s), 7.91 (1H, d, J=7.6 Hz), 7.47 (1H, d, J=7.6 Hz), 7.39 (1H, t, J=7.6 Hz), 7.20 (1H, dd, J=8.7, 2.6 Hz), 7.11 (1H, d, J=2.6 Hz), 6.79 (1H, d, J=8.7 Hz), 5.70 (1H, br), 5.32 (1H, d, J=17.3 Hz), 4.80 (1H, q, J=7.4 Hz), 4.06 (1H, d, J=17.3 Hz), 3.90 (3H, s), 3.82 (3H, s), 3.72-3.62 (1H, m), 3.34-3.29 (2H, m), 3.19 (1H, dd, J=13.9, 5.0 Hz), 2.60 (1H, dd, J=13.9, 8.6 Hz), 1.95-1.80 (2H, m), 0.92 (3H, t, J=7.3 Hz)
MS: 502 (M+H)$^+$

Example 219

Methyl rel-(1R,6R)-4-[1-({[6-(5-chloro-2-methoxybenzyl)-3,7-dioxo-1,4-diazepan-1-yl]carbonyl}amino)propyl]benzoate (Compound 219)

Instead of the starting material of Example 208, that is, the compound 196, the compound 113 was used for the similar procedure as in Example 208 to obtain the title compound.
NMR (CDCl$_3$): δ9.52 (1H, d, J=7.3 Hz), 7.99 (2H, d, J=8.2 Hz), 7.33 (2H, d, J=8.2 Hz), 7.20 (1H, dd, J=8.7, 2.5 Hz), 7.12 (1H, d, J=2.5 Hz), 6.79 (1H, d, J=8.7 Hz), 5.75 (1H, br), 5.33 (1H, d, J=17.5 Hz), 4.82 (1H, q, J=7.3 Hz), 4.06 (1H, d, J=17.5 Hz), 3.89 (3H, s), 3.81 (3H, s), 3.72-3.61 (1H, m), 3.35-3.30 (2H, m), 3.18 (1H, dd, J=13.9, 5.1 Hz), 2.61 (1H, dd, J=13.9, 8.4 Hz), 1.92-1.78 (2H, m), 0.91 (3H, t, J=7.4 Hz)
MS: 502 (M+H)$^+$

Example 220 tert-butyl {[2-({[6-(5-chloro-2-methoxybenzyl)-3,7-dioxo-1,4-diazepan-1-yl]carbonyl}amino)butanoyl]amino}acetate (Compound 220)

To the compound 119 (50 mg) in methylene chloride (3 ml) solution, glycine tert-butyl ester hydrochloride (41 mg), triethylamine (0.29 ml), and n-propyl phosphoric acid anhydride (25% ethyl acetate solution) (0.37 ml) were added and the mixture was stirred at room temperature for 3 hours. The reaction solution was concentrated, then ethyl acetate was added to the residue. The obtained solution was successively washed with distilled water, saturated potassium hydrogensulfate aqueous solution, saturated saline, saturated sodium hydrogencarbonate aqueous solution, and saturated saline, dried over with anhydrous sodium sulfate, then concentrated. The precipitate was washed with diethylether/hexane and collected by filtration to obtain the title compound (41.6 mg).
NMR (CDCl$_3$): δ9.44 (0.5H, d, 7.2 Hz), 9.40 (0.5H, d, 7.0 Hz), 7.23-7.20 (1H, m), 7.14 (0.5H, d, 2.6 Hz), 7.11 (0.5H, d, 2.5 Hz), 6.81 (1H, d, 8.7 Hz), 6.46 (1H, brd, 4.3 Hz), 5.76 (1H, brd, 4.3 Hz), 5.36 (0.5H, d, 17.6 Hz), 5.34 (0.5H, d, 17.6 Hz), 4.36-4.27 (1H, m), 4.14 (1H, d, 17.6 Hz), 3.98-3.92 (2H, m), 3.84 (1.5H, s), 3.83 (1.5H, s), 3.76-3.65 (1H, m), 3.37-3.29 (2H, m), 3.25-3.17 (1H, m), 2.67-2.57 (1H, m), 2.03-1.91 (1H, m), 1.85-1.75 (1H, m), 1.47 (9H, s), 1.05-0.98 (3H, m)
MS: 469 (M+H)$^+$

Example 221

6-(5-chloro-2-methoxybenzyl)-4-{[4-chloro-3-(4-morpholinylcarbonyl)phenyl]sulfonyl}-1,4-diazepan-2,5-dione (Compound 221)

Instead of the starting material of Example 220, that is, the compound 119, the compound 197 was used, while instead of the glycine tert-butyl ester hydrochloride, morpholine was used for the similar procedure as in Example 220 to obtain the title compound.
NMR (DMSO-d$_6$): δ8.00-7.94 (2H, m), 7.87-7.84 (2H, m), 7.26-7.19 (2H, m), 6.97 (1H, d, 8.9 Hz), 4.91-4.82 (1H, m), 4.57-4.52 (1H, m), 3.80-3.43 (7H, m), 3.75 (3H, s) 3.18-3.07 (2H, m), 3.04-2.98 (2H, m), 2.89-2.80 (1H, m), 2.59-2.50 (1H, m)
MS: 570 (M+H)+

Example 222

6-(5-chloro-2-methoxybenzyl)-4-{[4-chloro-3-(1-pyrrolidinylcarbonyl)phenyl]sulfonyl}-1,4-diazepan-2,5-dione (Compound 222)

Instead of the starting material of Example 220, that is, the compound 119, the compound 197 was used, while instead of the glycine tert-butyl ester hydrochloride, pyrrolidine was used for the similar procedure as in Example 220 to obtain the title compound.
NMR (DMSO-$d_6$): δ8.00-7.91 (2H, m), 7.89-7.80 (2H, m), 7.27-7.19 (2H, m), 6.97 (1H, d, 8.5 Hz), 4.87 (1H, d, 17.4 Hz), 4.54 (1H, d, 17.4 Hz), 3.75 (3H, s) 3.70-3.62 (1H, m), 3.52-3.47 (2H, m), 3.10-2.97 (4H, m), 2.87-2.78 (1H, m), 2.62-2.50 (1H, m), 1.94-1.79 (4H, m)
MS: 554 (M+H)+

Example 223 tert-butyl 4-(2-chloro-5-{[6-(5-chloro-2-methoxybenzyl)-3,7-dioxo-1,4-diazepan-1-yl]sulfonyl}benzoyl)-1-piperadine Carboxylate (Compound 223)

Instead of the starting material of Example 220, that is, the compound 119, the compound 197 was used, while instead of the glycine tert-butyl ester hydrochloride, N-(tert-butoxycarbonyl)piperadine was used for the similar procedure as in Example 220 to obtain the title compound.
NMR (DMSO-$d_6$): δ7.80-7.97 (1H, m), 7.98 (1H, d, 8.5 Hz), 7.87-7.84 (1H, m), 7.85 (1H, d, 8.5 Hz), 7.26-7.20 (2H, m), 6.97 (1H, d, 9.0 Hz), 4.87 (0.5H, d, 17.2 Hz), 4.85 (0.5H, d, 17.2 Hz), 4.53 (1H, d, 17.2 Hz), 3.75 (3H, s) 3.73-3.55 (3H, m), 3.50-3.39 (2H, m), 3.38-3.22 (2H, m), 3.15-3.05 (2H, m), 3.04-2.95 (2H, m), 2.89-2.79 (1H, m), 2.60-2.50 (1H, m)
MS: 613 (M+H)+

Example 224

2-chloro-5-{[6-(5-chloro-2-methoxybenzyl)-3,7-dioxo-1,4-diazepan-1-yl]sulfonyl}-N-(2-hydroxyethyl)benzamide (Compound 224)

Instead of the starting material of Example 220, that is, the compound 119, the compound 197 was used, while instead of the glycine tert-butyl ester hydrochloride, 2-hydroxyethylamine was used for the similar procedure as in Example 220 to obtain the title compound.
NMR (DMSO-$d_6$): δ8.64 (1H, t, 5.5 Hz), 7.98-7.92 (2H, m), 7.85 (1H, br), 7.79 (1H, d, 8.3 Hz), 7.29-7.24 (2H, m), 6.98 (1H, d, 9.5 Hz), 4.87 (1H, d, 17.5 Hz), 4.77 (1H, t, 5.5 Hz), 4.54 (1H, d, 17.5 Hz), 3.75 (3H, s) 3.70-3.63 (1H, m), 3.56-3.50 (2H, m), 3.43-3.30 (2H, m), 3.08-2.95 (2H, m), 2.85 (1H, dd, 14.3, 4.5 Hz), 2.59-2.49 (1H, m)
MS: 544 (M+H)+

Example 225

2-chloro-5-{[6-(5-chloro-2-methoxybenzyl)-3,7-dioxo-1,4-diazepan-1-yl]sulfonyl}-N-(3-pyridylmethyl)benzamide (Compound 225)

Instead of the starting material of Example 220, that is, the compound 119, the compound 197 was used, while instead of the glycine tert-butyl ester hydrochloride, 3-picolylamine was used for the similar procedure as in Example 220 to obtain the title compound.
NMR (DMSO-$d_6$): δ9.26 (1H, t, 5.9 Hz), 8.61 (1H, s), 8.51 (1H, d, 4.5 Hz), 8.01-7.98 (2H, m), 7.87-7.81 (3H, m), 7.44 (1H, dd, 7.8, 4.9 Hz), 7.29-7.24 (2H, m), 6.98 (1H, d, 9.5 Hz), 4.88 (1H, d, 17.7 Hz), 4.58-4.52 (3H, m), 3.75 (3H, s), 3.72-3.63 (1H, m), 3.13-2.95 (2H, m), 2.85 (1H, dd, 14.4, 4.6 Hz), 2.57-2.49 (1H, m)
MS: 591 (M+H)+

Example 226

2-chloro-5-{[6-(5-chloro-2-methoxybenzyl)-3,7-dioxo-1,4-diazepan-1-yl]sulfonyl}-N-methyl-N-phenylbenzamide (Compound 226)

Instead of the starting material of Example 220, that is, the compound 119, the compound 197 was used, while instead of the glycine tert-butyl ester hydrochloride, N-methylaniline was used for the similar procedure as in Example 220 to obtain the title compound.
NMR (DMSO-$d_6$): δ7.95 (1H, brs), 7.86 (1H, brs), 7.73 (1H, brd, 8.2 Hz), 7.57 (1H, brd, 8.2 Hz), 7.32-7.20 (6H, m), 7.15 (1H, brs), 7.00 (1H, brd, 9.1 Hz), 4.80 (1H, d, 17.3 Hz), 4.50 (1H, d, 17.3 Hz), 3.77 (3H, s), 3.72-3.62 (1H, m), 3.40 (3H, s), 3.07-2.94 (2H, m), 2.89-2.81 (1H, m), 2.70-2.50 (1H, m)
MS: 591 (M+H)+

Example 227

2-chloro-5-{[6-(5-chloro-2-methoxybenzyl)-3,7-dioxo-1,4-diazepan-1-yl]sulfonyl}-N-(2-methoxyethyl)benzamide (Compound 227)

Instead of the starting material of Example 220, that is, the compound 119, the compound 197 was used, while instead of the glycine tert-butyl ester hydrochloride, N-methoxyethylamine was used for the similar procedure as in Example 220 to obtain the title compound.
NMR (DMSO-$d_6$): δ8.74 (1H, t, 5.4 Hz), 7.96 (1H, dd, 8.4, 2.3 Hz), 7.88 (1H, d, 2.3 Hz), 7.85 (1H, br), 7.80 (1H, d, 8.4 Hz), 7.28-7.22 (2H, m), 6.98 (1H, d, 9.5 Hz), 4.87 (1H, d, 17.5 Hz), 4.54 (1H, d, 17.5 Hz), 3.75 (3H, s), 3.71-3.61 (1H, m), 3.50-3.35 (4H, m), 3.28 (3H, s), 3.09-2.94 (2H, m), 2.84 (1H, dd, 14.3, 5.4 Hz), 2.60-2.50 (1H, m)
MS: 558 (M+H)+

Example 228

2-chloro-5-{[6-(5-chloro-2-methoxybenzyl)-3,7-dioxo-1,4-diazepan-1-yl]sulfonyl}-N-(2-hydroxyethyl)-N-methylbenzamide (Compound 228)

Instead of the starting material of Example 220, that is, the compound 119, the compound 197 was used, while instead of the glycine tert-butyl ester hydrochloride, N-methyl-2-hydroxyethylamine was used for the similar procedure as in Example 220 to obtain the title compound.
NMR (DMSO-$d_6$): δ7.99-7.90 (2H, m), 7.89-7.80 (2H, m), 7.28-7.20 (2H, m), 6.97 (1H, dd, 8.5, 2.2 Hz), 4.93-4.72 (2H, m), 4.54 (0.5H, d, 17.5 Hz), 4.52 (0.5H, d, 17.5 Hz), 3.75 (3H, s), 3.74-3.60 (2H, m), 3.59-3.45 (1H, m), 3.43-3.28 (2H, m), 3.15-2.92 (2H, m), 3.04 (1.5H, s), 2.84 (1H, dd, 14.3, 4.5 Hz), 2.79 (1.5H, s), 2.61-2.46 (1H, m)
MS: 558 (M+H)+

Example 229

2-chloro-5-{[6-(5-chloro-2-methoxybenzyl)-3,7-dioxo-1,4-diazepan-1-yl]sulfonyl}-N-cyclopropylbenzamide (Compound 229)

Instead of the starting material of Example 220, that is, the compound 119, the compound 197 was used, while instead of the glycine tert-butyl ester hydrochloride, cyclopropylamine was used for the similar procedure as in Example 220 to obtain the title compound.

NMR (DMSO-$d_6$): δ8.69 (1H, d, 4.2 Hz), 7.96 (1H, dd, 8.6, 2.3 Hz), 7.89 (1H, d, 2.3 Hz), 7.86 (1H, br), 7.79 (1H, d, 8.6 Hz), 7.29-7.25 (2H, m), 6.98 (1H, d, 9.5 Hz), 4.87 (1H, d, 17.6 Hz), 4.55 (1H, d, 17.6 Hz), 3.75 (3H, s), 3.72-3.62 (1H, m), 3.09-2.96 (2H, m), 2.90-2.81 (2H, m), 2.60-2.50 (1H, m), 0.75-0.70 (1H, m), 0.59-0.54 (1H, m)

MS: 540 (M+H)$^+$

Example 230

2-chloro-5-{[6-(5-chloro-2-methoxybenzyl)-3,7-dioxo-1,4-diazepan-1-yl]sulfonyl}-N-phenylbenzamide (Compound 230)

Instead of the starting material of Example 220, that is, the compound 119, the compound 197 was used, while instead of the glycine tert-butyl ester hydrochloride, aniline was used for the similar procedure as in Example 220 to obtain the title compound.

NMR (DMSO-$d_6$): δ10.68 (1H, s), 8.10 (1H, d, 2.3 Hz), 8.04 (1H, dd, 8.5, 2.3 Hz), 7.91-7.87 (1H, m), 7.88 (1H, d, 8.5 Hz), 7.70 (2H, d, 7.7 Hz), 7.37 (2H, t, 7.7 Hz), 7.29-7.21 (2H, m), 7.14 (1H, t, 7.7 Hz), 6.98 (1H, d, 9.5 Hz), 4.88 (1H, d, 17.5 Hz), 4.57 (1H, d, 17.5 Hz), 3.75 (3H, s), 3.73-3.62 (1H, m), 3.09-2.95 (2H, m), 2.86 (1H, dd, 14.5, 4.8 Hz), 2.60-2.50 (1H, m)

MS: 576 (M+H)$^+$

Example 231

2-chloro-5-{[6-(5-chloro-2-methoxybenzyl)-3,7-dioxo-1,4-diazepan-1-yl]sulfonyl}-N-cyclohexylbenzamide (Compound 231)

Instead of the starting material of Example 220, that is, the compound 119, the compound 197 was used, while instead of the glycine tert-butyl ester hydrochloride, cyclohexylamine was used for the similar procedure as in Example 220 to obtain the title compound.

NMR (DMSO-$d_6$): δ8.53 (1H, d, 7.8 Hz), 7.95 (1H, dd, 8.5, 2.2 Hz), 7.89-7.81 (2H, m), 7.79 (1H, d, 8.5 Hz), 7.29-7.22 (2H, m), 6.98 (1H, d, 9.5 Hz), 4.88 (1H, d, 17.4 Hz), 4.54 (1H, d, 17.4 Hz), 3.80-3.65 (2H, m), 3.75 (3H, s), 3.08-2.95 (2H, m), 2.84 (1H, dd, 14.3, 4.6 Hz), 2.60-2.50 (1H, m), 1.90-1.80 (2H, m), 1.79-1.69 (2H, m), 1.60-1.55 (2H, m), 1.38-1.10 (1H, m)

MS: 582 (M+H)$^+$

Example 232

2-chloro-5-{[6-(5-chloro-2-methoxybenzyl)-3,7-dioxo-1,4-diazepan-1-yl]sulfonyl}-N-(2-pyridyl)benzamide (Compound 232)

Instead of the starting material of Example 220, that is, the compound 119, the compound 197 was used, while instead of the glycine tert-butyl ester hydrochloride, 2-aminopyridine was used for the similar procedure as in Example 220 to obtain the title compound.

NMR (DMSO-$d_6$): δ11.24 (1H, s), 8.40-8.36 (0.6H, m), 8.25-8.15 (0.6H, m), 8.10 (1H, s), 7.90-7.84 (3H, m), 7.82-7.70 (0.4H, m), 7.68-7.60 (0.4H, m), 7.29-7.18 (3H, m), 7.00-6.95 (1H, m), 4.87 (0.4H, d, 17.4 Hz), 4.86 (0.6H, d, 17.5 Hz), 4.59-4.49 (1H, m), 3.75 (3H, s), 3.72-3.61 (1H, m), 3.10-2.95 (2H, m), 2.90-2.80 (1H, m), 2.60-2.50 (1H, m)

MS: 577 (M+H)$^+$

Example 233

2-chloro-5-{[6-(5-chloro-2-methoxybenzyl)-3,7-dioxo-1,4-diazepan-1-yl]sulfonyl}-N-(2-pyridylmethyl)benzamide (Compound 233)

Instead of the starting material of Example 220, that is, the compound 119, the compound 197 was used, while instead of the glycine tert-butyl ester hydrochloride, 2-picolylamine was used for the similar procedure as in Example 220 to obtain the title compound.

NMR (DMSO-$d_6$): δ9.28 (1H, t, 5.9 Hz), 8.53 (1H, d, 4.6 Hz), 8.02-7.98 (2H, m), 7.89-7.79 (3H, m), 7.44 (1H, d, 7.8 Hz), 7.30 (1H, dd, 7.4, 4.6 Hz), 7.28-7.24 (2H, m), 6.98 (1H, d, 9.5 Hz), 4.88 (1H, d, 17.5 Hz), 4.59-4.53 (3H, m), 3.75 (3H, s), 3.72-3.64 (1H, m), 3.09-2.94 (2H, m), 2.85 (1H, dd, 14.2, 4.6 Hz), 2.59-2.49 (1H, m)

MS: 591 (M+H)$^+$

Example 234

N-(benzyloxo)-2-chloro-5-{[6-(5-chloro-2-methoxybenzyl)-3,7-dioxo-1,4-diazepan-1-yl]sulfonyl}benzamide (Compound 234)

Instead of the starting material of Example 220, that is, the compound 119, the compound 197 was used, while instead of the glycine tert-butyl ester hydrochloride, O-benzylhydroxylamine hydrochloride was used for the similar procedure as in Example 220 to obtain the title compound.

NMR (DMSO-$d_6$): δ11.82 (1H, s), 8.00 (1H, d, 8.4, 2.0 Hz), 7.92 (1H, d, 2.0 Hz), 7.87 (1H, br), 7.82 (1H, d, 8.4 Hz), 7.47 (2H, d 6.9 Hz), 7.45-7.38 (3H, m), 7.29-7.24 (2H, m), 6.98 (1H, d, 9.5 Hz), 4.97 (2H, s), 4.86 (1H, d, 17.6 Hz), 4.54 (1H, d, 17.6 Hz), 3.75 (3H, s), 3.70-3.64 (1H, m), 3.10-2.95 (2H, m), 2.85 (1H, dd, 14.2, 4.4 Hz), 2.60-2.50 (1H, m)

MS: 606 (M+H)$^+$

Example 235

N-[(1R)-2-anilino-1-methyl-2-oxoethyl]-6-(5-chloro-2-methoxybenzyl)-3,7-dioxo-1,4-diazepan-1-carboxamide (Compound 235)

Instead of the starting material of Example 220, that is, the compound 119, the compound 100 was used, while instead of the glycine tert-butyl ester hydrochloride, aniline was used for the similar procedure as in Example 220 to obtain the title compound.

NMR (CDCl$_3$): δ9.50 (0.5H, d, 6.8 Hz), 9.42 (0.5H, d, 6.9 Hz), 8.32 (0.5H, s), 8.23 (0.5H, s), 7.56-7.52 (2H, m), 7.34-7.29 (2H, m), 7.24-7.20 (1H, m), 7.15-7.10 (2H, m), 6.81 (0.5H, d, 8.7 Hz), 6.80 (0.5H, d, 8.8 Hz), 5.71 (0.5H, br), 5.69 (0.5H, br), 5.40 (0.5H, d, 17.5 Hz), 5.36 (0.5H, d, 17.5 Hz), 4.59-4.49 (1H, m), 4.17 (1H, d, 17.5 Hz), 3.84 (1.5H, s), 3.83

(1.5H, s), 3.75-3.65 (1H, m), 3.39-3.30 (2H, m), 3.25-3.19 (1H, m), 2.67-2.59 (1H, m), 1.537 (1.5H, d, 7.1 Hz), 1.530 (1.5H, d, 7.0 Hz)

MS: 473 (M+H)$^+$

Example 236

N-[(1R)-1-(anilinocarbonyl)propyl]-6-(5-chloro-2-methoxybenzyl)-3,7-dioxo-1,4-diazepan-1-carboxamide (Compound 236)

Instead of the starting material compound of Example 220, that is, glycine tert-butyl ester hydrochloride, aniline was used for the similar procedure as in Example 220 to obtain the title compound.

NMR (CDCl$_3$): δ9.51 (0.5H, d, 7.3 Hz), 9.43 (0.5H, d, 6.9 Hz), 8.20 (0.5H, s), 8.15 (0.5H, s), 7.53 (2H, d, 8.0 Hz), 7.34-7.29 (2H, m), 7.21 (1H, dd, 8.7, 2.6 Hz), 7.15-7.00 (2H, m), 6.81 (0.5H, d, 8.7 Hz), 6.80 (0.5H, d, 8.7 Hz), 5.85-5.78 (1H, m), 5.36 (0.5H, d, 17.4 Hz), 5.33 (0.5H, d, 17.4 Hz), 4.41-4.33 (1H, m), 4.16 (0.5H, d, 17.4 Hz), 4.15 (0.5H, d, 17.4 Hz), 3.84 (1.5H, s), 3.83 (1.5H, s), 3.77-3.65 (1H, m), 3.37-3.30 (2H, m), 3.25-3.16 (1H, m), 2.65-2.55 (1H, m), 2.10-1.99 (1H, m), 1.91-1.79 (1H, m), 1.10-1.00 (3H, m)

MS: 487 (M+H)$^+$

Example 237

6-(5-chloro-2-methoxybenzyl)-N-{(1R)-1-[(methylamino)carbonyl]propyl}-3,7-dioxo-1,4-diazepan-1-carboxamide (Compound 237)

Instead of the starting material compound of Example 220, that is, glycine tert-butyl ester hydrochloride, a methylamine 30% ethanol solution was used for the similar procedure as in Example 220 to obtain the title compound.

NMR (CDCl$_3$): δ9.40 (0.5H, d, 7.2 Hz), 9.35 (0.5H, d, 7.2 Hz), 7.24-7.20 (1H, m), 7.14 (0.5H, d, 2.6 Hz), 7.11 (0.5H, d, 2.5 Hz), 6.81 (1H, d, 8.8 Hz), 6.06 (1H, br), 5.77 (1H, br), 5.35 (0.5H, d, 17.7 Hz), 5.32 (0.5H, d, 17.7 Hz), 4.28-4.18 (1H, m), 4.14 (1H, d, 17.7 Hz), 3.83 (3H, s), 3.76-3.67 (1H, m), 3.38-3.30 (2H, m), 3.25-3.18 (1H, m), 2.83 (1.5H, s), 2.82 (1.5H, s), 2.66-2.57 (1H, m), 2.00-1.90 (1H, m), 1.83-1.73 (1H, m), 1.03-0.94 (3H, m)

MS: 425 (M+H)$^+$

Example 238

6-(5-chloro-2-methoxybenzyl)-N-{(1R)-1-[(methylanilino)carbonyl]propyl}-3,7-dioxo-1,4-diazepan-1-carboxamide (Compound 238)

Instead of the starting material compound of Example 220, that is, glycine tert-butyl ester hydrochloride, N-methylaniline was used for the similar procedure as in Example 220 to obtain the title compound.

NMR (CDCl$_3$): δ9.54 (0.5H, d, 7.7 Hz), 9.41 (0.5H, d, 7.1 Hz), 7.49-7.11 (7H, m), 6.81 (0.5H, d, 8.7 Hz), 6.80 (0.5H, d, 8.7 Hz), 5.72-5.66 (1H, m), 5.36 (0.5H, d, 17.4 Hz), 5.32 (0.5H, d, 17.4 Hz), 4.58-4.49 (0.5H, m), 4.48-4.00 (0.5H, m), 4.10 (1H, d, 17.4 Hz), 3.84 (1.5H, s), 3.82 (1.5H, s), 3.74-3.62 (1H, m), 3.42-3.13 (3H, m), 3.30 (1.5H, s), 3.29 (1.5H, s), 2.72-2.53 (1H, m), 2.05-1.81 (1H, m), 1.77-1.60 (1H, m), 0.85-0.74 (3H, m)

MS: 501 (M+H)$^+$

Example 239

6-(5-chloro-2-methoxybenzyl)-3,7-dioxo-N-{(1R)-1-[(1H-tetrazol-5-ylamino)carbonyl]propyl}-1,4-diazepan-1-carboxamide (Compound 239)

Instead of the starting material compound of Example 220, that is, glycine tert-butyl ester hydrochloride, 5-amino-1H-tetrazole was used for the similar procedure as in Example 220 to obtain the title compound.

NMR (DMSO-d$_6$): δ15.90 (1H, brs), 12.10 (1H, brs), 9.52-9.47 (1H, m), 7.67 (1H, br), 7.31 (1H, s), 7.249 (0.5H, d, 8.8 Hz), 7.243 (0.5H, d, 8.8 Hz), 6.98 (1H, d, 8.8 Hz), 4.75 (1H, d, 17.2 Hz), 4.56-4.46 (1H, m), 4.52 (1H, d, 17.2 Hz), 3.94-3.84 (1H, m), 3.77 (3H, s), 3.18-2.90 (3H, m), 2.68-2.58 (1H, m), 1.89-1.63 (2H, m), 0.90-0.75 (3H, m)

MS: 479 (M+H)$^+$

Melting point: 141-142° C.

Example 240

6-(5-chloro-2-methoxybenzyl)-3,7-dioxo-N-{(1R)-1-[(2-pyridylamino)carbonyl]propyl}-1,4-diazepan-1-carboxamide (Compound 240)

Instead of the starting material compound of Example 220, that is, glycine tert-butyl ester hydrochloride, 2-aminopyridine was used for the similar procedure as in Example 220 to obtain the title compound.

NMR (CDCl$_3$): δ9.59 (0.5H, d, 6.7 Hz), 9.54 (0.5H, d, 6.6 Hz), 8.49 (1H, s), 8.29-8.26 (1H, m), 8.23 (1H, d, 8.6 Hz), 7.71 (0.5H, d, 7.1 Hz), 7.69 (0.5H, d, 7.1 Hz), 7.24-7.19 (1H, m), 7.15 (0.5H, d, 2.5 Hz), 7.12 (0.5H, d, 2.6 Hz), 7.07-7.03 (1H, m), 6.82 (0.5H, d, 8.7 Hz), 6.81 (0.5H, d, 8.7 Hz), 5.84-5.77 (1H, m), 5.40 (0.5H, d, 17.1 Hz), 5.39 (0.5H, d, 17.1 Hz), 4.49-4.40 (1H, m), 4.16 (1H, d, 17.1 Hz), 3.85 (1.5H, s), 3.84 (1.5H, s), 3.75-3.65 (1H, m), 3.40-3.29 (2H, m), 3.28-3.19 (1H, m), 2.70-2.58 (1H, m), 2.11-2.00 (1H, m), 1.97-1.81 (1H, m), 1.10-1.02 (3H, m)

MS: 488 (M+H)$^+$

Example 241

N-{(1R)-1-[(tert-butoxyamino)carbonyl]propyl}-6-(5-chloro-2-methoxybenzyl)-3,7-dioxo-1,4-diazepan-1-carboxamide (Compound 241)

Instead of the starting material compound of Example 220, that is, glycine tert-butyl ester hydrochloride, O-(tert-butyl)hydroxylaminehydrochloride was used for the similar procedure as in Example 220 to obtain the title compound.

NMR (CDCl$_3$): δ9.34 (0.5H, d, 7.4 Hz), 9.28 (0.5H, d, 7.4 Hz), 8.42 (1H, s), 7.19 (1H, dd, 8.8, 2.5 Hz), 7.12 (0.5H, d, 2.5 Hz), 7.09 (0.5H, d, 2.5 Hz), 6.794 (0.5H, d, 8.8 Hz), 6.790 (0.5H, d, 8.8 Hz), 5.69 (1H, br), 5.31 (0.5H, d, 17.6 Hz), 5.28 (0.5H, d, 17.6 Hz), 4.15-4.01 (1H, m), 4.12 (1H, d, 17.6 Hz), 3.82 (1.5H, s), 3.81 (1.5H, s), 3.74-3.62 (1H, m), 3.55-3.25 (2H, m), 3.23-3.12 (1H, m), 2.63-2.53 (1H, m), 2.02-1.91 (1H, m), 1.83-1.72 (1H, m), 1.25 (9H, s), 1.01-0.95 (3H, m)

MS: 483 (M+H)$^+$

Example 242

6-(5-chloro-2-methoxybenzyl)-3,7-dioxo-N-{(1R)-1-[(3-pyridylamino)carbonyl]propyl}-1,4-diazepan-1-carboxamide (Compound 242)

Instead of the starting material compound of Example 220, that is, glycine tert-butyl ester hydrochloride, 3-aminopyridine was used for the similar procedure as in Example 220 to obtain the title compound.

NMR (CDCl$_3$): δ9.51 (0.5H, d, 7.2 Hz), 9.42 (0.5H, d, 6.8 Hz), 8.63-8.58 (2H, m), 8.31 (0.5H, s), 8.30 (0.5H, s), 8.15-8.10 (1H, m), 7.24-7.18 (2H, m), 7.13 (0.5H, d, 2.6 Hz), 7.10 (0.5H, d, 2.6 Hz), 6.795 (0.5H, d, 8.8 Hz), 6.791 (0.5H, d, 8.7 Hz), 5.88 (1H, br), 5.32 (0.5H, d, 17.5 Hz), 5.29 (0.5H, d, 17.5 Hz), 4.44-4.32 (1H, m), 4.17 (1H, d, 17.5 Hz), 3.82 (1.5H, s), 3.81 (1.5H, s), 3.75-3.65 (1H, m), 3.35-3.26 (2H, m), 3.22-3.15 (1H, m), 2.65-2.55 (1H, m), 2.10-1.98 (1H, m), 1.90-1.77 (1H, m), 1.08-0.99 (3H, m)

MS: 488 (M+H)$^+$

Example 243

6-(5-chloro-2-methoxybenzyl)-3,7-dioxo-N-{(1R)-1-[(4-pyridylamino)carbonyl]propyl}-1,4-diazepan-1-carboxamide (Compound 243)

Instead of the starting material compound of Example 220, that is, glycine tert-butyl ester hydrochloride, 4-aminopyridine was used for the similar procedure as in Example 220 to obtain the title compound.

NMR (CDCl$_3$): δ9.50 (0.5H, d, 7.1 Hz), 9.41 (0.5H, d6.8 Hz), 8.79 (0.5H, s), 8.76 (0.5H, s), 8.46 (2H, d, 6.0 Hz), 7.48 (1H, d, 6.0 Hz), 7.47 (1H, d, 6.0 Hz), 7.20 (1H, dd, 8.7, 2.5 Hz), 7.13 (0.5H, d, 2.5 Hz), 7.11 (0.5H, d, 2.5 Hz), 6.797 (0.5H, d, 8.7 Hz), 6.792 (0.5H, d, 8.7 Hz), 5.85 (1H, brd, 8.4 Hz), 5.32 (0.5H, d, 17.4 Hz), 5.29 (0.5H, d, 17.4 Hz), 4.39-4.30 (1H, m), 4.17 (1H, d, 17.4 Hz), 3.82 (1.5H, s), 3.81 (1.5H, s), 3.80-3.65 (1H, m), 3.35-3.30 (2H, m), 3.22-3.12 (1H, m), 2.66-2.56 (1H, m), 2.09-1.98 (1H, m), 1.89-1.79 (1H, m), 1.08-1.00 (3H, m)

MS: 488 (M+H)$^+$

Example 244

N-((1R)-1-{[3-(aminosulfonyl)anilino]carbonyl}propyl)-6-(5-chloro-2-methoxybenzyl)-3,7-dioxo-1,4-diazepan-1-carboxamide (Compound 244)

Instead of the starting material compound of Example 220, that is, glycine tert-butyl ester hydrochloride, 3-aminobenzenesulfonamide was used for the similar procedure as in Example 220 to obtain the title compound.

NMR (DMSO-d$_6$): δ10.47 (0.5H, s), 10.45 (0.5H, s), 9.48 (0.5H, d, 7.2 Hz), 9.44 (0.5H, d, 7.3 Hz), 8.18 (0.5H, s), 8.16 (0.5H, s), 7.72-7.66 (2H, m), 7.52-7.46 (2H, m), 7.37-7.29 (3H, m), 7.248 (0.5H, d, 8.8 Hz), 7.241 (0.5H, d, 8.8 Hz), 6.98 (1H, d, 8.8 Hz), 4.77 (1H, d, 17.1 Hz), 4.11 (1H, d, 17.1 Hz) 4.46-4.38 (1H, m), 3.93-3.82 (1H, m), 3.77 (3H, s), 3.18-3.07 (1H, m), 3.05-2.91 (2H, m), 2.69-2.60 (1H, m), 1.89-1.65 (2H, m), 0.91-0.80 (3H, m)

MS: 566 (M+H)$^+$

Example 245

{[2-({[6-(5-chloro-2-methoxybenzyl)-3,7-dioxo-1,4-diazepan-1-yl]carbonyl}amino)butanoyl]amino}acetic Acid (Compound 245)

A mixed solution of the compound 220 (33 mg) and 1N hydrogen chloride/acetic acid solution (2 ml) was stirred at room temperature for 5 hours. The reaction solution was concentrated, then the residue was diluted with ethyl acetate. The insoluble compound was filtered out, then the filtrate was concentrated. The residue was recrystallized from hexane/ethyl acetate to obtain the title compound (18 mg).

NMR (CDCl$_3$): δ9.42 (0.5H, d, 7.4 Hz), 9.39 (0.5H, d, 6.9 Hz), 7.25-7.05 (3.5H, m), 6.80 (1H, d, 8.9 Hz), 6.36 (0.5H, br), 5.28-5.16 (1H, m), 4.41-3.90 (5H, m), 3.83 (3H, s), 3.78-3.68 (1H, m), 3.38-3.30 (2H, m), 3.22-3.14 (1H, m), 3.67-3.55 (1H, m), 2.00-1.90 (1H, m), 1.85-1.74 (1H, m), 1.05-0.99 (3H, m)

MS: 469 (M+H)$^+$

Reference Example 174

3-amino-2-benzylpropanoic Acid Ethyl Hydrochloride (Compound S174)

To the (2E)-3-phenyl-2-cyano-2-propenoic acid ethyl (3 g) obtained by using benzaldehyde instead of the starting material compound of Reference Example 39, that is, the compound S1 for the similar procedure as with Reference Example 39, ethanol (100 ml), platinum oxide (170 mg), and 1N hydrochloric acid/acetic acid solution (20 ml) were added and the mixture was stirred under hydrogen atmosphere. The insolubles in the reaction solution were filtered out, the filtrate was concentrated, the residue was diluted with tetrahydrofuran (100 ml), tert-butyldicarbonate (3.4 g) and triethylamine (4.2 ml) were added, and the mixture was stirred at room temperature for 30 minutes. A small amount of N,N-dimethylethylenediamine was added, the mixture was stirred for 5 minutes, then the reaction solution was diluted with ethyl acetate and successively washed with 10% citric acid aqueous solution, water, saturated sodium hydrogencarbonate aqueous solution, and saturated saline. The organic layer was dried over with anhydrous sodium sulfate, the concentrated. To the ethyl 2-benzyl-3-[(tert-butoxycarbonyl)amino]propanoate (2.52 g) obtained by refining the obtained residue by silica gel column chromatography (hexane/ethyl acetate=7/1 to 5/1), 1M hydrogen chloride/acetic acid solution (15 ml) was added and the mixture was stirred at room temperature for 5 hours. The reaction solution was concentrated to obtain the title compound as a crude product (2.32 g).

Reference Example 175

3-[(allyloxycarbonyl)(2-tert-butoxycarbonylmethyl)amino]-2-benzylpropanoic Acid (Compound S175)

To the compound S174 (2.32 g), methylene chloride (15 ml), saturated sodium hydrogencarbonate aqueous solution (15 ml), and allyl chloroformate (0.92 ml) were added and the mixture was stirred at room temperature for 1 hour. The reaction solution was separated, the aqueous layer was extracted with chloroform. Then, the combined organic layer was successively washed with a 10% citric acid aqueous solution, water, saturated sodium hydrogencarbonate aqueous solution, and saturated saline, then was dried over with anhydrous sodium sulfate and concentrated. To 1.5 g of the obtained residue, dimethylformamide (15 ml), tert-butyl bromoacetate (1.1 ml), and sodium hydride (224 mg) were successively added under ice cooling and the mixture was stirred at room temperature for 2 hours. Ammonium chloride aqueous solution was added to the reaction solution, and the mixture was extracted with hexane-ethyl acetate (1:1). The combined extract was successively washed with water and saturated saline, dried over with anhydrous sodium sulfate, and concentrated, and the obtained residue was purified by silica gel column chromatography (hexane/ethyl acetate). To the thus obtained ethyl 3-[(allyloxycarbonyl)(2-tert-butoxycarbonylmethyl)amino]-2-benzylpropenoate (968 mg), ethanol (16 ml) and 2N sodium hydroxide aqueous solution (4 ml) were added and the mixture was stirred at room temperature for 1.5 hours. The reaction solution was diluted with ethyl acetate, acidified by 2N hydrochloric acid, then separated. The organic layer was washed with saturated saline, then dried over with anhydrous sodium sulfate and concentrated to obtain the title compound (877 mg).

Example 246

[6-benzyl-4-(4-chlorobenzenesulfonyl)-2,5-dioxo-1,4-diazepan-1-yl]acetic Acid (Compound 246)

To the tert-butyl [(2-benzyl-3-{[(4-chlorophenyl)sulfonyl]amino}-3-oxopropyl)(3-butenoyl)amino]acetate (505 mg), synthesized by using, instead of the starting material compound of Reference Example 117, that is, the compound S6, the compound S175 for the similar procedure as in Reference Example 117, in tetrahydrofuran (10 ml) solution, tetrakis(triphenylphosphine)palladium (0) (104 mg) and dimedone (1 g) were added and the mixture was stirred at room temperature for 1 hour. The reaction solution was concentrated and suspended in methanol-diethylether, and the precipitate was collected by filtration. The collected precipitate was used for the similar procedure was followed as in Reference Example 124, Example 1, and Example 251 to obtain the title compound.
NMR (CDCl$_3$): δ7.94 (2H, d, J=8.8 Hz), 7.59 (2H, d, J=8.8 Hz), 7.25-7.08 (5H, m), 4.91 (1H, d, J=17.5 Hz), 4.84 (1H, d, J=17.5 Hz), 4.01 (1H, d, J=17.5 Hz), 3.94 (1H, d, J=17.5 Hz), 3.85-3.70 (1H, m), 3.37-3.26 (2H, m), 3.07 (1H, dd, J=14.2, 5.6 Hz), 2.56 (1H, dd, J=14.2, 7.9 Hz)
MS: 451 (M+H)$^+$ Reference Example 176

3-[(allyloxycarbonyl)(2-tert-butoxycarbonylethyl)amino]-2-benzylpropanoic Acid (Compound S176)

To the compound S174 (2.32 g), ethanol (25 ml), triethylamine (1.4 ml), and tert-butyl acrylate (1.3 ml) were added and the mixture refluxed for 3 hours. This was cooled, then concentrated, then methylene chloride (15 ml), saturated sodium hydrogencarbonate aqueous solution (15 ml), and allyl chloroformate (0.92 ml) were added and the mixture was stirred at room temperature for 1 hour. The reaction solution was separated, the aqueous layer was extracted with chloroform, then the combined organic layer was successively washed with a 10% citric acid aqueous solution, water, saturated sodium hydrogencarbonate aqueous solution, and saturated saline. The organic layer was dried over with anhydrous sodium sulfate and concentrated, and the obtained residue was purified by silica gel column chromatography (hexane/ethyl acetate=5/1 to 3/1). To 1.94 g of the thus obtained ethyl 3-[(allyloxycarbonyl)(2-tert-butoxycarbonylethyl)amino]-2-benzylpropanoate (2.52 g), ethanol (40 ml) and 2N sodium hydroxide aqueous solution (10 ml) were added and the mixture was stirred at room temperature for 1.5 hours. The reaction solution was diluted with ethyl acetate, acidified by 2N hydrochloric acid, then separated. The organic layer was washed with saturated saline, then dried over with anhydrous sodium sulfate and concentrated to obtain the title compound as a crude product (1.82 g).

Example 247

3-[6-benzyl-4-(4-chlorobenzenesulfonyl)-2,5-dioxo-1,4-diazepan-1-yl]propanoic Acid (Compound 247)

Instead of the starting material compound of Reference Example 117, that is, the compound S6, the compound S176 was used for the similar procedure as in Reference Example 117 and Example 246 to obtain the title compound.
NMR (CDCl$_3$): δ7.95 (2H, d, J=8.7 Hz), 7.51 (2H, d, J=8.7 Hz), 7.33-7.22 (3H, m), 7.13 (2H, d, J=6.8 Hz), 4.89 (1H, d, J=17.5 Hz), 4.48 (1H, d, J=17.5 Hz), 3.57-3.30 (5H, m), 3.19 (1H, dd, J=14.3, 4.2 Hz); 2.60 (1H, dd, J=14.3, 7.8 Hz), 2.50-2.44 (2H, m)
MS: (M+H)$^+$ Example 248

6-(5-chloro-2-methoxybenzyl)-4-{[4-chloro-3-(1-piperadinylcarbonyl)phenyl]sulfonyl}-1,4-diazepan-2,5-dione Hydrochloride (Compound 248)

Instead of the starting material of Example 245, that is, the compound 220, the compound 223 was used for the similar procedure as in Example 245 to obtain the title compound.
NMR (DMSO-d$_6$): δ9.16 (2H, br), 8.14 (1H, d, 2.2 Hz), 7.99 (1H, d, 8.6 Hz), 7.89-7.85 (2H, m), 7.27-7.19 (2H, m), 6.98 (1H, d, 8.8 Hz), 4.92-4.81 (1H, m), 4.53 (1H, d, 17.4 Hz), 4.12-3.97 (1H, m), 3.82-3.60 (2H, m), 3.75 (3H, s) 3.45-3.10 (4H, m), 3.08-2.91 (4H, m), 2.89-2.76 (1H, m), 2.62-2.50 (1H, m)
MS: 569 (M+H)$^+$ Example 249

[4-chloro-2-({1-[(4-chlorophenyl)sulfonyl]-3,7-dioxo-1,4-diazepan-6-yl}methyl)phenoxy]acetic Acid (Compound 249)

Instead of the starting material compound of Example 29, that is, the compound 1, the compound 206 was used for the similar procedure as in Example 29 and Example 245 to obtain the title compound.
NMR (DMSO-d$_6$): δ7.92 (2H, d, J=8.6 Hz), 7.86-7.81 (1H, br), 7.73 (2H, d, J=8.6 Hz), 7.24-7.18 (2H, m), 6.94 (1H, d, J=8.6 Hz), 4.81 (1H, d, J=17.5 Hz), 4.73 (2H, dd, J=22.8, 16.5 Hz), 4.52 (1H, d, J=17.5 Hz), 3.98-3.90 (1H, m), 3.10-2.85 (3H, m)
MS: 501 (M+H)$^+$ Example 250

4-[(3-amino-4-methoxyphenyl)sulfonyl]-6-(5-chloro-2-methoxybenzyl)-1,4-diazepan-2,5-dione Hydrochloride (Compound 250)

Instead of the starting material of Example 245, that is, the compound 220, the compound 51 was used for the similar procedure as in Example 245 to obtain the title compound.

NMR (DMSO-d$_6$): δ7.79 (1H, br), 7.29-7.23 (3H, m), 7.17 (1H, d, 8.6 Hz), 7.03-6.96 (2H, m), 4.81 (1H, d, 17.5 Hz), 4.48 (1H, d, 17.5 Hz), 3.87 (3H, s), 3.75 (3H, s), 3.69-3.59 (1H, m), 3.01-2.95 (2H, m), 2.84 (1H, dd, 14.2, 4.7 Hz), 2.55-2.50 (1H, m)
MS: 468 (M+H)$^+$

Example 251

6-(5-chloro-2-methoxybenzyl)-N-{(1R)-1-[(hydroxyamino)carbonyl]propyl}-3,7-dioxo-1,4-diazepan-1-carboxamide (Compound 251)

To the compound 241 (30 mg), methylene chloride (1 ml) and trifluoroacetic acid (0.7 ml) were added and reacted for 6 days. The reaction solution was concentrated, hexane-ethyl acetate was added, and the precipitated crystal was collected by filtration to obtain the title compound (15 mg).
NMR (DMSO-d$_6$): δ10.79-10.65 (1H, br), 9.31 (0.5H, d, 7.4 Hz), 9.30 (0.5H, d, 7.7 Hz), 8.90 (1H, br), 7.64 (1H, br), 7.30 (0.5H, s), 7.29 (0.5H, s), 7.24 (0.5H, d, 8.8 Hz), 7.23 (0.5H, d, 8.8 Hz), 6.97 (1H, d, 8.8 Hz), 4.77 (0.5H, d, 17.0 Hz), 4.75 (0.5H, d, 17.0 Hz), 4.49 (1H, d, 17.0 Hz), 4.10-4.02 (1H, m), 3.90-3.80 (1H, m), 3.76 (3H, s), 3.15-3.06 (1H, m), 3.04-2.88 (2H, m), 2.66-2.57 (1H, m), 1.72-1.52 (2H, m), 0.87-0.74 (3H, m)
MS: 427 (M+H)$^+$ Example 252

(2S)-2-{[(2R)-2-({[6-(5-chloro-2-methoxybenzyl)-3,7-dioxo-1,4-diazepan-1-yl]carbonyl}amino)butanoyl]amino}propanoic Acid (Compound 252)

Instead of the starting material compound of Example 220, that is, the glycine tert-butyl ester hydrochloride, L-alanine tert-butyl ester hydrochloride was used for the similar procedure as in Example 220 and Example 245 to obtain the title compound.
NMR (DMSO-d$_6$): δ12.79-12.19 (1H, br), 9.40 (0.5H, d, 7.5 Hz), 9.35 (0.5H, d, 7.7 Hz), 8.45 (0.5H, d, 8.0 Hz), 8.43 (0.5H, d, 8.0 Hz), 7.64 (1H, br), 7.307 (0.5H, s), 7.301 (0.5H, s), 7.24 (0.5H, d, 8.8 Hz), 7.23 (0.5H, d, 8.8 Hz), 6.97 (1H, d, 8.8 Hz), 4.78 (0.5H, d, 17.0 Hz), 4.76 (0.5H, d, 17.0 Hz), 4.48 (1H, d, 17.0 Hz), 4.35-4.28 (1H, m), 4.25-4.15 (1H, m), 3.89-3.80 (1H, m), 3.76 (3H, s), 3.15-3.08 (1H, m), 3.03-2.91 (2H, m), 2.65-2.58 (1H, m), 1.72-1.57 (2H, m), 1.23 (3H, d, 7.3 Hz), 0.82-0.75 (3H, m)
MS: 483 (M+H)$^+$ Example 253

(2R)-2-{[(2R)-2-({[6-(5-chloro-2-methoxybenzyl)-3,7-dioxo-1,4-diazepan-1-yl]carbonyl}amino)butanoyl]amino}propanoic Acid (Compound 253)

Instead of the starting material compound of Example 220, that is, the glycine tert-butyl ester hydrochloride, D-alanine tert-butyl ester hydrochloride was used for the similar procedure as in Example 220 and Example 245 to obtain the title compound.
NMR (DMSO-d$_6$): δ12.75-12.21 (1H, br), 9.37 (0.5H, d, 7.4 Hz), 9.33 (0.5H, d, 7.7 Hz), 8.41 (0.5H, d, 7.6 Hz), 8.39 (0.5H, d, 8.0 Hz), 7.64 (1H, br), 7.30 (0.5H, s), 7.29 (0.5H, s), 7.24 (0.5H, d, 8.8 Hz), 7.23 (0.5H, d, 8.8 Hz), 6.97 (1H, d, 8.8 Hz), 4.77 (0.5H, d, 17.1 Hz), 4.76 (0.5H, d, 17.1 Hz), 4.48 (1H, d, 17.1 Hz), 4.35-4.26 (1H, m), 4.23-4.13 (1H, m), 3.89-3.80 (1H, m), 3.76 (3H, s), 3.16-3.05 (1H, m), 3.04-2.91 (2H, m), 2.67-2.57 (1H, m), 1.75-1.55 (2H, m), 1.25 (1.5H, d, 7.4 Hz), 1.24 (1.5H, d, 7.3 Hz), 0.88-0.81 (3H, m)
MS: 483 (M+H)$^+$ Example 254

N-{(1R)-1-[(3-aminoanilino)carbonyl]propyl}-6-(5-chloro-2-methoxybenzyl)-3,7-dioxo-1,4-diazepan-1-carboxamide (Compound 254)

Instead of the starting material compound of Example 220, that is, the glycine tert-butyl ester hydrochloride, 1-(tert-butoxycarbonyl)-1,3-phenylenediamine was used for the similar procedure as in Example 220 and Example 245 to obtain the title compound.
NMR (DMSO-d$_6$): δ9.83 (0.5H, s), 9.81 (0.5H, s), 9.45 (0.5H, d, 7.4 Hz), 9.41 (0.5H, d, 7.4 Hz), 7.65 (1H, d, 2.9 Hz), 7.316 (0.5H, s), 7.311 (0.5H, s), 7.24 (0.5H, d, 8.8 Hz), 7.23 (0.5H, d, 8.8 Hz), 6.98 (1H, d, 8.8 Hz), 6.91-6.87 (2H, m), 6.64 (1H, d, 7.8 Hz), 6.23 (1H, d, 7.8 Hz), 5.02 (2H, s), 4.78 (0.5H, d, 17.1 Hz), 4.77 (0.5H, d, 17.1 Hz), 4.50 (1H, d, 17.1 Hz), 4.45-4.37 (1H, m), 3.92-3.81 (1H, m), 3.77 (3H, s), 3.19-3.08 (1H, m), 3.07-2.91 (2H, m), 2.68-2.60 (1H, m), 1.82-1.65 (2H, m), 0.89-0.82 (3H, m)
MS: 502 (M+H)$^+$ Example 255

3-{[(2R)-2-({[6-(5-chloro-2-methoxybenzyl)-3,7-dioxo-1,4-diazepan-1-yl]carbonyl}amino)butanoyl]amino}benzoic Acid (Compound 255)

Instead of the starting material compound of Example 220, that is, the glycine tert-butyl ester hydrochloride, tert-butyl 3-aminobenzoate was used for the similar procedure as in Example 220 and Example 245 to obtain the title compound.
NMR (DMSO-d$_6$): δ13.10-12.47 (1H, br), 10.35 (0.5H, s), 10.33 (0.5H, s), 9.48 (0.5H, d, 7.2 Hz), 9.43 (0.5H, d, 7.3 Hz), 8.22-8.20 (1H, br), 7.78 (1H, d, 7.9), 7.65 (1H, s), 7.61 (1H, d, 7.9 Hz), 7.41 (1H, t, 7.9 Hz), 7.31 (1H, s), 7.24 (0.5H, d, 8.8 Hz), 7.23 (0.5H, d, 8.8 Hz), 6.98 (1H, d, 8.8 Hz), 4.78 (0.5H, d, 17.2 Hz), 4.77 (0.5H, d, 17.2 Hz), 4.51 (1H, d, 17.2 Hz), 4.49-4.39 (1H, m), 3.90-3.81 (1H, m), 3.77 (3H, s), 3.18-3.07 (1H, m), 3.05-2.91 (2H, m), 2.69-2.60 (1H, m), 1.89-1.67 (2H, m), 0.92-0.80 (3H, m)
MS: 531 (M+H)$^+$ Example 256

(2S)-2-{[(2R)-2-({[6-(5-chloro-2-methoxybenzyl)-3,7-dioxo-1,4-diazepan-1-yl]carbonyl}amino)butanoyl]amino}-4-methylpentanoic Acid (Compound 256)

Instead of the starting material compound of Example 220, that is, the glycine tert-butyl ester hydrochloride, L-leucine tert-butyl ester was used for the similar procedure as in Example 220 and Example 245 to obtain the title compound.
NMR (DMSO-d$_6$): δ12.81-12.25 (1H, br), 9.40 (0.5H, d, 7.5 Hz), 9.37 (0.5H, d, 7.6 Hz), 8.44-8.40 (1H, m), 7.64 (1H, d, 3.6 Hz), 7.309 (0.5H, s), 7.303 (0.5H, s), 7.24 (0.5H, d, 8.8 Hz), 7.23 (0.5H, d, 8.8 Hz), 6.97 (1H, d, 8.8 Hz), 4.78 (0.5H, d, 17.0 Hz), 4.75 (0.5H, d, 17.0 Hz), 4.48 (1H, d, 17.0 Hz), 4.38-4.30 (1H, m), 4.23-4.17 (1H, m), 3.89-3.80 (1H, m), 3.76 (3H, s), 3.14-3.08 (1H, m), 3.00-2.90 (2H, m), 2.68-2.58 (1H, m), 1.72-1.42 (5H, m), 0.90-0.85 (3H, m), 0.84-0.75 (6H, m)
MS: 525 (M+H)$^+$

Example 257

2-amino-5-{[(2R)-2-({[6-(5-chloro-2-methoxybenzyl)-3,7-dioxo-1,4-diazepan-1-yl]carbonyl}amino)butanoyl]amino}benzoic Acid Hydrochloride (Compound 257)

Instead of the starting material compound of Example 220, that is, the glycine tert-butyl ester hydrochloride, tert-butyl 2,5-diaminobenzoate was used for the similar procedure as in Example 220 and Example 245 to obtain the title compound.
NMR (DMSO-d$_6$): δ9.92 (0.5H, s), 9.89 (0.5H, s), 9.45 (0.5H, d, 7.4 Hz), 9.40 (0.5H, d, 7.4 Hz), 7.95-7.92 (1H, m), 7.66 (0.5H, s), 7.61 (0.5H, s), 7.427 (0.5H, d, 8.7 Hz), 7.421 (0.5H, d, 8.7 Hz), 7.31 (1H, s), 7.24 (0.5H, d, 8.8 Hz), 7.23 (0.5H, d, 8.8 Hz), 6.98 (1H, d, 8.8 Hz), 6.71 (1H, d, 8.7 Hz), 4.78 (0.5H, d, 17.1 Hz), 4.77 (0.5H, d, 17.1 Hz), 4.50 (1H, d, 17.1 Hz), 4.39-4.32 (1H, m), 3.91-3.79 (1H, m), 3.77 (3H, s), 3.17-3.07 (1H, m), 3.03-2.92 (2H, m), 2.68-2.60 (1H, m), 1.83-1.65 (2H, m), 0.89-0.81 (3H, m)
MS: 546 (M+H)$^+$

Example 258

N-{(1R)-1-[(4-aminoanilino)carbonyl]propyl}-6-(5-chloro-2-methoxybenzyl)-3,7-dioxo-1,4-diazepan-1-carboxamide (Compound 258)

Instead of the starting material compound of Example 220, that is, the glycine tert-butyl ester hydrochloride, 1-(tert-butoxycarbonyl)-1,4-phenylenediamine was used for the similar procedure as in Example 220 and Example 245 to obtain the title compound.
NMR (DMSO-d$_6$): δ9.72 (0.5H, s), 9.70 (0.5H, s), 9.43 (0.5H, d, 7.4 Hz), 9.39 (0.5H, d, 7.5 Hz), 7.65 (1H, d, 3.2 Hz), 7.31 (0.5H, s), 7.30 (0.5H, s), 7.24 (0.5H, d, 8.9 Hz), 7.23 (0.5H, d, 8.9 Hz), 7.17 (2H, d, 8.6 Hz), 6.98 (1H, d, 8.9 Hz), 6.48 (1H, d, 8.6 Hz), 6.46 (1H, d, 8.6 Hz), 4.847 (1H, s), 4.842 (1H, s), 4.79 (0.5H, d, 17.1 Hz), 4.77 (0.5H, d, 17.1 Hz), 4.50 (1H, d, 17.1 Hz), 4.39-4.32 (1H, m), 3.91-3.81 (1H, m), 3.77 (3H, s), 3.18-3.07 (1H, m), 3.03-2.92 (2H, m), 2.68-2.60 (1H, m), 1.80-1.62 (2H, m), 0.89-0.81 (3H, m)
MS: 502 (M+H)$^+$

Example 259

5-{[(2R)-2-({[6-(5-chloro-2-methoxybenzyl)-3,7-dioxo-1,4-diazepan-1-yl]carbonyl}amino)butanoyl]amino}-2-hydroxybenzoic Acid (Compound 259)

Instead of the starting material compound of Example 220, that is, the glycine tert-butyl ester hydrochloride, tert-butyl 4-amino-2-hydroxybenzoate was used for the similar procedure as in Example 220 and Example 245 to obtain the title compound.
NMR (DMSO-d$_6$): δ13.78-13.22 (1H, br), 11.43 (0.5H, s), 11.37 (0.5H, s), 9.53 (0.5H, d, 6.5 Hz), 9.46 (0.5H, d, 6.6 Hz), 8.46-8.40 (1H, m), 7.95 (1H, d, 7.5 Hz), 7.70-7.60 (1H, m), 7.57 (1H, t, 7.5 Hz), 7.35-7.31 (1H, m), 7.28-7.22 (1H, m), 7.15 (1H, t, 7.5 Hz), 6.99 (1H, d, 8.8 Hz), 4.77 (0.5H, d, 17.3 Hz), 4.73 (0.5H, d, 17.3 Hz), 4.53 (1H, d, 17.3 Hz), 4.31-4.25 (1H, m), 3.95-3.84 (1H, m), 3.77 (3H, s), 3.15-3.06 (1H, m), 3.05-2.91 (2H, m), 2.69-2.61 (1H, m), 1.94-1.72 (2H, m), 0.95-0.89 (3H, m)
MS: 547 (M+H)$^+$

Example 260

2-{[(2R)-2-({[6-(5-chloro-2-methoxybenzyl)-3,7-dioxo-1,4-diazepan-1-yl]carbonyl}amino)butanoyl] amino}benzoic Acid (Compound 260)

Instead of the starting material compound of Example 220, that is, the glycine tert-butyl ester hydrochloride, tert-butyl anthranilate was used for the similar procedure as in Example 220 and Example 245 to obtain the title compound.
NMR (DMSO-d$_6$): δ13.78-13.22 (1H, br), 11.43 (0.5H, s), 11.37 (0.5H, s), 9.53 (0.5H, d, 6.5 Hz), 9.46 (0.5H, d, 6.6 Hz), 8.46-8.40 (1H, m), 7.95 (1H, d, 7.5 Hz), 7.70-7.60 (1H, m), 7.57 (1H, t, 7.5 Hz), 7.35-7.31 (1H, m), 7.28-7.22 (1H, m), 7.15 (1H, t, 7.5 Hz), 6.99 (1H, d, 8.8 Hz), 4.77 (0.5H, d, 17.3 Hz), 4.73 (0.5H, d, 17.3 Hz), 4.53 (1H, d, 17.3 Hz), 4.31-4.25 (1H, m), 3.95-3.84 (1H, m), 3.77 (3H, s), 3.15-3.06 (1H, m), 3.05-2.91 (2H, m), 2.69-2.61 (1H, m), 1.94-1.72 (2H, m), 0.95-0.89 (3H, m)
MS: 531 (M+H)$^+$

Example 261

4-{[(2R)-2-({[6-(5-chloro-2-methoxybenzyl)-3,7-dioxo-1,4-diazepan-1-yl]carbonyl}amino)butanoyl] amino}benzoic Acid (Compound 261)

Instead of the starting material compound of Example 220, that is, the glycine tert-butyl ester hydrochloride, tert-butyl 4-aminobenzoate was used for the similar procedure as in Example 220 and Example 245 to obtain the title compound.
NMR (DMSO-d$_6$): δ12.88-12.35 (1H, br), 10.47 (0.5H, s), 10.45 (0.5H, s), 9.47 (0.5H, d, 7.2 Hz), 9.43 (0.5H, d, 7.3 Hz), 7.87 (2H, d, 8.6 Hz), 7.68 (2H, d, 8.6 Hz), 7.67 (1H, br), 7.31 (1H, s), 7.248 (0.5H, d, 8.8 Hz), 7.242 (0.5H, d, 8.8 Hz), 6.98 (1H, d, 8.8 Hz), 4.77 (1H, d, 17.1 Hz), 4.51 (1H, d, 17.1 Hz), 4.48-4.40 (1H, m), 3.92-3.81 (1H, m), 3.77 (3H, s), 3.18-3.08 (1H, m), 3.05-2.92 (2H, m), 2.65-2.59 (1H, m), 1.85-1.65 (2H, m), 0.90-0.85 (3H, m)
MS: 531 (M+H)$^+$

Example 262

4-{[(2R)-2-({[6-(5-chloro-2-methoxybenzyl)-3,7-dioxo-1,4-diazepan-1-yl]carbonyl}amino)butanoyl] amino}-1H-pyrrole-2-carboxylic Acid (Compound 262)

To 4-nitropyrrol-2-carboxylic acid (2.0 g), methylene chloride (15 ml), tert-butanol (15 ml), and O-tert-butyl-N,N'-diisopropylisourea (7 ml) were added and the mixture refluxed for 7 hours. The reaction solution was concentrated, and the obtained residue was purified by silica gel column chromatography (hexane/ethyl acetate=7/3). To the obtained 4-nitropyrrole-2-carboxylic acid tert-butyl ester (1.7 g), ethyl acetate (30 ml) and 10% palladium carbon (0.25 g) were added and the mixture was stirred under hydrogen atmosphere at room temperature for 8 hours. The reaction solution was filtered, the filtrate was concentrated, and the obtained residue was purified by silica gel column chromatography. The obtained 4-aminopyrrole-2-carboxylic acid tert-butyl ester was used, instead of the starting material compound of Example 220, that is, the glycine tert-butyl ester hydrochloride, for the similar procedure was in Example 220 and Example 245 to obtain the title compound.

NMR (DMSO-d$_6$): δ12.30-12.10 (1H, br), 11.46 (1H, s), 10.10 (0.5H, s), 10.07 (0.5H, s), 9.44 (0.5H, d, 7.4 Hz), 9.39 (0.5H, d, 7.4 Hz), 7.659 (0.5H, s), 7.651 (0.5H, s), 7.315 (0.5H, s), 7.310 (0.5H, s), 7.24 (0.5H, d, 8.9 Hz), 7.23 (0.5H, d, 8.9 Hz), 7.15 (1H, s), 6.98 (1H, d, 8.9 Hz), 6.61 (1H, s), 4.78 (0.5H, d, 17.1 Hz), 4.76 (0.5H, d, 17.1 Hz), 4.50 (1H, d, 17.1 Hz) 4.37-4.29 (1H, m), 3.91-3.80 (1H, m), 3.77 (3H, s), 3.12 (0.5H, t, 13.2 Hz), 3.11 (0.5H, t, 12.8 Hz), 3.03-2.92 (2H, m), 2.66-2.51 (1H, m), 1.80-1.62 (2H, m), 0.86-0.80 (3H, m)

MS: 520 (M+H)$^+$

Example 263

5-{[(2R)-2-({[6-(5-chloro-2-methoxybenzyl)-3,7-dioxo-1,4-diazepan-1-yl]carbonyl}amino)butanoyl]amino}-2-methylbenzoic Acid (Compound 263)

Instead of the starting material compound of Example 262, that is, the 4-nitropyrrole-2-carboxylic acid, 2-methyl-5-nitrobenzoic acid was used for the similar procedure as in Example 262 to obtain the title compound.

NMR (DMSO-d$_6$): δ12.91-12.49 (1H, br), 10.24 (0.5H, s), 10.21 (0.5H, s), 9.47 (0.5H, d, 7.3 Hz), 9.42 (0.5H, d, 7.4 Hz), 8.07 (0.5H, d, 3.7 Hz), 8.06 (0.5H, d, 2.5 Hz), 7.65-7.62 (2H, m), 7.31 (1H, s), 7.26-7.19 (2H, m), 6.98 (1H, d, 8.8 Hz), 4.78 (0.5H, d, 17.2 Hz), 4.77 (0.5H, d, 17.2 Hz), 4.50 (1H, d, 17.2 Hz) 4.44-4.36 (1H, m), 3.92-3.81 (1H, m), 3.77 (3H, s), 3.18-3.07 (1H, m), 3.05-2.94 (2H, m), 2.66-2.60 (1H, m), 2.29 (3H, s), 1.83-1.66 (2H, m), 0.90-0.83 (3H, m)

MS: 545 (M+H)$^+$

Melting point: 132-134° C.

Example 264

3-{[(2R)-2-({[6-(5-chloro-2-methoxybenzyl)-3,7-dioxo-1,4-diazepan-1-yl]carbonyl}amino)butanoyl]amino}-2-methoxybenzoic Acid (Compound 264)

To 2-hydroxy-3-nitrobenzoic acid (5.2 g), methylene chloride (30 ml), tert-butanol (30 ml), and O-tert-butyl-N,N'-diisopropylisourea (15 ml) were added and the mixture refluxed for 3 hours. The reaction solution was concentrated, and the obtained residue was purified by silica gel column chromatography (hexane/ethyl acetate=20/1 to 6/1). To 430 g of the obtained tert-butyl 2-hydroxy-3-nitrobenzoate (1.5 g), N,N'-dimethylformamide (10 ml), methyl iodide (0.13 ml), and potassium carbonate (0.29 g) were added and the mixture was stirred at room temperature for 5 hours. Water was added to the reaction solution, then the mixture was extracted with hexane/ethyl acetate=1/1 solution. The extract was dried over with anhydrous magnesium sulfate and concentrated. The obtained residue was purified by silica gel column chromatography (hexane/ethyl acetate=10/1). To the obtained tert-butyl 2-methoxy-3-nitrobenzoate (340 mg), ethanol (10 ml) and 10% palladium carbon (50 mg) were added and the mixture was stirred under hydrogen atmosphere at room temperature for 18 hours. The reaction solution was filtered, the filtrate was concentrated, and the obtained residue was purified by silica gel column chromatography. The obtained tert-butyl 3-amino-2-methoxybenzoate was used instead of the starting material compound of Example 220, that is, the glycine tert-butyl ester hydrochloride, for the similar procedure as with Example 220 and Example 245 to obtain the title compound.

NMR (DMSO-d$_6$): δ13.27-12.37 (1H, br), 9.66 (1H, s), 9.45 (0.5H, d, 7.3 Hz), 9.42 (0.5H, d, 7.3 Hz), 8.04 (0.5H, t, 8.4 Hz), 8.04 (0.5H, t, 7.0 Hz), 7.67 (1H, s), 7.43 (0.5H, d, 7.8 Hz), 7.42 (0.5H, d, 8.1 Hz), 7.319 (0.5H, s), 7.312 (0.5H, s), 7.24 (0.5H, d, 8.7 Hz), 7.23 (0.5H, d, 8.7 Hz), 7.15-7.10 (1H, m), 6.98 (1H, d, 8.7 Hz), 4.79 (0.5H, d, 17.1 Hz), 4.78 (0.5H, d, 17.1 Hz), 4.68-4.62 (1H, m), 4.21 (1H, d, 17.1 Hz), 3.91-3.83 (1H, m), 3.77 (3H, s), 3.70 (1.5H, s), 3.69 (1.5H, s), 3.17-3.07 (1H, m), 3.03-2.91 (2H, m), 2.68-2.59 (1H, m), 1.88-1.69 (2H, m), 0.94-0.88 (3H, m)

MS: 561 (M+H)$^+$

Example 265

3-{[(2R)-2-({[6-(5-chloro-2-methoxybenzyl)-3,7-dioxo-1,4-diazepan-1-yl]carbonyl}amino)butanoyl]amino}-4-methoxybenzoic Acid (Compound 265)

Instead of the starting material compound of Example 264, that is, 2-hydroxy-3-nitrobenzoic acid, 4-hydroxy-3-nitrobenzoic acid was used for the similar procedure as in Example 264 to obtain the title compound.

NMR (DMSO-d$_6$): δ12.80-12.40 (1H, br), 9.55 (1H, s), 9.44 (0.5H, d, 7.3 Hz), 9.40 (0.5H, d, 7.4 Hz), 8.467 (0.5H, d, 2.2 Hz), 8.460 (0.5H, d, 3.2 Hz), 7.72-7.65 (2H, m), 7.318 (0.5H, s), 7.312 (0.5H, s), 7.24 (1H, d, 8.8 Hz), 7.11 (1H, d, 8.6 Hz), 6.98 (1H, d, 8.8 Hz), 4.78 (1H, d, 17.4 Hz), 4.65-4.52 (1H, m), 4.51 (1H, d, 17.4 Hz), 3.95-3.82 (1H, m), 3.87 (3H, s), 3.77 (3H, s), 3.13 (0.5H, t, 12.9 Hz), 3.11 (0.5H, t, 13.0 Hz), 3.03-2.93 (2H, m), 2.67-2.62 (1H, m), 1.84-1.65 (2H, m), 0.93-0.85 (3H, m)

MS: 561 (M+H)$^+$

Example 266

3-{[(2R)-2-({[6-(5-chloro-2-methoxybenzyl)-3,7-dioxo-1,4-diazepan-1-yl]carbonyl}amino)butanoyl]amino}-4-fluorobenzoic Acid (Compound 266)

Instead of the starting material compound of Example 262, that is, 4-nitropyrrole-2-carboxylic acid, 4-fluoro-3-nitrobenzoic acid was used for the similar procedure as in Example 262 to obtain the title compound.

NMR (DMSO-d$_6$): δ12.90-12.20 (1H, br), 10.15 (0.5H, s), 10.14 (0.5H, s), 9.47 (0.5H, d, 7.3 Hz), 9.43 (0.5H, d, 7.2 Hz), 8.43 (1H, t, 5.6 Hz), 7.75-7.70 (1H, m), 7.65 (1H, s), 7.39-7.31 (2H, m), 7.24 (1H, d, 8.8 Hz), 6.98 (1H, d, 8.8 Hz), 4.78 (1H, d, 17.1 Hz), 4.65-4.56 (1H, m), 4.51 (1H, d, 17.1 Hz), 3.90-3.82 (1H, m), 3.77 (3H, s), 3.15-3.06 (1H, m), 3.05-2.93 (2H, m), 2.66-2.59 (1H, m), 1.88-1.69 (2H, m), 0.93-0.85 (3H, m)

MS: 549 (M+H)$^+$

Example 267

3-{[(2R)-2-({[6-(5-chloro-2-methoxybenzyl)-3,7-dioxo-1,4-diazepan-1-yl]carbonyl}amino)butanoyl]amino}-4-hydroxybenzoic Acid (Compound 267)

To the synthesis intermediate of Example 265, that is, tert-butyl 4-hydroxy-3-nitrobenzoate (0.42 g), methylene chloride (10 ml), chloromethylmethylether (0.16 ml), and N,N-diisopropylethylamine (0.37 ml) were added under ice cooling and the mixture was stirred at room temperature for 2 hours. The reaction solution was diluted with ethyl acetate and successively washed with water, a potassium hydrogensulfate aqueous solution, and saturated saline. The mixture was dried over with anhydrous magnesium sulfate, then concentrated. The obtained residue was purified by silica gel column chromatography (hexane/ethyl acetate=10/1). To the obtained tert-butyl 4-methoxymethyloxy-3-nitrobenzoate (0.26 g), ethanol (10 ml) and 10% palladium carbon (40 mg) were added and the mixture was stirred under hydrogen atmosphere at room temperature for 7 hours. The reaction solution was filtered, the filtrate was concentrated, and the obtained residue was purified by silica gel column chromatography (hexane/ethyl acetate=6/1 to 1/1). The obtained tert-butyl 3-amino-2-methoxymethyloxybenzoate was used, instead of the starting material compound of Example 220, that is, the glycine tert-butyl ester hydrochloride, for the similar procedure as in Example 220 and Example 245 to obtain the title compound.

NMR (DMSO-$d_6$): δ12.58-12.12 (1H, br), 10.6 (1H, s), 9.51 (0.5H, s), 9.50 (0.5H, s), 9.45 (0.5H, d, 7.3 Hz), 9.41 (0.5H, d, 7.3 Hz), 8.38 (1H, s), 7.65 (1H, s), 7.55 (1H, d, 8.3 Hz), 7.31 (1H, s), 7.24 (1H, d, 8.9 Hz), 6.98 (1H, d, 8.8 Hz), 6.90 (1H, d, 8.5 Hz), 4.78 (1H, d, 16.6 Hz), 4.65-4.61 (1H, m), 4.50 (1H, d, 17.1 Hz), 3.90-3.83 (1H, m), 3.77 (3H, s), 3.13 (0.5H, t, 12.6 Hz), 3.11 (0.5H, t, 12.4 Hz), 3.02-2.91 (2H, m), 2.68-2.60 (1H, m), 1.85-1.66 (2H, m), 0.91-0.85 (3H, m)

MS: 547 (M+H)$^+$

Example 268

3-amino-5-{[(2R)-2-({[6-(5-chloro-2-methoxybenzyl)-3,7-dioxo-1,4-diazepan-1-yl]carbonyl}amino)butanoyl]amino}benzoic Acid (Compound 268)

To 3-amino-5-nitrobenzoic acid (2.1 g), 1,4-dioxane (30 ml) and di-tert-butyldicarbonate (3.74 g) were added and the mixture refluxed for 3 days. The reaction solution was concentrated and diluted with ethyl acetate. The solution was washed with a potassium hydrogensulfate aqueous solution and saturated saline, dried over with anhydrous sodium sulfate, and concentrated. The thus obtained 3-(tert-butoxycarbonylamino)-5-nitrobenzoic acid was used instead of the starting material compound of Example 262, that is, the 4-nitropyrrole-2-carboxylic acid, for the similar procedure as in Example 262 to obtain the title compound.

NMR (DMSO-$d_6$): δ12.73-11.90 (1H, br), 10.1 (0.5H, s), 10.0 (0.5H, s), 9.46 (0.5H, d, 7.3 Hz), 9.42 (0.5H, d, 7.4 Hz), 7.65 (1H, d, 3.2 Hz), 7.32-7.22 (3H, m), 7.10 (0.5H, s), 7.09 (0.5H, s), 6.99 (0.5H, s), 6.97 (0.5H, s), 6.87 (0.5H, s), 6.86 (0.5H, s), 5.32 (2H, brs), 4.78 (1H, d, 17.3 Hz), 4.50 (1H, d, 17.1 Hz), 4.42-4.38 (1H, m), 3.90-3.82 (1H, m), 3.77 (3H, s), 3.17-3.07 (1H, m), 3.04-2.93 (2H, m), 2.67-2.62 (1H, m), 1.85-1.60 (2H, m), 0.88-0.81 (3H, m)

MS: 546 (M+H)$^+$

Example 269

Methyl [4-chloro-2-({1-[(4-chlorophenyl)sulfonyl]-3,7-dioxo-1,4-diazepan-6-yl}methyl)phenoxy]acetate (Compound 269)

Instead of the starting material of Example 208, that is, the compound 196, the compound 249 was used for the similar procedure as in Example 208 to obtain the title compound.

NMR (CDCl$_3$): δ7.95 (2H, d, J=8.7 Hz), 7.50 (2H, d, J=8.7 Hz), 7.16 (1H, dd, J=8.7, 2.6 Hz), 7.08 (1H, d, J=2.6 Hz), 6.64 (1H, d, J=8.7 Hz), 5.81-5.76 (1H, br), 4.98 (1H, d, J=17.5 Hz), 4.66 (2H, s), 4.60 (1H, d, J=17.5 Hz), 3.99-3.87 (1H, m), 3.79 (3H, s), 3.36-3.27 (1H, m), 3.20-3.10 (2H, m), 2.56 (1H, dd, J=14.0, 8.4 Hz)

MS: 515 (M+H)$^+$

Melting point: 138-140° C.

Example 270

2-{6-benzyl-4-[(4-chlorophenyl)sulfonyl]-2,5-dioxo-1,4-diazepan-1-yl}-N-phenylacetoamide (Compound 270)

To the compound 246 (14 mg) in N,N-dimethylformamide (0.3 ml) solution, aniline (5 μM), triethylamine (0.03 ml), and n-propylphosphonic acid anhydride (25% ethyl acetate solution) (0.03 ml) were added and the mixture was stirred at room temperature for 5 hours. The reaction solution was diluted with ethyl acetate, successively washed with 1N hydrochloric acid, saturated saline, saturated sodium hydrogencarbonate aqueous solution, and saturated saline, dried over with anhydrous sodium sulfate, then concentrated. The residue was recrystallized from methanol/diethylether to obtain the title compound (8.7 mg).

NMR (DMSO-$d_6$): δ10.00 (1H, s), 7.94 (2H, d, J=8.6 Hz), 7.70 (2H, d, J=8.6 Hz), 7.50 (2H, d, J=7.9 Hz), 7.34-7.15 (7H, m), 7.05 (1H, t, J=7.3 Hz), 5.11 (1H, d, J=17.4 Hz), 7.71 (1H, d, J=17.4 Hz), 4.08 (1H, d, J=16.4 Hz), 4.01-3.90 (1H, m), 3.96 (1H, d, J=16.4 Hz), 3.49-3.25 (2H, m), 2.96 (1H, dd, J=14.3, 5.5 Hz), 2.66-2.47 (1H, m)

MS: 548 (M+Na)$^+$

Example 271

2-[6-benzyl-4-(4-chlorobenzenesulfonyl)-2,5-dioxo-1,4-diazepan-1-yl]-N-methyl-N-phenylacetoamide (Compound 271)

Instead of the starting material compound of Example 270, that is, aniline, N-methylaniline was used for the similar procedure as in Example 270 to obtain the title compound.

NMR (CDCl$_3$): δ7.96 (2H, d, J=8.7 Hz), 7.50-7.35 (5H, m), 7.31-7.20 (5H, m), 7.12 (2H, d, J=6.8 Hz), 4.94 (1H, d, J=17.5 Hz), 4.54 (1H, d, J=17.5 Hz), 3.64 (2H, s), 3.53-3.45 (1H, m), 3.32-3.29 (2H, m), 3.23 (3H, s), 3.16 (1H, dd, J=14.3, 5.6 Hz), 2.56 (1H, dd, J=14.3, 7.7 Hz)

MS: 540 (M+H)$^+$

Example 272

N-benzyl-2-[6-benzyl-4-(4-chlorobenzenesulfonyl)-2,5-dioxo-1,4-diazepan-1-yl]acetoamide (Compound 272)

Instead of the starting material compound of Example 270, that is, aniline, benzylamine was used for the similar procedure as in Example 270 to obtain the title compound.

NMR (CDCl$_3$): δ7.92 (2H, d, J=8.6 Hz), 7.47 (2H, d, J=8.6 Hz), 7.37-7.19 (8H, m), 7.11 (2H, d, J=6.9 Hz), 6.20 (1H, m), 4.95 (1H, d, J=17.6 Hz), 4.51 (1H, d, J=17.6 Hz), 4.39 (1H, dd, J=14.8, 5.8 Hz), 4.34 (1H, dd, J=14.8, 5.8 Hz), 3.88 (1H, d, J=15.3 Hz), 3.81 (1H, d, J=15.3 Hz), 3.50-3.35 (3H, m), 3.17 (1H, dd, J=14.0, 3.9 Hz), 2.58 (1H, dd, J=14.0, 6.3 Hz)

MS: 540 (M+H)$^+$

Melting point: 187-190° C.

Example 273

3-[6-benzyl-4-(4-chlorobenzenesulfonyl)-2,5-dioxo-1,4-diazepan-1-yl]-N-phenylpropanamide (Compound 273)

Instead of the starting material compound of Example 270, that is, the compound 246, the compound 247 was used for the similar procedure as in Example 270 to obtain the title compound.

NMR (CDCl$_3$): δ7.89 (2H, d, J=8.7 Hz), 7.84 (1H, brs), 7.49 (2H, d, J=7.9 Hz), 7.43 (2H, d, J=8.7 Hz), 7.33 (2H, t, J=7.9 Hz), 7.30-7.19 (3H, m), 7.15-7.05 (3H, m), 4.85 (1H, d, J=17.5 Hz), 4.48 (1H, d, J=17.5 Hz), 3.69-3.53 (2H, m), 3.48-3.42 (2H, m), 3.38-3.28 (1H, m), 3.15 (1H, dd, J=14.3, 4.9 Hz), 2.61 (1H, dd, J=14.3, 8.1 Hz), 2.53 (2H, t, J=6.3 Hz)
MS: 540 (M+H)$^+$

Example 274

N-benzyl-3-[6-benzyl-4-(4-chlorobenzenesulfonyl)-2,5-dioxo-1,4-diazepan-1-yl]propanamide (Compound 274)

Instead of the starting material compound of Example 273, that is, aniline, benzylamine was used for the similar procedure as in Example 273 to obtain the title compound.

NMR (CDCl$_3$): δ7.94 (2H, d, J=8.7 Hz), 7.46 (2H, d, J=8.7 Hz), 7.38-7.22 (8H, m), 7.11 (2H, d, J=8.2 Hz), 5.87 (1H, br), 4.74 (1H, d, J=17.3 Hz), 4.45-4.30 (3H, m), 3.64-3.57 (1H, m), 3.52-3.25 (4H, m), 3.13 (1H, dd, J=14.3, 4.9 Hz), 2.63 (1H, dd, J=14.3, 8.0 Hz), 2.31 (2H, t, J=6.5 Hz)
MS: (M+H)$^+$

Example 275

3-[6-benzyl-4-(4-chlorobenzenesulfonyl)-2,5-dioxo-1,4-diazepan-1-yl]propanamide (Compound 275)

Instead of the starting material compound of Example 273, that is, aniline, 1,1,1,3,3,3-hexamethyldisilazane was used for the similar procedure as in Example 273 to obtain the title compound.

NMR (CDCl$_3$): δ7.95 (2H, d, J=8.6 Hz), 7.52 (2H, d, J=8.6 Hz), 7.23-7.21 (3H, m), 7.11 (2H, d, J=7.0 Hz), 5.79 (1H, br), 5.34 (1H, br), 4.80 (1H, d, J=17.4 Hz), 4.47 (1H, d, J=17.4 Hz), 3.64-3.55 (1H, m), 3.49-3.40 (2H, m), 3.39-3.28 (2H, m), 3.15 (1H, dd, J=14.4, 4.6 Hz), 2.61 (1H, dd, J=14.4, 8.3 Hz), 2.46-2.29 (2H, m)
MS: 464 (M+H)$^+$

Example 276

3-[6-benzyl-4-(4-chlorobenzenesulfonyl)-2,5-dioxo-1,4-diazepan-1-yl]-N-(3-pyridyl)propanamide (Compound 276)

Instead of the starting material compound of Example 273, that is, aniline, 3-aminopyridine was used for the similar procedure as in Example 273 to obtain the title compound.

NMR (DMSO-d$_6$): δ10.16 (1H, s), 8.66 (1H, d, J=2.1 Hz), 8.25 (1H, d, J=4.7 Hz), 7.97-7.93 (1H, m), 7.88 (2H, d, J=8.6 Hz), 7.70 (2H, d, J=8.6 Hz), 7.33 (1H, dd, J=8.2, 4.7 Hz), 7.25-7.12 (5H, m), 4.99 (1H, d, J=17.4 Hz), 4.65 (1H, d, J=17.4 Hz), 3.89-3.78 (1H, m), 3.59-3.49 (1H, m), 3.43-3.30 (4H, m), 2.95 (1H, dd, J=14.2, 5.6 Hz), 2.58-2.43 (2H, m)
MS: 541 (M+H)$^+$

Example 277

2-[4-chloro-2-({1-[(4-chlorophenyl)sulfonyl]-3,7-dioxo-1,4-diazepan-6-yl}methyl)phenoxy]-N-methylacetoamide (Compound 277)

Instead of the starting material of Example 270, that is, the compound 246, the compound 249 was used, while instead of aniline, methylamine hydrochloride was used for the similar procedure as in Example 270 to obtain the title compound.

NMR (CDCl$_3$): δ7.94 (2H, d, J=8.7 Hz), 7.51 (2H, d, J=8.7 Hz), 7.21 (1H, dd, J=8.7, 2.5 Hz), 7.07 (1H, d, J=2.5 Hz), 6.80-6.75 (1H, br), 6.73 (1H, d, J=8.7 Hz), 5.90-5.86 (1H, br), 4.91 (1H, d, J=17 Hz), 4.65 (1H, d, J=17 Hz), 4.48 (2H, s), 33.40-3.22 (3H, m), 2.88 (4H, d, J=4.8 Hz), 2.54 (1H, dd, J=13.8, 8.3 Hz)
MS: 514 (M+H)$^+$

Example 278

Ethyl 4-chloro-2-((E)-{1-[(4-chlorophenyl)sulfonyl]-3,7-dioxo-1,4-diazepan-6-ylidene}methyl)phenylcarbamate (Compound 278)

To the compound 204 (94 mg) in methylene chloride (1.9 ml) solution, pyridine (21 μM) and ethyl chlorocarbonate (25 μM) was added and the mixture was stirred at room temperature for 30 minutes. To the reaction solution, saturated ammonium chloride aqueous solution was added and the mixture was extracted with chloroform. The organic layer was successively washed with saturated saline, dried over with anhydrous sodium sulfate, then concentrated. The residue was recrystallized from hexane/ethyl acetate to obtain the title compound (74 mg).

NMR (CDCl$_3$): δ8.02 (2H, d, J=8.8 Hz), 7.82 (1H, d, J=8.8 Hz), 7.55 (1H, s), 7.53 (2H, d, J=8.8 Hz), 7.35 (1H, dd, J=8.8, 2.5 Hz), 7.03 (1H, d, J=2.5 Hz), 6.43 (1H, brs), 5.93-5.86 (1H, br), 4.75 (2H, s), 4.22-4.12 (4H, m), 1.28 (3H, t, J=7.1 Hz)
MS: 512 (M+H)$^+$

Example 279 ethyl-4-chloro-2-({1-[(4-chlorophenyl)sulfonyl]-3,7-dioxo-1,4-diazepan-6-yl}methyl)phenylcarbamate (Compound 279)

Instead of the starting material of Example 29, that is, the compound 1, the compound of Example 278 was used for the similar procedure as in Example 29 to obtain the title compound.

NMR (CDCl$_3$): δ7.93 (2H, d, J=8.6 Hz), 7.55-7.48 (1H, br), 7.49 (2H, d, J=8.6 Hz), 7.28 (1H, d, J=8.7 Hz), 7.21 (1H, dd, J=8.7, 2.4 Hz), 7.08 (1H, d, J=2.4 Hz), 5.83-5.79 (1H, br), 5.01 (1H, d, J=17.7 Hz), 4.43 (1H, d, J=17.7 Hz), 4.22 (2H, q, J=7.1 Hz), 3.51-3.40 (2H, m), 3.25 (1H, t, J=11.6 Hz), 3.10 (1H, dd, J=14.6, 7.8 Hz), 2.49 (1H, dd, J=14.5, 5.2 Hz), 1.33 (3H, t, J=7.1 Hz)
MS: 514 (M+H)$^+$

Example 280

Methyl 2-chloro-5-{[6-(5-chloro-2-methoxybenzyl)-3,7-dioxo-1,4-diazepan-1-yl]sulfonyl}phenylcarbamate (Compound 280)

Instead of the material of Example 278, that is, the compound 204, the compound S134 was used, while instead of ethyl chlorocarbonate, methyl chlorocarbonate was used for the similar procedure as in Example 278 to obtain the title compound.

NMR (DMSO-d$_6$): δ9.47 (1H, s), 8.24 (1H, d, J=2.2 Hz), 7.85 (1H, br), 7.76 (1H, d, J=8.5 Hz), 7.66 (1H, dd, J=8.5, 2.2 Hz), 7.28-7.23 (2H, m), 6.97 (1H, d, J=8.5 Hz), 4.87 (1H, d, J=17.4 Hz), 4.5 (1H, d, J=17.4 Hz), 3.75 (3H, s), 3.72 (3H, s), 3.70-3.62 (1H, m), 3.33-3.29 (1H, m), 3.04-2.94 (2H, m), 2.84 (1H, dd, J=14.2, 4.6 Hz)
MS: 530 (M+H)$^+$

Example 281

4-[(3-amino-4-chlorophenyl)sulfonyl]-6-(5-chloro-2-methoxybenzyl)-N-ethyl-2,5-dioxo-1,4-diazepan-1-carboxamide (Compound 281)

To the compound S134 (52 mg) in tetrahydrofuran (0.5 ml) solution, ethyl isocyanate (40 μl) was added under heating and reflux in two additions and the mixture was stirred for 21 hours. The reaction system was concentrated, and the residue was purified by silica gel column chromatography (hexane/ethyl acetate=3/1). The purified product was again purified by silica gel column chromatography (hexane/ethyl acetate=1/1→2/3). The purified product was recrystallized from chloroform/hexane to obtain the title compound (15.6 mg).

NMR (CDCl$_3$): δ8.64 (1H, br), 7.41 (1H, d, J=2.3 Hz), 7.37 (1H, d, J=8.3 Hz), 7.23 (1H, dd, J=8.3, 2.3 Hz), 7.18 (1H, dd, J=8.7, 2.5 Hz), 7.06 (1H, d, J=2.5 Hz), 6.77 (1H, d, J=8.7 Hz), 4.82 (1H, d, J=16.1 Hz), 4.61 (1H, d, J=16.1 Hz), 4.41-4.32 (3H, m), 3.79 (3H, s), 3.50 (1H, dd, J=15.6, 11.5 Hz), 3.35-3.21 (3H, m), 3.12 (1H, dd, J=13.8, 5.6 Hz), 2.94 (1H, dd, J=13.8, 7.2 Hz), 1.16 (3H, t, J=7.3 Hz)
MS: 543 (M+H)$^+$

Example 282

N-(2-chloro-5-{[6-(5-chloro-2-methoxybenzyl)-3,7-dioxo-1,4-diazepan-1-yl]sulfonyl}phenyl)acetoamide (Compound 282)

A mixed solution of the compound S134 (300 mg), anhydrous acetic acid (2 ml), and pyridine (2 ml) was stirred at room temperature for 18 hours. The reaction solution was concentrated, the residue was purified by silica gel column chromatography (hexane/ethyl acetate=1/3 to 0/1), and the purified product was recrystallized from hexane/ethyl acetate to obtain the title compound (170 mg).

NMR (CDCl$_3$): δ8.73 (1H, d, J=1.9 Hz), 7.80 (1H, dd, J=8.6, 1.9 Hz), 7.64 (1H, brs), 7.57 (1H, d, J=8.6 Hz), 7.18 (1H, dd, J=8.8, 2.7 Hz), 7.00 (1H, d, J=2.7 Hz), 6.77 (1H, d, J=8.8 Hz), 5.98-5.00 (1H, br), 5.04 (1H, d, J=17.8 Hz), 4.44 (1H, d, J=17.8 Hz), 3.80 (3H, s), 3.53-3.55 (1H, m), 3.31-3.20 (2H, m), 3.11 (1H, dd, J=14.0, 4.7 Hz), 2.46 (1H, dd, J=14.0, 9.0 Hz), 2.26 (3H, s)
MS: 514 (M+H)$^+$ Example 283

N-(5-{[6-(5-chloro-2-methoxybenzyl)-3,7-dioxo-1,4-diazepan-1-yl]sulfonyl}-2-methoxyphenyl)acetoamide (Compound 283)

Instead of the starting material of Example 282, that is, the compound S134, the compound 250 was used for the similar procedure as in Example 282 to obtain the title compound.

NMR (DMSO-d$_6$): δ9.43 (1H, s), 8.60 (1H, m), 7.81 (1H, br), 7.64 (1H, dd, 8.7, 2.4 Hz), 7.27-7.23 (3H, m), 6.97 (1H, d, 8.4 Hz), 4.83 (1H, d, 17.5 Hz), 4.49 (1H, d, 17.5 Hz), 3.94 (3H, s), 3.74 (3H, s), 3.69-3.59 (1H, m), 3.01-2.91 (2H, m), 2.82 (1H, dd, 14.3, 4.6 Hz), 2.59-2.45 (1H, m), 2.12 (3H, s)
MS: 510 (M+H)$^+$

Example 284

N-(5-{[6-(5-chloro-2-methoxybenzyl)-3,7-dioxo-1,4-diazepan-1-yl]sulfonyl}-2-methylphenyl)acetoamide (Compound 284)

Instead of the starting material of Example 282, that is, the compound S134, the compound 200 was used for the similar procedure as in Example 282 to obtain the title compound.

NMR (DMSO-d$_6$): δ9.52 (1H, s), 8.08 (1H, m), 7.83 (1H, br), 7.57 (1H, dd, 8.1, 1.7 Hz), 7.46 (1H, d, 8.1 Hz), 7.27-7.23 (2H, m), 6.97 (1H, d, 9.1 Hz), 4.85 (1H, d, 17.5 Hz), 4.50 (1H, d, 17.5 Hz), 3.74 (3H, s), 3.70-3.61 (1H, m), 3.03-2.93 (2H, m), 2.82 (1H, dd, 14.3, 4.7 Hz), 2.54-2.47 (1H, m), 2.30 (3H, s), 2.11 (9H, s)
MS: 494 (M+H)$^+$

Example 285

N-[3-(acetylamino)phenyl]-6-(5-chloro-2-methoxybenzyl)-3,7-dioxo-1,4-diazepan-1-carboxamide (Compound 285)

Instead of the starting material of Example 282, that is, the compound S134, the compound 171 was used for the similar procedure as in Example 282 to obtain the title compound.

NMR (CDCl$_3$): δ11.22 (1H, s), 7.72 (1H, s), 7.46 (1H, d, J=7.7 Hz), 7.35-7.20 (3H, m), 7.19-7.13 (2H, m), 6.82 (1H, d, J=8.7 Hz), 5.86 (1H, br), 5.44 (1H, d, J=17.6 Hz), 4.20 (1H, d, J=17.6 Hz), 3.85 (3H, s), 3.83-3.72 (1H, m), 3.40-3.35 (2H, m), 3.22 (1H, dd, J=13.8, 5.4 Hz), 2.64 (1H, dd, J=13.8, 7.9 Hz), 2.17 (3H, s)
MS: 459 (M+H)$^+$
Melting point: 130-131° C.

Example 286

N-[4-(acetylamino)phenyl]-6-(5-chloro-2-methoxybenzyl)-3,7-dioxo-1,4-diazepan-1-carboxamide (Compound 286)

Instead of the starting material of Example 282, that is, the compound S134, the compound 172 was used for the similar procedure as in Example 282 to obtain the title compound.

NMR (DMSO-d$_6$): δ10.97 (1H, s), 9.89 (1H, s), 7.72 (1H, d, J=3.7 Hz), 7.52 (2H, d, J=9.0 Hz), 7.42 (2H, d, J=9.0 Hz), 7.35 (1H, d, J=2.6 Hz), 7.26 (1H, dd, J=8.9, 2.6 Hz), 7.00 (1H, d, J=8.9 Hz), 4.80 (1H, d, J=17.3 Hz), 4.60 (1H, d, J=17.3 Hz), 3.99-3.89 (1H, m), 3.79 (3H, s), 3.21 (1H, t, J=12.7 Hz), 3.08-2.96 (2H, m), 2.66 (1H, dd, J=14.1, 9.1 Hz), 2.01 (3H, s)
MS: 459 (M+H)$^+$

Example 287

N-{1-[4-(acetylamino)phenyl]propyl}-6-(5-chloro-2-methoxybenzyl)-3,7-dioxo-1,4-diazepan-1-carboxamide (Compound 287) (Diastereomer of Compound 288)

Instead of the starting material of Example 282, that is, the compound S134, the compound 122 was used for the similar procedure as in Example 282 to obtain the title compound.

NMR (CDCl$_3$): δ9.43 (1H, d, J=7.8 Hz), 7.45 (2H, d, J=8.3 Hz), 7.28-7.13 (4H, m), 7.11 (1H, d, J=2.6 Hz), 6.80 (1H, d, J=8.7 Hz), 5.70 (1H, brs), 5.36 (1H, d, J=17.6 Hz), 4.75 (1H, dd, J=14.4, 7.1 Hz), 4.10 (1H, d, J=17.6 Hz), 3.82 (3H, s), 3.72-3.61 (1H, m), 3.31-3.22 (2H, m), 3.18 (1H, dd, J=14.0, 5.2 Hz), 2.59 (1H, dd, J=14.0, 8.4 Hz), 2.16 (3H, s), 1.90-1.74 (2H, m), 0.88 (3H, t, J=7.3 Hz)

MS: 501 (M+H)$^+$

Example 288

N-{1-[4-(acetylamino)phenyl]propyl}-6-(5-chloro-2-methoxybenzyl)-3,7-dioxo-1,4-diazepan-1-carboxamide (Compound 288) (Diastereomer of Compound 287)

Instead of the starting material of Example 282, that is, the compound S134, the compound 123 was used for the similar procedure as in Example 282 to obtain the title compound.

NMR (CDCl$_3$): δ9.44 (1H, d, J=7.7 Hz), 7.44 (2H, d, J=8.3 Hz), 7.27-7.17 (3H, m), 7.11 (1H, d, J=2.5 Hz), 7.13-7.04 (1H, br), 6.79 (1H, d, J=8.8 Hz), 5.59 (1H, brs), 5.36 (1H, d, J=17.4 Hz), 4.73 (1H, dd, J=14.4, 7.1 Hz), 4.05 (1H, d, J=17.4 Hz), 3.81 (3H, s), 3.72-3.61 (1H, m), 3.36-3.27 (2H, m), 3.18 (1H, dd, J=14.0, 5.0 Hz), 2.59 (1H, dd, J=14.0, 8.6 Hz), 2.16 (3H, s), 1.93-1.75 (2H, m), 0.90 (3H, t, J=7.3 Hz)

MS: 501 (M+H)$^+$

Example 289

N-(2-chloro-5-{[6-(5-chloro-2-methoxybenzyl)-3,7-dioxo-1,4-diazepan-1-yl]sulfonyl}phenyl)methane Sulfonamide (Compound 289)

To the compound 90 (51 mg) in pyridine (0.5 ml) solution, methanesulfonyl chloride (10 μM) was added under ice cooling and the mixture was stirred at room temperature for 1 hour. The reaction solution was diluted with ethyl acetate, then the mixture was successively washed with saturated potassium hydrogensulfate aqueous solution and saturated saline, dried over with anhydrous sodium sulfate, then concentrated. The residue was purified by silica gel column chromatography (hexane/ethyl acetate=3/1) to obtain the title compound (1.7 mg).

NMR (CDCl$_3$): δ7.99 (1H, d, J=2.1 Hz), 7.80 (1H, dd, J=8.5, 2.1 Hz), 7.61 (1H, d, J=8.5 Hz), 7.18 (1H, dd, J=8.7, 2.6 Hz), 7.04-6.96 (1H, br), 7.01 (1H, d, J=2.6 Hz), 6.77 (1H, d, J=8.7 Hz), 5.77 (1H, br), 4.99 (1H, d, J=17.7 Hz), 4.43 (1H, d, J=17.7 Hz), 3.80 (3H, s), 3.55-3.48 (2H, m), 3.25-3.18 (1H, m), 3.22 (3H, s), 3.09 (1H, dd, J=13.9, 5.0 Hz), 2.51 (1H, dd, J=13.9, 8.7 Hz)

MS: 550 (M+H)$^+$

Example 290

6-(5-chloro-2-methoxybenzyl)-N-(1-{4-[(methylsulfonyl)amino]phenyl}propyl)-3,7-dioxo-1,4-diazepan-1-carboxamide (Compound 290)

Instead of the starting material of Example 289, that is, compound 90, the compound 123 was used for the similar procedure as in Example 289 to obtain the title compound.

NMR (CDCl$_3$): δ9.48 (1H, d, J=7.4 Hz), 7.28 (2H, d, J=8.4 Hz), 7.22 (1H, dd, J=8.7, 2.6 Hz), 7.17 (2H, d, J=8.4 Hz), 7.14 (1H, d, J=2.6 Hz), 6.81 (1H, d, J=8.7 Hz), 6.37 (1H, s), 5.67 (1H, brs), 5.35 (1H, d, J=17.6 Hz), 4.76 (1H, dd, J=14.4, 7.1 Hz), 4.08 (1H, d, J=17.6 Hz), 3.83 (3H, s), 3.71-3.63 (1H, m), 3.37-3.30 (2H, m), 3.19 (1H, dd, J=14.0, 5.4 Hz), 3.00 (3H, s), 2.63 (1H, dd, J=14.0, 8.2 Hz), 1.90-1.75 (2H, m), 0.93 (3H, t, J=7.3 Hz)

MS: 537 (M+H)$^+$

Reference Example 177

(2E)-2-{[(tert-butoxycarbonyl)amino]methyl}-3-(5-fluoro-2-methoxyphenyl)-2-propenoic Acid (Compound S177)

Instead of the ingredient in Reference Example 2, that is, the compound S1, 5-fluoro-2-methoxybenzaldehyde was used for the similar procedure as in Reference Example 2 to Reference Example 5 and Reference Example 23 to obtain the title compound.

Reference Example 178

(2E)-2-{[(tert-butoxycarbonyl)amino]methyl}-3-(3-pyridyl)-2-propenoic Acid (Compound S178)

Instead of the starting material in Reference Example 2, that is, the compound S1, nicotine aldehyde was used for the similar procedure as in Reference Example 2 to Reference Example 5 and Reference Example 23 to obtain the title compound.

Reference Example 179

(2E)-2-{[(tert-butoxycarbonyl)amino]methyl}-3-(4-pyridyl)-2-propenoic Acid (Compound S179)

Instead of the starting material in Reference Example 2, that is, the compound S1, isonicotine aldehyde was used for the similar procedure as in Reference Example 2 to Reference Example 5 and Reference Example 23 to obtain the title compound.

Reference Example 180

(2E)-2-{[(tert-butoxycarbonyl)amino]methyl}-3-(6-fluoro-2-methoxyphenyl)-2-propenoic Acid (Compound S180)

Instead of the starting material in Reference Example 2, that is, the compound S1,5-fluoro-2-methoxybenzaldehyde was used for the similar procedure as in Reference Example 2 to Reference Example 5 and Reference Example 23 to obtain the title compound.

NMR (CDCl$_3$): δ7.75-7.45 (1H, m), 7.35-7.21 (1H, m), 6.80-6.68 (2H, m), 3.97 (2H, d, J=6.0 Hz), 3.86 (3H, s), 1.50-1.05 (9H, m)

Reference Example 181

(2E)-3-(4,5-dichloro-2-methoxyphenyl)-2-[[(trifluoroacetyl)amino]methyl}-2-propenoic Acid (Compound S181)

Instead of the starting material in Reference Example 2, that is, the compound S1, 4,5-dichloro-2-methoxybenzaldehyde was used for the similar procedure as in Reference Example 2 to Reference Example 6 to obtain the title compound.

NMR (CDCl₃): δ7.96 (1H, s), 7.57 (1H, s), 7.15-6.95 (2H, m), 4.33 (2H, d, J=6.1 Hz), 3.86 (3H, s)

Reference Example 182

(2E)-3-(3,5-difluoro-2-methoxyphenyl)-2-[[(trifluoroacetyl)amino]methyl}-2-propenoic Acid (Compound S182)

Instead of the starting material in Reference Example 2, that is, the compound S1, 3,5-difluoro-2-methoxybenzaldehyde was used for successively the similar procedures as in Reference Example 2 to Reference Example 6 to obtain the title compound.
NMR (CDCl₃): δ7.99 (1H, s), 7.08 (1H, br), 7.05-7.00 (1H, m), 6.99-6.90 (1H, m), 4.33 (2H, d, J=6.2 Hz), 3.89 (3H, s)

Reference Example 183

(2E)-3-(2-fluorophenyl)-2-[[(trifluoroacetyl)amino] methyl}-2-propenoic Acid (Compound S183)

Instead of the starting material in Reference Example 2, that is, the compound S1, 2-fluorobenzaldehyde was used for the similar procedure as in Reference Example 2 to Reference Example 6 to obtain the title compound.

Reference Example 184

(2E)-3-(5-chloro-4-fluoro-2-methoxyphenyl)-2-[[(trifluoroacetyl)amino]methyl}-2-propenoic Acid (Compound S184)

Instead of the starting material in Reference Example 2, that is, the compound S1, 5-chloro-4-fluoro-2-methoxybenzaldehyde was used for the similar procedure as in Reference Example 2 to Reference Example 6 to obtain the title compound.
NMR (CDCl₃): δ7.96 (1H, s), 7.55 (1H, d, J=8.2 Hz), 7.06 (1H, br), 6.77 (1H, d, J=10.6 Hz), 4.34 (2H, d, J=6.0 Hz), 3.85 (3H, s)

Reference Example 185

(2Z)-2-{[(tert-butoxycarbonyl)amino]ethyl}-3-(2-isopropoxy-5-chlorophenyl)-2-propenoic Acid (Compound S185)

Instead of the n-butyl iodide of Reference Example 53, i-propyl iodide was used for the similar procedure as in Reference Example 53 to obtain the title compound.

Example 291

4-[(4-chlorophenyl)sulfonyl]-6-(3-pyridinylmethyl)-1,4-diazepan-2,5-dione (Compound 291)

Instead of the starting material of Reference Example 119, that is, the compound S26, the compound S178 was used for the similar procedure as in Reference Example 119, Reference Example 120, Reference Example 124, Example 1, and Example 29 to obtain the title compound.
NMR (DMSO-d6): δ8.44 (1H, s), 8.4 (1H, d, J=4.7 Hz), 7.93 (2H, d, J=8.5 Hz), 7.86 (1H, br), 7.73 (2H, d, J=8.5 Hz), 7.63 (1H, d, J=7.9 Hz), 7.29 (1H, dd, J=7.9, 4.7 Hz), 4.9 (1H, d, J=17.6 Hz), 4.53 (1H, d, J=17.6 Hz), 3.88-3.74 (1H, m), 3.10-2.89 (3H, m), 2.60-2.47 (1H, m)
MS: 394 (M+H)⁺

Example 292

4-[(4-chlorophenyl)sulfonyl]-6-(4-pyridinylmethyl)-1,4-diazepan-2,5-dione (Compound 292)

Instead of the starting material of Reference Example 119, that is, the compound S26, the compound S179 was used for the similar procedure as in Reference Example 119, Reference Example 120, Reference Example 124, Example 1, and Example 29 to obtain the title compound.
NMR (DMSO-d6): δ8.44 (2H, d, J=5.3 Hz), 7.92 (2H, d, J=8.6 Hz), 7.87 (1H, br), 7.73 (2H, d, J=8.6 Hz), 7.24 (2H, d, J=5.3 Hz), 4.92 (1H, d, J=17.6 Hz), 4.54 (1H, d, J=17.6 Hz), 3.90-3.79 (1H, m), 3.09-2.90 (3H, m), 2.65-2.46 (1H, m)
MS: 394 (M+H)⁺

Example 293

6-(5-chloro-2-isopropoxybenzyl)-4-[(4-chlorophenyl)sulfonyl]-1,4-diazepan-2,5-dione (Compound 293)

Instead of the starting material of Reference Example 119, that is, the compound S26, the compound S185 was used for the similar procedure as in Reference Example 119, Reference Example 120, Reference Example 124, Example 1, and Example 29 to obtain the title compound.
NMR (CDCl₃): δ7.96 (2H, d, J=8.7 Hz), 7.52 (2H, d, J=8.7 Hz), 7.15 (1H, dd, J=8.8, 2.6 Hz), 7.02 (1H, d, J=2.6 Hz), 6.76 (1H, d, J=8.8 Hz), 5.69 (1H, br), 5.01 (1H, d, J=17.6 Hz), 4.58-4.48 (1H, m), 4.35 (1H, d, J=17.6 Hz), 3.53-3.43 (1H, m), 3.23 (1H, dt, J=13.0, 4.2 Hz), 3.14 (1H, d, J=13.0 Hz), 3.07 (1H, dd, J=14.2, 4.8 Hz), 2.54 (1H, dd, J=14.2, 9.1 Hz), 1.29 (6H, d, J=6.0 Hz)
MS: 485 (M+H)⁺

Example 294

4-[(4-chlorophenyl)sulfonyl]-6-(4,5-dichloro-2-methoxybenzyl)-1,4-diazepan-2,5-dione (Compound 294)

Instead of the starting material of Reference Example 119, that is, the compound S26, the compound S181 was used for the similar procedure as in Reference Example 117, Reference Example 122, Example 1, and Example 29 to obtain the title compound.
NMR (CDCl₃): δ7.96 (2H, d, J=8.7 Hz), 7.52 (2H, d, J=8.7 Hz), 7.12 (1H, s), 6.93 (1H, s), 5.7 (1H, br), 5 (1H, d, J=17.7 Hz), 4.39 (1H, d, J=17.7 Hz), 3.81 (3H, s), 3.49-3.38 (1H, m), 3.22 (1H, dt, J=11.7, 4.4 Hz), 3.16 (1H, d, J=11.7 Hz), 3.08 (1H, dd, J=14.2, 5.2 Hz), 2.53 (1H, dd, J=14.2, 8.6 Hz)
MS: 493 (M+H)⁺

Example 295

4-[(4-chlorophenyl)sulfonyl]-6-(3,5-difluoro-2-methoxybenzyl)-1,4-diazepan-2,5-dione (Compound 295)

Instead of the starting material of Reference Example 119, that is, the compound S26, the compound S182 was used for the similar procedure as in Reference Example 117, Reference Example 122, Example 1, and Example 29 to obtain the title compound.

NMR (CDCl$_3$): δ7.95 (2H, d, J=8.7 Hz), 7.52 (2H, d, J=8.7 Hz), 6.80-6.71 (1H, m), 6.65-6.59 (1H, m), 5.71 (1H, br), 5 (1H, d, J=17.6 Hz), 4.4 (1H, d, J=17.6 Hz), 3.85 (3H, s), 3.48-3.36 (1H, m), 3.24 (1H, dt, J=13.2, 4.4 Hz), 3.16 (1H, d, J=13.2 Hz), 3.09 (1H, dd, J=14.1, 5.1 Hz), 2.61 (1H, dd, J=14.1, 8.7 Hz)

MS: 459 (M+H)$^+$

Example 296

4-[(4-chlorophenyl)sulfonyl]-6-(2-fluorobenzyl)-1,4-diazepan-2,5-dione (Compound 296)

Instead of the starting material of Reference Example 119, that is, the compound S26, the compound S183 was used for the similar procedure as in Reference Example 117, Reference Example 122, Example 1, and Example 29 to obtain the title compound.

NMR (CDCl$_3$): δ7.96 (2H, d, J=8.7 Hz), 7.52 (2H, d, J=8.7 Hz), 7.29-7.21 (1H, m), 7.19-6.99 (3H, m), 5.8 (1H, br), 5 (1H, d, J=17.7 Hz), 4.42 (1H, d, J=17.7 Hz), 3.48-3.35 (1H, m), 3.32-3.12 (3H, m), 2.66 (1H, dd, J=14.4, 8.9 Hz)

MS: 411 (M+H)$^+$

Example 297

6-(5-chloro-4-fluoro-2-methoxybenzyl)-4-[(4-chlorophenyl)sulfonyl]-1,4-diazepan-2,5-dione (Compound 297)

Instead of the starting material of Reference Example 119, that is, the compound S26, the compound S184 was used for the similar procedure as in Reference Example 117, Reference Example 122, Example 1, and Example 29 to obtain the title compound.

NMR (CDCl$_3$): δ7.96 (2H, d, J=8.7 Hz), 7.52 (2H, d, J=8.7 Hz), 7.07 (1H, d, J=8.3 Hz), 6.68 (1H, d, J=10.7 Hz), 5.68 (1H, br), 5.01 (1H, d, J=17.7 Hz), 4.39 (1H, d, J=17.7 Hz), 3.08 (3H, s), 3.48-3.35 (1H, m), 3.23 (1H, dt, J=13.2, 4.0 Hz), 3.15 (1H, d, J=13.2 Hz), 3.08 (1H, dd, J=14.3, 5.3 Hz), 2.52 (1H, dd, J=14.3, 8.6 Hz)

MS: 475 (M+H)$^+$

Example 298

4-[(4-chlorophenyl)sulfonyl]-6-(2-fluoro-6-methoxybenzyl)-1,4-diazepan-2,5-dione (Compound 298)

Instead of the starting material of Reference Example 119, that is, the compound S26, the compound S180 was used for the similar procedure as in Reference Example 119, Reference Example 120, Reference Example 124, Example 1, and Example 29 to obtain the title compound.

NMR (CDCl$_3$): δ7.99 (2H, d, J=8.8 Hz), 7.54 (2H, d, J=8.8 Hz), 7.21 (1H, dd, J=8.4, 7.0 Hz), 6.71-6.64 (2H, m), 5.62 (1H, br), 5.02 (1H, d, J=17.6 Hz), 4.41 (1H, d, J=17.6 Hz), 3.82 (3H, s), 3.46-3.35 (1H, m), 3.25-3.10 (2H, m), 3.09-3.00 (1H, m), 2.82 (1H, dd, J=14.1, 10.9 Hz)

MS: 441 (M+H)$^+$

Reference Example 186 tert-butyl [4-(1-aminopropyl)phenyl]acetate Hydrochloride (Compound S186)

To tert-butyl(4-propionylphenyl)acetate (1 g) in ethanol (20 ml) solution, sodium acetate (0.7 g) and hydroxylamine hydrochloride (0.44 g) were added and the mixture was stirred at 90° C. for 3 hours. Distilled water was added to the reaction solution, and the mixture was extracted with ethyl acetate. The organic layer was washed with saturated saline, dried over with anhydrous sodium sulfate, then concentrated. Ethanol (22 ml) and 10% palladium carbon (0.6 g) were added to the residue, and the mixture was stirred under hydrogen atmosphere at 5 atm for 40 hours. The insoluble compound was filtered out, then a 4N hydrochloric acid/ethyl acetate solution was added to the filtrate and the mixture concentrated. Hexane/ethyl acetate was added to the residue, and the precipitated solid was collected by filtration to obtain the title compound (0.74 g).

NMR (DMSO-d6): δ8.34 (2H, br), 7.4 (2H, d, J=8.1 Hz), 7.3 (2H, d, J=8.1 Hz), 4.1 (1H, dd, J=9.0, 5.6 Hz), 3.58 (2H, s), 2.01-1.72 (2H, m), 1.39 (9H, s), 0.75 (3H, t, J=7.4 Hz)

Example 299

{4-[(1R)-1-({[(6R)-6-(5-chloro-2-methoxybenzyl)-3,7-dioxo-1,4-diazepan-1-yl]carbonyl}amino)propyl]phenyl}acetic Acid (Compound 299) (Diastereomer of Compound 300)

The compound S141C was used instead of the starting material compound of Reference Example 142A, that is, the compound S141A, and the compound S186 was used instead of the starting material compound of Reference Example 142A, that is, the compound S83, for the similar procedure as in Reference Example 142A and Example 91 to obtain the title compound.

NMR (DMSO-d6): δ9.45 (1H, d, J=7.5 Hz), 7.68 (1H, br), 7.33 (1H, d, J=2.4 Hz), 7.30-7.18 (5H, m), 7 (1H, d, J=8.8 Hz), 4.75 (1H, d, J=17.3 Hz), 4.66 (1H, q, J=7.5 Hz), 4.47 (1H, d, J=17.3 Hz), 3.90-3.81 (1H, m), 3.78 (3H, s), 3.54 (2H, s), 3.15 (1H, t, J=13.0 Hz), 3.06-2.92 (2H, m), 2.70-2.62 (1H, m), 1.86-1.70 (2H, m), 0.83 (3H, t, J=7.3 Hz)

MS: 502 (M+H)$^+$

Example 300

{4-[(1S)-1-({[(6R)-6-(5-chloro-2-methoxybenzyl)-3,7-dioxo-1,4-diazepan-1-yl]carbonyl}amino)propyl]phenyl}acetic Acid (Compound 300) (Diastereomer of Compound 299)

The compound S141B was used instead of the starting material compound of Reference Example 142A, that is, the compound S141A, and the compound S186 was used instead of the starting material compound of Reference Example 142A, that is, the compound S83, for the similar procedure as in Reference Example 142A and Example 91 to obtain the title compound.

NMR (DMSO-d6): δ9.42 (1H, d, J=7.7 Hz), 7.66 (1H, br), 7.33 (1H, d, J=2.7 Hz), 7.30-7.19 (5H, m), 7.01 (1H, d, J=8.8 Hz), 4.76 (1H, d, J=17.4 Hz), 4.67 (1H, q, J=7.7 Hz), 4.52 (1H, d, J=17.4 Hz), 3.93-3.82 (1H, m), 3.79 (3H, s), 3.54 (2H, s), 3.13 (1H, t, J=13.0 Hz), 3.04-2.92 (2H, m), 2.70-2.60 (1H, m), 1.86-1.70 (2H, m), 0.82 (3H, t, J=7.3 Hz)

MS: 502 (M+H)$^+$

Example 301

3-[(1R)-1-({[(6R)-6-(2-methoxybenzyl)-3,7-dioxo-1,4-diazepan-1-yl]carbonyl}amino)propyl]benzoic Acid (Compound 301)

To the compound 91 (100 mg) in tetrahydrofuran (2 ml) solution, a 10% palladium carbon catalyst (100 mg) was added and the mixture was stirred at a 5 kgf/cm² hydrogen atmosphere at room temperature for 36 hours. The reaction was incomplete, so the reaction was stopped once, the catalyst was filtered, and the residue was washed with ethyl acetate. The filtrate and the washings were combined, successively washed with saturated ammonium chloride aqueous solution, water, and saturated saline, dried over with anhydrous sodium sulfate, then concentrated. The residue was dissolved in tetrahydrofuran (2 ml), 10% palladium carbon catalyst (100 mg) was added, and the mixture was again stirred in 5 kgf/cm² hydrogen atmosphere at room temperature for 18 hours. The end of the reaction was confirmed, then the catalyst was filtered, and the residue was washed with ethyl acetate. The filtrate and the washings were combined, successively washed with saturated ammonium chloride aqueous solution, water, and saturated saline, dried over with anhydrous sodium sulfate, then concentrated. The residue was crystallized from ethyl acetate/hexane to obtain the title compound (63.9 mg).

NMR (DMSO-$d_6$): δ9.52 (1H, d, J=7.4 Hz), 7.87 (1H, s), 7.83 (1H, d, J=7.7 Hz), 7.71 (1H, d, J=3.6 Hz), 7.57 (1H, d, J=7.7 Hz), 7.47 (1H, dd, J=7.7, 7.7 Hz), 7.25-7.21 (2H, m), 6.98 (1H, d, J=8.2 Hz), 6.90 (1H, dd, J=7.3, 7.3 Hz), 4.75 (1H, dt, J=7.4, 7.4 Hz), 4.74 (1H, d, J=17.1 Hz), 4.47 (1H, d, J=17.1 Hz), 3.83 (1H, m), 3.79 (3H, s), 3.17 (1H, dd, J=12.7, 12.7 Hz), 3.02 (1H, m), 3.01 (1H, dd, J=14.4, 4.8 Hz), 2.65 (1H, dd, J=14.4, 9.2 Hz), 1.86-1.76 (2H, m), 0.85 (3H, t, J=7.4 Hz)

MS: 454 (M+H)⁺

Example 302

2-amino-4-[(1R)-1-({[(6R)-6-(2-methoxybenzyl)-3,7-dioxo-1,4-diazepan-1-yl]carbonyl}amino)propyl]benzoic Acid (Compound 302)

Instead of the starting material of Example 301, that is, the compound 91, the compound 178B was used for the similar procedure as in Example 301. The obtained crude product was crystallized from ethyl acetate/hexane to obtain the title compound.

NMR (DMSO-$d_6$): δ9.45 (1H, d, J=7.6 Hz), 7.71 (1H, d, J=4.2 Hz), 7.65 (1H, d, J=8.3 Hz), 7.25-7.21 (2H, m), 6.99 (1H, d, J=8.9 Hz), 6.90 (1H, dd, J=7.9, 7.9 Hz), 6.63 (1H, d, J=1.5 Hz), 6.44 (1H, dd, J=8.3, 1.5 Hz), 4.77 (1H, d, J=17.2 Hz), 4.54 (1H, dt, J=7.6, 7.1 Hz), 4.49 (1H, d, J=17.2 Hz), 3.84 (1H, m), 3.79 (3H, s), 3.19 (1H, m), 3.16 (1H, dd, J=12.7, 12.7 Hz), 3.00 (1H, dd, J=14.4, 4.5 Hz), 2.64 (1H, dd, J=14.4, 8.9 Hz), 1.78-1.72 (2H, m), 0.84 (3H, t, J=7.3 Hz)

MS: 469 (M+H)⁺

Example 303

2-amino-4-[(1R)-1-({[(6S)-6-(2-methoxybenzyl)-3,7-dioxo-1,4-diazepan-1-yl]carbonyl}amino)propyl]benzoic Acid Acetate Solvate (Compound 303)

Instead of the starting material of Example 301, that is, the compound 91, the compound 179B was used for the similar procedure as in Example 301. The obtained crude product was crystallized from acetic acid to obtain the title compound.

NMR (DMSO-$d_6$): δ9.44 (1H, d, J=7.4 Hz), 7.69 (1H, d, J=3.9 Hz), 7.66 (1H, d, J=8.3 Hz), 7.25-7.21 (2H, m), 6.99 (1H, d, J=8.4 Hz), 6.90 (1H, ddd, J=7.3, 7.3, 1.3 Hz), 6.63 (1H, d, J=1.5 Hz), 6.45 (1H, dd, J=8.3, 1.5 Hz), 4.79 (1H, d, J=17.2 Hz), 4.56 (1H, dt, J=7.9, 7.9 Hz), 4.51 (1H, d, J=17.2 Hz), 3.84 (1H, m), 3.79 (3H, s), 3.14 (1H, dd, J=12.6, 12.6 Hz), 3.02 (1H, m), 3.01 (1H, dd, J=14.4, 4.4 Hz), 2.64 (1H, dd, J=14.4, 9.2 Hz), 1.91 (3H, s), 1.77-1.72 (2H, m), 0.83 (3H, t, J=7.3 Hz)

MS: 469 (M+H)⁺

Reference Example 187

2-chlorophenyl(6E)-6-(5-chloro-2-methoxybenzylidene)-3,7-dioxo-4-(2,4,6-trimethoxybenzyl)-1,4-diazepan-1-carboxylate (Compound S187)

The compound S139 was used instead of the starting material compound of Reference Example 141A, that is, the compound S140A, for the similar procedure as in Reference Example 141A to obtain the title compound.

NMR (CDCl₃): δ7.68 (1H, s), 7.44 (1H, dd, J=7.8, 1.3 Hz), 7.35-7.18 (4H, m), 7.01 (1H, d, J=2.5 Hz), 6.83 (1H, d, J=8.7 Hz), 5.9 (2H, s), 4.76 (2H, s), 4.73 (2H, s), 4.04 (2H, s), 3.82 (3H, s), 3.79 (3H, s), 3.64 (6H, s)

Example 304

2-amino-4-[(1R)-1-({[(6E)-6-(5-chloro-2-methoxybenzylidene)-3,7-dioxo-1,4-diazepan-1-yl]carbonyl}amino)propyl]benzoic Acid (Compound 304)

The compound S187 was used instead of the starting material compound of Reference Example 142A, that is, the compound S141A, and the compound S101 was used instead of the starting material compound of Reference Example 142A, that is, the compound S83, for the similar procedure as in Reference Example 142A and Example 91 to obtain the title compound.

NMR (DMSO-d6): δ9.34 (1H, d, J=7.8 Hz), 7.66 (1H, br), 7.46 (1H, d, J=8.3 Hz), 7.33 (1H, s), 7.28 (1H, dd, J=8.8, 2.6 Hz), 7.18 (1H, d, J=2.6 Hz), 6.94 (1H, d, J=8.8 Hz), 6.45 (1H, s), 6.26 (1H, d, J=8.3 Hz), 4.38 (1H, q, J=7.8 Hz), 4.33 (2H, s), 4.05-4.00 (2H, m), 3.64 (3H, s), 1.63-1.50 (2H, m), 0.96 (3H, t, J=7.2 Hz)

MS: 501 (M+H)⁺

Example 305

4-[(1R)-1-({[(6S)-6-(5-chloro-2-methoxybenzyl)-3,7-dioxo-1,4-diazepan-1-yl]carbonyl}amino)propyl]-2-nitrobenzoic Acid (Compound 304)

The compound S162 was used instead of the starting material of Example 179A, that is, the compound S165, for the similar procedure as in Example 179A to obtain the title compound.

NMR (DMSO-d6): δ9.43 (1H, d, J=7.1 Hz), 7.95 (1H, d, J=1.3 Hz), 7.83 (1H, d, J=8.0 Hz), 7.73 (1H, dd, J=8.0, 1.3 Hz), 7.67 (1H, d, J=3.7 Hz), 7.34 (1H, d, J=2.6 Hz), 7.27 (1H, dd, J=8.8, 2.6 Hz), 7.01 (1H, d, J=8.8 Hz), 4.83 (1H, q, J=7.1 Hz), 4.71 (1H, d, J=17.2 Hz), 4.53 (1H, d, J=17.2 Hz), 3.93-3.82 (1H, m), 3.79 (3H, s), 3.15 (1H, t, J=12.9 Hz), 3.08-2.95 (2H, m), 2.66 (1H, dd, J=14.3, 9.1 Hz), 1.90-1.75 (2H, m), 0.87 (3H, t, J=7.3 Hz)

MS: 533 (M+H)⁺

Reference Example 188

1-{4-[(4-methoxybenzyl)sulfanyl]phenyl}-1-propanone (Compound S188)

To (4-methoxyphenyl)methane thiol (20 g) in N,N-dimethylformamide (200 ml) solution, sodium hydride (60% mineral oil dispersion) was added under ice cooling and the mixture was stirred for 10 minutes. 4-fluoropropiophenone was added to the reaction solution and the mixture was stirred at room temperature for 3 hours. 1N sodium hydroxide aqueous solution was added to the reaction solution, and the mixture was extracted with ethyl acetate. The organic layer was washed with saturated saline, dried over with anhydrous sodium sulfate, then concentrated. Methanol was added to the residue, and the precipitated solid was collected by filtration to obtain the title compound (37.4 g).

NMR (CDCl$_3$): δ7.84 (2H, d, J=8.2 Hz), 7.3 (2H, d, J=8.2 Hz), 7.27 (2H, d, J=8.9 Hz), 6.84 (2H, d, J=8.9 Hz), 4.16 (2H, s), 3.79 (3H, s), 3.00-2.90 (2H, m), 1.25-1.17 (3H, m)

Reference Example 189

1-{4-[(4-methoxybenzyl)sulfanyl]phenyl}-1-propanamine Hydrochloride (Compound S189)

To the compound S188 (5 g) in ethanol (100 ml) solution, sodium acetate (2.1 g) and hydroxylamine hydrochloride (1.3 g) were added and the mixture was stirred at 90° C. for 3 hours. Distilled water was added to the reaction solution, and the precipitated solid was collected by filtration. To 2.5 g of the solid, acetic acid (25 ml) and zinc (5 g) were added and the mixture was stirred at 80° C. for 1 hour. The insoluble compound was filtered out, and the filtrate was concentrated. Ethanol was added to the residue, then the precipitated solid was collected by filtration. The obtained solid was diluted with ethyl acetate, 4M hydrochloric acid/ethyl acetate solution was added, and the mixture was stirred at 60° C. This was allowed to cool and the precipitated solid was collected by filtration to obtain the title compound (0.7 g).

NMR (DMSO-d6): δ8.29 (3H, br), 7.41-7.32 (4H, m), 7.28 (2H, d, J=8.7 Hz), 6.85 (2H, d, J=8.7 Hz), 4.21 (2H, s), 4.15-4.05 (1H, m), 1.99-1.70 (2H, m), 0.74 (3H, t, J=7.4 Hz)

Reference Example 190

(6R)-6-(5-chloro-2-methoxybenzyl)-N-((1R)-1-{4-[(4-methoxybenzyl)sulfanyl]phenyl}-1-propyl)-3,7-dioxo-4-(2,4,6-trimethoxybenzyl)-1,4-diazepan-1-carboxamide (Compound S190)

The compound S141C was used instead of the starting material compound of Reference Example 142A, that is, the compound S141A, and the compound S189 was used instead of the starting material compound of Reference Example 142A, that is, the compound S83, for the similar procedure as in Reference Example 142A to obtain the title compound.

NMR (CDCl$_3$): δ9.43 (1H, d, J=8.0 Hz), 7.30-7.12 (7H, m), 6.91 (1H, d, J=2.6 Hz), 6.85-6.80 (1H, m), 6.74 (1H, d, J=8.7 Hz), 6.07 (2H, s), 5.31 (1H, d, J=17.4 Hz), 4.80-4.72 (2H, m), 4.32 (1H, d, J=13.8 Hz), 4.19 (1H, d, J=17.4 Hz), 4.05 (2H, s), 3.83 (3H, s), 3.78 (3H, s), 3.76 (3H, s), 3.7 (6H, s), 3.59-3.45 (2H, m), 3.15-3.09 (1H, m), 3.07-3.00 (2H, m), 2.39 (1H, dd, J=13.8, 9.5 Hz), 1.88-1.75 (2H, m), 0.87 (3H, t, J=7.4 Hz)

Reference Example 191

(6R)-6-(5-chloro-2-methoxybenzyl)-3,7-dioxo-N-[(1R)-1-(4-sulfanylphenyl)propyl]-1,4-diazepan-1-carboxamide (Compound S191)

To the compound S190 (290 mg), trifluoroacetic acid (5.8 ml), anisole (0.58 ml), and mercury acetate (II) (131 mg) were added and the mixture was stirred at room temperature for 5 hours. The reaction solution was concentrated, and the residue was purified by SH-silica gel column chromatography (SH Silica: Fuji Silicia Chemical) (ethyl acetate) and silica gel column chromatography (ethyl acetate) to obtain the title compound (117 mg).

NMR (DMSO-d6): δ9.39 (1H, d, J=7.6 Hz), 7.67 (1H, d, J=3.2 Hz), 7.37-7.30 (3H, m), 7.26 (1H, dd, J=8.8, 2.6 Hz), 7.09 (2H, d, J=8.2 Hz), 6.99 (1H, d, J=8.8 Hz), 4.74 (1H, d, J=17.1 Hz), 4.6 (1H, q, J=7.6 Hz), 4.47 (1H, d, J=17.1 Hz), 3.90-3.80 (1H, m), 3.77 (3H, s), 3.14 (1H, t, J=13.0 Hz), 3.05-2.92 (2H, m), 2.70-2.60 (1H, m), 1.80-1.69 (2H, m), 0.8 (3H, t, J=7.0 Hz)

Example 306

4-[(1R)-1-({[(6R)-6-(5-chloro-2-methoxybenzyl)-3,7-dioxo-1,4-diazepan-1-yl]carbonyl}amino)propyl]benzenesulfonic Acid (Compound 306)

To the compound S191 (110 mg) in acetic acid 1.1 (1.1 ml) solution, a 32% by weight peracetic acid/acetic acid solution (0.22 ml) was added and the mixture was stirred at room temperature for 2 hours. The reaction solution was concentrated, then acetone was added to the residue. The precipitated solid was collected by filtration to obtain the title compound (94 mg).

NMR (DMSO-d6): δ9.46 (1H, d, J=7.5 Hz), 7.68 (1H, br), 7.54 (2H, d, J=8.2 Hz), 7.33 (1H, d, J=2.6 Hz), 7.27 (1H, dd, J=8.8, 2.6 Hz), 7.22 (2H, d, J=8.2 Hz), 7 (1H, d, J=8.8 Hz), 4.75 (1H, d, J=17.1 Hz), 4.67 (1H, q, J=7.5 Hz), 4.47 (1H, d, J=17.1 Hz), 3.92-3.80 (1H, m), 3.78 (3H, s), 3.15 (1H, t, J=13.2 Hz), 3.06-2.92 (2H, m), 2.71-2.64 (1H, m), 1.90-1.69 (2H, m), 0.82 (3H, t, J=7.3 Hz)

MS: 524 (M+H)$^+$

Reference Example 192

({3-[(tert-butoxycarbonyl)amino]-2-hydroxypropanoyl}amino)ethyl Acetate (Compound S192)

Isoserine (454 mg) was dissolved in 2M sodium hydroxide aqueous solution (4 ml) and tetrahydrofuran (8 ml), then di-tert-butyldicarbonate (1 g) was added and the mixture was stirred at room temperature for 1.5 hours. Further, di-tert-butyldicarbonate (0.5 g) was added and the mixture was stirred at room temperature for 1 hour. To the reaction mixture, N,N-dimethylethylenediamine (0.5 ml) was added, the mixture was stirred at room temperature for 30 minutes, then tetrahydrofuran was distilled off. Saturated potassium hydrogensulfate aqueous solution was added to the obtained aqueous mixture to acidify the mixture, then the mixture was extracted with ethyl acetate. The extract was combined and successively washed with water and saturated saline, dried over with anhydrous sodium sulfate, and concentrated to obtain N-tert-butoxycarbonyl-isoserine as a crude product (829 mg). The obtained product (829 mg) was dissolved in dichloromethane (10 ml), glycine ethyl ester hydrochloride (850 mg), 1-hydroxybenztriazole (655 mg), and triethylamine (0.85 ml) were added to the solution, and the mixture was stirred at room temperature for 15 minutes. The reaction mixture was cooled to 0° C., then 1-(3-dimethylaminopropyl)-3-ethylcarbodiimide hydrochloride (930 mg) was added and the mixture was stirred at room temperature for 2 hours. The reaction mixture was diluted with ethyl acetate, the mixture was successively washed with water, saturated potassium hydrogensulfate aqueous solution, water, saturated sodium hydrogencarbonate aqueous solution, and saturated saline, and the organic layer was dried over with anhydrous sodium sulfate, then concentrated. The residue was purified by silica gel column chromatography (hexane/ethyl acetate=2/1→1/2) to obtain the title compound (441 mg).

NMR (CDCl$_6$): δ7.46 (1H, br), 5.23 (1H, br.s), 5.22 (1H, br.s), 4.23 (1H, m), 4.22 (2H, q, J=7.1 Hz), 4.11 (1H, dd, J=18.1, 5.1 Hz), 4.00 (1H, dd, J=18.1, 5.4 Hz), 3.63 (1H, ddd, J=14.8, 6.2, 2.9 Hz), 1.45 (9H, s), 1.29 (3H, t, J=7.1 Hz)

Reference Example 193

({3-[(tert-butoxycarbonyl)amino]-2-[(2-methoxyphenyl)sulfanyl]propanoyl}amino)ethyl Acetate (Compound S193)

(Step 1) The compound S192 (441 mg) was dissolved in pyridine (5 ml), the mixture was cooled to 0° C., then methanesulfonyl chloride (0.18 ml) was added and the mixture was stirred at 0° C. for 45 minutes. Further, methanesulfonyl chloride (0.18 ml) was added and the mixture was stirred at 0° C. for 45 minutes. Water (5 ml) was added and the mixture was stirred for 15 minutes, then the mixture was extracted with ethyl acetate. The extract was combined and successively washed with saturated potassium hydrogensulfate aqueous solution, water, and saturated saline, dried over with anhydrous sodium sulfate, and concentrated to obtain ({3-[(tert-butoxycarbonyl)amino]-2-[(methylsulfonyl)oxy]propanoyl}amino)ethyl acetate as a crude product.

NMR (CDCl$_6$): δ6.96 (1H, br), 5.10 (1H, dd, J=5.3, 5.3 Hz), 5.09 (1H, br), 4.23 (2H, q, J=7.1 Hz), 4.12 (1H, dd, J=18.1, 5.8 Hz), 4.01 (1H, dd, J=18.1, 5.3 Hz), 3.82 (1H, ddd, J=14.9, 7.1, 5.3 Hz), 3.59 (1H, ddd, J=14.9, 5.3, 5.3 Hz), 3.21 (3H, s), 1.44 (9H, s), 1.30 (3H, t, J=7.1 Hz)

(Step 2) To 2-methoxybenzenethiol (850 mg) in N,N-dimethylformamide (2 ml) solution, sodium hydride in 60% mineral oil dispersion (243 mg) a was added at 0° C., then N,N-dimethylformamide (2 ml) was further added and the temperature raised to room temperature. The ({3-[(tert-butoxycarbonyl)amino]-2-[(methylsulfonyl)oxy]propanoyl}amino)ethyl acetate obtained as a crude product (397 mg) at step 1 was added to the obtained solution, then the mixture was stirred at room temperature for 1.5 hours. Water (10 ml) was added to the reaction mixture and the mixture was extracted with a hexane-ethyl acetate (1:1) mixed solvent. The extract was combined and was successively washed with saturated potassium hydrogensulfate aqueous solution and saturated saline, dried over with anhydrous sodium sulfate, then concentrated. The residue was purified by silica gel column chromatography (hexane/ethyl acetate=2/1→1/2) to obtain the title compound (400 mg)

NMR (CDCl$_6$): δ7.48 (1H, d, J=7.3 Hz), 7.31 (1H, ddd, J=8.1, 7.6, 1.6 Hz), 7.20 (1H, br), 6.94-6.90 (2H, m), 5.33 (1H, br), 4.23 (2H, q, J=7.2 Hz), 4.06 (1H, dd, J=18.4, 5.4 Hz), 4.00 (1H, dd, J=18.4, 5.4 Hz), 3.94 (3H, s), 3.80 (1H, m), 3.62-3.56 (2H, m), 1.41 (9H, s), 1.29 (3H, t, J=7.2 Hz)

Reference Example 194

6-[(2-methoxyphenyl)sulfanyl]-1-(2,4,6-trimethoxybenzyl)-1,4-diazepan-2,5-dione (Compound S194)

Instead of the starting material of Reference Example 136, that is, the compound S135, the compound S193 was used for the similar procedure as in Examples 136 to 139 to obtain the title compound.

NMR (CDCl$_6$): δ7.30 (1H, ddd, J=7.6, 7.3, 1.8 Hz), 7.27 (1H, dd, J=7.6, 1.8 Hz), 6.86 (1H, ddd, J=7.3, 6.8, 1.8 Hz), 6.83 (1H, dd, J=6.8, 1.8 Hz), 6.04 (1H, dd, J=8.0, 4.1 Hz), 4.92 (1H, d, J=13.7 Hz), 4.26 (1H, d, J=13.7 Hz), 4.10 (1H, dd, J=15.4, 4.1 Hz), 3.83 (3H, s), 3.81 (3H, s), 3.70 (6H, s), 3.69 (1H, dd, J=15.2, 12.0 Hz), 3.53 (1H, dd, J=15.4, 8.0 Hz), 3.45 (1H, dd, J=12.0, 6.4 Hz), 3.32 (1H, dd, J=15.2, 6.4 Hz)

Reference Example 195 tert-butyl 4-[(1R)-1-({[6-[(2-methoxyphenyl)sulfanyl]-3,7-dioxo-4-(2,4,6-trimethoxybenzyl)-1,4-diazepan-1-yl]carbonyl}amino)propyl]-2-nitrobenzoate (Compound S195A) and (Compound S195B) (Compound 195A and Compound 195B are Diastereomers)

Instead of the starting material of Reference Example 141, that is, the compound S140, the compound S194 was used for the similar procedure as in Reference Examples 141 and 142 to obtain the title compound.
(Compound S195A)

NMR (CDCl$_6$): δ9.46 (1H, d, J=7.2 Hz), 7.68 (1H, d, J=7.9 Hz), 7.67 (1H, d, J=1.5 Hz), 7.54 (1H, dd, J=8.0, 1.5 Hz), 7.33 (1H, dd, J=7.8, 1.6 Hz), 7.36 (1H, ddd, J=8.0, 8.0, 1.6 Hz), 6.90-6.87 (2H, m), 6.07 (2H, s), 4.84 (1H, dt, J=7.3, 7.3 Hz), 4.75 (1H, d, J=16.0 Hz), 4.69 (1H, d, J=13.7 Hz), 4.56 (1H, d, J=16.0 Hz), 4.40 (1H, d, J=13.7 Hz), 4.16 (1H, dd, J=11.2, 7.2 Hz), 3.83 (3H, s), 3.82 (3H, s), 3.65 (6H, s), 3.47 (1H, dd, J=14.9, 11.2 Hz), 3.36 (1H, dd, J=14.9, 7.2 Hz), 1.79 (1H, dq, J=7.4, 7.2 Hz), 1.55 (9H, s), 0.91 (3H, t, J=7.4 Hz)
(Compound S195B)

NMR (CDCl$_6$): δ9.46 (1H, d, J=6.6 Hz), 7.70-7.67 (2H, m), 7.51 (1H, d, J=7.9 Hz), 7.35 (1H, ddd, J=7.4, 7.4, 1.3 Hz), 7.31 (1H, dd, J=8.0, 1.3 Hz), 6.87-6.83 (2H, m), 6.07 (2H, s), 4.83 (1H, dt, J=7.9, 7.5 Hz), 4.81 (1H, d, J=15.8 Hz), 4.68 (1H, d, J=13.7 Hz), 4.46 (1H, d, J=15.8 Hz), 4.44 (1H, d, J=13.7 Hz), 4.11 (1H, dd, J=11.0, 7.5 Hz), 3.83 (3H, s), 3.77 (3H, s), 3.66 (6H, s), 3.45 (1H, dd, J=15.1, 11.0 Hz), 3.36 (1H, dd, J=15.1, 7.5 Hz), 1.78 (1H, dq, J=7.5, 7.2 Hz), 1.55 (9H, s), 0.91 (3H, t, J=7.2 Hz)

Example 307

2-amino-4-{(1R)-1-[({6-[(2-methoxyphenyl)sulfanyl]-3,7-dioxo-1,4-diazepan-1-yl}carbonyl)amino]propyl}benzoic Acid (Compound 307) (Diastereomer of Compound 308)

Instead of the starting material of Reference Example 164, that is, the compound S161, the compound S195A was used for the similar procedure as in Reference Example 164 and Example 178. The obtained crude product was purified by preparative thin layer chromatography (chloroform/ethyl acetate/methanol/acetic acid=10/10/1/0.1 to obtain the title compound.

NMR (DMSO-d$_6$): δ9.17 (1H, d, J=7.6 Hz), 7.90 (1H, d, J=4.4 Hz), 7.66 (1H, d, J=8.0 Hz), 7.44 (1H, dd, J=7.7, 1.5 Hz), 7.33 (1H, ddd, J=7.7, 7.7, 1.5 Hz), 7.06 (1H, d, J=8.2 Hz), 6.98 (1H, dd, J=7.6, 7.6 Hz), 6.61 (1H, s), 6.43 (1H, d, J=8.2 Hz), 5.19 (1H, dd, J=11.3, 4.4 Hz), 4.73 (1H, d, J=17.0 Hz), 4.64 (1H, d, J=17.0 Hz), 4.53 (1H, dt, J=7.3, 7.6 Hz), 3.84 (3H, s), 3.47 (1H, m), 3.30 (1H, m), 1.77-1.69 (2H, m), 0.83 (3H, t, J=7.3 Hz)
MS: 487 (M+H)$^+$

Example 308

2-amino-4-{(1R)-1-[({6-[(2-methoxyphenyl)sulfanyl]-3,7-dioxo-1,4-diazepan-1-yl}carbonyl)amino]propyl}benzoic Acid (Compound 308) (Diastereomer of Compound 307)

Instead of the starting material of Reference Example 164, that is, the compound S161, the compound S195B was used for the similar procedure as in Reference Example 164 and Example 178. The obtained crude product was purified by preparative thin layer chromatography (chloroform/ethyl acetate/methanol/acetic acid=10/10/1/0.1 to obtain the title compound.

NMR (DMSO-$d_6$): δ9.16 (1H, d, J=7.8 Hz), 7.88 (1H, d, J=4.7 Hz), 7.67 (1H, d, J=8.1 Hz), 7.44 (1H, dd, J=7.6, 1.5 Hz), 7.33 (1H, ddd, J=7.8, 7.8, 1.5 Hz), 7.06 (1H, d, J=8.2 Hz), 6.97 (1H, dd, J=7.5, 7.5 Hz), 6.60 (1H, s), 6.43 (1H, d, J=7.9 Hz), 5.21 (1H, dd, J=11.3, 4.7 Hz), 4.74 (1H, d, J=17.3 Hz), 4.66 (1H, d, J=17.3 Hz), 4.54 (1H, dt, J=7.8, 7.6 Hz), 3.83 (3H, s), 3.45 (1H, m), 3.25 (1H, m), 1.80-1.71 (2H, m), 0.84 (3H, t, J=7.4 Hz)

MS: 487 (M+H)$^+$

Test Example 1

Measurement of Inhibitory Activity of Test Compound for Human Chymase

The inhibitory activity of the compounds of the present invention for recombinant human chymase was measured by the method of Pasztor et al. (Pasztor et al., Acta. Biol. Hung. 42: 285-95, 1991). That is, recombinant human chymase was diluted to an appropriate concentration by a 50 mM tris-hydrochloride buffer (pH 7.5), 1M sodium chloride, and 0.01% (v/v) Triton X-100 to obtain an enzyme solution. A 10 mM dimethyl sulfoxide (hereinafter referred to as DMSO) solution of Suc-Ala-Ala-Pro-Phe-MCA (Peptide Institute) was diluted 20-fold at the time of use by 50 mM tris-hydrochloride buffer (pH 7.5), 1M sodium chloride, and 0.01% (v/v) Triton X-100 to obtain the substrate solution. 75 μl of the enzyme solution was mixed with 5 μl of the test compound in a DMSO solution, and then incubated for 10 minutes. 20 μl of the substrate solution was added to the mixture, and incubated for a further 10 minutes at room temperature. The reaction was stopped by adding 50 μl of 30% (v/v) acetic acid. The intensity of the fluorescence (Ex380 nm, Em460 nm) of the fluorescent substance MCA produced by the degradation of the substrate was measured by a fluorescent photometer (Fluoroscan II, Labsystems Japan). Simultaneously, 5 μl of DMSO was added to a reaction instead of the test compound, and was used as a blank. The inhibitory activity for chymase was calculated based on the value of the blank. Further, the rate of inhibition and the 50% inhibition concentration (IC$_{50}$ value) were calculated. The IC$_{50}$ values of representative compounds are shown in Table XII.

TABLE XII

| | Tested compound | IC$_{50}$ value (μM) |
|---|---|---|
| 1 | Compound 4 | 1.1 |
| 2 | Compound 15 | 0.16 |
| 3 | Compound 29 | 0.034 |
| 4 | Compound 37 | 0.39 |
| 5 | Compound 61 | 0.26 |
| 6 | Compound 67 | 0.019 |
| 7 | Compound 90 | 0.093 |
| 8 | Compound 91 | 0.2 |
| 9 | Compound 150 | 0.16 |
| 10 | Compound 151 | 0.38 |
| 11 | Compound 178A | 0.3 |
| 12 | Compound 179B | 0.14 |
| 13 | Compound 214 | 0.019 |
| 14 | Compound 239 | 0.26 |
| 15 | Compound 263 | 0.46 |
| 16 | Compound 269 | 0.024 |
| 17 | Compound 272 | 2.4 |
| 18 | Compound 285 | 4.7 |

Test Example 2

Effect of Test Compounds on Dermatitis Model Induced by Repeated Application of Hapten Dinitrofluorobenzene (hereinafter referred to as "DNFB") was used as hapten, and dermatitis was induced in accordance with the method of Nagai et al. (Nagai et al., J. Pharmacol. Exp. Ther. 288: 43-50, 1999). That is, dermatitis was induced by repeated application of 12.5 μl of 0.15% (v/v) DNFB (Nacalai Tesque) dissolved in a mixture (ratio 1:3) of acetone (Wako Pure Chemicals) and olive oil (Wako Pure Chemicals) to both sides of the right ear, total 25 μl, once a week in 8 week old female C$_3$H/HeN mice (Crea Japan). As a control group, acetone:olive oil (1:3) was applied by the same protocol. Ear thickness was measured at every week before DNFB application and 24, 48 and 72 hours after DNFB application by using microgauge (Mitutoyo), and ear edema was evaluated by the increase in ear thickness compared to the ear thickness before the first DNFB application. Six compounds of chymase inhibitor (compound 91, compound 178A, compound 150, compound 179B, compound 29, and compound 90) were used as test compounds. The test compound was suspended in 0.5% hydroxypropylcellulose in distilled water (hereinafter referred to as "0.5% HPC-distilled water") and was administered orally at doses of 2 and 10 mg/kg once a day, every day from just before the first application of hapten to the end of the experiment. Further, as a control, 0.5% HPC-distilled water instead of the test compound was administered by the same methods. The number of mice used in this experiment was seven per group.

Transient skin reaction was induced by DNFB application, and this transient skin reaction was increased gradually with increasing the number of DNFB application. As a result of oral administration of test compound to this model, each test compound remarkably inhibited the transient skin reaction. For example, when compound 91, compound 178A, compound 150, compound 179B, compound 29, and compound 90 at a dose of 10 mg/kg were administered orally, the inhibition rates of the skin reaction at 24 hours after DNFB application at fifth application were 26.1%, 20.0%, 29.9%, 32.8%, 31.0%, and 25.1%, respectively.

INDUSTRIAL APPLICABILITY

The compound (I) or its salt or a solvate thereof of the present invention has chymase inhibitory activity and is useful as a pharmaceutical for the prevention and/or treatment of bronchial asthma, urticaria, atopic dermatitis, allergic conjunctivitis, rhinitis, rheumatoid arthritis, mastocytosis, scleroderma, heart failure, cardiac hypertrophy, congestive heart failure, hypertension, atherosclerosis, myocardial ischemia, myocardial infarction, restenosis after PTCA, restenosis after bypass graft surgery, ischemic peripheral circulatory disorders, hyperaldosteronism, diabetic retinopathy, diabetic nephropathy, nephritis, glomerulosclerosis, renal insufficiency, psoriasis, solid tumor, postoperative adhesion, glaucoma, and ocular hypertension, and other diseases. Further, according to the method of production of the present invention, the compound (I), or its salt or a solvate thereof can be efficiently produced with a high yield.

| Ex. No. | Structure |
|---------|-----------|
| 15 | 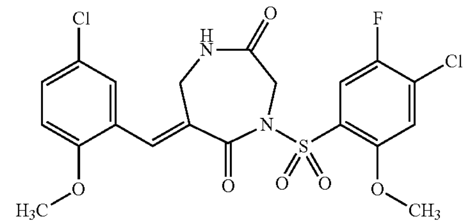 [SMILES: COc1ccc(Cl)cc1/C=C1\CNC(=O)CN(S(=O)(=O)c2cc(F)c(Cl)cc2OC)C1=O] |
| 16 | 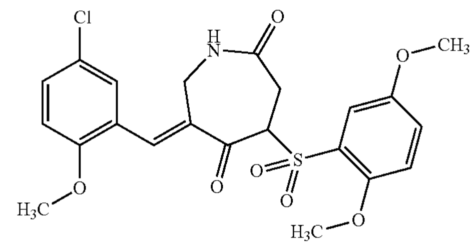 [SMILES: COc1ccc(OC)c(S(=O)(=O)C2CC(=O)NC/C(=C\c3cc(Cl)ccc3OC)C2=O)c1] |
| 17 | 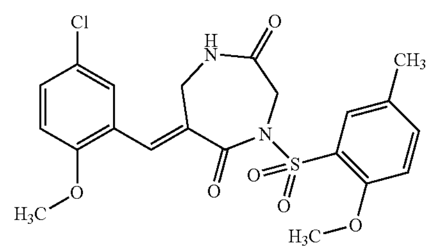 [SMILES: COc1ccc(Cl)cc1/C=C1\CNC(=O)CN(S(=O)(=O)c2cc(C)ccc2OC)C1=O] |
| 18 | 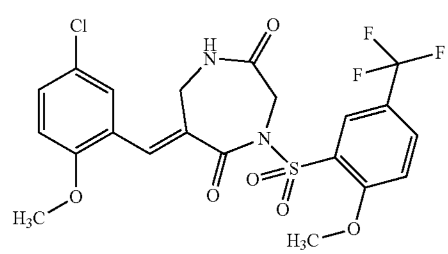 [SMILES: COc1ccc(Cl)cc1/C=C1\CNC(=O)CN(S(=O)(=O)c2cc(C(F)(F)F)ccc2OC)C1=O] |
| 19 | 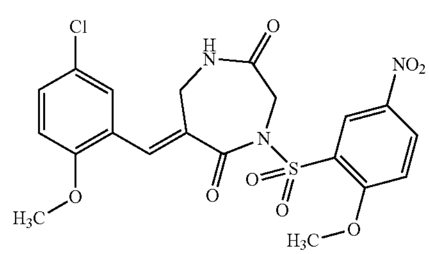 [SMILES: COc1ccc(Cl)cc1/C=C1\CNC(=O)CN(S(=O)(=O)c2cc([N+](=O)[O-])ccc2OC)C1=O] |

-continued
| Ex. No. | Structure |
|---|---|
| 20 | 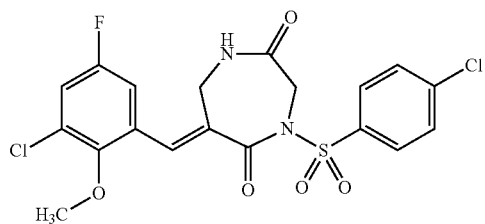 [SMILES: COc1c(Cl)cc(F)cc1/C=C1\CNC(=O)CN(S(=O)(=O)c2ccc(Cl)cc2)C1=O] |
| 21 | 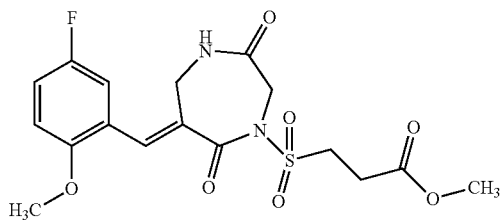 [SMILES: COC(=O)CCS(=O)(=O)N1CC(=O)NC/C(=C\c2cc(F)ccc2OC)C1=O] |
| 22 | 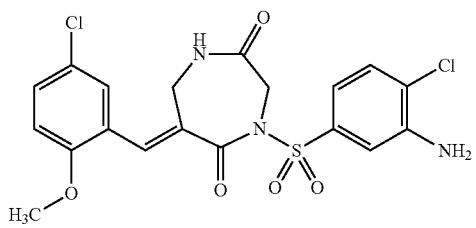 [SMILES: COc1ccc(Cl)cc1/C=C1\CNC(=O)CN(S(=O)(=O)c2ccc(Cl)c(N)c2)C1=O] |
| 23 | 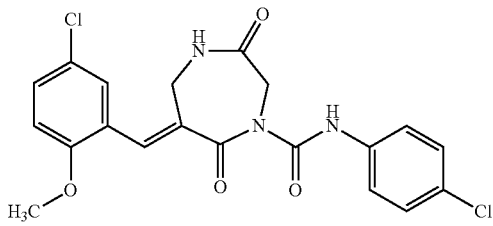 [SMILES: COc1ccc(Cl)cc1/C=C1\CNC(=O)CN(C(=O)Nc2ccc(Cl)cc2)C1=O] |
| 24 | 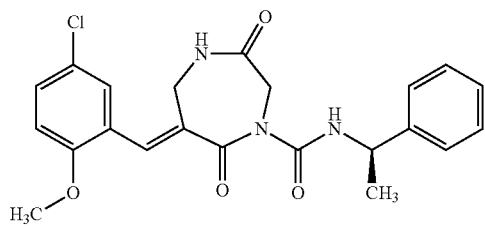 [SMILES: COc1ccc(Cl)cc1/C=C1\CNC(=O)CN(C(=O)N[C@H](C)c2ccccc2)C1=O] |
| 25 | 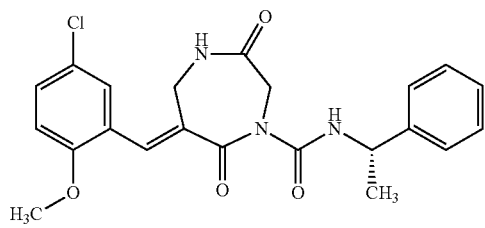 [SMILES: COc1ccc(Cl)cc1/C=C1\CNC(=O)CN(C(=O)N[C@@H](C)c2ccccc2)C1=O] |

-continued
| Ex. No. | Structure |
|---|---|
| 26 | 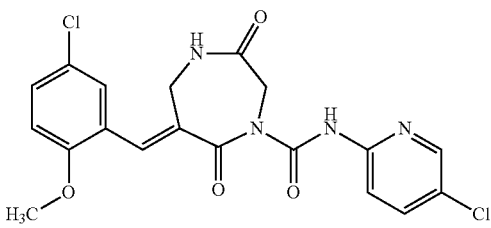 |
| 27 | 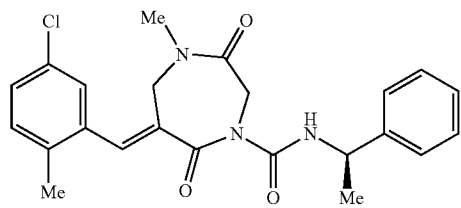 [SMILES: Cc1ccc(Cl)cc1/C=C1\CN(C)C(=O)CN(C(=O)N[C@H](C)c2ccccc2)C1=O] |
| 28 | 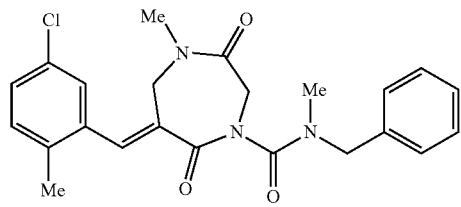 [SMILES: Cc1ccc(Cl)cc1/C=C1\CN(C)C(=O)CN(C(=O)N(C)Cc2ccccc2)C1=O] |
| 29 | 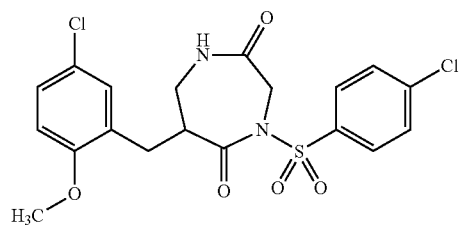 |
| 30 | 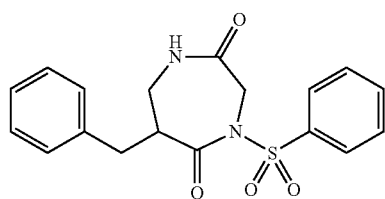 [SMILES: O=C1CN(S(=O)(=O)c2ccccc2)C(=O)C(Cc2ccccc2)CN1] |
| 31 | 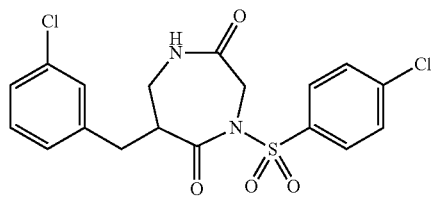 [SMILES: O=C1CN(S(=O)(=O)c2ccc(Cl)cc2)C(=O)C(Cc2cccc(Cl)c2)CN1] |
| 32 | 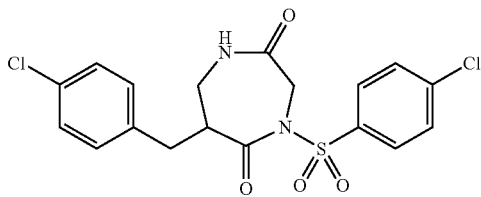 [SMILES: O=C1CN(S(=O)(=O)c2ccc(Cl)cc2)C(=O)C(Cc2ccc(Cl)cc2)CN1] |

| Ex. No. | Structure |
|---|---|
| 33 | 4-fluorobenzyl-substituted diazepane-2,5-dione with 4-chlorophenylsulfonyl group |
| 34 | 4-cyanobenzyl-substituted diazepane-2,5-dione with 4-chlorophenylsulfonyl group |
| 35 | naphthalen-2-ylmethyl-substituted diazepane-2,5-dione with 4-chlorophenylsulfonyl group |
| 36 | benzyl-substituted diazepane-2,5-dione with 4-cyanophenylsulfonyl group |
| 37 | 3-methylbenzyl-substituted diazepane-2,5-dione with 4-chlorophenylsulfonyl group |
| 38 | 3-(trifluoromethyl)benzyl-substituted diazepane-2,5-dione with 4-chlorophenylsulfonyl group |
| 39 | (5-chloro-2-ethoxyphenyl)methyl-substituted diazepane-2,5-dione with 4-chlorophenylsulfonyl group |

-continued
| Ex. No. | Structure |
|---|---|
| 40 | 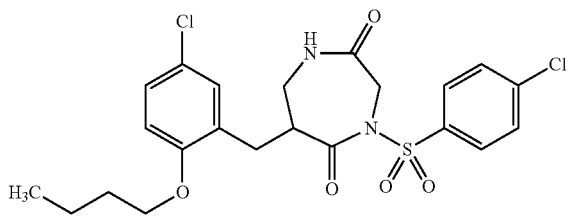 [SMILES: CCCCOc1ccc(Cl)cc1CC1CNC(=O)CN(S(=O)(=O)c2ccc(Cl)cc2)C1=O] |
| 41 | 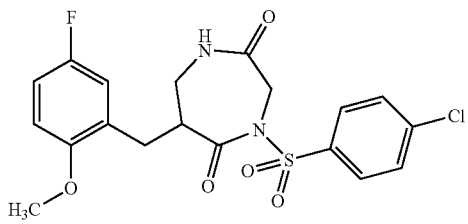 [SMILES: COc1ccc(F)cc1CC1CNC(=O)CN(S(=O)(=O)c2ccc(Cl)cc2)C1=O] |
| 42 | 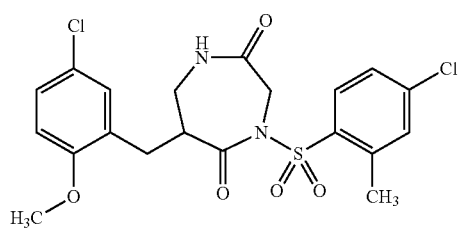 [SMILES: COc1ccc(Cl)cc1CC1CNC(=O)CN(S(=O)(=O)c2ccc(Cl)cc2C)C1=O] |
| 43 | 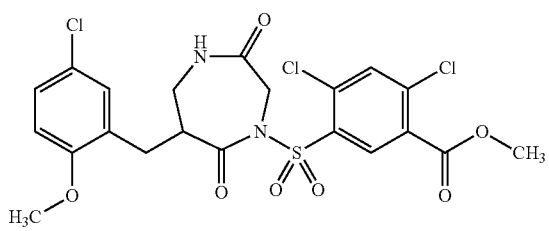 [SMILES: COC(=O)c1cc(S(=O)(=O)N2CC(=O)NCC(Cc3cc(Cl)ccc3OC)C2=O)c(Cl)cc1Cl] |
| 44 | 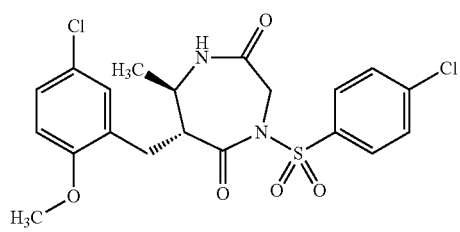 [SMILES: COc1ccc(Cl)cc1C[C@H]1C(=O)N(S(=O)(=O)c2ccc(Cl)cc2)CC(=O)N[C@@H]1C] |
| 45 | 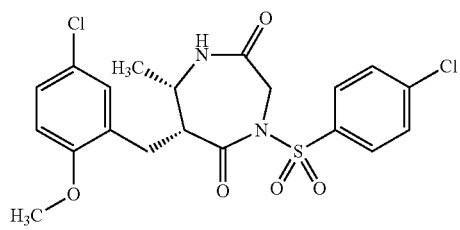 [SMILES: COc1ccc(Cl)cc1C[C@H]1C(=O)N(S(=O)(=O)c2ccc(Cl)cc2)CC(=O)N[C@H]1C] |

-continued
| Ex. No. | Structure |
|---|---|
| 46 | 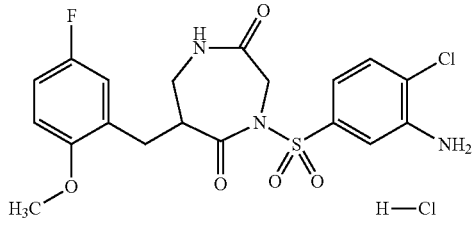 [SMILES: COc1ccc(F)cc1CC1CNC(=O)CN(S(=O)(=O)c2ccc(Cl)c(N)c2)C1=O ; Cl] |
| 47 | 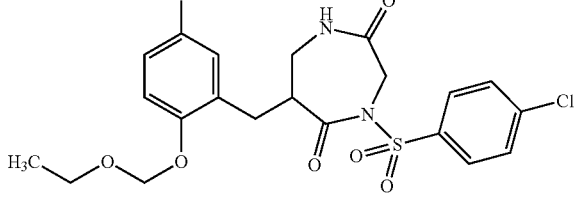 |
| 48 | 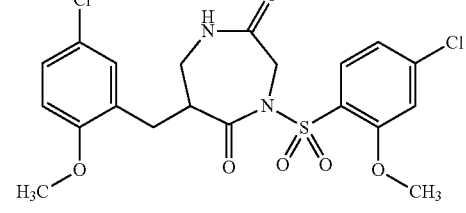 |
| 49 | 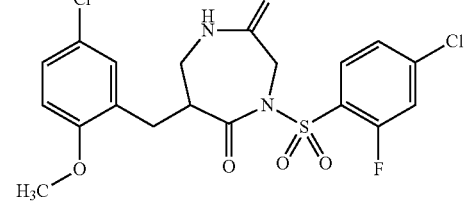 |
| 50 | 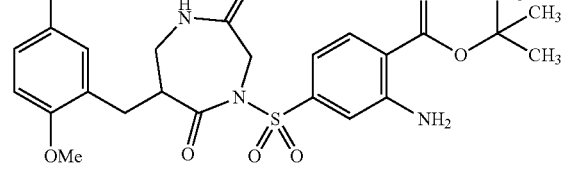 |
| 51 | 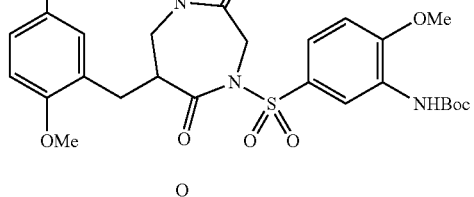 |
| 52 | 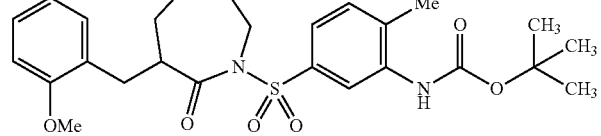 |

| Ex. No. | Structure |
|---|---|
| 53 | 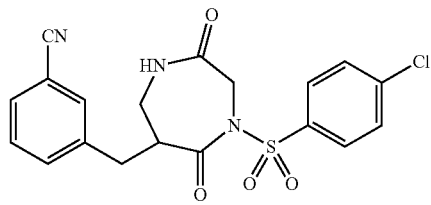 [SMILES: N#Cc1cccc(CC2CNC(=O)CN(S(=O)(=O)c3ccc(Cl)cc3)C2=O)c1] |
| 54 | 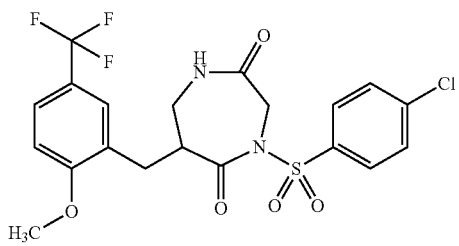 [SMILES: COc1ccc(C(F)(F)F)cc1CC1CNC(=O)CN(S(=O)(=O)c2ccc(Cl)cc2)C1=O] |
| 55 | 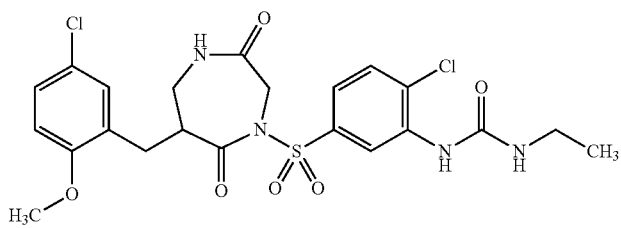 [SMILES: CCNC(=O)Nc1cc(S(=O)(=O)N2CC(=O)NCC(Cc3cc(Cl)ccc3OC)C2=O)ccc1Cl] |
| 56 | 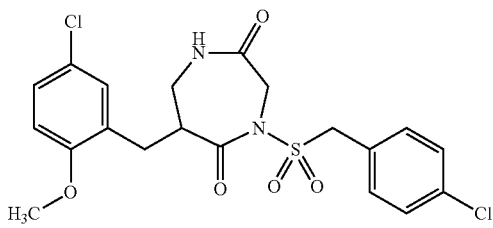 [SMILES: COc1ccc(Cl)cc1CC1CNC(=O)CN(S(=O)(=O)Cc2ccc(Cl)cc2)C1=O] |
| 57 | 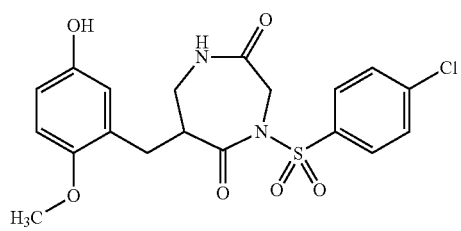 [SMILES: COc1ccc(O)cc1CC1CNC(=O)CN(S(=O)(=O)c2ccc(Cl)cc2)C1=O] |
| 58 | 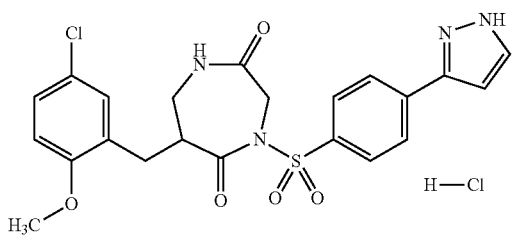 |

| Ex. No. | Structure |
|---|---|
| 59 | 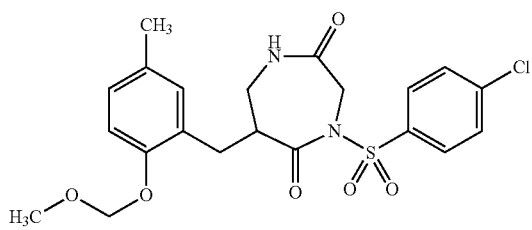 [SMILES: COCOc1ccc(C)cc1CC1CNC(=O)CN(S(=O)(=O)c2ccc(Cl)cc2)C1=O] |
| 60 | 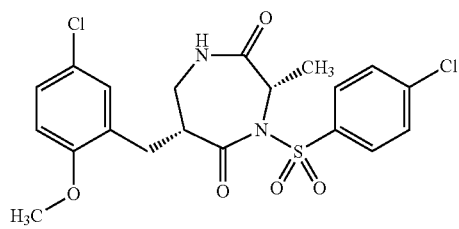 [SMILES: COc1ccc(Cl)cc1C[C@@H]1CNC(=O)[C@H](C)N(S(=O)(=O)c2ccc(Cl)cc2)C1=O] |
| 61 | 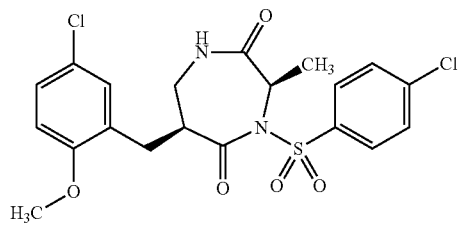 [SMILES: COc1ccc(Cl)cc1C[C@H]1CNC(=O)[C@@H](C)N(S(=O)(=O)c2ccc(Cl)cc2)C1=O] |
| 62 | 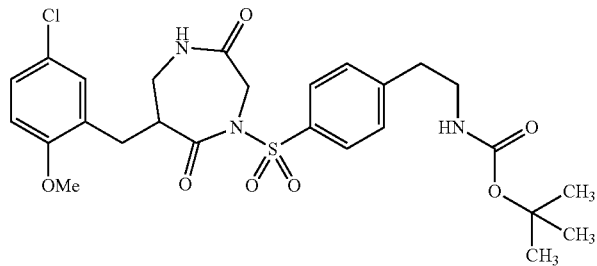 [SMILES: COc1ccc(Cl)cc1CC1CNC(=O)CN(S(=O)(=O)c2ccc(CCNC(=O)OC(C)(C)C)cc2)C1=O] |
| 63 | 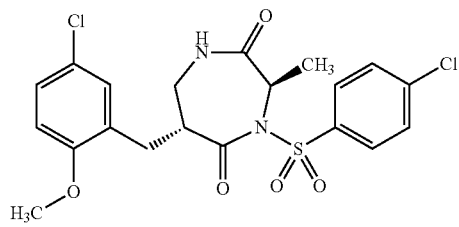 [SMILES: COc1ccc(Cl)cc1C[C@@H]1CNC(=O)[C@@H](C)N(S(=O)(=O)c2ccc(Cl)cc2)C1=O] |
| 64 | 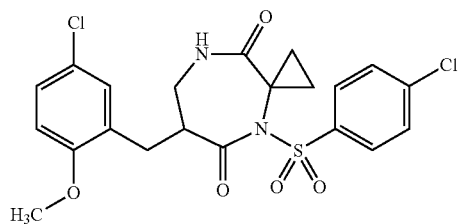 [SMILES: COc1ccc(Cl)cc1CC1CNC(=O)C2(CC2)N(S(=O)(=O)c2ccc(Cl)cc2)C1=O] |

US 8,507,714 B2
-continued
| Ex. No. | Structure |
|---|---|
| 65 | 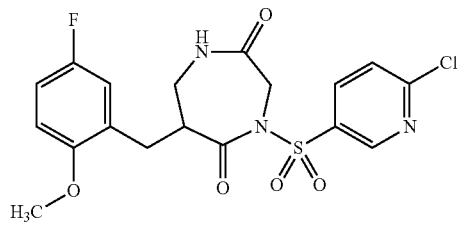 [SMILES: COc1ccc(F)cc1CC1CNC(=O)CN(S(=O)(=O)c2ccc(Cl)nc2)C1=O] |
| 66 | 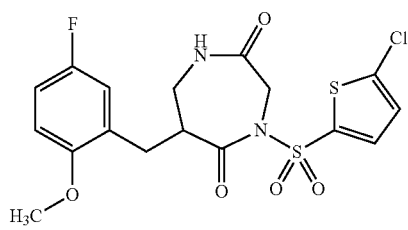 [SMILES: COc1ccc(F)cc1CC1CNC(=O)CN(S(=O)(=O)c2ccc(Cl)s2)C1=O] |
| 67 | 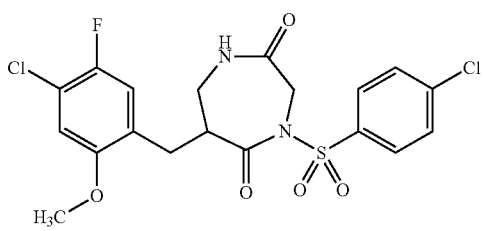 [SMILES: COc1cc(Cl)c(F)cc1CC1CNC(=O)CN(S(=O)(=O)c2ccc(Cl)cc2)C1=O] |
| 68 | 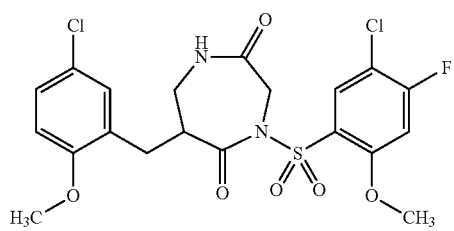 [SMILES: COc1ccc(Cl)cc1CC1CNC(=O)CN(S(=O)(=O)c2cc(Cl)c(F)cc2OC)C1=O] |
| 69 | 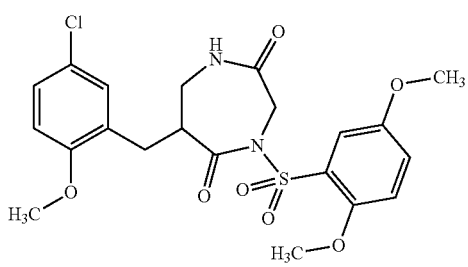 [SMILES: COc1ccc(OC)c(S(=O)(=O)N2CC(=O)NCC(Cc3cc(Cl)ccc3OC)C2=O)c1] |
| 70 | 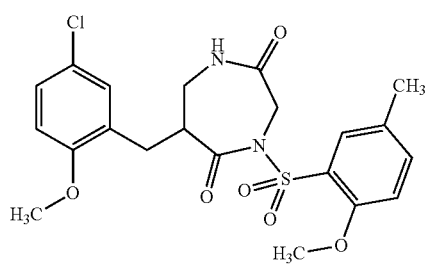 [SMILES: COc1ccc(Cl)cc1CC1CNC(=O)CN(S(=O)(=O)c2cc(C)ccc2OC)C1=O] |

-continued
| Ex. No. | Structure |
|---|---|
| 71 | 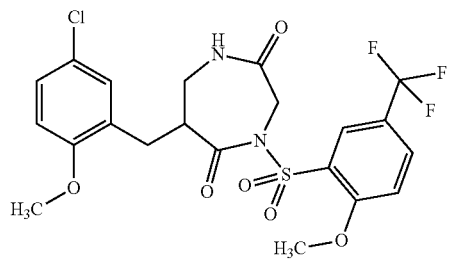 [SMILES: COc1ccc(Cl)cc1CC1CNC(=O)CN(S(=O)(=O)c2cc(C(F)(F)F)ccc2OC)C1=O] |
| 72 | 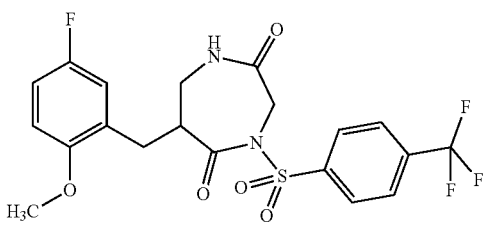 [SMILES: COc1ccc(F)cc1CC1CNC(=O)CN(S(=O)(=O)c2ccc(C(F)(F)F)cc2)C1=O] |
| 73 | 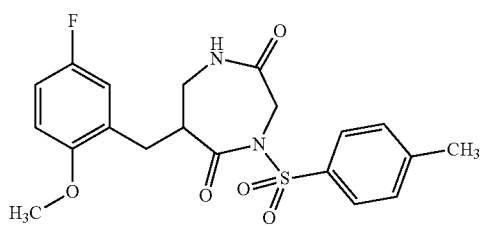 [SMILES: COc1ccc(F)cc1CC1CNC(=O)CN(S(=O)(=O)c2ccc(N)cc2)C1=O] |
| 74 | 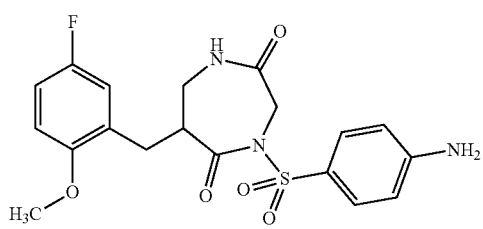 |
| 75 | 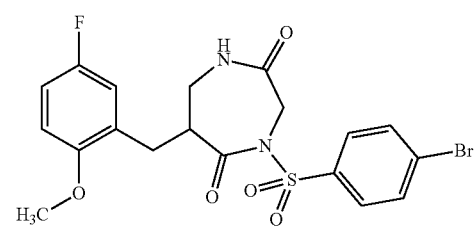 [SMILES: COc1ccc(F)cc1CC1CNC(=O)CN(S(=O)(=O)c2ccc(Br)cc2)C1=O] |
| 76 | 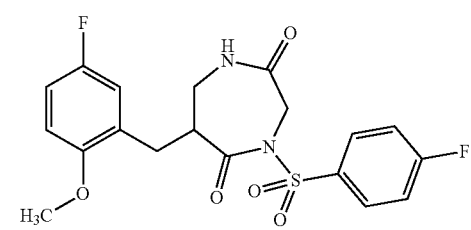 [SMILES: COc1ccc(F)cc1CC1CNC(=O)CN(S(=O)(=O)c2ccc(F)cc2)C1=O] |

-continued

| Ex. No. | Structure |
|---------|-----------|
| 77 | 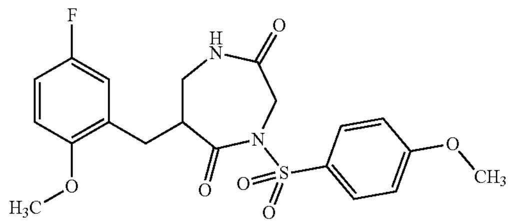 [SMILES: COc1ccc(S(=O)(=O)N2CC(=O)NCC(Cc3cc(F)ccc3OC)C2=O)cc1] |
| 78 | 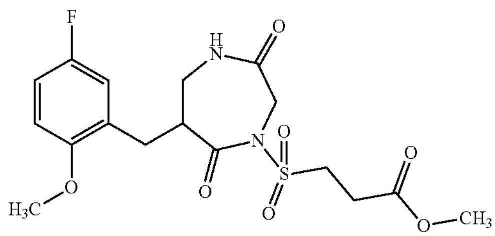 [SMILES: COC(=O)CCS(=O)(=O)N1CC(=O)NCC(Cc2cc(F)ccc2OC)C1=O] |
| 79 | 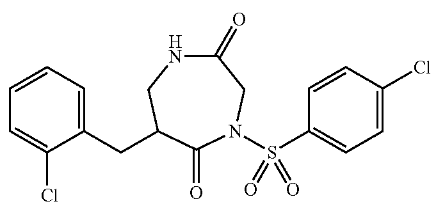 [SMILES: O=C1CN(S(=O)(=O)c2ccc(Cl)cc2)C(=O)C(Cc2ccccc2Cl)CN1] |
| 80 | 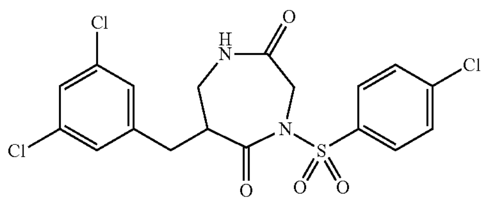 [SMILES: O=C1CN(S(=O)(=O)c2ccc(Cl)cc2)C(=O)C(Cc2cc(Cl)cc(Cl)c2)CN1] |
| 81 | 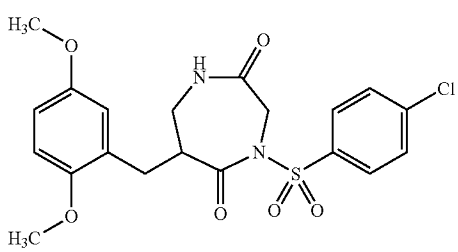 [SMILES: COc1ccc(OC)c(CC2CNC(=O)CN(S(=O)(=O)c3ccc(Cl)cc3)C2=O)c1] |
| 82 | 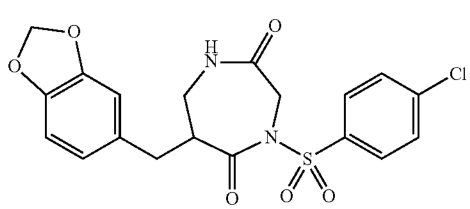 [SMILES: O=C1CN(S(=O)(=O)c2ccc(Cl)cc2)C(=O)C(Cc2ccc3c(c2)OCO3)CN1] |
| 83 | 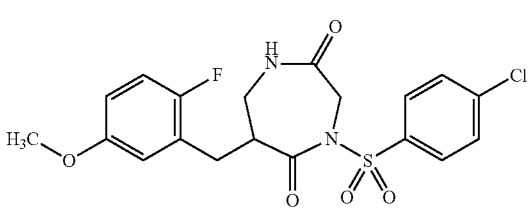 [SMILES: COc1ccc(F)c(CC2CNC(=O)CN(S(=O)(=O)c3ccc(Cl)cc3)C2=O)c1] |

-continued

| Ex. No. | Structure |
|---|---|
| 84 | (structure) |
| 85 | (structure) |
| 86 | (structure) |
| 87 | (structure) |
| 88 | (structure) |
| 89 | (structure) |
| 90 | (structure) |

-continued
| Ex. No. | Structure |
|---|---|
| 91 | 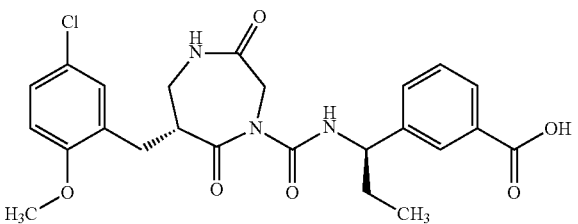 [SMILES: CC[C@@H](NC(=O)N1CC(=O)NC[C@@H](Cc2cc(Cl)ccc2OC)C1=O)c1cccc(C(=O)O)c1] |
| 92 | 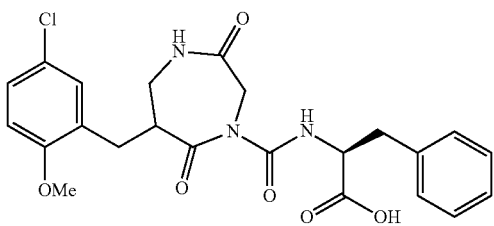 [SMILES: COc1ccc(Cl)cc1CC1CNC(=O)CN(C(=O)N[C@@H](Cc2ccccc2)C(=O)O)C1=O] |
| 93 | 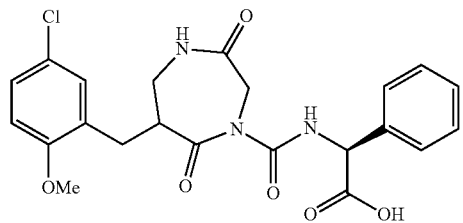 [SMILES: COc1ccc(Cl)cc1CC1CNC(=O)CN(C(=O)N[C@H](C(=O)O)c2ccccc2)C1=O] |
| 94 | 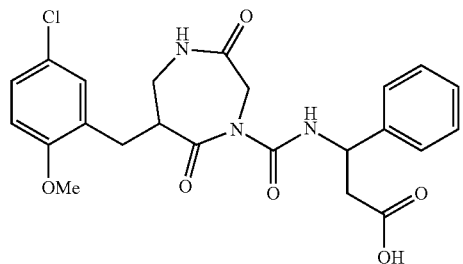 [SMILES: COc1ccc(Cl)cc1CC1CNC(=O)CN(C(=O)NC(CC(=O)O)c2ccccc2)C1=O] |
| 95 | 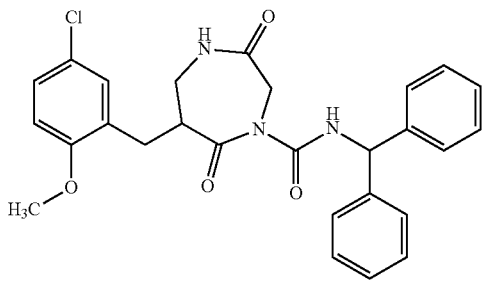 [SMILES: COc1ccc(Cl)cc1CC1CNC(=O)CN(C(=O)NC(c2ccccc2)c2ccccc2)C1=O] |
| 96 | 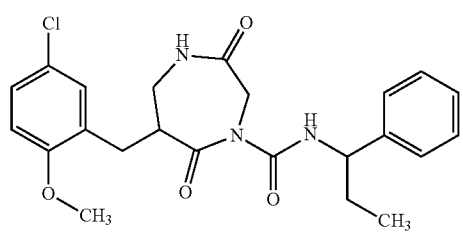 [SMILES: CCC(NC(=O)N1CC(=O)NCC(Cc2cc(Cl)ccc2OC)C1=O)c1ccccc1] |

-continued
| Ex. No. | Structure |
|---|---|
| 97 | 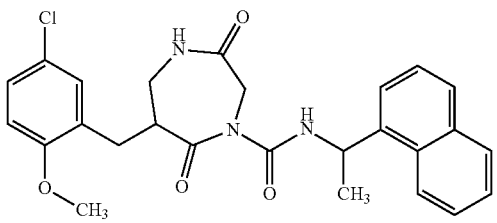 [SMILES: COc1ccc(Cl)cc1CC1CNC(=O)CN(C(=O)NC(C)c2cccc3ccccc23)C1=O] |
| 98 | 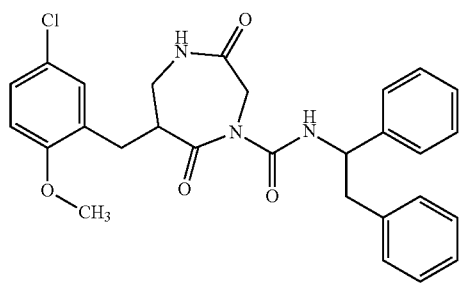 [SMILES: COc1ccc(Cl)cc1CC1CNC(=O)CN(C(=O)NC(Cc2ccccc2)c2ccccc2)C1=O] |
| 99 | 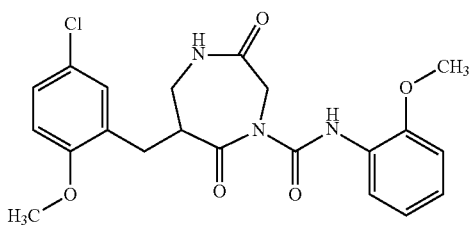 [SMILES: COc1ccc(Cl)cc1CC1CNC(=O)CN(C(=O)Nc2ccccc2OC)C1=O] |
| 100 | 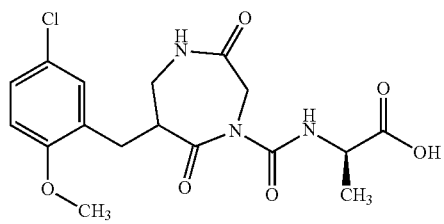 [SMILES: COc1ccc(Cl)cc1CC1CNC(=O)CN(C(=O)N[C@H](C)C(=O)O)C1=O] |
| 101 | 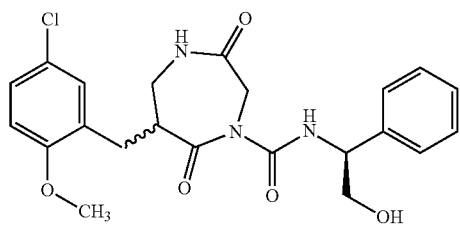 [SMILES: COc1ccc(Cl)cc1CC1CNC(=O)CN(C(=O)N[C@H](CO)c2ccccc2)C1=O] |
| 102 | 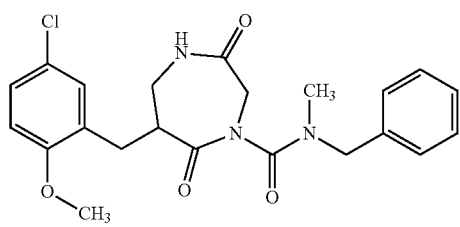 [SMILES: COc1ccc(Cl)cc1CC1CNC(=O)CN(C(=O)N(C)Cc2ccccc2)C1=O] |

-continued
| Ex. No. | Structure |
|---|---|
| 103 | 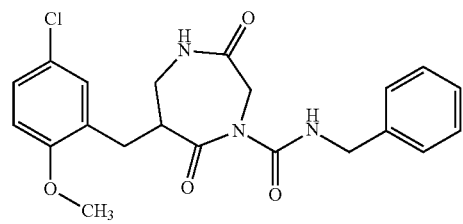 [SMILES: COc1ccc(Cl)cc1CC1CNC(=O)CN(C(=O)NCc2ccccc2)C1=O] |
| 104 | 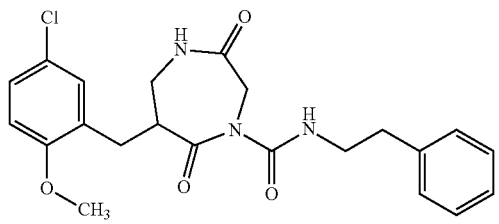 [SMILES: COc1ccc(Cl)cc1CC1CNC(=O)CN(C(=O)NCCc2ccccc2)C1=O] |
| 105 | 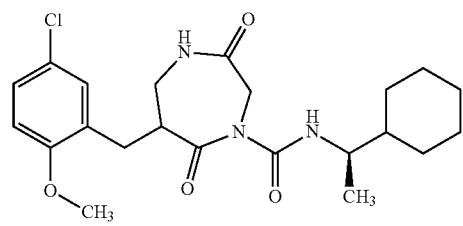 [SMILES: COc1ccc(Cl)cc1CC1CNC(=O)CN(C(=O)N[C@H](C)C2CCCCC2)C1=O] |
| 106 | 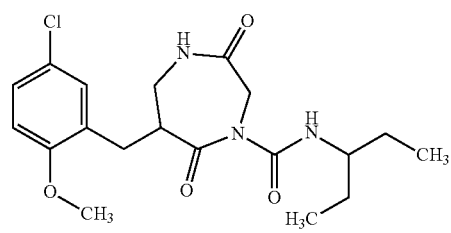 [SMILES: CCC(CC)NC(=O)N1CC(=O)NCC(Cc2cc(Cl)ccc2OC)C1=O] |
| 107 | 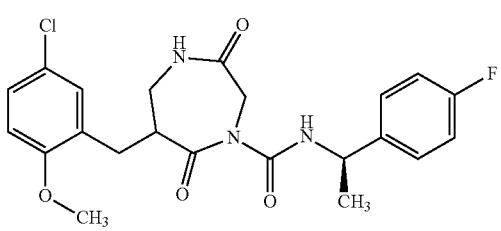 [SMILES: COc1ccc(Cl)cc1CC1CNC(=O)CN(C(=O)N[C@H](C)c2ccc(F)cc2)C1=O] |
| 108 | 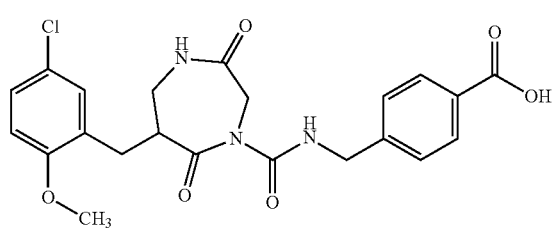 [SMILES: COc1ccc(Cl)cc1CC1CNC(=O)CN(C(=O)NCc2ccc(C(=O)O)cc2)C1=O] |

-continued
| Ex. No. | Structure |
|---|---|
| 109 | 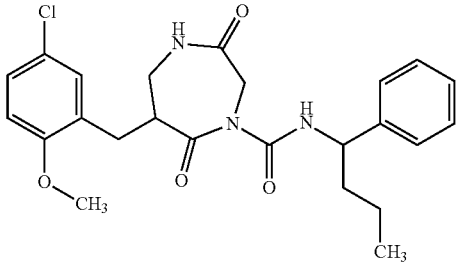 [SMILES: CCCC(NC(=O)N1CC(=O)NCC(Cc2cc(Cl)ccc2OC)C1=O)c1ccccc1] |
| 110 | 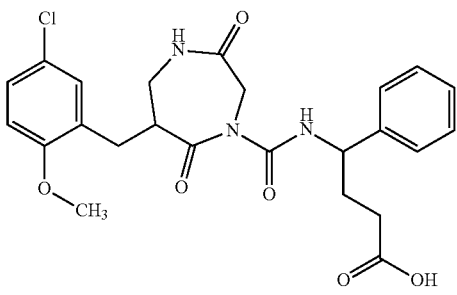 [SMILES: COc1ccc(Cl)cc1CC1CNC(=O)CN(C(=O)NC(CCC(=O)O)c2ccccc2)C1=O] |
| 111 | 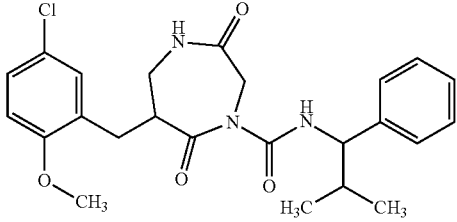 |
| 112 | 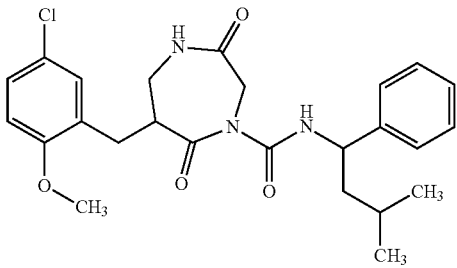 [SMILES: COc1ccc(Cl)cc1CC1CNC(=O)CN(C(=O)NC(CC(C)C)c2ccccc2)C1=O] |
| 113 | 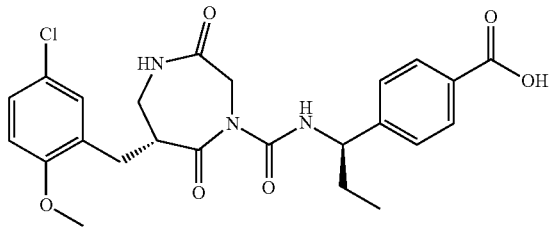 [SMILES: CC[C@@H](NC(=O)N1CC(=O)NC[C@@H](Cc2cc(Cl)ccc2OC)C1=O)c1ccc(C(=O)O)cc1] |
| 114 | 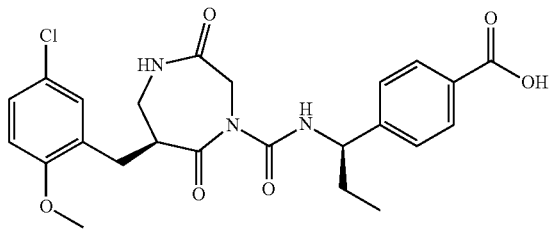 [SMILES: CC[C@@H](NC(=O)N1CC(=O)NC[C@H](Cc2cc(Cl)ccc2OC)C1=O)c1ccc(C(=O)O)cc1] |

| Ex. No. | Structure |
|---|---|
| 115 | 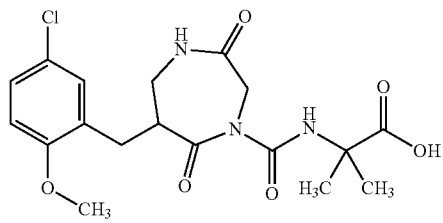 [SMILES: COc1ccc(Cl)cc1CC1CNC(=O)CN(C(=O)NC(C)(C)C(=O)O)C1=O] |
| 116 | 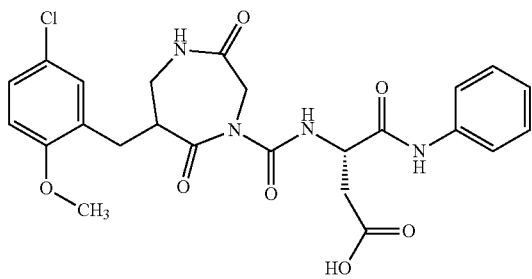 [SMILES: COc1ccc(Cl)cc1CC1CNC(=O)CN(C(=O)N[C@@H](CC(=O)O)C(=O)Nc2ccccc2)C1=O] |
| 117 | 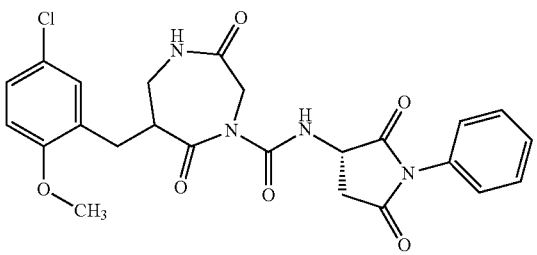 [SMILES: COc1ccc(Cl)cc1CC1CNC(=O)CN(C(=O)N[C@H]2CC(=O)N(c3ccccc3)C2=O)C1=O] |
| 118 | 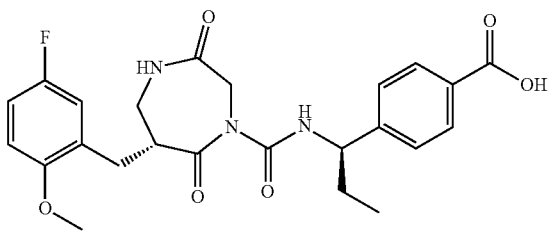 [SMILES: CC[C@@H](NC(=O)N1CC(=O)NC[C@@H](Cc2cc(F)ccc2OC)C1=O)c1ccc(C(=O)O)cc1] |
| 119 | 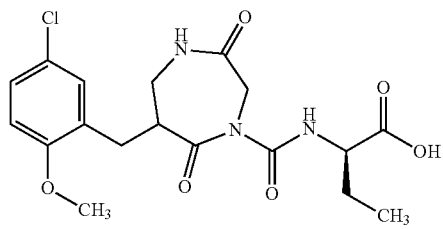 [SMILES: CC[C@@H](NC(=O)N1CC(=O)NCC(Cc2cc(Cl)ccc2OC)C1=O)C(=O)O] |
| 120 | 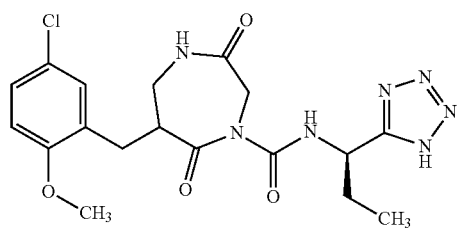 [SMILES: CC[C@@H](NC(=O)N1CC(=O)NCC(Cc2cc(Cl)ccc2OC)C1=O)c1nnn[nH]1] |

-continued
| Ex. No. | Structure |
|---|---|
| 121 | 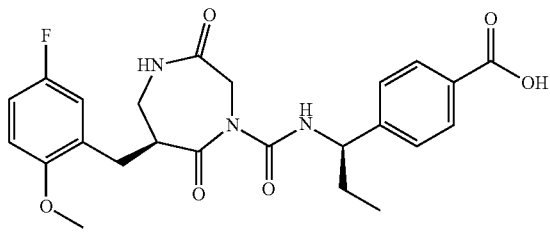 |
| 122 | 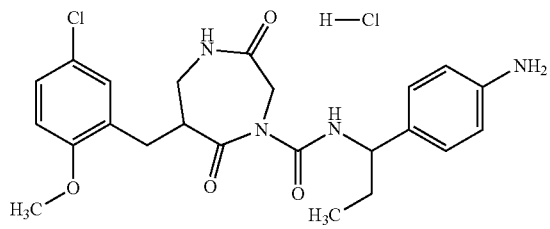 |
| 123 | 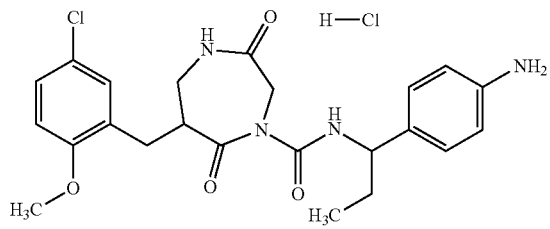 |
| 124 | 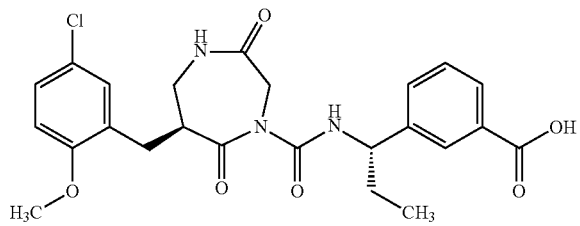 [SMILES: CC[C@H](NC(=O)N1CC(=O)NC[C@H](Cc2cc(Cl)ccc2OC)C1=O)c1cccc(C(=O)O)c1] |
| 125 | 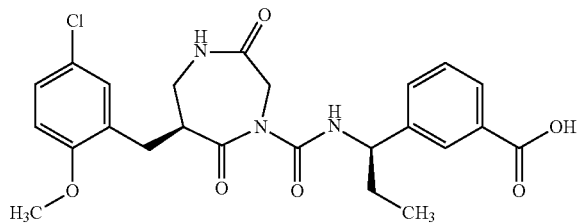 [SMILES: CC[C@@H](NC(=O)N1CC(=O)NC[C@H](Cc2cc(Cl)ccc2OC)C1=O)c1cccc(C(=O)O)c1] |
| 126 | 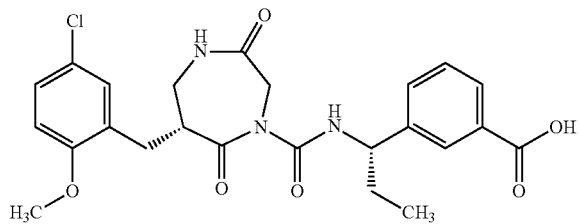 |

| Ex. No. | Structure |
|---|---|
| 127 | 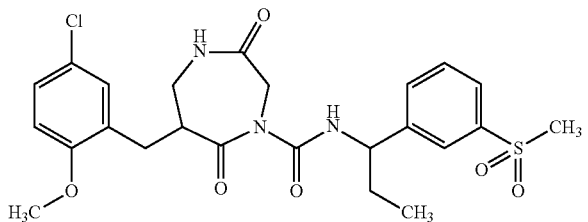 [SMILES: CCC(NC(=O)N1CC(=O)NCC(Cc2cc(Cl)ccc2OC)C1=O)c1cccc(S(C)(=O)=O)c1] |
| 128 | 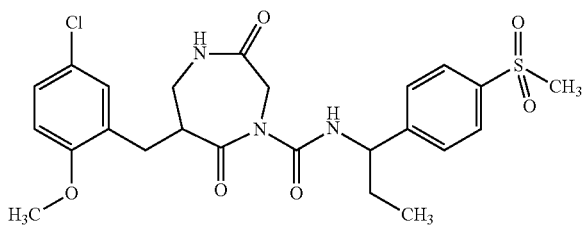 [SMILES: CCC(NC(=O)N1CC(=O)NCC(Cc2cc(Cl)ccc2OC)C1=O)c1ccc(S(C)(=O)=O)cc1] |
| 129 | 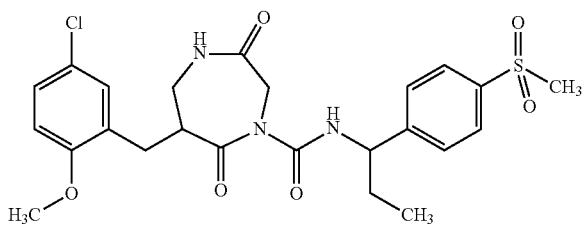 [SMILES: CCC(NC(=O)N1CC(=O)NCC(Cc2cc(Cl)ccc2OC)C1=O)c1ccc(S(C)(=O)=O)cc1] |
| 130 | 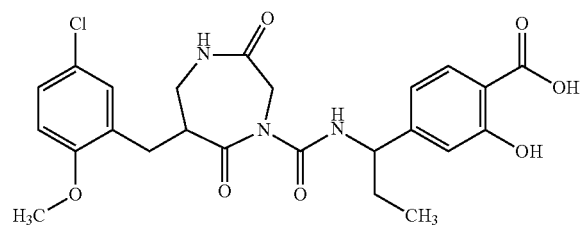 [SMILES: CCC(NC(=O)N1CC(=O)NCC(Cc2cc(Cl)ccc2OC)C1=O)c1ccc(C(=O)O)c(O)c1] |
| 131 | 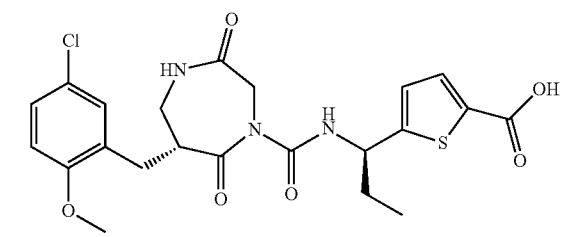 |
| 132 | 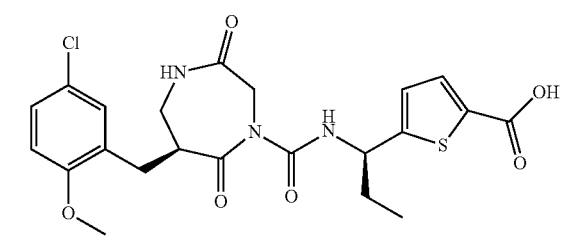 [SMILES: CC[C@@H](NC(=O)N1CC(=O)NC[C@H](Cc2cc(Cl)ccc2OC)C1=O)c1ccc(C(=O)O)s1] |

| Ex. No. | Structure |
|---|---|
| 133 | 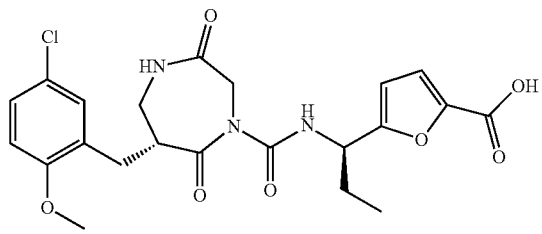 |
| 134 | 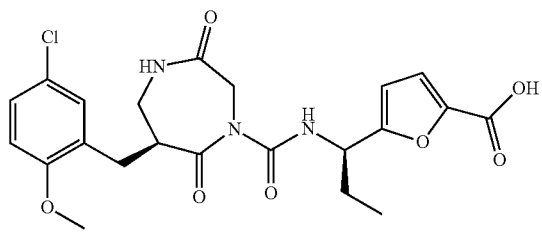 [SMILES: CC[C@@H](NC(=O)N1CC(=O)NC[C@H](Cc2cc(Cl)ccc2OC)C1=O)c1ccc(C(=O)O)o1] |
| 135 | 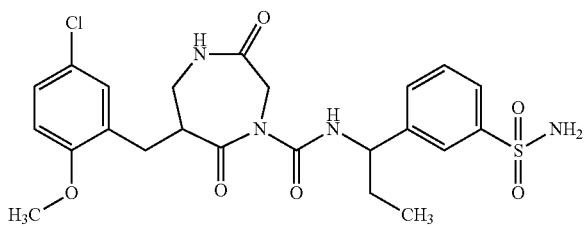 [SMILES: CCC(NC(=O)N1CC(=O)NCC(Cc2cc(Cl)ccc2OC)C1=O)c1cccc(S(N)(=O)=O)c1] |
| 136 | 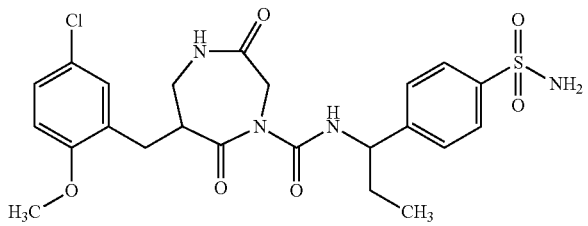 [SMILES: CCC(NC(=O)N1CC(=O)NCC(Cc2cc(Cl)ccc2OC)C1=O)c1ccc(S(N)(=O)=O)cc1] |
| 137 | 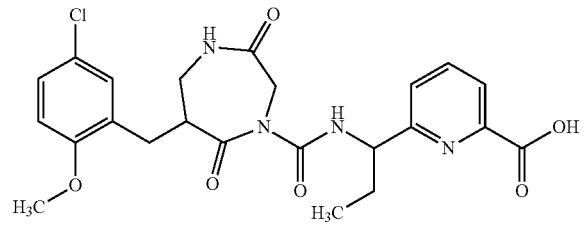 [SMILES: CCC(NC(=O)N1CC(=O)NCC(Cc2cc(Cl)ccc2OC)C1=O)c1cccc(C(=O)O)n1] |
| 138 | 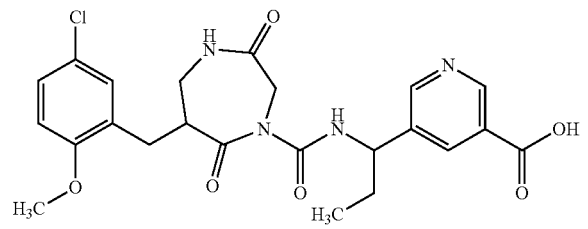 [SMILES: CCC(NC(=O)N1CC(=O)NCC(Cc2cc(Cl)ccc2OC)C1=O)c1cncc(C(=O)O)c1] |

| Ex. No. | Structure |
|---|---|
| 139 | 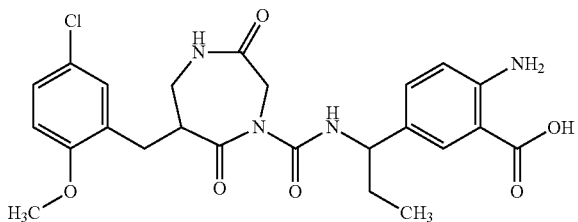 [SMILES: CCC(NC(=O)N1CC(=O)NCC(Cc2cc(Cl)ccc2OC)C1=O)c1ccc(N)c(C(=O)O)c1] |
| 140 | 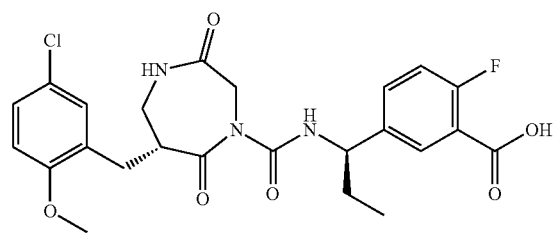 [SMILES: CC[C@@H](NC(=O)N1CC(=O)NC[C@@H](Cc2cc(Cl)ccc2OC)C1=O)c1ccc(F)c(C(=O)O)c1] |
| 141 | 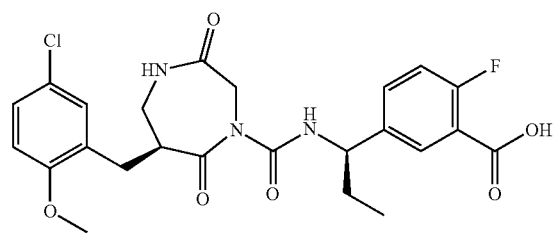 [SMILES: CC[C@@H](NC(=O)N1CC(=O)NC[C@H](Cc2cc(Cl)ccc2OC)C1=O)c1ccc(F)c(C(=O)O)c1] |
| 142 | 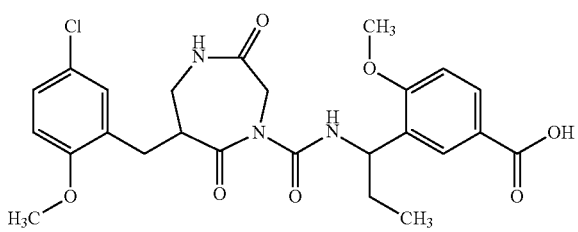 [SMILES: CCC(NC(=O)N1CC(=O)NCC(Cc2cc(Cl)ccc2OC)C1=O)c1cc(C(=O)O)ccc1OC] |
| 143 | 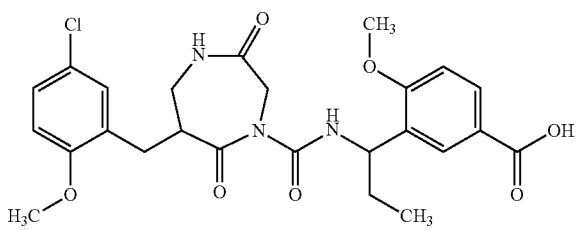 [SMILES: CCC(NC(=O)N1CC(=O)NCC(Cc2cc(Cl)ccc2OC)C1=O)c1cc(C(=O)O)ccc1OC] |
| 144 | 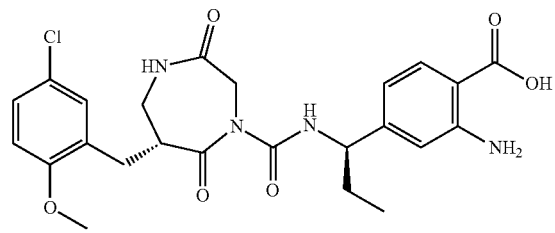 [SMILES: CC[C@@H](NC(=O)N1CC(=O)NC[C@@H](Cc2cc(Cl)ccc2OC)C1=O)c1ccc(C(=O)O)c(N)c1] |

| Ex. No. | Structure |
|---|---|
| 145 | 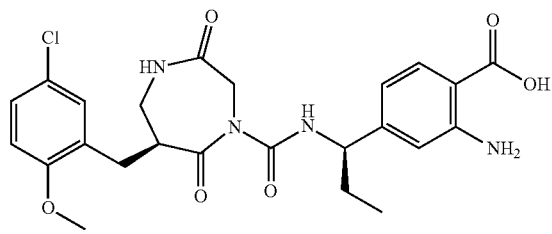 [SMILES: CC[C@@H](NC(=O)N1CC(=O)NC[C@H](Cc2cc(Cl)ccc2OC)C1=O)c1ccc(C(=O)O)c(N)c1] |
| 146 | 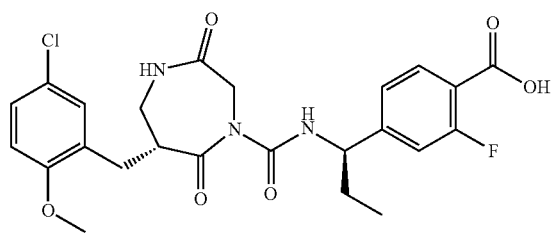 [SMILES: CC[C@@H](NC(=O)N1CC(=O)NC[C@@H](Cc2cc(Cl)ccc2OC)C1=O)c1ccc(C(=O)O)c(F)c1] |
| 147 | 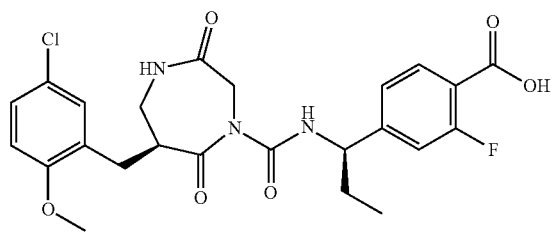 [SMILES: CC[C@@H](NC(=O)N1CC(=O)NC[C@H](Cc2cc(Cl)ccc2OC)C1=O)c1ccc(C(=O)O)c(F)c1] |
| 148 | 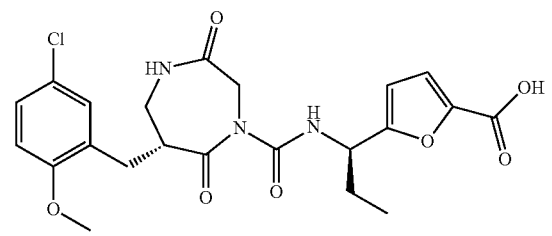 [SMILES: CC[C@@H](NC(=O)N1CC(=O)NC[C@@H](Cc2cc(Cl)ccc2OC)C1=O)c1ccc(C(=O)O)o1] |
| 149 | 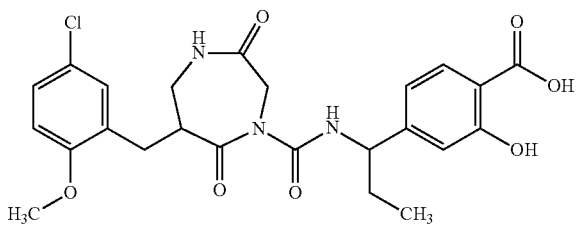 [SMILES: CCC(NC(=O)N1CC(=O)NCC(Cc2cc(Cl)ccc2OC)C1=O)c1ccc(C(=O)O)c(O)c1] |
| 150 | 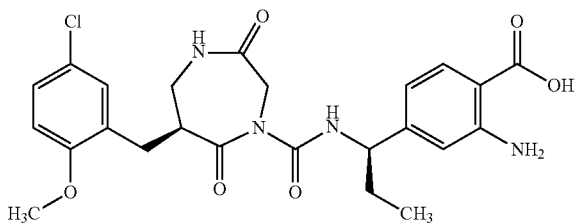 [SMILES: CC[C@@H](NC(=O)N1CC(=O)NC[C@H](Cc2cc(Cl)ccc2OC)C1=O)c1ccc(C(=O)O)c(N)c1] |

| Ex. No. | Structure |
|---|---|
| 151 | 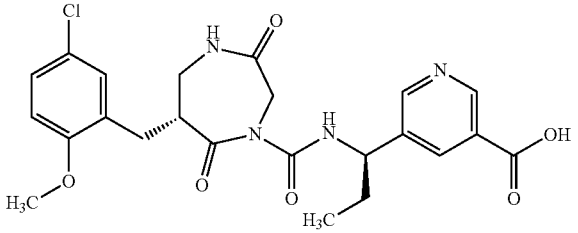 [SMILES: CC[C@@H](NC(=O)N1CC(=O)NC[C@@H](Cc2cc(Cl)ccc2OC)C1=O)c1cncc(C(=O)O)c1] |
| 152 | 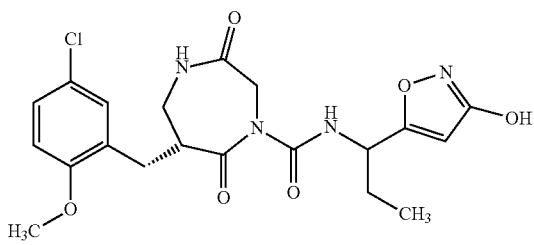 |
| 153 | 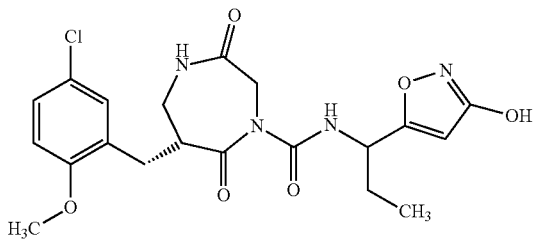 |
| 154 | 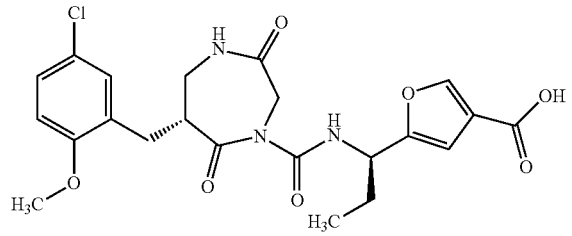 [SMILES: CC[C@@H](NC(=O)N1CC(=O)NC[C@@H](Cc2cc(Cl)ccc2OC)C1=O)c1cc(C(=O)O)co1] |
| 155 | 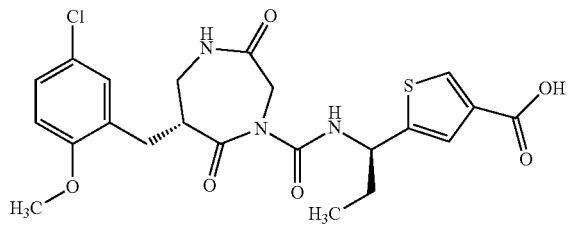 [SMILES: CC[C@@H](NC(=O)N1CC(=O)NC[C@@H](Cc2cc(Cl)ccc2OC)C1=O)c1cc(C(=O)O)cs1] |
| 156 | 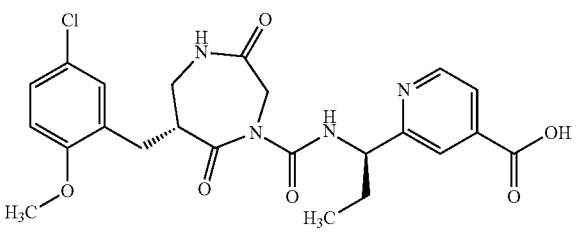 [SMILES: CC[C@@H](NC(=O)N1CC(=O)NC[C@@H](Cc2cc(Cl)ccc2OC)C1=O)c1cc(C(=O)O)ccn1] |

| Ex. No. | Structure |
|---|---|
| 157 | 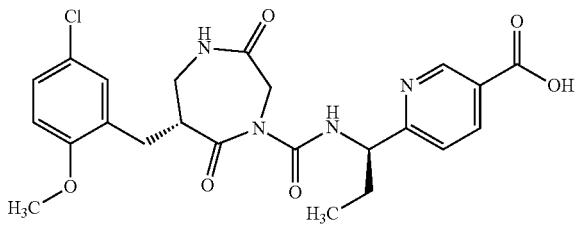 [SMILES: CC[C@@H](NC(=O)N1CC(=O)NC[C@@H](Cc2cc(Cl)ccc2OC)C1=O)c1ccc(C(=O)O)cn1] |
| 158 | 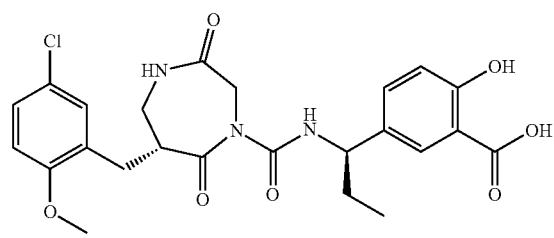 [SMILES: CC[C@@H](NC(=O)N1CC(=O)NC[C@@H](Cc2cc(Cl)ccc2OC)C1=O)c1ccc(O)c(C(=O)O)c1] |
| 159 | 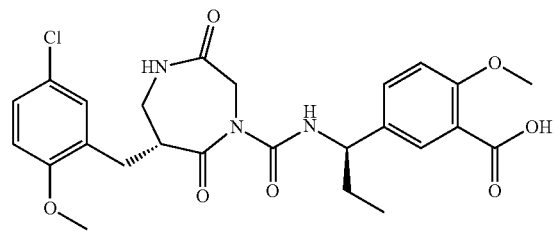 [SMILES: CC[C@@H](NC(=O)N1CC(=O)NC[C@@H](Cc2cc(Cl)ccc2OC)C1=O)c1ccc(OC)c(C(=O)O)c1] |
| 160 | 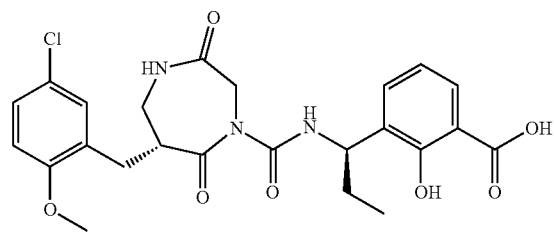 [SMILES: CC[C@@H](NC(=O)N1CC(=O)NC[C@@H](Cc2cc(Cl)ccc2OC)C1=O)c1cccc(C(=O)O)c1O] |
| 161 | 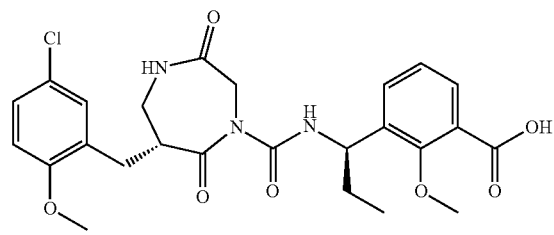 [SMILES: CC[C@@H](NC(=O)N1CC(=O)NC[C@@H](Cc2cc(Cl)ccc2OC)C1=O)c1cccc(C(=O)O)c1OC] |
| 162 | 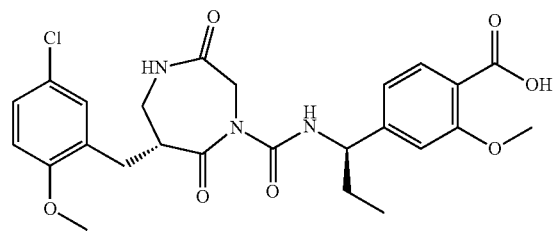 [SMILES: CC[C@@H](NC(=O)N1CC(=O)NC[C@@H](Cc2cc(Cl)ccc2OC)C1=O)c1ccc(C(=O)O)c(OC)c1] |

-continued
| Ex. No. | Structure |
|---|---|
| 163 | 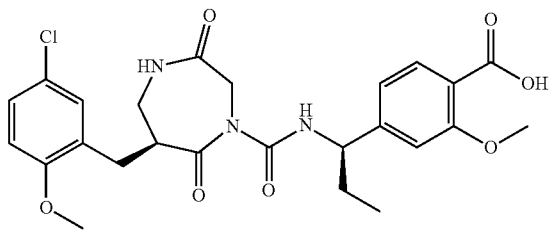 [SMILES: CC[C@@H](NC(=O)N1CC(=O)NC[C@H](Cc2cc(Cl)ccc2OC)C1=O)c1ccc(C(=O)O)c(OC)c1] |
| 164 | 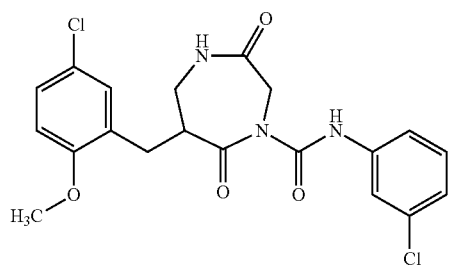 [SMILES: COc1ccc(Cl)cc1CC1CNC(=O)CN(C(=O)Nc2cccc(Cl)c2)C1=O] |
| 165 | 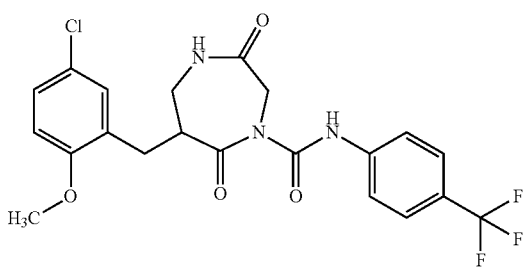 [SMILES: COc1ccc(Cl)cc1CC1CNC(=O)CN(C(=O)Nc2ccc(C(F)(F)F)cc2)C1=O] |
| 166 | 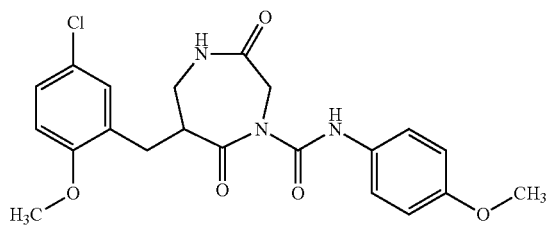 [SMILES: COc1ccc(NC(=O)N2CC(=O)NCC(Cc3cc(Cl)ccc3OC)C2=O)cc1] |
| 167 | 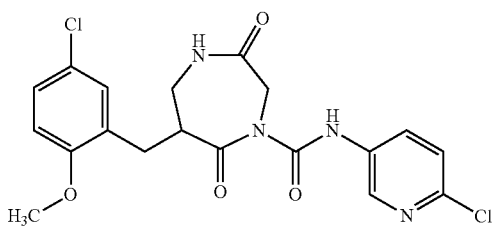 |
| 168 | 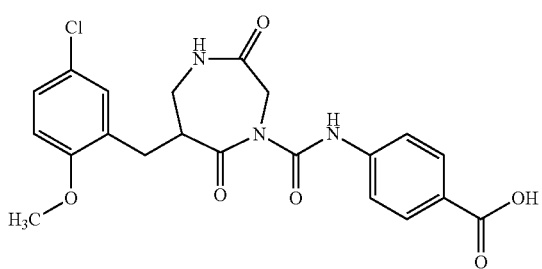 [SMILES: COc1ccc(Cl)cc1CC1CNC(=O)CN(C(=O)Nc2ccc(C(=O)O)cc2)C1=O] |

US 8,507,714 B2
251                                           252
-continued
| Ex. No. | Structure |
|---|---|
| 169 | 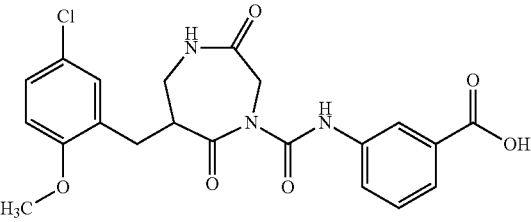 [SMILES: COc1ccc(Cl)cc1CC1CNC(=O)CN(C(=O)Nc2cccc(C(=O)O)c2)C1=O] |
| 170 | 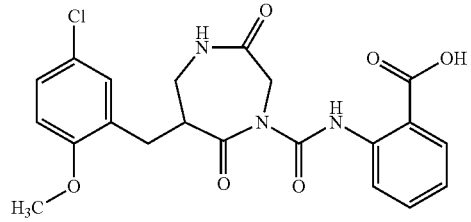 [SMILES: COc1ccc(Cl)cc1CC1CNC(=O)CN(C(=O)Nc2ccccc2C(=O)O)C1=O] |
| 171 | 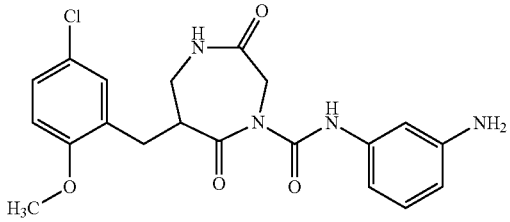 [SMILES: COc1ccc(Cl)cc1CC1CNC(=O)CN(C(=O)Nc2cccc(N)c2)C1=O] |
| 172 | 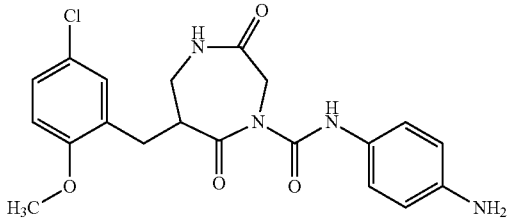 [SMILES: COc1ccc(Cl)cc1CC1CNC(=O)CN(C(=O)Nc2ccc(N)cc2)C1=O] |
| 173 | 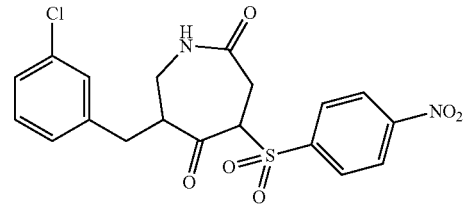 [SMILES: O=C1CC(S(=O)(=O)c2ccc([N+](=O)[O-])cc2)C(=O)C(Cc2cccc(Cl)c2)CN1] |
| 174 | 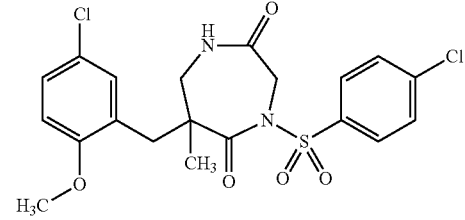 [SMILES: COc1ccc(Cl)cc1CC1(C)CNC(=O)CN(S(=O)(=O)c2ccc(Cl)cc2)C1=O] |
| 175 | 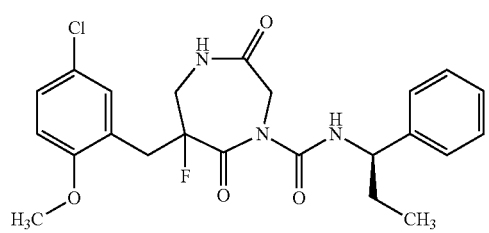 [SMILES: CC[C@@H](NC(=O)N1CC(=O)NCC(F)(Cc2cc(Cl)ccc2OC)C1=O)c1ccccc1] |

| Ex. No. | Structure |
|---|---|
| 176 | 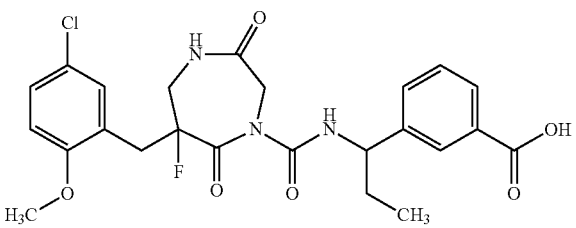 [SMILES: CCC(NC(=O)N1CC(=O)NCC(F)(Cc2cc(Cl)ccc2OC)C1=O)c1cccc(C(=O)O)c1] |
| 177 | 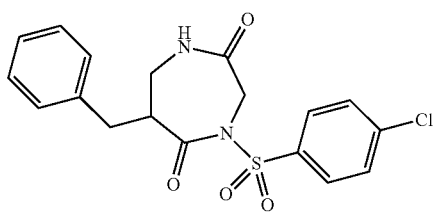 [SMILES: O=C1CN(S(=O)(=O)c2ccc(Cl)cc2)C(=O)C(Cc2ccccc2)CN1] |
| 178A | 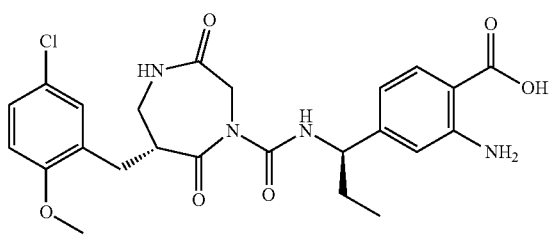 [SMILES: CC[C@@H](NC(=O)N1CC(=O)NC[C@@H](Cc2cc(Cl)ccc2OC)C1=O)c1ccc(C(=O)O)c(N)c1] |
| 178B | 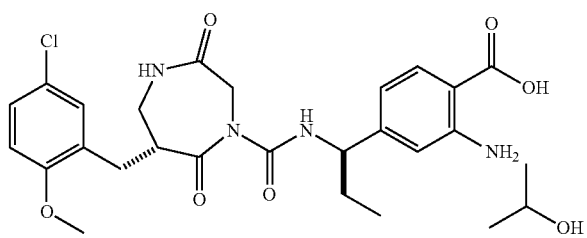 |
| 179A | 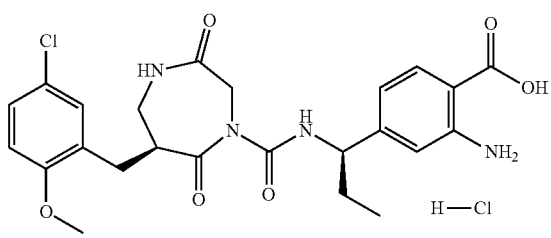 |
| 179B | 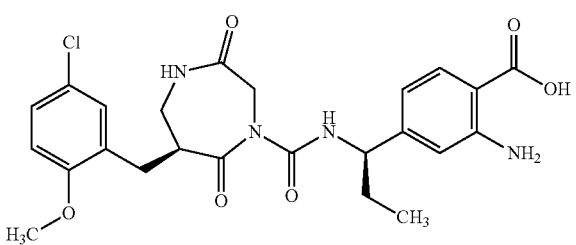 [SMILES: CC[C@@H](NC(=O)N1CC(=O)NC[C@H](Cc2cc(Cl)ccc2OC)C1=O)c1ccc(C(=O)O)c(N)c1] |

| Ex. No. | Structure |
|---|---|
| 179C | 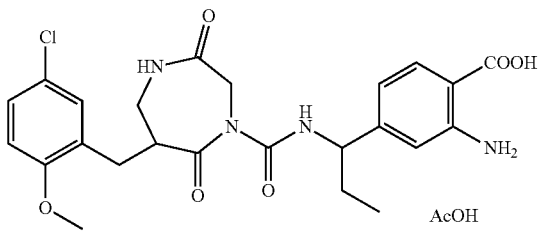 [SMILES: "AcOH" ; CCC(NC(=O)N1CC(=O)NCC(Cc2cc(Cl)ccc2OC)C1=O)c1ccc(C(=O)O)c(N)c1] AcOH |
| 180A | 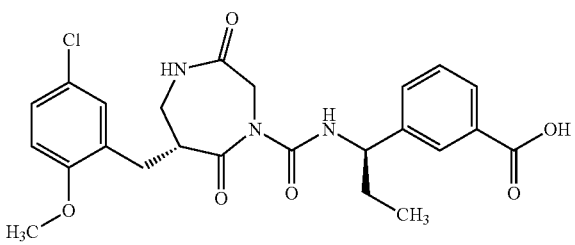 [SMILES: CC[C@@H](NC(=O)N1CC(=O)NC[C@@H](Cc2cc(Cl)ccc2OC)C1=O)c1cccc(C(=O)O)c1] |
| 180B | 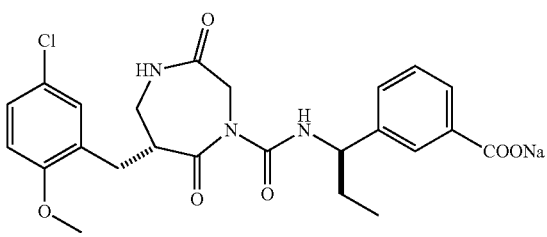 |
| 181 | 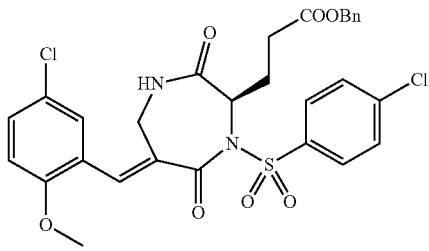 |
| 182 | 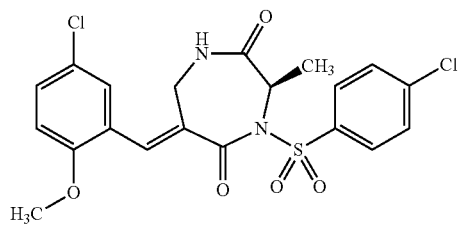 [SMILES: COc1ccc(Cl)cc1/C=C1\CNC(=O)[C@@H](C)N(S(=O)(=O)c2ccc(Cl)cc2)C1=O] |
| 183 | 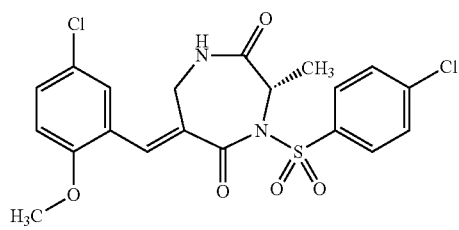 [SMILES: COc1ccc(Cl)cc1/C=C1\CNC(=O)[C@H](C)N(S(=O)(=O)c2ccc(Cl)cc2)C1=O] |

| Ex. No. | Structure |
| --- | --- |
| 184 | 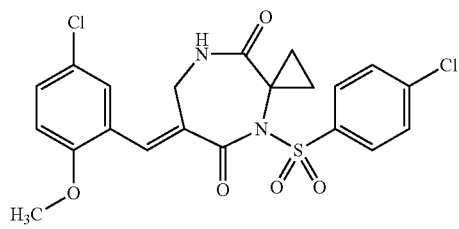 [SMILES: COc1ccc(Cl)cc1/C=C1\CNC(=O)C2(CC2)N(S(=O)(=O)c2ccc(Cl)cc2)C1=O] |
| 185 | 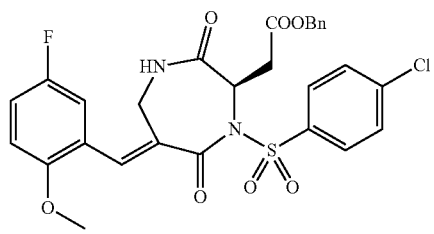 |
| 186 | 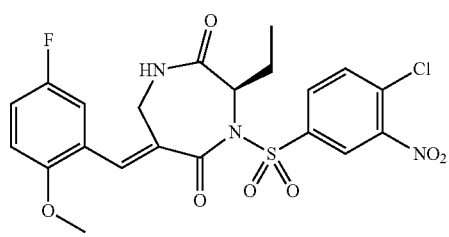 [SMILES: CC[C@@H]1C(=O)NC/C(=C\c2cc(F)ccc2OC)C(=O)N1S(=O)(=O)c1ccc(Cl)c([N+](=O)[O-])c1] |
| 187 | 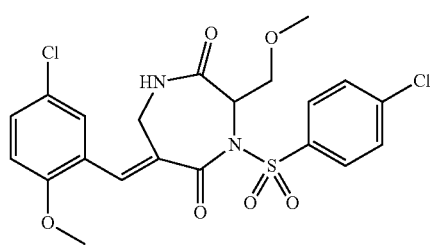 [SMILES: COCC1C(=O)NC/C(=C\c2cc(Cl)ccc2OC)C(=O)N1S(=O)(=O)c1ccc(Cl)cc1] |
| 188 | 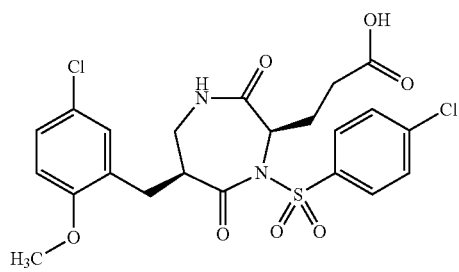 [SMILES: COc1ccc(Cl)cc1C[C@H]1CNC(=O)[C@@H](CCC(=O)O)N(S(=O)(=O)c2ccc(Cl)cc2)C1=O] |
| 189 | 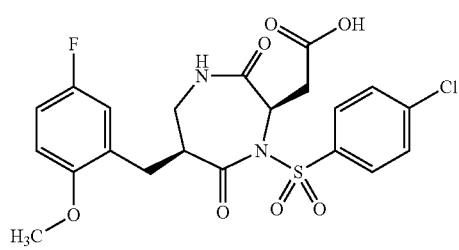 [SMILES: COc1ccc(F)cc1C[C@H]1CNC(=O)[C@@H](CC(=O)O)N(S(=O)(=O)c2ccc(Cl)cc2)C1=O] |

| Ex. No. | Structure |
|---|---|
| 190 | 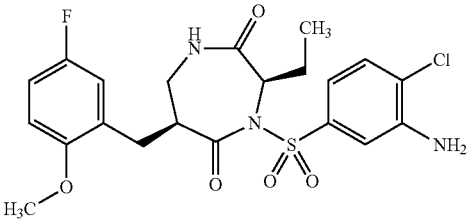 [SMILES: CC[C@@H]1C(=O)NC[C@H](Cc2cc(F)ccc2OC)C(=O)N1S(=O)(=O)c1ccc(Cl)c(N)c1] |
| 191 | 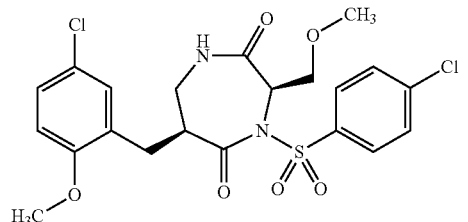 |
| 192 | 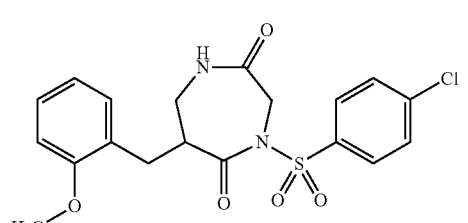 |
| 193 | 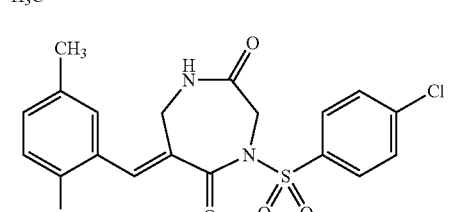 |
| 194 | 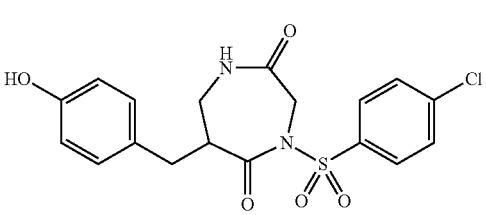 [SMILES: O=C1CN(S(=O)(=O)c2ccc(Cl)cc2)C(=O)C(Cc2ccc(O)cc2)CN1] |
| 195 | 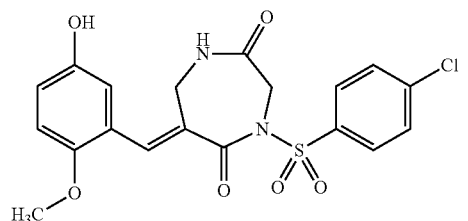 |
| 196 | 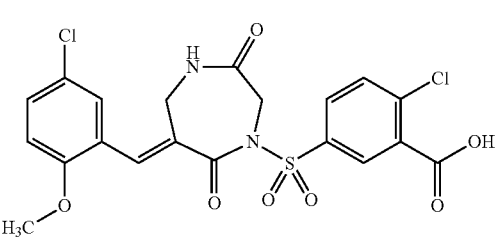 [SMILES: COc1ccc(Cl)cc1/C=C1\CNC(=O)CN(S(=O)(=O)c2ccc(Cl)c(C(=O)O)c2)C1=O] |

| Ex. No. | Structure |
|---|---|
| 197 | 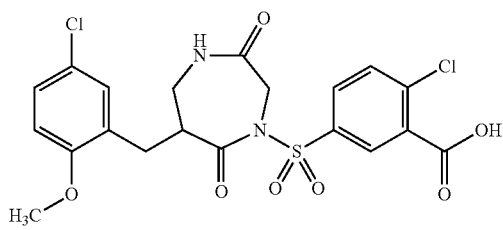 [SMILES: COc1ccc(Cl)cc1CC1CNC(=O)CN(S(=O)(=O)c2ccc(Cl)c(C(=O)O)c2)C1=O] |
| 198 | 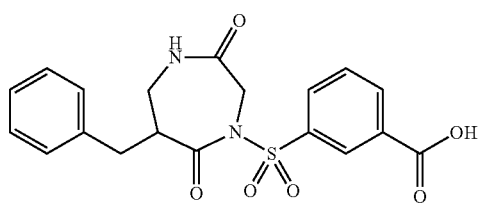 [SMILES: O=C1CN(S(=O)(=O)c2cccc(C(=O)O)c2)C(=O)C(Cc2ccccc2)CN1] |
| 199 | 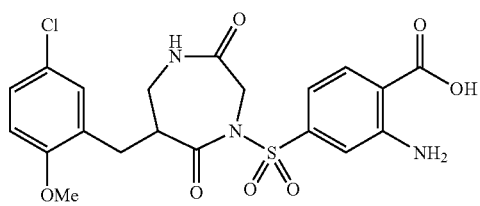 [SMILES: COc1ccc(Cl)cc1CC1CNC(=O)CN(S(=O)(=O)c2ccc(C(=O)O)c(N)c2)C1=O] |
| 200 | 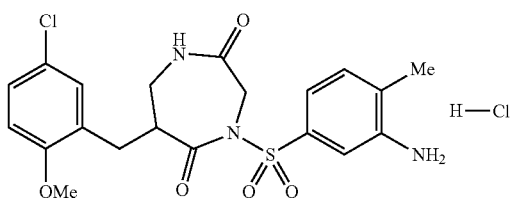 |
| 201 | 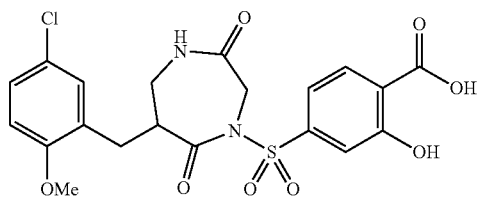 [SMILES: COc1ccc(Cl)cc1CC1CNC(=O)CN(S(=O)(=O)c2ccc(C(=O)O)c(O)c2)C1=O] |
| 202 | 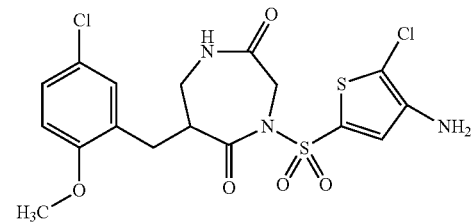 [SMILES: COc1ccc(Cl)cc1CC1CNC(=O)CN(S(=O)(=O)c2cc(N)c(Cl)s2)C1=O] |
| 203 | 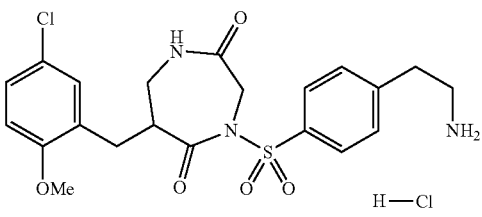 [SMILES: COc1ccc(Cl)cc1CC1CNC(=O)CN(S(=O)(=O)c2ccc(CCN)cc2)C1=O ; Cl] |

-continued
| Ex. No. | Structure |
|---|---|
| 204 | 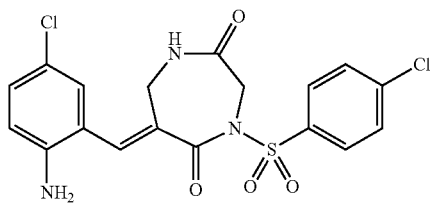 [SMILES: Nc1ccc(Cl)cc1/C=C1\CNC(=O)CN(S(=O)(=O)c2ccc(Cl)cc2)C1=O] |
| 205 | 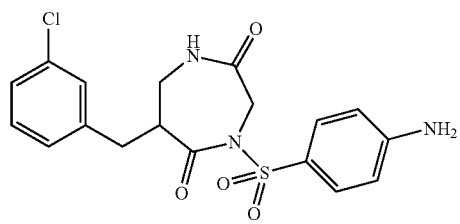 [SMILES: Nc1ccc(S(=O)(=O)N2CC(=O)NCC(Cc3cccc(Cl)c3)C2=O)cc1] |
| 206 | 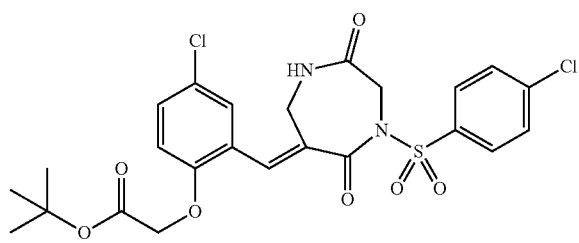 [SMILES: CC(C)(C)OC(=O)COc1ccc(Cl)cc1/C=C1\CNC(=O)CN(S(=O)(=O)c2ccc(Cl)cc2)C1=O] |
| 207 | 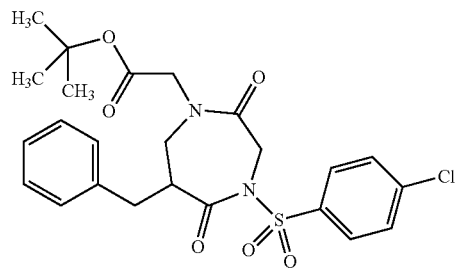 [SMILES: CC(C)(C)OC(=O)CN1CC(Cc2ccccc2)C(=O)N(S(=O)(=O)c2ccc(Cl)cc2)CC1=O] |
| 208 | 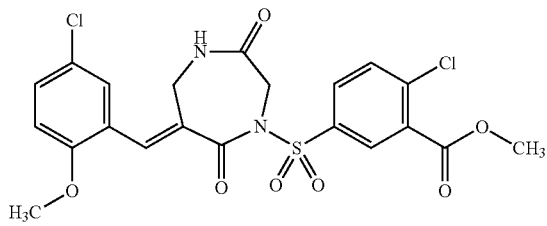 [SMILES: COC(=O)c1cc(S(=O)(=O)N2CC(=O)NC/C(=C\c3cc(Cl)ccc3OC)C2=O)ccc1Cl] |
| 209 | 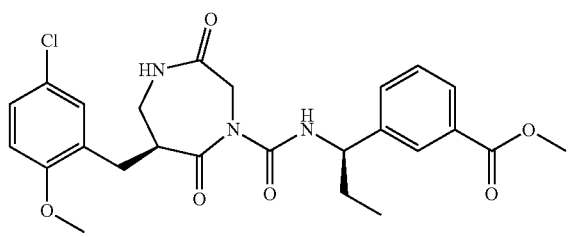 [SMILES: CC[C@@H](NC(=O)N1CC(=O)NC[C@H](Cc2cc(Cl)ccc2OC)C1=O)c1cccc(C(=O)OC)c1] |

-continued
| Ex. No. | Structure |
|---|---|
| 210 | 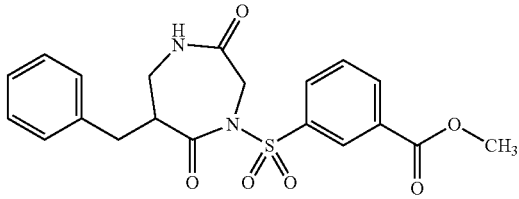 [SMILES: COC(=O)c1cccc(S(=O)(=O)N2CC(=O)NCC(Cc3ccccc3)C2=O)c1] |
| 211 | 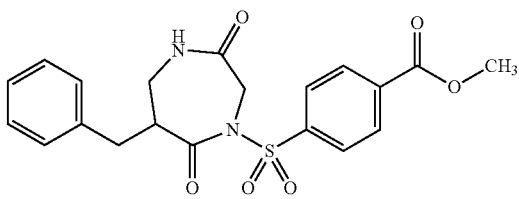 [SMILES: COC(=O)c1ccc(S(=O)(=O)N2CC(=O)NCC(Cc3ccccc3)C2=O)cc1] |
| 212 | 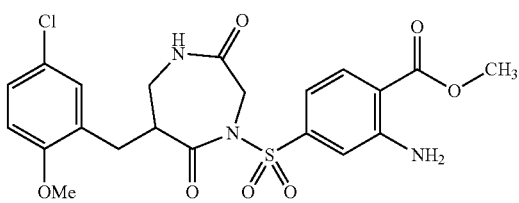 [SMILES: COC(=O)c1ccc(S(=O)(=O)N2CC(=O)NCC(Cc3cc(Cl)ccc3OC)C2=O)cc1N] |
| 213 | 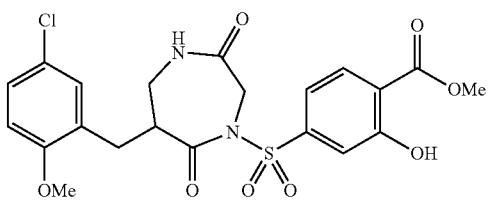 [SMILES: COC(=O)c1ccc(S(=O)(=O)N2CC(=O)NCC(Cc3cc(Cl)ccc3OC)C2=O)cc1O] |
| 214 | 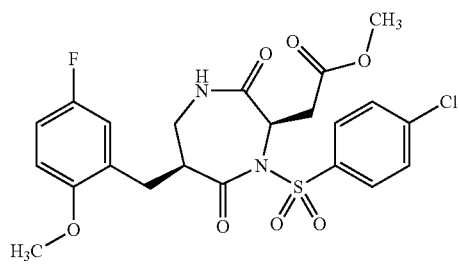 [SMILES: COC(=O)C[C@@H]1C(=O)NC[C@H](Cc2cc(F)ccc2OC)C(=O)N1S(=O)(=O)c1ccc(Cl)cc1] |
| 215 | 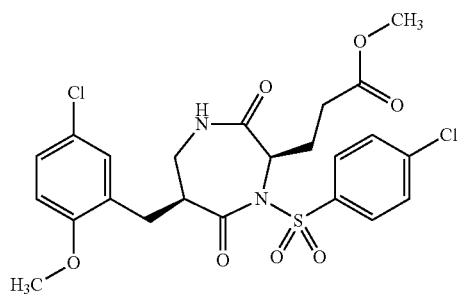 [SMILES: COC(=O)CC[C@@H]1C(=O)NC[C@H](Cc2cc(Cl)ccc2OC)C(=O)N1S(=O)(=O)c1ccc(Cl)cc1] |

| Ex. No. | Structure |
|---|---|
| 216 | 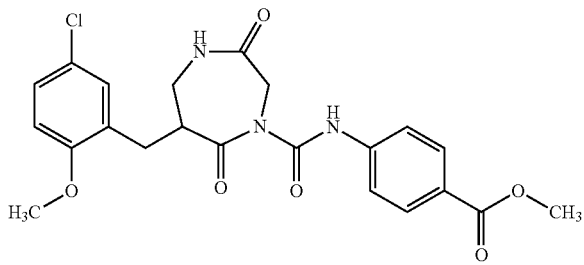 [SMILES: COC(=O)c1ccc(NC(=O)N2CC(=O)NCC(Cc3cc(Cl)ccc3OC)C2=O)cc1] |
| 217 | 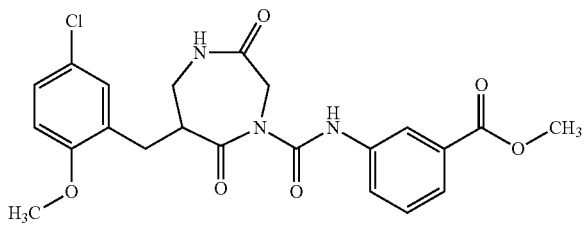 [SMILES: COC(=O)c1cccc(NC(=O)N2CC(=O)NCC(Cc3cc(Cl)ccc3OC)C2=O)c1] |
| 218 | 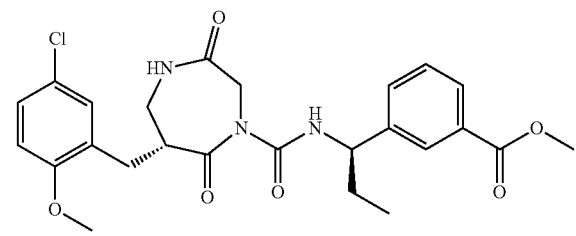 [SMILES: CC[C@@H](NC(=O)N1CC(=O)NC[C@@H](Cc2cc(Cl)ccc2OC)C1=O)c1cccc(C(=O)OC)c1] |
| 219 | 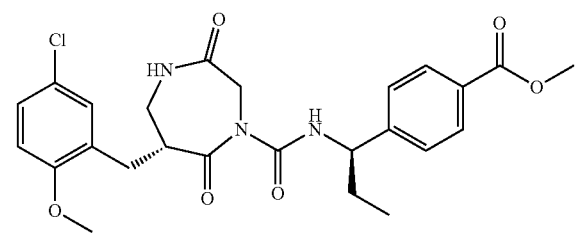 [SMILES: CC[C@@H](NC(=O)N1CC(=O)NC[C@@H](Cc2cc(Cl)ccc2OC)C1=O)c1ccc(C(=O)OC)cc1] |
| 220 | 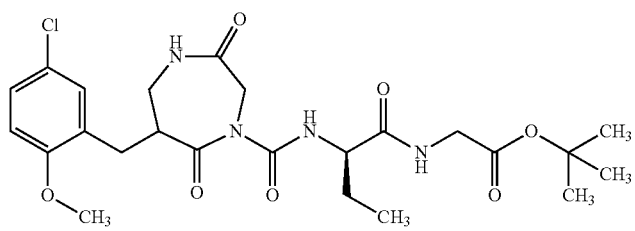 [SMILES: CC[C@@H](NC(=O)N1CC(=O)NCC(Cc2cc(Cl)ccc2OC)C1=O)C(=O)NCC(=O)OC(C)(C)C] |
| 221 | 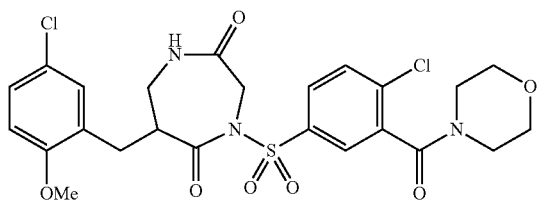 [SMILES: COc1ccc(Cl)cc1CC1CNC(=O)CN(S(=O)(=O)c2ccc(Cl)c(C(=O)N3CCOCC3)c2)C1=O] |

| Ex. No. | Structure |
|---|---|
| 222 | 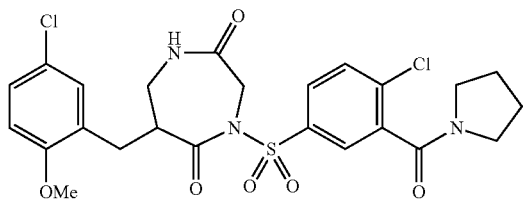 [SMILES: COc1ccc(Cl)cc1CC1CNC(=O)CN(S(=O)(=O)c2ccc(Cl)c(C(=O)N3CCCC3)c2)C1=O] |
| 223 | 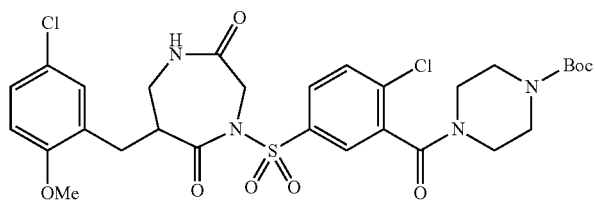 [SMILES: COc1ccc(Cl)cc1CC1CNC(=O)CN(S(=O)(=O)c2ccc(Cl)c(C(=O)N3CCN(C(=O)OC(C)(C)C)CC3)c2)C1=O] |
| 224 | 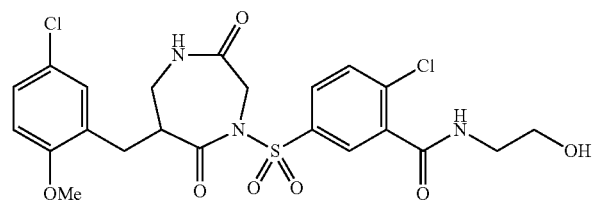 [SMILES: COc1ccc(Cl)cc1CC1CNC(=O)CN(S(=O)(=O)c2ccc(Cl)c(C(=O)NCCO)c2)C1=O] |
| 225 | 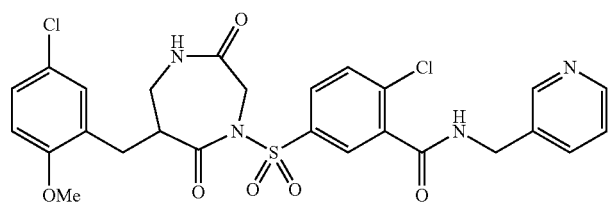 [SMILES: COc1ccc(Cl)cc1CC1CNC(=O)CN(S(=O)(=O)c2ccc(Cl)c(C(=O)NCc3cccnc3)c2)C1=O] |
| 226 | 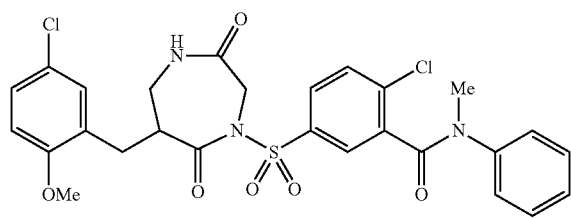 [SMILES: COc1ccc(Cl)cc1CC1CNC(=O)CN(S(=O)(=O)c2ccc(Cl)c(C(=O)N(C)c3ccccc3)c2)C1=O] |
| 227 | 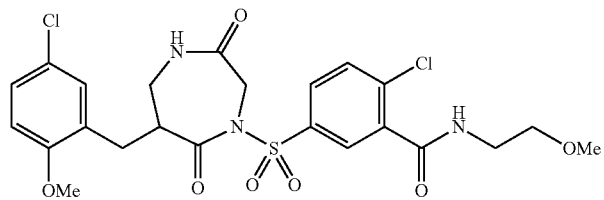 [SMILES: COCCNC(=O)c1cc(S(=O)(=O)N2CC(=O)NCC(Cc3cc(Cl)ccc3OC)C2=O)ccc1Cl] |
| 228 | 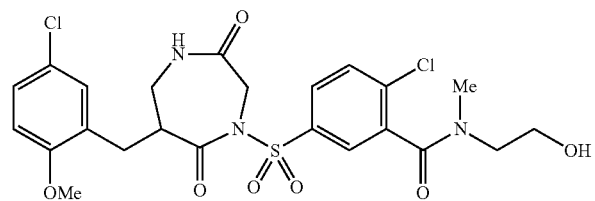 [SMILES: COc1ccc(Cl)cc1CC1CNC(=O)CN(S(=O)(=O)c2ccc(Cl)c(C(=O)N(C)CCO)c2)C1=O] |

| Ex. No. | Structure |
|---------|-----------|
| 229 | 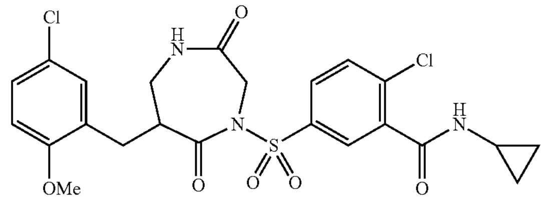 [SMILES: COc1ccc(Cl)cc1CC1CNC(=O)CN(S(=O)(=O)c2ccc(Cl)c(C(=O)NC3CC3)c2)C1=O] |
| 230 | 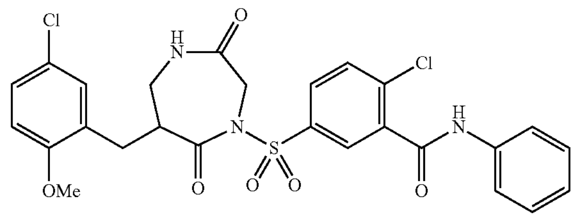 [SMILES: COc1ccc(Cl)cc1CC1CNC(=O)CN(S(=O)(=O)c2ccc(Cl)c(C(=O)Nc3ccccc3)c2)C1=O] |
| 231 | 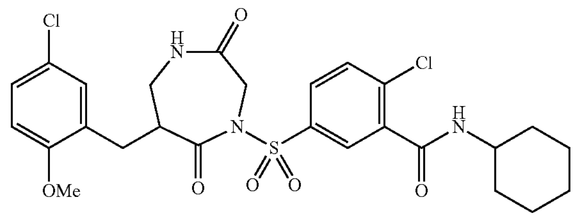 [SMILES: COc1ccc(Cl)cc1CC1CNC(=O)CN(S(=O)(=O)c2ccc(Cl)c(C(=O)NC3CCCCC3)c2)C1=O] |
| 232 | 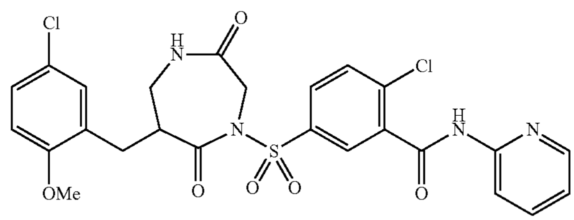 [SMILES: COc1ccc(Cl)cc1CC1CNC(=O)CN(S(=O)(=O)c2ccc(Cl)c(C(=O)Nc3ccccn3)c2)C1=O] |
| 233 | 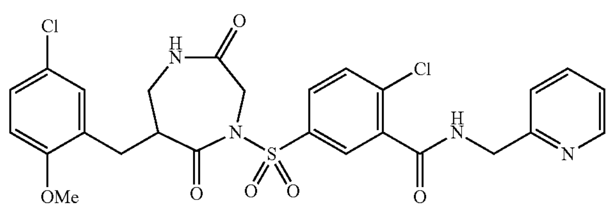 [SMILES: COc1ccc(Cl)cc1CC1CNC(=O)CN(S(=O)(=O)c2ccc(Cl)c(C(=O)NCc3ccccn3)c2)C1=O] |
| 234 | 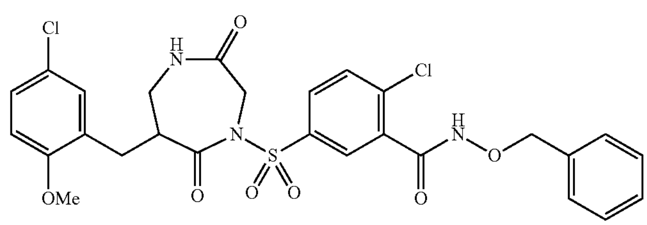 [SMILES: COc1ccc(Cl)cc1CC1CNC(=O)CN(S(=O)(=O)c2ccc(Cl)c(C(=O)NOCc3ccccc3)c2)C1=O] |
| 235 | 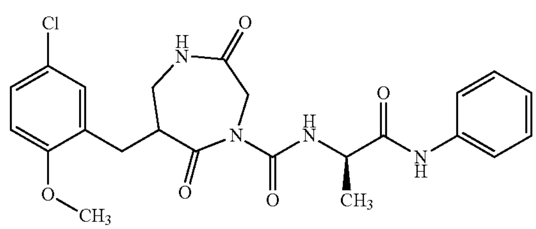 [SMILES: COc1ccc(Cl)cc1CC1CNC(=O)CN(C(=O)N[C@H](C)C(=O)Nc2ccccc2)C1=O] |

-continued
| Ex. No. | Structure |
|---|---|
| 236 | 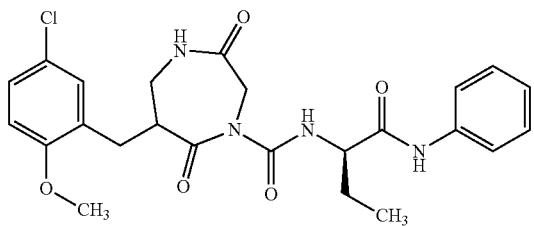 |
| 237 | 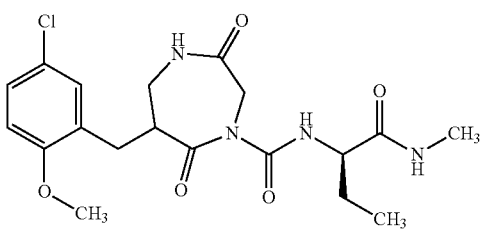 [SMILES: CC[C@@H](NC(=O)N1CC(=O)NCC(Cc2cc(Cl)ccc2OC)C1=O)C(=O)NC] |
| 238 | 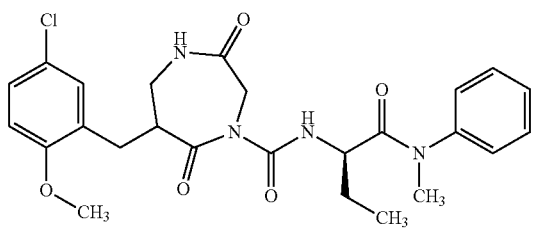 [SMILES: CC[C@@H](NC(=O)N1CC(=O)NCC(Cc2cc(Cl)ccc2OC)C1=O)C(=O)N(C)c1ccccc1] |
| 239 | 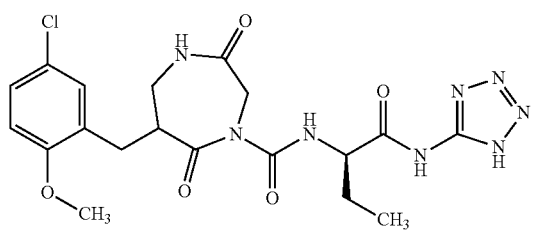 [SMILES: CC[C@@H](NC(=O)N1CC(=O)NCC(Cc2cc(Cl)ccc2OC)C1=O)C(=O)Nc1nnn[nH]1] |
| 240 | 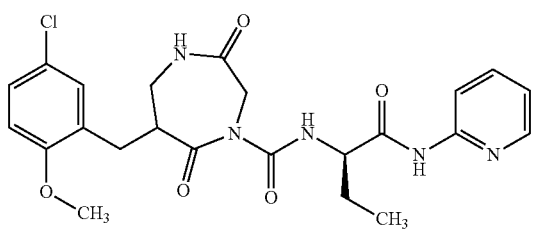 [SMILES: CC[C@@H](NC(=O)N1CC(=O)NCC(Cc2cc(Cl)ccc2OC)C1=O)C(=O)Nc1ccccn1] |
| 241 | 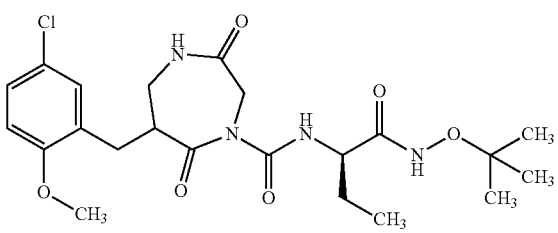 [SMILES: CC[C@@H](NC(=O)N1CC(=O)NCC(Cc2cc(Cl)ccc2OC)C1=O)C(=O)NOC(C)(C)C] |

| Ex. No. | Structure |
|---|---|
| 242 | 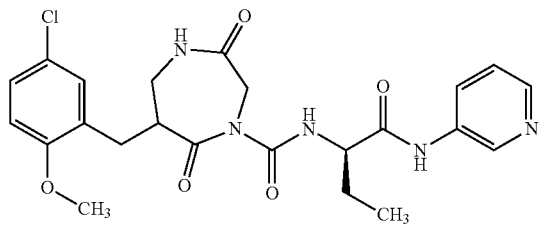 [SMILES: CC[C@@H](NC(=O)N1CC(=O)NCC(Cc2cc(Cl)ccc2OC)C1=O)C(=O)Nc1cccnc1] |
| 243 | 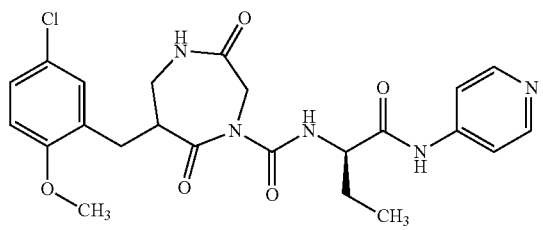 [SMILES: CC[C@@H](NC(=O)N1CC(=O)NCC(Cc2cc(Cl)ccc2OC)C1=O)C(=O)Nc1ccncc1] |
| 244 | 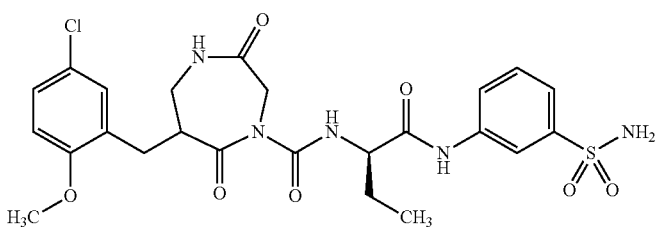 [SMILES: CC[C@@H](NC(=O)N1CC(=O)NCC(Cc2cc(Cl)ccc2OC)C1=O)C(=O)Nc1cccc(S(N)(=O)=O)c1] |
| 245 | 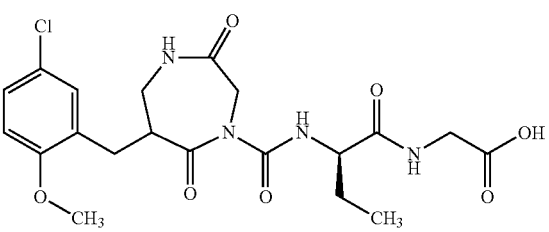 [SMILES: CC[C@@H](NC(=O)N1CC(=O)NCC(Cc2cc(Cl)ccc2OC)C1=O)C(=O)NCC(=O)O] |
| 246 | 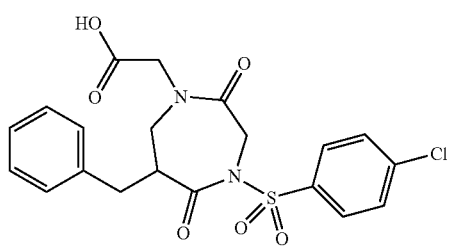 [SMILES: O=C(O)CN1CC(Cc2ccccc2)C(=O)N(S(=O)(=O)c2ccc(Cl)cc2)CC1=O] |
| 247 | 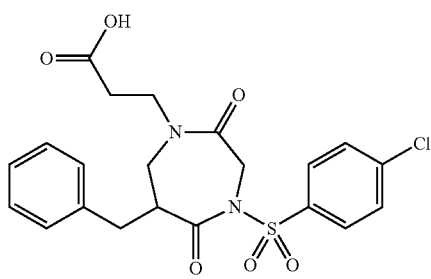 [SMILES: O=C(O)CCN1CC(Cc2ccccc2)C(=O)N(S(=O)(=O)c2ccc(Cl)cc2)CC1=O] |

| Ex. No. | Structure |
|---|---|
| 248 | 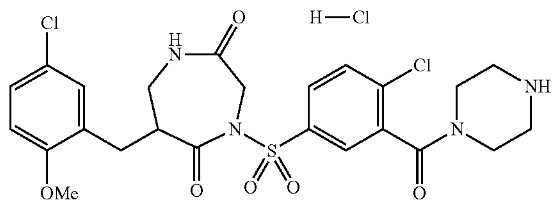 |
| 249 | 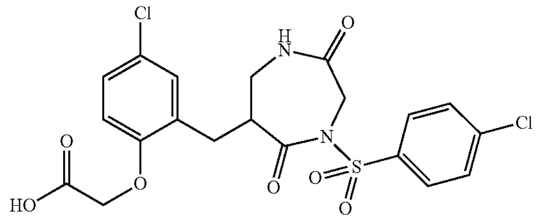 [SMILES: O=C(O)COc1ccc(Cl)cc1CC1CNC(=O)CN(S(=O)(=O)c2ccc(Cl)cc2)C1=O] |
| 250 | 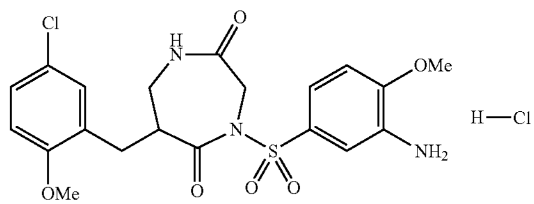 [SMILES: COc1ccc(S(=O)(=O)N2CC(=O)NCC(Cc3cc(Cl)ccc3OC)C2=O)cc1N ; Cl] |
| 251 | 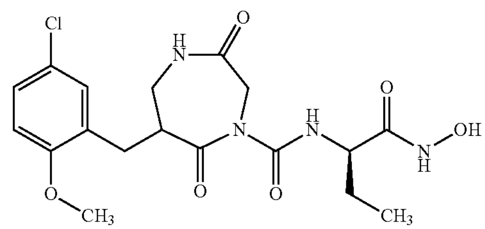 [SMILES: CC[C@@H](NC(=O)N1CC(=O)NCC(Cc2cc(Cl)ccc2OC)C1=O)C(=O)NO] |
| 252 | 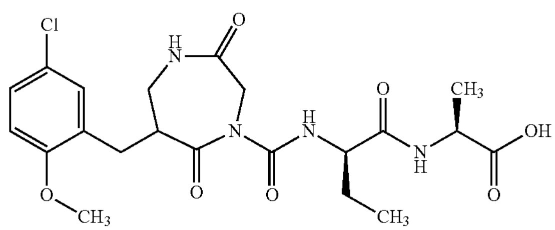 [SMILES: CC[C@@H](NC(=O)N1CC(=O)NCC(Cc2cc(Cl)ccc2OC)C1=O)C(=O)N[C@@H](C)C(=O)O] |
| 253 | 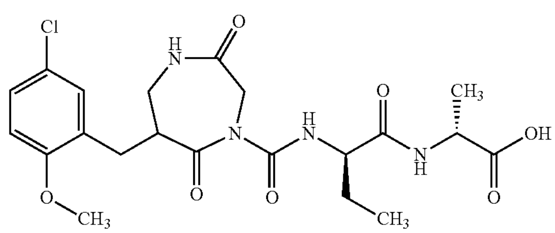 [SMILES: CC[C@@H](NC(=O)N1CC(=O)NCC(Cc2cc(Cl)ccc2OC)C1=O)C(=O)N[C@H](C)C(=O)O] |
| 254 | 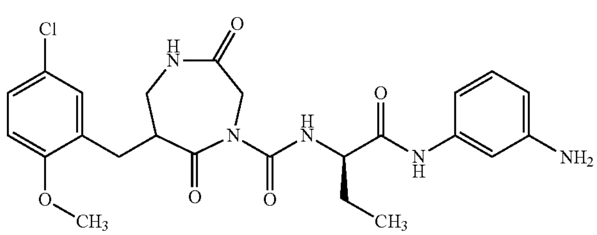 [SMILES: CC[C@@H](NC(=O)N1CC(=O)NCC(Cc2cc(Cl)ccc2OC)C1=O)C(=O)Nc1cccc(N)c1] |

| Ex. No. | Structure |
|---|---|
| 255 | 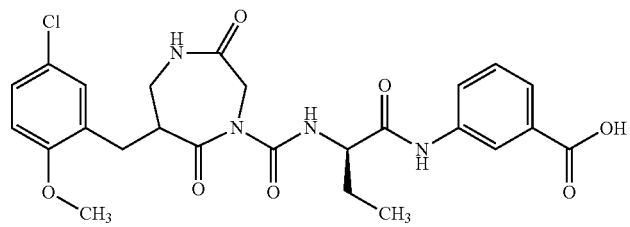 [SMILES: CC[C@@H](NC(=O)N1CC(=O)NCC(Cc2cc(Cl)ccc2OC)C1=O)C(=O)Nc1cccc(C(=O)O)c1] |
| 256 | 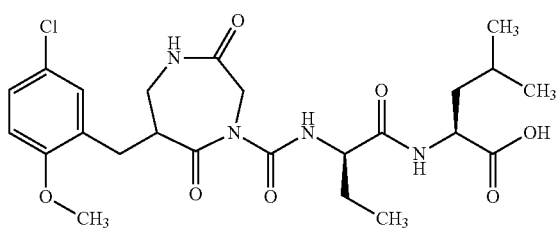 [SMILES: CC[C@@H](NC(=O)N1CC(=O)NCC(Cc2cc(Cl)ccc2OC)C1=O)C(=O)N[C@@H](CC(C)C)C(=O)O] |
| 257 | 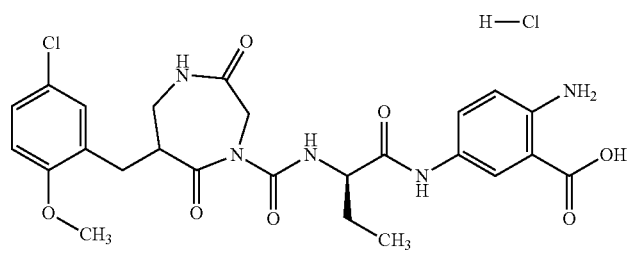 [SMILES: Cl ; CC[C@@H](NC(=O)N1CC(=O)NCC(Cc2cc(Cl)ccc2OC)C1=O)C(=O)Nc1ccc(N)c(C(=O)O)c1] |
| 258 | 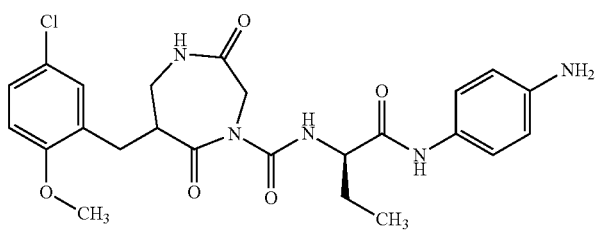 [SMILES: CC[C@@H](NC(=O)N1CC(=O)NCC(Cc2cc(Cl)ccc2OC)C1=O)C(=O)Nc1ccc(N)cc1] |
| 259 | 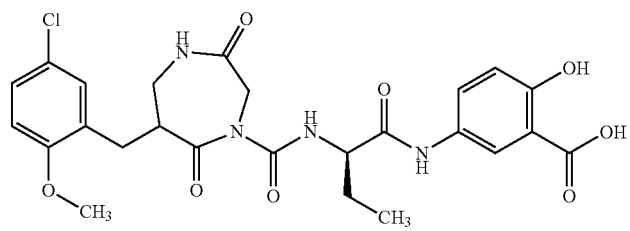 [SMILES: CC[C@@H](NC(=O)N1CC(=O)NCC(Cc2cc(Cl)ccc2OC)C1=O)C(=O)Nc1ccc(O)c(C(=O)O)c1] |
| 260 | 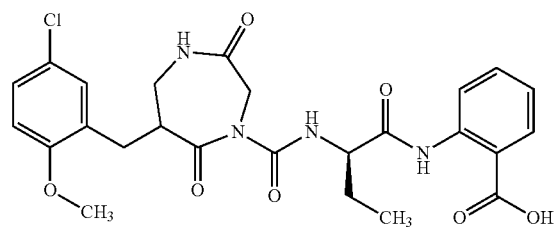 [SMILES: CC[C@@H](NC(=O)N1CC(=O)NCC(Cc2cc(Cl)ccc2OC)C1=O)C(=O)Nc1ccccc1C(=O)O] |

-continued
| Ex. No. | Structure |
|---|---|
| 261 | 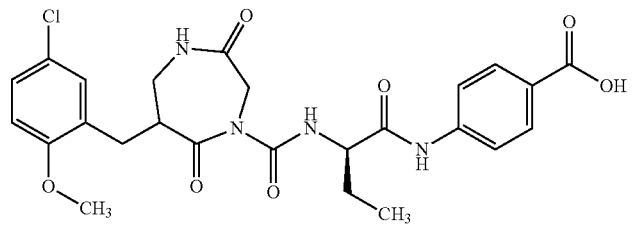 [SMILES: CC[C@@H](NC(=O)N1CC(=O)NCC(Cc2cc(Cl)ccc2OC)C1=O)C(=O)Nc1ccc(C(=O)O)cc1] |
| 262 | 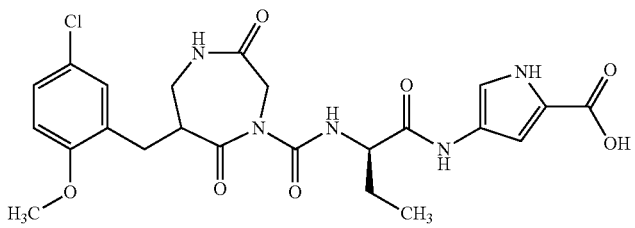 [SMILES: CC[C@@H](NC(=O)N1CC(=O)NCC(Cc2cc(Cl)ccc2OC)C1=O)C(=O)Nc1c[nH]c(C(=O)O)c1] |
| 263 | 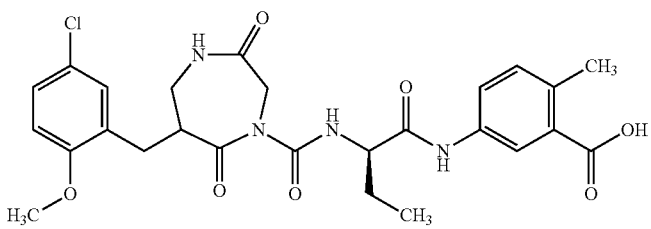 [SMILES: CC[C@@H](NC(=O)N1CC(=O)NCC(Cc2cc(Cl)ccc2OC)C1=O)C(=O)Nc1ccc(C)c(C(=O)O)c1] |
| 264 | 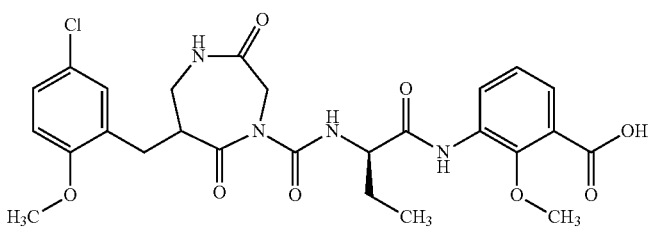 [SMILES: CC[C@@H](NC(=O)N1CC(=O)NCC(Cc2cc(Cl)ccc2OC)C1=O)C(=O)Nc1cccc(C(=O)O)c1OC] |
| 265 | 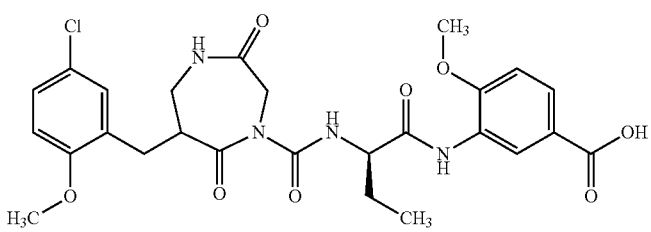 [SMILES: CC[C@@H](NC(=O)N1CC(=O)NCC(Cc2cc(Cl)ccc2OC)C1=O)C(=O)Nc1cc(C(=O)O)ccc1OC] |
| 266 | 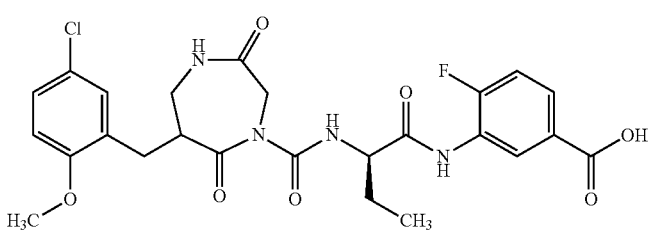 [SMILES: CC[C@@H](NC(=O)N1CC(=O)NCC(Cc2cc(Cl)ccc2OC)C1=O)C(=O)Nc1cc(C(=O)O)ccc1F] |

| Ex. No. | Structure |
|---|---|
| 267 | 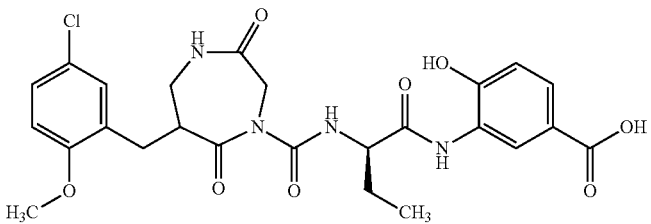 [SMILES: CC[C@@H](NC(=O)N1CC(=O)NCC(Cc2cc(Cl)ccc2OC)C1=O)C(=O)Nc1cc(C(=O)O)ccc1O] |
| 268 | 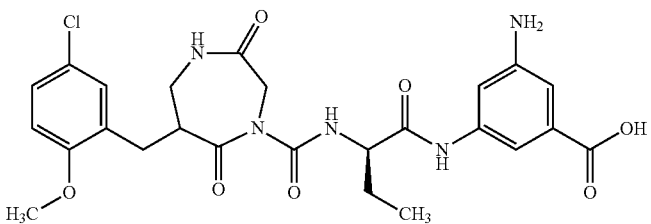 [SMILES: CC[C@@H](NC(=O)N1CC(=O)NCC(Cc2cc(Cl)ccc2OC)C1=O)C(=O)Nc1cc(N)cc(C(=O)O)c1] |
| 269 | 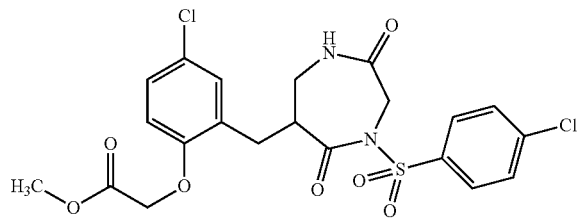 [SMILES: COC(=O)COc1ccc(Cl)cc1CC1CNC(=O)CN(S(=O)(=O)c2ccc(Cl)cc2)C1=O] |
| 270 | 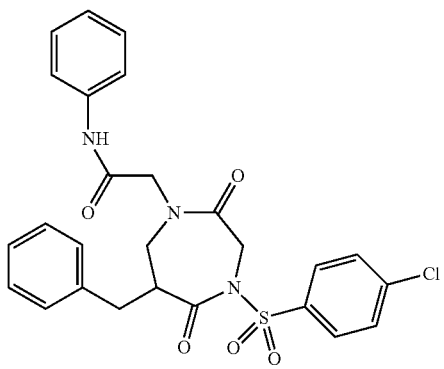 [SMILES: O=C(CN1CC(Cc2ccccc2)C(=O)N(S(=O)(=O)c2ccc(Cl)cc2)CC1=O)Nc1ccccc1] |
| 271 | 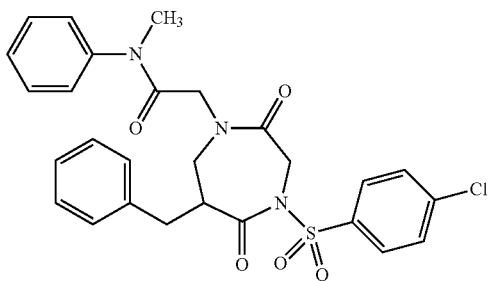 [SMILES: CN(C(=O)CN1CC(Cc2ccccc2)C(=O)N(S(=O)(=O)c2ccc(Cl)cc2)CC1=O)c1ccccc1] |

| Ex. No. | Structure |
|---|---|
| 272 | 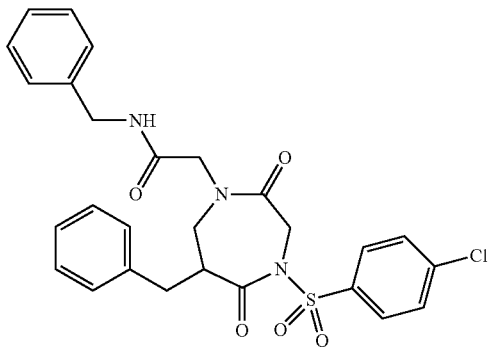 [SMILES: O=C(CN1CC(Cc2ccccc2)C(=O)N(S(=O)(=O)c2ccc(Cl)cc2)CC1=O)NCc1ccccc1] |
| 273 | 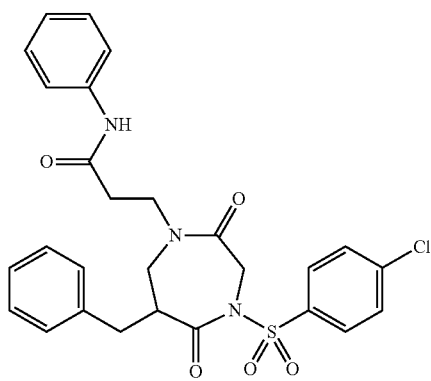 [SMILES: O=C(CCN1CC(Cc2ccccc2)C(=O)N(S(=O)(=O)c2ccc(Cl)cc2)CC1=O)Nc1ccccc1] |
| 274 | 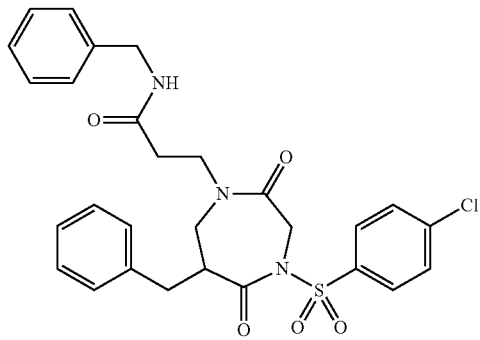 [SMILES: O=C(CCN1CC(Cc2ccccc2)C(=O)N(S(=O)(=O)c2ccc(Cl)cc2)CC1=O)NCc1ccccc1] |
| 275 | 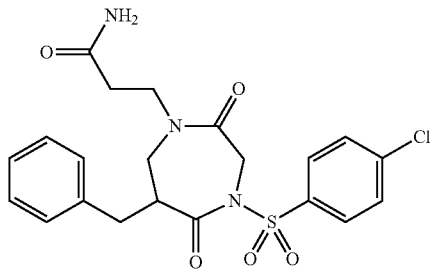 [SMILES: NC(=O)CCN1CC(Cc2ccccc2)C(=O)N(S(=O)(=O)c2ccc(Cl)cc2)CC1=O] |

-continued
| Ex. No. | Structure |
|---|---|
| 276 | 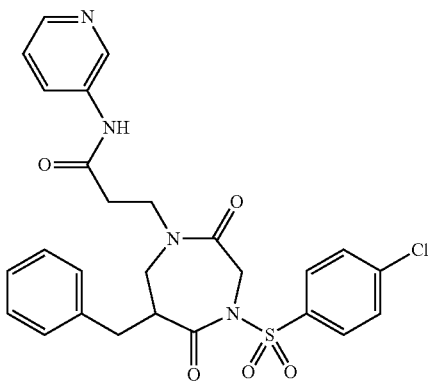 [SMILES: O=C(CCN1CC(Cc2ccccc2)C(=O)N(S(=O)(=O)c2ccc(Cl)cc2)CC1=O)Nc1cccnc1] |
| 277 | 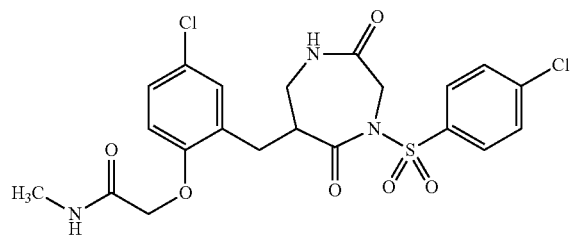 [SMILES: CNC(=O)COc1ccc(Cl)cc1CC1CNC(=O)CN(S(=O)(=O)c2ccc(Cl)cc2)C1=O] |
| 278 | 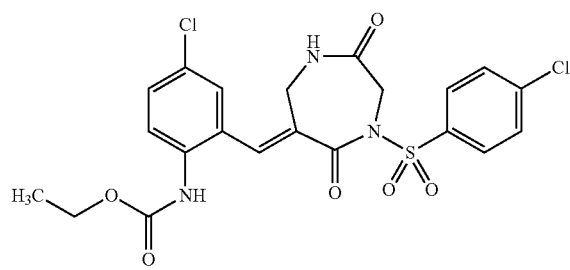 [SMILES: CCOC(=O)Nc1ccc(Cl)cc1/C=C1\CNC(=O)CN(S(=O)(=O)c2ccc(Cl)cc2)C1=O] |
| 279 | 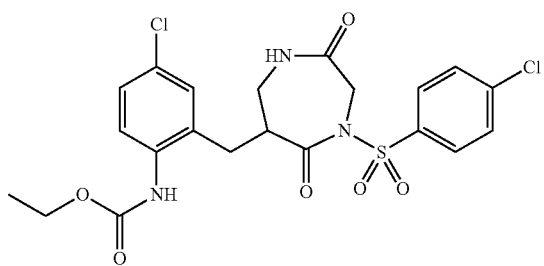 [SMILES: CCOC(=O)Nc1ccc(Cl)cc1CC1CNC(=O)CN(S(=O)(=O)c2ccc(Cl)cc2)C1=O] |
| 280 | 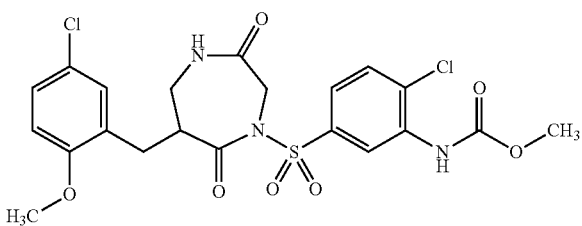 [SMILES: COC(=O)Nc1cc(S(=O)(=O)N2CC(=O)NCC(Cc3cc(Cl)ccc3OC)C2=O)ccc1Cl] |

| Ex. No. | Structure |
|---|---|
| 281 | 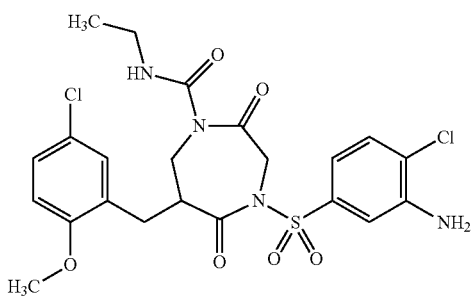 [SMILES: CCNC(=O)N1CC(Cc2cc(Cl)ccc2OC)C(=O)N(S(=O)(=O)c2ccc(Cl)c(N)c2)CC1=O] |
| 282 | 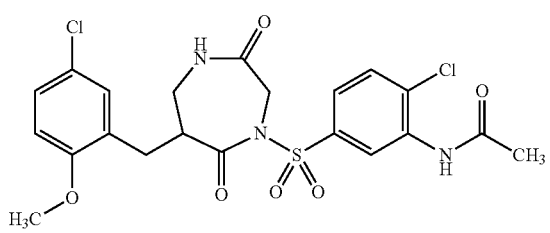 [SMILES: COc1ccc(Cl)cc1CC1CNC(=O)CN(S(=O)(=O)c2ccc(Cl)c(NC(C)=O)c2)C1=O] |
| 283 | 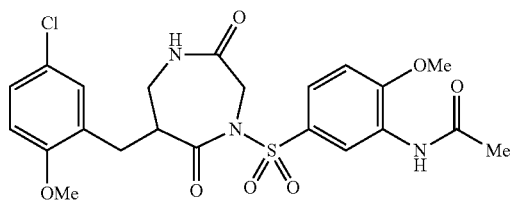 [SMILES: COc1ccc(Cl)cc1CC1CNC(=O)CN(S(=O)(=O)c2ccc(OC)c(NC(C)=O)c2)C1=O] |
| 284 | 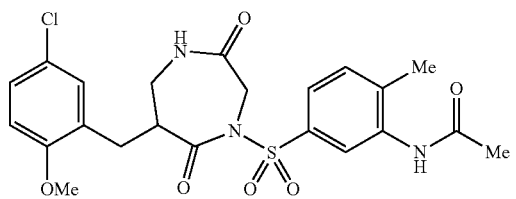 [SMILES: COc1ccc(Cl)cc1CC1CNC(=O)CN(S(=O)(=O)c2ccc(C)c(NC(C)=O)c2)C1=O] |
| 285 | 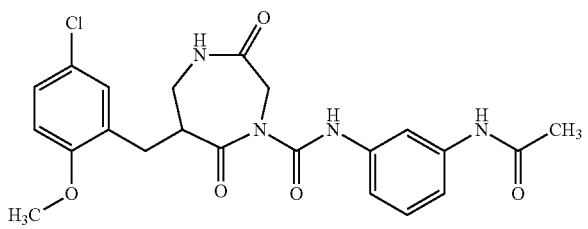 [SMILES: COc1ccc(Cl)cc1CC1CNC(=O)CN(C(=O)Nc2cccc(NC(C)=O)c2)C1=O] |
| 286 | 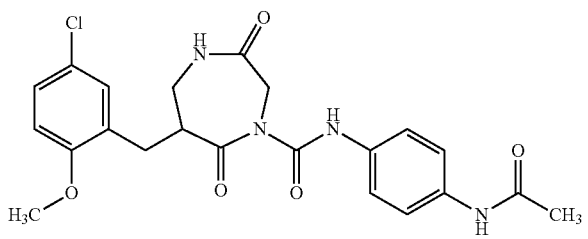 [SMILES: COc1ccc(Cl)cc1CC1CNC(=O)CN(C(=O)Nc2ccc(NC(C)=O)cc2)C1=O] |

-continued

| Ex. No. | Structure |
|---|---|
| 287 | (structure) |
| 288 | (structure) |
| 289 | (structure) |
| 290 | (structure) |
| 291 | (structure) |
| 292 | (structure) |
| 293 | (structure) |

| Ex. No. | Structure |
|---|---|
| 294 | 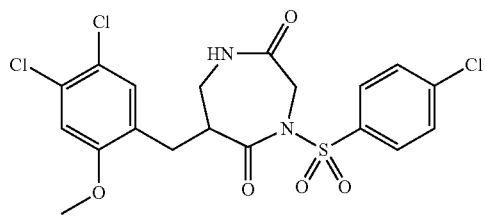 [SMILES: COc1cc(Cl)c(Cl)cc1CC1CNC(=O)CN(S(=O)(=O)c2ccc(Cl)cc2)C1=O] |
| 295 | 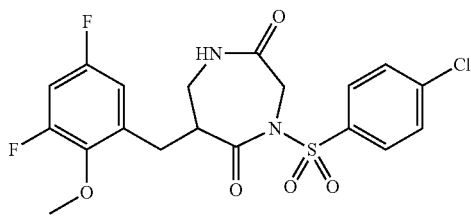 [SMILES: COc1c(F)cc(F)cc1CC1CNC(=O)CN(S(=O)(=O)c2ccc(Cl)cc2)C1=O] |
| 296 | 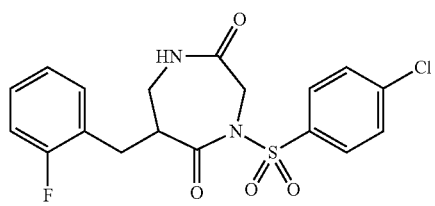 [SMILES: O=C1CN(S(=O)(=O)c2ccc(Cl)cc2)C(=O)C(Cc2ccccc2F)CN1] |
| 297 | 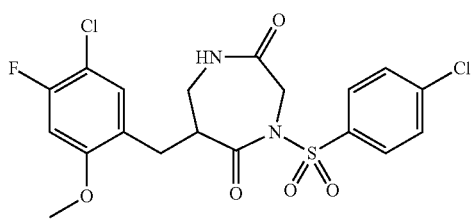 [SMILES: COc1cc(F)c(Cl)cc1CC1CNC(=O)CN(S(=O)(=O)c2ccc(Cl)cc2)C1=O] |
| 298 | 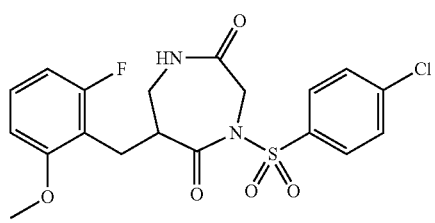 [SMILES: COc1cccc(F)c1CC1CNC(=O)CN(S(=O)(=O)c2ccc(Cl)cc2)C1=O] |
| 299 | 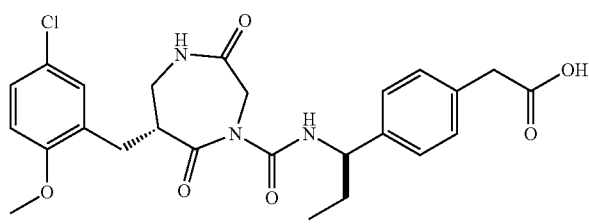 [SMILES: CC[C@@H](NC(=O)N1CC(=O)NC[C@@H](Cc2cc(Cl)ccc2OC)C1=O)c1ccc(CC(=O)O)cc1] |
| 300 | 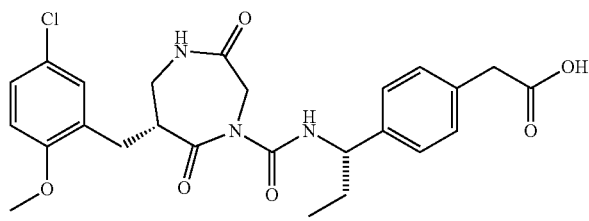 [SMILES: CC[C@H](NC(=O)N1CC(=O)NC[C@@H](Cc2cc(Cl)ccc2OC)C1=O)c1ccc(CC(=O)O)cc1] |

-continued

| Ex. No. | Structure |
|---|---|
| 301 | 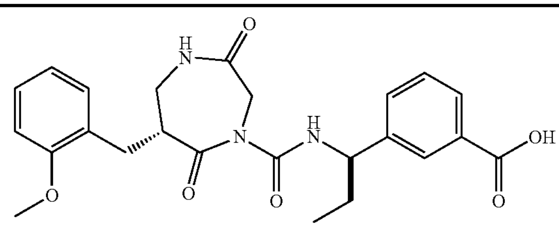 |
| 302 | 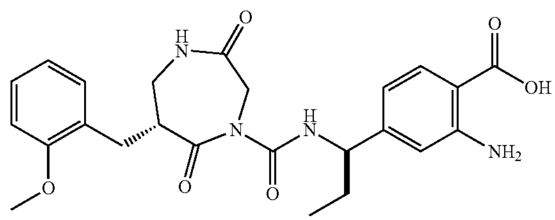 [SMILES: CC[C@@H](NC(=O)N1CC(=O)NC[C@@H](Cc2ccccc2OC)C1=O)c1ccc(C(=O)O)c(N)c1] |
| 303 | AcOH |
| 304 | 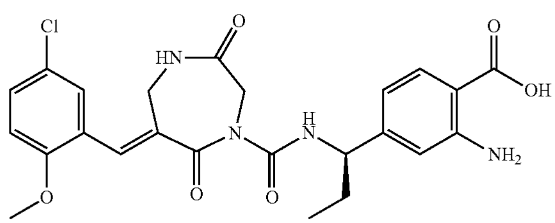 [SMILES: CC[C@@H](NC(=O)N1CC(=O)NC/C(=C\c2cc(Cl)ccc2OC)C1=O)c1ccc(C(=O)O)c(N)c1] |
| 305 | 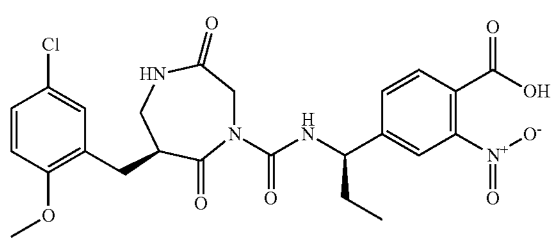 [SMILES: CC[C@@H](NC(=O)N1CC(=O)NC[C@H](Cc2cc(Cl)ccc2OC)C1=O)c1ccc(C(=O)O)c([N+](=O)[O-])c1] |
| 306 | 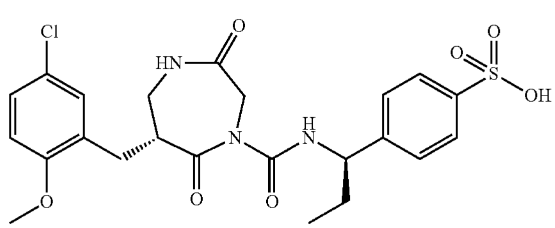 [SMILES: CC[C@@H](NC(=O)N1CC(=O)NC[C@@H](Cc2cc(Cl)ccc2OC)C1=O)c1ccc(S(=O)(=O)O)cc1] |
| 307 | 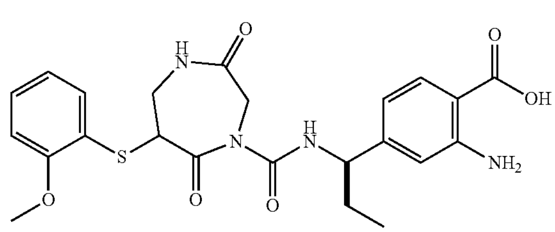 [SMILES: CC[C@@H](NC(=O)N1CC(=O)NCC(Sc2ccccc2OC)C1=O)c1ccc(C(=O)O)c(N)c1] |

| Ex. No. | Structure |
|---------|-----------|
| 308 | 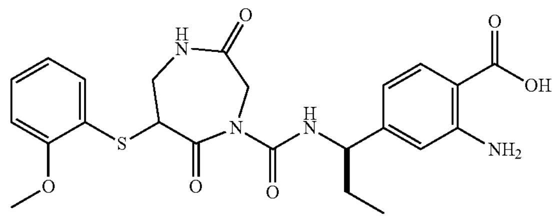 [SMILES: CC[C@@H](NC(=O)N1CC(=O)NCC(Sc2ccccc2OC)C1=O)c1ccc(C(=O)O)c(N)c1] |

The invention claimed is:

1. A compound, or its salt or a solvate thereof, having the formula (Va):

wherein W' indicates a phenyl,
wherein the $NH_2$—$CH(R^{18})$— group and $R^{19}O$—$C(=O)$— group of W' are 1,4 substituted; and
wherein the groups (1) and (2) of W' may optionally be substituted with 1 to 4 groups selected from the group consisting of (i) a halogen atom, (ii) nitro, (iii) cyano, (iv) $C_1$ to $C_6$ alkyl which may optionally be substituted with 1 to 3 groups selected from a halogen atom, amino, $C_1$ to $C_6$ alkoxycarbonyl, $C_1$ to $C_6$ alkoxycarbonylamino, and carboxyl, (v) $C_2$ to $C_6$ alkenyl which may optionally be substituted with 1 to 3 halogen atoms, (vi) $C_2$ to $C_6$ alkynyl which may optionally be substituted with 1 to 3 halogen atoms, (vii) $C_3$ to $C_6$ cycloalkyl, (viii) hydroxyl, (ix) $C_1$ to $C_6$ alkoxy which may optionally be substituted with 1 to 3 groups selected from a halogen atom, hydroxyl, $C_1$ to $C_6$ alkoxy, amino, and mono- or di-$C_1$ to $C_6$ alkylamino, (x) $C_1$ to $C_5$ alkylenedioxy, (xi) $C_1$ to $C_6$ alkylthio which may optionally be substituted with 1 to 3 groups selected from a halogen atom, hydroxyl, $C_1$ to $C_6$ alkoxy, amino, and mono- or di-$C_1$ to $C_6$ alkylamino, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xviii) $C_1$ to $C_6$ alkoxycarbonyl, (xix) $C_7$ to $C_{16}$ aralkyloxycarbonyl, (xx) carbamoyl, (xxi) mono-$C_1$ to $C_6$ alkylcarbamoyl which may optionally be substituted with 1 to 3 groups selected from a halogen atom, hydroxyl, carboxyl, $C_1$ to $C_6$ alkoxy, amino, and mono- or di-$C_1$ to $C_6$ alkylamino, (xxii) di-$C_1$ to $C_6$ alkylcarbamoyl which may optionally be substituted with hydroxyl, (xxiii) 5 to 6-membered cyclic aminocarbonyl which may optionally be substituted with $C_1$ to $C_6$ alkoxycarbonyl, (xxiv) $C_6$ to $C_{10}$ arylcarbamoyl, (xxv) $C_1$ to $C_{10}$ heteroarylcarbamoyl, (xxvi) $C_7$ to $C_{16}$ aralkylcarbamoyl, (xxvii) $C_1$ to $C_{10}$ heteroaryl-$C_1$ to $C_6$ alkylcarbamoyl, (xxviii) N—$C_1$ to $C_6$ alkyl-N—$C_6$ to $C_{12}$ arylcarbamoyl, (xxix) $C_3$ to $C_6$ cycloalkylcarbamoyl, (xxx) sulfo, (xxxi) $C_1$ to $C_6$ alkylsulfonyl, (xxxii) $C_1$ to $C_6$ alkylsulfonylamino, (xxxiii) $C_6$ to $C_{12}$ arylsulfonylamino which may be substituted with $C_1$ to $C_6$ alkyl, (xxxiv) $C_1$ to $C_{10}$ heteroarylsulfonylamino, (xxxv) $C_1$ to $C_6$ alkoxycarbonylamino, (xxxvi) $C_1$ to $C_6$ alkylcarbonylamino, (xxxvii) mono- or di-$C_1$ to $C_6$ alkylaminocarbonylamino, (xxxviii) $C_6$ to $C_{12}$ aryl, (xxxix) $C_1$ to $C_{10}$ heteroaryl, (xl) $C_6$ to $C_{10}$ aryloxy, (xli) $C_1$ to $C_{10}$ heteroaryloxy, (xlii) $C_7$ to $C_{16}$ aralkyloxy, (xliii) $C_1$ to $C_{10}$ heteroaryl-$C_1$ to $C_6$ alkyloxy, (xliv) aminosulfonyl, (xlv) mono- or di-$C_1$ to $C_6$ alkylaminosulfonyl, (xlvi) $C_7$ to $C_{16}$ aralkyloxycarbamoyl, and (xlvii) $C_1$ to $C_{10}$ heteroaryl-$C_1$ to $C_6$ alkyloxycarbamoyl, $R^{18}$ indicates a $C_2$ to $C_4$ alkyl group which may optionally be substituted with 1 to 3 halogen atoms, and $R^{19}$ indicates a hydrogen atom, $C_1$ to $C_6$ alkyl group which may optionally be substituted with 1 to 3 halogen atoms, or $C_7$ to $C_{16}$ aralkyl group which may optionally be substituted with 1 to 3 halogen atoms.

2. A compound, or its salt or a solvate thereof, as claimed in claim 1, wherein in the formula (Va),
W' is substituted with 1 to 4 groups selected from the group consisting of (ii) nitro, (iv) $C_1$ to $C_6$ alkyl substituted with 1 to 3 groups selected from amino, $C_1$ to $C_6$ alkoxycarbonyl, $C_1$ to $C_6$ alkoxycarbonylamino, and carboxyl, (v) $C_2$ to $C_6$ alkenyl which may optionally be substituted with 1 to 3 halogen atoms, (vi) $C_2$ to $C_6$ alkynyl which may optionally be substituted with 1 to 3 halogen atoms, (vii) $C_3$ to $C_6$ cycloalkyl, (viii) hydroxyl, (ix) $C_1$ to $C_6$ alkoxy substituted with 1 to 3 groups selected from hydroxyl, $C_1$ to $C_6$ alkoxy, amino, and mono- or di-$C_1$ to $C_6$ alkylamino, (x) $C_1$ to $C_5$ alkylenedioxy, (xi) $C_1$ to $C_6$ alkylthio which may optionally be substituted with 1 to 3 groups selected from a halogen atom, hydroxyl, $C_1$ to $C_6$ alkoxy, amino, and mono- or di-$C_1$ to $C_6$ alkylamino, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xviii) $C_1$ to $C_6$ alkoxycarbonyl, (xix) $C_7$ to $C_{16}$ aralkyloxycarbonyl, (xx) carbamoyl, (xxi) mono-$C_1$ to $C_6$ alkylcarbamoyl which may optionally be substituted with 1 to 3 groups selected from a halogen atom, hydroxyl, carboxyl, $C_1$ to $C_6$ alkoxy, amino, and mono- or di-$C_1$ to $C_6$ alkylamino, (xxii) di-$C_1$ to $C_6$ alkylcarbamoyl which may optionally be substituted with hydroxyl, (xxiii) 5- to 6-membered cyclic aminocarbonyl which may optionally be substituted with $C_1$ to $C_6$ alkoxycarbonyl, (xxiv) $C_6$ to $C_{10}$ arylcarbamoyl, (xxv) $C_1$ to $C_{10}$ heteroarylcarbamoyl, (xxvi) $C_7$ to $C_{16}$ aralkylcarbamoyl, (xxvii) $C_1$ to $C_{10}$ heteroaryl-$C_1$ to $C_6$ alkylcarbamoyl, (xxviii) N—$C_1$ to $C_6$ alkyl-N—$C_6$ to $C_{12}$ arylcarbamoyl, (xxix) $C_3$ to $C_6$ cycloalkylcarbamoyl, (xxx) sulfo, (xxxi) $C_1$ to $C_6$ alkylsulfonyl, (xxxii) $C_1$ to $C_6$ alkylsulfonylamino, (xxxiii) $C_6$ to $C_{12}$ arylsulfonylamino which may optionally be substituted with $C_1$ to $C_6$ alkyl, (xxxiv) $C_1$ to $C_{10}$ heteroarylsulfonylamino, (xxxv) $C_1$ to $C_6$ alkoxycarbonylamino, (xxxvi) $C_1$ to $C_6$ alkylcarbonylamino, (xxxvii) mono- or di-$C_1$ to $C_6$ alkylaminocarbonylamino, (xxxviii) $C_6$ to $C_{12}$ aryl, (xxxix) $C_1$ to $C_{10}$ heteroaryl, (xl) $C_6$ to $C_{10}$ aryloxy, (xli) $C_1$ to $C_{10}$ heteroaryloxy, (xlii) $C_7$ to $C_{16}$ aralkyloxy, (xliii) $C_1$ to $C_{10}$ heteroaryl-$C_1$ to $C_6$ alkyloxy, (xliv) aminosulfonyl, (xlv) mono- or di-$C_1$ to $C_6$ alkylaminosulfonyl, (xlvi) $C_7$ to $C_{16}$ aralkyloxycarbamoyl, and (xlvii) $C_1$ to $C_{10}$ heteroaryl-$C_1$ to $C_6$ alkyloxycarbamoyl.

3. A compound, or its salt or a solvate thereof, as claimed in claim 2, wherein, W' is substituted with (ii) nitro, (viii) hydroxyl, or (xii) amino.

\* \* \* \* \*